(12) United States Patent
Erra Sola et al.

(10) Patent No.: US 9,388,189 B2
(45) Date of Patent: Jul. 12, 2016

(54) PYRROLOTRIAZINONE DERIVATIVES AS PI3K INHIBITORS

(71) Applicant: ALMIRALL, S.A., Barcelona (ES)

(72) Inventors: Montserrat Erra Sola, Barcelona (ES); Marta Carrascal Riera, Barcelona (ES); Joan Taltavull Moll, Barcelona (ES); Juan Francisco Caturla Javaloyes, Barcelona (ES); Francisco Javier Bernal Anchuela, Barcelona (ES); Lluis Miquel Pages Santacana, Barcelona (ES); Marta Mir Cepeda, Barcelona (ES); Gaspar Casals Coll, Barcelona (ES); Maria Begoña Hernandez Olasagarre, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 14/435,851

(22) PCT Filed: Oct. 15, 2013

(86) PCT No.: PCT/EP2013/071551
§ 371 (c)(1),
(2) Date: Apr. 15, 2015

(87) PCT Pub. No.: WO2014/060432
PCT Pub. Date: Apr. 24, 2014

(65) Prior Publication Data
US 2015/0291595 A1    Oct. 15, 2015

Related U.S. Application Data

(60) Provisional application No. 61/718,782, filed on Oct. 26, 2012.

(30) Foreign Application Priority Data

Oct. 16, 2012    (EP) .................................... 12382399

(51) Int. Cl.
| | |
|---|---|
| C07D 487/04 | (2006.01) |
| C07D 519/00 | (2006.01) |
| A61K 31/53 | (2006.01) |
| A61P 11/06 | (2006.01) |
| A61P 11/00 | (2006.01) |
| A61K 45/06 | (2006.01) |

(52) U.S. Cl.
CPC .............. *C07D 487/04* (2013.01); *A61K 31/53* (2013.01); *A61K 45/06* (2013.01); *C07D 519/00* (2013.01)

(58) Field of Classification Search
CPC .. C07D 491/04; C07D 487/04; C07D 519/00; A61K 31/53
USPC .......................................... 544/183; 514/243
See application file for complete search history.

(56) References Cited

U.S. PATENT DOCUMENTS

| | | |
|---|---|---|
| 2002/0161014 A1 | 10/2002 | Sadhu et al. |
| 2003/0232832 A1 | 12/2003 | Lombardo et al. |
| 2010/0029693 A1 | 2/2010 | Douangpanya et al. |

FOREIGN PATENT DOCUMENTS

| | | |
|---|---|---|
| WO | WO 01/81346 | 11/2001 |
| WO | WO 03/035075 | 5/2003 |
| WO | WO 03/099286 | 12/2003 |
| WO | WO 2007/023186 | 3/2007 |
| WO | WO 2010/111432 A1 | 9/2010 |
| WO | WO 2011/058109 A | 5/2011 |
| WO | WO 2012/145666 A1 | 11/2012 |
| WO | WO 2014/015523 | 1/2014 |

OTHER PUBLICATIONS

Klempner et al.Cancer Discov. Dec. 2013;3(12):1345-54.*
Massacesi et al. Ann. N.Y. Acad. Sci. 1280 (2013) 19-23.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Hulikal, V. Deuterium Labeled Compounds in Drug Discovery Process-Abstract, www.hwb.gov.In/htmldocs/nahwd2010/L15.pdf.*
Pimlott SL., Nucl. Med. Commun. 26(3): 183-188, 2005 (PubMed Abstract provided).*
PCT International Search Report for International Application No. PCT/EP2013/071551, Nov. 22, 2013 (3 pages).
Kim, Kyoung Soon et al., "Synthesis and SAR of Pyrrolotriazine-4-one Based Eg5 Inhibitors," *Biorganic & Medical Chemistry Letters*, vol. 26, No. 15, pp. 3937-3942 (2006).

(Continued)

*Primary Examiner* — Venkataraman Balasubramanian
(74) *Attorney, Agent, or Firm* — Finnegan, Henderson, Farabow, Garrett & Dunner

(57) ABSTRACT

New pyrrolotriazinone derivatives having the chemical structure of Formula (I) are disclosed; as well as process for theft preparation, pharmaceutical compositions comprising them and their use in therapy as inhibitors of Phosphoinositide 3-Kinases (PI3Ks).

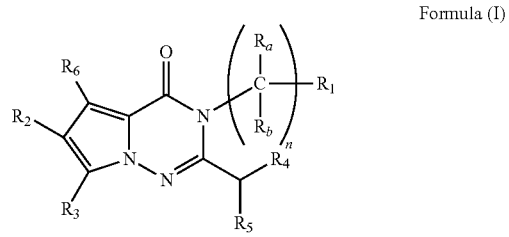

Formula (I)

20 Claims, No Drawings

(56) References Cited

OTHER PUBLICATIONS

McNeill, Helen et al., "When Pathways Collide: Collaboration and Connivance Among Signaling Proteins in Development," *Nature Reviews Mollecular Cell Biology, Nature Publishing GB*, vol. 11, No. 6, pp. 404-413.
Liu, Xuesong et al., "Akt Inhibitor A-443654 Interferes with Mitotic Progression by Regulating Aurora A Kinase Expression" *NEOPLASIA* Aug. 10, 2008(8) pp. 828-837 (2008).
International Search Report of International Application No. PCT/EP2012/057671, Jun. 8, 2012.
Stearns, Ralph A. et al., "Evidence for a 1,3-Hydride Shift in the Microsomal Metabolism of the Heterocycle L-158,338, a NonPeptide Anglotensin II Receptor Antagonist", *Drug Metabolism and Disposition*, vol. 21, No. 4, pp. 670-676 (1993).
Kok, Klaartje, et al., "Regulation of Phosphoinositide 3-kinase Expression in Health and Disease" *trends Biochem Sci.*, vol. 34, No. 3, pp. 115-127 (2009).
Kumar, Amit et al., "New Function for P13K in the Control of Cell Division," *Cell Cycle*, vol. 6, issue 14, pp. 1696-1698 (2007).

* cited by examiner

PYRROLOTRIAZINONE DERIVATIVES AS PI3K INHIBITORS

This application is a national stage filing under 35 U.S.C. §371 of International Application No. PCT/EP2013/071551, filed on Oct. 15, 2013, which claims priority of European Patent Application No. 12382399.9, filed on Oct. 16, 2012, and also claims priority of U.S. Provisional Patent Application No. 61/718,782 filed on Oct. 26, 2012. The contents of these applications are each incorporated herein by reference.

When cells are activated by extracellular stimuli, intracellular signalling cascades involving the regulation of second messengers are initiated that eventually produce a response of the cell to the stimuli. Phosphoinositide 3-Kinases (PI3Ks) are among the enzymes involved in early signalling events to a plethora of different types of stimuli. PI3Ks phosphorylate the 3-hydroxyl group of the inositol ring of phosphatidylinositol (Ptdlns), Ptdlns-4-phosphate (Ptdlns4P), and Ptdlns-4,5-bisphosphate (Ptdlns(4,5)P2). The resulting 3-phosphoinositides mediate correct localization and subsequent activation of a number of downstream effector proteins that bind to the lipids via specific lipid binding sequences such as the pleckstrin homology (PH) domain (Vanhaesebroeck B, 2010, *Nat Rev Mol Cell Biol* 5:11381-6).

The PI3K family is divided into 3 different classes (PI3K class I, class II, and class III), depending on substrate preference and structural features.

The best characterized is the PI3K class I with the preferential substrate Ptdlns-(4,5)P2. It englobes 4 different isoforms which originally were further subdivided into class IA (p110a, p110b, p110d), binding to a p85 type of regulatory subunit, and class IB (p110g) which is regulated by p101 and p87 subunits. Whereas p110a (PI3Ka or PI3Kα) and p110b (PI3Kb or PI3Kβ) isoforms are expressed ubiquitously, p110g (PI3Kg or PI3Kγ) and especially p110d (PI3Kd or PI3Kδ) have a more restricted expression pattern and seem to play a major role in leukocytes (Kok K, *Trends Biochem Science* 34:115-127, 2009).

Both, PI3Kd and PI3Kg are involved in activation of immune cells by a large variety of different stimuli. Pharmacological inhibition or genetic deficiency in active p110d has been shown to inhibit T cell proliferation and cytokine production in response to different stimuli such as anti-CD3, anti-CD3/CD28, superantigen or antigen in vitro (Ji H, Blood 2007; Okkenhaug K, Science 2002; Garcon F, 2009; Soond D R, Blood 2010; Herman S E M, Blood Jun. 3, 2010; William 0, Chemistry & Biology 17, 2010) and to suppress concanavalin A and anti-CD3 induced cytokine production as well as antigen-dependent tissue retention in vivo (Soond D R, Blood 2010; Jarmin S J, JCI 2008). In addition, B cell function is critically dependent on functional PI3Kd activity as demonstrated by suppressed B cell proliferation and cytokine release in vitro in response to anti-IgM (Bilancio A, Blood 107, 2006), toll like receptor agonists such as LPS and oligodeoxynucleotides (Dil N, Mol Immunol 46, 2009) or impaired ability to stimulate antigen-specific T cells (Al-Alwan M, JI 2007) in the absence of functional p110d or pharmacological inhibition. In vivo, PI3Kg deficient mice display partially suppressed antibody production upon immunization (Garcon F, 2009; Durand C A, JI 2009). Further studies have demonstrated an important role of PI3Kd in inhibition of T cell apoptosis and in TH17 differentiation (Haylock-Jacobs S, J. Autoimmun 2010).

In addition, mast cell degranulation was reduced in cells from mice with inactivated PI3Kd or by pharmacological inhibition of PI3Kd (Ali K, Nature 431:1007-1011, 2004; Ali K, Journal of Immunology 180:2538-2544, 2008) and basophil activation via the FcE receptor is suppressed by pharmacological inhibition of PI3Kd (Lannutti B J, Blood October 2010).

In terms of neutrophil function, PI3Kd inhibition inhibits migration of mouse neutrophils to fMLP in an under-agarose migration assay by inhibiting cell polarization and directional movement (Sadhu C, JI 170, 2003) and mouse PI3Kd deficient or inhibitor treated neutrophils show slightly (25%) reduced in vitro chemotaxis to LTB4, whereas in vivo accumulation in the lung in response to LPS was reduced by more than 80%, indicating an important role of PI3Kd in endothelial cells for mediating PMN transendothelial migration (Puri K D, Blood 103, 2004). Furthermore, TNF induced neutrophil infiltration to an air pouch in mice and elastase release is partially inhibited by a PI3Kd selective inhibitor (Sadhu C, Biochem Biophys Res Comm 308, 2003). In addition, TNF mediated priming of oxidative burst by human neutrophils depends on PI3Kd activity (Condliffe A M, Blood 106, 2005).

In contrast to the dominant role of PI3Kd in lymphocyte activation, PI3Kg seems to affect primarily chemotaxis of different immune cells induced by various mediators and chemokines (Martin A L, JI 180, 2008; Thomas M S, J Leukoc Biol 84, 2008; Jarmin S J, JCI 2008; Matthew T, Immunology 126, 2008), as well as degranulation and oxidative burst of innate immuce cells induced by GPCR mediated stimuli such as fMLP, IL-8 or C5a (Condliffe A M, Blood 106, 2005; Yum H K, JI 167, 2001; Pinho V, JI 179, 2007

The above mentioned findings suggest that selective PI3Kd or dual PI3Kd/PI3Kg pharmacological inhibition represents a promising approach for treating a variety of diseases such as respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, blistering diseases including but not limited to bullous pemphigoid, scleroderma, dermatomyositis, etc.), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelo-dysplastic syndrome; myeloproliferative disorders (MPDS); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

There is substantial experimental evidence supporting this view. In rodent models of allergic lung inflammation, genetic or pharmacological inactivation of PI3Kd or dual PI3Kd/g dual inhibition reduces cell influx, mucus production, cytokine production and airway hyperreactivity (Nashed et a. 2007, *Eur J Immunol* 37:416; Lee et al. 2006, FASEB J 20:455 & Lee K S et al. 2006, J Allergy Clin Immunol 118:403; Doukas J, JPET 2009; 328:758; Par S J, ERJ 2010). Moreover, LPS induced lung neutrophil infiltration is blocked by PI3Kd inhibition (Puri K D, Blood 2004; 103:3448) and inflammation in response to LPS or tobacco smoke exposure is suppressed by a dual PI3Kd/g inhibitor (Doukas J, JPET 2009; 328:758). Moreover, PI3Kd seems to be involved in the reduction of responsiveness to corticosteroid treatment associated with oxidative stress and chronic obstructive pulmonary disease (COPD). This notion is based on the findings that tobacco smoke induced inflammation remains responsive to treatment with budesonide, whereas wild type or PI3Kg deficient mice develop resistance to corticosteroid treatment (Marwick J A, JRCCM 179:542-548, 2009). Similar results were obtained with a PI3Kd selective inhibitor (To Y, AJRCCM 182:897-904, 2010). In addition, in vitro induction of corticosteroid resistance by oxidative stress is prevented by PI3Kd inhibition (To Y, AJRCCM 2010). In COPD patients, lung macrophages display increased expression of PI3Kd and phosphorylation of its downstream effector Akt and non-selective PI3K or PI3Kd-selective inhibition restored the impaired inhibitory efficacy of dexamethasone in PBMC from COPD patients (To Y, AJRCCM 182:897-904, 2010; Marwick J A, JACI 125:1146-53, 2010).

Furthermore, PI3Kd inhibition was effective in a model of contact hypersensitivity (Soond D R, Blood January 2010). In a model of experimental autoimmune encephalomyelitis, PI3Kd deficiency or pharmacological inhibition of PI3Kd attenuated T cell activation and function and reduced T cell numbers in the CNS, suggesting a therapeutic benefit of PI3Kd inhibitor in multiple sclerosis and other Th17-mediated autoimmune diseases (Haylock-Jacobs S, J. Autoimmun 2010). In line with that, genetic deficiency or pharmacological inhibition of PI3Kd diminished joint erosion in a mouse model of inflammatory arthritis (Randis T M, Eur J Immunol 38, 2008). Concerning metabolic diseases, PI3Kd overexpression seems to contribute to excessive vascular contraction and PI3Kd inhibition normalized vascular contractive responses in a mouse model of type I diabetes, suggesting a therapeutic potential of PI3Kd blockade to treat vascular dysfunction in diabetic patients (Pinho J F, Br. J. Pharmacol 161, 2010).

There is also substantial experimental evidence supporting that genetic of pharmacological inactivation of PI3Kd or dual PI3Kd/g dual inhibition is effective in the treatment of cancers including but not restricted to leukemias, such as chronic lymphocytic leukemia, B-cell acute lymphoblastic leukemia, T-cell acute lymphoblastic leukaemia, non-hodgkins lymphoma, B-cell lymphoma, acute myeloid leukaemia, myelodysplastic syndrome or myelo-proliferative diseases. In this aspect, the selective PI3Kd inhibitor CAL-101 demonstrated anti-proliferative properties on different tumor cells in vitro and efficacy in cancer patients with a dysregulated PI3Kd activity, such as chronic lymphocytic leukemia (Hermann S E, Blood 116:2078-88, 2010; Lannutti B J, Blood October 2010).

Conditions in which targeting of the PI3K pathway or modulation of the PI3 Kinases, particularly PI3Kd or PI3Kd/g, are contemplated to be therapeutically useful for the treatment or prevention of diseases including: respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune-mediated diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, scleroderma, dermatomyositis and blistering diseases including but not limited to bullous pemphigoid), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelo-dysplastic syndrome; myeloproliferative disorders (MPDS); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

In view of the numerous conditions that are contemplated to benefit by treatment involving modulation of the PI3K pathway or modulation of the PI3 Kinases it is immediately apparent that new compounds that modulate PI3K pathways and use of these compounds should provide substantial therapeutic benefits to a wide variety of patients.

Provided herein are novel pyrrolotriazinone derivatives for use in the treatment of conditions in which targeting of the PI3K pathway or inhibition of PI3 Kinases can be therapeutically useful.

The compounds described in the present invention are potent PI3K inhibitors, particularly PI3Kd or dual PK3Kd/g inhibitors. This property makes them useful for the treatment or prevention of pathological conditions or diseases such as respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, scleroderma, cutaneous vasculitis, cutaneous lupus erythematosus, dermatomyositis and blistering diseases including but not limited to *pemphigus vulgaris*, bullous pemphigoid and epidermolysis bullosa), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelodysplastic syndrome; myeloproliferative disorders (such as polycythemia vera, essential thrombocythemia or mielofibrosis); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

The compounds described in the present invention are particularly useful for the treatment or prevention of pathological conditions or diseases such as neoplastic diseases (e.g. leukemia, lymphomas, solid tumors); transplant rejection, bone marrow transplant applications (e.g., graft-versus-host disease); autoimmune diseases (e.g. rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis and blistering diseases including but not limited to *pemphigus vulgaris*, bullous pemphigoid and epidermolysis bullosa; respiratory inflammation diseases (e.g. asthma, chronic obstructive pulmonary disease, cystic fibrosis, idiopathic pulmonary fibrosis, sarcoidosis); skin inflammatory diseases (e.g., atopic dermatitis, contact dermatitis, eczema or psoriasis); premalignant and malignant skin conditions (e.g. basal cell carcinoma (BCC), squamous cell carcinoma (SCC) or actinic keratosis (AK)); neurological disorders and pain (such as pain associated with rheumatoid arthritis or osteoarthritis, back pain, general inflammatory pain, inflammatory neuropathic pain, trigeminal neuralgia or central pain)

The compounds described in the present invention are particularly useful for the treatment or prevention of pathological conditions or diseases selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

It has now been found that certain pyrrolotriazinone derivatives are novel and potent PI3K inhibitors and can therefore be used in the treatment or prevention of these diseases.

Thus the present invention is directed to compounds of formula (I), or a pharmaceutically acceptable salt, or N-oxide, or isotopically-labeled derivate thereof:

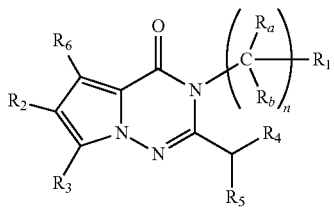

Formula (I)

wherein, n represents 0, 1, 2 or 3;

$R_a$ and $R_b$ each independently represent a hydrogen atom, a $C_1$-$C_4$ haloalkyl group, a $C_1$-$C_4$ hydroxyalkyl group or a linear or branched $C_1$-$C_4$ alkyl group;

$R_1$ represents a $C_3$-$C_{10}$ cycloalkyl group, a $C_3$-$C_{10}$ cycloalkenyl group, a phenyl group, a 5- to 7-membered heteroaryl group containing at least one heteroatom selected from O, S and N, or a 5- to 7-membered heterocyclyl group containing at least one heteroatom selected from O, S and N, wherein the cycloalkyl, cycloalkenyl, aryl, heteroaryl, and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, $R_2$ and $R_3$ each independently represent a hydrogen atom, a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a $C_1$-$C_4$ alkoxy group, a —$NH_2$ group, a —$N(CH_3)H$ group or a —$N(CH_3)_2$ group;

$R_7$ and $R_8$ each independently represent a hydrogen atom, a $C_1$-$C_4$ haloalkyl group, a $C_1$-$C_4$ hydroxyalkyl group or a linear or branched $C_1$-$C_4$ alkyl group;

and a)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —C(O)—$(CH_2)_{0-3}$—$R_8$ group or a —C(O)—$(CH_2)_{0-3}$—$NR_7R_8$ group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}NR_7R_8$ group; a —$(CH_2)_{1-3}$—O($C_1$-$C_4$ alkyl group); a —$(CH_2)_{0-3}$—OC (O)—($C_1$-$C_4$ alkyl group); a —$(CH_2)_{0-3}$—C(O)O—($C_1$-$C_4$ alkyl group); a —C(O)—$(CH_2)_{0-3}$—$NR_7R_8$ group; a —$(CH_2)_{0-3}$—C(O)OH group; a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N); a $C_2$-$C_4$ alkynyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;
  wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;
$R_5$ represents a moiety of formula (II-1), (II-2), (II-3), or (II-4):

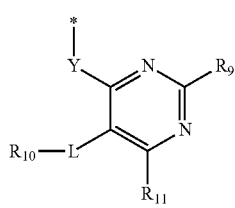

formula (II-1)

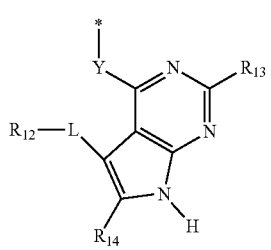

formula (II-2)

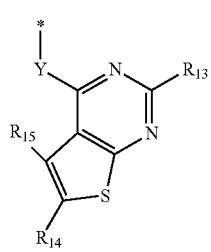

formula (II-3)

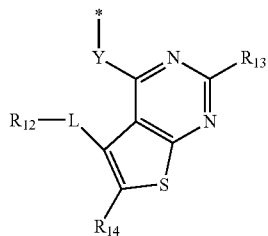

formula (II-4)

wherein:
$R_9$, $R_{11}$, $R_{13}$, $R_{14}$ and $R_{15}$ each independently represent a hydrogen atom, a —$(CH_2)_{0-3}$CN group, a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group, a $C_1$-$C_4$ hydroxyalkyl group or a linear or branched $C_1$-$C_4$ alkyl group;
$R_{10}$ and $R_{12}$ each independently represent a phenyl group or a 5- to 14-membered heteroaryl group containing at least one heteroatom selected from O, S and N,
  wherein the phenyl and heteroaryl groups are unsubstituted or substituted by one or more substituents selected from a halogen atom, hydroxyl group, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 14-membered heteroaryl group containing at least one heteroatom selected from O, S and N, a 5- to 14-membered heterocyclyl group containing at least one heteroatom selected from O, S and N, a —$(CH_2)_{1-3}$CN group, a —$(CH_2)_{0-3}$—OR' group, a —C(O) group, a —$(CH_2)_{0-3}$NR'R" group, a —$(CH_2)_{0-3}$—C(O)—$(CH_2)_{1-3}$—CN group, a —$(CH_2)_{0-3}$—C(O)OH group, a —$(CH_2)_{0-3}$—C(O)—$(CH_2)_{0-3}$—R' group, a —$(CH_2)_{0-3}$—C(O)—$(CH_2)_{0-3}$—NR'R"group, a —$(CH_2)_{0-3}$NR'—S(O)$_2$R" group or a —$(CH_2)_{0-3}$—S(O)$_2$$(CH_2)_{0-3}$NR'R" group; wherein R' and R" each independently represent a hydrogen atom, a hydroxyl group, a $C_1$-$C_4$ haloalkyl group, a $C_1$-$C_4$ alkoxy group, a $C_1$-$C_4$ hydroxyalkyl group, a linear or branched $C_1$-$C_4$ alkyl group or a phenyl group, which phenyl group is unsubstituted or substituted by one or more substituents selected from a halogen atom, a hydroxyl group, a cyano group, a $C_1$-$C_4$ hydroxyalkyl group, a $C_1$-$C_4$ haloalkyl group, a $C_1$-$C_4$ alkoxy group, a $C_3$-$C_4$ cycloalkyl group or a linear or branched $C_1$-$C_4$ alkyl group;
L represents a direct bound or a linker selected from —O—, —S—, a —$(CH_2)_{0-3}$NR'— group, a —C(O)—NR'— group, a —$(CH_2)_{0-3}$NR'—C(O)— group, a —C(O)—O— group, a —O—C(O)— group or a —$(CH_2)_{1-4}$ group; wherein R' represents hydrogen or a linear or branched $C_1$-$C_4$ alkyl group;
Y represents a —NR'— group; wherein R' represents hydrogen or a linear or branched $C_1$-$C_4$ alkyl group;
or
b)
$R_4$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a C$_1$-C$_4$ alkoxy group; a C$_1$-C$_4$ haloalkyl group; a linear or branched C$_1$-C$_4$ hydroxyalkyl group; a C$_3$-C$_7$ cycloalkyl group; a —(CH$_2$)$_{0-3}$NR$_7$R$_8$ group; a —(CH$_2$)$_{1-3}$—O(C$_1$-C$_4$ alkyl group); a —(CH$_2$)$_{0-3}$—OC(O)—(C$_1$-C$_4$ alkyl group); a —(CH$_2$)$_{0-3}$—C(O)O—(C$_1$-C$_4$ alkyl group); a —C(O)—(CH$_2$)$_{0-3}$—NR$_7$R$_8$ group; a —(CH$_2$)$_{0-3}$—C(O)OH group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_5$ represents a moiety of formula (II-1), (II-2), (II-3), (II-4), (II-5) or (II-6):

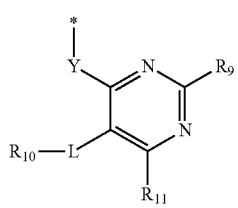

formula (II-1)

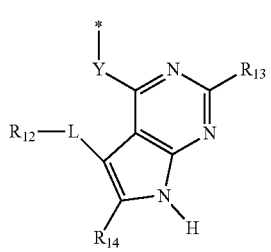

formula (II-2)

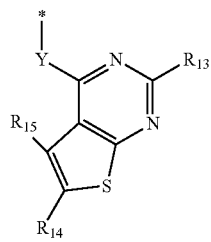

formula (II-3)

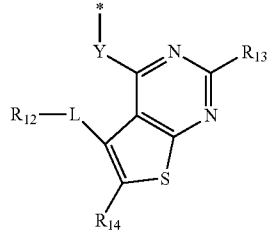

formula (II-4)

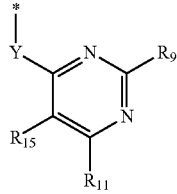

formula (II-5)

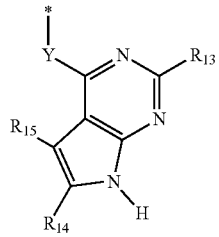

formula (II-6)

wherein:
R$_9$, R$_{11}$, R$_{13}$, R$_{14}$, R$_{15}$, R$_{10}$, R$_{12}$, L and Y are as defined above;

or c) R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group, which alkyl group is unsubstituted or substituted by one or more substituents selected from a C$_1$-C$_4$ alkoxy group, a cyano group, a C$_3$-C$_4$ cycloalkyl group, a —C(O)—(CH$_2$)$_{0-3}$—R$_8$ group or a —C(O)—(CH$_2$)$_{0-3}$—NR$_7$R$_8$ group;

wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

$R_6$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3), (II-4), (II-5) or (II-6):

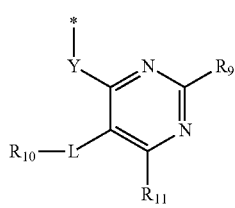

formula (II-1)

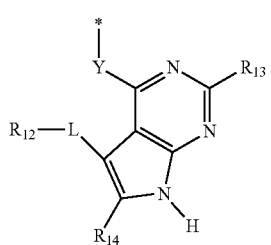

formula (II-2)

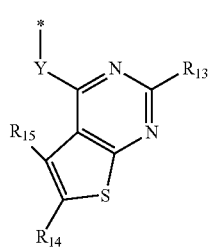

formula (II-3)

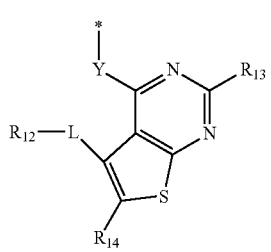

formula (II-4)

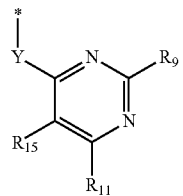

formula (II-5)

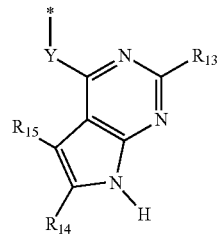

formula (II-6)

wherein:
$R_9$, $R_{11}$, $R_{13}$, $R_{14}$, $R_{15}$, $R_{10}$, $R_{12}$, L and Y are as defined above.

The invention further provides synthetic processes and intermediates described herein, which are useful for preparing said compounds.

The invention is also directed to a compound of the invention as described herein for use in the treatment of the human or animal body by therapy.

The invention also provides a pharmaceutical composition comprising the compounds of the invention and a pharmaceutically-acceptable diluent or carrier.

The invention is also directed to the compounds of the invention as described herein, for use in the treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK).

The invention is also directed to use of the compounds of the invention as described herein, in the manufacture of a medicament for treatment of a pathological condition or disease susceptible to amelioration by inhibition of Phosphoinositide 3-Kinases (PI3Ks), in particular wherein the pathological condition or disease is as defined above. The invention also provides a method of treatment of a pathological condition or disease susceptible to amelioration by inhibition of Phosphoinositide 3-Kinases (PI3Ks), in particular wherein the pathological condition or disease is as defined above.

The invention also provides a combination product comprising (i) the compounds of the invention as described herein; and (ii) one or more additional active substances which are known to be useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelodysplastic syndrome; myeloproliferative disorders (MPDS); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK).

As used herein the term $C_1$-$C_6$ alkyl embraces linear or branched radicals having 1 to 6 carbon atoms, preferably 1 to 4 carbon atoms. Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

When it is mentioned that the alkyl radical may be optionally substituted it is meant to include linear or branched alkyl radical as defined above, which may be unsubstituted or substituted in any position by one or more substituents, for example by 1, 2 or 3 substituents. When two or more substituents are present, each substituent may be the same or different.

As used herein, the term $C_1$-$C_4$ haloalkyl group is an alkyl group, for example a $C_1$-$C_4$ or $C_1$-$C_2$ alkyl group, which is bonded to one or more, preferably 1, 2 or 3 halogen atoms. Preferably, said haloakyl group is chosen from —$CCl_3$, —$CHF_2$ and —$CF_3$.

As used herein, the term $C_1$-$C_4$ hydroxyalkyl embraces linear or branched alkyl radicals having 1 to 4 carbon atoms, any one of which may be substituted by one or more, preferably 1 or 2, more preferably 1 hydroxyl radicals. Examples of such radicals include hydroxymethyl, hydroxyethyl, hydroxypropyl, and hydroxybutyl.

As used herein, the term $C_1$-$C_4$ alkoxy (or alkyloxy) embraces linear or branched oxy-containing radicals each having alkyl portions of 1 to 4 carbon atoms.

As used herein, the term $C_3$-$C_{10}$ cycloalkyl embraces saturated monocyclic or polycyclic carbocyclic radicals having from 3 to 10 carbon atoms, preferably from 3 to 7 carbon atoms. An optionally substituted $C_3$-$C_{10}$ cycloalkyl radical is typically unsubstituted or substituted by 1, 2 or 3 substituents which may be the same or different. When a $C_3$-$C_{10}$ cycloalkyl radical carries 2 or more substituents, the substituents may be the same or different. Typically the substituents on a $C_3$-$C_{10}$ cycloalkyl group are themselves unsubstituted.

Polycyclic cycloalkyl radicals contains two or more fused cycloalkyl groups, preferably two cycloalkyl groups. Typically, polycyclic cycloalkyl radicals are selected from decahydronaphthyl (decalyl), bicyclo[2.2.2]octyl, adamantly, camphyl or bornyl groups.

Examples of monocyclic cycloalkyl groups include cyclopropyl, cyclobutyl, cyclopentyl, cyclohexyl, cycloheptyl, cyclooctyl, cyclononyl and cyclodecyl.

As used herein, the term $C_3$-$C_{10}$ cycloalkenyl embraces partially unsaturated carbocyclic radicals having from 3 to 10 carbon atoms, preferably from 3 to 7 carbon atoms. A $C_3$-$C_{10}$ cycloalkenyl radical is typically unsubstituted or substituted by 1, 2 or 3 substituents which may be the same or different. When a $C_3$-$C_{10}$ cycloalkenyl radical carries 2 or more substituents, the substituents may be the same or different. Typically, the substituents on a cycloalkenyl group are themselves unsubstituted.

Examples include cyclobutenyl, cyclopentenyl, cyclohexenyl, cycloheptenyl, cyclooctenyl, cyclononenyl and cyclodecenyl.

As used herein, the term $C_6$-$C_{14}$ aryl radical embraces typically a $C_6$-$C_{14}$, more preferably $C_6$-$C_{10}$ monocyclic or bicyclic aryl radical such as phenyl, naphthyl, anthranyl and phenanthryl. Phenyl is preferred. A said optionally substituted $C_6$-$C_{14}$ aryl radical is typically unsubstituted or substituted by 1, 2 or 3 substituents which may be the same or different. When a $C_6$-$C_{14}$ aryl radical carries 2 or more substituents, the substituents may be the same or different. Unless otherwise specified, the substituents on a $C_6$-$C_{14}$ aryl group are typically themselves unsubstituted.

As used herein, the term 5- to 14-membered heteroaryl radical embraces typically a 5- to 14-membered ring system, preferably a 5- to 10-membered ring system, more preferably a 5- to 6-membered ring system, comprising at least one heteroaromatic ring and containing at least one heteroatom selected from O, S and N. A 5- to 14-membered heteroaryl radical may be a single ring or two fused rings wherein at least one ring contains a heteroatom.

A said optionally substituted 5- to 14-membered heteroaryl radical is typically unsubstituted or substituted by 1, 2 or 3 substituents which may be the same or different. When a 5- to 14-membered heteroaryl radical carries 2 or more substituents, the substituents may be the same or different. Unless otherwise specified, the substituents on a 5- to 14-membered heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo [3,4-d]pyrimidinyl, 1H-pyrazolo[3,4-d]pyrimidinyl, thieno [2,3-d]pyrimidinyl and the various pyrrolopyridyl radicals.

As used herein, the term 5- to 14-membered heterocyclyl radical embraces typically a non-aromatic, saturated or unsaturated $C_5$-$C_{14}$ carbocyclic ring system, preferably $C_5$-$C_{10}$ carbocyclic ring system, more preferably $C_5$-$C_6$ carbocyclic ring system, in which one or more, for example 1, 2, 3 or 4 of the carbon atoms preferably 1 or 2 of the carbon atoms are replaced by a heteroatom selected from N, O and S. A heterocyclyl radical may be a single ring or two fused rings wherein at least one ring contains a heteroatom. When a 5 to 14-membered heterocyclyl radical carries 2 or more substituents, the substituents may be the same or different.

A said optionally substituted 5- to 14-membered heterocyclyl radical is typically unsubstituted or substituted by 1, 2 or 3 substituents which may be the same or different. Typically, the substituents on a 5 to 14-membered heterocyclyl radical are themselves unsubstituted.

Examples of 5- to 14-membered heterocyclyl radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1 (3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiephanyl, azepanyl, 1,4-dioxepnayl, 1,4-oxathiepanyl, 1,4-oxaazepanyl, 1,4-dithiepanyl, 1,4-thiezepanyl, 1,4-diazepanyl, tropanyl, (1S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

Where a 5- to 14-membered heterocyclyl radical carries 2 or more substituents, the substituents may be the same or different.

As used herein, the bicyclic N-containing heteroaryl group is a $C_8$-$C_{10}$ membered ring system where two rings have been fused and wherein at least in one ring one of the carbon atoms is replaced by N and optionally in which 1, 2, 3, or 4, preferably 1, 2, or 3 further carbon atoms of any ring which form the group are replaced by N.

Examples include indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-d]pyridinyl, pyrazolo[3,4-c]pyridinyl, pyrazolo[3,4-b]pyridinyl, isoindolinyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolyl, isoquinolyl, cinnolinyl, azaquinazolinyl, quinoxalinyl, phthalazinyl, naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrazolo[1,5-a]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

Also included within the scope of the invention are the isomers, polymorphs, pharmaceutically acceptable salts, N-oxides, isotopes, solvates and prodrugs of the compounds of formula (I). Any reference to a compound of formula (I) throughout the present specification includes a reference to any isomer, polymorph, pharmaceutically acceptable salt, N-oxide, isotope, solvate or prodrug of such compound of formula (I).

Isomers

Compounds containing one or more chiral centre may be used in enantiomerically or diastereoisomerically pure form, in the form of racemic mixtures and in the form of mixtures enriched in one or more stereoisomer. The compounds of Formula (I) as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereoisomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; *Topics in Stereochemistry* 1983, 1) defined atropisomers as conformers that interconvert with a half-life of more than 1000 seconds at a given temperature. The scope of the invention as described and claimed encompasses the racemic forms of the compounds as well as the individual atropisomers (an atropisomer "substantially free" of its corresponding enantionmer) and stereoisomer-enriched mixtures, i.e. mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

The compounds of Formula (I) may exhibit the phenomena of tautomerism and structural isomerism. Tautomers exist as mixtures of a tautomeric set in solution. In solid form, usually one tautomer predominates. Even though one tautomer may be described, the present invention includes all tautomers of the compounds of Formula (I).

Polymorphs

The compounds of formula (I) may exist in different physical forms, i.e. amorphous and crystalline forms.

Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula (I), including all polymorphic forms ("polymorphs") or amorphous forms thereof, are included within the scope of the invention.

Pharmaceutically Acceptable Salts

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion (X−) is associated with the positive charge of the N atom. X− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X− is preferably an anion selected from chloride, bromide, iodide, sulphate, nitrate, acetate, maleate, oxalate, succinate or trifluoroacetate. More preferably X− is chloride, bromide, trifluoroacetate or methanesulphonate.

N-Oxides

As used herein, an N-oxide is formed from the tertiary basic amines or imines present in the molecule, using a convenient oxidising agent.

Isotopes

The invention also includes isotopically-labeled derivatives of the compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as 2H and 3H, carbon, such as 11C, 13C and 14C, chlorine, such as 36Cl, fluorine, such as 18F, iodine, such as 123I and 125I, nitrogen, such as 13N and 15N, oxygen, such as 15O, 17O and 18O, phosphorus, such as 32P, and sulfur, such as 35S. Certain isotopically-labeled compounds of the invention, for example, those incorporating a radioactive isotope, are useful in drug and/or substrate tissue distribution studies. The radioactive isotopes tritium, 3H, and carbon-14, 14C, are particularly useful for this purpose in view of their ease of incorporation and ready means of detection. Substitution with heavier isotopes such as deuterium, 2H, may afford certain therapeutic advantages resulting from greater metabolic stability, for example, increased in vivo half-life or reduced dosage requirements, and hence may be preferred in some circumstances. Substitution with positron emitting isotopes, such as 11C, 18F, 15O and 13N, can be useful in Positron Emission Topography (PET) studies for examining substrate receptor occupancy.

Isotopically-labeled derivatives of the compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled derivatives include deuterated derivatives of the compounds of the invention. As used herein, the term deuterated derivative embraces compounds of the invention where in a particular position at least one hydrogen atom is replaced by deuterium. Deuterium (D or 2H) is a stable isotope of hydrogen which is present at a natural abundance of 0.015 molar %.

Solvates

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

Prodrugs

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in Design of Prodrugs by H. Bundgaard (Elsevier, 1985).

As used herein, the term PI3Kd inhibitor generally refers to a compound that inhibits the activity of the PI3Kd isoform more effectively than other isoforms of the PI3K family.

As used herein, the term PI3Kd/g inhibitor generally refers to a compound that inhibits the activity of both the PI3Kd isoform and the PI3Kg isoform more effectively than other isoforms of the PI3K family.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value.

Accordingly, a PI3Kd inhibitor alternatively can be understood to refer to a compound that exhibits a 50% inhibitory concentration ($IC_{50}$) with respect to PI3Kd that is at least of less than about 100 μM, preferably of less than about 50 μM, more preferably of less than about 20 μM, even more preferably of less than about 10 μM PI3K HTRF assay (as described in Gray et al. *Anal Biochem*, 2003; 313: 234-45)

Typically, in the compound of formula (I), $R_a$ and $R_b$ each independently represent a hydrogen atom, a $C_1$-$C_4$ haloalkyl group, a $C_1$-$C_4$ hydroxyalkyl group or a linear or branched $C_1$-$C_4$ alkyl group.

Preferably, $R_a$ and $R_b$ each independently represent a hydrogen atom or a linear or branched $C_1$-$C_4$ alkyl group. More preferably $R_a$ and $R_b$ each independently represent a hydrogen atom, a methyl group or an ethyl group.

Typically, n represents 0, 1 or 2, preferably 0 or 1, more preferably 0.

Typically, in the compound of formula (I) $R_1$ represents a $C_3$-$C_{10}$ cycloalkyl group, a $C_3$-$C_{10}$ cycloalkenyl group, a phenyl group, a 5- to 7-membered heteroaryl group containing at least one heteroatom selected from O, S and N, or a 5- to 7-membered heterocyclyl group containing at least one heteroatom selected from O, S and N; wherein the cycloalkyl, cycloalkenyl, phenyl, heteroaryl, and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group.

Preferably, $R_1$ represents a phenyl group, which phenyl group is unsubstituted or substituted by one, two or three substituents selected from a halogen atom or a linear or branched $C_1$-$C_3$ alkyl group.

Preferably, when $R_1$ represents a phenyl group, said phenyl group is directly bonded to the pyrrolotriazinone group. In other words, the linker —($R_a$—C—$R_b$)$_n$— is not present.

Typically, in the compound of formula (I) $R_2$ represents a hydrogen atom, a halogen atom, a hydroxyl group, a $C_1$-$C_3$ alkoxy group, a linear or branched $C_1$-$C_4$ alkyl group, a $C_1$-$C_3$ haloalkyl group, a $C_3$-$C_4$ cycloalkyl group or a —NH$_2$ group.

Preferably, $R_2$ represents a hydrogen atom, a halogen atom, a hydroxyl group, or a linear or branched $C_1$-$C_4$ alkyl group. More preferably $R_2$ represents a hydrogen atom.

Typically, in the compound of formula (I) $R_3$ represents a hydrogen atom, a halogen atom, a hydroxyl group, a $C_1$-$C_3$ alkoxy group, a linear or branched $C_1$-$C_4$ alkyl group, a $C_1$-$C_3$ haloalkyl group, a $C_3$-$C_4$ cycloalkyl group or a —NH$_2$ group.

Preferably, $R_3$ represents a hydrogen atom, a halogen atom, a hydroxyl group, or a linear or branched $C_1$-$C_4$ alkyl group. More preferably $R_2$ represents a hydrogen atom.

Typically, in the compound of formula (I), $R_7$ and $R_8$ each independently represent a hydrogen atom, a $C_1$-$C_4$ haloalkyl group, a $C_1$-$C_4$ hydroxyalkyl group or a linear or branched $C_1$-$C_4$ alkyl group.

Preferably, in the compound of formula (I), $R_7$ and $R_8$ each independently represent a hydrogen atom or a linear or branched $C_1$-$C_4$ alkyl group.

Typically, in the compound of formula (I), $R_4$, $R_5$ and $R_6$ are selected from the group consisting of a)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched $C_1$-$C_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; hydroxyl group; a cyano group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a $C_2$-$C_4$ alkynyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3) or (II-4):

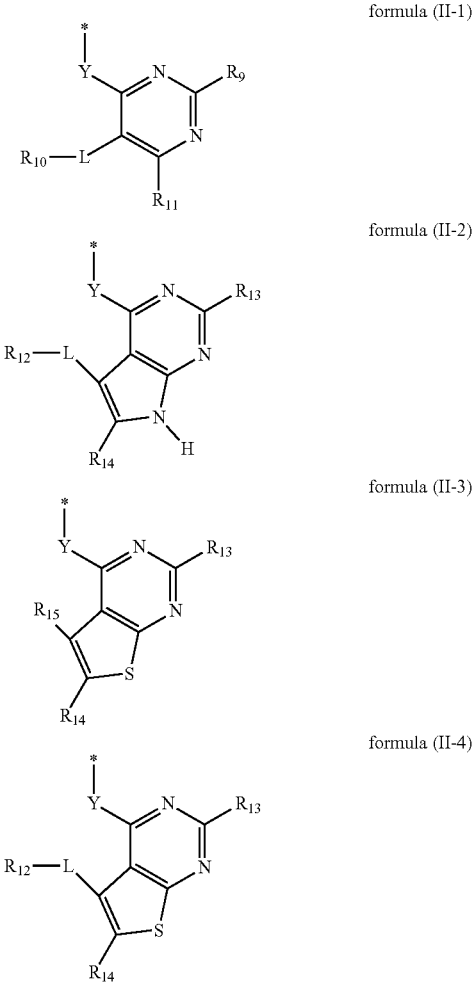

wherein:

$R_9$, $R_{11}$, $R_{13}$, $R_{14}$ and $R_{15}$ each independently represent a hydrogen atom, a —$(CH_2)_{0-3}$CN group, a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group, a $C_1$-$C_4$ hydroxyalkyl group or a linear or branched $C_1$-$C_4$ alkyl group;

$R_{10}$ and $R_{12}$ each independently represent a phenyl group or a 5- to 14-membered heteroaryl group containing at least one heteroatom selected from O, S and N,
wherein the phenyl and heteroaryl groups are unsubstituted or substituted by one or more substituents selected from a halogen atom, hydroxyl group, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 14-membered heteroaryl group containing at least one heteroatom selected from O, S and N, a 5- to 14-membered heterocyclyl group containing at least one heteroatom selected from O, S and N, a —$(CH_2)_{1-3}$ CN group, a —$(CH_2)_{0-3}$—OR' group, a —$C(O)$ group, a —$(CH_2)_{0-3}$NR'R" group, a —$(CH_2)_{0-3}$—$C(O)$—$(CH_2)_{1-3}$—CN group, a —$(CH_2)_{0-3}$—$C(O)OH$ group, a $(CH_2)_{0-3}$—$C(O)$—$(CH_2)_{0-3}$—R' group, a —$(CH_2)_{0-3}$—$C(O)$—$(CH_2)_{0-3}$—NR'R" group, a —$(CH_2)_{0-3}$NR'—$S(O)_2$R" group or a —$(CH_2)_{0-3}$—$S(O)_2(CH_2)_{0-3}$NR'R" group; wherein R' and R" each independently represent a hydrogen atom, a hydroxyl group, a $C_1$-$C_4$ haloalkyl group, a $C_1$-$C_4$ alkoxy group, a $C_1$-$C_4$ hydroxyalkyl group, a linear or branched $C_1$-$C_4$ alkyl group or a phenyl group, which phenyl group is unsubstituted or substituted by one or more substituents selected from a halogen atom, a hydroxyl group, a cyano group, a $C_1$-$C_4$ hydroxy alkyl group, a $C_1$-$C_4$ haloalkyl group, a $C_1$-$C_4$ alkoxy group, a $C_3$-$C_4$ cycloalkyl group or a linear or branched $C_1$-$C_4$ alkyl group;

L represents a direct bound or a linker selected from —O—, —S—, a —$(CH_2)_{0-3}$NR'— group, a —$C(O)$—NR'— group, a —$(CH_2)_{0-3}$NR'—$C(O)$— group, a —$C(O)$—O— group, a —O—$C(O)$— group or a —$(CH_2)_{1-4}$ group; wherein R' represents hydrogen or a linear or branched $C_1$-$C_4$ alkyl group, and R'" represents a linear or branched $C_1$-$C_4$ alkyl group;

Y represents a —NR'— group; wherein R' represents hydrogen or a linear or branched $C_1$-$C_4$ alkyl group.

or b)

$R_4$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_5$ represents a moiety of formula (II-1), (II-2), (II-3), (II-4), (II-5) or (II-6):

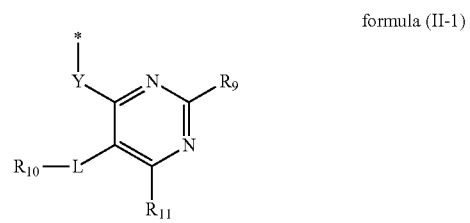

-continued

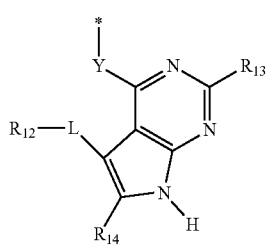
formula (II-2)

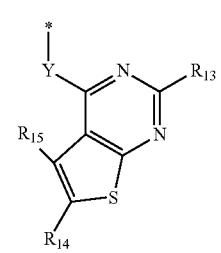
formula (II-3)

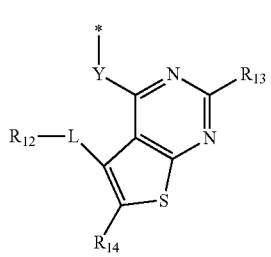
formula (II-4)

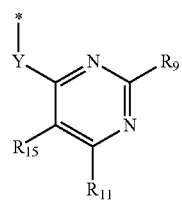
formula (II-5)

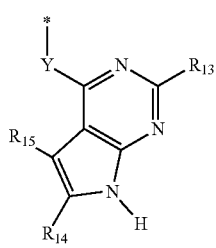
formula (II-6)

wherein:
$R_9$, $R_{11}$, $R_{13}$, $R_{14}$, $R_{15}$, $R_{10}$, $R_{12}$, L and Y are as defined above;
or
c)
$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3), (II-4), (II-5) or (II-6):

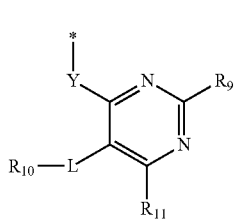
formula (II-1)

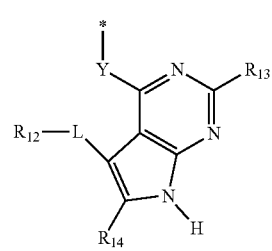
formula (II-2)

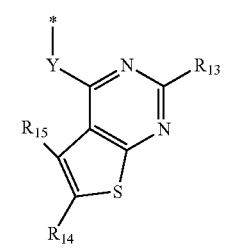
formula (II-3)

-continued formula (II-4)

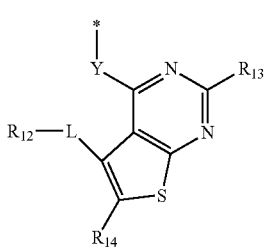

formula (II-5)

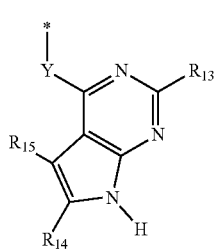

formula (II-6)

wherein:
R$_9$, R$_{11}$, R$_{13}$, R$_{14}$, R$_{15}$, R$_{10}$, R$_{12}$, L and Y are as defined above.

In a particular embodiment, in the compound of formula (I),

R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group;
wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;
wherein the phenyl, heteroaryl, heterocyclyl and alkynyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group, a —(CH$_2$)$_{0-3}$—NR$_7$—(CH$_2$)$_{0-3}$—NR$_7$R$_8$ group, a —(CH$_2$)$_{0-3}$—C(O)—(CH$_2$)$_{0-3}$-(5- to 7-membered heteroaryl group containing at least one heteroatom selected from O, S and N) or a —(CH$_2$)$_{0-3}$-(5- to 7-membered heterocyclyl group containing at least one heteroatom selected from O, S and N); wherein the heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group;

R$_5$ represents a moiety of formula (II-1), (II-2), (II-3) or (II-4):

formula (II-1)

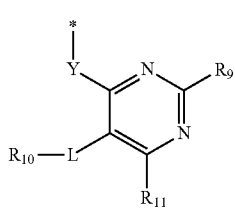

formula (II-2)

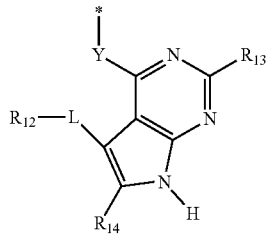

formula (II-3)

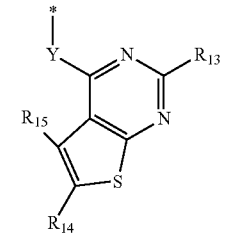

formula (II-4)

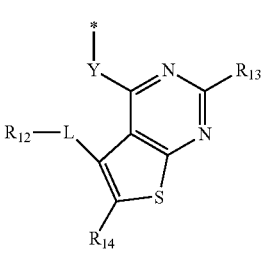

wherein:
R$_9$, R$_{11}$, R$_{13}$, R$_{14}$, R$_{15}$, R$_{10}$, R$_{12}$, L and Y are as defined above.

In another particular embodiment, in the compound of formula (I), $R_4$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_5$ represents a moiety of formula (II-1), (II-2), (II-3), (II-4), (II-5) or (II-6):

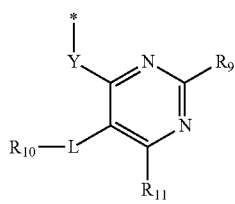

formula (II-1)

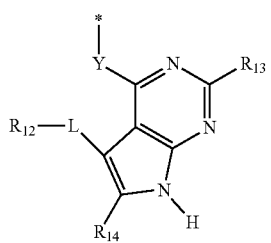

formula (II-2)

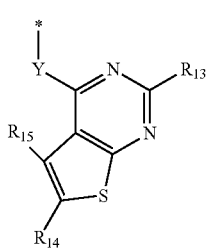

formula (II-3)

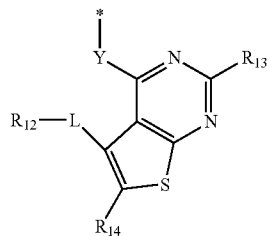

formula (II-4)

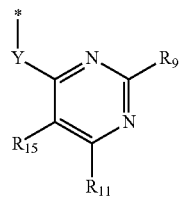

formula (II-5)

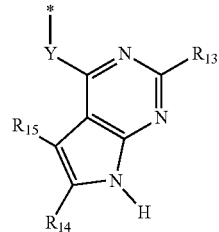

formula (II-6)

wherein:
$R_9$, $R_{11}$, $R_{13}$, $R_{14}$, $R_{15}$, $R_{10}$, $R_{12}$, L and Y are as defined above.

In another particular embodiment, in the compound of formula (I), $R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl, heterocyclyl and alkynyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group, a —$(CH_2)_{0-3}$—$NR_7$—$(CH_2)_{0-3}$—$NR_7R_8$ group, a —$(CH_2)_{0-3}$—$C(O)$—$(CH_2)_{0-3}$-(5- to 7-membered heteroaryl group containing at least one heteroatom selected from O, S and N) or a —$(CH_2)_{0-3}$-(5- to 7-membered heterocyclyl group containing at least one heteroatom selected from O, S and N); wherein the heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group;

$R_5$ represents a moiety of formula (II-1), (II-2), (II-3), (II-4), (II-5) or (II-6):

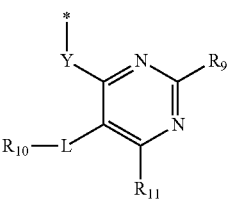

formula (II-1)

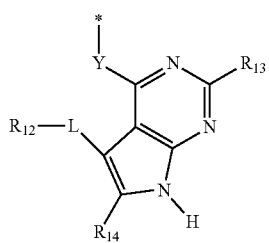

formula (II-2)

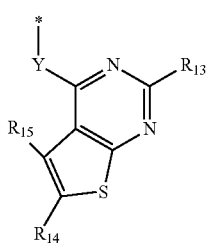

formula (II-3)

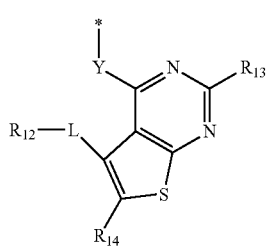

formula (II-4)

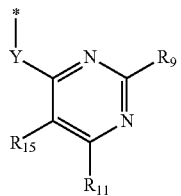

formula (II-5)

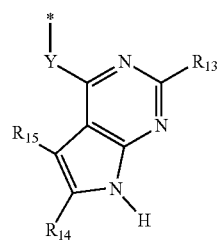

formula (II-6)

wherein:
$R_9$, $R_{11}$, $R_{13}$, $R_{14}$, $R_{15}$, $R_{10}$, $R_{12}$, L and Y are as defined above.

In one embodiment, in the compound of formula (I), $R_4$, $R_5$ and $R_6$ are selected from the group consisting of a)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —$C(O)$—$(CH_2)_{0-3}$—$R_8$ group or a —$C(O)$—$(CH_2)_{0-3}$—$NR_7R_8$ group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}NR_7R_8$ group; a —$(CH_2)_{1-3}$—O($C_1$-$C_4$ alkyl group); a —$(CH_2)_{0-3}$—OC(O)—($C_1$-$C_4$ alkyl group); a —$(CH_2)_{0-3}$—C(O)O—($C_1$-$C_4$ alkyl group); a —$C(O)$—$(CH_2)_{0-3}$—$NR_7R_8$ group; a —$(CH_2)_{0-3}$—C(O)OH group; a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;
   wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_5$ represents a moiety of formula (II-1), (II-2), (II-3), or (II-4):

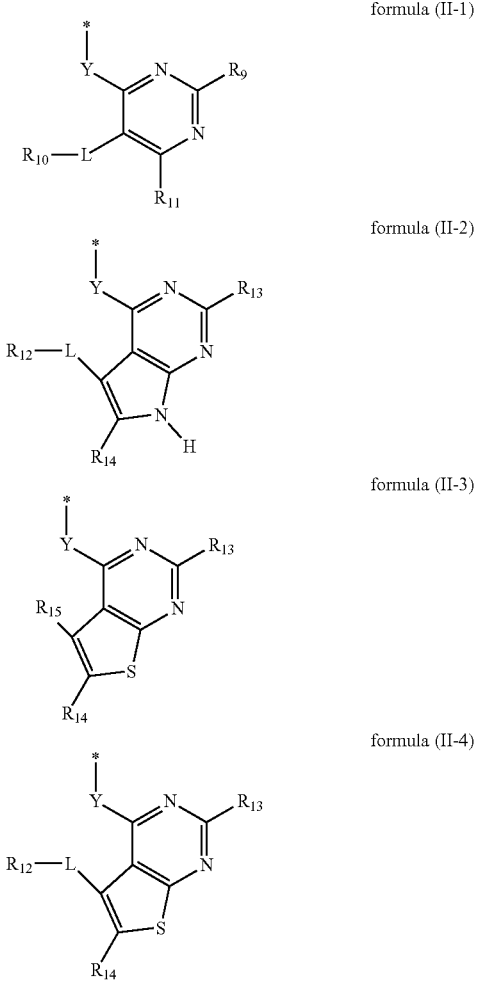

formula (II-1)

formula (II-2)

formula (II-3)

formula (II-4)

wherein:
R$_9$, R$_{11}$, R$_{13}$, R$_{14}$ and R$_{15}$ each independently represent a hydrogen atom, a —(CH$_2$)$_{0-3}$CN group, a —(CH$_2$)$_{0-3}$NR'R" group, or a linear or branched C$_1$-C$_4$ alkyl group; wherein R' and R" each independently represent a hydrogen atom, a hydroxyl group, a C$_1$-C$_4$ alkoxy group, a C$_1$-C$_4$ hydroxyalkyl group or a linear or branched C$_1$-C$_4$ alkyl group;

R$_{10}$ and R$_{12}$ each independently represent a phenyl group or a 5- to 14-membered heteroaryl group containing at least one heteroatom selected from O, S and N,
   wherein the phenyl and heteroaryl groups are unsubstituted or substituted by one or more substituents selected from a halogen atom, hydroxyl group, a cyano group, a linear or branched C$_1$-C$_6$ alkyl group, a C$_1$-C$_4$ haloalkyl group, a C$_1$-C$_4$ hydroxyalkyl group, a C$_3$-C$_7$ cycloalkyl group, a phenyl group, a 5- to 14-membered heteroaryl group containing at least one heteroatom selected from O, S and N, a 5- to 14-membered heterocyclyl group containing at least one heteroatom selected from O, S and N, a —(CH$_2$)$_{1-3}$CN group, a —(CH$_2$)$_{0-3}$—OR' group, a —C(O) group, a —(CH$_2$)$_{0-3}$NR'R" group, a —(CH$_2$)$_{0-3}$ —C(O)—(CH$_2$)$_{1-3}$—CN group, a —(CH$_2$)$_{0-3}$—C(O)OH group, a —(CH$_2$)$_{0-3}$—C(O)—(CH$_2$)$_{0-3}$—R' group, a —(CH$_2$)$_{0-3}$—C(O)—(CH$_2$)$_{0-3}$—NR'R" group, a —(CH$_2$)$_{0-3}$NR'—S(O)$_2$R" group or a —(CH$_2$)$_{0-3}$—S(O)$_2$(CH$_2$)$_{0-3}$NR'R" group; wherein R' and R" each independently represent a hydrogen atom, a hydroxyl group, a C$_1$-C$_4$ haloalkyl group, a C$_1$-C$_4$ alkoxy group, a C$_1$-C$_4$ hydroxyalkyl group, a linear or branched C$_1$-C$_4$ alkyl group or a phenyl group, which phenyl group is unsubstituted or substituted by one or more substituents selected from a halogen atom, a hydroxyl group, a cyano group, a C$_1$-C$_4$ hydroxyalkyl group, a C$_1$-C$_4$ haloalkyl group, a C$_1$-C$_4$ alkoxy group, a C$_3$-C$_4$ cycloalkyl group or a linear or branched C$_1$-C$_4$ alkyl group;

L represents a direct bound or a linker selected from —O—, —S—, a —(CH$_2$)$_{0-3}$NR'— group, a —C(O)—NR'— group, a —(CH$_2$)$_{0-3}$NR'—C(O)— group, a —C(O)—O— group, a —O—C(O)— group or a —(CH$_2$)$_{1-4}$ group; wherein R' represents hydrogen or a linear or branched C$_1$-C$_4$ alkyl group;

Y represents a —NR'— group; wherein R' represents hydrogen or a linear or branched C$_1$-C$_4$ alkyl group;

or b)

R$_4$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N),
   wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a C$_1$-C$_4$ alkoxy group; a C$_1$-C$_4$ haloalkyl group; a linear or branched C$_1$-C$_4$ hydroxyalkyl group; a C$_3$-C$_7$ cycloalkyl group; a —(CH$_2$)$_{0-3}$NR$_7$R$_8$ group; a —(CH$_2$)$_{1-3}$—O(C$_1$-C$_4$ alkyl group); a —(CH$_2$)$_{0-3}$—OC (O)—(C$_1$-C$_4$ alkyl group); a —(CH$_2$)$_{0-3}$—C(O)O—(C$_1$-C$_4$ alkyl group); a —C(O)—(CH$_2$)$_{0-3}$—NR$_7$R$_8$ group; a —(CH$_2$)$_{0-3}$—C(O)OH group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_5$ represents a moiety of formula (II-1), (II-2), (II-3), (II-4), (II-5) or (II-6):

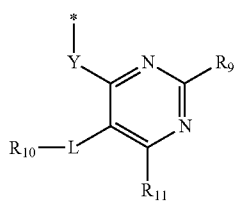

formula (II-1)

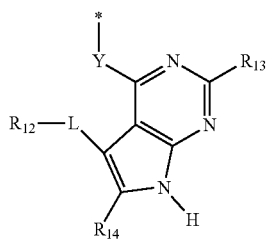

formula (II-2)

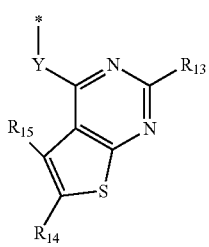

formula (II-3)

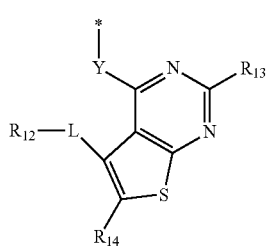

formula (II-4)

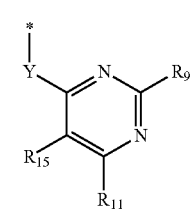

formula (II-5)

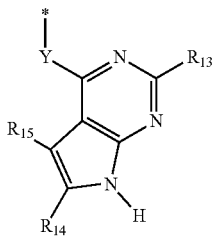

formula (II-6)

wherein:
R$_9$, R$_{11}$, R$_{13}$, R$_{14}$, R$_{15}$, R$_{10}$, R$_{12}$, L and Y are as defined above;

or c)

R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group, which alkyl group is unsubstituted or substituted by one or more substituents selected from a C$_1$-C$_4$ alkoxy group, a cyano group, a C$_3$-C$_4$ cycloalkyl group, a —C(O)—(CH$_2$)$_{0-3}$—R$_8$ group or a —C(O)—(CH$_2$)$_{0-3}$—NR$_7$R$_8$ group;

wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N) or a C$_2$-C$_4$ alkynyl group;

wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

$R_5$ represents a moiety of formula (II-1), (II-2), (II-3), (II-4), (II-5) or (II-6):

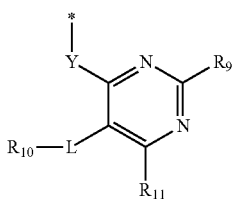

formula (II-1)

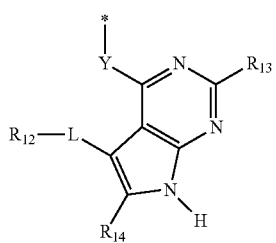

formula (II-2)

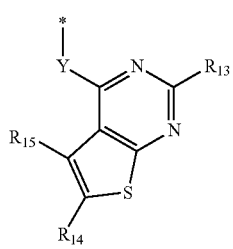

formula (II-3)

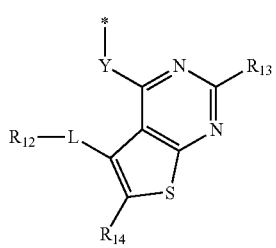

formula (II-4)

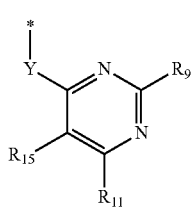

formula (II-5)

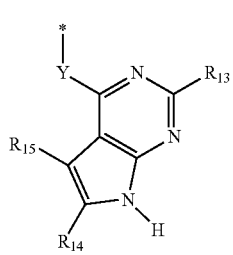

formula (II-6)

wherein:
$R_9$, $R_{11}$, $R_{13}$, $R_{14}$, $R_{15}$, $R_{10}$, $R_{12}$, L and Y are as defined above.

In this embodiment, it is particularly preferred that in the compound of formula (I), $R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N); a $C_2$-$C_4$ alkynyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group; and $R_5$ represents a moiety of formula (II-1), (II-2), (II-3) or (II-4):

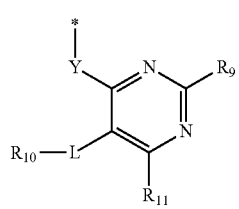

formula (II-1)

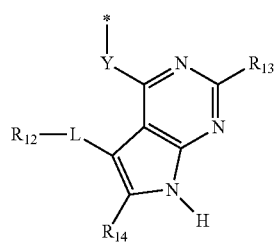
formula (II-2)

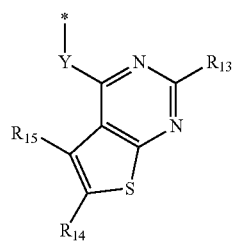
formula (II-3)

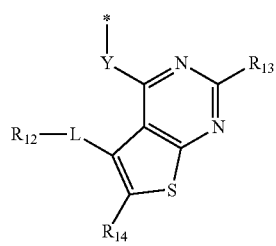
formula (II-4)

wherein:

$R_9$, $R_{11}$, $R_{13}$, $R_{14}$, $R_{15}$, $R_{10}$, $R_{12}$, L and Y are as defined above.

In this embodiment, it is further particularly preferred that in the compound of formula (I), $R_4$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_5$ represents a moiety of formula (II-1), (II-2), (II-3), (II-4), (II-5) or (II-6):

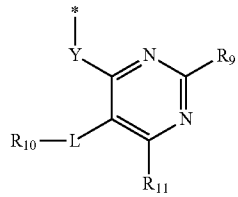
formula (II-1)

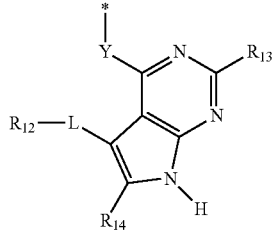
formula (II-2)

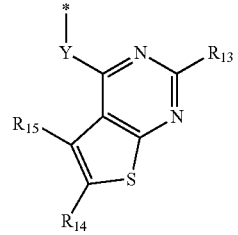
formula (II-3)

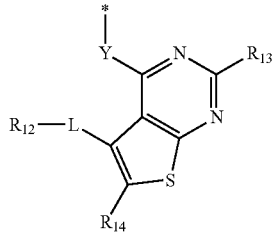
formula (II-4)

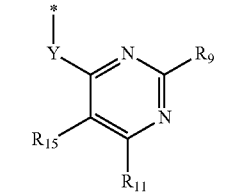
formula (II-5)

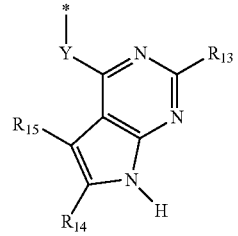
formula (II-6)

wherein:

$R_9$, $R_{11}$, $R_{13}$, $R_{14}$, $R_{15}$, $R_{10}$, $R_{12}$, L and Y are as defined above.

In another particular embodiment, in the compound of formula (I), $R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group;
  wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;
R$_6$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N) or a C$_2$-C$_4$ alkynyl group;
  wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;
R$_5$ represents a moiety of formula (II-1), (II-2), (II-3), (II-4), (II-5) or (II-6):

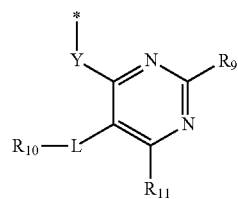

formula (II-1)

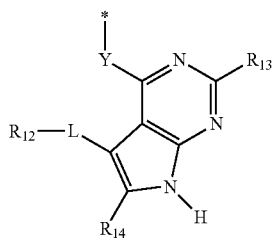

formula (II-2)

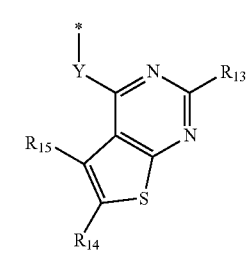

formula (II-3)

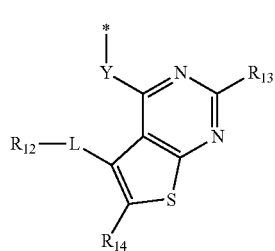

formula (II-4)

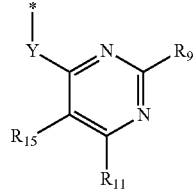

formula (II-5)

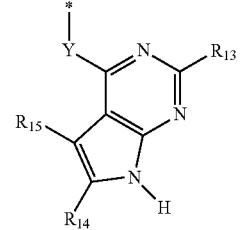

formula (II-6)

wherein:
  R$_9$, R$_{11}$, R$_{13}$, R$_{14}$, R$_{15}$, R$_{10}$, R$_{12}$, L and Y are as defined above.
  Typically, in the compound of formula (I)
n represents 0, 1, 2 or 3;
R$_a$ and R$_b$ each independently represent a hydrogen atom, a C$_1$-C$_4$ haloalkyl group, a C$_1$-C$_4$ hydroxyalkyl group or a linear or branched C$_1$-C$_4$ alkyl group;
R$_1$ represents a C$_3$-C$_{10}$ cycloalkyl group, a C$_3$-C$_{10}$ cycloalkenyl group, a phenyl group, a 5- to 7-membered heteroaryl group containing at least one heteroatom selected from O, S and N, or a 5- to 7-membered heterocyclyl group containing at least one heteroatom selected from O, S and N,
  wherein the cycloalkyl, cycloalkenyl, phenyl, heteroaryl, and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group,
R$_2$ and R$_3$ each independently represent a hydrogen atom, a halogen atom, a hydroxyl group, a C$_1$-C$_3$ alkoxy group, a linear or branched C$_1$-C$_4$ alkyl group, a C$_1$-C$_3$ haloalkyl group, a C$_3$-C$_4$ cycloalkyl group or a —NH$_2$ group;
R$_7$ and R$_8$ each independently represent a hydrogen atom, a C$_1$-C$_4$ haloalkyl group, a C$_1$-C$_4$ hydroxyalkyl group or a linear or branched C$_1$-C$_4$ alkyl group;
and
a)
R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group;

wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

wherein the phenyl, heteroaryl, heterocyclyl and alkynyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group, a —(CH$_2$)$_{0-3}$—NR$_7$—(CH$_2$)$_{0-3}$—NR$_7$R$_8$ group, a —(CH$_2$)$_{0-3}$—C(O)—(CH$_2$)$_{0-3}$-(5- to 7-membered heteroaryl group containing at least one heteroatom selected from O, S and N) or a —(CH$_2$)$_{0-3}$-(5- to 7-membered heterocyclyl group containing at least one heteroatom selected from O, S and N); wherein the heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group;

R$_5$ represents a moiety of formula (II-1), (II-2), (II-3) or (II-4):

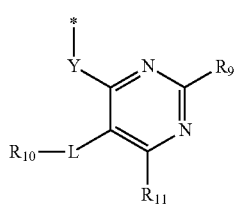

formula (II-1)

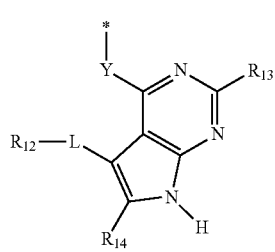

formula (II-2)

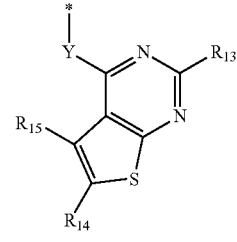

formula (II-3)

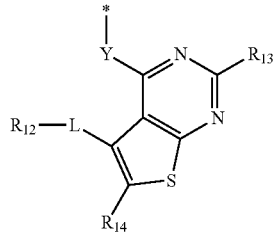

formula (II-4)

wherein:
R$_9$, R$_{11}$, R$_{13}$, R$_{14}$ and R$_{15}$ each independently represent a hydrogen atom, a —(CH$_2$)$_{0-3}$CN group, a —(CH$_2$)$_{0-3}$NR'R" group, or a linear or branched C$_1$-C$_4$ alkyl group; wherein R' and R" each independently represent a hydrogen atom, a hydroxyl group, a C$_1$-C$_4$ alkoxy group, a C$_1$-C$_4$ hydroxyalkyl group or a linear or branched C$_1$-C$_4$ alkyl group;

R$_{10}$ and R$_{12}$ each independently represent a phenyl group or a 5- to 14-membered heteroaryl group containing at least one heteroatom selected from O, S and N,
wherein the phenyl and heteroaryl groups are unsubstituted or substituted by one or more substituents selected from a halogen atom, a hydroxyl group, a cyano group, a linear or branched C$_1$-C$_6$ alkyl group, a C$_1$-C$_4$ haloalkyl group, a linear or branched C$_1$-C$_6$ hydroxyalkyl group, a C$_3$-C$_7$ cycloalkyl group, a —(CH$_2$)$_{0-3}$-(phenyl group), a —(CH$_2$)$_{0-3}$-(5- to 14-membered heteroaryl group containing at least one heteroatom selected from O, S and N), a —(CH$_2$)$_{0-3}$-(5- to 14-membered heterocyclyl group containing at least one heteroatom selected from O, S and N), a —(CH$_2$)$_{1-3}$CN group, a —(CH$_2$)$_{0-3}$—O—(CH$_2$)$_{0-3}$—R' group, a —C(O) group, a —(CH$_2$)$_{0-3}$NR'R" group, a —(CH$_2$)$_{0-3}$—C(O)—(CH$_2$)$_{1-3}$—CN group, a —(CH$_2$)$_{0-3}$—C(O)OH group, a —(CH$_2$)$_{0-3}$—C(O)—(CH$_2$)$_{0-3}$—R' group, a —(CH$_2$)$_{0-3}$—C(O)—(CH$_2$)$_{0-3}$—NR'R"group, a —(CH$_2$)$_{0-3}$NR'—C(O)—(CH$_2$)$_{0-3}$—NR'R" group, a —(CH$_2$)$_{0-3}$NR'—C(O)—(CH$_2$)$_{0-3}$—R"group, a —(CH$_2$)$_{0-3}$NR'—S(O)$_2$ —(CH$_2$)$_{0-3}$—R" group, a —(CH$_2$)$_{0-3}$NR'—(CH$_2$)$_{0-3}$ NR'—SO$_2$—(CH$_2$)$_{0-3}$—NR'R" group, a —(CH$_2$)$_{0-3}$ —S(O)$_2$—(CH$_2$)$_{0-3}$—R"group or a —(CH$_2$)$_{0-3}$—S(O)$_2$(CH$_2$)$_{0-3}$NR'R" group; wherein the phenyl, heterocyclyl and heteroaryl groups are unsubstituted or substituted by one or more substituents selected from a halogen atom, a hydroxyl group, a cyano group, a linear or branched $C_1$-$C_6$ alkyl group, a $C_1$-$C_4$ haloalkyl group, a $C_1$-$C_4$ alkoxy group, a $NH_2$ group, a —NH($C_1$-$C_4$ alkyl) group, a —N($C_1$-$C_4$ alkyl)$_2$ group, or a linear or branched $C_1$-$C_6$ hydroxyalkyl group; and wherein R' and R" each independently represent a hydrogen atom, a hydroxyl group, a $C_1$-$C_4$ haloalkyl group, a $C_1$-$C_4$ alkoxy group, a $C_1$-$C_4$ hydroxyalkyl group, a linear or branched $C_1$-$C_4$ alkyl group, a —N($C_1$-$C_4$ alkyl)$_2$ group, a 5- to 7-membered heteroaryl group containing at least one heteroatom selected from O, S and N, a 5- to 7-membered heterocyclyl group containing at least one heteroatom selected from O, S and N, or a phenyl group, which phenyl group is unsubstituted or substituted by one or more substituents selected from a halogen atom, a hydroxyl group, a cyano group, a $C_1$-$C_4$ hydroxyalkyl group, a $C_1$-$C_4$ haloalkyl group, a $C_1$-$C_4$ alkoxy group, a $C_3$-$C_4$ cycloalkyl group or a linear or branched $C_1$-$C_4$ alkyl group;

L represents a direct bound or a linker selected from —O—, —S—, a —(CH$_2$)$_{0-3}$—SO$_2$—(CH$_2$)$_{0-3}$ group, a —(CH$_2$)$_{0-3}$—SO$_2$—NR'—(CH$_2$)$_{0-3}$, a —(CH$_2$)$_{0-3}$NR'—(CH$_2$)$_{0-3}$— group, a —C(O)—(CH$_2$)$_{0-3}$ group, a —C(O)—NR'—(CH$_2$)$_{0-3}$ group, a —(CH$_2$)$_{0-3}$NR'—C(O)—(CH$_2$)$_{0-3}$ group, a —(CH$_2$)$_{0-3}$—C(O)—O—(CH$_2$)$_{0-3}$ group, a —(CH$_2$)$_{0-3}$—O—C(O)—(CH$_2$)$_{0-3}$ group or a —(CH$_2$)$_{1-4}$ group; wherein R' represents hydrogen or a linear or branched $C_1$-$C_4$ alkyl group;

Y represents a —NR'— group; wherein R' represents hydrogen or a linear or branched $C_1$-$C_4$ alkyl group;

or b)

$R_4$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_5$ represents a moiety of formula (II-1), (II-2), (II-3), (II-4), (II-5) or (II-6):

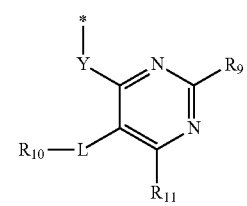

formula (II-1)

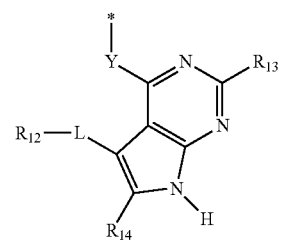

formula (II-2)

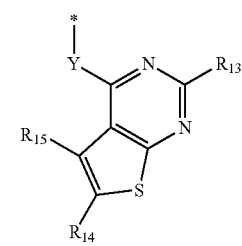

formula (II-3)

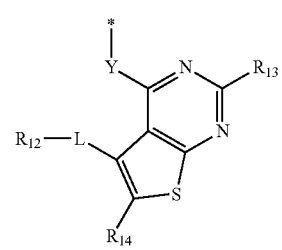

formula (II-4)

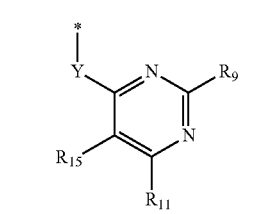

formula (II-5)

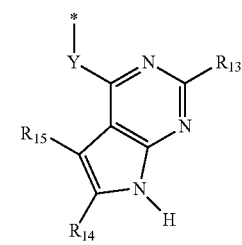

formula (II-6)

wherein:

$R_9$, $R_{11}$, $R_{13}$, $R_{14}$, $R_{15}$, $R_{10}$, $R_{12}$, L and Y are as defined above;

or c)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group;

wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N) or a C$_2$-C$_4$ alkynyl group;

wherein the phenyl, heteroaryl, heterocyclyl and alkynyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group, a —(CH$_2$)$_{0-3}$—NR$_7$—(CH$_2$)$_{0-3}$—NR$_7$R$_8$ group, a —(CH$_2$)$_{0-3}$—C(O)—(CH$_2$)$_{0-3}$-(5- to 7-membered heteroaryl group containing at least one heteroatom selected from O, S and N) or a —(CH$_2$)$_{0-3}$-(5- to 7-membered heterocyclyl group containing at least one heteroatom selected from O, S and N); wherein the heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_1$-C$_4$ alkoxy group;

R$_5$ represents a moiety of formula (II-1), (II-2), (II-3), (II-4), (II-5) or (II-6):

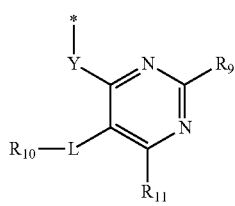

formula (II-1)

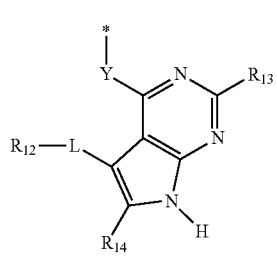

formula (II-2)

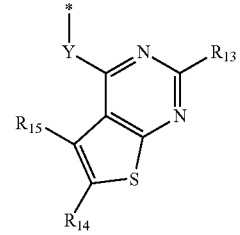

formula (II-3)

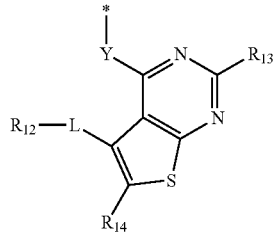

formula (II-4)

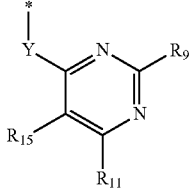

formula (II-5)

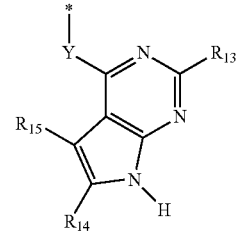

formula (II-6)

wherein:
R$_9$, R$_{11}$, R$_{13}$, R$_{14}$, R$_{15}$, R$_{10}$, R$_{12}$, L and Y are as defined above.

Typically, in the compound of formula (I), L represents a direct bound or a linker selected from —O—, —S—, a —(CH$_2$)$_{0-3}$—SO$_2$—(CH$_2$)$_{0-3}$ group, a —(CH$_2$)$_{0-3}$—SO$_2$—NR'—(CH$_2$)$_{0-3}$, a —(CH$_2$)$_{0-3}$NR'—(CH$_2$)$_{0-3}$— group, a —C(O)—(CH$_2$)$_{0-3}$ group, a —C(O)—NR'—(CH$_2$)$_{0-3}$ group, a —(CH$_2$)$_{0-3}$NR'—C(O)—(CH$_2$)$_{0-3}$ group, a —(CH$_2$)$_{0-3}$—C(O)—O—(CH$_2$)$_{0-3}$ group, a —(CH$_2$)$_{0-3}$—O—C(O)—(CH$_2$)$_{0-3}$ group or a —(CH$_2$)$_{1-4}$ group; wherein R' represents hydrogen or a linear or branched C$_1$-C$_4$ alkyl group.

Preferably, L represents a direct bound or a linker selected from —O—, —S—, a —SO$_2$— group, a —NH— group, a —C(O)—NR'—(CH$_2$)$_{0-3}$ group, a —(CH$_2$)$_{0-3}$—C(O)—O—(CH$_2$)$_{0-3}$ group, or a —(CH$_2$)$_{1-4}$ group.

In one embodiment, in the compound of formula (I), L represents a direct bound or a linker selected from —O—, —S—, a —$(CH_2)_{0-3}$NR'— group, a —C(O)—NR'— group, a —$(CH_2)_{0-3}$NR'—C(O)— group, a —C(O)—O— group, a —O—C(O)— group or a —$(CH_2)_{1-4}$ group; wherein R' represents hydrogen or a linear or branched $C_1$-$C_4$ alkyl group.

In this embodiment it is preferred that L represents a direct bound or a linker selected from —O—, —S—, a —NH— group or a —$(CH_2)_{1-4}$ group.

Typically, in the compound of formula (I), Y represents a —NR'— group; wherein R' represents hydrogen or a linear or branched $C_1$-$C_4$ alkyl group.

Preferably Y represents a —NH— group.

When R' and/or R" are attached to a nitrogen atom, preferably R' and/or R" do not represent a hydroxyl group or alkoxy group.

Where any of the above moieties represent —$(CH_2)_{0-3}$—C(O)—$R^8$ or —$(CH_2)_{0-3}$—C(O)—$(CH_2)_{0-3}$—R', it is preferable that $R^8$ and R' do not represent a hydrogen atom if the alkylene spacer moiety is absent.

In one particular embodiment, in the compound of formula (I)

n represents 0, 1, or 2;

$R_a$ and $R_b$ each independently represent a hydrogen atom or a linear or branched $C_1$-$C_4$ alkyl group;

$R_1$ represents a $C_3$-$C_7$ cycloalkyl group, a phenyl group, a pyridinyl group, a piperidinyl group or a tetrahydropyranyl group;

wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(CH_2)_{0-3}$—$NR_7R_8$ group;

$R_2$ and $R_3$ each independently represent a hydrogen atom, a halogen atom or a hydroxyl group or a linear or branched $C_1$-$C_4$ alkyl group;

$R_7$ and $R_8$ each independently represent a hydrogen atom, a —$NH_2$ group, a —$N(CH_3)H$ group, a —$N(CH_3)_2$ group, or a linear or branched $C_1$-$C_4$ alkyl group;

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a linear or branched $C_1$-$C_3$ alkyl group, a —$(CH_2)_{0-3}$—S—$(CH_2)_{0-3}$-(phenyl) group, a —$(CH_2)_{0-3}$—S—$(CH_2)_{0-3}$-(5- to 7-membered heteroaryl group containing at least one heteroatom selected from O, S and N), a —$(CH_2)_{0-3}$—O—$(CH_2)_{0-3}$-(phenyl) group, a —$(CH_2)_{0-3}$—O—$(CH_2)_{0-3}$-(5- to 7-membered heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}$—S—$(CH_2)_{0-3}$-(phenyl) group; a —$(CH_2)_{0-3}$—S—$(CH_2)_{0-3}$-(5- to 7-membered monocyclic or bicyclic heteroaryl group containing at least one heteroatom selected from O, S and N); a —$(CH_2)_{0-3}$—O—$(CH_2)_{0-3}$-(phenyl) group; a —$(CH_2)_{0-3}$—O—$(CH_2)_{0-3}$-(5- to 7-membered monocyclic or bicyclic heteroaryl group containing at least one heteroatom selected from O, S and N);

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2) or (II-3):

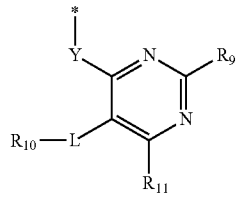

formula (II-1)

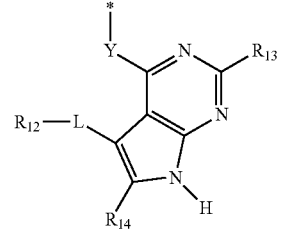

formula (II-2)

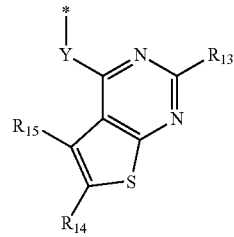

formula (II-3)

wherein:

$R_9$, $R_{11}$, $R_{13}$, $R_{14}$, $R_{15}$, $R_{10}$, $R_{12}$, L and Y are as defined above.

In one particular preferred embodiment, in the compound of formula (I)

n is 0 or 1;

$R_1$ represents a phenyl group, which phenyl group is unsubstituted or substituted by one or more substituents selected from a halogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom, a linear or branched $C_1$-$C_3$ alkyl group, a —$(CH_2)_{0-3}$—S—$(CH_2)_{0-3}$-(phenyl) group or a —$(CH_2)_{0-3}$—O—$(CH_2)_{0-3}$-(phenyl) group;

$R_6$ represents a hydrogen atom, a halogen atom, a cyano group, a linear or branched $C_1$-$C_3$ alkyl group, or a —S-phenyl group;

$R_5$ represents a moiety of formula (II-1), (II-2) or (II-3):

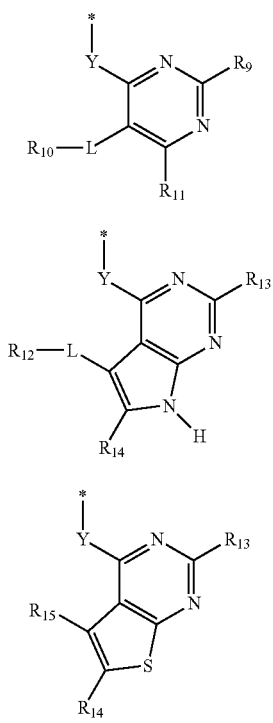

formula (II-1)

formula (II-2)

formula (II-3)

wherein:

R$_9$, R$_{11}$, R$_{13}$, R$_{14}$ and R$_{15}$ each independently represent a hydrogen atom, a —NH$_2$ group, or a linear or branched C$_1$-C$_4$ alkyl group;

R$_{10}$ and R$_{12}$ each independently represent a phenyl group or a 5- to 9-membered heteroaryl group containing at least one heteroatom selected from O, S and N, wherein the phenyl and heteroaryl groups are unsubstituted or substituted by one or more substituents selected from a halogen atom, a hydroxyl group, a cyano group, a linear or branched C$_1$-C$_6$ alkyl group, a C$_1$-C$_4$ haloalkyl group, a linear or branched C$_1$-C$_6$ hydroxyalkyl group, a —(CH$_2$)$_{0-3}$-(phenyl) group, a —(CH$_2$)$_{0-3}$-(morpholinyl) group, a —(CH$_2$)$_{0-3}$-(piperidinyl)-N(C$_1$-C$_3$ alkyl)$_2$ group, a —(CH$_2$)$_{0-3}$-(oxazolyl) group, a —(CH$_2$)$_{0-3}$-(oxadiazolyl)-R' group, a —O—(C$_1$-C$_3$ alkyl) group, a —O—(C$_1$-C$_3$ haloalkyl) group, a —(CH$_2$)$_{0-3}$—O—(CH$_2$)$_{0-3}$—N(C$_1$-C$_3$ alkyl)$_2$ group, a —C(O) group, a —NH$_2$ group, a —NH(C$_1$-C$_3$ alkyl) group, a —N(C$_1$-C$_3$ alkyl)$_2$ group, a —(CH$_2$)$_{0-3}$—C(O)OH group, a —C(O)—N(C$_1$-C$_3$ alkyl)$_2$ group, a —C(O)—NH-(phenyl) group, a —NH—C(O)—NH$_2$— group, a —NH—C(O)—NH-(pyridine) group, a —NH—C(O)-(phenyl) group, a N(CH$_3$)—S(O)$_2$—CH$_3$ group, a —NH—S(O)$_2$—(CH$_2$)$_{0-3}$—R'' group, a —S(O)$_2$ R''group, or a —S(O)$_2$NH(C$_1$-C$_3$ alkyl) group; wherein R' represents a linear or branched C$_1$-C$_4$ alkyl group or a NH$_2$ group, and wherein R'' represents a hydroxyl group, a C$_1$-C$_4$ haloalkyl group, a C$_1$-C$_4$ alkoxy group, a linear or branched C$_1$-C$_4$ alkyl group, a —NH$_2$ group, a —N(C$_1$-C$_3$ alkyl)$_2$ group, a phenyl group, a tetrahydropyranyl group, or a morpholinyl group; and wherein each phenyl group independently is unsubstituted or substituted by one or more substituents selected from a halogen atom, a hydroxyl group, a C$_1$-C$_4$ haloalkyl group, a C$_1$-C$_4$ alkoxy group, a linear or branched C$_1$-C$_4$ alkyl group, a C$_1$-C$_4$ haloalkyl group, or a linear or branched C$_1$-C$_6$ hydroxyalkyl group;

L represents a direct bound or a linker selected from —S—, a —SO$_2$— group, a —C(O)—NH—(CH$_2$)$_{0-3}$ group, a —(CH$_2$)$_{0-3}$—C(O)—O—(CH$_2$)$_{0-3}$ group, or a —(CH$_2$)$_{1-3}$ group;

Y represents a —NH— group.

In one particular embodiment, in the compound of formula (I)

n represents 0, 1, or 2;

R$_a$ and R$_b$ each independently represent a hydrogen atom or a linear or branched C$_1$-C$_4$ alkyl group;

R$_1$ represents a C$_3$-C$_7$ cycloalkyl group, a phenyl group, a pyridinyl group, a piperidinyl group or a tetrahydropyranyl group;

wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group, a —(CH$_2$)$_{0-3}$OR$_8$ group, a —(CH$_2$)$_{0-3}$NR$_7$R$_8$ group, a —C(O)—(CH$_2$)$_{0-3}$—R$_8$ group or a —C(O)—(CH$_2$)$_{0-3}$—NR$_7$R$_8$ group;

R$_2$ and R$_3$ each independently represent a hydrogen atom, a halogen atom or a hydroxyl group or a linear or branched C$_1$-C$_4$ alkyl group;

R$_7$ and R$_8$ each independently represent a hydrogen atom, a —NH$_2$ group, a —N(CH$_3$)H group, a —N(CH$_3$)$_2$ group, or a linear or branched C$_1$-C$_4$ alkyl group;

R$_4$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a C$_1$-C$_4$ alkoxy group; a C$_1$-C$_4$ haloalkyl group; a linear or branched C$_1$-C$_4$ hydroxyalkyl group; a C$_3$-C$_7$ cycloalkyl group; or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

R$_5$ represents a moiety of formula (II-1), (II-2), (II-3), (II-4), (II-5) or (II-6):

formula (II-1)
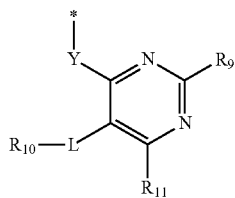

formula (II-2)
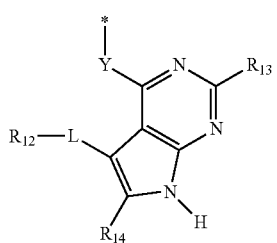

formula (II-3)
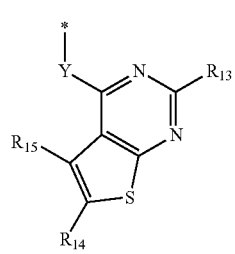

formula (II-4)
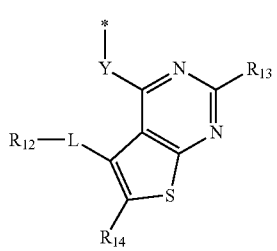

formula (II-5)
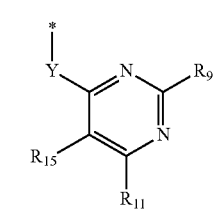

formula (II-6)
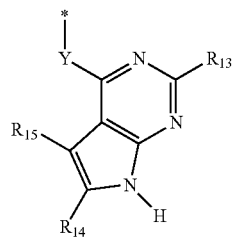

wherein:
$R_9$, $R_{11}$, $R_{13}$, $R_{14}$, $R_{15}$, $R_{10}$, $R_{12}$, L and Y are as defined above.

In one particular preferred embodiment, in the compound of formula (I)
n is 0 or 1;
$R_1$ represents a phenyl group, which phenyl group is unsubstituted or substituted by one or more substituents selected from a halogen atom or a linear or branched $C_1$-$C_3$ alkyl group;
$R_2$ and $R_3$ each independently represent a hydrogen atom or a linear or branched $C_1$-$C_3$ alkyl group;
$R_4$ represents a —$(CH_2)_{0-3}$—S—$(CH_2)_{0-3}$-(phenyl) group or a —$(CH_2)_{0-3}$—O—$(CH_2)_{0-3}$-(phenyl) group;
$R_6$ represents a hydrogen atom, a halogen atom, a cyano group, or a linear or branched $C_1$-$C_3$ alkyl group;
$R_5$ represents a moiety of formula (II-1) or (II-5):

formula (II-1)
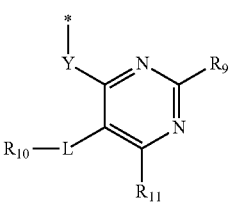

formula (II-5)
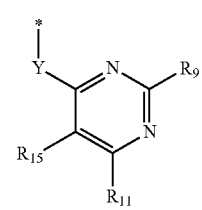

wherein:
$R_9$, $R_{11}$ and $R_{15}$ each independently represent a hydrogen atom, a cyano group, a —$NH_2$ group, or a linear or branched $C_1$-$C_4$ alkyl group;
$R_{10}$ represents a phenyl group,
wherein the phenyl group is unsubstituted or substituted by one or more substituents selected from a halogen atom, a hydroxyl group, a linear or branched $C_1$-$C_4$ alkyl group;
L represents a direct bound;
Y represents a —NH— group.
In one particular embodiment, in the compound of formula (I)
n represents 0, 1, or 2;
$R_a$ and $R_b$ each independently represent a hydrogen atom or a linear or branched $C_1$-$C_4$ alkyl group;
$R_1$ represents a $C_3$-$C_7$ cycloalkyl group, a phenyl group, a pyridinyl group, a piperidinyl group or a tetrahydropyranyl group;
wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(CH_2)_{0-3}$—$NR_7R_8$ group;
$R_2$ and $R_3$ each independently represent a hydrogen atom, a halogen atom or a hydroxyl group or a linear or branched $C_1$-$C_4$ alkyl group;
$R_7$ and $R_8$ each independently represent a hydrogen atom, a —$NH_2$ group, a —$N(CH_3)H$ group, a —$N(CH_3)_2$ group, or a linear or branched $C_1$-$C_4$ alkyl group;

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —C(O)—(CH$_2$)$_{0-3}$—R$_8$ group or a —C(O)—(CH$_2$)$_{0-3}$—NR$_7$R$_8$ group;

$R_6$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl, heterocyclyl and alkynyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group, a —(CH$_2$)$_{0-3}$—NR$_7$—(CH$_2$)$_{0-3}$—NR$_7$R$_8$ group, a —(CH$_2$)$_{0-3}$—C(O)—(CH$_2$)$_{0-3}$-(5- to 7-membered heteroaryl group containing at least one heteroatom selected from O, S and N) or a —(CH$_2$)$_{0-3}$-(5- to 7-membered heterocyclyl group containing at least one heteroatom selected from O, S and N); wherein the heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group;

$R_5$ represents a moiety of formula (II-1), (II-2), (II-3), (II-4), (II-5) or (II-6):

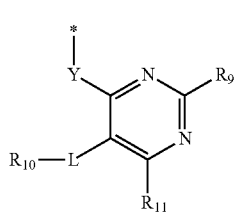

formula (II-1)

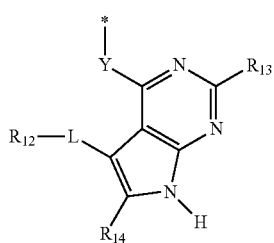

formula (II-2)

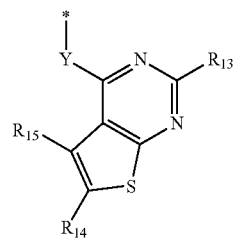

formula (II-3)

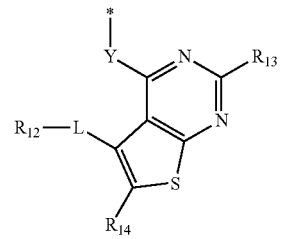

formula (II-4)

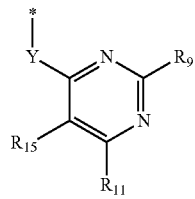

formula (II-5)

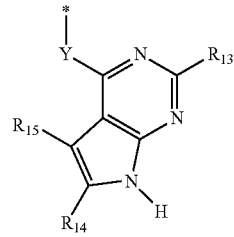

formula (II-6)

wherein:

$R_9$, $R_{11}$, $R_{13}$, $R_{14}$, $R_{15}$, $R_{10}$, $R_{12}$, L and Y are as defined above.

In one particular preferred embodiment, in the compound of formula (I)

n is 0 or 1;

$R_1$ represents a phenyl group, which phenyl group is unsubstituted or substituted by one or more substituents selected from a halogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom or a linear or branched $C_1$-$C_3$ alkyl group;

$R_6$ represents a —(CH$_2$)$_{0-3}$—S—(CH$_2$)$_{0-3}$-(phenyl) group, a —(CH$_2$)$_{0-3}$—O—(CH$_2$)$_{0-3}$-(phenyl) group, a —(CH$_2$)$_{0-3}$-(phenyl group), or a $C_2$-$C_4$ alkynyl group; wherein the phenyl and alkynyl groups are unsubstituted or substituted by one or more substituents selected from a halogen atom, a hydroxyl group, a linear or branched $C_1$-$C_3$ alkyl group or a $C_1$-$C_3$ alkoxy group, a —NH—(CH$_2$)$_{0-3}$—N($C_1$-$C_3$ alkyl)$_2$ group, or a —(CH$_2$)$_{0-3}$—C(O)—(CH$_2$)$_{0-3}$-(piperazinyl)-(linear or branched C$_1$-C$_4$ alkyl) group;

R$_5$ represents a moiety of formula (II-1) or (II-5):

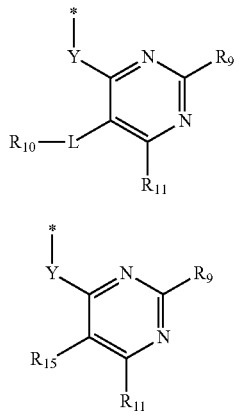

formula (II-1)

formula (II-5)

wherein:
R$_9$, R$_{11}$ and R$_{15}$ each independently represent a hydrogen atom, a cyano group, a —NH$_2$ group, or a linear or branched C$_1$-C$_4$ alkyl group;
R$_{10}$ represents a phenyl group,
  wherein the phenyl group is substituted by one or more substituents selected from a halogen atom, a hydroxyl group, a linear or branched C$_1$-C$_4$ alkyl group;
L represents a direct bound;
Y represents a —NH— group.

In one particular preferred embodiment, in the compound of formula (I)
wherein,
n is 0 or 1;
R$_a$ and R$_b$ each independently represent a hydrogen atom or a linear or branched C$_1$-C$_4$ alkyl group;
R$_1$ represents a phenyl group, which phenyl group is unsubstituted or substituted by one or more substituents selected from a halogen atom or a linear or branched C$_1$-C$_3$ alkyl group;
R$_2$ and R$_3$ each independently represent a hydrogen atom or a linear or branched C$_1$-C$_3$ alkyl group;
and
a)
R$_4$ represents a hydrogen atom, a linear or branched C$_1$-C$_3$ alkyl group, a —(CH$_2$)$_{0-3}$—S—(CH$_2$)$_{0-3}$-(phenyl) group or a —(CH$_2$)$_{0-3}$—O—(CH$_2$)$_{0-3}$-(phenyl) group;
R$_6$ represents a hydrogen atom, a halogen atom, a cyano group, a linear or branched C$_1$-C$_3$ alkyl group, or a —S-phenyl group;
R$_5$ represents a moiety of formula (II-1), (II-2) or (II-3):

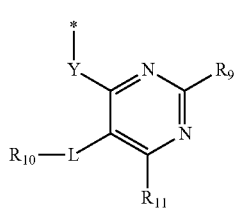

formula (II-1)

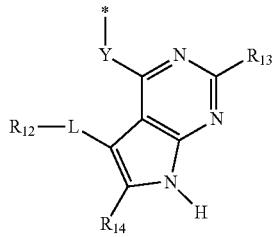

formula (II-2)

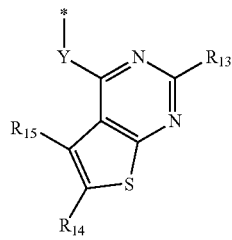

formula (II-3)

wherein:
R$_9$, R$_{11}$, R$_{13}$, R$_{14}$ and R$_{15}$ each independently represent a hydrogen atom, a —NH$_2$ group, or a linear or branched C$_1$-C$_4$ alkyl group;
R$_{10}$ and R$_{12}$ each independently represent a phenyl group or a 5- to 9-membered heteroaryl group containing at least one heteroatom selected from O, S and N,
  wherein the phenyl and heteroaryl groups are unsubstituted or substituted by one or more substituents selected from a halogen atom, a hydroxyl group, a cyano group, a linear or branched C$_1$-C$_6$ alkyl group, a C$_1$-C$_4$ haloalkyl group, a linear or branched C$_1$-C$_6$ hydroxyalkyl group, a —(CH$_2$)$_{0-3}$-(phenyl) group, a —(CH$_2$)$_{0-3}$-(morpholinyl) group, a —(CH$_2$)$_{0-3}$-(piperidinyl)-N(C$_1$-C$_3$ alkyl)$_2$ group, a —(CH$_2$)$_{0-3}$-(oxazolyl) group, a —(CH$_2$)$_{0-3}$-(oxadiazolyl)-R' group, a —O—(C$_1$-C$_3$ alkyl) group, a —O—(C$_1$-C$_3$ haloalkyl) group, a —(CH$_2$)$_{0-3}$—O—(CH$_2$)$_{0-3}$—N(C$_1$-C$_3$ alkyl)$_2$ group, a —C(O) group, a —NH$_2$ group, a —NH(C$_1$-C$_3$ alkyl) group, a —N(C$_1$-C$_3$ alkyl)$_2$ group, a —(CH$_2$)$_{0-3}$—C(O)OH group, a —C(O)—N(C$_1$-C$_3$ alkyl)$_2$ group, a —C(O)—NH-(phenyl) group, a —NH—C(O)—NH$_2$— group, a —NH—C(O)—NH-(pyridine) group, a —NH—C(O)-(phenyl) group, a N(CH$_3$)—S(O)$_2$—CH$_3$ group, a —NH—S(O)$_2$—(CH$_2$)$_{0-3}$—R" group, a —S(O)$_2$R"group, or a —S(O)$_2$NH(C$_1$-C$_3$ alkyl) group;
  wherein R' represents a linear or branched C$_1$-C$_4$ alkyl group or a NH$_2$ group, and wherein R" represents a hydroxyl group, a C$_1$-C$_4$ haloalkyl group, a C$_1$-C$_4$ alkoxy group, a linear or branched C$_1$-C$_4$ alkyl group, a —NH$_2$ group, a —N(C$_1$-C$_3$ alkyl)$_2$ group, a phenyl group, a tetrahydropyranyl group, or a morpholinyl group; and wherein each phenyl group independently is unsubstituted or substituted by one or more substituents selected from a halogen atom, a hydroxyl group, a C$_1$-C$_4$ haloalkyl group, a C$_1$-C$_4$ alkoxy group, a linear or branched C$_1$-C$_4$ alkyl group, a C$_1$-C$_4$ haloalkyl group, or a linear or branched C$_1$-C$_6$ hydroxyalkyl group;

L represents a direct bound or a linker selected from —S—, a —SO$_2$— group, a —C(O)—NH—(CH$_2$)$_{0-3}$ group, a —(CH$_2$)$_{0-3}$—C(O)—O—(CH$_2$)$_{0-3}$ group, or a —(CH$_2$)$_{1-3}$ group;

Y represents a —NH— group.

or b)

R$_4$ represents a —(CH$_2$)$_{0-3}$—S—(CH$_2$)$_{0-3}$-(phenyl) group or a —(CH$_2$)$_{0-3}$—O—(CH$_2$)$_{0-3}$-(phenyl) group;

R$_6$ represents a hydrogen atom, a halogen atom, a cyano group, or a linear or branched C$_1$-C$_3$ alkyl group;

R$_5$ represents a moiety of formula (II-1) or (II-5):

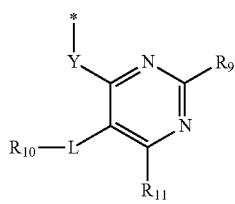

formula (II-1)

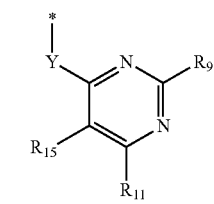

formula (II-5)

wherein:

R$_9$, R$_{11}$ and R$_{15}$ each independently represent a hydrogen atom, a cyano group, a —NH$_2$ group, or a linear or branched C$_1$-C$_4$ alkyl group;

R$_{10}$ represents a phenyl group,
wherein the phenyl group is unsubstituted or substituted by one or more substituents selected from a halogen atom, a hydroxyl group, a linear or branched C$_1$-C$_4$ alkyl group;

L represents a direct bound;

Y represents a —NH— group.

or c)

R$_4$ represents a hydrogen atom or a linear or branched C$_1$-C$_3$ alkyl group;

R$_6$ represents a —(CH$_2$)$_{0-3}$—S—(CH$_2$)$_{0-3}$-(phenyl) group, a —(CH$_2$)$_{0-3}$—O—(CH$_2$)$_{0-3}$-(phenyl) group, a —(CH$_2$)$_{0-3}$-(phenyl group), or a C$_2$-C$_4$ alkynyl group; wherein the phenyl and alkynyl groups are unsubstituted or substituted by one or more substituents selected from a halogen atom, a hydroxyl group, a linear or branched C$_1$-C$_3$ alkyl group or a C$_1$-C$_3$ alkoxy group, a —NH—(CH$_2$)$_{0-3}$—N(C$_1$-C$_3$ alkyl)$_2$ group, or a —(CH$_2$)$_{0-3}$—C(O)—(CH$_2$)$_{0-3}$-(piperazinyl)-(linear or branched C$_1$-C$_4$ alkyl) group;

R$_5$ represents a moiety of formula (II-1) or (II-5):

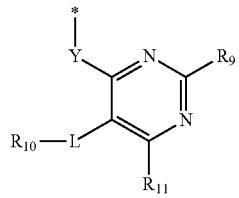

formula (II-1)

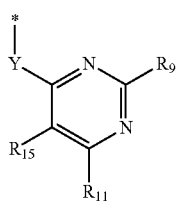

formula (II-5)

wherein:

R$_9$, R$_{11}$ and R$_{15}$ each independently represent a hydrogen atom, a cyano group, a —NH$_2$ group, or a linear or branched C$_1$-C$_4$ alkyl group;

R$_{10}$ represents a phenyl group,
wherein the phenyl group is substituted by one or more substituents selected from a halogen atom, a hydroxyl group, a linear or branched C$_1$-C$_4$ alkyl group;

L represents a direct bound;

Y represents a —NH— group.

In one embodiment, in the compound of formula (I)

n represents 0, 1, 2 or 3;

R$_a$ and R$_b$ each independently represent a hydrogen atom, a C$_1$-C$_4$ haloalkyl group, a C$_1$-C$_4$ hydroxyalkyl group or a linear or branched C$_1$-C$_4$ alkyl group;

R$_1$ represents a C$_3$-C$_{10}$ cycloalkyl group, a C$_3$-C$_{10}$ cycloalkenyl group, a phenyl group, a 5- to 7-membered heteroaryl group containing at least one heteroatom selected from O, S and N, or a 5- to 7-membered heterocyclyl group containing at least one heteroatom selected from O, S and N,
wherein the cycloalkyl, cycloalkenyl, phenyl, heteroaryl, and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group, R$_2$ and R$_3$ each independently represent a hydrogen atom, a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group, a C$_1$-C$_4$ alkoxy group, a —NH$_2$ group, a —N(CH$_3$)H group or a —N(CH$_3$)$_2$ group;

R$_7$ and R$_8$ each independently represent a hydrogen atom, a C$_1$-C$_4$ haloalkyl group, a C$_1$-C$_4$ hydroxyalkyl group or a linear or branched C$_1$-C$_4$ alkyl group;

and a)

R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-

(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group, which alkyl group is unsubstituted or substituted by one or more substituents selected from a C$_1$-C$_4$ alkoxy group, a cyano group, a C$_3$-C$_4$ cycloalkyl group, a —C(O)—(CH$_2$)$_{0-3}$—R$_8$ group or a —C(O)—(CH$_2$)$_{0-3}$—NR$_7$R$_8$ group;

wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a C$_1$-C$_4$ alkoxy group; a C$_1$-C$_4$ haloalkyl group; a linear or branched C$_1$-C$_4$ hydroxyalkyl group; a C$_3$-C$_7$ cycloalkyl group; a —(CH$_2$)$_{0-3}$NR$_7$R$_8$ group; a —(CH$_2$)$_{1-3}$—O(C$_1$-C$_4$ alkyl group); a —(CH$_2$)$_{0-3}$—OC(O)—(C$_1$-C$_4$ alkyl group); a —(CH$_2$)$_{0-3}$—C(O)O—(C$_1$-C$_4$ alkyl group); a —C(O)—(CH$_2$)$_{0-3}$—NR$_7$R$_8$ group; a —(CH$_2$)$_{0-3}$—C(O)OH group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a C$_2$-C$_4$ alkynyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_5$ represents a moiety of formula (II-1), (II-2), (II-3), or (II-4):

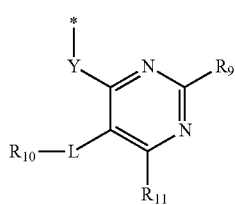

formula (II-1)

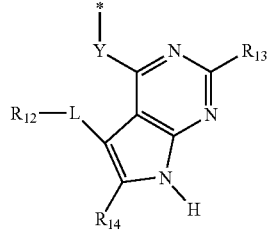

formula (II-2)

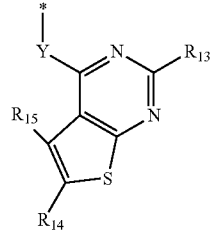

formula (II-3)

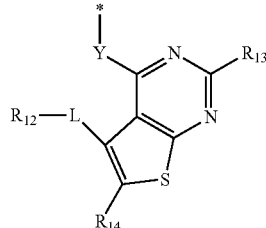

formula (II-4)

wherein:

R$_9$, R$_{11}$, R$_{13}$, R$_{14}$ and R$_{15}$ each independently represent a hydrogen atom, a —(CH$_2$)$_{0-3}$CN group, a —(CH$_2$)$_{0-3}$NR'R" group, or a linear or branched C$_1$-C$_4$ alkyl group; wherein R' and R" each independently represent a hydrogen atom, a hydroxyl group, a C$_1$-C$_4$ alkoxy group, a C$_1$-C$_4$ hydroxyalkyl group or a linear or branched C$_1$-C$_4$ alkyl group;

R$_{10}$ and R$_{12}$ each independently represent a phenyl group or a 5- to 14-membered heteroaryl group containing at least one heteroatom selected from O, S and N, wherein the phenyl and heteroaryl groups are unsubstituted or substituted by one or more substituents selected from a halogen atom, hydroxyl group, a cyano group, a linear or branched C$_1$-C$_6$ alkyl group, a C$_1$-C$_4$ haloalkyl group, a C$_1$-C$_4$ hydroxyalkyl group, a C$_3$-C$_7$ cycloalkyl group, a phenyl group, a 5- to 14-membered heteroaryl group containing at least one heteroatom selected from O, S and N, a 5- to 14-membered heterocyclyl group containing at least one heteroatom selected from O, S and N, a —(CH$_2$)$_{1-3}$CN group, a —(CH$_2$)$_{0-3}$—OR' group, a —C(O) group, a —(CH$_2$)$_{0-3}$NR'R" group, a —(CH$_2$)$_{0-3}$—C(O)—(CH$_2$)$_{1-3}$—CN group, a —(CH$_2$)$_{0-3}$—C(O)OH group, a —(CH$_2$)$_{0-3}$—C(O)—(CH$_2$)$_{0-3}$—R' group, a —(CH$_2$)$_{0-3}$—C(O)—(CH$_2$)$_{0-3}$—NR'R"group, a —(CH$_2$)$_{0-3}$NR'—S(O)$_2$R" group or a —(CH$_2$)$_{0-3}$—S(O)$_2$(CH$_2$)$_{0-3}$NR' R" group; wherein R' and R" each independently represent a hydrogen atom, a hydroxyl group, a C$_1$-C$_4$ haloalkyl group, a C$_1$-C$_4$ alkoxy group, a C$_1$-C$_4$ hydroxyalkyl group, a linear or branched C$_1$-C$_4$ alkyl group or a phenyl group, which phenyl group is unsubstituted or substituted by one or more substituents selected from a halogen atom, a hydroxyl group, a cyano group, a $C_1$-$C_4$ hydroxyalkyl group, a $C_1$-$C_4$ haloalkyl group, a $C_1$-$C_4$ alkoxy group, a $C_3$-$C_4$ cycloalkyl group or a linear or branched alkyl group;

L represents a direct bound or a linker selected from —O—, —S—, a —(CH$_2$)$_{0-3}$NR'— group, a —C(O)—NR'— group, a —(CH$_2$)$_{0-3}$NR'—C(O)— group, a —C(O)—O— group, a —O—C(O)— group or a —(CH$_2$)$_{1-4}$ group; wherein R' represents hydrogen or a linear or branched $C_1$-$C_4$ alkyl group;

Y represents a —NR'— group; wherein R' represents hydrogen or a linear or branched $C_1$-$C_4$ alkyl group;

or b)

$R_4$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —(CH$_2$)$_{0-3}$NR$_7$R$_8$ group; a —(CH$_2$)$_{1-3}$—O(C$_1$-$C_4$ alkyl group); a —(CH$_2$)$_{0-3}$—OC(O)—(C$_1$-$C_4$ alkyl group); a —(CH$_2$)$_{0-3}$—C(O)O—(C$_1$-$C_4$ alkyl group); a —C(O)—(CH$_2$)$_{0-3}$—NR$_7$R$_8$ group; a —(CH$_2$)$_{0-3}$—C(O)OH group; a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); a $C_2$-$C_4$ alkynyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3), (II-4), (II-5) or (II-6):

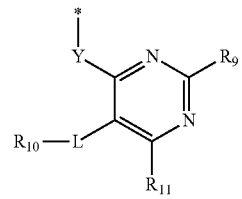

formula (II-1)

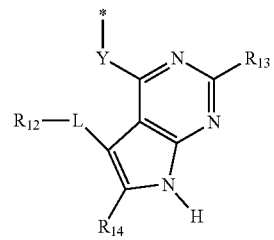

formula (II-2)

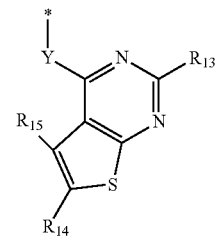

formula (II-3)

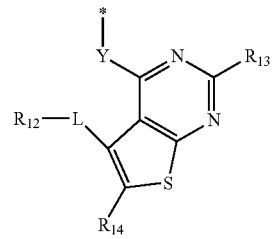

formula (II-4)

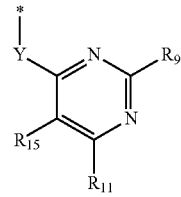

formula (II-5)

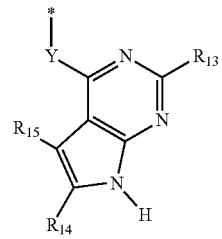

formula (II-6)

wherein:

$R_9$, $R_{11}$, $R_{13}$, $R_{14}$, $R_{15}$, $R_{10}$, $R_{12}$, L and Y are as defined above;

or c)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —C(O)—$(CH_2)_{0-3}$—$R_8$ group or a —C(O)—$(CH_2)_{0-3}$—$NR_7R_8$ group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3), (II-4), (II-5) or (II-6):

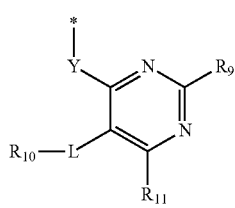

formula (II-1)

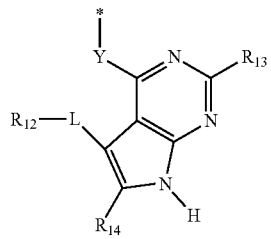

formula (II-2)

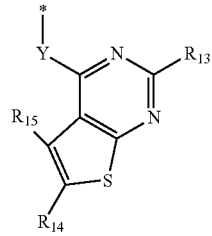

formula (II-3)

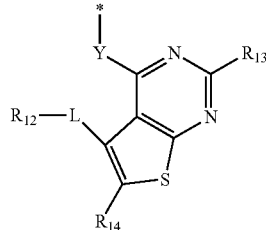

formula (II-4)

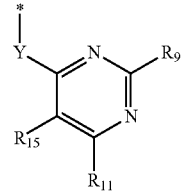

formula (II-5)

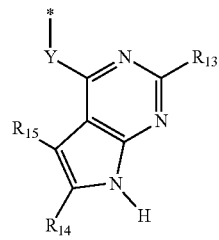

formula (II-6)

wherein:

$R_9$, $R_{11}$, $R_{13}$, $R_{14}$, $R_{15}$, $R_{10}$, $R_{12}$, L and Y are as defined above.

In this embodiment, it is preferred that in the compound of formula (I)

n represents 0, 1, 2 or 3;

$R_a$ and $R_b$ each independently represent a hydrogen atom, a $C_1$-$C_4$ haloalkyl group, a $C_1$-$C_4$ hydroxyalkyl group or a linear or branched $C_1$-$C_4$ alkyl group;

$R_1$ represents a $C_3$-$C_{10}$ cycloalkyl group, a $C_3$-$C_{10}$ cycloalkenyl group, a phenyl group, a 5- to 7-membered heteroaryl group containing at least one heteroatom selected from O, S and N, or a 5- to 7-membered heterocyclyl group containing at least one heteroatom selected from O, S and N, wherein the cycloalkyl, cycloalkenyl, phenyl, heteroaryl, and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, $R_2$ and $R_3$ each independently represent a hydrogen atom, a halogen atom, a hydroxyl group, a $C_1$-$C_3$ alkoxy group, a linear or branched $C_1$-$C_4$ alkyl group, a $C_1$-$C_3$ haloalkyl group, a $C_3$-$C_4$ cycloalkyl group or a —$NH_2$ group;

$R_7$ and $R_8$ each independently represent a hydrogen atom, a $C_1$-$C_4$ haloalkyl group, a $C_1$-$C_4$ hydroxyalkyl group or a linear or branched $C_1$-$C_4$ alkyl group;

and a)

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N), or a linear or branched $C_1$-$C_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N); a $C_2$-$C_4$ alkynyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3) or (II-4):

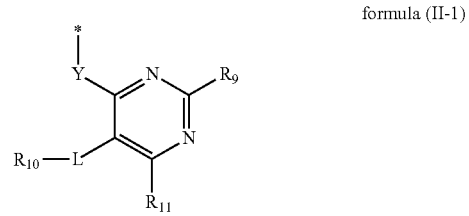

formula (II-1)

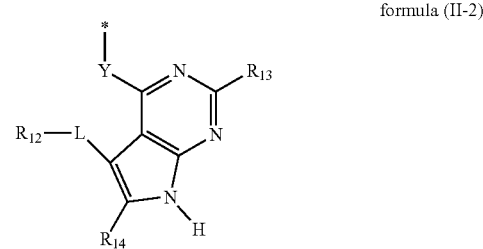

formula (II-2)

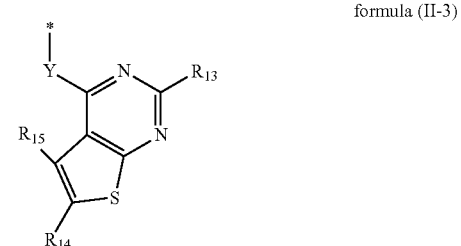

formula (II-3)

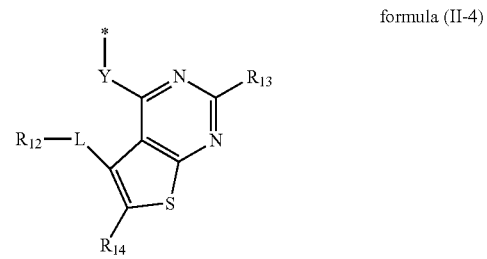

formula (II-4)

wherein:

$R_9$, $R_{11}$, $R_{13}$, $R_{14}$ and $R_{15}$ each independently represent a hydrogen atom, a —$(CH_2)_{0-3}CN$ group, a —$(CH_2)_{0-3}NR'R''$ group, or a linear or branched $C_1$-$C_4$ alkyl group; wherein R' and R'' each independently represent a hydrogen atom, a hydroxyl group, a $C_1$-$C_4$ alkoxy group, a $C_1$-$C_4$ hydroxyalkyl group or a linear or branched $C_1$-$C_4$ alkyl group;

$R_{10}$ and $R_{12}$ each independently represent a phenyl group or a 5- to 14-membered heteroaryl group containing at least one heteroatom selected from O, S and N, wherein the phenyl and heteroaryl groups are unsubstituted or substituted by one or more substituents selected from a halogen atom, hydroxyl group, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 14-membered heteroaryl group containing at least one heteroatom selected from O, S and N, a 5- to 14-membered heterocyclyl group containing at least one heteroatom selected from O, S and N, a —$(CH_2)_{1-3}CN$ group, a —$(CH_2)_{0-3}$—$OR'$ group, a —$C(O)$ group, a —$(CH_2)_{0-3}NR'R''$ group, a —$(CH_2)_{0-3}$—$C(O)$—$(CH_2)_{1-3}$—$CN$ group, a —(CH$_2$)$_{0-3}$—C(O)OH group, a (CH$_2$)$_{0-3}$—C(O)—(CH$_2$)$_{0-3}$—R' group, a —(CH$_2$)$_{0-3}$—C(O)—(CH$_2$)$_{0-3}$—NR'R"group, a —(CH$_2$)$_{0-3}$NR'—S(O)$_2$R" group or a —(CH$_2$)$_{0-3}$—S(O)$_2$(CH$_2$)$_{0-3}$NR'R" group; wherein R' and R" each independently represent a hydrogen atom, a hydroxyl group, a C$_1$-C$_4$ haloalkyl group, a C$_1$-C$_4$ alkoxy group, a C$_1$-C$_4$ hydroxyalkyl group, a linear or branched C$_1$-C$_4$ alkyl group or a phenyl group, which phenyl group is unsubstituted or substituted by one or more substituents selected from a halogen atom, a hydroxyl group, a cyano group, a C$_1$-C$_4$ hydroxy alkyl group, a C$_1$-C$_4$ haloalkyl group, a C$_1$-C$_4$ alkoxy group, a C$_3$-C$_4$ cycloalkyl group or a linear or branched C$_1$-C$_4$ alkyl group;

L represents a direct bound or a linker selected from —O—, —S—, a —(CH$_2$)$_{0-3}$NR'— group, a —C(O)—NR'— group, a —(CH$_2$)$_{0-3}$NR'—C(O)— group, a —C(O)—O— group, a —O—C(O)— group or a —(CH$_2$)$_{1-4}$ group; wherein R' represents hydrogen or a linear or branched C$_1$-C$_4$ alkyl group, and R''' represents a linear or branched C$_1$-C$_4$ alkyl group;

Y represents a —NR'— group; wherein R' represents hydrogen or a linear or branched C$_1$-C$_4$ alkyl group.

or b)

R$_4$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;

R$_6$ represents a hydrogen atom; a halogen atom; a hydroxyl group; a cyano group; a C$_1$-C$_4$ alkoxy group; a C$_1$-C$_4$ haloalkyl group; a linear or branched C$_1$-C$_4$ hydroxyalkyl group; a C$_3$-C$_7$ cycloalkyl group; or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

R$_5$ represents a moiety of formula (II-1), (II-2), (II-3), (II-4), (II-5) or (II-6):

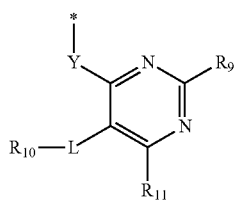

formula (II-1)

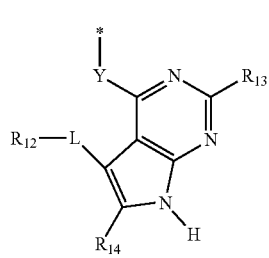

formula (II-2)

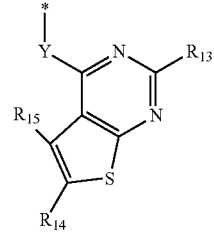

formula (II-3)

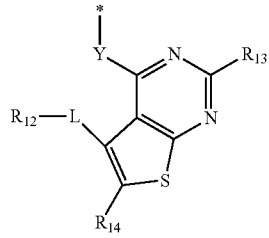

formula (II-4)

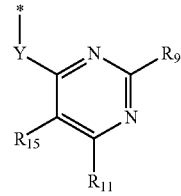

formula (II-5)

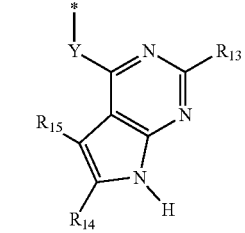

formula (II-6)

wherein:
R$_9$, R$_{11}$, R$_{13}$, R$_{14}$, R$_{15}$, R$_{10}$, R$_{12}$, L and Y are as defined above;

or c)

R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N), a —(CH$_2$)$_{0-3}$-(phenyl group), a —(CH$_2$)$_{0-3}$-(5- to 14-membered monocyclic or bicyclic heteroaryl group containing at least one heteroatom selected from O, S and N), or a linear or branched C$_1$-C$_4$ alkyl group;

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N); a —$(CH_2)_{0-3}$-(phenyl group); a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N) or a $C_2$-$C_4$ alkynyl group;

wherein the phenyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2), (II-3), (II-4), (II-5) or (II-6):

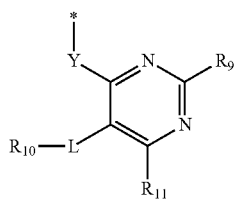

formula (II-1)

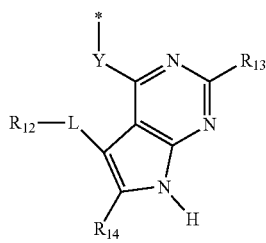

formula (II-2)

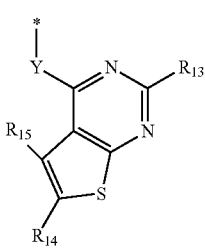

formula (II-3)

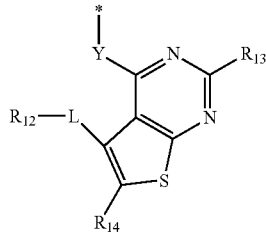

formula (II-4)

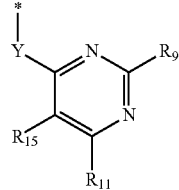

formula (II-5)

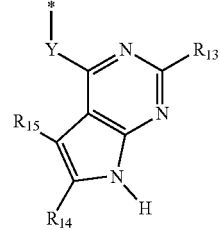

formula (II-6)

wherein:
$R_9$, $R_{11}$, $R_{13}$, $R_{14}$, $R_{15}$, $R_{10}$, $R_{12}$, L and Y are as defined above.

In a particular preferred embodiment, in the compound of formula (I)

n represents 0, 1, or 2;

$R_a$ and $R_b$ each independently represent a hydrogen atom or a linear or branched $C_1$-$C_4$ alkyl group;

$R_1$ represents a $C_3$-$C_7$ cycloalkyl group, a phenyl group, a pyridinyl group, a piperidinyl group or a tetrahydropyranyl group;

wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(CH_2)_{0-3}$—$NR_7R_8$ group;

$R_2$ and $R_3$ each independently represent a hydrogen atom, a halogen atom or a hydroxyl group or a linear or branched $C_1$-$C_4$ alkyl group;

$R_7$ and $R_8$ each independently represent a hydrogen atom, a —$NH_2$ group, a —$N(CH_3)H$ group, a —$N(CH_3)_2$ group, or a linear or branched $C_1$-$C_4$ alkyl group;

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a linear or branched $C_1$-$C_3$ alkyl group, a —$(CH_2)_{0-3}$—S—$(CH_2)_{0-3}$-(phenyl) group, a —$(CH_2)_{0-3}$—S—$(CH_2)_{0-3}$-(5- to 7-membered heteroaryl group containing at least one heteroatom selected from O, S and N), a —$(CH_2)_{0-3}$—O—$(CH_2)_{0-3}$-(phenyl) group, a —$(CH_2)_{0-3}$—O—$(CH_2)_{0-3}$-(5- to 7-membered heteroaryl group containing at least one heteroatom selected from O, S and N), wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}$—S—$(CH_2)_{0-3}$-(phenyl) group; a —$(CH_2)_{0-3}$—S—$(CH_2)_{0-3}$-(5- to 7-membered monocyclic or bicyclic heteroaryl group containing at least one heteroatom selected from O, S and N); a —$(CH_2)_{0-3}$—O—$(CH_2)_{0-3}$-(phenyl) group; a —$(CH_2)_{0-3}$—O—$(CH_2)_{0-3}$-(5- to 7-membered monocyclic or bicyclic heteroaryl group containing at least one heteroatom selected from O, S and N);

wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_5$ represents a moiety of formula (II-1), (II-2) or (II-3):

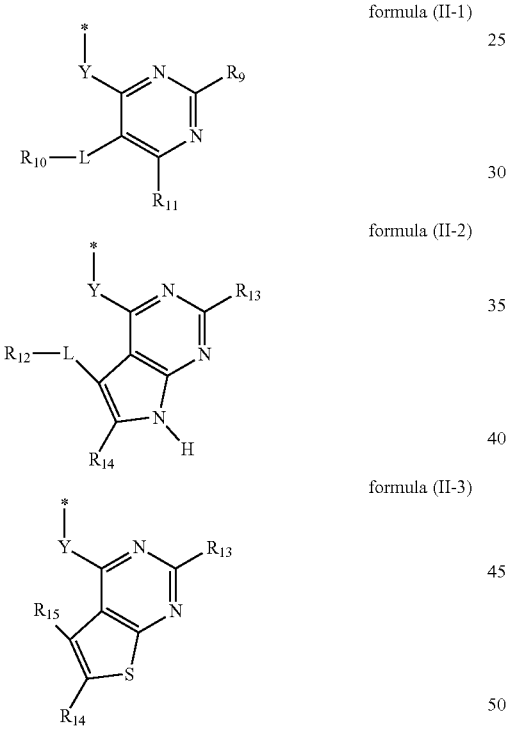

wherein:

$R_9$, $R_{11}$, $R_{13}$, $R_{14}$, $R_{15}$, $R_{10}$, $R_{12}$, L and Y are as defined in claim 1.

In another particularly preferred embodiment, in the compound of formula (I)

n is 0 or 1;

$R_1$ represents a phenyl group, which phenyl group is unsubstituted or substituted by one or more substituents selected from a halogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom, a linear or branched $C_1$-$C_3$ alkyl group, a —$(CH_2)_{0-3}$—S—$(CH_2)_{0-3}$-(phenyl) group or a —$(CH_2)_{0-3}$—O—$(CH_2)_{0-3}$-(phenyl) group;

$R_6$ represents a hydrogen atom, a halogen atom, a cyano group, a linear or branched $C_1$-$C_3$ alkyl group, or a —S-phenyl group;

$R_5$ represents a moiety of formula (II-1), (II-2) or (II-3):

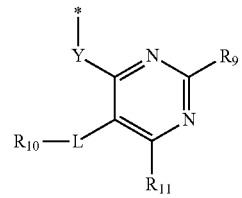

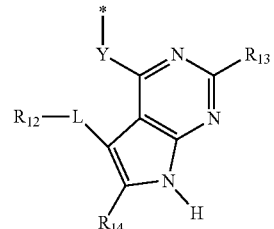

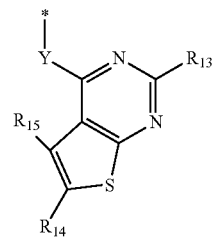

wherein:

$R_9$, $R_{11}$, $R_{13}$, $R_{14}$ and $R_{15}$ each independently represent a hydrogen atom, a —$NH_2$ group, or a linear or branched $C_1$-$C_4$ alkyl group;

$R_{10}$ and $R_{12}$ each independently represent a phenyl group, a 5- to 9-membered heteroaryl group containing at least one heteroatom selected from O, S and N, wherein the phenyl and heteroaryl groups are unsubstituted or substituted by one or more substituents selected from a halogen atom, hydroxyl group, a linear or branched $C_1$-$C_4$ alkyl group, a $C_1$-$C_4$ haloalkyl group, a $C_1$-$C_4$ hydroxyalkyl group, a —O—($C_1$-$C_3$ alkyl group) group, a —C(O) group, a —$NH_2$ group, a —$(CH_2)_{0-3}$—C(O)OH group, or a —$(CH_2)_{0-3}$NR'—S(O)$_2$R" group, wherein each n' and n are 0, 1 or 2; and wherein R' represents a hydrogen atom or a linear or branched $C_1$-$C_3$ and wherein R" represents a linear or branched $C_1$-$C_3$ alkyl group or a phenyl group, which phenyl group is unsubstituted or substituted by one or more substituents selected from a halogen atom, a hydroxyl group or a linear or branched $C_1$-$C_4$ alkyl group;

L represents a direct bound or a linker selected from —S—, a —C(O)—NH— group, a —C(O)—O— group or a —$(CH_2)_{1-3}$ group;

Y represents a —NH— group.

In a particular preferred embodiment, in the compound of formula (I)

n represents 0, 1, or 2;

$R_a$ and $R_b$ each independently represent a hydrogen atom or a linear or branched $C_1$-$C_4$ alkyl group;

$R_1$ represents a $C_3$-$C_7$ cycloalkyl group, a phenyl group, a pyridinyl group, a piperidinyl group or a tetrahydropyranyl group;
  wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(CH_2)_{0-3}$—$NR_7R_8$ group;

$R_2$ and $R_3$ each independently represent a hydrogen atom, a halogen atom or a hydroxyl group or a linear or branched $C_1$-$C_4$ alkyl group;

$R_7$ and $R_8$ each independently represent a hydrogen atom, a —$NH_2$ group, a —$N(CH_3)H$ group, a —$N(CH_3)_2$ group, or a linear or branched $C_1$-$C_4$ alkyl group;

$R_4$ represents a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom selected from O, S and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom selected from O, S and N), a —$(CH_2)_{0-3}$-(phenyl group), a —$(CH_2)_{0-3}$-(5- to 14-membered monocyclic or bicyclic heteroaryl group containing at least one heteroatom selected from O, S and N),
  wherein the phenyl and heteroaryl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group or a $C_1$-$C_4$ alkoxy group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_5$ represents a moiety of formula (II-1), (II-2), (II-3), (II-4), (II-5) or (II-6):

formula (II-1)

formula (II-2)

formula (II-3)

formula (II-4)

formula (II-5)

formula (II-6)

wherein:
  $R_9$, $R_{11}$, $R_{13}$, $R_{14}$, $R_{15}$, $R_{10}$, $R_{12}$, L and Y are as defined above.

In another particularly preferred embodiment, in the compound of formula (I)
n is 0 or 1;
$R_1$ represents a phenyl group, which phenyl group is unsubstituted or substituted by one or more substituents selected from a halogen atom or a linear or branched $C_1$-$C_3$ alkyl group;
$R_2$ and $R_3$ each independently represent a hydrogen atom or a linear or branched $C_1$-$C_3$ alkyl group;
$R_4$ represents a —$(CH_2)_{0-3}$—S—$(CH_2)_{0-3}$-(phenyl) group or a —$(CH_2)_{0-3}$—O—$(CH_2)_{0-3}$-(phenyl) group;
$R_6$ represents a hydrogen atom, a halogen atom, a cyano group, or a linear or branched $C_1$-$C_3$ alkyl group;
$R_5$ represents a moiety of formula (II-1) or (II-5):

formula (II-1)

formula (II-5)

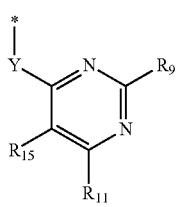

wherein:
R$_9$, R$_{11}$ and R$_{15}$ each independently represent a hydrogen atom, a cyano group, a —NH$_2$ group, or a linear or branched C$_1$-C$_4$ alkyl group;
R$_{10}$ represents a phenyl group,
wherein the phenyl group is unsubstituted or substituted by one or more substituents selected from a halogen atom, a hydroxyl group, a linear or branched C$_1$-C$_4$ alkyl group;
L represents a direct bound;
Y represents a —NH— group.

In a particular preferred embodiment, in the compound of formula (I)
n represents 0, 1, or 2;
R$_a$ and R$_b$ each independently represent a hydrogen atom or a linear or branched C$_1$-C$_4$ alkyl group;
R$_1$ represents a C$_3$-C$_7$ cycloalkyl group, a phenyl group, a pyridinyl group, a piperidinyl group or a tetrahydropyranyl group;
wherein the cycloalkyl, phenyl, pyridinyl, piperidinyl, or tetrahydropyranyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group, a —(CH$_2$)$_{0-3}$OR$_8$ group, a —(CH$_2$)$_{0-3}$NR$_7$R$_8$ group, a —C(O)—(CH$_2$)$_{0-3}$—R$_8$ group or a —C(O)—(CH$_2$)$_{0-3}$—NR$_7$R$_8$ group;
R$_2$ and R$_3$ each independently represent a hydrogen atom, a halogen atom or a hydroxyl group or a linear or branched C$_1$-C$_4$ alkyl group;
R$_7$ and R$_8$ each independently represent a hydrogen atom, a —NH$_2$ group, a —N(CH$_3$)H group, a —N(CH$_3$)$_2$ group, or a linear or branched C$_1$-C$_4$ alkyl group;
R$_4$ represents a hydrogen atom, a C$_1$-C$_4$ alkoxy group, a C$_1$-C$_4$ haloalkyl group, a C$_1$-C$_4$ hydroxyalkyl group, a C$_3$-C$_7$ cycloalkyl group, or a linear or branched C$_1$-C$_4$ alkyl group, which alkyl group is unsubstituted or substituted by one or more substituents selected from a C$_1$-C$_4$ alkoxy group, a cyano group, a C$_3$-C$_4$ cycloalkyl group, a —C(O)—(CH$_2$)$_{0-3}$—R$_8$ group or a —C(O)—(CH$_2$)$_{0-3}$—NR$_7$R$_8$ group;
R$_6$ represents a —(CH$_2$)$_{0-3}$—S—(CH$_2$)$_{0-3}$-(phenyl group), a —(CH$_2$)$_{0-3}$—S—(CH$_2$)$_{0-3}$-(5- to 14-membered monocyclic or bicyclic heteroaryl group containing at least one heteroatom selected from O, S and N), a —(CH$_2$)$_{0-3}$—O—(CH$_2$)$_{0-3}$-(phenyl group), a —(CH$_2$)$_{0-3}$—O—(CH$_2$)$_{0-3}$-(5- to 14-membered monocyclic or bicyclic heteroaryl group containing at least one heteroatom selected from O, S and N); a —(CH$_2$)$_{0-3}$-(phenyl group); a —(CH$_2$)$_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N) or a C$_2$-C$_4$ alkynyl group;
wherein the phenyl, heteroaryl and heterocyclyl groups are unsubstituted or substituted by one or more substituents selected from a halogen atom, a hydroxyl group, a cyano group, a linear or branched C$_1$-C$_4$ alkyl group, a C$_1$-C$_4$ haloalkyl group, a C$_1$-C$_4$ hydroxyalkyl group or a C$_1$-C$_4$ alkoxy group;
R$_5$ represents a moiety of formula (II-1), (II-2), (II-3), (II-4), (II-5) or (II-6):

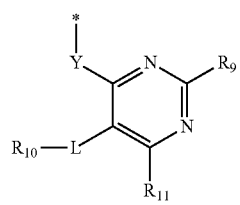

formula (II-1)

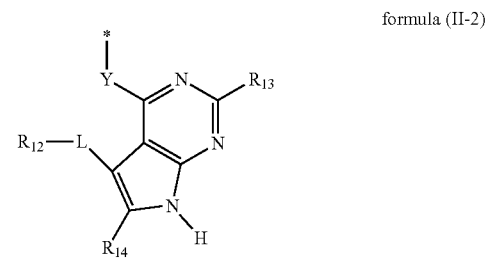

formula (II-2)

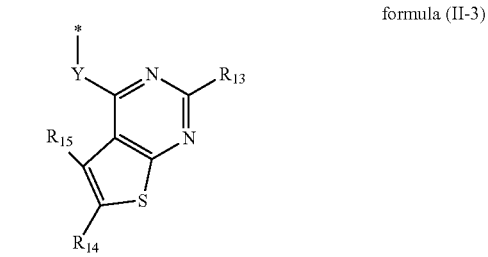

formula (II-3)

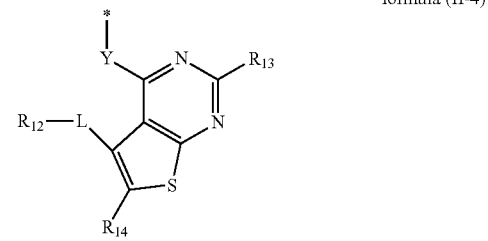

formula (II-4)

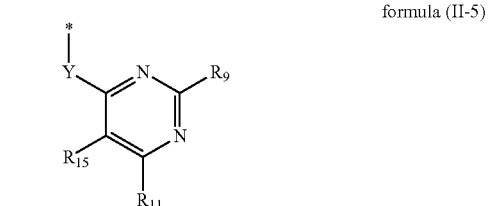

formula (II-5)

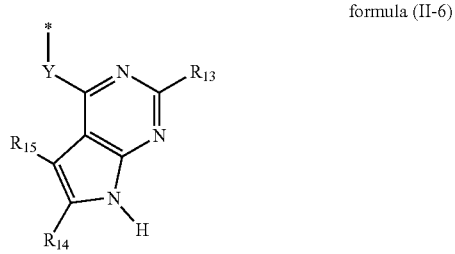

formula (II-6)

wherein:
R$_9$, R$_{11}$, R$_{13}$, R$_{14}$, R$_{15}$, R$_{10}$, R$_{12}$, L and Y are as defined above.

In another particularly preferred embodiment, in the compound of formula (I)
n is 0 or 1;
R$_1$ represents a phenyl group, which phenyl group is unsubstituted or substituted by one or more substituents selected from a halogen atom or a linear or branched C$_1$-C$_3$ alkyl group;
R$_2$ and R$_3$ each independently represent a hydrogen atom or a linear or branched C$_1$-C$_3$ alkyl group;
R$_4$ represents a hydrogen atom or a linear or branched C$_1$-C$_3$ alkyl group;
R$_6$ represents a —(CH$_2$)$_{0-3}$—S—(CH$_2$)$_{0-3}$-(phenyl) group or a —(CH$_2$)$_{0-3}$—O—(CH$_2$)$_{0-3}$-(phenyl) group; which phenyl group is unsubstituted or substituted by one or more substituents selected from a halogen atom, a hydroxyl group, a linear or branched C$_1$-C$_3$ alkyl group or a C$_1$-C$_3$ alkoxy group;
R$_5$ represents a moiety of formula (II-1) or (II-5):

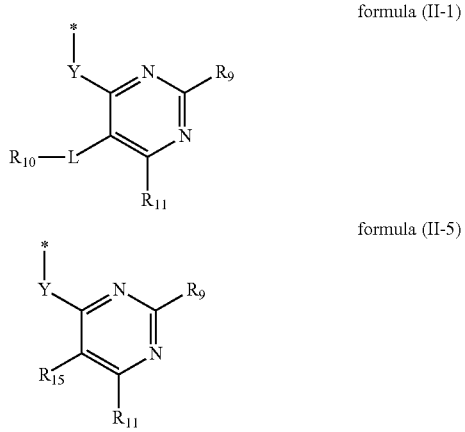

formula (II-1)

formula (II-5)

wherein:
R$_9$, R$_{11}$ and R$_{15}$ each independently represent a hydrogen atom, a cyano group, a —NH$_2$ group, or a linear or branched C$_1$-C$_4$ alkyl group;
R$_{10}$ represents a phenyl group,
  wherein the phenyl group is substituted by one or more substituents selected from a halogen atom, a hydroxyl group, a linear or branched C$_1$-C$_4$ alkyl group;
L represents a direct bound;
Y represents a —NH— group.

Particular individual compounds of the invention include:
(S)-2-(1-(6-Amino-5-(1H-tetrazol-5-yl)pyrimidin-4-ylamino)ethyl)-3-phenylpyrrolo[1,2-f][1,2,4]triazin-4(3H)-one
(S)-2-(1-((6-Amino-5-(thiazol-2-yl)pyrimidin-4-yl)amino)ethyl)-3-phenylpyrrolo[2,1-f][1,2,4]triazin-4(3H)-one
(S)-2-(1-((6-Amino-5-(6-aminopyridin-3-yl)pyrimidin-4-yl)amino)ethyl)-3-phenylpyrrolo[2,1-f][1,2,4]triazin-4(3H)-one
(S)-2-(1-((6-Amino-5-(1H-pyrazol-4-yl)pyrimidin-4-yl)amino)ethyl)-3-phenylpyrrolo[2,1-f][1,2,4]triazin-4(3H)-one
(S)-2-(1-((6-Amino-5-(1-(2-hydroxyethyl)-1H-pyrazol-4-yl)pyrimidin-4-yl)amino)ethyl)-3-phenylpyrrolo[2,1-f][1,2,4]triazin-4(3H)-one
(S)-2-(1-(6-amino-5-(3-hydroxyphenyl)pyrimidin-4-ylamino)ethyl)-3-phenylpyrrolo[1,2-f][1,2,4]triazin-4(3H)-one;
(S)-2-(1-(6-Amino-5-(3-fluoro-5-hydroxyphenyl)pyrimidin-4-ylamino)ethyl)-3-phenylpyrrolo[1,2-f][1,2,4]triazin-4(3H)-one;
(S)—N-(5-(4-Amino-6-(1-(5-bromo-4-oxo-3-phenyl-3,4-dihydropyrrolo[1,2-f][1,2,4]triazin-2-yl)ethylamino)pyrimidin-5-yl)-2-methoxypyridin-3-yl)methanesulfonamide;
(S)-2-(1-((6-amino-5-(3-fluoro-4-hydroxyphenyl)pyrimidin-4-yl)amino)ethyl)-3-phenylpyrrolo[2,1-f][1,2,4]triazin-4(3H)-one;
(S)-2-(1-((6-amino-5-(4-hydroxyphenyl)pyrimidin-4-yl)amino)ethyl)-5-methyl-3-phenylpyrrolo[2,1-f][1,2,4]triazin-4(3H)-one;
(S)-2-(1-((6-amino-5-(3-fluoro-5-hydroxyphenyl)pyrimidin-4-yl)amino)ethyl)-5-methyl-3-phenylpyrrolo[2,1-f][1,2,4]triazin-4(3H)-one;
(S)-4-amino-6-((1-(5-((3-hydroxyphenyl)thio)-4-oxo-3-phenyl-3,4-dihydropyrrolo[2,1-f][1,2,4]triazin-2-yl)ethyl)amino)pyrimidine-5-carbonitrile;
(S)-2-(1-((6-amino-5-(3-fluoro-4-hydroxyphenyl)pyrimidin-4-yl)amino)ethyl)-5-methyl-3-phenylpyrrolo[2,1-f][1,2,4]triazin-4(3H)-one;
(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide;
(S)-2-(1-((6-amino-5-(1H-indol-6-yl)pyrimidin-4-yl)amino)ethyl)-5-methyl-3-phenylpyrrolo[2,1-f][1,2,4]triazin-4(3H)-one;
(S)-2-(1-((2',6-diamino-[5,5'-bipyrimidin]-4-yl)amino)ethyl)-5-methyl-3-phenylpyrrolo[2,1-f][1,2,4]triazin-4(3H)-one;
(S)-2-(1-((6-amino-5-cyanopyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile;
(S)-2-(1-((5-(3-fluoro-5-hydroxyphenyl)pyrimidin-4-yl)amino)ethyl)-3-phenylpyrrolo[2,1-f][1,2,4]triazin-4 (3H)-one;
(S)-4-amino-6-((3-(benzylthio)-1-(4-oxo-3-phenyl-3,4-dihydropyrrolo[2,1-f][1,2,4]triazin-2-yl)propyl)amino)pyrimidine-5-carbonitrile;
(S)-4-amino-6-((1-(4-oxo-3-phenyl-3,4-dihydropyrrolo[2,1-f][1,2,4]triazin-2-yl)-3-phenoxypropyl)amino)pyrimidine-5-carbonitrile;
(S)-3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxybenzoic acid;
(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-fluorobenzenesulfonamide;
(S)-2-(1-((6-amino-5-(3,4-difluoro-5-hydroxyphenyl)pyrimidin-4-yl)amino)ethyl)-5-methyl-3-phenylpyrrolo[2,1-f][1,2,4]triazin-4(3H)-one;
(S)-2-(1-((6-amino-5-(3-fluoro-5-hydroxyphenyl)pyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile;
(S)-4-amino-6-((3-(benzyloxy)-1-(5-methyl-4-oxo-3-phenyl-3,4-dihydropyrrolo[2,1-f][1,2,4]triazin-2-yl)propyl)amino)pyrimidine-5-carbonitrile;
(S)-2-(1-((6-amino-5-(3,5-difluoro-4-hydroxyphenyl)pyrimidin-4-yl)amino)ethyl)-5-methyl-3-phenylpyrrolo[2,1-f][1,2,4]triazin-4(3H)-one;

(S)-2-(1-((5-(3-fluoro-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-hydroxy-5-(trifluoromethyl)phenyl)pyrimidin-4-yl)amino)ethyl)-5-methyl-3-phenylpyrrolo[2,1-f][1,2,4]triazin-4(3H)-one;

(S)-2-(1-((5-(2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-chloro-5-hydroxyphenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzenesulfonamide;

(S)-2-(1-((5-(1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-fluoro-5-hydroxyphenyl)pyrimidin-4-yl)amino)ethyl)-3-phenyl-5-(phenylthio)pyrrolo[2,1-f]triazin-4(3H)-one;

(S)-2-(1-((5-(3-fluoro-5-hydroxyphenyl)pyrimidin-4-yl)amino)ethyl)-5-methyl-3-phenylpyrrolo[2,1-f][1,2,4]triazin-4(3H)-one;

(S)-3-hydroxyphenyl 4-amino-6-((1-(5-methyl-4-oxo-3-phenyl-3,4-dihydropyrrolo[2,1-f][1,2,4]triazin-2-yl)ethyl)amino)pyrimidine-5-carboxamide;

(S)-benzyl 4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylate (S)-2-(1-((5-(2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-fluorophenyl)-7H-pyrrolo[2,3-d]pyrimidin-4-yl)amino)ethyl)-5-methyl-3-phenylpyrrolo[2,1-f][1,2,4]triazin-4(3H)-one;

(S)-4-amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile;

(S)-2-(1-((5-(4-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-fluoro-2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-((3-hydroxyphenyl)thio)pyrimidin-4-yl)amino)ethyl)-5-methyl-3-phenylpyrrolo[2,1-f][1,2,4]triazin-4(3H)-one;

(S)—N-(2-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide;

(S)-2-(1-((5-(3-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)methanesulfonamide;

(S)-4-amino-6-((1-(5-((2-hydroxyphenyl)thio)-4-oxo-3-phenyl-3,4-dihydropyrrolo[2,1-f][1,2,4]triazin-2-yl)ethyl)amino)pyrimidine-5-carbonitrile;

(S)-2-(1-((5-(5-amino-6-methoxypyridin-3-yl)-7H-pyrrolo[2,3-d]pyrimidin-4-yl)amino)ethyl)-5-methyl-3-phenylpyrrolo[2,1-f][1,2,4]triazin-4(3H)-one;

2-((1S)-1-((5-(2-fluoro-6-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(6-methoxypyridin-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-5-(4-amino-6-((1-(5-methyl-4-oxo-3-phenyl-3,4-dihydropyrrolo[2,1-f][1,2,4]triazin-2-yl)ethyl)amino)pyrimidin-5-yl)benzo[d]oxazol-2(3H)-one;

(S)-2-(1-((5-(5-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((6-methylthieno[2,3-d]pyrimidin-4-yl)amino)ethyl)-3-phenylpyrrolo[2,1-f][1,2,4]triazin-4(3H)-one;

(S)-2-(1-((2-butyl-6-methylthieno[2,3-d]pyrimidin-4-yl)amino)ethyl)-5-methyl-3-phenylpyrrolo[2,1-f][1,2,4]triazin-4(3H)-one;

(S)-2-(1-((2,6-dimethylthieno[2,3-d]pyrimidin-4-yl)amino)ethyl)-5-methyl-3-phenylpyrrolo[2,1-f][1,2,4]triazin-4(3H)-one;

(S)-5-methyl-3-phenyl-2-(1-(thieno[2,3-d]pyrimidin-4-ylamino)ethyl)pyrrolo[2,1-f][1,2,4]triazin-4(3H)-one;

(S)-2-(1-((5-(2-hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one (S)-5-methyl-2-(1-((2-methylthieno[2,3-d]pyrimidin-4-yl)amino)ethyl)-3-phenylpyrrolo[2,1-f][1,2,4]triazin-4(3H)-one;

(S)-5-methyl-2-(1-((5-(6-oxo-1,6-dihydropyridin-2-yl)-7H-pyrrolo[2,3-d]pyrimidin-4-yl)amino)ethyl)-3-phenylpyrrolo[2,1-f][1,2,4]triazin-4(3H)-one;

(S)-2-(1-((5-(1H-indol-7-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-hydroxybenzyl)pyrimidin-4-yl)amino)ethyl)-5-methyl-3-phenylpyrrolo[2,1-f][1,2,4]triazin-4(3H)-one;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(2-hydroxy-5-(trifluoromethyl)phenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-methoxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2,4-dihydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(1-methyl-1H-pyrazol-4-yl)-7H-pyrrolo[2,3-d]pyrimidin-4-yl)amino)ethyl)-3-phenylpyrrolo[2,1-f][1,2,4]triazin-4(3H)-one;

(S)-4-amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile;

N'-[3-methoxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

(S)-4-amino-6-((1-(5-(3-hydroxybenzyl)-4-oxo-3-phenyl-3,4-dihydropyrrolo[2,1-f][1,2,4]triazin-2-yl)ethyl)amino)pyrimidine-5-carbonitrile;

(S)—N-benzyl-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)—N-(3-(dimethylamino)-5-(4-((1-(5-methyl-4-oxo-3-phenyl-3,4-dihydropyrrolo[2,1-f][1,2,4]triazin-2-yl)amino)-7H-pyrrolo[2,3-d]pyrimidin-5-yl)phenyl)methanesulfonamide;

(S)-2-(1-((6-amino-5-((3-fluoro-4-hydroxyphenyl)thio)pyrimidin-4-yl)amino)ethyl)-5-methyl-3-phenylpyrrolo[2,1-f][1,2,4]triazin-4(3H)-one;

(S)-2-(1-((5-(3-fluoro-5-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-methyl-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-5-methyl-3-phenyl-2-(1-((5-(phenylethynyl)-7H-pyrrolo[2,3-d]pyrimidin-4-yl)amino)ethyl)pyrrolo[2,1-f][1,2,4]triazin-4(3H)-one;

(S)-4-amino-6-((1-(5-((3-fluoro-4-hydroxyphenyl)thio)-4-oxo-3-phenyl-3,4-dihydropyrrolo[2,1-f][1,2,4]triazin-2-yl)ethyl)amino)pyrimidine-5-carbonitrile;

(S)—N-(3-hydroxyphenyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)-4-amino-N-(3-fluoro-4-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-4-amino-N-(3-fluoro-5-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-5-methyl-2-(1-((5-(3-(morpholinosulfonyl)phenyl)-7H-pyrrolo[2,3-d]pyrimidin-4-yl)amino)ethyl)-3-phenylpyrrolo[2,1-f][1,2,4]triazin-4(3H)-one;

2-((1S)-1-((6-amino-5-(1H-indol-4-yl)pyrimidin-4-yl)amino)ethyl)-5-methyl-3-phenylpyrrolo[2,1-f][1,2,4]triazin-4(3H)-one;

(S)-4-amino-N-(3-hydroxybenzyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)—N-((1H-pyrazol-4-yl)ethyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)-4-amino-N-(2-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)methanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-1,1,1-trifluoromethanesulfonamide;

(S)-4-amino-6-((1-(5-((2-((2-(dimethylamino)ethyl)amino)phenyl)thio)-4-oxo-3-phenyl-3,4-dihydropyrrolo[2,1-f][1,2,4]triazin-2-yl)ethyl)amino)pyrimidine-5-carbonitrile;

(S)-1-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea;

(S)—N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(4-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((2-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((4-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-4-amino-N-(3,5-dihydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-4-amino-N-(5-carbamoyl-2-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-2-(1-((5-(1-(2-hydroxyethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-amino-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-hydroxyphenyl)-4-((1-(5-methyl-4-oxo-3-phenyl-3,4-dihydropyrrolo[2,1-f][1,2,4]triazin-2-yl)ethyl)amino)pyrimidine-5-carboxamide;

(S)—N-(3-hydroxy-5-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-pyrazol-1-yl)phenyl)methanesulfonamide;

(S)-2-(1-((5-(3-chloro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide;

(S)-2-(1-((5-(1-(2-(dimethylamino)ethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)butane-1-sulfonamide;

(S)-4-hydroxy-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)-4-methoxy-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)-2-(1-((5-(1-(3-(dimethylamino)propyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-4-amino-N-(3-hydroxy-4-(oxazol-5-yl)phenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-2-(1-((6-amino-5-(5-(trifluoromethyl)pyridin-3-yl)pyrimidin-4-yl)amino)ethyl)-5-methyl-3-phenylpyrrolo[2,1-f][1,2,4]triazin-4(3H)-one;

(S)—N-(3-(2-(dimethylamino)ethoxy)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((6-amino-5-(1-(2-hydroxyethyl)-1H-pyrazol-4-yl)pyrimidin-4-yl)amino)ethyl)-5-methyl-3-phenylpyrrolo[2,1-f][1,2,4]triazin-4(3H)-one;

(S)-2-(1-((6-amino-5-(3-hydroxy-5-(trifluoromethoxy)phenyl)pyrimidin-4-yl)amino)ethyl)-5-methyl-3-phenylpyrrolo[2,1-f][1,2,4]triazin-4(3H)-one;

(S)-4-amino-N-(4-(3-(dimethylamino)propoxy)-3-hydroxyphenyl)-6-((1-(8-methyl-1-oxo-2-phenyl-1,2-dihydropyrrolo[2,1-f][1,2,4]triazin-3-yl)ethyl)amino)pyrimidine-5-carboxamide;

3-((S)-1-((6-amino-5-((S)-3-hydroxypyrrolidine-1-carbonyl)pyrimidin-4-yl)amino)ethyl)-8-methyl-2-phenylpyrrolo[2,1-f][1,2,4]triazin-1(2H)-one;

(S)-2-(1-((5-(5-(ethylamino)-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(5-(difluoromethyl)pyridin-3-yl)pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-1,1,1-trifluoromethanesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-hydroxybenzenesulfonamide;

(S)-2-(1-(((6-amino-5-(5-hydroxypyridin-3-yl)pyrimidin-4-yl)amino)ethyl)-5-methyl-3-phenylpyrrolo[2,1-f][1,2,4]triazin-4(3H)-one;

(S)-4-hydroxy-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-hydroxybenzenesulfonamide;

(S)-2-(1-((6-amino-5-(5-(difluoromethoxy)pyridin-3-yl)pyrimidin-4-yl)amino)ethyl)-5-methyl-3-phenylpyrrolo[2,1-f][1,2,4]triazin-4(3H)-one;

(S)-4-amino-6-((1-(5-(6-(4-isopropylpiperazin-1-yl)-6-oxohex-1-yn-1-yl)-4-oxo-3-phenyl-3,4-dihydropyrrolo[2,1-f][1,2,4]triazin-2-yl)ethyl)amino)pyrimidine-5-carbonitrile;

(S)-2-(1-((5-((5-fluoro-2-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-2,4-difluorobenzenesulfonamide;

(S)-5-methyl-2-(1-((5-(2-methyloxazol-5-yl)-7H-pyrrolo[2,3-d]pyrimidin-4-yl)amino)ethyl)-3-phenylpyrrolo[2,1-f][1,2,4]triazin-4(3H)-one;

(S)-2-(1-((6-amino-5-(5-(2,2,2-trifluoroethoxyl)pyridin-3-yl)pyrimidin-4-yl)amino)ethyl)-5-methyl-3-phenylpyrrolo[2,1-f][1,2,4]triazin-4(3H)-one;

(S)-2-(1-((5-(1-(2-hydroxyethyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(5-amino-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-(difluoromethyl)-5-hydroxyphenyl)pyrimidin-4-yl)amino)ethyl)-5-methyl-3-phenylpyrrolo[2,1-f][1,2,4]triazin-4(3H)-one;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide;

(S)-2-(1-((6-amino-5-(2-methoxy-6-(trifluoromethyl)pyridin-4-yl)pyrimidin-4-yl)amino)ethyl)-5-methyl-3-phenylpyrrolo[2,1-f][1,2,4]triazin-4(3H)-one;

(S)—N-methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide;

(S)-2-(1-((5-(1H-pyrrolo[2,3-b]pyridin-5-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1-(3-hydroxypropyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-2,4-difluorobenzenesulfonamide;

(S)-2-(1-((6-amino-5-(2-hydroxy-6-(trifluoromethyl)pyridin-4-yl)pyrimidin-4-yl)amino)ethyl)-5-methyl-3-phenylpyrrolo[2,1-f][1,2,4]triazin-4(3H)-one;

N-[3-hydroxy-5-(4-{[(1S)-1-(5-methyl-4-oxo-3-phenyl-3,4-dihydropyrrolo[2,1-f][1,2,4]triazin-2-yl]ethyl]amino}-7H-pyrrolo[2,3-d]pyrimidin-5-yl)phenyl]sulfamide;

(S)-5-methyl-2-(1-((5-(1-(2-morpholinoethyl)-1H-pyrazol-3-yl)-7H-pyrrolo[2,3-d]pyrimidin-4-yl)amino)ethyl)-3-phenylpyrrolo[2,1-f][1,2,4]triazin-4(3H)-one;

(S)-5-methyl-3-phenyl-2-(1-((5-(1-(2,2,2-trifluoroethyl)-1H-pyrazol-3-yl)-7H-pyrrolo[2,3-d]pyrimidin-4-yl)amino)ethyl)pyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-2-fluoro-4-hydroxybenzenesulfonamide;

(S)-3-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzonitrile;

(S)-3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzonitrile;

(S)-2-(1-((6-amino-5-(2-(trifluoromethyl)pyridin-4-yl)pyrimidin-4-yl)amino)ethyl)-5-methyl-3-phenylpyrrolo[2,1-f][1,2,4]triazin-4(3H)-one;

- (S)-2-(dimethylamino)-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)ethanesulfonamide;
- (S)-5-methyl-2-(1-((5-(1-methyl-3-(trifluoromethyl)-1H-pyrazol-5-yl)-7H-pyrrolo[2,3-d]pyrimidin-4-yl)amino)ethyl)-3-phenylpyrrolo[2,1-f][1,2,4]triazin-4(3H)-one;
- (S)-tert-butyl 4-(4-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)piperazine-1-carboxylate;
- (S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)-2-(1-((5-(1-(2-methoxybenzyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;
- (S)-2-(1-((5-(1-(3-hydroxy-2,2-dimethylpropyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;
- (S)-3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxy-N,N-dimethylbenzamide;
- (S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzenesulfonamide;
- (S)—N-(3-hydroxy-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)-2-(1-((5-(1-(2-hydroxybenzyl)-1H-pyrazol-3-yl)-7H-pyrrolo[2,3-d]pyrimidin-4-yl)amino)ethyl)-3-phenylpyrrolo[2,1-f][1,2,4]triazin-4(3H)-one;
- (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)-1-(4-fluorophenyl)methanesulfonamide;
- (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-fluorobenzenesulfonamide;
- (S)-2-(1-(((6-amino-5-(4-(piperazin-1-yl)phenyl)pyrimidin-4-yl)amino)ethyl)-5-methyl-3-phenylpyrrolo[2,1-f][1,2,4]triazin-4(3H)-one;
- (S)-2-(1-((5-(1-(3-hydroxyphenyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;
- (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-fluorophenyl)-4-hydroxybenzenesulfonamide;
- (S)—N-(4-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide;
- (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-fluorophenyl)methanesulfonamide;
- (S)-2-(1-((5-(1-((3-hydroxyphenyl)sulfonyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;
- (S)-3-(4-amino-6-((1-(5-methyl-4-oxo-3-phenyl-3,4-dihydropyrrolo[2,1-f][1,2,4]triazin-2-yl)ethyl)amino)pyrimidin-5-yl)-N-(3-hydroxyphenyl)benzamide;
- 2-(((6-amino-5-(5-(difluoromethyl)pyridin-3-yl)pyrimidin-4-yl)amino)methyl)-5-methyl-3-phenylpyrrolo[2,1-f][1,2,4]triazin-4(3H)-one;
- (S)—N-(4-hydroxy-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)-2-(1-(((6-amino-5-(1-((2-fluoro-4-hydroxyphenyl)sulfonyl)-4-hydroxy-1H-indol-6-yl)pyrimidin-4-yl)amino)ethyl)-5-methyl-3-phenylpyrrolo[2,1-f][1,2,4]triazin-4(3H)-one;
- N-(3-(4-amino-6-(((5-methyl-4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide;
- (S)-1-(4-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-fluorophenyl)-3-(pyridin-4-yl)urea;
- 2-(((6-amino-5-(3-(difluoromethyl)-5-hydroxyphenyl)pyrimidin-4-yl)amino)methyl)-5-methyl-3-phenylpyrrolo[2,1-f][1,2,4]triazin-4(3H)-one;
- (S)-1-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea;
- (S)-3-(Methylsulfonamido)-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl methanesulfonate;
- (S)—N-(3-hydroxy-5-(4-((3-hydroxy-1-(5-methyl-4-oxo-3-phenyl-3,4-dihydropyrrolo[2,1-f][1,2,4]triazin-2-yl)propyl)amino)-7H-pyrrolo[2,3-d]pyrimidin-5-yl)phenyl)methanesulfonamide;
- (S)-3-hydroxy-N-methyl-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide;
- (S)-3-hydroxy-N,N-dimethyl-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzamide;
- (S)—N-(3-Fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indazol-6-yl)methanesulfonamide;
- (S)—N-methyl-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-morpholinophenyl)methanesulfonamide;
- N-[4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)-1H-indol-6-yl]sulfamide;
- (S)—N-(2-hydroxy-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;
- (S)-2-(1-(((6-amino-5-(1-((4-methoxyphenyl)sulfonyl)-1H-indazol-6-yl)pyrimidin-4-yl)amino)ethyl)-5-methyl-3-phenylpyrrolo[2,1-f][1,2,4]triazin-4(3H)-one;
- (S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-ethoxypyridin-3-yl)-4-hydroxybenzenesulfonamide;

(S)-5-methyl-2-(1-((5-(3-(5-methyl-1,3,4-oxadiazol-2-yl)phenyl)-7H-pyrrolo[2,3-d]pyrimidin-4-yl)amino)ethyl)-3-phenylpyrrolo[2,1-f][1,2,4]triazin-4(3H)-one;

N'-[3-hydroxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

(S)—N-(6-(4-amino-6-((1-(5-methyl-4-oxo-3-phenyl-3,4-dihydropyrrolo[2,1-f][1,2,4]triazin-2-yl)ethyl)amino)pyrimidin-5-yl)-1H-indol-4-yl)-4-methoxybenzenesulfonamide;

(S)—N-(6-(4-amino-6-((1-(5-methyl-4-oxo-3-phenyl-3,4-dihydropyrrolo[2,1-f][1,2,4]triazin-2-yl)ethyl)amino)pyrimidin-5-yl)-1H-indol-4-yl)-4-hydroxybenzenesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-ethylpyridin-3-yl)-4-hydroxybenzenesulfonamide;

(S)—N-(3-cyano-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((6-amino-5-(1H-indazol-6-yl)pyrimidin-4-yl)amino)ethyl)-5-methyl-3-phenylpyrrolo[2,1-f][1,2,4]triazin-4(3H)-one;

(S)-3-hydroxy-5-(methylsulfonamido)phenyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate;

(S)-2-(1-((5-((2-hydroxyphenyl)sulfonyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide;

(S)-2-(1-((5-(2-aminopyridin-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(1-((4-methoxyphenyl)sulfonyl)-1H-indol-6-yl)pyrimidin-4-yl)amino)ethyl)-5-methyl-3-phenylpyrrolo[2,1-f][1,2,4]triazin-4(3H)-one;

(S)-4-(N-methylsulfamoyl)phenyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate;

(S)-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-(methylsulfonamido)phenyl methanesulfonate;

(S)-2-(1-((5-(3-hydroxy-5-(5-methyl-1,3,4-oxadiazol-2-yl)phenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-(5-amino-1,3,4-oxadiazol-2-yl)-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(4-methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-((4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide;

(S)-4-amino-6-((1-(5-methyl-4-oxo-3-phenyl-3,4-dihydropyrrolo[2,1-f][1,2,4]triazin-2-yl)ethyl)amino)-N-(4-(N-methylsulfamoyl)phenyl)pyrimidine-5-carboxamide;

(S)-2-(1-((6-amino-5-(1-((4-hydroxyphenyl)sulfonyl)-1H-indol-6-yl)pyrimidin-4-yl)amino)ethyl)-5-methyl-3-phenylpyrrolo[2,1-f][1,2,4]triazin-4(3H)-one;

(S)—N-(6-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-4-yl)methanesulfonamide;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-2-yl)-1-(tetrahydro-2H-pyran-4-yl)methanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxy-3-methylbenzenesulfonamide;

(S)-4-methoxybenzyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate;

(S)-1-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)urea;

(S)-2-(1-((6-amino-5-(3-(morpholinosulfonyl)phenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-2,4-difluorobenzenesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-2,4-dihydroxybenzenesulfonamide;

(S)-1-(2-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)urea;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-(ethylamino)pyridin-3-yl)-4-hydroxybenzenesulfonamide;

(S)—N,N-dimethyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-(methylsulfonamido)benzamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-hydroxybenzamide;

(S)-4-amino-N-(3-methoxy-5-(methylsulfonamido)phenyl)-6-((1-(5-methyl-4-oxo-3-phenyl-3,4-dihydropyrrolo[2,1-f][1,2,4]triazin-2-yl)ethyl)amino)pyrimidine-5-carboxamide N-[3-fluoro-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]sulfamide;

(S)—N-(4-((4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-(trifluoromethyl)phenyl)methanesulfonamide;

(S)-2-(1-((5-(2-(4-(dimethylamino)piperidin-1-yl)pyridin-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(1-(methylsulfonyl)-1H-pyrrolo[2,3-b]pyridin-4-yl)-7H-pyrrolo[2,3-d]pyrimidin-4-yl)amino)ethyl)-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-(difluoromethyl)phenyl)methanesulfonamide;

(S)-1-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)urea;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-3-methoxybenzamide;

(S)—N-(3-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-1-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)urea;

(S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-hydroxyethanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-3-hydroxybenzamide (S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-methoxyethanesulfonamide (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxy-3-methylbenzenesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-methylphenyl)methanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-ethoxypyridin-3-yl)-4-hydroxy-3-methylbenzenesulfonamide;

(S)—N-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-1-(tetrahydro-2H-pyran-4-yl)methanesulfonamide;

N'-[3-hydroxy-4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

or a pharmaceutically acceptable salt, or N-oxide, or isotopically-labeled derivate thereof.

Examples of the preferred compounds are:

(S)-2-(1-((6-amino-5-(3-fluoro-5-hydroxyphenyl)pyrimidin-4-yl)amino)ethyl)-5-methyl-3-phenylpyrrolo[2,1-f][1,2,4]triazin-4(3H)-one;

(S)-2-(1-((6-amino-5-(3-fluoro-4-hydroxyphenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-fluorobenzenesulfonamide;

(S)-2-(1-((6-amino-5-(3,4-difluoro-5-hydroxyphenyl)pyrimidin-4-yl)amino)ethyl)-5-methyl-3-phenylpyrrolo[2,1-f][1,2,4]triazin-4(3H)-one;

(S)-4-amino-6-((3-(benzyloxy)-1-(5-methyl-4-oxo-3-phenyl-3,4-dihydropyrrolo[2,1-f][1,2,4]triazin-2-yl)propyl)amino)pyrimidine-5-carbonitrile;

(S)-2-(1-((6-amino-5-(3-hydroxy-5-(trifluoromethyl)phenyl)pyrimidin-4-yl)amino)ethyl)-5-methyl-3-phenylpyrrolo[2,1-f][1,2,4]triazin-4(3H)-one;

(S)-2-(1-((6-amino-5-(3-chloro-5-hydroxyphenyl)pyrimidin-4-yl)amino)ethyl)-5-methyl-3-phenylpyrrolo[2,1-f][1,2,4]triazin-4(3H)-one;

(S)-4-amino-N-(3-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-2-(1-((5-(3-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)methanesulfonamide;

(S)-2-(1-((5-(1H-indazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(2-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indol-4-yl)-7H-pyrrolo[2,3-d]pyrimidin-4-yl)amino)ethyl)-5-methyl-3-phenylpyrrolo[2,1-f][1,2,4]triazin-4(3H)-one;

N'-[3-methoxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

(S)—N-(3-(dimethylamino)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(1-(2-hydroxyethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide;

(S)—N-(3-hydroxy-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)-1-(4-fluorophenyl)methanesulfonamide;

N-[4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)-1H-indol-6-yl]sulfamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-ethoxypyridin-3-yl)-4-hydroxybenzenesulfonamide;

(S)-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-(methylsulfonamido)phenyl methanesulfonate;

(S)—N-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-4-amino-N-(3-methoxy-5-(methylsulfonamido)phenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-5-methyl-2-(1-((5-(1-(methylsulfonyl)-1H-pyrrolo[2,3-b]pyridin-4-yl)-7H-pyrrolo[2,3-d]pyrimidin-4-yl)amino)ethyl)-3-phenylpyrrolo[2,1-f][1,2,4]triazin-4(3H)-one;

(S)—N-(3-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-hydroxyethanesulfonamide;

(S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-methoxyethanesulfonamide;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxy-3-methylbenzenesulfonamide;

or a pharmaceutically acceptable salt, or N-oxide, or isotopically-labeled derivate thereof.

In one embodiment, particular individual compounds of the invention include:

(S)-2-(1-(6-Amino-5-(1H-tetrazol-5-yl)pyrimidin-4-ylamino)ethyl)-3-phenylpyrrolo[1,2-f][1,2,4]triazin-4(3H)-one;

(S)-2-(1-(6-Amino-5-(thiazol-2-yl)pyrimidin-4-ylamino)ethyl)-3-phenylpyrrolo[1,2-f][1,2,4]triazin-4(3H)-one:

(S)-2-(1-(6-Amino-5-(6-aminopyridin-3-yl)pyrimidin-4-ylamino)ethyl)-3-phenylpyrrolo[1,2-f][1,2,4]triazin-4(3H)-one;

(S)-2-(1-(6-Amino-5-(1H-pyrazol-4-yl)pyrimidin-4-ylamino)ethyl)-3-phenylpyrrolo[1,2-f][1,2,4]triazin-4(3H)-one;

(S)-2-(1-(6-Amino-5-(1-(2-hydroxyethyl)-1H-pyrazol-4-yl)pyrimidin-4-ylamino)ethyl)-3-phenylpyrrolo[1,2-f][1,2,4]triazin-4(3H)-one;

(S)-2-(1-(6-amino-5-(3-hydroxyphenyl)pyrimidin-4-ylamino)ethyl)-3-phenylpyrrolo[1,2-f][1,2,4]triazin-4(3H)-one;

(S)-2-(1-(6-Amino-5-(3-fluoro-5-hydroxyphenyl)pyrimidin-4-ylamino)ethyl)-3-phenylpyrrolo[1,2-f][1,2,4]triazin-4(3H)-one;

(S)—N-(5-(4-Amino-6-(1-(5-bromo-4-oxo-3-phenyl-3,4-dihydropyrrolo[1,2-f][1,2,4]triazin-2-yl)ethylamino)pyrimidin-5-yl)-2-methoxypyridin-3-yl)methanesulfonamide;

(S)-2-(1-((6-amino-5-(3-fluoro-4-hydroxyphenyl)pyrimidin-4-yl)amino)ethyl)-3-phenylpyrrolo[2,1-f][1,2,4]triazin-4(3H)-one;

(S)-2-(1-((6-amino-5-(4-hydroxyphenyl)pyrimidin-4-yl)amino)ethyl)-5-methyl-3-phenylpyrrolo[2,1-f][1,2,4]triazin-4(3H)-one;

(S)-2-(1-((6-amino-5-(3-fluoro-5-hydroxyphenyl)pyrimidin-4-yl)amino)ethyl)-5-methyl-3-phenylpyrrolo[2,1-f][1,2,4]triazin-4(3H)-one;

(S)-4-amino-6-((1-(5-((3-hydroxyphenyl)thio)-4-oxo-3-phenyl-3,4-dihydropyrrolo[2,1-f][1,2,4]triazin-2-yl)ethyl)amino)pyrimidine-5-carbonitrile;

(S)-2-(1-((6-amino-5-(3-fluoro-4-hydroxyphenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide;

(S)-2-(1-((6-amino-5-(1H-indol-6-yl)pyrimidin-4-yl)amino)ethyl)-5-methyl-3-phenylpyrrolo[2,1-f][1,2,4]triazin-4(3H)-one;

(S)-2-(1-((2',6-diamino-[5,5'-bipyrimidin]-4-yl)amino)ethyl)-5-methyl-3-phenylpyrrolo[2,1-f][1,2,4]triazin-4(3H)-one;

(S)-2-(1-((6-amino-5-cyanopyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile;

(S)-2-(1-((5-(3-fluoro-5-hydroxyphenyl)pyrimidin-4-yl)amino)ethyl)-3-phenylpyrrolo[2,1-f][1,2,4]triazin-4(3H)-one;

(S)-4-amino-6-((3-(benzylthio)-1-(oxo-3-phenyl-3,4-dihydropyrrolo[2,1-f][1,2,4]triazin-2-yl)propyl)amino)pyrimidine-5-carbonitrile;

(S)-4-amino-6-((1-(4-oxo-3-phenyl-3,4-dihydropyrrolo[2,1-f][1,2,4]triazin-2-yl)-3-phenoxypropyl)amino)pyrimidine-5-carbonitrile;

(S)-3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxybenzoic acid;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-fluorobenzenesulfonamide;

(S)-2-(1-((6-amino-5-(3,4-difluoro-5-hydroxyphenyl)pyrimidin-4-yl)amino)ethyl)-5-methyl-3-phenylpyrrolo[2,1-f][1,2,4]triazin-4(3H)-one;

(S)-2-(1-((6-amino-5-(3-fluoro-5-hydroxyphenyl)pyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile;

(S)-4-amino-6-((3-(benzyloxy)-1-(5-methyl-4-oxo-3-phenyl-3,4-dihydropyrrolo[2,1-f][1,2,4]triazin-2-yl)propyl)amino)pyrimidine-5-carbonitrile;

(S)-2-(1-((6-amino-5-(3,5-difluoro-4-hydroxyphenyl)pyrimidin-4-yl)amino)ethyl)-5-methyl-3-phenylpyrrolo[2,1-f][1,2,4]triazin-4(3H)-one;

(S)-2-(1-((5-(3-fluoro-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-hydroxy-5-(trifluoromethyl)phenyl)pyrimidin-4-yl)amino)ethyl)-5-methyl-3-phenylpyrrolo[2,1-f][1,2,4]triazin-4(3H)-one;

(S)-2-(1-((5-(2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-chloro-5-hydroxyphenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzenesulfonamide;

(S)-2-(1-((5-(1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-fluoro-5-hydroxyphenyl)pyrimidin-4-yl)amino)ethyl)-3-phenyl-5-(phenylthio)pyrrolo[2,1-f][1,2,4]triazin-4(3H)-one;

(S)-2-(1-((5-(3-fluoro-5-hydroxyphenyl)pyrimidin-4-yl)amino)ethyl)-5-methyl-3-phenylpyrrolo[2,1-f][1,2,4]triazin-4(3H)-one;

(S)-3-hydroxyphenyl 4-amino-6-((1-(5-methyl-4-oxo-3-phenyl-3,4-dihydropyrrolo[2,1-f][1,2,4]triazin-2-yl)ethyl)amino)pyrimidine-5-carboxamide;

(S)-benzyl 4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylate (S)-2-(1-((5-(2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-fluorophenyl)-7H-pyrrolo[2,3-d]pyrimidin-4-yl)amino)ethyl)-5-methyl-3-phenylpyrrolo[2,1-f][1,2,4]triazin-4(3H)-one;

(S)-4-amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile;

(S)-2-(1-((5-(4-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-fluoro-2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-((3-hydroxyphenyl)thio)pyrimidin-4-yl)amino)ethyl)-5-methyl-3-phenylpyrrolo[2,1-f][1,2,4]triazin-4(3H)-one;

(S)—N-(2-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide;

(S)-2-(1-((5-(3-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)methanesulfonamide;

(S)-4-amino-6-((1-(5-((2-hydroxyphenyl)thio)-4-oxo-3-phenyl-3,4-dihydropyrrolo[2,1-f][1,2,4]triazin-2-yl)ethyl)amino)pyrimidine-5-carbonitrile;

(S)-2-(1-((5-(5-amino-6-methoxypyridin-3-yl)-7H-pyrrolo[2,3-d]pyrimidin-4-yl)amino)ethyl)-5-methyl-3-phenylpyrrolo[2,1-f][1,2,4]triazin-4(3H)-one;

2-((1S)-1-((5-(2-fluoro-6-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(6-methoxypyridin-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-5-(4-amino-6-((1-(5-methyl-4-oxo-3-phenyl-3,4-dihydropyrrolo[2,1-f][1,2,4]triazin-2-yl)ethyl)amino)pyrimidin-5-yl)benzo[d]oxazol-2(3H)-one;

(S)-2-(1-((5-(5-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((6-methylthieno[2,3-d]pyrimidin-4-yl)amino)ethyl)-3-phenylpyrrolo[2,1-f][1,2,4]triazin-4(3H)-one;

(S)-2-(1-((2-butyl-6-methylthieno[2,3-d]pyrimidin-4-yl)amino)ethyl)-5-methyl-3-phenylpyrrolo[2,1-f][1,2,4]triazin-4(3H)-one;

(S)-2-(1-((2,6-dimethylthieno[2,3-d]pyrimidin-4-yl)amino)ethyl)-5-methyl-3-phenylpyrrolo[2,1-f][1,2,4]triazin-4(3H)-one;

(S)-5-methyl-3-phenyl-2-(1-(thieno[2,3-d]pyrimidin-4-ylamino)ethyl)pyrrolo[2,1-f][1,2,4]triazin-4(3H)-one;

(S)-2-(1-((5-(2-hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one (S)-5-methyl-2-(1-((2-methylthieno[2,3-d]pyrimidin-4-yl)amino)ethyl)-3-phenylpyrrolo[2,1-f][1,2,4]triazin-4(3H)-one;

(S)-5-methyl-2-(1-((5-(6-oxo-1,6-dihydropyridin-2-yl)-7H-pyrrolo[2,3-d]pyrimidin-4-yl)amino)ethyl)-3-phenylpyrrolo[2,1-f][1,2,4]triazin-4(3H)-one;

(S)-2-(1-((5-(1H-indol-7-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((6-amino-5-(3-hydroxybenzyl)pyrimidin-4-yl)amino)ethyl)-5-methyl-3-phenylpyrrolo[2,1-f][1,2,4]triazin-4(3H)-one;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(2-hydroxy-5-(trifluoromethyl)phenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-methoxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2,4-dihydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(1-methyl-1H-pyrazol-4-yl)-7H-pyrrolo[2,3-d]pyrimidin-4-yl)amino)ethyl)-3-phenylpyrrolo[2,1-f][1,2,4]triazin-4(3H)-one;

(S)-4-amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile;

or a pharmaceutically acceptable salt, or N-oxide, or isotopically-labeled derivate thereof.

Examples of the preferred compounds in this embodiment are:

(S)-2-(1-(((6-amino-5-(3-fluoro-5-hydroxyphenyl)pyrimidin-4-yl)amino)ethyl)-5-methyl-3-phenylpyrrolo[2,1-f][1,2,4]triazin-4(3H)-one;

(S)-2-(1-(((6-amino-5-(3-fluoro-4-hydroxyphenyl)pyrimidin-4-yl)amino)ethyl)-5-methyl-3-phenylpyrrolo[2,1-f][1,2,4]triazin-4(3H)-one;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide;

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-fluorobenzenesulfonamide;

(S)-2-(1-(((6-amino-5-(3,4-difluoro-5-hydroxyphenyl)pyrimidin-4-yl)amino)ethyl)-5-methyl-3-phenylpyrrolo[2,1-f][1,2,4]triazin-4(3H)-one;

(S)-4-amino-6-((3-(benzyloxy)-1-(5-methyl-4-oxo-3-phenyl-3,4-dihydropyrrolo[2,1-f][1,2,4]triazin-2-yl)propyl)amino)pyrimidine-5-carbonitrile;

(S)-2-(1-(((6-amino-5-(3-hydroxy-5-(trifluoromethyl)phenyl)pyrimidin-4-yl)amino)ethyl)-5-methyl-3-phenylpyrrolo[2,1-f][1,2,4]triazin-4(3H)-one;

(S)-2-(1-(((6-amino-5-(3-chloro-5-hydroxyphenyl)pyrimidin-4-yl)amino)ethyl)-5-methyl-3-phenylpyrrolo[2,1-f][1,2,4]triazin-4(3H)-one;

(S)-4-amino-N-(3-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide;

(S)-2-(1-((5-(3-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)methanesulfonamide;

(S)-2-(1-((5-(1H-indazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(2-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indol-4-yl)-7H-pyrrolo[2,3-d]pyrimidin-4-yl)amino)ethyl)-5-methyl-3-phenylpyrrolo[2,1-f][1,2,4]triazin-4(3H)-one;

or a pharmaceutically acceptable salt, or N-oxide, or isotopically-labeled derivate thereof.

The invention is also directed to the compounds of the invention as described herein, for use in the treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK).

The invention is also directed to use of the compounds of the invention as described herein, in the manufacture of a medicament for treatment of a pathological condition or disease susceptible to amelioration by inhibition of Phosphoinositide 3-Kinases (PI3Ks), in particular wherein the pathological condition or disease is as defined above.

The invention also provides a method of treatment of a pathological condition or disease susceptible to amelioration by inhibition of Phosphoinositide 3-Kinases (PI3Ks), in particular wherein the pathological condition or disease is as defined above, which comprises administering to said subject a therapeutically effective amount of a compound of the invention as described herein.

As used herein, the term therapeutically effective amount refers to an amount sufficient to effect treatment when administered to a patient in need of treatment.

As used herein, the term treatment refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

The term amino-protecting group refers to a protecting group suitable for preventing undesired reactions at amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS), 2-(trimethylsilyl) ethoxymethyl (SEM) and tert-butyldimethylsilyl (TBS); and the like.

The term hydroxy-protecting group refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

According to one embodiment of the present invention, compounds of general Formula (I) may be prepared by the synthetic route illustrated in Scheme 1, from compounds of Formula (III), where the group $Z_1$ represents —NR'— group; wherein R' represents hydrogen or a linear or branched $C_1$-$C_4$ alkyl group;

In one embodiment of the present invention compounds of Formula (I) can be obtained from compounds of Formula (III) by treatment with compounds of Formula (II-1a) (II-2a) (II-3a) (II-4a) (II-5a) (II-6a), where $Z_2$ represents an halogen, in the presence of a suitable base such as potassium carbonate, diisopropylethylamine or sodium hydride in an appropriate solvent such as tert-butanol, N,N-dimethylformamide or tetrahydrofuran at temperatures ranging from room temperature to 160° C., with or without the use of microwaves irradiation and with or without the use of a catalytic amount of cesium fluoride.

Compounds of Formula (II) can either be commercial or prepared as shown in Scheme 8 from compounds of Formula (XX-1) (XX-2) (XX-3) where Z3 is an halogen or carboxylic acid following the standard methods described as it follows, with or without the use of protecting groups.

Alternatively, compounds of Formula (I) can be obtained in two step synthesis from compounds of Formula (V-1)(V-2) (V-3). Where compounds of Formula (V) can be obtained from reaction of compounds of Formula (III) with compounds of Formula (IV-1) (IV-2) (IV-3), where $Z_2$ represents an halogen, in the presence of a suitable base such as potassium carbonate, diisopropylethylamine or sodium hydride in an appropriate solvent such as tert-butanol, N,N-dimethylformamide or tetrahydrofuran at temperatures ranging from room temperature to 160° C., with or without the use of microwaves irradiation and with or without the use of a catalytic amount of cesium fluoride.

In the particular case of compounds of general Formula (I) where L represents a direct bond or a —$(CH_2)_{1-4}$ group, compounds of Formula (I) can be prepared in the two steps synthesis from compounds of Formula (V-1) (V-2) (V-3) where $Z_3$ represents an halogen by reaction with the corresponding boronic acids or boronic esters using standard Suzuki coupling conditions.

In the particular case of compounds of general Formula (I) where L represents a linker selected from —O—, —S—, —NH— group, compounds can be obtained from compounds of Formula (V-1) (V-2) (V-3) by reacting with the corresponding aniline or thiophenol or phenol by using copper or palladium catalysed coupling methods well known for those skilled in the art.

Boronic acids or esters, anilines, thiophenols or phenols can be commercial or prepared by standard methods and can be used in a protected form to prevent certain functional groups from undergoing undesired reactions. In these cases, standard methods for the removal of these protecting groups can be used at the suitable step of the synthesis. Numerous protecting groups, their introduction and their removal are described in T. W. Greene and G. M. Wuts, Protecting Groups in Organic Synthesis, Third Edition, Wiley, New York, 1999, and references cited therein.

In the particular case of compounds of general Formula (I) where the group L represents a —C(O)—NR'— group or a —C(O)—O— group; wherein R' represents hydrogen or a linear or branched $C_1$-$C_4$ alkyl group; can be prepared from compounds of Formula (V-1) (V-2) (V-3) where $Z_3$ represents a carboxylic acid by preparing the corresponding amide or ester by treatment of the carboxylic acid with an activating agent by methods and conditions well described in the literature, for example using T3P®, EDC or HATU as an activating agent in a solvent such as dimethylformamide, tetrahydrofuran, ethyl acetate or dichloromethane at temperatures ranging from room temperature to 80° C.

Scheme 1

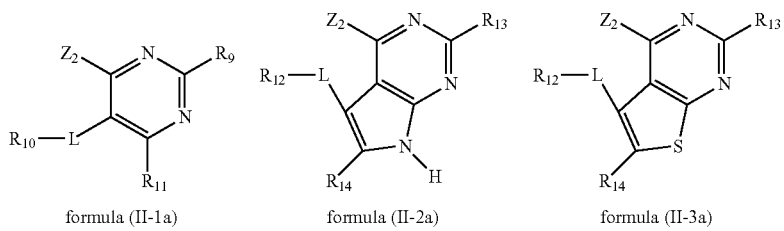

formula (II-1a)  formula (II-2a)  formula (II-3a)

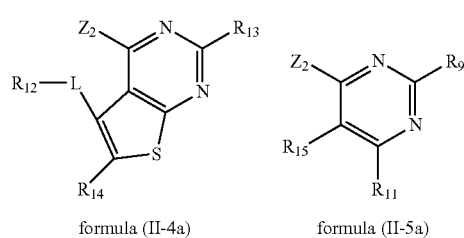
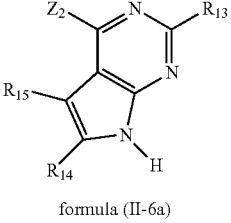

formula (II-4a)    formula (II-5a)    formula (II-6a)

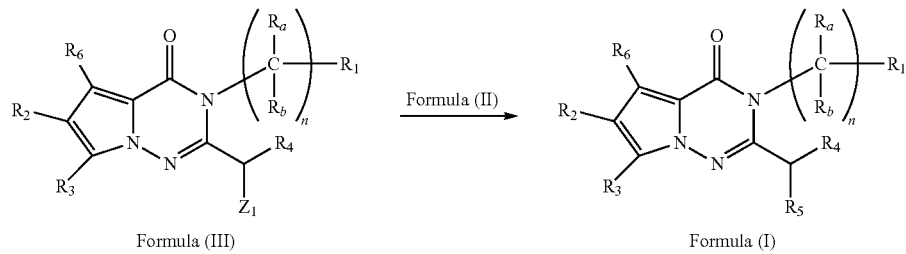

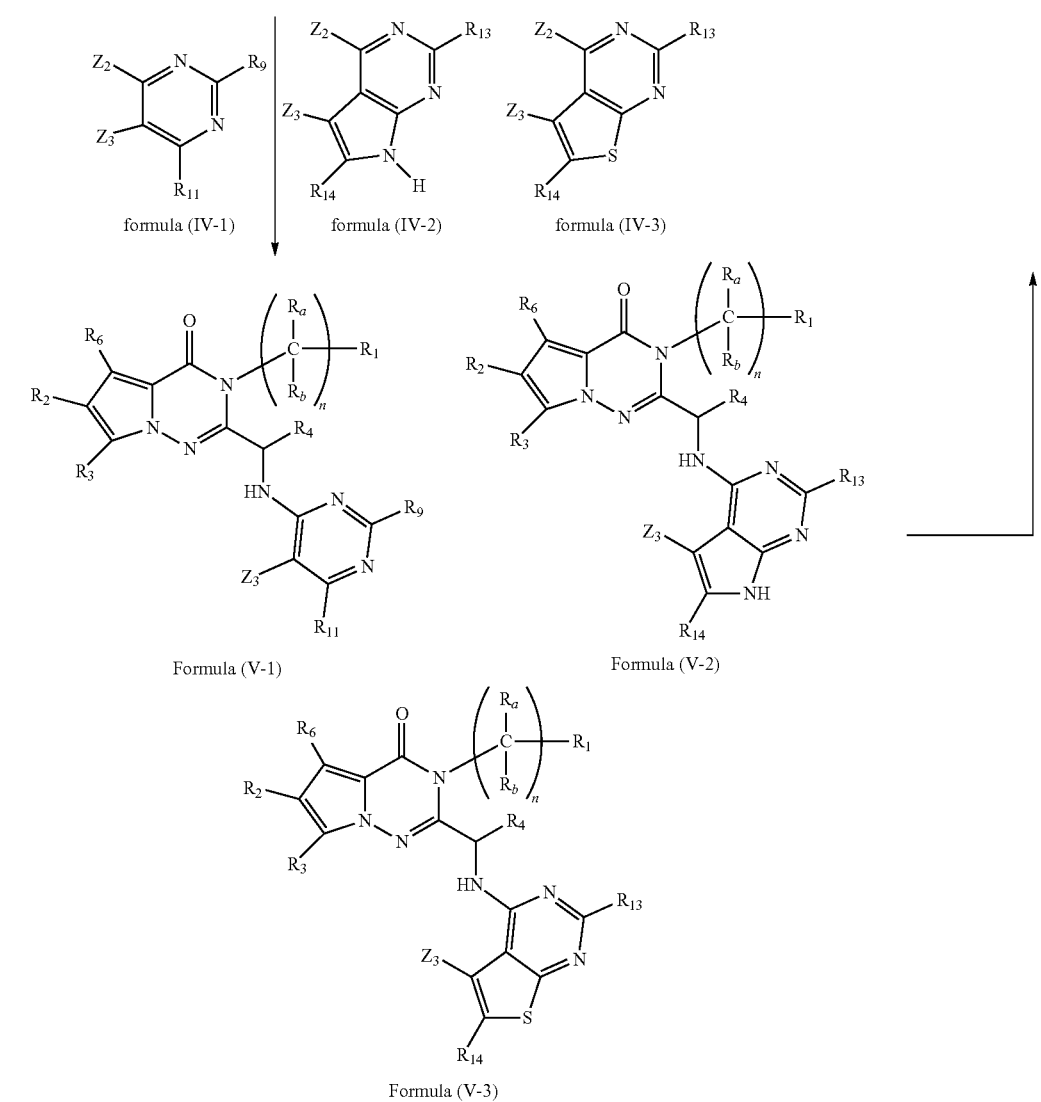

Compounds of general Formula (III) can be prepared directly from compounds of Formula (VII) as illustrated in Scheme 2 by treatment of compounds with Formula (VII) with the appropriate acid chlorides of Formula (VIII) in a solvent such as acetic acid or, alternatively, in toluene or xylene with the presence of pyridinium p-toluenesulfonate at a temperature ranging from room temperature to 150° C. with or without the use of microwaves irradiation.

Alternatively, compounds of Formula (III) can be obtained in two steps from compounds of Formula (VII), isolating the intermediate amides of Formula (VI).

Compounds of Formula (VII) can be transformed in amides of Formula (VI) by treatment with carboxylic acids of Formula (IX) in the presence of an activating agent by methods and conditions well described in the literature, for example using T3P®, EDC HCl or HATU as an activating agent in a solvent such as dimethylformamide, tetrahydrofuran or dichloromethane or mixtures of these solvents at temperatures ranging from room temperature to 80° C.

Alternatively, amides of Formula (VI) can be obtained from compounds of Formula (VII) by treatment with acid chlorides of Formula (VIII) at room temperature in a suitable solvent such as acetic acid or 1,4-dioxane or alternatively in the presence of a base such as triethylamine in a suitable solvent such as dichloromethane.

In a second step, compounds of Formula (VI) can yield compounds of Formula (III) by treatment with phosphorous oxychloride at temperatures ranging from room temperature to 100° C., with or without a subsequent treatment with a solution of a base such as ammonia, pirrolidine, piperidine or potassium carbonate in a solvent such as methanol, ethyl acetate or N,N-dimethylformamide at a temperature between room temperature and 100° C. Alternatively, pyridinium p-toluenesulfonate can be used in toluene or xylene as a solvent at temperature between 80° C. and 130° C.

Alternatively, compounds of Formula (VI) can yield compounds of Formula (III) by treatment of compounds of Formula (VI) with the complex resulting from the treatment of triphenylphosphine with bromine in a solvent such as dichloromethane in the presence of a base such as triethylamine at a temperature from room temperature to reflux, with or without a subsequent treatment with a base such as ammonia, pirrolidine, piperidine or potassium carbonate or a nucleophile such us sodium methanethiolate in a solvent such as methanol, ethyl acetate or N,N-dimethylformamide at a temperature between room temperature and 100° C.

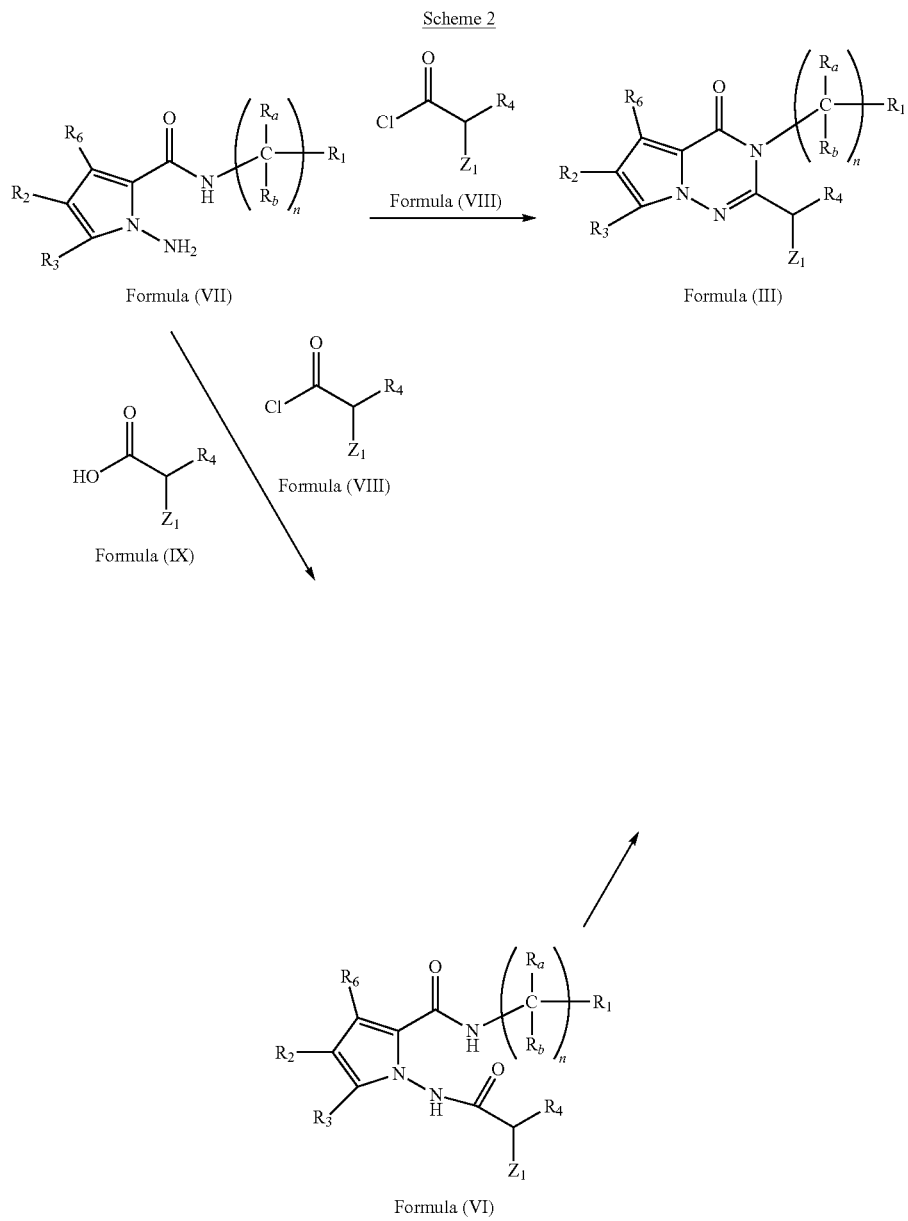

Scheme 2

The acid chlorides of Formula (VIII) and the carboxylic acids of Formula (IX) can be used in a protected form to prevent certain functional groups from undergoing undesired reactions. In these cases, standard methods for the removal of these protecting groups can be used at the suitable step of the synthesis. Numerous protecting groups, their introduction and their removal are described in T. W. Greene and G. M. Wuts, Protecting Groups in Organic Synthesis, Third Edition, Wiley, New York, 1999, and references cited therein.

Compounds of Formula (VII) can be prepared from carboxylic acids of Formula (XII) following the scheme described in Scheme 3.

Carboxylic acids (XII) can be activated with any activating reagent described in the literature such as thionyl chloride, oxalyl chloride, phosphorous oxychloride, EDC HCl, HATU or T3P® and treated with amines of Formula (XI) in the presence of a base such as diisopropylethylamine when needed in a suitable solvent such as dioxane, dichloromethane, N,N-dimethylformamide or tetrahydrofuran at temperatures ranging from 0° C. to reflux to give amides of Formula (X).

Subsequently, amides of Formula (X) can be aminated on the nitrogen atom in position 1 by any of the aminating reagents described in the literature, such as O-(mesitylene-sulfonyl)hydroxylamine, O-(p-nitrobenzoyl)-hydroxylamine, O-(diphenyl-phosphinyl)-hydroxylamine, O-(2,4-dinitrophenyl)-hydroxylamine, hydroxylamine-O-sulfonic acid using a suitable base such as triethylamine, potassium carbonate, sodium hydride or butyl lithium in an appropriate solvent such as N,N'-dimethylformamide, tetrahydrofuran, 1,4-dioxane at temperatures ranging from −78 to 100° C. Alternatively, the amination reaction can be carried out in a biphasic system using an aqueous solution of ammonia, sodium hydroxide, ammonium chloride and sodium hypochlorite and a suitable organic solvent such as dialkyl ethers and adding a phase transfer catalyst such as Aliquat 336® at temperatures ranging from 0° C. to room temperature.

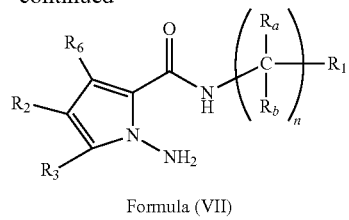

Formula (VII)

Compounds (XII) can be either commercially available compounds or can be prepared by the synthetic scheme illustrated in Scheme 4. In the particular case when $R_5$ represents a $C_3$-$C_7$ cycloalkyl group, or a linear or branched $C_1$-$C_4$ alkyl group, compounds (XIIa) can be prepared, as illustrated in Scheme 4, from bromopyrrol of Formula (XIV)[2] by Suzuki coupling with the corresponding alkyl or cycloalkylboronic acids in the presence of a palladium catalyst such as tetrakis(triphenylphosphane) palladium(0) and appropriate base such as potassium carbonate and in a suitable solvent such as toluene at a temperature ranging from 60° C. to 150° C. Compounds of Formula (XIIa) can be obtained by simultaneous cleavage of the sulphone and ester groups of compounds of Formula (XIII) by means of a base such as lithium hydroxide in a suitable solvent or mixture of solvents such as water or tetrahydrofuran at temperatures ranging from room temperature to 220° C., with or without the use of microwaves irradiation. Alternatively, the cleavage of the sulphone and ester groups of compounds of Formula (XIII) can be done sequentially by treatment of compounds (XIII) with tetrabutylammonium fluoride in an appropriate solvent such as tetrahydrofuran at a temperature from room temperature to reflux and subsequent hydrolysis of the ester group by any of the methods well known in the literature.

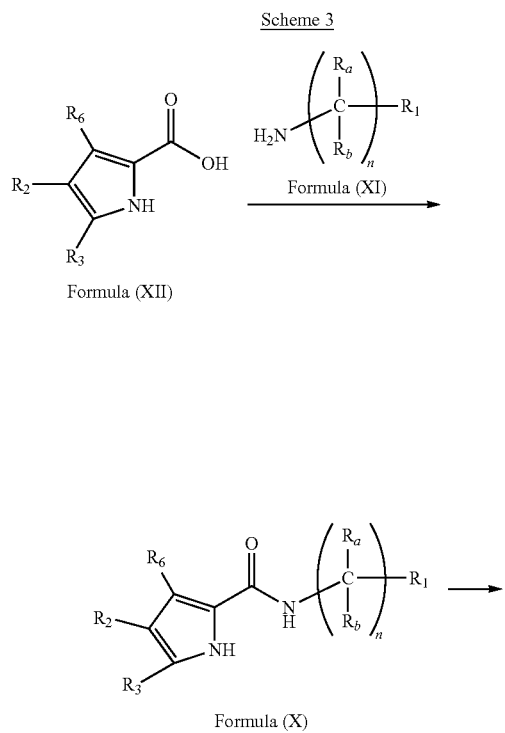

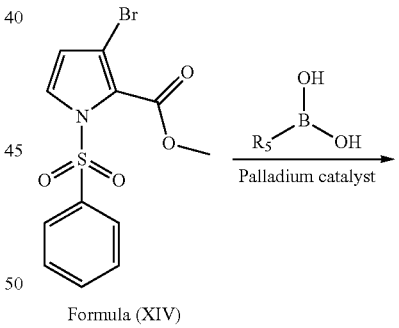

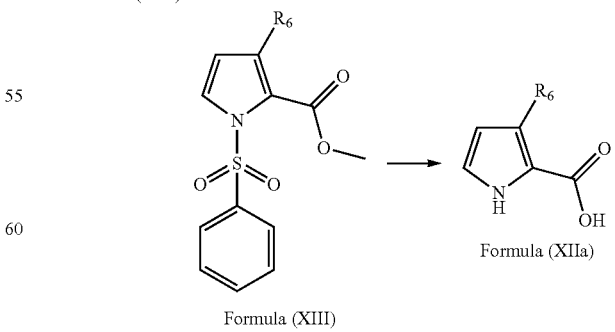

In the particular case when $R_6$ represents hydrogen or $C_3$-$C_7$ cycloalkyl group, or a linear or branched $C_1$-$C_4$ alkyl group, and $R_2$ independently represents hydrogen or $C_3$-$C_7$ cycloalkyl group, or a linear or branched $C_1$-$C_4$ alkyl group, compounds of Formula (Xa) can be prepared, as illustrated in Scheme 5, from pyrroles of Formula (XVI). Pyrroles of Formula (XVI) can be reacted with 2,2,2-trichloroacetyl chloride in a suitable solvent such as diethyl ether at a temperature ranging from room temperature to reflux affording ketones of Formula (XV). These intermediate compounds of Formula (XV) can be reacted with the corresponding amines of Formula (XI) with or without solvent in the presence of a base such as triethylamine at a temperature ranging from room temperature to 150° C. to afford compounds of Formula (Xa).

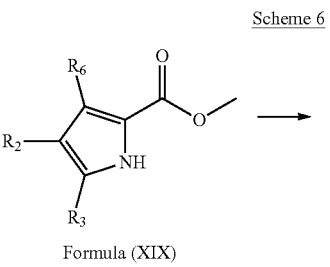

Scheme 6

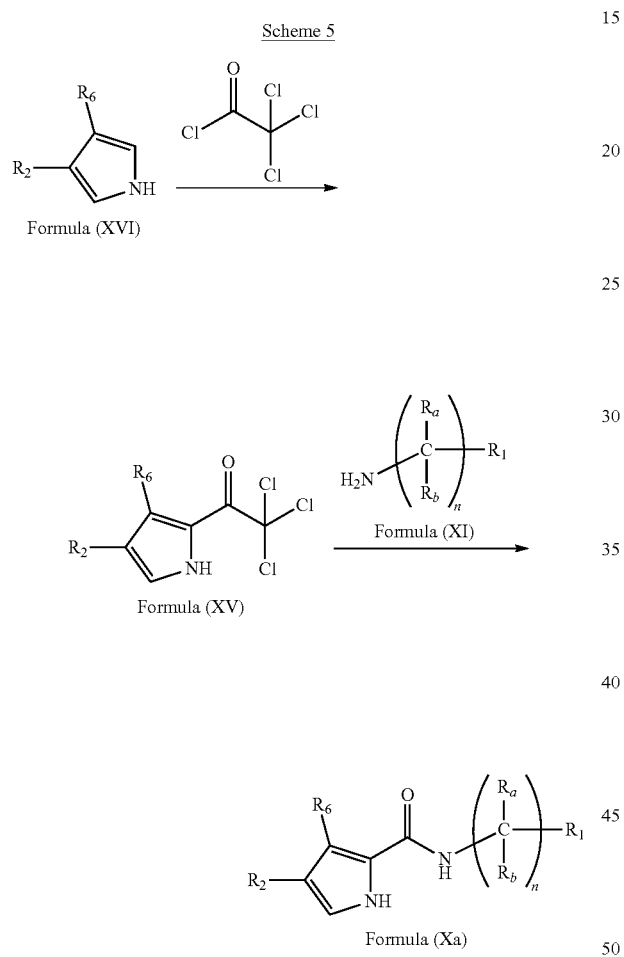

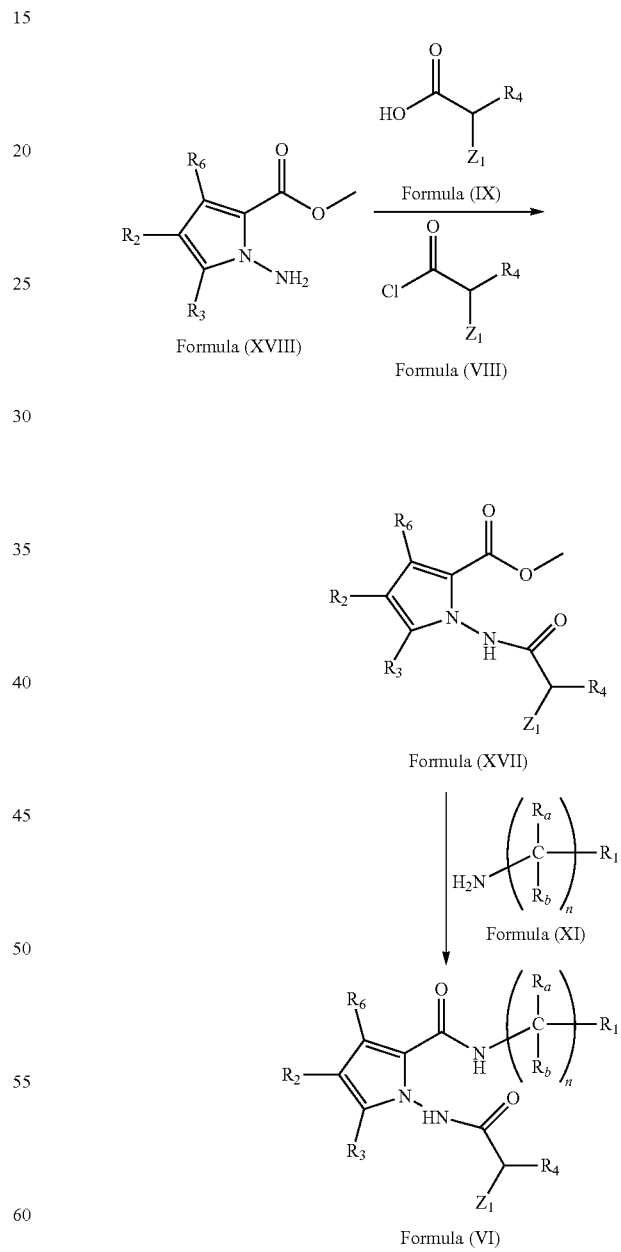

Alternatively, compounds of general Formula (VI) may be prepared by the synthetic route illustrated in Scheme 6. Thus, compounds of Formula (VI) can be prepared from compounds of Formula (XVII), where compounds of Formula (XVII) can be treated with the corresponding amines of Formula (XI) in the presence or not of a suitable base such as sodium hexamethyldisilazide or a Lewis acid such as trimethyl aluminium at a temperature ranging from room temperature to 150° C. in an appropriate solvent such as 1,4-dioxane, tetrahydrofuran or dichloromethane.

Compounds of Formula (XVII) can be prepared by the coupling methods previously described from compounds of Formula (XVIII). Compounds of Formula (XVIII) can be obtained by amination of compounds of Formula (XIX) by the methods already described.

In another embodiment of the present invention, compounds of general Formula (IIIb) can also be synthesized from compounds of Formula (IIIa) as shown in Scheme 7 by the general methods described as it follows.

Scheme 7

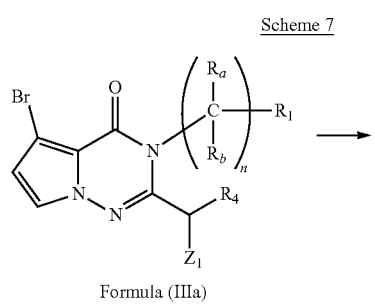

Formula (IIIa)

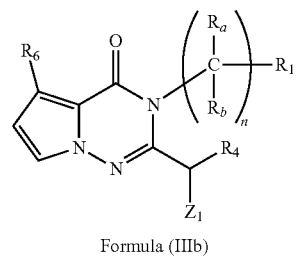

Formula (IIIb)

In the particular case where $R_6$ is a trifluoromethyl group, the bromine atom of compound of Formula (IIIa) can be converted first into a iodine atom by treatment of (IIIa) with sodium iodide in the presence of a catalysts such as copper (I) iodide and a chelating amine such as trans-1,2-bis(methylamino)cyclohexane in an appropriate solvent such as 1,4-dioxane at a temperature ranging from 60° C. to reflux. Next, treatment of iodine intermediate with methyl 2,2-difluoro-2-(fluorosulfonyl)acetate or any other trifluoromethylating agent using a suitable catalyst such as copper (I) iodide in the presence or not of a chelating agent such as hexamethylphosphoramide and in an appropriate solvent such as N,N'-dimethylformamide afford compounds of Formula (IIIb).

In the particular case where $R_6$ is a alkyl or cycloalkyl group, or an aromatic or heteroaromatic ring compounds of Formula (IIIb) can be obtained from compound of Formula (IIIa) by standard Suzuki or Stille couplings with the corresponding boronic acid or organotin compound in the presence of a palladium catalyst such as tetrakis(triphenylphosphane)palladium(0) or palladium acetate with or without an appropriate base such as potassium carbonate or cesium carbonate and in a suitable solvent such as toluene or dioxane or N,N-dimethylformamide at temperatures ranging from 60° C. to 150° C.

In the particular case where $R_6$ is a fluorine, compounds of Formula (IIIb) can be obtained from compounds of Formula (IIIa) by treatment with a lithiating agent such as n-BuLi, in a non protic solvent such as hexanes and at a temperature between −78° C. and 0° C. and subsequently treated with a suitable fluorine source such as N-fluoro-N-(phenylsulfonyl)-benzenesulfonamide at a temperature between −78° C. and room temperature.

In the particular case of compounds of Formula (IIIb) where $R_6$ is hydrogen, compounds can alternatively be obtained by hydrogenolysis of compounds of Formula (IIIa) using an appropriate catalyst such as 10% palladium on charcoal in a suitable solvent such as an alkyl alcohol under a hydrogen atmosphere at pressures ranging from atmospheric pressure to 60 psi and at temperatures ranging from room temperature to 60° C.

In the particular case of compounds of Formula (IIIb) where $R_6$ is a thiophenol, compounds of Formula (IIIa) can be converted first into a iodine following the general methods previously described. The iodine intermediate can then react with the corresponding thiophenol in the presence of copper (I) iodide and a base such as potassium carbonate in solvent such as DMF and at temperatures ranging from room temperature to 150° C.

In the particular case of compounds of Formula (IIIb) where $R_6$ is a $C_2$-$C_4$ alkynyl group, wherein the alkynyl group is unsubstituted or substituted as described in claim 1, compounds of Formula (IIIb) can be obtained by reacting compounds of Formula (IIIa) with the corresponding alkyne derivative in the presence of a palladium catalyst such as bis(triphenylphosphine)palladium(II) chloride and copper (I) iodide in a suitable solvent such as diethylamine at temperatures ranging from room temperature to 100° C.

Finally, compounds of Formula (II) can be obtained from compounds of Formula (XX) as shown in Scheme 8 following the different general methods just described for each particular case of $R_6$.

Scheme 8

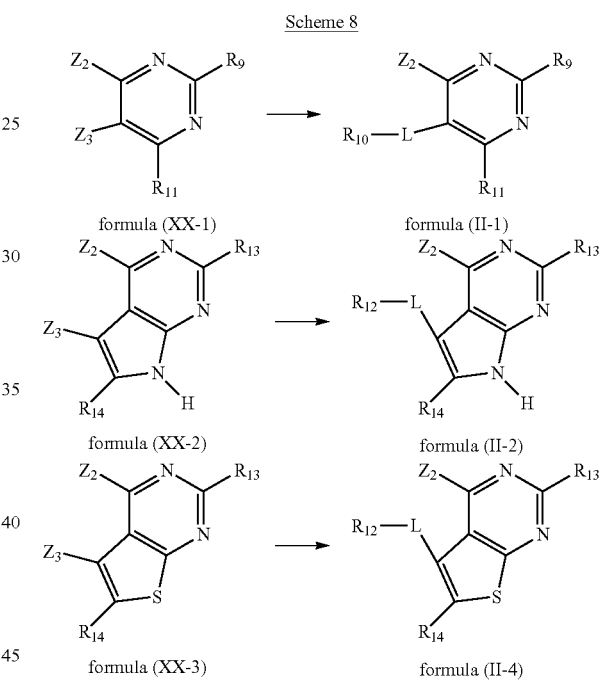

EXAMPLES

General

The syntheses of the compounds of the invention and of the intermediates for use therein are illustrated by the following Examples (1-239) (including Preparation Examples (Preparations 1-259)) and are given in order to provide a person skilled in the art with a sufficiently clear and complete explanation of the present invention, but should not be considered as limiting of the essential aspects of its subject, as set out in the preceding portions of this description.

Reagents, starting materials, and solvents were purchased from commercial suppliers and used as received. Concentration or evaporation refers to evaporation under vacuum using a Büchi rotatory evaporator.

Reaction products were purified, when necessary, by flash or reverse phase chromatography in a Biotage SP1® or Isolera® automatic purification systems.

Purifications in reverse phase were made in a Biotage SP1® automated purification system equipped with a C18 column and using a gradient of water-acetonitrile/MeOH (1:1) (0.1% v/v ammonium formate both phases) from 0% to 100% acetonitrile/MeOH (1:1) in 40 column volumes. The conditions "formic acid buffer" refer to the use of 0.1% v/v formic acid in both phases. The appropriate fractions were collected and the solvents evaporated under reduced pressure and/or liofilized.

Preparative HPLC-MS were performed on a Waters instrument equipped with a 2767 injector/collector, a 2525 binary gradient pump, a 2996 PDA detector, a 515 pump as a make-up pump and a ZQ4000 Mass spectrometer detector.

The HPLC chromatographic separations were obtained using a Waters 2795 system equipped with a Symmetry C18 (2.1×50 mm, 3.5 μM) column for methods A, B and C and a Symmetry C18 (2.1×100 mm, 3.5 μM) for method D. The mobile phases were (B): formic acid (0.4 mL), ammonia (0.1 mL), methanol (500 mL) and acetonitrile (500 mL) and (A): formic acid (0.5 mL), ammonia (0.125 mL) and water (1000 mL) (A), the gradients are specified in the following table for each method used.

| Method | Run time | 0% B | 0 to 95% B | 95% B |
|--------|----------|------|------------|-------|
| A | 5 min | 0.2 min | 3 min | 0.8 min |
| B | 9 min | 0.5 min | 6.5 min | 1 min |
| C | 15 min | 0 min | 10.5 min | 1.5 min |
| D | 30 min | 0 min | 20 min | 4 min |

The flow rate was 0.8 mL/min for method A and 0.4 mL/min for method B, C and D. The injection volume was 5 microliter. A Waters 2996 diode array was used as a UV detector. Chromatograms were processed at 210 nM or 254 nM. Mass spectra of the chromatograms were acquired using positive and negative electrospray ionization in a Micromass ZMD or in a Waters ZQ detectors coupled to the HPLC.

The UPLC chromatographic separations were obtained using a Waters Acquity UPLC system coupled to a SQD mass spectrometer detector. The system was equipped with an ACQUITY UPLC BEH C-18 (2.1×50 mm, 1.7 μm) column. The mobile phase was formic acid (0.4 mL), ammonia (0.1 mL), methanol (500 mL) and acetonitrile (500 mL) (B) and formic acid (0.5 mL), ammonia (0.125 mL) and water (1000 mL) (A). A gradient between 0 to 95% of B was used. The run time was 3 or 5 minutes The injection volume was 0.5 microliter. Chromatograms were processed at 210 nM or 254 nM. Mass spectra of the chromatograms were acquired using positive and negative electrospray ionization.

$^1$H Nuclear Magnetic Resonance Spectra were recorded on a Varian Mercury plus operating at a frequency of 400 MHz for the $^1$H spectra. Samples were dissolved in the specified deuterated solvent. Tetramethylsilane was used as reference.

Abbreviations:
DMF Dimethylformamide
DMSO-d6 Deuterated Dimethylsulfoxide
CDCl$_3$ Deuterated chloroform
CD$_3$OD Deuterated methanol
NMR Nuclear magnetic resonance
s Singlet
d Doublet
dd Doublet of doublets
td Triplet of doublets
br Broad
q Quartet
t Triplet
m Multiplet
LRMS Low resolution mass spectrometry
h Hour
min Minutes
NMM N-Methylmorpholine
DMF N,N-Dimethylformamide
DCM Dichloromethane, methylene chloride
AcOEt Ethyl acetate
DMSO Dimethylsufoxide
EDC.HCl 3-((Ethylimino)methyleneamino)-N,N-dimethyl-propan-1-aminium chloride
THF Tetrahydrofuran
TEA Triethylamine
DIEA Diisopropylethylamine
HOBt 1-Hydroxybenzotriazole hydrate
MeOH Methanol
DPPONH$_2$ P,P-Diphenylphosphinic amide
DAST Diethylaminosulfur trifluoride
PPTS Pyridinium p-toluenesulphonate
Pd(PPh$_3$)$_4$ Tetrakis(triphenylphosphane) palladium(0)
HMPA Hexamethylphosphoramide
Celite® Diatomaceous earth
BINAP 2,2'-Bis(diphenylphosphino)-1,1'-binaphthyl
T3P® 2,4,6-Tripropyl-1,3,5,2,4,6-trioxatriphosphorinane-2,4,6-trioxide
HATU 2-(1H-7-Azabenzotriazol-1-yl)-1,1,3,3-tetramethyl uronium hexafluorophosphate
Psi Pounds per square inch Preparation 1

(S)-2-(1-Aminoethyl)-5-bromo-3-phenylpyrrolo[2,1-f][1,2,4]triazin-4(3H)-one (S)-tert-Butyl 1-(5-bromo-4-oxo-3-phenyl-3,4-dihydro-pyrrolo[1,2-f][1,2,4]triazin-2-yl)ethylcarbamate (2.73 g, 1.70 mol) was dissolved in 10 ml dioxane. A solution of hydrochloric acid (4M in dioxane, 8.50 mL, 34 mol) was added and the reaction was stirred at room temperature overnight. The mixture was partitioned between dichloromethane and water. The aqueous phase was basified with sodium hydroxide 2N and was extracted with dichloromethane. The organics were washed with brine and dried over sodium sulphate, evaporated to dryness to give 0.72 g (99% yield) of the title compound as a solid.

LRMS (m/z): 333, 335 (M+1)$^+$.

Preparation 2

(S)-2-(1-((6-Amino-5-iodopyrimidin-4-yl)amino)ethyl)-5-bromo-3-phenylpyrrolo[2,1-f][1,2,4]triazin-4(3H)-one (S)-2-(1-Aminoethyl)-5-bromo-3-phenylpyrrolo[2,1-f][1,2,4]triazin-4(3H)-one (0.72 g, 2.16 mol) was treated with 6-chloro-5-iodopyrimidin-4-amine (1.55 g, 4.31 mol), cesium fluoride (0.66 g, 4.34 mol), N,N-diisopropylethylamine (1.88 mL, 10.79 mol) according to Preparation 13. The residue was purified using SP1® Purification System (0% to 70%, hexane-ethyl acetate) to give 0.39 g (32% yield) of the title compound as a solid. Purity 93%.

LRMS (m/z): 552, 554 (M+1)$^+$.

Preparation 3

(S)-2-(1-((6-Amino-5-(3-fluoro-4-hydroxyphenyl)pyrimidin-4-yl)amino)ethyl)-5-bromo-3-phenylpyrrolo[2,1-f][1,2,4]triazin-4(3H)-one (S)-2-(1-((6-Amino-5-iodopyrimidin-4-yl)amino)ethyl)-5-bromo-3-phenylpyrrolo[2,1-f][1,2,4]triazin-4(3H)-one (90 mg, 0.16 mol) was treated with (3-fluoro-4-hydroxyphenyl)boronic acid (38 mg, 0.24 mol), 1,1'-bis(diphenylphosphino)ferrocene-palladium(II)dichloride dichloromethane complex (22 mg, 0.02 mol) and a solution of sodium carbonate (2M, 317 µl, 0.73 mol) according to the method described in Example 3 to give 150 mg of the title compound that was used in the next step without any further purification.

LRMS (m/z): 536, 538 (M+1)$^+$.

Preparation 4

1-Amino-3-methyl-N-phenyl-1H-pyrrole-2-carboxamide a) 3-Methyl-1H-pyrrole-2-carboxylic acid Methyl 3-methyl-1H-pyrrole-2-carboxylate (10 g, 0.07 mol, purchased at Aurora Building Blocks, reference number A00.567.027) was dissolved in 200 mL methanol and a solution of sodium hydroxide (2N, 108 mL, 0.22 mol) was added. The mixture was heated at 60° C. overnight. The solvent was evaporated and the residue was acidified to pH 2-3 with 2N hydrochloric acid. A white precipitate was formed and filtered and washed with cool water. The solid was dried in a vacuum oven to give 6.97 g (77% yield) of the desired compound. Purity 100%.

LRMS (m/z): 126 (M+1)$^+$.

b) 3-Methyl-N-phenyl-1H-pyrrole-2-carboxamide

3-Methyl-1H-pyrrole-2-carboxylic acid (6.97 g, 0.06 mol) was dissolved in 150 mL dichloromethane and 1 mL dimethylformamide. Oxalyl chloride (7.26 mL, 0.08 mol) dissolved in 50 mL dichloromethane was added dropwise over 60 min and the mixture was stirred at room temperature for 2 h. The mixture was concentrated to dryness and was re-dissolved in 150 mL dichloromethane. A solution of aniline (5.71 g, 0.06 mol) and N,N-diisopropylethylamine (14.5 mL, 0.08 mol) dissolved in 50 mL dichloromethane was added dropwise and the reaction was stirred at room temperature for 2 h.

The mixture was washed sequentially with water and brine, dried over sodium sulphate, filtered and evaporated under reduced pressure. The residue was purified using the Isolera® Purification System (0% to 40%, hexane-ethyl acetate) to give 6.66 g (60% yield) of the title compound as a brown solid.

LRMS (m/z): 201 (M+1)$^+$.

c) 1-Amino-3-methyl-N-phenyl-1H-pyrrole-2-carboxamide

In a three-necked flask it was placed aqueous solution of sodium hydroxide (32%, 95 mL, 665 mmol), ammonium hydroxide solution (8M, 31 mL, 250 mmol), ammonium chloride (10.7 g, 200 mmol) and Aliquat 336 (1.34 g, 3.3 mmol). Afterwards, a solution of 3-methyl-N-phenyl-1H-pyrrole-2-carboxamide (6.6 g, 33.2 mmol) dissolved in 140 mL diethyl ether and 70 mL methyl tert-butyl ether was added and the mixture was cooled at 0° C. affording a suspension. Over this suspension, a 10% aqueous solution of sodium hypochlorite (10%, 224 mL, 300 mmol) was added dropwise over 60 min with vigorous stirring. The reaction mixture was stirred at room temperature overnight. The reaction crude was diluted with ethyl acetate until no suspended material was observed. The layers were separated and the organic phase was washed with water and brine, dried over sodium sulphate and concentrated under reduce pressure to give 7.54 g (90% yield) of the title compound that was used in the next step without any further purification.

LRMS (m/z): 216 (M+1)$^+$.

Preparation 5

(S)-tert-Butyl (1-(5-methyl-4-oxo-3-phenyl-3,4-dihydropyrrolo[2,1-f][1,2,4]triazin-2-yl)ethyl)carbamate a) (S)-tert-Butyl (1-((3-methyl-2-(phenylcarbamoyl)-1H-pyrrol-1-yl)amino)-1-oxopropan-2-yl)carbamate 1-Amino-3-methyl-N-phenyl-1H-pyrrole-2-carboxamide (5.30 g, 24.62 mmol) was dissolved in 35 mL ethyl acetate and (S)-2-((tert-butoxycarbonyl)amino)propanoic acid (6.50 g, 34.35 mmol) was added. The mixture was cooled in an ice bath and N,N-diisopropylethylamine (19.8 mL, 113.68 mmol) was added dropwise. After 15 min stirring, maintaining the reaction temperature at 0° C., T3P® (50% in ethyl acetate, 14.3 mL, 48.04 mmol) was added dropwise and the reaction was stirred at room temperature for 3 h. Further (S)-2-((tert-butoxycarbonyl)amino)propanoic acid (3.25 g, 17.17 mmol) was added and the mixture was stirred at room temperature overnight. Further N,N-diisopropylethylamine (20 mL, 114 mmol) and T3P® (50% in ethyl acetate, 14.3 mL, 48.04 mmol) were added dropwise at 0° C. and the reaction was stirred at room temperature overnight. The reaction was poured into water and extracted with ethyl acetate. The organic phase was dried over sodium sulphate, filtered and concentrated under reduced pressure. The residue was purified using Isolera® Purification System (0% to 60% hexane-ethyl acetate) to obtain 7.15 g (75% yield) of the desired product as a solid.

LRMS (m/z): 387 (M+1)$^+$.

b) (S)-tert-Butyl (1-(5-methyl-4-oxo-3-phenyl-3,4-dihydropyrrolo[2,1-f][1,2,4]triazin-2-yl)ethyl)carbamate Triphenylphosphine (6.8 g, 25.93 mmol) was dissolved in 50 mL dichloromethane. Bromine (1.33 mL, 25.97 mmol) was added dropwise and the reaction was stirred at room temperature for 30 min. Triethylamine (10.3 mL, 73.9 mmol) and (S)-tert-butyl (1-((3-methyl-2-(phenylcarbamoyl)-1H-pyrrol-1-yl)amino)-1-oxopropan-2-yl)carbamate (7.15 g, 18.5 mmol) suspended in 100 mL dichloromethane was added and the reaction mixture was stirred at 60° C. for 2 h. The mixture was concentrated to dryness and was re-dissolved in a pressure reactor with a solution of ammonia (7M in methanol, 350 mL, 2415 mmol). The mixture was heated at 100° C. for 32 h, then cooled at room temperature and evaporated under reduced pressure. The residue was partitioned between ethyl acetate and water. The organic layer was washed with water, brine and dried over sodium sulphate, filtered and concentrated. The residue was purified using Isolera® Purification System (0% to 50%, hexane-ethyl acetate) to obtain 0.95 g (14% yield) of the title compound as a yellow solid.

LRMS (m/z): 367 (M+1)$^+$.

Preparation 6

(S)-2-(1-Aminoethyl)-5-methyl-3-phenylpyrrolo[2,1-f][1,2,4]triazin-4(3H)-one (S)-tert-Butyl (1-(5-methyl-4-oxo-3-phenyl-3,4-dihydropyrrolo[2,1-f][1,2,4]triazin-2-yl)ethyl)carbamate (950 mg, 2.58 mmol) was dissolved in 5 mL dichloromethane and trifluoroacetic acid (993 µl, 12.89 mmol) was added. The mixture was stirred at room temperature overnight. The reaction mixture was evaporated to dryness and was partitioned between ethyl acetate and potassium bicarbonate. The organic layer was washed with water, brine and dried over sodium sulphate, filtered and concentrated under reduced pressure to give 0.55 g (78% yield) of the title compound that was used in the next step without any further purification. Purity 97%.

LRMS (m/z): 269 (M+1)$^+$.

Preparation 7

(S)-2-(1-((6-Amino-5-iodopyrimidin-4-yl)amino)ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (0.55 g, 2.05 mmol) was treated with 6-chloro-5-iodopyrimidin-4-amine (1 g, 3.29 mol), cesium fluoride (0.62 g, 4.08 mmol), N,N-diisopropylethylamine (1.79 mL, 10.28 mol) according to Preparation 13. The residue was purified using SP1® Purification System (0% to 100%, hexane-ethyl acetate) to give 0.59 g (59% yield) of the title compound as a solid. Purity 100%.

LRMS (m/z): 488 (M+1)$^+$.

Preparation 8

1-Amino-N-phenyl-1H-pyrrole-2-carboxamide a) N-Phenyl-1H-pyrrole-2-carboxamide

Prepared following the experimental method described in Preparation 4b starting from 10.0 g (90.0 mmol) of 1H-pyrrole-2-carboxylic acid (purchased from Aldrich®, cat. no. P7,360-9) and 9.22 g (99.0 mmol) of aniline. 13.0 g (78% yield) of the title compound were obtained as a brownish solid.

LRMS (m/z): 187 (M+1)$^+$.

b) 1-Amino-N-phenyl-1H-pyrrole-2-carboxamide

The title compound was prepared from 12.9 g (69.8 mmol) of N-phenyl-1H-pyrrole-2-carboxamide following the experimental procedure described in Preparation 4c. 10.3 g (73% yield) of the title compound were obtained as a solid.

LRMS (m/z): 202 (M+1)$^+$.

Preparation 9

(S)-2-(1-Aminoethyl)-3-phenylpyrrolo[1,2-f][1,2,4]triazin-4(3H)-one a) (S)-tert-Butyl 1-oxo-1-(2-(phenylcarbamoyl)-1H-pyrrol-1-ylamino)propan-2-ylcarbamate 2.00 g (9.94 mmol) of 1-amino-N-phenyl-1H-pyrrole-2-carboxamide were dissolved in 50 mL dimethylformamide. To this solution, 2.07 g (10.94 mmol) of (S)-2-(tert-butoxycarbonylamino)propanoic acid (purchased from Aldrich®, cat. no. 13,451-1) and 2.10 g (10.95 mmol) of EDC.HCl were added and the resulting reaction mixture was stirred at room temperature overnight. The solvent was then evaporated under vacuum, the residue was taken up in ethyl acetate and washed with an aqueous solution of sodium bicarbonate and brine, it was dried over magnesium sulphate, filtered and the solvent was evaporated. The product was purified by flash chromatography (0-5%, methanol-dichloromethane). 2.21 g (60% yield) of the final product were obtained as a white solid.

LRMS (m/z): 373 (M+1)$^+$.

b) (S)-2-(1-Aminoethyl)-3-phenylpyrrolo[1,2-f][1,2,4]triazin-4(3H)-one 2.21 g (5.93 mmol) of (S)-tert-butyl 1-oxo-1-(2-(phenylcarbamoyl)-1H-pyrrol-1-ylamino)propan-2-ylcarbamate were treated with 27 mL of phosphorous oxychloride at 80° C. for 6 hours and then it was evaporated under vacuum until a dark solid was formed. This residue was dissolved in chloroform and then treated with an aqueous solution of sodium bicarbonate. After stirring the mixture for 1 hour, the two layers were separated and the organic phase was washed with water and brine, dried over magnesium sulphate and the solvent was evaporated under vacuum. The residue was then treated in a sealed vessel with 30 mL of a 7M methanolic solution of ammonia at 80° C. overnight. The solvent was then evaporated and the product was purified by reverse phase chromatography using SP1® Purification System to obtain the title compound (350 mg, 23%) as a white solid.

LRMS (m/z): 255 (M+1)$^+$.

Preparation 10

1-Amino-3-bromo-N-phenyl-1H-pyrrole-2-carboxamide a) 3-Bromo-N-phenyl-1-(phenylsulfonyl)-1H-pyrrole-2-carboxamide In a three-necked round-bottom flask aniline (1.57 mL, 17.20 mmol) was dissolved in 80 mL of toluene under inert atmosphere. To this solution was added trimethyl aluminium (7.82 mL, 15.64 mmol) and the mixture was stirred at room temperature during 10 min. Afterwards, a solution of methyl 3-bromo-1-(phenylsulfonyl)-1H-pyrrole-2-carboxylate (2.0 g, 5.81 mmol) in 20 mL of toluene was added and the reaction mixture was heated at 80° C. for 3 h. Next, the mixture was allowed to cool to room temperature and 20-30 mL of water and a 0.5M aqueous solution of disodium tartrate dihydrate were added to hydrolize unreacted trimethyl aluminium. After stirring for a while, the two layers were separated and the aqueous phase was extracted with ethyl acetate. The organic mixture was washed with the same 0.5M aqueous solution of disodium tartrate dihydrate (200 mL), water and brine, dried and concentrated in vacuum to afford 2.7 g of a residue that was used in the following step without further purification.

LRMS (m/z): 405, 407 (M+1)$^+$.

b) 3-Bromo-N-phenyl-1H-pyrrole-2-carboxamide

To a solution of 3-bromo-N-phenyl-1-(phenylsulfonyl)-1H-pyrrole-2-carboxamide (2.70 g of crude material) in 50 mL of methanol was added 15 mL of an aqueous 1N solution of sodium hydroxide and the mixture was stirred at room temperature during 1.5 h. At the end of this period, no starting material was detected and the reaction was elaborated in the following way: methanol was evaporated and a precipitate was formed which was filtered off and washed several times with water. The solid was dried in the vacuum oven to afford 1.14 g of the title compound that was used in the following step without any further purification.

LRMS (m/z): 265, 267 (M+1)$^+$.

c)
1-Amino-3-bromo-N-phenyl-1H-pyrrole-2-carboxamide

This compound was prepared starting from 3-bromo-N-phenyl-1H-pyrrole-2-carboxamide (1.11 g, 4.19 mmol) and following the experimental procedure described in Preparation 4c to afford 0.78 g (67% yield) of the title compound that was used in the next step without any further purification.

LRMS (m/z): 280, 282 (M+1)$^+$.

Preparation 11

(S)-tert-Butyl 1-(5-bromo-4-oxo-3-phenyl-3,4-dihydropyrrolo[1,2-f][1,2,4]triazin-2-yl)ethylcarbamate a) (S)-tert-Butyl 1-(3-bromo-2-(phenylcarbamoyl)-1H-pyrrol-1-ylamino)-1-oxopropan-2-ylcarbamate The title compound was prepared following the experimental procedure described in Preparation 9a from 810 mg (2.89 mmol) of 1-amino-3-bromo-N-phenyl-1H-pyrrole-2-carboxamide and 656 mg (3.47 mmol) of (S)-2-(tert-butoxycarbonylamino)propanoic acid (purchased from Aldrich). The crude product was purified by flash chromatography in hexane-ethyl acetate to afford 670 mg (49% yield) of the title compound.

LRMS (m/z): 306, 308 (M+1)$^+$.

b) (S)-tert-Butyl 1-(5-bromo-4-oxo-3-phenyl-3,4-dihydropyrrolo[1,2-f][1,2,4]triazin-2-yl)ethylcarbamate This compound was prepared starting from (S)-tert-butyl 1-(3-bromo-2-(phenylcarbamoyl)-1H-pyrrol-1-ylamino)-1-oxopropan-2-ylcarbamate (670 mg, 1.48 mmol) and following the experimental procedure described in Preparation 5b. The residue was purified by flash chromatography in hexane-ethyl acetate to afford 500 mg (78% yield) of the title compound.

LRMS (m/z): 433, 435 (M+1)$^+$.

Preparation 12

6-Chloro-5-iodopyrimidin-4-amine

To a solution of 3.03 g (23.39 mmol) of 6-chloropyrimidin-4-amine in 60 mL of dimethylformamide was added dropwise a solution of iodine monochloride (2.34 mL, 46.70 mmol) in 40 mL of dimethylformamide. Then the mixture was stirred at 45° C. overnight. The solvent was evaporated under reduced pressure and the residue was partitioned between dichloromethane and a 4% aqueous solution of sodium bicarbonate. The organic layer was washed with water and brine, dried over magnesium sulphate, filtered and the solvent was removed in vacuum. The product was purified by flash chromatography (0% to 20%, methanol-dichloromethane) to obtain 4.28 g (72% yield) of the title compound.

LRMS (m/z): 256 (M+1)$^+$.

Preparation 13

(S)-2-(1-(6-Amino-5-iodopyrimidin-4-ylamino)ethyl)-3-phenylpyrrolo[2,1-f][1,2,4]triazin-4(3H)-one 460 mg (1.81 mmol) of (S)-2-(1-aminoethyl)-3-phenylpyrrolo[1,2-f][1,2,4]triazin-4(3H)-one, 924 mg (3.62 mmol) of 6-chloro-5-iodopyrimidin-4-amine and 550 mg (3.62 mmol) of cesium iodide were suspended in 10 mL of tert-butanol. 1.58 mL (9.07 mmol) of N,N-diisopropylethylamine were added and the mixture was stirred at 140° C. in a sealed vessel for 40 hours. The reaction mixture was partitioned between water and ethyl acetate and the organic layer was washed with water and brine, dried over magnesium sulphate, filtered and the solvents were removed in vacuum. The product was purified by reverse phase chromatography using SP1® Purification System to furnish 481 mg (56% yield) of the title compound.

LRMS (m/z): 474 (M+1)$^+$.
$^1$H NMR (400 MHz, CDCl3) δ 7.84 (s, 1H), 7.58-7.34 (m, 5H), 7.31 (d, 1H), 7.07 (dd, 1H), 6.55 (dd, 1H), 5.56 (d, 1H), 5.04 (s, 2H), 5.01-4.94 (m, 1H), 1.41 (d, J=6.7 Hz, 3H).

Preparation 14

2-(4-(4,4,5,5-Tetramethyl-1,3,2-dioxaborolan-2-yl)-1H-pyrazol-1-yl)ethanol 4-(4,4,5,5-Tetramethyl-1,3,2-dioxaborolan-2-yl)-1H-pyrazole (1.00 g, 5.15 mmol) and cesium carbonate (5.04 g, 15.47 mmol) were suspended in 10 mL of dimethylformamide. 2-Bromoethanol (0.73 mL, 10.30 mmol) was added and the mixture was stirred at 70° C. for 3 hours. Additional amounts of cesium carbonate (5.04 g, 15.47 mmol) and 2-bromoethanol (0.73 mL, 10.30 mmol) were added and the mixture was left at 70° C. overnight. The solvent was evaporated under reduced pressure and the residue was partitioned between water and ethyl acetate. The organic layer was washed with water and brine, dried over magnesium sulphate, filtered and the solvent was evaporated to give 770 mg (63% yield) of a yellowish oil that was used in the next step without further purification.

LRMS (m/z): 239 (M+1)$^+$.

Preparation 15

N-(2-Methoxy-5-(4,4,5,5-tetramethyl-1,3,2-dioxaborolan-2-yl)pyridin-3-yl)methanesulfonamide a) 2-Methoxy-5-(4,4,5,5-tetramethyl-1,3,2-dioxaborolan-2-yl)pyridin-3-amine 5-Bromo-2-methoxypyridin-3-amine (1.73 g, 6.82 mmol) was dissolved in 50 mL dioxane. Bis(pinacolato)diboron (4.4 g, 17.33 mmol) and potassium acetate (2.5 g, 25.47 mmol) were added and the mixture was submitted to three vacuum-argon cycles. Then bis(diphenylphosphino)ferrocene-palladium(II)dichloride dichloromethane complex (0.9 g, 0.16 mmol) was added under argon conditions and the mixture heated at 80° C. for 2 h. The reaction mixture was partitioned between ethyl acetate and water and filtered through a plug of celite. The organic phase was dried over sodium sulphate, filtered and evaporated under reduced pressure. The residue was purified using SP1® Purification System (0% to 20%, hexane-ethyl acetate) to obtain 1.43 g. This solid was triturated with hexane, filtered and dried in the vacuum oven to give 0.94 g (55% yield) of the desired product as a solid. Purity 100%.

LRMS (m/z): 251 (M+1)$^+$.

b) N-(2-Methoxy-5-(4,4,5,5-tetramethyl-1,3,2-dioxaborolan-2-yl)pyridin-3-yl)methanesulfonamide 2-Methoxy-5-(4,4,5,5-tetramethyl-1,3,2-dioxaborolan-2-yl)pyridin-3-amine (940 mg, 3.76 mol) was dissolved in 20 mL pyridine. The mixture was submitted to three vacuum-argon cycles and was cooled at 0° C. with an ice bath. Methanesulfonyl chloride (600 µl, 7.75 mol) was added dropwise and the reaction mixture was stirred overnight. The solvent was concentrated and the residue was partitioned between dichloromethane and a saturated sodium bicarbonate solution. The organic phase was dried over sodium sulphate and evaporated under reduced pressure. The semi-solid was crystallized with diethyl ether and isopropyl ether to obtain a solid that was filtered and dried in the oven to give 720 mg (58% yield) of the final compound as a mixture of boronic acid and boronate. Purity 100%.

LRMS (m/z): 329 (M+1)$^+$.

Preparation 16

Methyl 3-hydroxy-5-(4,4,5,5-tetramethyl-1,3,2-dioxaborolan-2-yl)benzoate

Methyl 3-bromo-5-hydroxybenzoate (1 g, 4.33 mmol) was dissolved in 40 mL dioxane. Bis(pinacolato)diboron (2.2 g, 8.66 mmol) and potassium acetate (1.27 g, 12.94 mmol) were added and the mixture was submitted to three vacuum-argon cycles. Bis(diphenylphosphino)ferrocene-palladium(II) dichloride dichloromethane complex (0.18 g, 0.22 mmol) was added under argon conditions. The mixture was heated at 90° C. overnight. The mixture was partitioned between ethyl acetate and water. The organic phase was dried over sodium sulphate, filtered and evaporated under reduced pressure. The residue was purified using SP1® Purification System (0% to 10%, dichloromethane-methanol) to obtain 1 g (83% yield) of the title compound as a brown solid. Purity 100%.

LRMS (m/z): 279 (M+1)$^+$.

Preparation 17

(S)-Methyl 3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxybenzoate (S)-2-(1-((6-Amino-5-iodopyrimidin-4-yl)amino)ethyl)-5-methyl-3-phenylpyrrolo[2,1-f][1,2,4]triazin-4(3H)-one (100 mg, 0.16 mmol) and methyl 3-hydroxy-5-(4,4,5,5-tetramethyl-1,3,2-dioxaborolan-2-yl)benzoate (64 mg, 0.23 mmol) were dissolved in 10 mL dioxane in a microwave vessel. A solution of sodium carbonate (2 M, 365 µl, 0.73 mmol) was added and the mixture was submitted to three vacuum-argon cycles. 2'-(Dimethylamino)-2-biphenylyl-palladium(II) chloride dinorbornylphosphine complex (5 mg, 0.01 mmol) was added and the mixture was submitted to three more vacuum-argon cycles. The reaction mixture was then heated at 120° C. under microwave conditions for 5 h. Further 2'-(dimethylamino)-2-biphenylyl-palladium(II) chloride dinorbornylphosphine complex (5 mg, 0.01 mmol) and sodium carbonate (2 M, 365 µl, 0.73 mmol) were added and the reaction mixture heated at 120° C. under microwave conditions 2 h more. The reaction mixture was cooled at room temperature and partitioned between ethyl acetate and water. The organic phase was washed with water, brine and dried over sodium sulphate, filtered and evaporated under reduced pressure. The residue was purified by reverse phase using SP1® Purification System to obtain 35 mg (42% yield) of the title compound. Purity 100%.

LRMS (m/z): 512 (M+1)$^+$.

Preparation 18

(S)-2-(1-((6-Amino-5-(3,4-difluoro-5-methoxyphenyl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (200 mg, 0.3 mmol) was treated with (3,4-difluoro-5-methoxyphenyl)boronic acid (93 mg, 0.49 mmol), 1,1-bis(diphenylphosphino)ferrocene-palladium(II)dichloride dichloromethane complex (29 mg, 0.03 mmol) and aqueous solution of sodium carbonate (2M, 492 µl, 0.98 mmol) in dioxane. The reaction mixture was submitted at vacuum-argon cycles and heated at 100° C. overnight. The solvent was cooled at room temperature and diluted with ethyl acetate. The organic phase was dried over sodium sulphate, filtered and evaporated under reduced pressure. The residue was purified by reverse phase using SP1® Purification System to obtain 87 mg (53% yield) of the title compound.

LRMS (m/z): 504 (M+1)$^+$.

Preparation 19

Methyl 3-bromo-1H-pyrrole-2-carboxylate

Methyl 3-bromo-1-(phenylsulfonyl)-1H-pyrrole-2-carboxylate (6.59 g, 19.15 mmol) was dissolved in 132 mL anhydrous methanol under nitrogen atmosphere and it was cooled at 0° C. Sodium methoxide (1.55 g, 28.69 mmol) was added and the reaction mixture was stirred at room temperature for 4 h. The reaction was poured into a saturated ammonium chloride solution and extracted twice with ethyl acetate. The organics were combined and washed with water, brine, dried over sodium sulphate, filtered and evaporated under reduced pressure. The crude was purified using SP1® Purification System (0% to 30%, hexane-ethyl acetate) to obtain 3.32 g (85% yield) of the title compound as a white solid.

LRMS (m/z): 204, 206 (M+1)$^+$.

Preparation 20

Methyl 1-amino-3-bromo-1H-pyrrole-2-carboxylate

Methyl 3-bromo-1H-pyrrole-2-carboxylate (1.74 g, 8.53 mmol) was treated with an aqueous solution of sodium hydroxide (32%, 25 mL, 172.3 mmol), ammonium hydroxide solution (8M, 8 mL, 63.5 mmol), ammonium chloride (2.74 g, 51.2 mmol), aliquat 336 (312 µl, 0.68 mmol) and a 10% aqueous solution of sodium hypochlorite (10%, 56 mL, 75.4 mmol) according to the method of Preparation 4c to give 600 mg (23% yield) of the title product. Purity 70%.

LRMS (m/z): 219, 221 (M+1)$^+$.

Preparation 21

(S)-Methyl 1-(4-(benzyloxy)-2-((tert-butoxycarbonyl)amino)butanamido)-3-bromo-1H-pyrrole-2-carboxylate Methyl 1-amino-3-bromo-1H-pyrrole-2-carboxylate (2.83 g, 12.92 mmol) was treated with (S)-4-(benzyloxy)-2-((tert-butoxycarbonyl)amino)butanoic acid (4 g, 12.93 mmol), N,N-diisopropylethylamine (7.4 mL, 42.6 mmol) and T3P® (50% in ethyl acetate, 10.8 mL, 18.14 mmol) according to the method of Preparation 5a to give 6.77 g (84% yield) of the desired compound. Purity 81%.

LRMS (m/z): 510, 512 (M+1)$^+$.

Preparation 22

(S)-tert-Butyl (4-(benzyloxy)-1-((3-bromo-2-((3,5-difluorophenyl)carbamoyl)-1H-pyrrol-1-yl)amino)-1-oxobutan-2-yl)carbamate (S)-Methyl 1-(4-(benzyloxy)-2-((tert-butoxycarbonyl)amino)butanamido)-3-bromo-1H-pyrrole-2-carboxylate (4 g, 7.84 mmol) was treated with 3,5-difluoroaniline (5.06 g, 39.19 mmol) and trimethyl aluminium (2 M in toluene, 19.6 mL, 39.18 mmol) according to the method of Preparation 10a. The residue was purified using SP1® Purification System (0% to 50% hexane-ethyl acetate) to obtain 2.18 g (41% yield) of the title compound as a white solid. Purity 88%.

LRMS (m/z): 607 (M+1)$^+$.

Preparation 23

(S)-tert-Butyl (3-(benzyloxy)-1-(5-bromo-3-(3,5-difluorophenyl)-4-oxo-3,4-dihydropyrrolo[2,1-f][1,2,4]triazin-2-yl)propyl)carbamate Triphenylphosphine (1.29 g, 4.92 mmol) was dissolved in 21 mL anhydrous dichloromethane. Bromine (253 µl, 4.94 mmol) was added dropwise under argon atmosphere and the reaction was stirred at room temperature for 30 min. Triethylamine (1.96 mL, 4 mmol) and (S)-tert-butyl (4-(benzyloxy)-1-((3-bromo-2-((3,5-difluorophenyl)carbamoyl)-1H-pyrrol-1-yl)amino)-1-oxobutan-2-yl)carbamate (2.15 g, 3.52 mmol) were added and the reaction mixture was heated at 60° C. for 2 h. The mixture was poured into 75 mL 4% aqueous solution sodium bicarbonate and extracted with dichlorometane. The organics were dried over sodium sulphate, filtered and evaporated. The residue was re-dissolved in 19 mL tetrahydrofuran and 2 mL dichloromethane and, under argon conditions, sodium methanethiolate was added and the reaction was stirred at room temperature for 1 h. The mixture was poured into 4% aqueous solution sodium bicarbonate and extracted with ethyl acetate. The organic layer was washed with water, brine and dried over sodium sulphate, filtered and concentrated. The residue was purified using Isolera® Purification System (0% to 20%, hexane-ethyl acetate) to obtain 1.66 g (74% yield) of the title compound as a white solid.

LRMS (m/z): 589, 591 (M+1)$^+$.

Preparation 24

(S)-tert-Butyl (3-(benzyloxy)-1-(5-cyano-3-(3,5-difluorophenyl)-4-oxo-3,4-dihydropyrrolo[2,1-f][1,2,4]triazin-2-yl)propyl)carbamate In a reactor vessel (S)-tert-butyl (3-(benzyloxy)-1-(5-bromo-3-(3,5-difluorophenyl)-4-oxo-3,4-dihydropyrrolo[2,1-f][1,2,4]triazin-2-yl)propyl)carbamate (0.81 g, 1.37 mmol) was dissolved in 32 mL dimethylformamide. Dicyanozinc (0.4 g, 3.49 mmol) and tetrakis(triphenylphosphine)palladium(0) (0.64 g, 0.55 mmol) were added under argon conditions. The reaction was stirred at 120° C. overnight. The crude was filtered through a plug of Celite and washed several times with ethyl acetate. The combinated filtrates were evaporated and washed with water, brine, dried over sodium sulphate, filtered and concentrated under reduced pressure. The residue was purified using SP1 ® Purification System (0% to 40%, hexane-ethyl acetate) to obtain 0.58 g (77% yield) of the title compound as a white solid. Purity 98%.

LRMS (m/z): 536 (M+1)$^+$.

Preparation 25

(S)-2-(1-Amino-3-(benzyloxy)propyl)-3-(3,5-difluorophenyl)-4-oxo-3,4-dihydropyrrolo[2,1-f][1,2,4]triazine-5-carbonitrile (S)-tert-Butyl (3-(benzyloxy)-1-(5-cyano-3-(3,5-difluorophenyl)-4-oxo-3,4-dihydropyrrolo[2,1-f][1,2,4]triazin-2-yl)propyl)carbamate (50 mg, 0.09 mmol) was treated with a solution of hydrochloric acid in dioxane (4M, 350 µl, 1.4 mmol) according to the method described in Preparation 1 to obtain 42 mg (92% yield) of the title compound as a yellow solid. Purity 96%.

LRMS (m/z): 436 (M+1)$^+$.

Preparation 26

(S)-2-(1-((6-Amino-5-iodopyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile (S)-2-(1-Amino-3-(benzyloxy)propyl)-3-(3,5-difluorophenyl)-4-oxo-3,4-dihydropyrrolo[2,1-f][1,2,4]triazine-5-carbonitrile (51 mg, 0.12 mmol) was treated with 6-chloro-5-iodopyrimidin-4-amine (50 mg, 0.2 mmol), cesium fluoride (55 mg, 0.36 mmol) and N,N-diisopropylethylamine (170 µl, 0.98 mmol) according to the method of Preparation 13. The residue was purified by reverse phase using SP1® Purification System to give 12 mg (16% yield) of the title compound.

LRMS (m/z): 655 (M+1)$^+$.

Preparation 27

(S)-tert-Butyl (4-(benzyloxy)-1-oxo-1-((2-(phenylcarbamoyl)-1H-pyrrol-1-yl)amino)butan-2-yl)carbamate 1-Amino-N-phenyl-1H-pyrrole-2-carboxamide (0.65 g, 3.23 mmol) was treated with (S)-4-(benzyloxy)-2-((tert-butoxycarbonyl)amino)butanoic acid (1 g, 3.23 mmol), N,N-diisopropylethylamine (1.9 mL, 10.66 mmol) and T3P® (50% in ethyl acetate, 2.7 mL, 4.52 mmol) according to the method of Preparation 5a to give 1.57 g (98% yield) of the desired compound. Purity 97%.

LRMS (m/z): 493 (M+1)+.

Preparation 28

(S)-tert-Butyl (3-(benzyloxy)-1-(4-oxo-3-phenyl-3,4-dihydropyrrolo[2,1-f][1,2,4]triazin-2-yl)propyl)carbamate (S)-tert-Butyl (4-(benzyloxy)-1-oxo-1-((2-(phenylcarbamoyl)-1H-pyrrol-1-yl)amino)butan-2-yl)carbamate (1.57 g, 3.19 mmol) was treated with triphenylphosphine (1.17 g, 4.46 mmol), bromine (229 µl, 4.47 mmol), triethylamine (1.78 mL, 12.77 mmol) and a solution of ammonia solution (7M in methanol, 150 mL, 1000 mmol) according to the method of Preparation 5b. The residue was purified using SP1® Purification System (0% to 30%, hexane-ethyl acetate) to give 0.81 g (53.5%) of the title compound as a white solid. Purity 100%.

LRMS (m/z): 475 (M+1)+.

Preparation 29

(S)-tert-Butyl (3-hydroxy-1-(4-oxo-3-phenyl-3,4-dihydropyrrolo[2,1-f][1,2,4]triazin-2-yl)propyl)carbamate (S)-tert-Butyl (3-(benzyloxy)-1-(4-oxo-3-phenyl-3,4-dihydropyrrolo[2,1-f][1,2,4]triazin-2-yl)propyl)carbamate (0.65 g, 1.37 mmol) was dissolved in 33 mL methanol. Palladium on carbon (10%, 0.65 g, 6.11 mmol) was added and the mixture was hydrogenated at 30 psi overnight. The crude was filtered through a plug of Celite, washing several times with ethyl acetate. The combined filtrates were evaporated to give 0.52 g (99% yield) of the title compound as a white solid. Purity 100%.

LRMS (m/z): 385 (M+1)+.

Preparation 30

(S)-tert-Butyl (3-bromo-1-(4-oxo-3-phenyl-3,4-dihydropyrrolo[2,1-f][1,2,4]triazin-2-yl)propyl)carbamate Triphenylphosphine (170 mg, 0.44 mmol) was dissolved in 2 mL anhydrous dichloromethane. Bromine (32 µl, 0.62 mmol) was added dropwise under argon atmosphere and the reaction was stirred at room temperature for 30 min. Triethylamine (247 µl, 1.77 mmol) and (S)-tert-butyl (3-hydroxy-1-(4-oxo-3-phenyl-3,4-dihydropyrrolo[2,1-f][1,2,4]triazin-2-yl)propyl)carbamate (170 mg, 0.44 mmol) were added and the reaction mixture was stirred at room temperature for 2 h. The mixture was poured into water and extracted with dichlorometane. The organics were dried over sodium sulphate, filtered and evaporated. The residue purified using SP1® Purification System (0% to 30%, hexane-ethyl acetate) to obtain 147 mg (74% yield) of the title compound as a white solid. Purity 100%.

LRMS (m/z): 447, 449 (M+1)+.

Preparation 31

(S)-tert-Butyl (1-(4-oxo-3-phenyl-3,4-dihydropyrrolo[2,1-f][1,2,4]triazin-2-yl)-3-phenoxypropyl)carbamate Phenol (6 mg, 0.06 mmol) was dissolved in 450 µl of N,N-dimethylformamide. Potassium carbonate (6 mg, 0.05 mmol) was added and the reaction was stirred at room temperature for 30 min. (S)-tert-Butyl (3-bromo-1-(4-oxo-3-phenyl-3,4-dihydropyrrolo[2,1-f][1,2,4]triazin-2-yl)propyl)carbamate (45 mg, 0.03 mmol) and potassium iodide (1 mg, 0.001 mmol) were added and the reaction was heated at 70° C. for 3 h. The mixture was poured into a 4% aqueous sodium bicarbonate and extracted with ethyl acetate. The combined organic phases were washed with water, brine, dried over sodium sulphate and evaporated under reduced pressure. The crude was purified by SP1® Purification System (0% to 50%, hexane-ethyl acetate) to give 8 mg (57% yield) of the title compound. Purity 98%.

LRMS (m/z): 461 (M+1)+.

Preparation 32

(S)-2-(1-Amino-3-phenoxypropyl)-3-phenylpyrrolo[2,1-f][1,2,4]triazin-4(3H)-one (S)-tert-Butyl (1-(4-oxo-3-phenyl-3,4-dihydropyrrolo[2,1-f][1,2,4]triazin-2-yl)-3-phenoxypropyl)carbamate (8 mg, 0.02 mmol) was treated with a solution of hydrochloric acid in dioxane (4M, 109 µl, 0.43 mmol) according to the method described in Preparation 1 to obtain 6 mg (87% yield) of the title compound as a solid. Purity 100%.

LRMS (m/z): 361 (M+1)+.

Preparation 33

(S)-tert-Butyl (3-(benzylthio)-1-(4-oxo-3-phenyl-3,4-dihydropyrrolo[2,1-f][1,2,4]triazin-2-yl)propyl)carbamate (S)-tert-Butyl (3-bromo-1-(4-oxo-3-phenyl-3,4-dihydropyrrolo[2,1-f][1,2,4]triazin-2-yl)propyl)carbamate (45 mg, 0.03 mmol) was treated with benzyl hydrosulfide (7 µl, 0.06 mmol) and potassium carbonate (6 mg, 0.05 mmol) according to the method described in Preparation 31. The residue was purified using SP1® Purification System (0% to 50%, hexane-ethyl acetate) to give 12 mg (81% yield) of the title compound. Purity 70%.

LRMS (m/z): 491 (M+1)+.

Preparation 34

(S)-2-(1-Amino-3-(benzylthio)propyl)-3-phenylpyrrolo[2,1-f][1,2,4]triazin-4(3H)-one (S)-tert-Butyl (3-(benzylthio)-1-(4-oxo-3-phenyl-3,4-dihydropyrrolo[2,1-f][1,2,4]triazin-2-yl)propyl)carbamate (12 mg, 0.02 mmol) was treated with a solution of hydrochloric acid in dioxane (4M, 92 µl, 0.37 mmol) according to the method described in Preparation 1 to obtain 10 mg (96% yield) of the title compound as a yellow solid. Purity 100%.

LRMS (m/z): 391 (M+1)+.

Preparation 35

4-Fluoro-N-(2-methoxy-5-(4,4,5,5-tetramethyl-1,3,2-dioxaborolan-2-yl)pyridin-3-yl)benzenesulfonamide 2-Methoxy-5-(4,4,5,5-tetramethyl-1,3,2-dioxaborolan-2-yl)pyridin-3-amine (200 mg, 0.8 mmol) was treated with 4-fluorobenzenesulfonyl chloride (311 mg, 1.6 mmol)

according to the method described In Preparation 15b to give 124 mg (37.5% yield) of the title compound as an oil. Purity 88%.

LRMS (m/z): 409 (M+1)$^+$.

Preparation 36

(S)-2-(1-((6-Amino-5-bromopyrimidin-4-yl)amino) ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (300 mg, 1.12 mmol) was treated 5-bromo-6-chloropyrimidin-4-amine (373 mg, 1.79 mmol), cesium fluoride (340 mg, 2.24 mmol), N,N-diisopropylethylamine (0.974 mL, 5.59 mol) according to Preparation 13. The residue was purified using SP1® Purification System (0% to 10%, dichloromethane-methanol) to give 0.26 g (60% yield) of the title compound as a solid. Purity 98%.

LRMS (m/z): 440, 442 (M+1)$^+$.

Preparation 37

4-Methoxy-N-(2-methoxy-5-(4,4,5,5-tetramethyl-1,3,2-dioxaborolan-2-yl)pyridin-3-yl)benzenesulfonamide 2-Methoxy-5-(4,4,5,5-tetramethyl-1,3,2-dioxaborolan-2-yl)pyridin-3-amine (200 mg, 0.8 mmol) was treated with 4-methoxybenzene-1-sulfonyl chloride (331 mg, 1.6 mmol) according to the method of Preparation 15b to give 270 mg (77% yield) of the title compound as an oil. Purity 96%.

LRMS (m/z): 421 (M+1)$^+$.

Preparation 38

(S)—N-(5-(4-Amino-6-((1-(5-methyl-4-oxo-3-phenyl-3,4-dihydropyrrolo[2,1-f][1,2,4]triazin-2-yl) ethyl)amino)pyrimidin-5-yl)-2-methoxypyridin-3-yl)-4-methoxybenzenesulfonamide (S)-2-(1-((6-Amino-5-bromopyrimidin-4-yl)amino) ethyl)-5-methyl-3-phenylpyrrolo[2,1-f][1,2,4]triazin-4(3H)-one (100 mg, 0.23 mmol) was treated with 4-methoxy-N-(2-methoxy-5-(4,4,5,5-tetramethyl-1,3,2-dioxaborolan-2-yl) pyridin-3-yl)benzenesulfonamide (149 mg, 0.34 mmol), sodium carbonate (2M, 511 µl, 1.02 mmol) and 1,1'-bis(diphenylphosphino)ferrocene-palladium(II)dichloride dichloromethane complex (28 mg, 0.03 mmol) according to the method described in Example 3 to give 82 mg (55% yield) of the title compound as a solid. Purity 100%.

LRMS (m/z): 654 (M+1)$^+$

Preparation 39

(S)-2-(1-((5-Iodopyrimidin-4-yl)amino)ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (400 mg, 1.49 mmol) was treated 4-chloro-5-iodopyrimidine (538 mg, 2.24 mmol), cesium fluoride (453 mg, 2.98 mmol) and N,N-diisopropylethylamine (1.3 mL, 7.46 mol) according to Preparation 13. The residue was purified by reverse phase using SP1® Purification System to give 230 mg (33% yield) of the title compound as a solid. Purity 100%.

LRMS (m/z): 473 (M+1)$^+$

Preparation 40

4-Chloro-5-iodopyrimidine a) 5-Iodopyrimidin-4(3H)-one

Pyrimidin-4(3H)-one (1 g, 10.41 mmol) was dissolved in 10 ml water. Sodium hydroxide (0.54 g, 13.50 mmol) and iodine (2.64 g, 10.40 mmol) were added and the reaction mixture heated at 85° C. for 72 h. The reaction mixture was filtered and washed with water. The solid formed was dried in the vacuum oven to give 1.01 g (44% yield) of the title compound. Purity 100%.

LRMS (m/z): 223 (M+1)$^+$ b) 4-Chloro-5-iodopyrimidine

Oxalyl chloride (1.27 ml, 14.61 mmol) was added dropwise in 707 ml dimethylformamide and 20 ml dichloroethane. 5-Iodopyrimidin-4(3H)-one (1 g, 4.55 mmol) was added and the reaction was heated at reflux for 2 h. The reaction mixture was dissolved in dichloromethane, washed with water, dried over sodium sulphate, filtered and concentrated under reduced pressure to give 0.91 g (83% yield) of the title compound as a solid. Purity 100%.

LRMS (m/z): 241 (M+1)$^+$

Preparation 41

(S)-2-(1-((5-(2,4-Dimethoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (2,4-dimethoxyphenyl)boronic acid (147 mg, 0.81 mmol), sodium carbonate (86 mg, 0.81 mmol) and bis(triphenylphosphine)palladium(II) dichloride (24 mg, 0.03 mmol) according to the method described in Preparation 62. The residue was purified using SP1® Purification System (0% to 20%, dichloromethane-ethyl acetate) to give 95 mg (87% yield) of the title compound. Purity 87%.

LRMS (m/z): 652 (M+1)$^+$.

Preparation 42

1-(2-Hydroxy-5-(4,4,5,5-tetramethyl-1,3,2-dioxaborolan-2-yl)phenyl)urea 1-(5-Bromo-2-hydroxyphenyl)urea (300 mg, 1.30 mmol) was treated with bis(pinacolato)diboron (430 mg, 1.69 mmol), potassium acetate (382 mg, 2.99 mmol) and bis(diphenylphosphino)ferrocene-palladium(II)dichloride dichloromethane complex (318 mg, 0.39 mmol) according to the method described in Preparation 16. The residue was purified by reverse phase using SP1® Purification System to give 38 mg (35% yield) of the title compound as a solid. Purity 82%.

Preparation 43

(S)-tert-Butyl (1-(5-iodo-4-oxo-3-phenyl-3,4-dihydropyrrolo[2,1-f][1,2,4]triazin-2-yl)ethyl)carbamate (S)-tert-Butyl (1-(5-bromo-4-oxo-3-phenyl-3,4-dihydropyrrolo[2,1-f][1,2,4]triazin-2-yl)ethyl)carbamate (1 g, 2.31 mmol) was dissolved in 25 mL anhydrous dioxane in a Schlenk vessel. Sodium iodide (1.38 g, 3.9 mmol), copper(I) iodide (0.13 g, 0.68 mmol) and trans-N,N'-dimethylcyclohexane-1,2-diamine (0.2 g, 1.41 mmol) were added under argon conditions and the mixture was further submitted to three vacuum-argon cycles. The reaction vessel was sealed and the mixture was heated at 120° C. for 7 h. The mixture was cooled to room temperature, diluted with ethyl acetate and filtered through celite. The organic phase was washed with 1N hydrochloric acid, water, brine and dried over sodium sulphate, filtered and evaporated under reduced pressure to obtain 1.43 g (88% yield) of the title compound as a oil. Purity 68%.

LRMS (m/z): 481 (M+1)$^+$

Preparation 44

(S)-tert-Butyl (1-(4-oxo-3-phenyl-5-(phenylthio)-3,4-dihydropyrrolo[2,1-f][1,2,4]triazin-2-yl)ethyl)carbamate (S)-tert-Butyl (1-(5-iodo-4-oxo-3-phenyl-3,4-dihydropyrrolo[2,1-f][1,2,4]triazin-2-yl)ethyl)carbamate (700 mg, 1.46 mmol) was dissolved in 50 mL dimethylformamide in a pressure reactor. Phenyl hydrosulfide (241 mg, 2.19 mmol), potassium carbonate (302 mg, 2.19 mmol) and copper(I) iodide (416 mg, 2.18 mmol) were added under argon atmosphere and the reaction mixture heated at 70° C. overnight. The reaction mixture was cooled at room temperature and partitioned between ethyl acetate and water. The organic phase was washed with water, brine, dried over sodium sulphate, filtered and concentrated under reduced pressure. The residue was purified by reverse phase using Isolera® Purification System to give 190 mg (28% yield) to the title compound. Purity 100%.

LRMS (m/z): 463 (M+1)$^+$

Preparation 45

(S)-2-(1-Aminoethyl)-3-phenyl-5-(phenylthio)pyrrolo[2,1-f][1,2,4]triazin-4(3H)-one (S)-tert-Butyl (1-(4-oxo-3-phenyl-5-(phenylthio)-3,4-dihydropyrrolo[2,1-f][1,2,4]triazin-2-yl)ethyl)carbamate (190 mg, 0.41 mmol) was treated with trifluoroacetic acid (316 µl, 4.10 mmol) according to the method of Preparation 6 to obtain 142 mg (95% yield) of the title compound as a oil. Purity 95%.

LRMS (m/z): 363 (M+1)$^+$

Preparation 46

(S)-2-(1-((6-Amino-5-bromopyrimidin-4-yl)amino)ethyl)-3-phenyl-5-(phenylthio)pyrrolo[2,1-f][1,2,4]triazin-4(3H)-one (S)-2-(1-Aminoethyl)-3-phenyl-5-(phenylthio)pyrrolo[2,1-f][1,2,4]triazin-4(3H)-one (142 mg, 0.39 mmol) was treated with treated 5-bromo-6-chloropyrimidin-4-amine (245 mg, 1.18 mmol), cesium fluoride (178 mg, 1.17 mmol), N,N-diisopropylethylamine (341 µl, 1.96 mol) according to Preparation 13 to give 0.23 g (75% yield) of the title compound as a solid.

LRMS (m/z): 534, 536 (M+1)$^+$

Preparation 47

Ethyl 2-cyano-3,3-bis(methylthio)acrylate

A solution of sodium ethanolate was prepared from sodium (3.4 g) and ethanol (50 mL). In a three necked flask it was placed 500 mL of sodium ethanolate and ethyl 2-cyanoacetate (9 mL, 0.08 mmol) was added dropwise and the reaction mixture was cooled at 0° C. with an ice bath. Carbon disulfide (4.5 mL, 0.07 mmol) was added dropwise and the reaction was stirred at 0° C. for 30 min. Dimethyl sulphate (14 mL, 0.15 mmol) was then added dropwise at 0° C. and the reaction mixture was stirred at room temperature for 2 h. The reaction mixture was then poured into 300 mL water and extracted with DCM. The organic phase was washed with water, brine, dried over sodium sulphate, filtered and concentrated under reduced pressure. The semi-solid was triturated several times with hexane to obtain 9.2 g (57% yield) of the title compound as an orange semi solid.

LRMS (m/z): 218 (M+1)$^+$

Preparation 48

(E)-Ethyl 2-cyano-3-((4-methoxybenzyl)amino)-3-(methylthio)acrylate

Ethyl 2-cyano-3,3-bis(methylthio)acrylate (3.8 g, 17.49 mmol) was dissolved in 70 mL ethanol and (4-methoxyphenyl)methanamine (2.88 g, 20.99 mmol) was added. The reaction was stirred at reflux for 2 h. The solvent was evaporated to give 6.5 g (100% yield) of the title compound that was used in the next step without any further purification. Purity 80%.

LRMS (m/z): 307 (M+1)$^+$

Preparation 49

(E)-Ethyl 3-((E)-(aminomethylene)amino)-2-cyano-3-((4-methoxybenzyl)amino)acrylate (E)-Ethyl 2-cyano-3-((4-methoxybenzyl)amino)-3-(methylthio)acrylate was dissolved in 65 mL ethanol. N,N-Diisopropylethylamine (13 mL, 74.44 mmol) and formamidine hydrochloride (2.12 g, 26.33 mmol) were added and the reaction mixture was stirred at room temperature for 48 h. The solvent was concentrated and the residue was directly purified using SP1® Purification System (0% to 10%, dichloromethane-methanol) to give 0.96 g (25% yield) of the title compound as a yellow oil. Purity 85%.

LRMS (m/z): 303 (M+1)$^+$

Preparation 50

Ethyl 4-chloro-6-((4-methoxybenzyl)amino)pyrimidine-5-carboxylate (E)-Ethyl 3-((E)-(aminomethylene)amino)-2-cyano-3-((4-methoxybenzyl)amino)acrylate (1.24 g, 3.49 mmol) was dissolved in 23 mL hydrochloride acid (4M in dioxane, 90.64 mmol) and the mixture was stirred at room temperature overnight. The mixture was poured into 400 mL water and extracted with ethyl acetate. The organic phase was washed with water, brine, dried over sodium sulphate, filtered and evaporated under reduced pressure. The crude was purified using SP1® Purification System (0% to 25%, hexane-ethyl acetate) to give 376 mg (34% yield) of the title compound as a white solid.

LRMS (m/z): 322 (M+1)$^+$

Preparation 51

(S)-Ethyl 4-((4-methoxybenzyl)amino)-6-((1-(5-methyl-4-oxo-3-phenyl-3,4-dihydropyrrolo[2,1-f][1,2,4]triazin-2-yl)ethyl)amino)pyrimidine-5-carboxylate (S)-2-(1-Aminoethyl)-5-methyl-3-phenylpyrrolo[2,1-f][1,2,4]triazin-4(3H)-one was treated with ethyl 4-chloro-6-((4-methoxybenzyl)amino)pyrimidine-5-carboxylate (6 mg, 0.02 mmol), N,N-diisopropylethylamine (16 µl, 0.09 mmol) and ethanol as a solvent according to the method described in Example 17. The solvent was concentrated and the solid was suspended in ethanol and filtered. The white solid obtained was washed with ether and dried in the oven to give 281 mg (82% yield) of the title compound as a white solid.

LRMS (m/z): 554 (M+1)$^+$

Preparation 52

(S)-4-((4-Methoxybenzyl)amino)-6-((1-(5-methyl-4-oxo-3-phenyl-3,4-dihydropyrrolo[2,1-f][1,2,4]triazin-2-yl)ethyl)amino)pyrimidine-5-carboxylic acid (S)-Ethyl 4-((4-methoxybenzyl)amino)-6-((1-(5-methyl-4-oxo-3-phenyl-3,4-dihydropyrrolo[2,1-f][1,2,4]triazin-2-yl)ethyl)amino)pyrimidine-5-carboxylate (281 mg, 0.51 mmol) was dissolved in 2 mL ethanol and 3 mL tetrahydrofuran. Lithium hydroxide (213 mg, 50.8 mmol) in 3 mL water was added and the mixture was heated at 50° C. overnight. Further lithium hydroxide (213 mg, 50.8 mmol) in 3 mL water was added and the reaction mixture heated at 50° C. for 4 h more. The reaction mixture was diluted with water and acidified to pH 5 with hydrochloric acid 5N. The aqueous phase was extracted with ethyl acetate and the organics were washed with brine, dried over sodium sulphate, filtered and concentrated under reduced pressure to give 300 mg (99% yield) of the title compound as a white solid. Purity 90%.

LRMS (m/z): 526 (M+1)$^+$

Preparation 53

(S)-4-((4-Methoxybenzyl)amino)-N-(3-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide

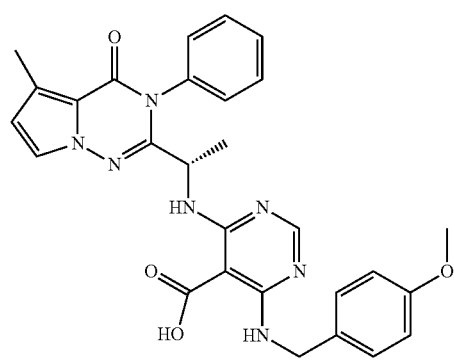

+

-continued

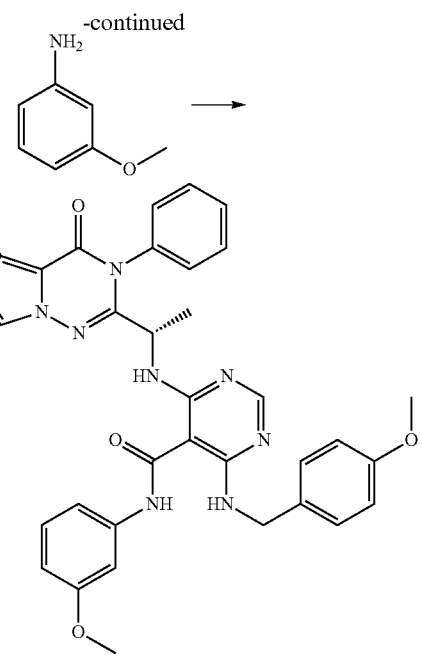

(S)-4-((4-Methoxybenzyl)amino)-6-((1-(5-methyl-4-oxo-3-phenyl-3,4-dihydropyrrolo[2,1-f][1,2,4]triazin-2-yl)ethyl)amino)pyrimidine-5-carboxylic acid (300 mg, 0.51 mmol) was dissolved in 7 mL dimethylformamide. N,N-Diisopropylethylamine (150 µl, 1.10 mmol) and HATU (400 mg, 1.05 mmol) were added and the reaction mixture was stirred at room temperature for 30 min. Then, 3-methoxyaniline (95 µl, 0.85 mmol) was added and the reaction mixture stirred at room temperature overnight. The crude was diluted with water and extracted with ethyl acetate. The organic layer was washed with water, brine, dried over sodium sulphate and concentrated under reduced pressure. A semi-solid was obtained and purified using SP1® Purification System (0% to 50%, hexane-ethyl acetate) to obtain 265 mg (82% yield) of the title compound. Purity 100%.

LRMS (m/z): 631 (M+1)$^+$

Preparation 54

(S)-4-Amino-N-(3-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-4-((4-Methoxybenzyl)amino)-N-(3-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (120 mg, 0.19 mmol) was dissolved in 5 mL trifluoroacetic acid. The reaction mixture was stirred at room temperature overnight. The trifluoroacetic acid was evaporated and the crude was partitioned between ethyl acetate and water. The organic phase was washed with brine, dried over sodium sulphate, filtered and concentrated. The residue was purified by reverse phase using SP1® Purification System to obtain 27 mg (28% yield) of the title compound.

LRMS (m/z): 511 (M+1)$^+$

Preparation 55

(S)-tert-Butyl (4-(benzyloxy)-1-((3-bromo-2-(phenylcarbamoyl)-1H-pyrrol-1-yl)amino)-1-oxobutan-2-yl)carbamate (S)-Methyl 1-(4-(benzyloxy)-2-((tert-butoxycarbonyl)amino)butanamido)-3-bromo-1H-pyrrole-2-carboxylate (1 g, 1.96 mmol) was treated with aniline (893 µl, 9.8 mmol) and trimethyl aluminium (2 M in toluene, 4.9 mL, 9.8 mmol) according to the method of Preparation 10a. The residue was purified using SP1® Purification System (0% to 30%, hexane-ethyl acetate) a to obtain 0.71 g (63% yield) of the title compound. Purity 100%.

LRMS (m/z): 572 (M+1)+

Preparation 56

(S)-tert-Butyl (3-(benzyloxy)-1-(5-bromo-4-oxo-3-phenyl-3,4-dihydropyrrolo[2,1-f][1,2,4]triazin-2-yl)propyl)carbamate (S)-tert-Butyl (4-(benzyloxy)-1-((3-bromo-2-(phenylcarbamoyl)-1H-pyrrol-1-yl)amino)-1-oxobutan-2-yl)carbamate (0.7 g, 1.22 mmol) was treated with triphenylphosphine (0.45 g, 1.72 mmol), bromine (88 µl, 1.72 mmol), triethylamine (683 µl, 4.90 mmol) and sodium methanethiolate (0.17 g, 2.45 mmol) according to the method of Preparation 23. The residue was purified using Isolera® Purification System (0% to 20%, hexane-ethyl acetate) to give 0.61 g (90% yield) of the title compound. Purity 100%.

LRMS (m/z): 554 (M+1)+

Preparation 57

(S)-tert-Butyl (3-(benzyloxy)-1-(5-methyl-4-oxo-3-phenyl-3,4-dihydropyrrolo[2,1-f][1,2,4]triazin-2-yl)propyl)carbamate (S)-tert-Butyl (3-(benzyloxy)-1-(5-bromo-4-oxo-3-phenyl-3,4-dihydropyrrolo[2,1-f][1,2,4]triazin-2-yl)propyl)carbamate (0.6 g, 1.08 mmol) was dissolved in 36 mL anhydrous dimethylformamide in a pressure reactor vessel. 2,4,6-Trimethylboroxine (1.36 mL, 9.76 mmol), potassium carbonate (3 g, 21.68 mmol) and tetrakis(triphenylphosphine)palladium (0) (0.13 g, 0.11 mmol) were added under argon conditions. The reaction mixture was heated at 120° C. for 2 h and then cooled and filtered through a plug of Celite, washing several times with ethyl acetate. The combinated filtrates were washed with water, saturated ammonium chloride solution and brine, dried over sodium sulphate, filtered and evaporated under reduced pressure. The residue was purified using SP1® Purification System (0% to 20%, hexane-ethyl acetate) to give 0.45 g (85% yield) of the title compound as a white solid.

LRMS (m/z): 489 (M+1)+.

Preparation 58

(S)-2-(1-Amino-3-(benzyloxy)propyl)-5-methyl-3-phenylpyrrolo[2,1-f][1,2,4]triazin-4(3H)-one (S)-tert-Butyl (3-(benzyloxy)-1-(5-methyl-4-oxo-3-phenyl-3,4-dihydropyrrolo[2,1-f][1,2,4]triazin-2-yl)propyl)carbamate (30 mg, 0.06 mmol) was treated with a solution of hydrochloric acid in dioxane (4M, 230 µl, 0.92 mmol) according to the method described in Preparation 1 to obtain 24 mg (91% yield) of the title compound. Purity 98%.

LRMS (m/z): 389 (M+1)+.

Preparation 59

5-Bromo-4-chloro-7H-pyrrolo[2,3-d]pyrimidine

4-Chloro-7H-pyrrolo[2,3-d]pyrimidine (2 g, 13.02 mmol) was dissolved in 20 mL dimethylformamide. N-Bromosuccinimide (2.55 g, 14.33 mmol) was added under argon atmosphere. The reaction was stirred at room temperature overnight. The crude was poured into water and the precipitate formed was filtered and washed with water. The yellow solid obtained was dried in the vacuum oven to give 2.77 g (91.5% yield) of the title compound. Purity 99%.

LRMS (m/z): 232 (M+1)+.

Preparation 60

5-Bromo-4-chloro-7-((2-(trimethylsilyl)ethoxy)methyl)-7H-pyrrolo[2,3-d]pyrimidine Sodium hydride (60% dispersion in mineral oil, 0.205 g, 5.13 mmol) was suspended in 5 mL dimethylformamide. The mixture was stirred for 10 min and then cooled at 0° C. with an ice bath. 5-Bromo-4-chloro-7H-pyrrolo[2,3-d]pyrimidine (1 g, 4.30 mmol) dissolved in 5 mL dimethylformamide was added dropwise and the mixture was stirred for 30 min. At the same temperature [2-(chloromethoxy)ethyl](trimethyl)silane (0.9 g, 5.4 mmol) dissolved in 5 mL dimethylformamide was added dropwise and stirred for 30 min at 0° C. The mixture was poured into water and extracted twice with ethyl acetate. The organics were dried over sodium sulphate and concentrated under reduced pressure. The residue was purified using SP1® Purification System (0% to 100%, hexane-ethyl acetate) to give 1.18 g (76% yield) of the title compound as a white solid. Purity 100%.

LRMS (m/z): 362, 364 (M+1)+.

Preparation 61

(S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (330 mg, 1.08 mmol) was treated with 5-bromo-4-chloro-7-((2-(trimethylsilyl)ethoxy)methyl)-7H-pyrrolo[2,3-d]pyrimidine (430 mg, 1.19 mmol), cesium fluoride (33 mg, 0.22 mmol), N,N-diisopropylethylamine (1.1 mL, 6.49 mol) and 1-butanol according to Preparation 13. The residue was purified using SP1® Purification System (0% to 30%, hexane-ethyl acetate) to give 0.24 g (38% yield) of the title compound. Purity 100%.

LRMS (m/z): 594 (M+1)+.

Preparation 62

(S)-2-(1-((5-(3-Fluoro-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (110 mg, 0.19 mmol) was dissolved in 1.32 mL 1,2-dimethoxyethane and 0.33 mL water. (3-Fluoro-5-hydroxyphenyl)boronic acid (69 mg, 0.44 mmol), sodium carbonate (47 mg, 0.44 mmols) and bis(triphenylphosphine)palladium(II) dichloride (13 mg, 0.02 mmol) were added under argon atmosphere and the mixture was heated at 70° C. for 2 h. The reaction mixture was poured into a saturated ammonium chloride solution and extracted twice with water. The organics were washed with water, brine, dried over sodium sulphate, filtered and evaporated under reduced pressure. The residue was purified using SP1® Purification System (0% to 50%, hexane-ethyl acetate) to give 61 mg (53% yield) of the title compound. Purity 99%.

LRMS (m/z): 626 (M+1)$^+$.

Preparation 63

(S)-2-(1-((5-(2-Hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with 2-(4,4,5,5-tetramethyl-1,3,2-dioxaborolan-2-yl)phenol (68 µl, 0.32 mmol), sodium carbonate (34 mg, 0.32 mmols) and bis(triphenylphosphine)palladium(II) dichloride (9 mg, 0.01 mmol) according to the method described in Preparation 62. The residue was purified using SP1® Purification System (0% to 60%, hexane-ethyl acetate) to give 52 mg (64% yield) of the title compound. Purity 93%.

LRMS (m/z): 608 (M+1)$^+$.

Preparation 64

(S)-2-(1-((5-(4-Hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with (4-hydroxyphenyl)boronic acid (45 mg, 0.32 mmol), sodium carbonate (34 mg, 0.32 mmols) and bis(triphenylphosphine)palladium(II) dichloride (9 mg, 0.01 mmol) according to the method described in Preparation 62. The residue was purified using SP1® Purification System (0% to 60%, hexane-ethyl acetate) to give 48 mg (58% yield) of the title compound. Purity 96%.

LRMS (m/z): 608 (M+1)$^+$.

Preparation 65

(S)-2-(1-((5-(1H-Pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (57 mg, 0.10 mmol) was treated with (1H-pyrazol-4-yl)boronic acid (64 mg, 0.58 mmol), sodium carbonate (65 mg, 0.61 mmols) and bis(triphenylphosphine)palladium(II) dichloride (33 mg, 0.03 mmol) according to the method described in Preparation 62. The residue was purified using SP1® Purification System (0% to 100%, hexane-ethyl acetate) to give 23 mg (41% yield) of the title compound. Purity 99%.

LRMS (m/z): 582 (M+1)$^+$.

Preparation 66

(S)-2-(1-((5-(2-Methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with (2-methoxyphenyl)boronic acid (49 mg, 0.32 mmol), sodium carbonate (34 mg, 0.32 mmols) and bis(triphenylphosphine)palladium(II) dichloride (9 mg, 0.01 mmol) according to the method described in Preparation 62. The residue was purified using SP1® Purification System (0% to 40%, hexane-ethyl acetate) to give 76 mg (90% yield) of the title compound. Purity 98%.

LRMS (m/z): 622 (M+1)$^+$.

Preparation 67

(S)-2-(1-((5-(4-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (4-fluoro-2-methoxyphenyl)boronic acid (69 mg, 0.4 mmol), sodium carbonate (43 mg, 0.4 mmols) and bis(triphenylphosphine)palladium(II) dichloride (12 mg, 0.02 mmol) according to the method described in Preparation 62.

The residue was purified using SP1® Purification System (0% to 40%, hexane-ethyl acetate) to give 91 mg (85% yield) of the title compound. Purity 91%.

LRMS (m/z): 640 (M+1)$^+$.

Preparation 68

(S)-2-(1-((5-(3-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (3-fluoro-2-methoxyphenyl)boronic acid (69 mg, 0.4 mmol), sodium carbonate (43 mg, 0.4 mmols) and bis(triphenylphosphine)palladium(II) dichloride (12 mg, 0.02 mmol) according to the method described in Preparation 62. The residue was purified using SP1® Purification System (0% to 100%, dichloromethane-ethyl acetate) to give 79 mg (73% yield) of the title compound. Purity 100%.

LRMS (m/z): 640 (M+1)$^+$.

Preparation 69

2-((1S)-1-((5-(2-Fluoro-6-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (2-fluoro-6-methoxyphenyl)boronic acid (137 mg, 0.81 mmol), sodium carbonate (86 mg, 0.81 mmols) and bis(triphenylphosphine)palladium(II) dichloride (24 mg, 0.03 mmol) according to the method described in Preparation 62. The residue was purified using SP1® Purification System (0% to 100%, dichloromethane-ethyl acetate) to give 50 mg (46% yield) of the title compound. Purity 87%.
LRMS (m/z): 640 (M+1)$^+$.

Preparation 70

Benzyl 4-chloro-7H-pyrrolo[2,3-d]pyrimidine-5-carboxylate

In a three-neck reactor 4-chloro-5-iodo-7H-pyrrolo[2,3-d]pyrimidine (1 g, 3.58 mmol) was dissolved in 36 mL tetrahydrofuran. The mixture was cooled at −78° C. and butyllithium solution (2.5 M in hexane, 3.20 mL, 8 mmol) dissolved in 10 mL was added dropwise over 15 min. The reaction was stirred at −78° C. for 20 min. Then benzyl carbonochloridate (570 μl, 3.99 mmol) was added dropwise. The reaction was stirred overnight. Water was added and the mixture evaporated. The crude was partitioned between ethyl acetate and water, brine, dried over sodium sulphate, filtered and concentrated under reduced pressure. The residue was purified using SP1® Purification System (0% to 20%, hexane-ethyl acetate) to give 490 mg (48% yield) of the title compound. Purity 100%.
LRMS (m/z): 288 (M+1)$^+$.

Preparation 71

(S)-2-(1-((5-(2-Fluorophenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one

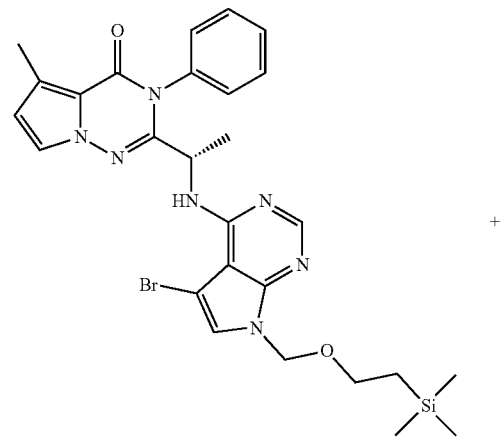

+

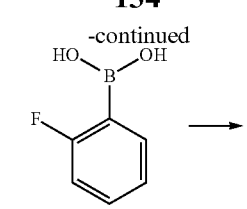

→

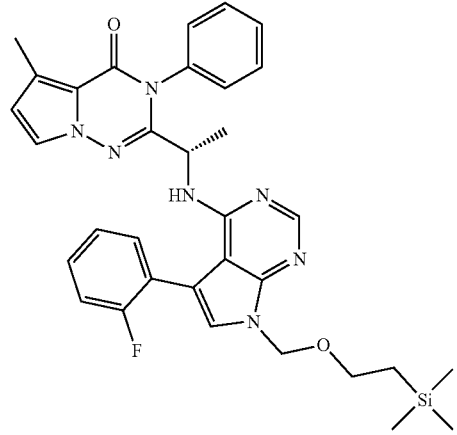

(S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (60 mg, 0.10 mmol) was treated with (2-fluorophenyl)boronic acid (34 mg, 0.24 mmol), sodium carbonate (25 mg, 0.24 mmol) and bis(triphenylphosphine)palladium(II) dichloride (7 mg, 0.01 mmol) according to the method described in Preparation 62. The residue was purified using SP1® Purification System (0% to 20%, hexane-ethyl acetate) to give 34 mg (56% yield) of the title compound. Purity 93%.
LRMS (m/z): 610 (M+1)$^+$.

Preparation 72

(S)-2-(1-((5-(3-Methoxybenzyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (140 mg, 0.17 mmol) was treated with 2-(3-methoxybenzyl)-4,4,5,5-tetramethyl-1,3,2-dioxaborolane (100 mg, 0.17 mmol), cesium carbonate (164 mg, 0.50 mmols) and 1,1'-bis(diphenylphosphino)ferrocene-palladium(II)dichloride dichloromethane complex (14 mg, 0.02 mmol) according to the method described in Preparation 62. The residue was purified using SP1® Purification System (0% to 50%, hexane-ethyl acetate) to obtain 55 mg of the title compound. Purity 50%.
LRMS (m/z): 636 (M+1)$^+$.

Preparation 73

(S)—N-(2-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with N-(2-methoxy-5-(4,4,5,5-tetramethyl-1,3,2-dioxaborolan-2-yl)pyridin-3-yl)methanesulfonamide (132 mg, 0.4 mmol), sodium carbonate (43 mg, 0.41 mmols) and bis(triphenylphosphine)palladium(II) dichloride (12 mg, 0.02 mmol) according to the method described in Preparation 62. The residue was purified using SP1® Purification System (0% to 50%, hexane-ethyl acetate) to give 83 mg (68% yield) of the title compound. Purity 100%.
LRMS (m/z): 716 (M+1)$^+$.

Preparation 74

(S)-2-(1-((5-(5-Amino-6-methoxypyridin-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with 2-methoxy-5-(4,4,5,5-tetramethyl-1,3,2-dioxaborolan-2-yl)pyridin-3-amine (101 mg, 0.4 mmol), sodium carbonate (43 mg, 0.41 mmols) and bis(triphenylphosphine)palladium(II) dichloride (12 mg, 0.02 mmol) according to the method described in Preparation 62. The residue was purified using SP1® Purification System (0% to 30%, hexane-ethyl acetate) to give 63 mg (59% yield) of the title compound. Purity 100%.
LRMS (m/z): 638 (M+1)$^+$.

Preparation 75

(S)-2-(1-((5-(1H-Indazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with 4-(4,4,5,5-tetramethyl-1,3,2-dioxaborolan-2-yl)-1H-indazole (78 mg, 0.32 mmol), sodium carbonate (43 mg, 0.41 mmols) and bis(triphenylphosphine)palladium(II) dichloride (12 mg, 0.02 mmol) according to the method described in Preparation 62. The residue was purified using SP1® Purification System (0% to 50%, hexane-ethyl acetate) to give 44 mg (51% yield) of the title compound. Purity 83%.
LRMS (m/z): 632 (M+1)$^+$.

Preparation 76

(S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with 3-(4,4,5,5-tetramethyl-1,3,2-dioxaborolan-2-yl)-1H-pyrazole (78 mg, 0.32 mmol), sodium carbonate (43 mg, 0.41 mmols) and tetrakis(triphenylphosphine)palladium(0) (12 mg, 0.02 mmol) in 1.5 mL dimethylformamide under argon conditions. The mixture was heated at 130° C. overnight. The mixture was poured into water and was extracted twice with ethyl acetate. The organics were dried over sodium sulphate, filtered and concentrated under reduced pressure. The residue was purified using SP1® Purification System (0% to 30%, hexane-ethyl acetate) to give 39 mg (66% yield) of the title compound. Purity 100%.
LRMS (m/z): 582 (M+1)$^+$.

Preparation 77

(S)-2-(1-((5-(5-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with (5-fluoro-2-methoxyphenyl)boronic acid (55 mg, 0.32 mmol), sodium carbonate (34 mg, 0.32 mmols) and bis(triphenylphosphine)palladium(II) dichloride (10 mg, 0.01 mmol) according to the method described in Preparation 62. The residue was purified using SP1® Purification System (0% to 30%, hexane-ethyl acetate) to give 55 mg (64% yield) of the title compound. Purity 92%.
LRMS (m/z): 640 (M+1)$^+$.

Preparation 78

(S)-2-(1-((5-(6-Methoxypyridin-2-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with 2-methoxy-6-(4,4,5,5-tetramethyl-1,3,2-dioxaborolan-2-yl)pyridine (190 mg, 0.81 mmol), sodium carbonate (86 mg, 0.81 mmols) and bis(triphenylphosphine)palladium(II) dichloride (24 mg, 0.03 mmol) according to the method described in Preparation 62. The residue was purified using SP1® Purification System (0% to 20%, dichloromethane-ethyl acetate) to give 61 mg (59% yield) of the title compound. Purity 632%.
LRMS (m/z): 623 (M+1)$^+$.

Preparation 79

(S)-2-(1-((5-(2-Methoxy-5-methyl phenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (60 mg, 0.10 mmol) was treated with (2-methoxy-5-methylphenyl)boronic acid (42 mg, 0.25 mmol), sodium carbonate (26 mg, 0.25 mmols) and bis(triphenylphosphine)palladium(II) dichloride (8 mg, 0.11 mmol) according to the method described in Preparation 62. The residue was purified using SP1® Purification System (0% to 100%, hexane-ethyl acetate) to give 45 mg (70% yield) of the title compound. Purity 94%.
LRMS (m/z): 636 (M+1)$^+$.

Preparation 80

(S)-2-(1-((5-(1H-Indol-7-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (1H-indol-7-yl)boronic acid (65 mg, 0.28 mmol), sodium carbonate (43 mg, 0.40 mmols) and bis(triphenylphosphine)palladium(II) dichloride (12 mg, 0.02 mmol) according to the method described in Preparation 62. The residue was purified using SP1® Purification System (0% to 25%, hexane-ethyl acetate) to give 91 mg (81% yield) of the title compound. Purity 94%.

LRMS (m/z): 631 (M+1)⁺.

Preparation 81

(S)—N-(3-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (90 mg, 0.15 mmol) was treated with (3-(methylsulfonamido)phenyl)boronic acid (216 mg, 0.73 mmol), sodium carbonate (77 mg, 0.73 mmols) and bis(triphenylphosphine)palladium(II) dichloride (22 mg, 0.03 mmol) according to the method described in Preparation 62. The residue was purified using SP1® Purification System (0% to 25%, dichloromethane-ethyl acetate) to give 79 mg (73% yield) of the title compound. Purity 95%.

LRMS (m/z): 685 (M+1)⁺.

Preparation 82

(S)-2-(1-((6-Bromothieno[2,3-d]pyrimidin-4-yl)amino)ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (219 mg, 0.72 mmol) was treated with 6-bromo-4-chlorothieno[2,3-d]pyrimidine (179 mg, 0.72 mmol), N,N-diisopropylethylamine (751 µl, 4.31 mmol) and tert-butanol as a solvent according to the method described in Example 17. The crude was purified using SP1® Purification (0% to 30%, hexane-ethyl acetate) to give 148 mg (42% yield) of the title compound as a white solid. Purity 97%.

LRMS (m/z): 481, 483 (M+1)⁺

Preparation 83

(S)-2-(1-((6-Amino-5-(3-methoxybenzyl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino)ethyl)-5-methyl-3-phenylpyrrolo[2,1-f][1,2,4]triazin-4(3H)-one (250 mg, 0.57 mmol) was treated with 2-(3-methoxybenzyl)-4,4,5,5-tetramethyl-1,3,2-dioxaborolane (211 mg, 0.85 mmol), sodium carbonate (2M, 1.28 mL, 2.56 mmol) and 1,1'-bis(diphenylphosphino)ferrocene-palladium(II)dichloride dichloromethane complex (70 mg, 0.09 mmol) according to the method described in Example 3 to give 70 mg (26% yield) of the title compound as a solid. Purity 100%.

LRMS (m/z): 482 (M+1)⁺

Preparation 84

(S)-2-(1-((5-(2-Hydroxy-3-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (60 mg, 0.10 mmol) was treated with (2-hydroxy-3-methoxyphenyl)boronic acid (41 mg, 0.24 mmol), sodium carbonate (26 mg, 0.25 mmols) and bis(triphenylphosphine)palladium(II) dichloride (7 mg, 0.01 mmol) according to the method described in Preparation 62. The residue was purified using SP1® Purification System (0% to 50%, hexane-ethyl acetate) to give 71 mg (99% yield) of the title compound. Purity 71%.

LRMS (m/z): 638 (M+1)⁺.

Preparation 85

5-Bromo-4-chloro-7-((2-(trimethylsilyl)ethoxy)methyl)-7H-pyrrolo[2,3-d]pyrimidine Sodium hydride (60% dispersion in mineral oil, 172 mg, 4.3 mmol) was suspended in 5 mL dimethylformamide. The mixture was stirred 10 min and cooled at 0° C. with an ice bath. 4-Chloro-5-iodo-7H-pyrrolo[2,3-d]pyrimidine (1 g, 3.58 mmol) dissolved in 5 mL dimethylformamide was added dropwise and the mixture was stirred 30 min. At the same temperature [2-(chloromethoxy)ethyl](trimethyl)silane (0.8 mL, 4.52 mmol) dissolved in 5 mL dimethylformamide was added dropwise and stirred 30 min at 0° C. The reaction was stirred at room temperature overnight. The mixture was poured into water and extracted twice with ethyl acetate. The organics were dried over sodium sulphate and concentrated under reduced pressure. The solid was washed with hexane, filtered and dried in the oven to give 1.1 g (75% yield) of the title compound as a white solid. Purity 100%.

LRMS (m/z): 410 (M+1)⁺.

Preparation 86

4-Chloro-5-((3-methoxyphenyl)thio)-7-((2-(trimethylsilyl)ethoxy)methyl)-7H-pyrrolo[2,3-d]pyrimidine 5-Bromo-4-chloro-7-((2-(trimethylsilyl)ethoxy)methyl)-7H-pyrrolo[2,3-d]pyrimidine (300 mg, 0.74 mmol) was dissolved in 3 mL dimethylformamide. 3-Methoxybenzenethiol (140 mg, 1.10 mmol), copper(I) iodide (205 mg, 1.1 mmol) and potassium carbonate (152 mg, 1.1 mmol) were added. The reaction vessel was sealed and submitted to three vacuum-nitrogen cycles. The reaction was heated at 70° C. for 5 h. The mixture was poured into water-ice and extracted twice with ethyl acetate. The organics were dried over sodium sulphate, filtered and concentrated under reduced pressure.

Preparation 87

(S)-2-(1-((5-((3-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (60 mg, 0.22 mmol) was treated with 4-chloro-5-((3-methoxyphenyl)thio)-7-((2-(trimethylsilyl)ethoxy)methyl)-7H-pyrrolo[2,3-d]pyrimidine (109 mg, 0.26 mmol), N,N-diisopropylethylamine (195 µl, 1.12 mmol), cesium fluoride (41 mg, 0.27 mmol) and tert-butanol as a solvent according to the method described in Example 17. The crude was purified using SP1® Purification (0% to 50%, hexane-ethyl acetate) to give 51 mg (35% yield) of the title compound as a white solid. Purity 100%.
LRMS (m/z): 654 (M+1)$^+$

Preparation 88

(S)-2-(1-((5-(2-Methoxy-5-(trifluoromethyl)phenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (2-methoxy-5-(trifluoromethyl)phenyl)boronic acid (89 mg, 0.40 mmol), sodium carbonate (43 mg, 0.40 mmols) and bis(triphenylphosphine)palladium(II) dichloride (12 mg, 0.02 mmol) according to the method described in Preparation 62. The residue was purified using SP1® Purification System (0% to 100%, dichloromethane-ethyl acetate) to give 99 mg (85% yield) of the title compound. Purity 100%.
LRMS (m/z): 690 (M+1)$^+$.

Preparation 89

(S)-tert-Butyl (1-(5-((3-methoxyphenyl)thio)-4-oxo-3-phenyl-3,4-dihydropyrrolo[2,1-f][1,2,4]triazin-2-yl)ethyl)carbamate (S)-tert-Butyl (1-(5-iodo-4-oxo-3-phenyl-3,4-dihydropyrrolo[2,1-f][1,2,4]triazin-2-yl)ethyl)carbamate (500 mg, 1.04 mmol) was treated with 3-methoxybenzenethiol (219 mg, 1.56 mmol), potassium carbonate (216 mg, 1.56 mmol) and copper(I) iodide (297 mg, 1.56 mmol) according to the method described in Preparation 44. The residue was purified by reverse phase using Isolera® Purification System to give 154 mg (30% yield) to the title compound. Purity 100%.
LRMS (m/z): 493 (M+1)$^+$

Preparation 90

(S)-2-(1-Aminoethyl)-5-((3-methoxyphenyl)thio)-3-phenyl pyrrolo[2,1-f][1,2,4]triazin-4(3H)-one (S)-tert-Butyl (1-(5-((3-methoxyphenyl)thio)-4-oxo-3-phenyl-3,4-dihydropyrrolo[2,1-f][1,2,4]triazin-2-yl)ethyl)carbamate (154 mg, 0.31 mmol) was treated with trifluoroacetic acid (240 µl, 3.12 mmol) according to the method of Preparation 6 to obtain 103 mg (78% yield) of the title compound as an oil. Purity 92%.
LRMS (m/z): 393 (M+1)$^+$

Preparation 91

4-Amino-6-chloropyrimidine-5-carbonitrile 4,6-Dichloropyrimidine-5-carbonitrile (4.8 g, 27.59 mols) was suspended in 30 mL dioxane and the mixture was cooled at 0° C. in an ice bath. Ammonia solution (7N in methanol, 20 mL, 140 mmol) was added dropwise over 20 min. The mixture was stirred at 0° C. for 30 min. The solvent was evaporated and the crude was re-dissolved in tetrahydrofuran. A precipite was formed and filtered and washed with more tetrahydrofuran. The organics were evaporated under reduced pressure. The residue was purified using a SP1® Purification System (20%-80%, hexane-ethyl acetate) to give 2.38 g (56% yield) of the title compound as a white solid. Purity 100%.
LRMS (m/z): 155 (M+1)$^+$

Preparation 92

(S)-4-Amino-6-((1-(5-((3-methoxyphenyl)thio)-4-oxo-3-phenyl-3,4-dihydropyrrolo[2,1-f][1,2,4]triazin-2-yl)ethyl)amino)pyrimidine-5-carbonitrile (S)-2-(1-Aminoethyl)-5-((3-methoxyphenyl)thio)-3-phenylpyrrolo[2,1-f][1,2,4]triazin-4(3H)-one (103 mg, 0.24 mmol) was treated with 4-amino-6-chloropyrimidine-5-carbonitrile (55 mg, 0.36 mmol),), N,N-diisopropylethylamine (126 µl, 0.72 mmol) and tert-butanol as a solvent according to the method described in Example 17. The crude was purified by reverse phase using SP1® Purification to give 70 mg (57% yield) of the title compound as a white solid. Purity 100%.
LRMS (m/z): 511 (M+1)$^+$

Preparation 93

(S)-tert-Butyl (1-(5-((2-hydroxyphenyl)thio)-4-oxo-3-phenyl-3,4-dihydropyrrolo[2,1-f][1,2,4]triazin-2-yl)ethyl)carbamate (S)-tert-Butyl (1-(5-iodo-4-oxo-3-phenyl-3,4-dihydropyrrolo[2,1-f][1,2,4]triazin-2-yl)ethyl)carbamate (250 mg, 0.52 mmol) was treated with 2-mercaptophenol (80 µl, 0.80 mmol), potassium carbonate (110 mg, 0.8 mmol) and copper (I) iodide (150 mg, 0.79 mmol) according to the method described in Preparation 44. The crude was purified using SP1® Purification System (0%-25%, hexane-ethyl acetate) to give 252 mg (64% yield) to the title compound as an oil.
LRMS (m/z): 479 (M+1)$^+$

Preparation 94

(S)-2-(1-Aminoethyl)-5-((2-hydroxyphenyl)thio)-3-phenylpyrrolo[2,1-f][1,2,4]triazin-4(3H)-one (S)-tert-Butyl (1-(5-((2-hydroxyphenyl)thio)-4-oxo-3-phenyl-3,4-dihydropyrrolo[2,1-f][1,2,4]triazin-2-yl)ethyl)carbamate (252 mg, 0.33 mmol) was treated with a solution of hydrochloric acid in dioxane (4M, 2 mL, 8 mmol) according to the method described in Preparation 1 to obtain 193 mg (99% yield) of the title compound. Purity 99%.
LRMS (m/z): 379 (M+1)$^+$.

Preparation 95

(S)-5-Methyl-2-(1-((5-(1-methyl-1H-pyrazol-4-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with 1-methyl-4-(4,4,5,5-tetramethyl-1,3,2-dioxaborolan-2-yl)-1H-pyrazole (44 mg, 0.21 mmol), sodium carbonate (22 mg, 0.21 mmols) and bis(triphenylphosphine)palladium(II) dichloride (6 mg, 0.01 mmol) according to the method described in Preparation 62. The residue was purified using SP1® Purification System (0% to 50%, hexane-ethyl acetate) to give 37 mg (74% yield) of the title compound. Purity 100%.
LRMS (m/z): 596 (M+1)$^+$.

Preparation 96

(S)-tert-Butyl (1-(5-(3-methoxybenzyl)-4-oxo-3-phenyl-3,4-dihydropyrrolo[2,1-f][1,2,4]triazin-2-yl)ethyl)carbamate (S)-tert-Butyl 1-(5-bromo-4-oxo-3-phenyl-3,4-dihydropyrrolo[1,2-f][1,2,4]triazin-2-yl)ethylcarbamate (150 mg, 0.35 mmol) was treated with 2-(3-methoxybenzyl)-4,4,5,5-tetramethyl-1,3,2-dioxaborolane (205 mg, 0.25 mmol), cesium carbonate (2M, 519 µl, 1.04 mmols) and 1,1'-bis(diphenylphosphino)ferrocene-palladium(II)dichloride dichloromethane complex (30 mg, 0.04 mmol) according to the method described in Preparation 62. The residue was purified using SP1® Purification System (0% to 20%, hexane-ethyl acetate) to obtain 129 mg (94% yield) of the title compound as an oil. Purity 84%.
LRMS (m/z): 475 (M+1)$^+$.

Preparation 97

(S)-2-(1-Aminoethyl)-5-(3-methoxybenzyl)-3-phenylpyrrolo[2,1-f][1,2,4]triazin-4(3H)-one (S)-tert-Butyl (1-(5-(3-methoxybenzyl)-4-oxo-3-phenyl-3,4-dihydropyrrolo[2,1-f][1,2,4]triazin-2-yl)ethyl)carbamate (129 mg, 0.23 mmol) was treated with a solution of hydrochloric acid in dioxane (4M, 2 mL, 8 mmol) according to the method described in Preparation 1 to obtain 120 mg (99% yield) of the title compound as a hydrochloride salt that was used in the following step without further purification.
LRMS (m/z): 375 (M+1)$^+$.

Preparation 98

(S)-2-(1-((5-(1H-Indol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with 4-(4,4,5,5-tetramethyl-1,3,2-dioxaborolan-2-yl)-1H-indole (196 mg, 0.81 mmol), sodium carbonate (86 mg, 0.81 mmols) and bis(triphenylphosphine)palladium(II) dichloride (24 mg, 0.03 mmol) according to the method described in Preparation 62. The residue was purified using SP1® Purification System (0% to 30%, dichloromethane-ethyl acetate) to give 75 mg (65% yield) of the title compound. Purity 89%.
LRMS (m/z): 631 (M+1)$^+$.

Preparation 99

(S)-2-(1-((6-Amino-5-((3-fluoro-4-methoxyphenyl)thio)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (220 mg, 0.45 mmol) and methyl 3-fluoro-4-methoxybenzenethiol (107 mg, 0.68 mmol) were dissolved in 10 mL dimethylformamide in a microwave vessel. Potassium carbonate (94 mg, 0.68 mmol) and copper(I) iodide (129 mg, 0.68 mmol) were added and the mixture was heated overnight at 70° C. The reaction mixture was cooled at room temperature and diluted with ethyl acetate. The organic phase was washed with 2N HCl, 4% sodium bicarbonate solution, water and brine and dried over sodium sulphate, filtered and evaporated under reduced pressure. The residue (0.26 g, 87%) was used in the next synthetic step without further purification. Purity 78%.
LRMS (m/z): 518 (M+1)$^+$.

Preparation 100

(S)-tert-Butyl (1-(5-((3-fluoro-4-methoxyphenyl)thio)-4-oxo-3-phenyl-3,4-dihydropyrrolo[2,1-f][1,2,4]triazin-2-yl)ethyl)carbamate (S)-tert-Butyl (1-(5-iodo-4-oxo-3-phenyl-3,4-dihydropyrrolo[2,1-f][1,2,4]triazin-2-yl)ethyl)carbamate (286 mg, 0.60 mmol) was treated with 3-fluoro-4-methoxybenzenethiol (141 mg, 0.89 mmol), potassium carbonate (123 mg, 0.89 mmol) and copper(I) iodide (170 mg, 0.89 mmol) according to the method described in Preparation 44. The crude was purified using SP1® Purification System (0%-25%, hexane-ethyl acetate) to give 226 mg (71% yield) to the title compound as an oil.
LRMS (m/z): 511 (M+1)$^+$ Preparation 101

(S)-2-(1-Aminoethyl)-5-((3-fluoro-4-methoxyphenyl)thio)-3-phenylpyrrolo[2,1-f][1,2,4]triazin-4(3H)-one (S)-tert-Butyl (1-(5-((3-fluoro-4-methoxyphenyl)thio)-4-oxo-3-phenyl-3,4-dihydropyrrolo[2,1-f][1,2,4]triazin-2-yl)ethyl)carbamate (226 mg, 0.44 mmol) was treated with a solution of hydrochloric acid in dioxane (4M, 2.2 mL, 8.8 mmol) according to the method described in Preparation 1 to obtain 293 mg (95% purity, 98% yield) of the title compound as a hydrochloride salt that was used in the following step without further purification.

LRMS (m/z): 448 (M+1)⁺.

Preparation 102

(S)-4-Amino-6-((1-(5-((3-fluoro-4-methoxyphenyl) thio)-4-oxo-3-phenyl-3,4-dihydropyrrolo[2,1-f][1,2, 4]triazin-2-yl)ethyl)amino)pyrimidine-5-carbonitrile (S)-2-(1-Aminoethyl)-5-((3-fluoro-4-methoxyphenyl) thio)-3-phenylpyrrolo[2,1-f][1,2,4]triazin-4(3H)-one (203 mg, 0.43 mmol), 4-amino-6-chloropyrimidine-5-carbonitrile (102 mg, 0.66 mmol) and DIEA (230 µl, 1.32 mmol) in 10 ml of tert-BuOH were heated at 80° C. for 72 h. After evaporation of the solvent under reduced pressure, the residue (158 mg, 35% yield) was used in the next synthetic step without further purification. Purity 50%.

LRMS (m/z): 529 (M+1)⁺

Preparation 103

4-Amino-6-bromo-N-(3-fluoro-4-hydroxyphenyl) pyrimidine-5-carboxamide a) 4,6-Dichloro-N-(3-fluoro-4-methoxyphenyl)pyrimidine-5-carboxamide 4,6-Dichloropyrimidine-5-carbonyl chloride (890 mg, 4.21 mmol, prepared according to E. V. Tarasov et al. *Synlett* 2000, 5, 625-626) was dissolved in dichloromethane (3 ml) and TEA (587 µl, 4.21 mmol) was added. To this solution, 3-fluoro-4-methoxyaniline (594 mg, 4.21 mmol) dissolved in 3 ml dichloromethane was added dropwise and the mixture was stirred for 30 min. The reaction mixture was then diluted with dichloromethane, washed with 4% sodium bicarbonate solution, dried over magnesium sulphate, filtered and evaporated. The crude was purified using SP1® Purification System (0%-40%, hexane-ethyl acetate) to give 720 mg (56% yield) to the title compound as an oil.

LRMS (m/z): 317 (M+1)⁺ b) 4-Amino-6-chloro-N-(3-fluoro-4-methoxyphenyl) pyrimidine-5-carboxamide 4,6-Dichloro-N-(3-fluoro-4-methoxyphenyl)pyrimidine-5-carboxamide (720 mg, 2.28 mmol) was dissolved in dioxane (10 ml) and cooled in an ice bath. Ammonia solution (1.63 mL, 7N in MeOH) was added dropwise and the mixture was stirred at 0° C. for 6 h and overnight at room temperature. After evaporation of the solvent under reduced pressure, the residue (675 mg, 100%) was used in the next synthetic step without further purification.

LRMS (m/z): 298 (M+1)⁺ c) 4-Amino-6-bromo-N-(3-fluoro-4-hydroxyphenyl) pyrimidine-5-carboxamide

4-Amino-6-chloro-N-(3-fluoro-4-methoxyphenyl)pyrimidine-5-carboxamide (675 mg, 2.28 mmol) was treated with boron tribromide (1M in dichloromethane, 6.80 ml, 6.80 mmol) and using dichloromethane (10 ml) as a solvent according to the method described in Example 23. The solid residue (280 mg, 38% yield) was used in the next synthetic step without further purification. Purity 99%.

LRMS (m/z): 328 (M+1)⁺

Preparation 104

4-Amino-6-bromo-N-(3-fluoro-5-hydroxyphenyl) pyrimidine-5-carboxamide a) 4,6-Dichloro-N-(3-fluoro-5-methoxyphenyl)pyrimidine-5-carboxamide 4,6-Dichloropyrimidine-5-carbonyl chloride (590 mg, 2.79 mmol, prepared according to E. V. Tarasov et al. *Synlett* 2000, 5, 625-626) was dissolved in dichloromethane (3 ml) and TEA (389 µl, 2.79 mmol) was added. To this solution, 3-fluoro-5-methoxyaniline (394 mg, 2.79 mmol) dissolved in 3 ml dichloromethane was added dropwise and the mixture was stirred for 30 min. The reaction mixture was then diluted with dichloromethane, washed with 4% sodium bicarbonate solution, dried over magnesium sulphate, filtered and evaporated. The crude (800 mg, 56% purity, 51% yield) was used in the next synthetic step without further purification.

LRMS (m/z): 317 (M+1)⁺ b) 4-Amino-6-chloro-N-(3-fluoro-5-methoxyphenyl) pyrimidine-5-carboxamide 4,6-Dichloro-N-(3-fluoro-5-methoxyphenyl)pyrimidine-5-carboxamide (800 mg, 1.42 mmol) was dissolved in dioxane (5 ml) and cooled in an ice bath. Ammonia solution (1 ml, 7N in MeOH) was added dropwise and the mixture was stirred at 0° C. for 6 h and overnight at room temperature. After evaporation of the solvent under reduced pressure, the residue (458 mg, 100%) was used in the next synthetic step without further purification.

LRMS (m/z): 298 (M+1)⁺ c) 4-Amino-6-bromo-N-(3-fluoro-5-hydroxyphenyl) pyrimidine-5-carboxamide

4-Amino-6-chloro-N-(3-fluoro-5-methoxyphenyl)pyrimidine-5-carboxamide (458 mg, 1.54 mmol) was treated with boron tribromide (1M in dichloromethane, 0.46 ml, 4.6 mmol) an using dichloromethane (7 ml) as a solvent according to the method described in Example 23. The solid residue (394 mg, 71% yield) was used in the next synthetic step without further purification. Purity 91%.

LRMS (m/z): 328 (M+1)⁺

Preparation 105

N-(3-Hydroxy-5-(4,4,5,5-tetramethyl-1,3,2-dioxaborolan-2-yl)phenyl)methanesulfonamide N-(3-Bromo-5-hydroxyphenyl)methanesulfonamide (0.87 g, 3.27 mmol, prepared as described at C. Cannizzaro et al. U.S. Pat. No. 7,417,055 B2 20080826) was treated with bis(pinacolato)diboron (1.25 g, 4.90 mmol), potassium acetate (0.96 g, 9.81 mmol) and bis(diphenylphosphino)ferrocene-palladium(II)dichloride dichloromethane complex (0.27 g, 0.33 mmol) according to the method described in Preparation 16. The crude was purified using SP1® Purification System (0%-100%, hexane-ethyl acetate) to give 390 mg (31% yield) to the title compound as a solid.

LRMS (m/z): 312 (M−1)⁻

Preparation 106

(S)-2-(1-Aminoethyl)-5-((2-((2-(dimethylamino) ethyl)amino)phenyl)thio)-3-phenylpyrrolo[2,1-f][1,2,4]triazin-4(3H)-one a) (S)-tert-Butyl (1-(5-((2-((2-(dimethylamino)ethyl) amino)phenyl)thio)-4-oxo-3-phenyl-3,4-dihydropyrrolo[2,1-f][1,2,4]triazin-2-yl)ethyl)carbamate (S)-tert-Butyl (1-(5-iodo-4-oxo-3-phenyl-3,4-dihydropyrrolo[2,1-f][1,2,4]triazin-2-yl)ethyl)carbamate (560 mg, 0.87 mmol) was treated with 2-(2-(dimethylamino)ethylamino) benzenethiol (258 mg, 1.31 mmol), potassium carbonate (181 mg, 1.31 mmol) and copper(I) iodide (250 mg, 1.31 mmol) according to the method described in Preparation 44. The crude was purified using SP1® Purification System (0%-100%, hexane-ethyl acetate) to give 432 mg (90% yield) of the title compound as an oil.
LRMS (m/z): 550 (M+1)$^+$ b) (S)-2-(1-Aminoethyl)-5-((2-((2-(dimethylamino) ethyl)amino)phenyl)thio)-3-phenylpyrrolo[2,1-f][1,2,4]triazin-4(3H)-one (S)-tert-Butyl (1-(5-((2-((2-(dimethylamino)ethyl)amino) phenyl)thio)-4-oxo-3-phenyl-3,4-dihydropyrrolo[2,1-f][1,2,4]triazin-2-yl)ethyl)carbamate (432 mg, 0.79 mmol) was treated with a solution of hydrochloric acid in dioxane (4M, 3.9 mL, 15.76 mmol) according to the method described in Preparation 1 to obtain 267 mg (90% purity, 63% yield) of the title compound as a hydrochloride salt that was used in the following step without further purification.
LRMS (m/z): 486 (M+1)$^+$.

Preparation 107

(S)-4-Amino-N-(3,5-dimethoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide a) 4,6-Dichloro-N-(3,5-dimethoxyphenyl)pyrimidine-5-carboxamide 4,6-Dichloropyrimidine-5-carbonyl chloride (590 mg, 2.79 mmol, prepared according to E. V. Tarasov et al. *Synlett* 2000, 5, 625-626) was dissolved in dichloromethane (3 ml) and TEA (283 µl, 2.03 mmol) was added. To this solution, 3,5-dimethoxyaniline (312 mg, 2.04 mmol) dissolved in 3 ml dichloromethane was added dropwise and the mixture was stirred for 60 min. The reaction mixture was then diluted with dichloromethane, washed with 4% sodium bicarbonate solution, dried over magnesium sulphate, filtered and evaporated. The crude (684 mg, 62% purity, 64% yield) was used in the next synthetic step without further purification.
LRMS (m/z): 329 (M+1)$^+$ b) 4-Amino-6-chloro-N-(3,5-dimethoxyphenyl)pyrimidine-5-carboxamide 4,6-Dichloro-N-(3,5-dimethoxyphenyl)pyrimidine-5-carboxamide (684 mg, 1.21 mmol) was dissolved in dioxane (5 ml) and cooled in an ice bath. Ammonia solution (0.86 ml, 7N in MeOH) was added dropwise and the mixture was stirred at 0° C. for 6 h and overnight at room temperature. After dilution with ethyl acetate, this organic phase was washed with water and brine, dried over magnesium sulphate, filtered and the solvents evaporated under reduced pressure, to yield an oil as a residue (575 mg, 66% purity, 100% yield) which was used in the next synthetic step without further purification.
LRMS (m/z): 310 (M+1)$^+$ c) (S)-4-Amino-N-(3,5-dimethoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (200 mg, 0.75 mmol), 4-amino-6-chloro-N-(3,5-dimethoxyphenyl)pyrimidine-5-carboxamide (575 mg, 1.23 mmol), DIEA (650 µl, 3.73 mmol) and cesium fluoride (227 mg, 1.49 mmol) were suspended in tert-butanol (7 ml) and the mixture was heated overnight at 120° C. in a sealed tube. The reaction mixture was diluted with ethyl acetate and washed with water and brine. After evaporation of the solvent, the residue (720 mg, 33% purity, 58% yield) was used in the next synthetic step without further purification.
LRMS (m/z): 542 (M+1)$^+$

Preparation 108

(S)-4-Amino-N-(5-carbamoyl-2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide a) N-(5-Carbamoyl-2-methoxyphenyl)-4,6-dichloropyrimidine-5-carboxamide 4,6-Dichloropyrimidine-5-carbonyl chloride (430 mg, 2.03 mmol, prepared according to E. V. Tarasov et al. *Synlett* 2000, 5, 625-626) was dissolved in dichloromethane (3 ml) and TEA (283 µl, 2.03 mmol) was added. To this solution, 3-amino-4-methoxybenzamide (338 mg, 2.03 mmol) dissolved in 3 ml dichloromethane was added dropwise and the mixture was stirred for 60 min. The reaction mixture was then diluted with dichloromethane, washed with 4% sodium bicarbonate solution, dried over magnesium sulphate, filtered and evaporated. The crude (366 mg, 93% purity, 66% yield) was used in the next synthetic step without further purification.
LRMS (m/z): 329 (M+1)$^+$ b) 4-Amino-N-(5-Carbamoyl-2-methoxyphenyl)-6-dichloropyrimidine-5-carboxamide N-(5-Carbamoyl-2-methoxyphenyl)-4,6-dichloropyrimidine-5-carboxamide (490 mg, 1.44 mmol) was dissolved in dioxane (5 ml) and cooled in an ice bath. Ammonia solution (1.03 ml, 7N in MeOH) was added dropwise and the mixture was stirred at 0° C. for 6 h and overnight at room temperature. After dilution with dichloromethane, this organic phase was successively washed with water and brine, dried over magnesium sulphate, filtered and the solvents evaporated under reduced pressure, to yield a solid as a residue (216 mg, 95% purity, 44% yield) which was used in the next synthetic step without further purification.
LRMS (m/z): 323 (M+1)$^+$ c) (S)-4-Amino-N-(5-carbamoyl-2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (125 mg, 0.44 mmol), 4-amino-N-

(5-carbamoyl-2-methoxyphenyl)-6-chloropyrimidine-5-carboxamide (216 mg, 0.67 mmol), DIEA (385 µl, 2.21 mmol) and cesium fluoride (134 mg, 0.88 mmol) were suspended in tert-butanol (7 ml) and the mixture was heated overnight at 120° C. in a sealed tube. The reaction mixture was diluted with ethyl acetate and washed with water and brine. After evaporation of the solvent, the residue (400 mg, 49% purity, 80% yield) was used in the next synthetic step without further purification.

LRMS (m/z): 555 (M+1)$^+$

Preparation 109

4-Amino-6-chloro-N-(3-morpholinopropyl)pyrimidine-5-carboxamide a) 4,6-Dichloro-N-(3-morpholinopropyl)pyrimidine-5-carboxamide 4,6-Dichloropyrimidine-5-carbonyl chloride (600 mg, 2.84 mmol, prepared according to E. V. Tarasov et al. *Synlett* 2000, 5, 625-626) was dissolved in dichloromethane (10 ml) and TEA (395 µl, 2.83 mmol) was added. To this solution, 3-morpholinopropan-1-amine (410 mg, 2.84 mmol) was added dropwise and the mixture was stirred for 30 min. The reaction mixture was then diluted with dichloromethane, washed with 4% sodium bicarbonate solution, dried over magnesium sulphate, filtered and evaporated. The crude (1.13 g, 87% purity, 100% yield) was used in the next synthetic step without further purification.

LRMS (m/z): 320 (M+1)$^+$ b) 4-Amino-6-chloro-N-(3-morpholinopropyl)pyrimidine-5-carboxamide 4,6-Dichloro-N-(3-morpholinopropyl)pyrimidine-5-carboxamide (1.13 g, 3.08 mmol) was dissolved in dioxane (10 ml) and cooled in an ice bath. Ammonia solution (2.2 ml, 7N in MeOH) was added dropwise and the mixture was stirred at 0° C. for 15 min and 4 h at room temperature. After dilution with ethyl acetate, this organic phase was washed with water and brine, dried over magnesium sulphate, filtered and the solvents evaporated under reduced pressure, to yield an oil which was rejected. The aqueous phase was neutralized with 2N HCl, extracted with DCM, dried over magnesium sulphate, filtered and the solvent evaporated. An oil was obtained (450 mg, 70% purity, 34% yield) which was used in the next synthetic step without further purification.

LRMS (m/z): 301 (M+1)$^+$

Preparation 110

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-methoxybenzenesulfonamide a) 4-Methoxy-N-(3-(4,4,5,5-tetramethyl-1,3,2-dioxaborolan-2-yl)phenyl)benzenesulfonamide 3-(4,4,5,5-Tetramethyl-1,3,2-dioxaborolan-2-yl)aniline (450 mg, 2.05 mmol, prepared as described at Wing Kin Chow et al. *Chemistry—A European Journal*, 2011, 17(25), 6913-6917) was treated with 4-methoxybenzene-1-sulfonyl chloride (850 mg, 4.11 mmol) according to the method described In Preparation 15b to give 788 mg (99% yield) of the title compound as an oil. Purity 99%.

LRMS (m/z): 390 (M+1)$^+$.

b) (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-methoxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (215 mg, 0.49 mmol) was treated with 4-methoxy-N-(3-(4,4,5,5-tetramethyl-1,3,2-dioxaborolan-2-yl)phenyl)benzenesulfonamide (291 mg, 0.75 mmol), sodium carbonate (159 mg, 3.08 mmol) and tetrakis(triphenylphosphino)palladium(0) (29 mg, 0.03 mmol) according to the method described in Example 3 to give 145 mg (48% yield) of the title compound as a solid. Purity 100%.

LRMS (m/z): 623 (M+1)$^+$

Preparation 111

4-Amino-6-bromo-N-(3-hydroxy-4-(oxazol-5-yl)phenyl)pyrimidine-5-carboxamide a) 4,6-Dichloro-N-(3-methoxy-4-(oxazol-5-yl)phenyl)pyrimidine-5-carboxamide 4,6-Dichloropyrimidine-5-carbonyl chloride (600 mg, 2.84 mmol, prepared according to E. V. Tarasov et al. *Synlett* 2000, 5, 625-626) was dissolved in dichloromethane (5 ml) and TEA (395 µl, 2.83 mmol) was added. To this solution, 3-methoxy-4-(oxazol-5-yl)aniline (540 mg, 2.84 mmol, prepared according to S. H. Watterson et al. *Bio. Med. Chem. Lett.* 12 (2002) 2879-2882) in 5 ml DCM was dropwise added and the mixture was stirred for 30 min. The reaction mixture was then diluted with dichloromethane, washed with 4% sodium bicarbonate solution, dried over magnesium sulphate, filtered and evaporated. The crude (844 mg, 87% purity, 71% yield) was used in the next synthetic step without further purification.

LRMS (m/z): 366 (M+1)$^+$ b) 4-Amino-6-chloro-N-(3-methoxy-4-(oxazol-5-yl)phenyl)pyrimidine-5-carboxamide 4,6-Dichloro-N-(3-methoxy-4-(oxazol-5-yl)phenyl)pyrimidine-5-carboxamide (844 mg, 2.01 mmol) was dissolved in dioxane (10 ml) and cooled in an ice bath. Ammonia solution (1.44 ml, 7N in MeOH) was added dropwise and the mixture was stirred at 0° C. for 20 min and 4 h at room temperature. After dilution with ethyl acetate, this organic phase was successively washed with water and brine, dried over magnesium sulphate, filtered and the solvents evaporated under reduced pressure, to yield a solid as a residue (788 mg, 86% purity, 98% yield) which was used in the next synthetic step without further purification.

LRMS (m/z): 355 (M+1)$^+$ c) 4-Amino-6-bromo-N-(3-hydroxy-4-(oxazol-5-yl)phenyl)pyrimidine-5-carboxamide 4-Amino-6-chloro-N-(3-methoxy-4-(oxazol-5-yl)phenyl)pyrimidine-5-carboxamide (788 mg, 1.74 mmol) was treated with boron tribromide (1 M in dichloromethane, 11.8 ml, 11.8 mmol) with dichloromethane (10 ml) as a solvent according to the method described in Example 23. In this reaction conditions the chlorine atom was transformed into bromine. The solid residue (220 mg, 33% yield) was used in the next synthetic step without further purification. Purity 99%.

LRMS (m/z): 377 (M+1)$^+$

Preparation 112

(S)-4-Amino-N-(3-methoxybenzyl)-6-((1-(5-methyl-4-oxo-3-phenyl-3,4-dihydropyrrolo[2,1-f][1,2,4]triazin-2-yl)ethyl)amino)pyrimidine-5-carboxamide a) 4,6-Dichloro-N-(3-methoxybenzyl)pyrimidine-5-carboxamide 4,6-Dichloropyrimidine-5-carbonyl chloride (587 mg, 2.78 mmol, prepared according to E. V. Tarasov et al. *Synlett* 2000, 5, 625-626) was dissolved in dichloromethane (2.5 ml) and TEA (400 μl, 2.87 mmol) was added. To this solution, (3-methoxyphenyl)methanamine (379 mg, 2.76 mmol) in 3 ml DCM was added dropwise and the mixture was stirred for 30 min at room temperature. The reaction mixture was then diluted with dichloromethane, washed with 4% sodium bicarbonate solution, dried over magnesium sulphate, filtered and evaporated. After evaporation of the solvent, the residue was purified by flash chromatography using SP1® Purification System (10% to 30%, hexane-ethyl acetate) to obtain 534 mg (61% yield) of the title compound.

LRMS (m/z): 313 (M+1)$^+$ b) 4-Amino-6-chloro-N-(3-methoxybenzyl)pyrimidine-5-carboxamide 4,6-Dichloro-N-(3-methoxybenzyl)pyrimidine-5-carboxamide (523 mg, 1.68 mmol) was dissolved in dioxane (8 ml) and cooled in an ice bath. Ammonia solution (1.2 ml, 8.40 mmol, 7N in MeOH) was added dropwise and the mixture was stirred at 0° C. for 6 h. After evaporation of the solvent under reduced pressure, the residue was suspended in ethyl acetate and filtered, washing several times with ethyl acetate. The organics were evaporated under reduced pressure to yield the final compound as a solid (424 mg, 97% purity, 84% yield) which was used in the next synthetic step without further purification.

LRMS (m/z): 293 (M+1)$^+$ c) (S)-4-Amino-N-(3-methoxybenzyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (92 mg, 0.34 mmol), 4-amino-6-chloro-N-(3-methoxybenzyl)pyrimidine-5-carboxamide (100 mg, 0.34 mmol), DIEA (360 μl, 2.07 mmol) and cesium fluoride (157 mg, 1.03 mmol) were suspended in tert-butanol (10 ml) and the mixture was heated to reflux for 48 h. The solvent was evaporated under reduced pressure and the crude was diluted with ethyl acetate and washed with saturated ammonium chloride solution and brine. After evaporation of the solvent, the residue was purified by flash chromatography using SP1® Purification System (0% to 40%, dichloromethane-ethyl acetate) to obtain 106 mg (59% yield) of the title compound.

LRMS (m/z): 525 (M+1)$^+$

Preparation 113

(S)-4-Amino-N-(2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide a) 4,6-Dichloro-N-(2-methoxyphenyl)pyrimidine-5-carboxamide 4,6-Dichloropyrimidine-5-carbonyl chloride (587 mg, 2.78 mmol, prepared according to E. V. Tarasov et al. *Synlett* 2000, 5, 625-626) was dissolved in dichloromethane (2.5 ml) and TEA (400 μl, 2.87 mmol) was added. To this solution, 2-methoxyaniline (340 mg, 2.76 mmol) in 3 ml DCM was added dropwise and the mixture was stirred for 30 min at room temperature. The reaction mixture was then diluted with dichloromethane, washed with 4% sodium bicarbonate solution, dried over magnesium sulphate, filtered and evaporated. After evaporation of the solvent, the residue was purified by flash chromatography using SP1® Purification System (10% to 40%, hexane-ethyl acetate) to obtain 630 mg (77% yield) of the title compound.

LRMS (m/z): 299 (M+1)$^+$ b) 4-Amino-6-chloro-N-(2-methoxyphenyl)pyrimidine-5-carboxamide 4,6-Dichloro-N-(2-methoxyphenyl)pyrimidine-5-carboxamide (506 mg, 1.70 mmol) was dissolved in dioxane (8 ml) and cooled in an ice bath. Ammonia solution (1.25 ml, 8.75 mmol, 7N in MeOH) was added dropwise and the mixture was stirred at 0° C. for 6 h. After evaporation of the solvent under reduced pressure, the residue was suspended in ethyl acetate and filtered, washing successively with ethyl acetate. The solvent of the filtrate is evaporated under reduced pressure to yield the final compound as a solid (454 mg, 93% purity, 89% yield) which was used in the next synthetic step without further purification.

LRMS (m/z): 279 (M+1)$^+$ c) (S)-4-Amino-N-(2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (97 mg, 0.36 mmol), 4-amino-6-chloro-N-(2-methoxyphenyl)pyrimidine-5-carboxamide (100 mg, 0.36 mmol), DIEA (400 μl, 2.3 mmol) and cesium fluoride (166 mg, 1.09 mmol) were suspended in tert-butanol (10 ml) and the mixture was heated at 150° C. in a microwave oven for 35 min. The solvent was evaporated under reduced pressure and the reaction mixture was diluted with ethyl acetate and washed with saturated ammonium chloride solution and brine. After evaporation of the solvent, the residue was purified by flash chromatography using SP1® Purification System (30% to 70%, dichloromethane-ethyl acetate) to obtain 67 mg (37% yield) of the title compound.

LRMS (m/z): 511 (M+1)$^+$

Preparation 114

(S)—N-(3-Methoxyphenyl)-4-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (15 mg, 0.06 mmol), 4-chloro-N-(3- methoxyphenyl)pyrimidine-5-carboxamide (14 mg, 0.05 mmol, prepared according to R. Tadiparthi et al PCT Int. Appl. 2007031829, 22 Mar. 2007), DIEA (50 µl, 0.29 mmol) and cesium fluoride (17 mg, 0.11 mmol) were suspended in tert-butanol (2 ml) and the mixture was heated at 120° C. in a sealed tube for 18 h. The solvent was evaporated under reduced pressure and the reaction mixture was diluted with ethyl acetate and washed with saturated ammonium chloride solution and brine. After evaporation of the solvent, the residue was purified by flash chromatography using SP1® Purification System (0% to 10%, dichloromethane-methanol) to obtain 6 mg (5% yield) of the title compound.

LRMS (m/z): 496 (M+1)$^+$

Preparation 115

(S)-4-Amino-6-((1-(5-methyl-4-oxo-3-phenyl-3,4-dihydropyrrolo[2,1-f][1,2,4]triazin-2-yl)ethyl)amino)pyrimidine-5-carboxylic acid (S)-2-(1-Aminoethyl)-5-methyl-3-phenylpyrrolo[2,1-f][1,2,4]triazin-4(3H)-one (270 mg, 0.89 mmol), 4-amino-6-chloropyrimidine-5-carboxylic acid (190 mg, 0.88 mmol, prepared according to Lan, Ruoxi et al from PCT Int. Appl. (2013), WO 2013040059 A1 20130321), DIEA (1.54 ml, 8.84 mmol) and cesium fluoride (403 mg, 2.65 mmol) were suspended in ethanol (10 ml) and the mixture was heated to reflux for 72 h. The solvent was evaporated under reduced pressure and the residue was purified by flash chromatography using SP1® Purification System (0% to 70%, ethyl acetate-methanol) to obtain 106 mg (27% yield) of the title compound. Purity: 90%.

LRMS (m/z): 406 (M+1)$^+$

Preparation 116

5-Amino-2-(3-(dimethylamino)propoxy)phenol a) 3-(2-Methoxy-4-nitrophenoxy)-N, N-dimethyl propan-1-amine 3-(Dimethylamino)propan-1-ol (1 g, 10.6 mmol) was dissolved in dimethylsulfoxide (20 ml) and sodium hydride (0.42 g, 10.5 mmol) was added. After stirring at room temperature for 15 min, 1-chloro-2-methoxy-4-nitrobenzene (1 g, 5.3 mmol) in dimethylsulfoxide (10 ml) was added and the reaction mixture stirred 4 h at room temperature. The reaction mixture was diluted with water, extracted with ethyl acetate, and the organic phase dried over magnesium sulphate and filtered. After evaporation of the solvent, the residue was purified by flash chromatography using SP1® Purification System (0% to 85%, ethyl acetate-methanol) to obtain 480 mg (34% yield) of the title compound as an oil.

LRMS (m/z): 255 (M+1)$^+$ b) 2-(3-(Dimethylamino)propoxy)-5-nitrophenol 3-(2-Methoxy-4-nitrophenoxy)-N,N-dimethylpropan-1-amine (480 mg, 1.89 mmol) was heated at 100° C. overnight in 3 ml of bromhydric acid (48% in water). Once at room temperature, 4% sodium bicarbonate solution was added and extracted with ethyl acetate. The organic phase was successively washed with water and brine, dried over magnesium sulphate, filtered and the solvent evaporated under reduced pressure. 0.22 mg (44% yield) of the title compound were obtained and used in the next synthetic step without further purification. Purity: 91%

LRMS (m/z): 241 (M+1)$^+$ c) 5-Amino-2-(3-(dimethylamino)propoxy)phenol 2-(3-(Dimethylamino)propoxy)-5-nitrophenol (220 mg 0.92 mmol), ammonium chloride (232 mg, 4.34 mmol) and powdered iron (242 mg, 4.33 mmol) were suspended in THF (5 ml) and water (10 ml) and the mixture was stirred at 70° C. overnight. The reaction mixture was diluted with water, neutralised to pH=6 with sodium carbonate and extracted with ethyl acetate (×3). The organic phase was washed successively with water and brine, dried over magnesium sulphate, filtered and the solvent evaporated under reduced pressure. 75 mg (24% yield, 61% purity) of the title compound were obtained and used in the next synthetic step without further purification.

LRMS (m/z): 211 (M+1)$^+$

Preparation 117

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-methoxybenzenesulfonamide a) N-(3-bromo-5-hydroxyphenyl)-4-methoxybenzenesulfonamide 3-Amino-5-bromophenol (0.75 g, 3.99 mmol, prepared according to WO 2011119704 A1 20110929) was treated with 4-methoxybenzene-1-sulfonyl chloride (1.61 g, 7.79 mmol) according to the method described In Preparation 15b to give 1.24 g (77% yield) of the title compound as an oil. Purity 89%.

LRMS (m/z): 359 (M+1)$^+$.

b) N-(3-Hydroxy-5-(4,4,5,5-tetramethyl-1,3,2-dioxaborolan-2-yl)phenyl)-4-methoxybenzenesulfonamide N-(3-Bromo-5-hydroxyphenyl)-4-methoxybenzenesulfonamide (1.21 g, 3.38 mmol), bis(pinacolato)diboron (1.29 g, 5.08 mmol), potassium acetate (0.99 g, 10.12 mmol), and bis(diphenylphosphino)ferrocene-palladium(II)dichloride dichloromethane complex (0.28 g, 0.34 mmol) were suspended in dioxane (30 ml) and the mixture heated to 140° C. for 20 min under microwave conditions. After usual workup with water and ethyl acetate, the reaction crude was purified by flash chromatography using SP1® Purification System (0% to 50%, hexane-ethyl acetate) to obtain 0.33 g of the title compound as an oil. (19% yield). Purity: 80%.

LRMS (m/z): 406 (M+1)$^+$ c) (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-methoxybenzenesulfonamide (S)-2-(1-((6-Amino-5-iodopyrimidin-4-yl)amino)ethyl)-5-methyl-3-phenylpyrrolo[2,1-f][1,2,4]triazin-4(3H)-one (70 mg, 0.14 mmol) was treated with N-(3-hydroxy-5-(4,4,5,5-tetramethyl-1,3,2-dioxaborolan-2-yl)phenyl)-4-methoxybenzenesulfonamide (87 mg, 0.21 mmol), 2M sodium carbonate (216 µl, 0.43 mmol) and tetrakis(triphenylphosphino)palladium(0) (8 mg, 0.01 mmol) according to the method

Preparation 118

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-methoxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (65 mg, 0.15 mmol) was treated with 4-methoxy-N-(5-(4,4,5,5-tetramethyl-1,3,2-dioxaborolan-2-yl)pyridin-3-yl)benzenesulfonamide (87 mg, 0.22 mmol, prepared from 5-(4,4,5,5-tetramethyl-1,3,2-dioxaborolan-2-yl)-3-pyridinamine, as described in WO 2009155527 A2 20091223, and 4-methoxybenzene-1-sulfonyl chloride according to the method described In Preparation 15b), 2M sodium carbonate (221 μl, 0.44 mmol) and tetrakis(triphenylphosphino)palladium(0) (9 mg, 0.01 mmol) according to the method described in Example 3 to give 92 mg (76% yield) of the title compound as a solid. Purity 53%.

LRMS (m/z): 624 (M+1)$^+$

Preparation 119

2,4-Difluoro-N-(3-hydroxy-5-(4,4,5,5-tetramethyl-1,3,2-dioxaborolan-2-yl)phenyl)benzenesulfonamide a) N-(3-Bromo-5-hydroxyphenyl)-2,4-difluorobenzenesulfonamide

3-Amino-5-bromophenol (600 mg, 2.87 mmol, prepared according to WO 2011119704 A1 20110929) was treated with 2,4-difluorobenzene-1-sulfonyl chloride (386 μl, 2.87 mmol) according to the method described in Preparation 15b to give 1.27 g (99% yield) of the title compound as an oil. Purity 70%.

LRMS (m/z): 365 (M+1)$^+$.

b) 2,4-Difluoro-N-(3-hydroxy-5-(4,4,5,5-tetramethyl-1,3,2-dioxaborolan-2-yl)phenyl)benzenesulfonamide N-(3-Bromo-5-hydroxyphenyl)-2,4-difluorobenzenesulfonamide (1.23 g, 3.38 mmol), bis(pinacolato)diboron (1.72 g, 6.77 mmol), potassium acetate (1.0 g, 10.19 mmol), diphenylphosphino)ferrocene (0.19 g, 0.34 mmol) and bis(diphenylphosphino)ferrocene-palladium(II)dichloride dichloromethane complex (0.28 g, 0.34 mmol) were suspended in dioxane (50 ml) and heated overnight at 100° C. After usual work-up with water and ethyl acetate, the reaction crude was purified by flash chromatography using SP1® Purification System (0% to 5%, dichloromethane-methanol) to obtain 1.09 g of the title compound as an oil. (67% yield). Purity: 88%.

LRMS (m/z): 406 (M+1)$^+$

Preparation 120

2,4-Difluoro-N-(3-hydroxy-5-(4,4,5,5-tetramethyl-1,3,2-dioxaborolan-2-yl)pyridine-3-yl)benzenesulfonamide a) N-(5-Bromopyridin-3-yl)-2,4-difluorobenzenesulfonamide

5-Bromopyridin-3-amine (500 mg, 2.89 mmol) was treated with 2,4-difluorobenzene-1-sulfonyl chloride (390 μl, 2.90 mmol) according to the method described in Preparation 15b to give 1.03 g (100% yield) of the title compound as an oil. Purity 74%.

LRMS (m/z): 350 (M+1)$^+$.

b) 2,4-Difluoro-N-(3-hydroxy-5-(4,4,5,5-tetramethyl-1,3,2-dioxaborolan-2-yl)pyridine-3-yl)benzenesulfonamide N-(3-Bromopyridin-3-yl)-2,4-difluorobenzenesulfonamide (705 mg, 2.02 mmol), bis(pinacolato)diboron (780 mg, 3.07 mmol), potassium acetate (115 mg, 1.17 mmol), and bis(diphenylphosphino)ferrocene-palladium(II)dichloride dichloromethane complex (740 mg, 0.91 mmol) were suspended in dioxane (5 ml) and heated overnight at 100° C. After evaporation of the solvent under reduced pressure, ethyl acetate (20 ml) was added to the residue and the precipitated salts were eliminated by filtration. The solvent was evaporated under reduced pressure and hexane (30 ml) was added to the residue. The solid formed was filtered off and this operation was repeated with the organic phase (another 30 ml of hexane were added after evaporation), to obtain 1.12 g (97% yield, 40% purity), which was used in the next synthetic step without further purification.

LRMS (m/z): 397 (M+1)$^+$

Preparation 121

4-Hydroxy-N-(2-methoxy-5-(4,4,5,5-tetramethyl-1,3,2-dioxaborolan-2-yl)pyridine-3-yl)benzenesulfonamide a) N-(5-Bromo-2-chloropyridin-3-yl)-4-methoxybenzenesulfonamide

5-Bromo-2-chloropyridin-3-amine (1 g, 4.82 mmol) was dissolved in THF (5.5 ml) and a solution of sodium bis(trimethylsilyl)amide (1M in THF, 14.5 ml, 14.5 mmol) was added dropwise. Ten minutes later, 4-methoxybenzene-1-sulfonyl chloride (3 g, 14.5 mmol) was added and the reaction mixture stirred for 2 h. A saturated solution of sodium bicarbonate was then added dropwise and the reaction mixture extracted with dichloromethane (×3). The organic phase was dried over magnesium sulphate, filtered and the solvent evaporated under reduced pressure. The resulting crude was purified by flash chromatography using SP1® Purification System (0% to 10%, dichloromethane-ethyl acetate) to obtain 1.49 g (82% yield) of the title compound. Purity: 100%

LRMS (m/z): 378 (M+1)$^+$.

b) N-(5-Bromo-2-chloropyridin-3-yl)-4-hydroxybenzenesulfonamide

N-(5-Bromo-2-chloropyridin-3-yl)-4-methoxybenzenesulfonamide (1.49 g, 3.95 mmol) was treated with boron tribromide (1M in dichloromethane, 20 ml, 20 mmol) with dichloromethane (10 ml) as a solvent according to the method described in Example 23. The resulting crude was purified by flash chromatography using SP1® Purification System (0% to 30%, dichloromethane-ethyl acetate) to obtain 0.6 g (42% yield) of the title compound. Purity: 100%

LRMS (m/z): 364 (M+1)$^+$ c) N-(5-Bromo-2-methoxypyridin-3-yl)-4-hydroxybenzenesulfonamide

N-(5-Bromo-2-chloropyridin-3-yl)-4-hydroxybenzenesulfonamide (587 mg, 1.61 mmol) and sodium methoxide (25% in methanol, 10 ml, 43.73 mmol) were stirred at 120° C. for 20 min under microwave conditions. The reaction mixture was poured into sodium bicarbonate saturated solution, neutralized with concentrated chlorhydric acid and extracted with ethyl acetate (×3). The organic phase was dried over magnesium sulphate, filtered and the solvent evaporated under reduced pressure to obtain 475 mg (82% yield, 100% purity) of the title compound, which was used in the next synthetic step without further purification.
LRMS (m/z): 360 (M+1)+ d) 4-Hydroxy-N-(2-methoxy-5-(4,4,5,5-tetramethyl-1,3,2-dioxaborolan-2-yl)pyridine-3-yl)benzenesulfonamide N-(5-Bromo-2-methoxypyridin-3-yl)-4-hydroxybenzenesulfonamide (475 mg, 1.32 mmol), bis(pinacolato)diboron (437 mg, 1.72 mmol), potassium acetate (390 mg, 3.97 mmol), and bis(diphenylphosphino)ferrocene-palladium(II) dichloride dichloromethane complex (81 mg, 0.10 mmol) were suspended in dioxane (14 ml) and stirred overnight at 100° C. After evaporation of the solvent under reduced pressure, ethyl acetate (20 ml) was added to the residue and the precipitated salts were eliminated by filtration. The organics were washed with water and brine, dried over magnesium sulphate and evaporated under reduced pressure. The resulting crude was purified by flash chromatography using SP1® Purification System (0% to 30%, dichloromethane-ethyl acetate) to obtain 272 mg (51% yield) of the title compound. Purity: 100%
LRMS (m/z): 407 (M+1)+

Preparation 122

(S)-2-(1-(5-Bromo-7-((2-(trimethylsilyl)ethoxy)methyl)-7H-pyrrolo[2,3-d]pyrimidin-4-ylamino)ethyl)-3-phenylpyrrolo[2,1-f][1,2,4]triazin-4(3H)-one (S)-2-(1-Aminoethyl)-3-phenylpyrrolo[2,1-f][1,2,4]triazin-4(3H)-one (370 mg, 1.46 mmol) was treated with 5-bromo-4-chloro-7-((2-(trimethylsilyl)ethoxy)methyl)-7H-pyrrolo[2,3-d]pyrimidine (793 mg, 2.19 mmol), cesium fluoride (120 mg, 0.79 mmol), N,N-diisopropylethylamine (2.3 ml, 13.20 mol) and tert-butanol (10 ml) as a solvent according to Preparation 13. The residue was purified using SP1® Purification System (0% to 35%, hexane-ethyl acetate) to give 0.61 g (72% yield) of the title compound. Purity 100%.
LRMS (m/z): 581 (M+1)+.

Preparation 123

(S)—N-(3-hydroxy-5-(4-((1-(4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (160 mg, 0.28 mmol) was treated with N-(3-hydroxy-5-(4,4,5,5-tetramethyl-1,3,2-dioxaborolan-2-yl)phenyl)methanesulfonamide (220 mg, 0.70 mmol), sodium carbonate (86.3 mg, 0.81 mmols) and bis(triphenylphosphine)palladium(II) dichloride (81.8 mg, 0.1 mmol) according to the method described in Preparation 62. The residue was purified using SP1® Purification System (0% to 80%, hexane-ethyl acetate) to give 160 mg (79% yield) of the title compound. Purity 94%.
LRMS (m/z): 687 (M+1)+.

Preparation 124

4-Fluoro-N-(3-hydroxy-5-(4,4,5,5-tetramethyl-1,3,2-dioxaborolan-2-yl)phenyl)benzenesulfonamide a) N-(3-Bromo-5-hydroxyphenyl)-4-fluorobenzenesulfonamide 3-Amino-5-bromophenol (300 mg, 1.4 mmol, prepared according to WO 2011119704 A1 20110929) was treated with 4-fluorobenzene-1-sulfonyl chloride (326 mg, 1.68 mmol) according to the method described in Preparation 15b to give 507 mg (99% yield) of the title compound as an oil. Purity 70%.
LRMS (m/z): 347 (M+1)+.

b) 4-Fluoro-N-(3-hydroxy-5-(4,4,5,5-tetramethyl-1,3,2-dioxaborolan-2-yl)phenyl)benzenesulfonamide N-(3-Bromo-5-hydroxyphenyl)-4-fluorobenzenesulfonamide (507 mg, 1.46 mmol), bis(pinacolato)diboron (558 mg, 2.20 mmol), potassium acetate (435 mg, 4.43 mmol), and bis(diphenylphosphino)ferrocene-palladium(II)dichloride dichloromethane complex (121 mg, 0.15 mmol) were suspended in dioxane (14 ml) and heated to 100° C. for 4.5 h. After usual work-up with water and ethyl acetate, the reaction crude was purified by flash chromatography using SP1® Purification System (0% to 50%, dichloromethane-ethyl acetate) to obtain 349 mg of the title compound as an oil. (60% yield). Purity: 100%.
LRMS (m/z): 394 (M+1)+

Preparation 125

N-(3-Fluoro-5-(4,4,5,5-tetramethyl-1,3,2-dioxaborolan-2-yl)phenyl)-4-hydroxybenzenesulfonamide a) N-(3-Bromo-5-fluorophenyl)-4-methoxybenzenesulfonamide 3-Bromo-5-fluoroaniline (500 mg, 2.63 mmol) was treated with 4-methoxybenzene-1-sulfonyl chloride (572 mg, 2.77 mmol) according to the method described in Preparation 15b to give 832 mg (88% yield) of the title compound as an oil. Purity 70%.
LRMS (m/z): 361 (M+1)+.

b) N-(3-Bromo-5-fluorophenyl)-4-hydroxybenzenesulfonamide

N-(3-Bromo-5-fluorophenyl)-4-methoxybenzenesulfonamide (507 mg, 1.41 mmol) was treated with boron tribromide (1M in dichloromethane, 7.0 ml, 7 mmol) using dichloromethane (10 ml) as a solvent according to the method described in Example 23. The resulting crude was purified by flash chromatography using SP1® Purification System (0% to 40%, dichloromethane-ethyl acetate) to obtain 480 mg (99% yield) of the title compound. Purity: 100%
LRMS (m/z): 347 (M+1)+ c) N-(3-Fluoro-5-(4,4,5,5-tetramethyl-1,3,2-dioxaborolan-2-yl)phenyl)-4-hydroxybenzenesulfonamide N-(3-Bromo-5-fluorophenyl)-4-hydroxybenzenesulfonamide (480 mg, 1.39 mmol), bis(pinacolato)diboron (532 mg, 2.09 mmol), potassium acetate (412 mg, 4.2 mmol), and bis(diphenylphosphino)ferrocene-palladium(II)dichloride dichloromethane complex (115 mg, 0.14 mmol) were suspended in dioxane (10 ml) and heated to 100° C. for 2 h. After usual work-up with water and ethyl acetate, the reaction crude was purified by flash chromatography using SP1® Purification System (0% to 50%, dichloromethane-ethyl acetate) to obtain 348 mg of the title compound as an oil. (64% yield). Purity: 100%.

LRMS (m/z): 394 (M+1)+

Preparation 126

(S)—N-(4-(4-((1-(4-Oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (125 mg, 0.22 mmol) was treated with N-(4-(4,4,5,5-tetramethyl-1,3,2-dioxaborolan-2-yl)-1H-indol-6-yl)methanesulfonamide (187 mg, 0.56 mmol, prepared from N-(4-bromo)-1H-indol-6-yl) methanesulfonamide, which is described at WO 2009147188 A1 20091210, and bis(pinacolato)diboron according to Preparation 119b), sodium carbonate (60 mg, 0.57 mmols) and bis(triphenylphosphine)palladium(II) dichloride (50 mg, 0.06 mmol) according to the method described in Preparation 62. The residue was purified using SP1® Purification System (0% to 80%, hexane-ethyl acetate) to give 152 mg (98% yield) of the title compound. Purity 98%.

LRMS (m/z): 710 (M+1)+.

Preparation 127

(S)—N-(4-Hydroxy-3-(4-((1-(5-methyl-4-oxo-3-phenyl-3,4-dihydropyrrolo[2,1-f][1,2,4]triazin-2-yl) ethyl)amino)-7-((2-(trimethylsilyl)ethoxy)methyl)-7H-pyrrolo[2,3-d]pyrimidin-5-yl)phenyl) methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with 2-hydroxy-5-(methylsulfonamido)phenylboronic acid (95 mg, 0.41 mmol, described at WO 2012013727 A1 20120202), sodium carbonate (52 mg, 0.49 mmols) and bis(triphenylphosphine)palladium(II) dichloride (41 mg, 0.05 mmol) according to the method described in Preparation 62. The residue was purified using SP1® Purification System (0% to 100%, hexane-ethyl ether) to give 102 mg (87% yield) of the title compound. Purity 100%.

LRMS (m/z): 701 (M+1)+.

Preparation 128

(S)-3-(Methylsulfonamido)-5-(4-((1-(4-oxo-3-phenyl-3,4-dihydropyrrolo[2,1-f][1,2,4]triazin-2-yl) ethyl)amino)-7-((2-(trimethylsilyl)ethoxy)methyl)-7H-pyrrolo[2,3-d]pyrimidin-5-yl)phenyl methanesulfonate (S)-2-(1-((5-Bromo-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (170 mg, 0.29 mmol) was treated with 3-(methylsulfonamido)-5-(4,4,5,5-tetramethyl-1,3,2-dioxaborolan-2-yl)phenyl methanesulfonate (230 mg, 0.73 mmol, prepared from the title compound of Preparation 105 and methanesulfonyl chloride according to Preparation 37), sodium carbonate (95 mg, 3.06 mmols) and bis(triphenylphosphine)palladium(II) dichloride (70 mg, 0.09 mmol) according to the method described in Preparation 62. The residue was purified using SP1® Purification System (0% to 80%, hexane-ethyl acetate) to give 82 mg (37% yield) of the title compound. Purity 98%.

LRMS (m/z): 765 (M+1)+.

Preparation 129

(S)—N-(3-Fluoro-5-(4-((1-(5-methyl-4-oxo-3-phenyl-3,4-dihydropyrrolo[2,1-f][1,2,4]triazin-2-yl) ethyl)amino)-7-((2-(trimethylsilyl)ethoxy)methyl)-7H-pyrrolo[2,3-d]pyrimidin-5-yl)phenyl) methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with N-(3-fluoro-5-(4,4,5,5-tetramethyl-1,3,2-dioxaborolan-2-yl)phenyl)methanesulfonamide (67 mg, 0.21 mmol, described at WO 2004052847 A2 20040624), sodium carbonate (23 mg, 0.22 mmols) and bis (triphenylphosphine)palladium(II) dichloride (21 mg, 0.03 mmol) according to the method described in Preparation 62. The residue was purified using SP1® Purification System (0% to 100%, hexane-ethyl ether) to give 36 mg (61% yield) of the title compound. Purity 100%.

LRMS (m/z): 703 (M+1)+.

Preparation 130

(S)—N-Methyl-N-(3-(4-((1-(5-methyl-4-oxo-3-phenyl-3,4-dihydropyrrolo[2,1-f][1,2,4]triazin-2-yl) ethyl)amino)-7-((2-(trimethylsilyl)ethoxy)methyl)-7H-pyrrolo[2,3-d]pyrimidin-5-yl)phenyl) methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (131 mg, 0.22 mmol) was treated with N-methyl-N-(3-(4,4,5,5-tetramethyl-1,3,2-dioxaborolan-2-yl)phenyl)methanesulfonamide (170 mg, 0.55 mmol, prepared according to WO 2006015829 A1 20060216), sodium carbonate (62 mg, 0.58 mmols) and bis(triphenylphosphine)palladium(II) dichloride (55 mg, 0.07 mmol) according to the method described in Preparation 62. The residue was purified using SP1® Purification System (0% to 100%, hexane-ethyl ether) to give 143 mg (92% yield) of the title compound. Purity 99%.

LRMS (m/z): 699 (M+1)+.

Preparation 131

(S)—N-(3-(4-((1-(5-Methyl-4-oxo-3-phenyl-3,4-dihydropyrrolo[2,1-f][1,2,4]triazin-2-yl)ethyl) amino)-7-((2-(trimethylsilyl)ethoxy)methyl)-7H-pyrrolo[2,3-d]pyrimidin-5-yl)-5-morpholinophenyl) methanesulfonamide a) 3-Iodo-5-morpholinoaniline 4-(3-Iodo-5-nitrophenyl)morpholine (200 mg, 0.60 mmol, prepared according to WO 2008104754 A1 20080904) and powdered iron (142 mg, 2.54 mmol) were suspended in ethanol (2 ml) and acetic acid (240 μl, 4.20 mmol) and heated 3 h to 95° C. The reaction mixture was diluted with water, neutralised to pH=6 with sodium carbonate and extracted with ethyl acetate (×3). The organic phase was washed successively with water and brine, dried over magnesium sulphate, filtered and the solvent evaporated under reduced pressure. 179 mg (81% yield, 82% purity) of the title compound were obtained and used in the next synthetic step without further purification.

LRMS (m/z): 305 (M+1)$^+$ b) N-(3-Iodo-5-morpholinophenyl)methanesulfonamide

3-Iodo-5-morpholinoaniline (279 mg, 0.76 mmol) was treated with methanesulfonyl chloride (82 μl, 1.06 mmol) according to the method described in Preparation 15b to give 305 mg (95% yield) of the title compound as an oil. Purity 90%.

LRMS (m/z): 383 (M+1)$^+$.

c) N-(3-morpholino-5-(4,4,5,5-tetramethyl-1,3,2-dioxaborolan-2-yl)phenyl)methanesulfonamide N-(3-Iodo-5-morpholinophenyl)methanesulfonamide (139 mg, 0.33 mmol), bis(pinacolato)diboron (134.4 mg, 0.53 mmol), potassium acetate (108 mg, 1.1 mmol), and bis(diphenylphosphino)ferrocene-palladium(II)dichloride dichloromethane complex (27.4 mg, 0.03 mmol) were suspended in dioxane (5 ml) and stirred at 90° C. for 48 h. After usual work-up with water and ethyl acetate, the reaction crude was purified by flash chromatography (0% to 100%, hexane-ethyl acetate) to obtain 44 mg of the title compound as an oil. (35% yield). Purity: 100%.

LRMS (m/z): 394 (M+1)$^+$ d) (S)—N-(3-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-5-morpholinophenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (45 mg, 0.08 mmol) was treated with N-(3-morpholino-5-(4,4,5,5-tetramethyl-1,3,2-dioxaborolan-2-yl)phenyl)methanesulfonamide (44 mg, 0.12 mmol), sodium carbonate (22 mg, 0.21 mmols) and bis(triphenylphosphine)palladium(II) dichloride (21 mg, 0.03 mmol) according to the method described in Preparation 62. The residue was purified using SP1® Purification System (0% to 100%, hexane-ethyl ether) to give 27 mg (32% yield) of the title compound. Purity 70%.

LRMS (m/z): 770 (M+1)$^+$.

Preparation 132

N-(2-Hydroxy-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (61 mg, 0.10 mmol) was treated with N-(2-hydroxy-3-(4,4,5,5-tetramethyl-1,3,2-dioxaborolan-2-yl)phenyl)methanesulfonamide (200 mg, 0.26 mmol, prepared from N-(3-bromo-2-hydroxyphenyl)-methanesulfonamide and bis(pinacolato) diboron according to Preparation 19b), sodium carbonate (27 mg, 0.25 mmols) and bis(triphenylphosphine)palladium(II) dichloride (25 mg, 0.03 mmol) according to the method described in Preparation 62. The residue was purified using SP1® Purification System (0% to 100%, hexane-ethyl ether) to give 12 mg (15% yield) of the title compound. Purity 90%.

LRMS (m/z): 701 (M+1)$^+$.

Preparation 133

N-(2-Ethoxy-5-(4,4,5,5-tetramethyl-1,3,2-dioxaborolan-2-yl)pyridin-3-yl)-4-hydroxybenzenesulfonamide a) N-(5-Bromo-2-ethoxypyridin-3-yl)-4-hydroxybenzenesulfonamide N-(5-Bromo-2-chloropyridin-3-yl)-4-hydroxybenzenesulfonamide (264 mg, 0.55 mmol) and sodium ethoxide (21% in ethanol, 10 ml, 27 mmol) were stirred at 120° C. for 90 min under microwave conditions. The reaction mixture was poured into sodium bicarbonate saturated solution, neutralized with concentrated chlorhydric acid and extracted with ethyl acetate (×3). The organic phase was dried over magnesium sulphate, filtered and the solvent evaporated under reduced pressure to obtain 211 mg (94% yield, 91% purity) of the title compound, which was used in the next synthetic step without further purification.

LRMS (m/z): 374 (M+1)$^+$ b) N-(2-Ethoxy-5-(4,4,5,5-tetramethyl-1,3,2-dioxaborolan-2-yl)pyridin-3-yl)-4-hydroxybenzenesulfonamide N-(5-Bromo-2-ethoxypyridin-3-yl)-4-hydroxybenzenesulfonamide (211 mg, 0.51 mmol), bis(pinacolato)diboron (210 mg, 1.60 mmol), potassium acetate (172 mg, 1.75 mmol), and bis(diphenylphosphino)ferrocene-palladium(II) dichloride dichloromethane complex (45 mg, 0.06 mmol) were suspended in dioxane (7 ml) and stirred overnight at 90° C. After filtration of the reaction mixture through Celite® and evaporation of the solvent under reduced pressure, the resulting crude was purified by flash chromatography using SP1® Purification System (0% to 100%, hexane-ethyl acetate) to obtain 116 mg (36% yield) of the title compound. Purity: 67%

LRMS (m/z): 421 (M+1)$^+$

Preparation 134

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethylpyridin-3-yl)-4-methoxybenzenesulfonamide a) N-(5-Bromo-2-ethylpyridin-3-yl)-4-methoxybenzenesulfonamide 5-Bromo-2-ethyl-3-pyridinamine (285 mg, 1.42 mmol, prepared according to WO 2008157191 A2 20081224) was treated with 4-methoxybenzene-1-sulfonyl chloride (323 mg, 1.56 mmol) according to the method described In Preparation 15b to give 461 mg (75% yield) of the title compound as an oil. Purity 85%.

LRMS (m/z): 372 (M+1)$^+$.

b) N-(2-Ethyl-5-(4,4,5,5-tetramethyl-1,3,2-dioxaborolan-2-yl)pyridin-3-yl)-4-methoxybenzenesulfonamide N-(5-Bromo-2-ethylpyridin-3-yl)-4-methoxybenzenesulfonamide (461 mg, 1.06 mmol), bis(pinacolato)diboron (400 mg, 1.58 mmol), potassium acetate (310 mg, 3.16 mmol), and bis(diphenylphosphino)ferrocene-palladium(II) dichloride dichloromethane complex (40 mg, 0.05 mmol) were suspended in dioxane (10 ml) and stirred overnight at 100° C. After usual work-up with water and ethyl acetate, the reaction crude was purified by flash chromatography using SP1® Purification System (0% to 100%, hexane-ethyl acetate) to obtain 246 mg of the title compound as a solid (56% yield). Purity: 99%.
LRMS (m/z): 419 (M+1)+ c) (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethylpyridin-3-yl)-4-methoxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (180 mg, 0.41 mmol) was treated with N-(2-ethyl-5-(4,4,5,5-tetramethyl-1,3,2-dioxaborolan-2-yl)pyridin-3-yl)-4-methoxybenzenesulfonamide (250 mg, 0.60 mmol), 2M cesium carbonate (410 µl, 0.82 mmol) and 1,1'-bis(diphenylphosphino)ferrocene-palladium(II)dichloride dichloromethane complex (30 mg, 0.04 mmol) according to the method described in Example 3 to give 146 mg (55% yield) of the title compound as a solid. Purity 100%.
LRMS (m/z): 652 (M+1)+

Preparation 135

(S)—N-(3-Cyano-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (138 mg, 0.23 mmol) was treated with N-(3-cyano-5-(4,4,5,5-tetramethyl-1,3,2-dioxaborolan-2-yl)phenyl)methanesulfonamide (545 mg, 0.62 mmol, prepared from N-(3-bromo-5-cyanophenyl)methanesulfonamide, described at WO 2009015369 A2 20090129, and bis(pinacolato)diboron according to Preparation 119b), sodium carbonate (58 mg, 0.55 mmols) and bis(triphenylphosphine)palladium(II)dichloride (61 mg, 0.07 mmol) according to the method described in Preparation 62. The residue was purified by reverse phase chromatography using SP1® Purification System (C-18 silica from Waters®, water/1:1 acetonitrile-methanol as eluents [0.1% v/v formic acid buffered] 0% to 100%) to give 145 mg (88% yield) of the title compound. Purity 100%.
LRMS (m/z): 710 (M+1)+.

Preparation 136

(S)—N-(3-(4-Amino-6-((1-(4-oxo-3-phenyl-3,4-dihydropyrrolo[2,1-f][1,2,4]triazin-2-yl)ethyl)amino)pyrimidin-5-yl)phenyl)-4-methoxybenzenesulfonamide (S)-2-(1-((6-Amino-5-bromopyrimidin-4-yl)amino)ethyl)-3-phenylpyrrolo[2,1-f][1,2,4]triazin-4(3H)-one (150 mg, 0.35 mmol) was treated with 4-methoxy-N-(3-(4,4,5,5-tetramethyl-1,3,2-dioxaborolan-2-yl)phenyl)benzenesulfonamide (205 mg, 0.53 mmol), 2M cesium carbonate (360 µl, 0.72 mmol) and bis(diphenylphosphino)ferrocene-palladium(II)dichloride dichloromethane complex (28 mg, 0.03 mmol) according to the method described in Example 3 to give 126 mg (59% yield) of the title compound as a solid. Purity 100%.
LRMS (m/z): 609 (M+1)+

Preparation 137

(S)-3-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-5-(methylsulfonamido)phenyl methanesulfonate (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (170 mg, 0.29 mmol) was treated with 3-(methylsulfonamido)-5-(4,4,5,5-tetramethyl-1,3,2-dioxaborolan-2-yl)phenyl methanesulfonate (300 mg, 0.67 mmol, prepared from the title compound of Preparation 105 and methanesulfonyl chloride according to Preparation 37), 2M cesium carbonate (450 µl, 0.90 mmols) and bis(diphenylphosphino)ferrocene-palladium(II)dichloride dichloromethane (50 mg, 0.06 mmol) according to the method described in Preparation 62. The residue was purified using SP1® Purification System (0% to 80%, hexane-ethyl acetate) to give 169 mg (66% yield) of the title compound. Purity 87%.
LRMS (m/z): 779 (M+1)+.

Preparation 138

(S)—N-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (170 mg, 0.29 mmol) was treated with N-(3-methoxy-4-(4,4,5,5-tetramethyl-1,3,2-dioxaborolan-2-yl)phenyl)methanesulfonamide (190 mg, 0.58 mmol, described at WO 2012015723 A1 20120202), sodium carbonate (100 mg, 0.94 mmols) and bis(diphenylphosphino)ferrocene-palladium(II) dichloride dichloromethane complex (50 mg, 0.06 mmol) according to the method described in Preparation 62. The residue was purified using SP1® Purification System (0% to 80%, hexane-ethyl acetate) to give 159 mg (71% yield) of the title compound. Purity 91%.
LRMS (m/z): 715 (M+1)+.

Preparation 139

4-Hydroxy-N-(2-methoxy-5-(4,4,5,5-tetramethyl-1,3,2-dioxaborolan-2-yl)pyridine-3-yl)-3-methylbenzenesulfonamide a) N-(5-Bromo-2-methoxypyridin-3-yl)-4-hydroxy-3-methylbenzenesulfonamide

5-Bromo-2-methoxypyridin-3-amine (1.08 g, 5.32 mmol) was dissolved in THF (2.5 ml) and cooled with an ice bath. A solution of sodium bis(trimethylsilyl)amide (1 M in THF, 8 ml, 8 mmol) was added dropwise. Ten minutes later, 4-hydroxy-3-methylbenzene-1-sulfonyl chloride (1.65 g, 5.91 mmol, prepared according to JP 47015818 B4 19720511) in THF (3 ml) was added and the reaction mixture was allowed to reach room temperature. After stirring for 1 h, a saturated solution of sodium bicarbonate was added dropwise and the reaction mixture was extracted with dichloromethane (×3). The organic phase was dried over magnesium sulphate, filtered and the solvent evaporated under reduced pressure. The resulting residue was purified by reverse phase chromatography using SP1® Purification System (C-18 silica from Waters®, water/1:1 acetonitrile-methanol as eluents [0.1% v/v formic acid buffered] 0% to 100%) to give 230 mg (12% yield) of the title compound. Purity 100%.

LRMS (m/z): 374 (M+1)$^+$.

b) 4-Hydroxy-N-(2-methoxy-5-(4,4,5,5-tetramethyl-1,3,2-dioxaborolan-2-yl)pyridine-3-yl)-3-methylbenzenesulfonamide N-(5-Bromo-2-methoxypyridin-3-yl)-4-hydroxy-3-methylbenzenesulfonamide (230 mg, 0.62 mmol), bis(pinacolato)diboron (205 mg, 0.81 mmol), potassium acetate (182 mg, 1.85 mmol), and bis(diphenylphosphino)ferrocene-palladium(II)dichloride dichloromethane complex (40 mg, 0.05 mmol) were suspended in dioxane (7 ml) and stirred at 100° C. for 3 h. After evaporation of the solvent under reduced pressure, ethyl acetate (20 ml) was added to the residue and the precipitated salts were eliminated by filtration. The solvents were evaporated under reduced pressure. The resulting crude was purified by flash chromatography using SP1® Purification System (0% to 10%, dichloromethane-ethyl acetate) to obtain 180 mg (70% yield) of the title compound. Purity: 100%.

LRMS (m/z): 407 (M+1)$^+$

Preparation 140

(5-(Difluoromethoxy)pyridin-3-yl)boronic acid a) 5-Bromopyridin-3-ol

3-Bromo-5-methoxypyridine (5 g, 26 mmol) was treated with hydrogen bromide (48% in water, 90 ml, 795 mmol) and the reaction mixture was heated at 130° C. for 3 days. It was then added over ice-water and treated with NaOH 8 N to pH 6. The white precipitate was filtered, washed with water and dried under vacuum at 35° C. with P2O5 to obtain 3.7 g (78% yield) of the title compound.

Purity 97%.
LRMS (m/z): 175 (M+1)$^+$ b) 3-Bromo-5-(difluoromethoxy)pyridine

A mixture of 5-bromopyridin-3-ol (3.7 g, 21 mmol) and potassium carbonate (8.8 g, 64 mmol) in DMF (50 ml) was treated with 2-chloro-2,2-difluoroacetic acid (2.16 ml, 25 mmol) and the reaction mixture was heated at 100° C. overnight. Further potassium carbonate (4.4 g, 32 mmol) and 2-chloro-2,2-difluoroacetic acid (1.08 ml, 12.5 mmol) were added and the reaction mixture stirred at 100° C. overnight. Water and ethyl acetate were added and the organic phase was washed with brine, dried over magnesium sulphate and the solvent was removed under vacuum. The resulting crude was purified by flash chromatography using SP1® Purification System (0% to 15% in 25 CV, hexane-ethyl acetate) to obtain 0.81 g (17% yield) of the title compound. Purity: 100%

LRMS (m/z): 225 (M+1)$^+$ c) (5-(Difluoromethoxy)pyridin-3-yl)boronic acid

3-Bromo-5-(difluoromethoxy)pyridine (813 mg, 3.63 mmol), 4,4,4',4',5,5,5',5'-octamethyl-2,2'-bi(1,3,2-dioxaborolane) (1.84 g, 7.25 mmol), potassium acetate (1.07 g, 11 mmol), and bis(diphenylphosphino)ferrocene-palladium(II) dichloride dichloromethane complex (296 mg, 0.36 mmol) and 1,1'-bis(diphenylphosphino)ferrocene (201 mg, 0.36 mmol) were suspended in dioxane (35 ml) and stirred at 90° C. overnight. After usual work-up with water and ethyl acetate, the reaction crude was purified by reverse phase chromatography (C-18 silica from Waters®, water/1:1 acetonitrile-methanol as eluents [0.1% v/v formic acid buffered] 0% to 100%) to give 495 mg (72% yield) of the title compound as a yellow oil. Purity 95%.

LRMS (m/z): 191 (M+1)$^+$

Preparation 141

(S)-2-(1-Aminoethyl)-5-(6-(4-isopropylpiperazin-1-yl)-6-oxohex-1-yn-1-yl)-3-phenylpyrrolo[2,1-f][1,2,4]triazin-4(3H)-one a) (S)-tert-Butyl (1-(5-(6-(4-isopropylpiperazin-1-yl)-6-oxohex-1-yn-1-yl)-4-oxo-3-phenyl-3,4-dihydropyrrolo[2,1-f][1,2,4]triazin-2-yl)ethyl)carbamate A mixture of (S)-tert-butyl (1-(5-bromo-4-oxo-3-phenyl-3,4-dihydropyrrolo[2,1-f][1,2,4]triazin-2-yl)ethyl)carbamate (140 mg, 0.32 mmol), 1-(4-isopropylpiperazin-1-yl)hex-5-yn-1-one (88 mg, 0.36 mmol), bis(triphenylphosphine)palladium(II) chloride (23 mg, 0.03 mmol) and copper iodide (6 mg, 0.03 mmol) in diethylamine (6 ml) was heated at 60° C. for 3 days. The solvent was removed and the crude purified by reverse phase chromatography (C-18 silica from Waters®, water/1:1 acetonitrile-methanol as eluents [0.1% v/v formic acid buffered] 0% to 100%) to give 134 mg (72% yield) of the title compound. Purity 100%.

LRMS (m/z): 575 (M+1)$^+$ b) (S)-2-(1-Aminoethyl)-5-(6-(4-isopropylpiperazin-1-yl)-6-oxohex-1-yn-1-yl)-3-phenylpyrrolo[2,1-f][1,2,4]triazin-4(3H)-one (S)-tert-Butyl (1-(5-(6-(4-isopropylpiperazin-1-yl)-6-oxohex-1-yn-1-yl)-4-oxo-3-phenyl-3,4-dihydropyrrolo[2,1-f][1,2,4]triazin-2-yl)ethyl)carbamate (134 mg, 0.23 mmol) was dissolved in hydrogen chloride (4M in dioxane, 2.5 ml, 10 mmol) and stirred at room temperature overnight. The solvent was removed and tert-butanol and DIEA were added to the crude and the reaction mixture was stirred at 120° C. overnight. The solvents were removed and this crude was used in the following step without further purification. Purity 10%

LRMS (m/z): 475 (M+1)$^+$

Preparation 142

1-(4-Isopropyl piperazin-1-yl)hex-5-yn-1-one

1-Isopropylpiperazine (228 mg, 1.78 mmol) was added over a mixture of hex-5-ynoic acid (200 mg, 1.78 mmol), N-(3-Dimethylaminopropyl)-N'-ethylcarbodiimide hydrochloride (393 mg, 2.05 mmol) and N,N-dimethylpyridin-4-amine (10 mg, 0.05 mmol) in dichloromethane (10 ml) at 0° C. and the resulting mixture was stirred at room temperature overnight. 100 ml of dichloromethane were added and washed with sodium bicarbonate 4%. Then a solution of hydrogen chloride 0.5 N was added to the organic phase. The aquose phase was separated and neutralised with a solution of NaOH 2N and treated with ethyl acetate. The ethyl acetate phase was washed with water and brine, dried over magnesium sulphate and the solvent removed to give 152 mg (34% yield) of the title compound. Purity 90%.

LRMS (m/z): 223 (M+1)$^+$

Preparation 143

3-(Difluoromethyl)-5-(4,4,5,5-tetramethyl-1,3,2-dioxaborolan-2-yl)phenol a) 3-Bromo-5-hydroxybenzaldehyde 3-Bromo-5-methoxybenzaldehyde (1 g, 4.65 mmol) was dissolved in 20 mL dichloromethane. A solution of boron tribromide (1M in dichloromethane, 23 ml, 23 mmol) was added dropwise and the reaction was stirred at room temperature overnight. The mixture was diluted with ethyl acetate and washed with a solution of 4% sodium bicarbonate, water, brine and dried over sodium sulphate, filtered and evaporated under reduced pressure. A mixture of ethyl ether and diisopropyl ether was added and the precipitate was filtered to give 1.1 g (68% yield) of the title compound as an orange solid. Purity 99%.

LRMS (m/z): 200 (M−1)$^-$ b) 3-Bromo-5-(difluoromethyl)phenol

A mixture of 3-bromo-5-hydroxybenzaldehyde (1.1 g, 3.37 mmol) and DAST (2.45 ml, 18.7 mmol) in anhydrous dichloromethane (25 ml) was heated at 40° C. in a pressure vessel overnight. The mixture was diluted with dichloromethane and washed with a solution of 4% sodium bicarbonate, water, brine and dried over sodium sulphate, filtered and evaporated under reduced pressure to give 1.13 g (60% yield) of the title compound as a dark oil. This crude was used in the following step without further purification. Purity 44%.

LRMS (m/z): 224 (M+1)$^+$ c) 3-(Difluoromethyl)-5-(4,4,5,5-tetramethyl-1,3,2-dioxaborolan-2-yl)phenol 3-Bromo-5-(difluoromethyl)phenol (300 mg, 1.35 mmol), 4,4,4',4',5,5,5',5'-octamethyl-2,2'-bi(1,3,2-dioxaborolane) (1.37 g, 5.39 mmol), potassium acetate (660 mg, 6.73 mmol), bis(diphenylphosphino)ferrocene-palladium(II)dichloride dichloromethane complex (165 mg, 0.2 mmol) and 1,1'-bis(diphenylphosphino)ferrocene (112 mg, 0.2 mmol) were suspended in dioxane (12 ml) and heated to 90° C. overnight. After usual work-up with water and ethyl acetate, the reaction crude was purified by reverse phase chromatography (C-18 silica from Waters®, water/1:1 acetonitrile-methanol as eluents [0.1% v/v formic acid buffered] 0% to 100%) to give 363 mg (95% yield) of the title compound as a mixture of the boronate ester and the boronic acid. Purity 95%.

LRMS (m/z): 271 (M+1)$^+$

Preparation 144

(S)-2-(1-((6-Amino-5-bromopyrimidin-4-yl)amino)ethyl)-3-phenylpyrrolo[2,1-f][1,2,4]triazin-4(3H)-one (S)-2-(1-Aminoethyl)-3-phenylpyrrolo[2,1-f][1,2,4]triazin-4(3H)-one (1.2 g, 4.72 mmol) was treated 5-bromo-6-chloropyrimidin-4-amine (2 g, 9.6 mmol), cesium fluoride (1.44 g, 9.48 mmol), N,N-diisopropylethylamine (4.2 mL, 24.11 mol) according to Preparation 13. The residue was purified by flash chromatography using Isolera® Purification System (0% to 50%, dichloromethane-ethyl acetate) to give 1.43 g (71% yield) of the title compound as a solid. Purity 100%.

LRMS (m/z): 426, 428 (M+1)$^+$.

Preparation 145

Benzyl ((5-bromo-4-oxo-3-phenyl-3,4-dihydropyrrolo[2,1-f][1,2,4]triazin-2-yl)ethyl)carbamate a) Benzyl (2-((3-bromo-2-(phenylcarbamoyl)-1H-pyrrol-1-yl)amino)-2-oxoethyl)carbamate DIEA (10.5 ml, 60 mmol) was added at 0° C. over a mixture of 1-amino-3-bromo-N-phenyl-1H-pyrrole-2-carboxamide (5.1 g, 18 mmol) and 2-(benzyloxycabonylamino)acetic acid (5.33 g, 25 mmol) in anhydrous ethyl acetate (100 ml). After 15 min T3P® solution (50% AcOEt, 15 ml) was slowly added and stirred 20 min at 0° C. and then at room temperature overnight. Further DIEA (5 ml, 30 mmol), 2-(benzyloxycabonylamino)acetic acid (2.66 g, 25 mmol) and T3P® solution (50% AcOEt, 7 ml) were added and the reaction mixture was stirred at room temperature overnight. More ethyl acetate was added and the reaction crude was washed with water and brine, dried over magnesium sulphate and the solvent was removed under vacuum. The residue was purified by flash chromatography using Isolera® Purification System (0-40%, hexane-AcOEt) to give 7.81 g (41% yield) of the final product with a purity of 45% that was used in the next step without further purification.

LRMS (m/z): 472 (M+1)$^+$.

b) Benzyl ((5-bromo-4-oxo-3-phenyl-3,4-dihydropyrrolo[2,1-f][1,2,4]triazin-2-yl)ethyl)carbamate To a solution of benzyl (2-((3-bromo-2-(phenylcarbamoyl)-1H-pyrrol-1-yl)amino)-2-oxoethyl)carbamate (7.81 g, purity 45%, 7.48 mmol) in toluene (80 ml) in a reactor equipped with a Dean-Stark destilator was added pyridinium p-toluene sulfonate (1.88 g, 7.48 g) and the reaction mixture was stirred at 120° C. for 3 days. The crude was diluted with ethyl acetate and washed with water and brine, dried over magnesium sulphate and the solvent was removed to give 7.39 g (100% yield) of the final product as a dark oil. Estimated purity 46%. This crude was used in the next step without further purification.

LRMS (m/z): 454 (M+1)$^+$.

Preparation 146

2-(((6-Amino-5-bromopyrimidin-4-yl)amino)methyl)-5-methyl-3-phenylpyrrolo[2,1-f][1,2,4]triazin-4(3H)-one a) 2-(Aminomethyl)-5-methyl-3-phenylpyrrolo[2,1-f][1,2,4]triazin-4(3H)-one Benzyl ((5-bromo-4-oxo-3-phenyl-3,4-dihydropyrrolo[2,1-f][1,2,4]triazin-2-yl)ethyl)carbamate (2.7 g, 5.96 mmol)

was dissolved in 95 mL anhydrous dimethylformamide. 2,4,6-Trimethylboroxine (7.48 mL, 53.6 mmol), potassium carbonate (16.5 g, 119.38 mmol) and tetrakis(triphenylphosphine)palladium(0) (0.69 g, 0.6 mmol) were added under argon conditions. The mixture was heated at 125° C. overnight. The mixture was allowed to cool and filtered through a plug of Celite, washing several times with ethyl acetate. The combinated filtrates were washed with water and brine, dried over sodium sulphate, filtered and evaporated under reduced pressure. The residue was purified by reverse phase chromatography using SP1® Purification System (C-18 silica from Waters®, water/1:1 acetonitrile-methanol as eluents [0.1% v/v formic acid buffered] 0% to 100%) to give 420 mg (30% yield) of the final product. Purity 100%.

LRMS (m/z): 255 (M+1)$^+$.

b) 2-(((6-Amino-5-bromopyrimidin-4-yl)amino)methyl)-5-methyl-3-phenylpyrrolo[2,1-f][1,2,4]triazin-4(3H)-one 2-(Aminomethyl)-5-methyl-3-phenylpyrrolo[2,1-f][1,2,4]triazin-4(3H)-one (420 mg, 0.97 mmol) was treated with 5-bromo-6-chloropyrimidin-4-amine (304 mg, 1.46 mmol), cesium fluoride (222 mg, 1.46 mmol) and N,N-diisopropylethylamine (0.508 mL, 2.92 mol) according to Preparation 13. The residue was purified using SP1® Purification System (0% to 10%, dichloromethane-methanol) to give 394 m g (95% yield) of the title compound as a solid. Purity 100%.

LRMS (m/z): 426, 428 (M+1)$^+$.

Preparation 147

3-(Difluoromethyl)-5-(4,4,5,5-tetramethyl-1,3,2-dioxaborolan-2-yl)phenol a) 6-Bromo-1-((2-fluoro-4-methoxyphenyl)sulfonyl)-4-methoxy-1H-indole 6-Bromo-4-methoxy-1H-indole (300 mg, 1.63 mmol) and tetrabutylammonium hydrogensulphate (67 mg, 0.2 mmol) were dissolved in toluene (5 mL) and sodium hydroxide (8N, 5 mL, 39 mmol). After 10 min 2-fluoro-4-methoxybenzene-1-sulfonil chloride (447 mg, 1.99 mmol) was added and the reaction mixture was stirred at room temperature overnight. The mixture was diluted with ethyl acetate and washed with water and brine, dried over sodium sulphate, filtered and evaporated under reduced pressure. The residue was purified using Isolera® Purification System (0% to 20%, hexane-ethyl acetate) to give 550 mg (69% yield) of the title compound. Purity 69%.

LRMS (m/z): 414, 416 (M+1)$^+$ b) 1-((2-Fluoro-4-methoxyphenyl)sulfonyl)-4-methoxy-6-(4,4,5,5-tetramethyl-1,3,2-dioxaborolan-2-yl)-1H-indole 6-Bromo-1-((2-fluoro-4-methoxyphenyl)sulfonyl)-4-methoxy-1H-indole (150 mg, 0.36 mmol), 4,4,4',4',5,5,5',5'-octamethyl-2,2'-bi(1,3,2-dioxaborolane) (183 mg, 0.72 mmol), potassium acetate (106 mg, 1.09 mmol), bis(diphenylphosphino)ferrocene-palladium(II)dichloride dichloromethane complex (14 mg, 0.05 mmol) and 1,1'-bis(diphenylphosphino)ferrocene (10 mg, 0.05 mmol) were suspended in dioxane (5 ml) and stirred at 90° C. overnight. The mixture was diluted with ethyl acetate and washed with water and brine, dried over sodium sulphate, filtered and evaporated under reduced pressure to give 303 mg (90% yield) of the title compound. Purity 90%.

LRMS (m/z): 462 (M+1)$^+$ c) 3-(Difluoromethyl)-5-(4,4,5,5-tetramethyl-1,3,2-dioxaborolan-2-yl)phenol 1-((2-Fluoro-4-methoxyphenyl)sulfonyl)-4-methoxy-6-(4,4,5,5-tetramethyl-1,3,2-dioxaborolan-2-yl)-1H-indole (100 g, 0.11 mmol) was dissolved in dichloromethane (2 ml). A solution of boron tribromide (1M in dichloromethane, 1.08 mL, 1.08 mmol) was added dropwise and the reaction was stirred at room temperature overnight. The mixture was diluted with dichloromethane and washed with a solution of 4% sodium bicarbonate, water, brine and dried over sodium sulphate, filtered and evaporated under reduced pressure. The product was purified by reverse phase using SP1® Purification System to give 23 mg (60% yield) of the title compound. Purity 99%.

LRMS (m/z): 350 (M−1)$^-$

Preparation 148

(3-(4-Hydroxyphenylsulfonamido)phenyl)boronic acid

4-Methoxy-N-(3-(4,4,5,5-tetramethyl-1,3,2-dioxaborolan-2-yl)phenyl)benzenesulfonamide (168 mg, 0.43 mmol) was dissolved in dichloromethane (4 ml). A solution of boron tribromide (1M in dichloromethane, 4.32 mL, 4.32 mmol) was added dropwise and the reaction was stirred at room temperature overnight. The mixture was diluted with dichloromethane and washed with a solution of 4% sodium bicarbonate, water, brine and dried over sodium sulphate, filtered and evaporated under reduced pressure. The product was purified by reverse phase using SP1® Purification System to give 30 mg (23% yield) of the title compound. Purity 100%.

LRMS (m/z): 294 (M−1)$^-$

Preparation 149

1-(2-Fluoro-4-(4,4,5,5-tetramethyl-1,3,2-dioxaborolan-2-yl)phenyl)-3-(pyridin-4-yl)urea A mixture of 2-fluoro-4-(4,4,5,5-tetramethyl-1,3,2-dioxaborolan-2-yl)aniline (100 mg, 0.42 mmol) and 4-isocyanatopyridine (56 mg, 0.47 mmol) in tetrahydrofuran (2 ml) was stirred at room temperature overnight. The mixture was diluted with ethyl acetate and washed with water, brine, dried over sodium sulphate, filtered and evaporated under reduced pressure to give 193 mg (100% yield) of the title compound. This crude was used in the following step without any further purification. Purity 77%.

LRMS (m/z): 358 (M+1)$^+$

Preparation 150

2,4-Difluoro-N-(2-methoxy-5-(4,4,5,5-tetramethyl-1,3,2-dioxaborolan-2-yl)pyridin-3-yl)benzenesulfonamide 2-Methoxy-5-(4,4,5,5-tetramethyl-1,3,2-dioxaborolan-2-yl)pyridin-3-amine (200 mg, 0.8 mmol) was treated with 2,4-difluorobenzene-1-sulfonyl chloride (220 µl, 1.6 mmol)

according to the method of Preparation 15b to give 287 mg (66% yield) of the title compound as an oil. Purity 78%.
LRMS (m/z): 427 (M+1)+.

Preparation 151

(S)—N-(3-(4-Amino-6-((1-(5-methyl-4-oxo-3-phenyl-3,4-dihydropyrrolo[2,1-f][1,2,4]triazin-2-yl) ethyl)amino)pyrimidin-5-yl)phenyl)-2,4-dimethoxybenzenesulfonamide a) 2,4-Dimethoxy-N-(3-(4,4,5,5-tetramethyl-1,3,2-dioxaborolan-2-yl)phenyl)benzenesulfonamide 3-(4,4,5,5-Tetramethyl-1,3,2-dioxaborolan-2-yl)aniline (450 mg, 2.05 mmol, prepared as described at Wing Kin Chow et al. *Chemistry—A European Journal*, 2011, 17(25), 6913-6917) was treated with 2,4-dimethoxybenzene-1-sulfonyl chloride (850 mg, 3.5 mmol) according to the method described in Preparation 15b to give 568 mg (77% yield) of the title compound as an oil. Purity 99%.
LRMS (m/z): 420 (M+1)+.

b) (S)—N-(3-(4-Amino-6-((1-(5-methyl-4-oxo-3-phenyl-3,4-dihydropyrrolo[2,1-f][1,2,4]triazin-2-yl) ethyl)amino)pyrimidin-5-yl)phenyl)-2,4-dimethoxybenzenesulfonamide (S)-2-(1-((6-Amino-5-bromopyrimidin-4-yl)amino) ethyl)-5-methyl-3-phenylpyrrolo[2,1-f][1,2,4]triazin-4(3H)-one (100 mg, 0.23 mmol) was treated with 2,4-dimethoxy-N-(3-(4,4,5,5-tetramethyl-1,3,2-dioxaborolan-2-yl)phenyl) benzenesulfonamide (191 mg, 0.45 mmol), 2N cesium carbonate (340 µl, 3.08 mmol) and bis(diphenylphosphino) ferrocene-palladium(II)dichloride dichloromethane complex (20 mg, 0.02 mmol) according to the method described in Example 3 to give 108 mg (73% yield) of the title compound as a solid. Purity 100%.
LRMS (m/z): 653 (M+1)+

Preparation 152

(S)—N-(5-(4-Amino-6-((1-(5-methyl-4-oxo-3-phenyl-3,4-dihydropyrrolo[2,1-f][1,2,4]triazin-2-yl) ethyl)amino)pyrimidin-5-yl)-2-(ethylamino)pyridin-3-yl)-4-methoxybenzenesulfonamide a) N-(5-Bromo-2-(ethylamino)pyridin-3-yl)-4-methoxybenzenesulfonamide 5-Bromo-N²-ethylpyridine-2,3-diamine (290 mg, 1.34 mmol, purchased from Aurora Building Blocks reference A01.414.067) was treated with 4-methoxybenzene-1-sulfonyl chloride (280 mg, 1.35 mmol) according to the method described in Preparation 15b to give 180 mg (35% yield) of the title compound as an oil. Purity 99%.
LRMS (m/z): 387 (M+1)+.

b) N-(2-(Ethylamino)-5-(4,4,5,5-tetramethyl-1,3,2-dioxaborolan-2-yl)pyridin-3-yl)-4-methoxybenzenesulfonamide N-(5-Bromo-2-(ethylamino)pyridin-3-yl)-4-methoxybenzenesulfonamide (176 mg, 0.46 mmol), bis(pinacolato)diboron (180 mg, 0.71 mmol), potassium acetate (135 mg, 1.38 mmol), and bis(diphenylphosphino)ferrocene-palladium(II) dichloride dichloromethane complex (20 mg, 0.02 mmol)

were suspended in dioxane (3 ml) and stirred overnight at 100° C. After evaporation of the solvent under reduced pressure, ethyl acetate (20 ml) was added to the residue and the precipitated salts were eliminated by filtration. The solvent was evaporated under reduced pressure and the residue was purified by reverse phase chromatography using SP1® Purification System (C-18 silica from Waters®, water/1:1 acetonitrile-methanol as eluents [0.1% v/v formic acid buffered] 0% to 100%) to give 72 mg (24% yield) of the final product. Purity 65%.
LRMS (m/z): 434 (M+1)+ c) (S)—N-(5-(4-Amino-6-((1-(5-methyl-4-oxo-3-phenyl-3,4-dihydropyrrolo[2,1-f][1,2,4]triazin-2-yl) ethyl)amino)pyrimidin-5-yl)-2-(ethylamino)pyridin-3-yl)-4-methoxybenzenesulfonamide (S)-2-(1-((6-Amino-5-bromopyrimidin-4-yl)amino) ethyl)-5-methyl-3-phenylpyrrolo[2,1-f][1,2,4]triazin-4(3H)-one (25 mg, 0.06 mmol) was treated with 6-(ethylamino)-5-(4-methoxyphenylsulfonamido)pyridin-3-ylboronic acid (30 mg, 0.09 mmol), 2M cesium carbonate (60 µl, 0.12 mmol) and bis(diphenylphosphino)ferrocene-palladium(II)dichloride dichloromethane complex (3 mg, 0.01 mmol) according to the method described in Example 3 to give 18 mg (48% yield) of the title compound as a solid. Purity 100%.
LRMS (m/z): 667 (M+1)+

Preparation 153

(S)—N,N-Dimethyl-3-(4-((1-(5-methyl-4-oxo-3-phenyl-3,4-dihydropyrrolo[2,1-f][1,2,4]triazin-2-yl) ethyl)amino)-7-((2-(trimethylsilyl)ethoxy)methyl)-7H-pyrrolo[2,3-d]pyrimidin-5-yl)-5-(methylsulfonamido)benzamide a) 3-Bromo-5-(methylsulfonamido)benzoic acid 3-Amino-5-bromobenzoic acid (1 g, 4.63 mmol, prepared according to EP 2394998 A1 20111214) was suspended in a saturated solution of sodium bicarbonate (6.4 ml). Sulfonyl chloride (0.54 ml, 6.94 mmol) was added dropwise at 0° C. After 2 h of stirring at this temperature, concentrated HCl was added dropwise to the reaction mixture until pH=7 and the resultant dissolution was directly purified by reverse phase chromatography using SP1® Purification System (C-18 silica from Waters®, water/1:1 acetonitrile-methanol as eluents [0.1% v/v formic acid buffered] 0% to 100%), to obtain 360 mg of the final compound as a white solid. Purity: 99%
LRMS (m/z): 323 (M+1)+ b) 3-Bromo-N,N-dimethyl-5-(methylsulfonamido) benzamide

To a mixture of 3-bromo-5-(methylsulfonamido)benzoic acid (360 mg, 1.22 mmol), HATU (490 mg, 1.29 mmol) and DIEA (260 µl, 1.49 mmol) in DMF (5 ml) was added dimethylamine (3.10 ml, 6.20 mmol, 2N in THF) and the resulting mixture was stirred at room temperature overnight. 30 ml of dichloromethane were added and washed with sodium bicarbonate 4%. The aqueous phase was further extracted with ethyl acetate. The organics were washed with water and brine, dried over magnesium sulphate and the solvent was removed to give a residue which purified by reverse phase chromatography using SP1® Purification System (C-18 silica from Waters®, water/1:1 acetonitrile-methanol as eluc) N,N-Dimethyl-3-(methylsulfonamido)-5-(4,4,5,5-tetramethyl-1,3,2-dioxaborolan-2-yl)benzamide 3-Bromo-N,N-dimethyl-5-(methylsulfonamido)benzamide (325 mg, 1.01 mmol), bis(pinacolato)diboron (335 mg, 1.32 mmol), potassium acetate (300 mg, 3.06 mmol), and bis(diphenylphosphino)ferrocene-palladium(II)dichloride dichloromethane complex (65 mg, 0.08 mmol) were suspended in dioxane (10 ml) and stirred overnight at 100° C. After evaporation of the solvent under reduced pressure, ethyl acetate (20 ml) was added to the residue and the precipitated salts were eliminated by filtration. The solvent was evaporated under reduced pressure and the residue was purified using SP1® Purification System (0% to 40%, dichloromethane-ethyl acetate) to give 262 mg (70% yield) of the final product. Purity 99%.
LRMS (m/z): 369 (M+1)$^+$ d) (S)—N,N-Dimethyl-3-(4-((1-(5-methyl-4-oxo-3-phenyl-3,4-dihydropyrrol o[2,1-f][1,2,4]triazin-2-yl)ethyl)amino)-7-((2-(trimethylsilyl)ethoxy)methyl)-7H-pyrrolo[2,3-d]pyrimidin-5-yl)-5-(methylsulfonamido)benzamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (170 mg, 0.29 mmol) was treated with N, N-dimethyl-3-(methylsulfonamido)-5-(4,4,5,5-tetramethyl-1,3,2-dioxaborolan-2-yl)benzamide (262 mg, 0.71 mmol), sodium carbonate (75 mg, 0.71 mmols) and bis(diphenylphosphino)ferrocene-palladium(II)dichloride dichloromethane complex (74 mg, 0.09 mmol) according to the method described in Preparation 62. The residue was purified using SP1® Purification System (0% to 100%, dichloromethane-ethyl acetate) to give 233 mg (99% yield) of the title compound. Purity 92%.
LRMS (m/z): 756 (M+1)$^+$.

Preparation 154

4-Hydroxy-3-methyl-N-(3-(4,4,5,5-tetramethyl-1,3,2-dioxaborolan-2-yl)phenyl)benzenesulfonamide a) N-(3-Bromophenyl)-4-hydroxy-3-methyl benzenesulfonamide 5-Bromopyridin-3-amine (400 mg, 2.33 mmol) was treated with 4-hydroxy-3-methylbenzene-1-sulfonyl chloride (506 mg, 2.45 mmol, prepared as described at JP 47015818 B4 19720511) according to the method described in Preparation 15b to give 582 mg (73% yield) of the title compound as an oil. Purity 99%.
LRMS (m/z): 340 (M−1)$^−$.

b) 4-Hydroxy-3-methyl-N-(3-(4,4,5,5-tetramethyl-1,3,2-dioxaborolan-2-yl)phenyl)benzenesulfonamide N-(3-Bromophenyl)-4-hydroxy-3-methylbenzenesulfonamide (582 mg, 1.70 mmol), bis(pinacolato)diboron (561 mg, 2.21 mmol), potassium acetate (294 mg, 5.1 mmol), and bis(diphenylphosphino)ferrocene-palladium(II)dichloride dichloromethane complex (108 mg, 0.13 mmol) were suspended in dioxane (17 ml) and stirred overnight at 100° C. After evaporation of the solvent under reduced pressure, ethyl acetate (20 ml) was added to the residue and the precipitated salts were eliminated by filtration. The solvent was evaporated under reduced pressure and hexane (30 ml) was added to the residue. The precipitate was filtered and this operation was repeated with the organic phase (another 30 ml of hexane were added after evaporation), to obtain 630 mg (66% yield, 93% purity), which was used in the next synthetic step without further purification.
LRMS (m/z): 388 (M−1)$^−$ Preparation 155

N-(2-Ethoxy-5-(4,4,5,5-tetramethyl-1,3,2-dioxaborolan-2-yl)pyridin-3-yl)-4-hydroxy-3-methyl benzenesulfonamide a) 5-Bromo-2-ethoxy-3-nitropyridine 5-Bromo-2-chloro-3-nitropyridine (1 g, 4.21 mmol) was dissolved in EtOH (5 ml) and a solution of sodium ethoxyde (21% m/v in EtOH, 1.5 ml, 4.63 mmol) was added dropwise. Once the addition was finished, the solvent was evaporated under reduced pressure and water was added tot the residue. The reaction mixture was extracted with dichloromethane (×3). The organic phase was dried over magnesium sulphate, filtered and the solvent evaporated under reduced pressure. The resulting crude (805 mg, 77% yield) was pure enough to perform the next synthetic step. Purity: 100%
LRMS (m/z): 248 (M+1)$^+$.

b) 5-Bromo-2-ethoxypyridin-3-amine

5-Bromo-2-ethoxy-3-nitropyridine (805 mg, 3.26 mmol), ammonium chloride (732 mg, 13.68 mmol) and powdered iron (764 mg, 13.68 mmol) were suspended in EtOH (3.4 ml) and water (3.4 ml) and stirred for 90 min at 100° C. The reaction mixture was filtered through Celite after dilution with EtOH. The solvent was evaporated under reduced pressure, water was added and the mixture neutralised to pH=6 with sodium carbonate and extracted with dichloromethane (×3). The organic phase was washed successively with water and brine, dried over magnesium sulphate, filtered and the solvent evaporated under reduced pressure. 708 mg (83% yield, 92% purity) of the titled compound were obtained and used in the next synthetic step without further purification.
LRMS (m/z): 263 (M+1)$^+$ c) N-(5-Bromo-2-ethoxypyridin-3-yl)-4-hydroxy-3-methylbenzenesulfonamide 5-Bromo-2-ethoxypyridin-3-amine (506 mg, 2.33 mmol) was treated with 4-hydroxy-3-methylbenzene-1-sulfonyl chloride (506 mg, 2.45 mmol, prepared as described at JP 47015818 B4 19720511) according to the method described in Preparation 15b to give 902 mg (100% yield) of the title compound as an oil. Purity 99%.
LRMS (m/z): 387 (M−1)$^−$.

d) N-(2-Ethoxy-5-(4,4,5,5-tetramethyl-1,3,2-dioxaborolan-2-yl)pyridin-3-yl)-4-hydroxy-3-methylbenzenesulfonamide N-(5-Bromo-2-ethoxypyridin-3-yl)-4-hydroxy-3-methylbenzenesulfonamide (631 mg, 1.63 mmol), bis(pinacolato)diboron (538 mg, 2.12 mmol), potassium acetate (480 mg, 4.89 mmol), and bis(diphenylphosphino)ferrocene-palladium(II)dichloride dichloromethane complex (104 mg, 0.12 mmol) were suspended in dioxane (16 ml) and stirred overnight at 100° C. After evaporation of the solvent under reduced pressure, ethyl acetate (20 ml) was added to the residue and the precipitated salts were eliminated by filtration. The organics were washed with water and brine, dried over magnesium sulphate and evaporated under reduced pressure. The resulting crude was purified by flash chromatography using SP1® Purification System (0% to 30%, dichloromethane-ethyl acetate) to obtain 309 mg (44% yield) of the title compound. Purity: 93%.

LRMS (m/z): 433 (M−1)⁻

Preparation 156

2-(3-Fluoro-5-methoxybenzyl)-4,4,5,5-tetramethyl-1,3,2-dioxaborolane 1-(Bromomethyl)-3-fluoro-5-methoxybenzene (250 mg, 1.14 mmol) was dissolved in 3.4 mL tert-butanol and 308 µl water. Bis(pinacolato)diboron (348 mg, 1.37 mmol), di-tert-butyl(methyl)phosphonium tetrafluoroborate (8 mg, 0.03 mmol) and potassium phosphate tribasic (485 mg, 2.28 mmol) were added and the mixture was submitted to three vacuum-argon cycles. Tris(dibenzylideneacetone)dipalladium(0) (10 mg, 0.01 mmol) was added under argon conditions. The mixture was stirred at 60° C. overnight. The reaction was poured into a saturated ammonium chloride solution and extracted twice with ethyl acetate. The organics were combined and washed with water, brine, dried over sodium sulphate, filtered and evaporated under reduced pressure to obtain 269 mg (68% yield, 77% purity) of the title compound as an oil.

LRMS (m/z): 267 (M+1)⁺

Preparation 157

2-(3-Methoxybenzyl)-4,4,5,5-tetramethyl-1,3,2-dioxaborolane 1-(Bromomethyl)-3-methoxybenzene (140 µl, 1.00 mmol) was treated with bis(pinacolato)diboron (305 mg, 1.20 mmol), di-tert-butyl(methyl)phosphonium tetrafluoroborate (7 mg, 0.03 mmol), potassium phosphate tribasic (424 mg, 2.00 mmol) and tris(dibenzylideneacetone)dipalladium(0) (5 mg, 0.01 mmol) according to the method described in Preparation 156 to obtain 164 mg (66% yield) of the title compound as an oil.

LRMS (m/z): 249 (M+1)⁺

Preparation 158

(S)-2-(1-((5-(3-Fluoro-5-methoxybenzyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (93 mg, 0.16 mmol) was treated with 2-(3-fluoro-5-methoxybenzyl)-4,4,5,5-tetramethyl-1,3,2-dioxaborolane (130 mg, 0.38 mmol), sodium carbonate (40 mg, 0.38 mmols) and 1,1'-bis(diphenylphosphino)ferrocene-palladium(II)dichloride dichloromethane complex (11 mg, 0.02 mmol) in a mixture of 1,2-dimethoxyethane (1.1 ml) and water (0.3 ml) according to the method described in Preparation 62. The residue was purified using SP1® Purification System (0% to 40%, hexane-ethyl acetate) to give 14 mg (9% yield, 68% purity) of the title compound.

LRMS (m/z): 654 (M+1)⁺.

Preparation 159

(S)-5-Methyl-3-phenyl-2-(1-((5-(phenylethynyl)-7-((2-(trimethylsilyl)ethoxy)methyl)-7H-pyrrolo[2,3-d]pyrimidin-4-yl)amino)ethyl)pyrrolo[2,1-f][1,2,4]triazin-4(3H)-one a) 4-Chloro-5-(phenylethynyl)-7-((2-(trimethylsilyl)ethoxy)methyl)-7H-pyrrolo[2,3-d]pyrimidine 4-Chloro-5-iodo-7-((2-(trimethylsilyl)ethoxy)methyl)-7H-pyrrolo[2,3-d]pyrimidine (50 mg, 0.12 mmol) was dissolved in 140 µl tetrahydrofuran and 160 µl triethylamine. Ethynylbenzene (16 µl, 0.15 mmol), bis(triphenylphosphine)palladium(II) dichloride (9 mg, 0.01 mmol) and copper(I) iodide (5 mg, 0.02 mmol) were added and the mixture was stirred at room temperature during 2 h. The reaction was poured into a 4% aqueous solution of sodium bicarbonate and extracted twice with ethyl acetate. The organics were combined and washed with water, brine, dried over sodium sulphate, filtered and evaporated under reduced pressure. The residue was purified using SP1® Purification System (0% to 15%, hexane-ethyl acetate) to give 45 mg (95% yield) of the title compound.

LRMS (m/z): 384 (M+1)+.

b) (S)-5-Methyl-3-phenyl-2-(1-((5-(phenylethynyl)-7-((2-(trimethylsilyl)ethoxy)methyl)-7H-pyrrolo[2,3-d]pyrimidin-4-yl)amino)ethyl)pyrrolo[2,1-f][1,2,4]triazin-4(3H)-one (S)-1-(5-Methyl-4-oxo-3-phenyl-3,4-dihydropyrrolo[2,1-f][1,2,4]triazin-2-yl)ethanaminium chloride (36 mg, 0.12 mmol) was treated with 4-chloro-5-iodo-7-((2-(trimethylsilyl)ethoxy)methyl)-7H-pyrrolo[2,3-d]pyrimidine (45 mg, 0.12 mmol), cesium fluoride (7 mg, 0.05 mmol), N,N-diisopropylethylamine (247 µl, 1.42 mmol) and tert-butanol (720 µl) as a solvent according to Preparation 13 but stirring the reaction mixture at 100° C. overnight. The residue was purified using SP1® Purification System (0% to 100%, hexane-ethyl acetate) to give 9 mg (12% yield) of the title compound.

LRMS (m/z): 616 (M+1)⁺.

Preparation 160

(S)—N-(3-Hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with N-(3-hydroxy-5-(4,4,5,5-tetramethyl-1,3,2-dioxaborolan-2-yl)phenyl)methanesulfonamide (101 mg, 0.32 mmol), sodium carbonate (34 mg, 0.32 mmols) and 1,1'-bis(diphenylphosphino)ferrocene-palladium(II)dichloride dichloromethane complex (8 mg, 0.01 mmol) using 1,2-dimethoxyethane (0.96 ml) and water (0.24 ml) as solvents according to the method described in Preparation 62. The residue was purified using SP1® Purification

Preparation 161

(S)-2-(1-((5-(4-Hydroxy-3-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.13 mmol) was treated with 2-methoxy-4-(4,4,5,5-tetramethyl-1,3,2-dioxaborolan-2-yl)phenol (101 mg, 0.32 mmol), sodium carbonate (34 mg, 0.32 mmols) and 1,1'-bis(diphenylphosphino)ferrocene-palladium(II)dichloride dichloromethane complex (8 mg, 0.01 mmol) using 1,2-dimethoxyethane (0.96 ml) and water (0.24 ml) as a solvents according to the method described in Preparation 62. The residue was purified using SP1® Purification System (0% to 80%, hexane-ethyl acetate) to give 63 mg (68% yield) of the title compound.

LRMS (m/z): 638 (M+1)$^+$.

Preparation 162

(S)-2-(1-((5-((2-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 4-Chloro-5-((2-methoxyphenyl)thio)-7H-pyrrolo[2,3-d]pyrimidine

4-Chloro-5-iodo-7-((2-(trimethylsilyl)ethoxy)methyl)-7H-pyrrolo[2,3-d]pyrimidine (110 mg, 0.27 mmol) was treated with 2-methoxybenzenethiol (49 µl, 0.40 mmol), copper(I) iodide (77 mg, 0.40 mmol) and potassium carbonate (74 mg, 0.54 mmol) in 2.2 mL dimethylformamide according to the method described in Preparation 86 but heating the reaction mixture at 50° C. overnight. The residue was purified using SP1® Purification System (0% to 15%, hexane-ethyl acetate) to give 69 mg (60% yield) of the title compound.

LRMS (m/z): 423 (M+1)$^+$.

b) (S)-2-(1-((5-((2-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-1-(5-Methyl-4-oxo-3-phenyl-3,4-dihydropyrrolo[2,1-f][1,2,4]triazin-2-yl)ethanaminium chloride (50 mg, 0.16 mmol) was treated with 4-chloro-5-((2-methoxyphenyl)thio)-7H-pyrrolo[2,3-d]pyrimidine (69 mg, 0.16 mmol), cesium fluoride (10 mg, 0.07 mmol), N,N-diisopropylethylamine (171 µl, 0.98 mmol) and tert-butanol (1 ml) as a solvent according to the method described in Preparation 87 but stirring the reaction mixture at 125° C. overnight. The residue was purified using SP1® Purification System (0% to 50%, hexane-ethyl acetate) to give 57 mg (52% yield) of the title compound.

LRMS (m/z): 654 (M+1)$^+$.

Preparation 163

(S)-2-(1-((5-((4-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 4-Chloro-5-((4-methoxyphenyl)thio)-7-((2-(trimethylsilyl)ethoxy)methyl)-7H-pyrrolo[2,3-d]pyrimidine 4-Chloro-5-iodo-7-((2-(trimethylsilyl)ethoxy)methyl)-7H-pyrrolo[2,3-d]pyrimidine (110 mg, 0.27 mmol) was treated with 4-methoxybenzenethiol (50 µl, 0.40 mmol), copper(I) iodide (77 mg, 0.40 mmol) and potassium carbonate (74 mg, 0.54 mmol) in 2.2 mL dimethylformamide according to method described in Preparation 86 but stirring the reaction mixture at 50° C. overnight. The residue was purified using SP1® Purification System (0% to 15%, hexane-ethyl acetate) to give 57 mg (43% yield, 85% purity) of the title compound.

LRMS (m/z): 423 (M+1)$^+$.

b) (S)-2-(1-((5-((4-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-1-(5-Methyl-4-oxo-3-phenyl-3,4-dihydropyrrolo[2,1-f][1,2,4]triazin-2-yl)ethanaminium chloride (35 mg, 0.11 mmol) was treated with 4-chloro-5-((4-methoxyphenyl)thio)-7H-pyrrolo[2,3-d]pyrimidine (57 mg, 0.11 mmol), cesium fluoride (7 mg, 0.05 mmol), N,N-diisopropylethylamine (120 µl, 0.89 mmol) and tert-butanol (0.70 ml) as a solvent according to Preparation 13 but stirring the reaction mixture at 125° C. overnight. The residue was purified using SP1® Purification System (0% to 50%, hexane-ethyl acetate) to give 65 mg (87% yield) of the title compound.

LRMS (m/z): 654 (M+1)$^+$.

Preparation 164

(S)-2-(1-((5-(3-Chloro-2-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was treated with 2-chloro-6-(4,4,5,5-tetramethyl-1,3,2-dioxaborolan-2-yl)phenol (52 mg, 0.30 mmol), sodium carbonate (32 mg, 0.30 mmols) and 1,1'-bis(diphenylphosphino)ferrocene-palladium(II)dichloride dichloromethane complex (9 mg, 0.01 mmol) in 1,2-dimethoxyethane (900 µl) and water (225 µl) according to the method described in Preparation 62. The residue was purified using SP1® Purification System (0% to 35%, hexane-ethyl acetate) to give 58 mg (55% yield, 77% purity) of the title compound.

LRMS (m/z): 643 (M+1)$^+$.

Preparation 165

(S)—N-(5-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was dissolved in 1.9 mL N,N-dimethylformamide. N-(5-(4,4,5,5-Tetramethyl-1,3,2-dioxaborolan-2-yl)pyridin-3-yl)methanesulfonamide (225 mg, 0.76 mmol) and sodium carbonate (86 mg, 0.81 mmol) were added and the mixture was submitted to three vacuum-argon cycles. Tetrakis(triphenylphosphine)palladium(0) (44 mg, 0.04 mmol) was added under argon conditions. The mixture was stirred at 130° C. during 1.5 h. The reaction was poured into a saturated ammonium chloride solution and extracted twice with ethyl acetate. The organics were combined and washed with water, brine, dried over sodium sulphate, filtered and evaporated under reduced pressure. The residue was purified using SP1® Purification System (0% to 100%, hexane-ethyl acetate) to give 53 mg (45% yield, 73% purity) of the title compound.
LRMS (m/z): 686 (M+1)$^+$.

Preparation 166

(S)-4-Methoxy-N-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)benzenesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was treated with 4-methoxy-N-(3-(4,4,5,5-tetramethyl-1,3,2-dioxaborolan-2-yl)phenyl)benzenesulfonamide (236 mg, 0.61 mmol), sodium carbonate (64 mg, 0.61 mmols) and 1,1'-bis(diphenylphosphino)ferrocene-palladium(II)dichloride dichloromethane complex (18 mg, 0.03 mmol) in 1,2-dimethoxyethane (1.2 ml) and water (0.30 ml) according to the method described in Preparation 62. The residue was purified using SP1® Purification System (0% to 35%, hexane-ethyl acetate) to give 82 mg (81% yield, 73% purity) of the title compound.
LRMS (m/z): 777 (M+1)$^+$.

Preparation 167

1-((4-Methoxyphenyl)sulfonyl)-6-(4,4,5,5-tetramethyl-1,3,2-dioxaborolan-2-yl)-1H-indazole a) 6-Bromo-1-((4-methoxyphenyl)sulfonyl)-1H-indazole 6-Bromo-1H-indazole (500 mg, 2.54 mmol) was treated with 4-methoxybenzene-1-sulfonyl chloride (576 mg, 2.79 mmol) according to the method described in Preparation 15b to give 820 mg (81% yield) of the title compound. Purity 92%.
LRMS (m/z): 467, 469 (M+1)$^+$.

b) 1-((4-Methoxyphenyl)sulfonyl)-6-(4,4,5,5-tetramethyl-1,3,2-dioxaborolan-2-yl)-1H-indazole 6-Bromo-1-((4-methoxyphenyl)sulfonyl)-1H-indazole (720 mg, 1.76 mmol), bis(pinacolato)diboron (896 mg, 3.53 mmol), potassium acetate (519 mg, 5.29 mmol), bis(diphenylphosphino)ferrocene-palladium(II)dichloride dichloromethane complex (144 mg, 0.18 mmol) and 1,1'-bis(diphenylphosphino)ferrocene (97 mg, 0.18 mmol) were suspended in dioxane (12 ml) and stirred overnight at 100° C. After evaporation of the solvent under reduced pressure, ethyl acetate (100 ml) was added to the residue and the precipitated salts were eliminated by filtration. The solvent was evaporated under reduced pressure and the residue was purified by flash chromatography using SP1® Purification System (0% to 15%, hexane-ethyl acetate) to obtain 925 mg (78% yield) of the title compound, that was used in the next step without further purification. Purity: 70%
LRMS (m/z): 333 (M+1)$^+$

Preparation 168

4-Methoxy-N-(6-(4,4,5,5-tetramethyl-1,3,2-dioxaborolan-2-yl)-1H-indol-4-yl)benzenesulfonamide a) 6-Bromo-1H-indol-4-amine 6-Bromo-4-nitro-1H-indole (1 g, 4.15 mmol) was treated with iron powder (1.16 g, 20 mmol) in acetic acid (60 ml) and stirred at room temperature. After 1 h the crude was filtered over Celite and the solvent was removed under reduced pressure. A mixture of a solution of sodium bicarbonate (4%) and ethyl acetate was added and the resulting mixture was filtered over Celite. The organic phase was washed with water and brine, dried over magnesium sulphate and the solvent was removed to give 1.05 g (100% yield) of the title compound as a dark solid, that was used in the next step without further purification. Purity 83%.
LRMS (m/z): 211, 213 (M+1)$^+$.

b) N-(6-Bromo-1H-indol-4-yl)-4-methoxybenzenesulfonamide

6-Bromo-1H-indol-4-amine (500 mg, 1.97 mmol) was treated with 4-methoxybenzene-1-sulfonyl chloride (446 mg, 2.16 mmol) according to the method described in Preparation 15b to give 890 mg (100% yield) of the title compound. Purity 87%.
LRMS (m/z): 467, 469 (M+1)$^+$.

c) 4-Methoxy-N-(6-(4,4,5,5-tetramethyl-1,3,2-dioxaborolan-2-yl)-1H-indol-4-yl)benzenesulfonamide N-(6-Bromo-1H-indol-4-yl)-4-methoxybenzenesulfonamide (790 mg, 1.80 mmol), bis(pinacolato)diboron (915 mg, 3.53 mmol), potassium acetate (519 mg, 3.61 mmol), bis(diphenylphosphino)ferrocene-palladium(II)dichloride dichloromethane complex (147 mg, 0.18 mmol) and 1,1'-bis(diphenylphosphino)ferrocene (99 mg, 0.18 mmol) were suspended in dioxane (10 ml) and stirred overnight at 120° C. After evaporation of the solvent under reduced pressure, ethyl acetate (100 ml) was added to the residue and the precipitated salts were eliminated by filtration. The solvent was evaporated under reduced pressure and the residue was purified by flash chromatography using SP1® Purification System (0% to 50%, hexane-ethyl acetate) to obtain 241 mg (26% yield) of the title compound. Purity: 85%
LRMS (m/z): 429 (M+1)$^+$

Preparation 169

N-(6-Chloro-1-((2-(trimethylsilyl)ethoxy)methyl)-1H-indol-4-yl)-4-methoxy benzenesulfonamide a) 6-Chloro-4-nitro-1-((2-(trimethylsilyl)ethoxy)methyl)-1H-indole

Sodium hydride (60% dispersion in mineral oil, 0.17 g, 6.61 mmol) was suspended in 30 mL dimethylformamide. The mixture was stirred for 15 min and was cooled at 0° C. with an ice bath. 6-Chloro-4-nitro-1H-indole (1 g, 5.09 mmol) dissolved in 5 mL dimethylformamide was added dropwise and the mixture was stirred 30 min. At the same temperature [2-(chloromethoxy)ethyl](trimethyl)silane (1.1 g, 6.61 mmol) dissolved in 5 mL dimethylformamide was added dropwise and stirred for 30 min at 0° C. The mixture was poured into water and extracted twice with ethyl acetate. The organic were dried over sodium sulphate and concentrated under reduced pressure to give 1.82 g (100% yield) of the title compound as a yellow oil. Purity 96%.

LRMS (m/z): 325, 327 (M−1)⁻.

b) 6-Chloro-1-((2-(trimethylsilyl)ethoxy)methyl)-1H-indol-4-amine

6-Chloro-4-nitro-1-((2-(trimethylsilyl)ethoxy)methyl)-1H-indole (1.82 g, 5.35 mmol) was treated with iron powder (1.49 g, 27 mmol) in acetic acid (80 ml) and stirred at room temperature. After 1 h the crude was filtered over Celite and the solvent was removed in vacuum. A mixture of a solution of sodium bicarbonate 4% and ethyl acetate was added and the resulting mixture was filtered over Celite. The organic phase was washed with water and brine, dried over magnesium sulphate and the solvent was removed to give 1.76 g (93% yield) of the title compound as a dark solid, that was used in the next step without further purification. Purity 85%.

LRMS (m/z): 297, 299 (M+1)⁺.

c) N-(6-Chloro-1-((2-(trimethylsilyl)ethoxy)methyl)-1H-indol-4-yl)-4-methoxy benzenesulfonamide 6-Chloro-1-((2-(trimethylsilyl)ethoxy)methyl)-1H-indol-4-amine (880 mg, 2.52 mmol) was treated with 4-methoxybenzene-1-sulfonyl chloride (572 mg, 2.77 mmol) according to the method described in Preparation 15b to give 1.48 mg (97% yield) of the title compound. Purity 85%.

LRMS (m/z): 467, 469 (M+1)⁺.

Preparation 170

(S)—N-(6-(4-Amino-6-((1-(5-methyl-4-oxo-3-phenyl-3,4-dihydropyrrolo[2,1-f][1,2,4]triazin-2-yl)ethyl)amino)pyrimidin-5-yl)-1-((2-(trimethylsilyl)ethoxy)methyl)-1H-indol-4-yl)-4-methoxybenzenesulfonamide a) 4-Methoxy-N-(6-(4,4,5,5-tetramethyl-1,3,2-dioxaborolan-2-yl)-1-((2-(trimethylsilyl)ethoxy)methyl)-1H-indol-4-yl)benzenesulfonamide N-(6-Chloro-1-((2-(trimethylsilyl)ethoxy)methyl)-1H-indol-4-yl)-4-methoxy benzenesulfonamide (600 mg, 1.09 mmol), bis(pinacolato)diboron (554 mg, 2.18 mmol), potassium acetate (321 mg, 3.28 mmol), bis(diphenylphosphino)ferrocene-palladium(II)dichloride dichloromethane complex (89 mg, 0.11 mmol) and 1,1′-bis(diphenylphosphino)ferrocene (104 mg, 0.22 mmol) were suspended in dioxane (10 ml) and heated overnight to 120° C. After evaporation the solvent under reduced pressure, ethyl acetate (100 ml) was added to the residue and the precipitated salts were eliminated by filtration. The solvent was evaporated under reduced pressure and the residue was purified by flash chromatography (0% to 50%, hexane-ethyl acetate) to obtain 560 mg (78% yield) of the title compound. Purity 85%.

LRMS (m/z): 558 (M+1)⁺ b) (S)—N-(6-(4-amino-6-((1-(5-methyl-4-oxo-3-phenyl-3,4-dihydropyrrolo[2,1-f][1,2,4]triazin-2-yl)ethyl)amino)pyrimidin-5-yl)-1-((2-(trimethylsilyl)ethoxy)methyl)-1H-indol-4-yl)-4-methoxybenzenesulfonamide A solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added 4-methoxy-N-(6-(4,4,5,5-tetramethyl-1,3,2-dioxaborolan-2-yl)-1-((2-(trimethylsilyl)ethoxy)methyl)-1H-indol-4-yl)benzenesulfonamide (194 mg, 0.30 mmol), 1,1′-bis(diphenylphosphino)ferrocene-palladium(II)dichloride dichloromethane complex (18 mg, 0.02 mmol) and 227 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1® Purification System (0% to 75%, hexane-ethyl acetate) to obtain 115 mg (60% yield) of the title compound as a white solid. Purity 95%.

LRMS (m/z): 792 (M+1)⁺.

Preparation 171

(S)—N-(3-Hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-4-methoxybenzenesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (70 mg, 0.12 mmol) was treated with N-(3-hydroxy-5-(4,4,5,5-tetramethyl-1,3,2-dioxaborolan-2-yl)phenyl)-4-methoxybenzenesulfonamide (229 mg, 0.57 mmol), sodium carbonate (60 mg, 0.57 mmols), 1,1′-bis(diphenylphosphino)ferrocene-palladium(II)dichloride dichloromethane complex (17 mg, 0.02 mmol) and 1.12 ml 1,2-dimethoxyethane and 0.28 ml water as a solvents according to the method described in Preparation 62. The residue was purified using SP1® Purification System (0% to 80%, hexane-ethyl acetate) to give 40 mg (33% yield, 77% purity) of the title compound.

LRMS (m/z): 793 (M+1)⁺.

Preparation 172

(S)-2-(1-((5-((5-Fluoro-2-methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 4-Chloro-5-((5-fluoro-2-methoxyphenyl)thio)-7-((2-(trimethylsilyl)ethoxy)methyl)-7H-pyrrolo[2,3-d]pyrimidine 4-Chloro-5-iodo-7-((2-(trimethylsilyl)ethoxy)methyl)-7H-pyrrolo[2,3-d]pyrimidine (200 mg, 0.49 mmol), 5-fluoro- 2-methoxybenzenethiol (96 μl, 0.73 mmol), copper(I) iodide (139 mg, 0.73 mmol), potassium carbonate (135 mg, 0.98 mmol) and 2 ml dimethylformamide as solvent according to Preparation 86 but heating the reaction mixture at 50° C. overnight. The residue was purified using SP1® Purification System (0% to 15%, hexane-ethyl acetate) to give 56 mg (26% yield) of the title compound.
LRMS (m/z): 423 (M+1)$^+$.

b) (S)-2-(1-((5-((5-Fluoro-2-methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-1-(5-Methyl-4-oxo-3-phenyl-3,4-dihydropyrrolo[2,1-f][1,2,4]triazin-2-yl)ethanaminium chloride (39 mg, 0.13 mmol) was treated with 4-chloro-5-((5-fluoro-2-methoxyphenyl)thio)-7-((2-(trimethylsilyl)ethoxy)methyl)-7H-pyrrolo[2,3-d]pyrimidine (56 mg, 0.13 mmol), cesium fluoride (8 mg, 0.05 mmol), N,N-diisopropylethylamine (201 μl, 1.15 mmol) and tert-butanol (0.78 ml) as a solvent according to Preparation 13 but heating the reaction mixture at 125° C. overnight. The residue was purified using SP1® Purification System (0% to 40%, hexane-ethyl acetate) to give 63 mg (73% yield) of the title compound.
LRMS (m/z): 672 (M+1)$^+$.

Preparation 173

(S)—N-Methyl-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzenesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was treated with (3-(N-methylsulfamoyl)phenyl) boronic acid (68 mg, 0.32 mmol), sodium carbonate (33 mg, 0.32 mmols), 1,1'-bis(diphenylphosphino)ferrocene-palladium(11)dichloride dichloromethane complex (17 mg, 0.02 mmol) and 1.12 ml 1,2-dimethoxyethane and 0.28 ml water as a solvents according to the method described in Preparation 62. The residue was purified using SP1® Purification System (0% to 80%, hexane-ethyl acetate) to give 40 mg (33% yield, 77% purity) of the title compound.
LRMS (m/z): 685 (M+1)$^+$.

Preparation 174

(S)-2-(1-((5-(3-Amino-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 3-Amino-5-(4,4,5,5-tetramethyl-1,3,2-dioxaborolan-2-yl)phenol 3-Amino-5-bromophenol (0.75 g, 3.99 mmol), prepared as described at C. Cannizzaro et al. U.S. Pat. No. 7,417,055 B2 20080826), was dissolved in 19 ml 1,4-dioxane. Bis(pinacolato)diboron (1.52 g, 5.99 mmol) and potassium acetate (1.17 g, 11.96 mmol were added and the mixture was submitted to three vacuum-argon cycles. 1,1'-Bis(diphenylphosphino)ferrocene-palladium(II)dichloride dichloromethane complex (0.33 g, 0.40 mmol) was added under argon conditions. The mixture was heated under microwave irradiation at 120° C. during 20 minutes. The reaction was filtered through a plug of Celite and the filtered was partitioned between ethyl acetate and water. The organic phase was extracted, washed with brine, dried over sodium sulphate, filtered and evaporated under reduced pressure. The residue was purified using SP1® Purification System (0% to 15% dichloromethane-2-propanol) to obtain 0.61 g (63% yield) of the title compound.
LRMS (m/z): 236 (M+1)$^+$.

b) (S)-2-(1-((5-(3-Amino-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (0.53 g, 0.89 mmol) was treated with 3-amino-5-(4,4,5,5-tetramethyl-1,3,2-dioxaborolan-2-yl)phenol (0.52 g, 2.22 mmol), sodium carbonate (0.24 g, 2.22 mmol), 1,1'-bis(diphenylphosphino)ferrocene-palladium(II)dichloride dichloromethane complex (0.22 g, 0.27 mmol) and 22 ml 1,2-dimethoxyethane and 5 ml water as a solvents according to the method described in Preparation 62. The residue was purified using SP1® Purification System (0% to 15% dichloromethane-2-propanol) to obtain 0.36 g (62% yield) of the title compound.
LRMS (m/z): 622 (M+1)$^+$.

Preparation 175

N-[3-Hydroxy-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]sulfamide (S)-2-(1-((5-(3-Amino-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was dissolved in 0.75 ml tetrahydrofuran. Pyridine (10 μl, 0.12 mmol) and sulfamoyl chloride (11 mg, 0.10 mmol) were added and the mixture was stirred at room temperature during 2 h. The reaction was poured into water and extracted twice with ethyl acetate. The organics were combined and washed with water, brine, dried over sodium sulphate, filtered and evaporated under reduced pressure. The residue was purified using SP1® Purification System (0% to 100% hexane-ethyl acetate) to obtain 38 mg (66% yield) of the title compound.
LRMS (m/z): 702 (M+1)$^+$.

Preparation 176

N-(3,5-Dihydroxyphenyl)methanesulfonamide a) N-(3,5-Dimethoxyphenyl)methanesulfonamide 3,5-Dimethoxyaniline (1 g mg, 6.53 mmol) was dissolved in pyridine (48 ml) and was treated with methanesulfonyl chloride (0.56 ml, 7.18 mmol). The reaction mixture was stirred at room temperature overnight. Methanesulfonyl chloride (0.28 ml, 3.59 mmol) was added and the mixture was stirred at room temperature overnight. The solvent was removed to give 1.7 mg (100% yield) of the title compound as a dark oil. Purity 89%.
LRMS (m/z): 232 (M+1)$^+$ b) N-(3,5-Dihydroxyphenyl)methanesulfonamide

N-(3,5-Dimethoxyphenyl)methanesulfonamide (1.7 g, 6.53 mmol) was dissolved in dichloromethane (28 ml). A solution of boron tribromide (1 M in dichloromethane, 33 mL, 33 mmol) was added dropwise and the reaction was stirred at room temperature overnight. Boron tribromide (1M in dichloromethane, 10 ml, 10 mmol) was added and the mixture was stirred for 3 hours. The mixture was diluted with ethyl acetate and washed with a solution of 4% sodium bicarbonate, water, brine and dried over sodium sulphate, filtered and evaporated under reduced pressure. The product was purified by reverse phase using SP1® Purification System to give 344 mg (26% yield) of the title compound. Purity 99%.
LRMS (m/z): 202 (M−1)⁻

Preparation 177

3-Hydroxy-5-(methylsulfonamido)phenyl 4-amino-6-chloropyrimidine-5-carboxylate a) 3-Hydroxy-5-(methylsulfonamido)phenyl 4,6-dichloropyrimidine-5-carboxylate N-(3,5-Dihydroxyphenyl)methanesulfonamide (260 mg, 1.28 mmol) was dissolved in tetrahydrofuran (5 ml) and triethylamine (214 μl, 1.52 mmol) was added. Then a solution of 4,6-dichloropyrimidine-5-carbonyl chloride (298 mg, 1.40 mmol, prepared according to E. V. Tarasov et al. *Synlett* 2000, 5, 625-626) was dropwise added. The reaction mixture was stirred at room temperature over 48 hours. The reaction mixture was then diluted with dichloromethane, washed with 4% sodium bicarbonate solution, dried over magnesium sulphate, filtered and evaporated. The product was purified by reverse phase using SP1® Purification System to give 280 mg (18% yield) of the title compound. Purity 100%.
LRMS (m/z): 379 (M+1)⁺ b) 3-Hydroxy-5-(methylsulfonamido)phenyl 4-amino-6-chloropyrimidine-5-carboxylate 3-Hydroxy-5-(methylsulfonamido)phenyl 4,6-dichloropyrimidine-5-carboxylate (110 mg, 0.29 mmol) was dissolved in dioxane (5 ml) and cooled in an ice bath. Ammonia (0.86 ml, 7N in MeOH) was dropwise added and the mixture was stirred at 0° C. and overnight at room temperature. After dilution with ethyl acetate, this organic phase was successively washed with water and brine, dried over magnesium sulphate, filtered and the solvents evaporated under reduced pressure, to yield an oil as a residue (148 mg, 49% purity, 70% yield) which was used in the next synthetic step without further purification.
LRMS (m/z): 359 (M+1)⁺

Preparation 178

(S)-3-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzonitrile (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with (3-cyano-5-methoxyphenyl)boronic acid (74 mg, 0.42 mmol), sodium carbonate (45 mg, 0.42 mmols), 1,1'-bis(diphenylphosphino)ferrocene-palladium(II)dichloride dichloromethane complex (41 mg, 0.05 mmol) and 4 ml 1,2-dimethoxyethane and 1 ml water as a solvents according to the method described in Preparation 62. The residue was purified using SP1® Purification System (0% to 50% hexane-ethyl acetate) to obtain 54 mg (43% yield, 87% purity) of the title compound.
LRMS (m/z): 647 (M+1)⁺.

Preparation 179

(S)-2-(1-(Dimethylamino)-N-(3-hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)ethanesulfonamide (S)-2-(1-((5-(3-Amino-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.12 mmol) was dissolved in 3.75 ml tetrahydrofuran. Triethylamine (50 μl, 0.36 mmol) and 2-chloroethanesulfonyl chloride (15 μL, 0.14 mmol) were added and the mixture was stirred at room temperature during 2 h. Dimethylamine 2M in tetrahydrofuran (301 μl, 0.60 mmol) was added and the mixture was stirred again at room temperature during 4 h. The reaction was poured into water and extracted twice with ethyl acetate. The organics were combined and washed with water, brine, dried over sodium sulphate, filtered and evaporated under reduced pressure. The residue was purified using SP1® Purification System (0% to 30% dichloromethane-2-propanol) to obtain 15 mg (13% yield, 77% purity) of the title compound.
LRMS (m/z): 758 (M+1)⁺.

Preparation 180

(S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was treated with N-(4-(4,4,5,5-tetramethyl-1,3,2-dioxaborolan-2-yl)phenyl)methanesulfonamide (94 mg, 0.32 mmol), sodium carbonate (33 mg, 0.32 mmols), 1,1'-bis(diphenylphosphino)ferrocene-palladium(II)dichloride dichloromethane complex (31 mg, 0.04 mmol) and 3 ml 1,2-dimethoxyethane and 0.75 ml water as a solvents according to the method described in Preparation 62. The residue was purified using SP1® Purification System (0% to 50% hexane-ethyl acetate) to obtain 65 mg (62% yield, 82% purity) of the title compound.
LRMS (m/z): 685 (M+1)⁺.

Preparation 181

(S)-1-(3-Hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)urea To a suspension of (S)-2-(1-((5-(3-amino-5-hydroxyphenyl)-7-((2-(trimethylsilyl)ethoxy)methyl)-7H-pyrrolo[2,3- d]pyrimidin-4-yl)amino)ethyl)-5-methyl-3-phenylpyrrolo[2,1-f][1,2,4]triazin-4(3H)-one (50 mg, 0.08 mmol) in 403 μl water and 208 μl acetic acid was added potassium isocyanate (10 mg, 0.12 mmol) The mixture was heated 35° C. overnight. The reaction was poured into water and extracted twice with ethyl acetate. The organics were combined and washed with water, brine, dried over sodium sulphate, filtered and evaporated under reduced pressure. The residue was purified using SP1® Purification System (0% to 100% hexane-ethyl acetate) to obtain 18 mg (33% yield) of the title compound.

LRMS (m/z): 666 (M+1)$^+$.

Preparation 182

(S)-2-(1-((6-Amino-5-(1H-indol-6-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (120 mg, 0.27 mmol) were added (1H-indol-6-yl)boronic acid (65 mg, 0.41 mmol), 1,1'-bis(diphenylphosphino)ferrocene-palladium(11)dichloride dichloromethane complex (22 mg, 0.03 mmol) and 272 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1® Purification System (50% to 100%, hexane-ethyl acetate) to obtain 125 mg (94% yield) of the title compound as a white solid. Purity 98%.

LRMS (m/z): 477 (M−1)$^-$.

Preparation 183

4-Hydroxy-N-methyl benzenesulfonamide a) 4-Methoxy-N-methylbenzenesulfonamide

4-Methoxybenzene-1-sulfonyl chloride (1 g, 4.84 mmol) was dissolved in dichloromethane (15 mL) and was treated with methanamine (9.7 ml, 19.40 mmol). The reaction mixture was stirred at room temperature for two hours. The crude was filtered and washed with dichloromethane to give 1.02 g (100% yield) of the title compound as a white solid. Purity 95%.

LRMS (m/z): 202 (M+1)$^+$ b) 4-Hydroxy-N-methylbenzenesulfonamide

4-Methoxy-N-methylbenzenesulfonamide (1.02 g, 4.82 mmol) was dissolved in dichloromethane (50 ml). A solution of boron tribromide (1M in dichloromethane, 14.5 mL, 14.5 mmol) was added dropwise and the reaction was stirred at room temperature overnight. The mixture was diluted with ethyl acetate and washed with a solution of 4% sodium bicarbonate, water, brine and dried over sodium sulphate, filtered and evaporated under reduced pressure. The product was purified by reverse phase using SP1® Purification System to give 650 mg (68% yield) of the title compound. Purity 95%.

LRMS (m/z): 186 (M−1)$^-$

Preparation 184

4-(N-Methylsulfamoyl)phenyl 4-amino-6-chloropyrimidine-5-carboxylate a) 4-(N-methylsulfamoyl)phenyl 4,6-dichloropyrimidine-5-carboxylate 4-Hydroxy-N-methylbenzenesulfonamide (650 mg, 3.47 mmol) was dissolved in tetrahydrofuran (18 ml) and triethylamine (1.06 ml, 7.61 mmol) was added. Then a solution of 4,6-dichloropyrimidine-5-carbonyl chloride (808 mg, 3.82 mmol, prepared according to E. V. Tarasov et al. *Synlett* 2000, 5, 625-626) was dropwise added. The reaction mixture was stirred at room temperature overnight. The reaction mixture was then diluted with dichloromethane, washed with 4% sodium bicarbonate solution, dried over magnesium sulphate, filtered and evaporated to give 1.4 g (91% yield) of the title compound, that was used in the next step without further purification. Purity 82%.

LRMS (m/z): 363 (M+1)$^+$ b) 4-(N-Methylsulfamoyl)phenyl 4-amino-6-chloropyrimidine-5-carboxylate 4-(N-methylsulfamoyl)phenyl 4,6-dichloropyrimidine-5-carboxylate (1.4 g, 3.18 mmol) was dissolved in dioxane (16 ml) and cooled in an ice bath. Ammonia (2.27 ml, 7N in MeOH) was dropwise added and the mixture was stirred at 0° C. for 6 h. The solvent was removed and ethyl acetate added. The solid precipitate was filtered and washed with ethyl acetate to give 750 mg (69% yield) of the title compound. Purity 100%

LRMS (m/z): 343 (M+1)$^+$

Preparation 185

4-Amino-6-chloro-N-(4-(N-methylsulfamoyl)phenyl)pyrimidine-5-carboxamide a) 4,6-Dichloro-N-(4-(N-methylsulfamoyl)phenyl) pyrimidine-5-carboxamide 4-Amino-N-methylbenzenesulfonamide (244 mg, 1.31 mmol) was dissolved in tetrahydrofuran (12 ml) and triethylamine (402 μl, 2.88 mmol) was added. Then a solution of 4,6-dichloropyrimidine-5-carbonyl chloride (300 mg, 1.42 mmol, prepared according to E. V. Tarasov et al. *Synlett* 2000, 5, 625-626) was dropwise added. After 2 h more triethylamine (202 μl, 1.44 mmol) and 4,6-dichloropyrimidine-5-carbonyl chloride (150 mg, 0.71 mmol) were added. The reaction mixture was stirred at room temperature overnight. The reaction mixture was then diluted with dichloromethane, washed with 4% sodium bicarbonate solution, dried over magnesium sulphate, filtered and evaporated. The crude was purified by flash chromatography (0% to 60%, hexane-ethyl acetate) using a SP1® Purification System to give 238 mg (50% yield) of the title compound. Purity 100%.

LRMS (m/z): 362 (M+1)$^+$ b) 4-Amino-6-chloro-N-(4-(N-methylsulfamoyl) phenyl)pyrimidine-5-carboxamide 4,6-Dichloro-N-(4-(N-methylsulfamoyl)phenyl)pyrimidine-5-carboxamide (238 m g, 0.66 mmol) was dissolved in dioxane (3 ml) and cooled in an ice bath. Ammonia (0.47 ml, 7N in MeOH, 3.3 mmol) was dropwise added and the mixture was stirred at 0° C. for 6 h and at room temperature overnight. The solvent was removed and ethyl acetate added. The solid precipitate was filtered and washed with ethyl acetate to give 181 mg (80% yield) of the title compound. Purity 100%

LRMS (m/z): 342 (M+1)+

Preparation 186

(S)—N-(6-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-4-yl)methanesulfonamide To a solution of (S)-2-(1-(((6-amino-5-bromopyrimidin-4-yl)amino)ethyl)-5-methyl-3-phenylpyrrolo[2,1-f][1,2,4]triazin-4(3H)-one (88 mg, 0.15 mmol) were added N-(6-(4,4,5,5-tetramethyl-1,3,2-dioxaborolan-2-yl)-1H-indol-4-yl)methanesulfonamide (55 mg, 0.16 mmol), tetrakis(triphenylphosphine)palladium(0) (52 mg, 0.04 mmol) and 187 µl of a 2M aqueous solution of sodium carbonate in dimethylformamide (3 ml). The mixture was stirred under argon atmosphere at 90° C. for 6 hours and then diluted with ethyl acetate. The resulting solution was washed with water and brine, dried over magnesium sulphate, filtered and the solvents were removed under reduced pressure. The crude was purified by reverse phase using SP1® Purification System to give 37 mg (34% yield) of the title compound as a white solid. Purity 100%.

LRMS (m/z): 724 (M+1)+.

Preparation 187

N-(6-(4,4,5,5-Tetramethyl-1,3,2-dioxaborolan-2-yl)-1H-indol-4-yl)methanesulfonamide a) N-(6-Bromo-1H-indol-4-yl)methanesulfonamide 6-Bromo-1H-indol-4-amine (500 mg, 1.97 mmol) was treated with methanesulfonyl chloride (167 µl, 2.16 mmol) according to the method described in Preparation 15b to give 580 mg (91% yield) of the title compound. Purity 89%.

LRMS (m/z): 287, 289 (M+1)+.

b) N-(6-(4,4,5,5-Tetramethyl-1,3,2-dioxaborolan-2-yl)-1H-indol-4-yl)methanesulfonamide N-(6-Bromo-1H-indol-4-yl)methanesulfonamide (580 mg, 1.79 mmol), bis(pinacolato)diboron (906 mg, 3.57 mmol), potassium acetate (525 mg, 5.36 mmol), bis(diphenylphosphino)ferrocene-palladium(II)dichloride dichloromethane complex (145 mg, 0.18 mmol) and 1,1'-bis(diphenylphosphino)ferrocene (99 mg, 0.18 mmol) were suspended in dioxane (8 ml) and heated at 120° C. for 48 h. After evaporation of the solvent under reduced pressure, ethyl acetate (100 ml) is added to the residue and the precipitated salts are eliminated by filtration. The solvent is evaporated under reduced pressure and the residue was purified by flash chromatography (50% to 100%, hexane-ethyl acetate) to obtain 65 mg (10% yield) of the title compound. Purity: 95%

LRMS (m/z): 337 (M+1)+

Preparation 188

4-Methoxybenzyl 4-amino-6-chloropyrimidine-5-carboxylate a) 4-Methoxybenzyl 4,6-dichloropyrimidine-5-carboxylate (4-Methoxyphenyl)methanol (356 mg, 2.58 mmol) was dissolved in tetrahydrofuran (10 ml) and triethylamine (790 µl, 5.67 mmol) was added. Then a solution of 4,6-dichloropyrimidine-5-carbonyl chloride (600 mg, 2.84 mmol, prepared according to E. V. Tarasov et al. *Synlett* 2000, 5, 625-626) in tetrahydrofuran (4 ml) was dropwise added. The reaction mixture was stirred at room temperature for 3 days. The reaction mixture was then diluted with dichloromethane, washed with 4% sodium bicarbonate solution, dried over magnesium sulphate, filtered and evaporated to give 732 mg (81% yield) of the title compound, that was used in the next step without further purification. Purity 84%.

UPLC 3 min: rt 1.78 min b) 4-Methoxybenzyl 4-amino-6-chloropyrimidine-5-carboxylate 4-Methoxybenzyl 4,6-dichloropyrimidine-5-carboxylate (732 m g, 1.97 mmol) was dissolved in dioxane (14 ml) and cooled in an ice bath. Ammonia (1.41 ml, 7N in MeOH, 9.87 mmol) was dropwise added and the mixture was stirred at 0° C. and then stirred at room temperature overnight. The solvent was removed to give 691 mg (94% yield) of the title compound, that was used in the next step without further purification. Purity 79%

LRMS (m/z): 294 (M+1)+

Preparation 189

3-Hydroxy-N,N-dimethyl-5-(4-(((5-methyl-4-oxo-3-phenyl-3,4-dihydropyrrolo[2,1-f][1,2,4]triazin-2-yl)methyl)amino)-7-((2-(trimethylsilyl)ethoxy)methyl)-7H-pyrrolo[2,3-d]pyrimidin-5-yl)benzamide (S)-2-(1-(((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.13 mmol) was treated with 3-hydroxy-N,N-dimethyl-5-(4,4,5,5-tetramethyl-1,3,2-dioxaborolan-2-yl)benzamide (92 mg, 0.32 mmol), sodium carbonate (33 mg, 0.32 mmol), 1,1'-bis(diphenylphosphino)ferrocene-palladium(II)dichloride dichloromethane complex (31 mg, 0.04 mmol) and 3 ml 1,2-dimethoxyethane and 0.75 ml water as a solvents according to the method described in Preparation 62. The residue was purified using SP1® Purification System (0% to 100% hexane-ethyl acetate) to obtain 44 mg (46% yield, 89% purity) of the title compound.

LRMS (m/z): 679 (M+1)+.

Preparation 190

N'-[3-Hydroxy-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]-N,N-dimethylsulfamide (S)-2-(1-((5-(3-Amino-5-hydroxyphenyl)-7-((2-(trimethylsilyl)ethoxy)methyl)-7H-pyrrolo[2,3-d]pyrimidin-4-yl)

amino)ethyl)-5-methyl-3-phenylpyrrolo[2,1-f][1,2,4]triazin-4(3H)-one (71 mg, 0.11 mmol) was treated with pyridine (30 µl, 0.36 mmol), dimethylsulfamoyl chloride (31 µl, 0.28 mmol) and 1.1 ml tetrahydrofuran as a solvent according to the method described in Preparation 175 but heating at 70° C. overnight. The residue was purified using SP1® Purification System (0% to 100% hexane-ethyl acetate) to obtain 8 mg (10% yield) of the title compound.
LRMS (m/z): 730 (M+1)+.

Preparation 191

(S)-2-(1-((5-(3-Amino-5-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 3-Methoxy-5-(4,4,5,5-tetramethyl-1,3,2-dioxaborolan-2-yl)aniline 3-Bromo-5-methoxyaniline (0.90 g, 4.45 mmol) was treated with bis(pinacolato)diboron (1.70 g, 6.69 mmol), potassium acetate (1.31 g, 13.35 mmol), 1,1'-bis(diphenylphosphino)ferrocene-palladium(II)dichloride dichloromethane complex (0.36 g, 0.44 mmol) and 24 ml 1,4-dixane as a solvent according to the method described in Preparation 174a. The residue was purified using SP1® Purification System (0% to 40% hexane-ethyl acetate) to obtain 0.69 g (62% yield) of the title compound.
LRMS (m/z): 250 (M+1)+.

b) (S)-2-(1-((5-(3-Amino-5-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (0.25 g, 0.42 mmol) was treated with 3-methoxy-5-(4,4,5,5-tetramethyl-1,3,2-dioxaborolan-2-yl)aniline (0.26 g, 1.05 mmol), sodium carbonate (0.11 g, 1.05 mmol), 1,1'-bis(diphenylphosphino)ferrocene-palladium(II)dichloride dichloromethane complex (0.10 g, 0.13 mmol) and 10.6 ml 1,2-dimethoxyethane and 2.4 ml water as a solvents according to the method described in Preparation 62. The residue was purified using SP1® Purification System (0% to 100% n-hexane-ethyl acetate) to obtain 0.15 g (54% yield) of the title compound.
LRMS (m/z): 637 (M+1)+

Preparation 192

(S)—N-(3-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-(3-Amino-5-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with pyridine (22 µl, 0.27 mmol), methanesulfonyl chloride (18 µl, 0.23 mmol) and 0.75 ml tetrahydrofuran as a solvent according to the method described in Preparation 175 but heating at 45° C. during 48 h. The residue was purified using SP1® Purification System (0% to 70% hexane-ethyl acetate) to obtain 42 mg (67% yield, 89% purity) of the title compound.
LRMS (m/z): 715 (M+1)+.

Preparation 193

(S)-1-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)urea To a suspension of (S)-2-(1-((5-(6-amino-1H-indol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) in 403 µl water and 208 µl acetic acid was added potassium isocyanate (17 mg, 0.21 mmol) according to the method described in Preparation 181. The residue was purified using SP1® Purification System (0% to 100% hexane-ethyl acetate) to obtain 40 mg (75% yield) of the title compound.
LRMS (m/z): 689 (M+1)$^+$.

Preparation 194

(S)—N-(3-Fluoro-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-2-methoxyethanesulfonamide a) 3-Fluoro-5-(4,4,5,5-tetramethyl-1,3,2-dioxaborolan-2-yl)aniline 3-Bromo-5-fluoroaniline (0.90 g, 4.74 mmol) was treated with bis(pinacolato)diboron (1.80 g, 7.09 mmol), potassium acetate (1.39 g, 14.20 mmol) and 1,1'-bis(diphenylphosphino)ferrocene-palladium(II)dichloride dichloromethane complex (0.39 g, 0.48 mmol) in 1,4-dioxane (24 ml) according to the method described in Preparation 174a. The residue was purified using SP1® Purification System (0% to 40% hexane-ethyl acetate) to obtain 0.84 g (68% yield, 91% purity) of the title compound.
LRMS (m/z): 238 (M+1)$^+$.

b) N-(3-Fluoro-5-(4,4,5,5-tetramethyl-1,3,2-dioxaborolan-2-yl)phenyl)-2-methoxyethanesulfonamide 3-Fluoro-5-(4,4,5,5-tetramethyl-1,3,2-dioxaborolan-2-yl)aniline (250 mg, 1.05 mmol) was treated with 2-methoxyethanesulfonyl chloride (326 mg, 2.06 mmol) and 1 ml pyridine as a solvent according to the method described in Preparation 15b but stirring at 45° C. during 3 h. The residue was purified using SP1® Purification System (0% to 100% hexane-ethyl acetate) to obtain 80 mg (17% yield, 81% purity) of the title compound.
LRMS (m/z): 360 (M+1)+.

c) (S)—N-(3-Fluoro-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-2-methoxyethanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (53 mg, 0.09 mmol) was treated with N-(3-fluoro-5-(4,4,5,5-tetramethyl-1,3,2-dioxaborolan-2-yl)phenyl)-2-methoxyethanesulfonamide (80 mg, 0.22 mmol), sodium carbonate (24 mg, 0.22 mmol) and 1,1'-Bis(diphenylphosphino)ferrocene-palladium(II)dichloride dichloromethane complex (22 mg, 0.03 mmol) in 1,2-dimethoxyethane (2 ml) and water (0.5 ml) according to the method described in Preparation 62. The residue was purified using SP1® Purification System (0% to 70% n-hexane-ethyl acetate) to obtain 59 mg (69% yield, 78% purity) of the title compound.

LRMS (m/z): 747 (M+1)+

Preparation 195

(S)-2-(1-((6-Amino-5-(3-amino-5-methoxyphenyl) pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (150 mg, 0.34 mmol) were added (3-methoxy-5-(4,4,5,5-tetramethyl-1,3,2-dioxaborolan-2-yl)aniline (86 mg, 0.34 mmol), 1,1'-bis(diphenylphosphino)ferrocene-palladium(II)dichloride dichloromethane complex (27 mg, 0.03 mmol) and 340 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by reverse phase using SP1® Purification System to give 87 mg (52% yield) of the title compound as a white solid. Purity 98%.

LRMS (m/z): 483 (M+1)+.

Preparation 196

(5-(4-Hydroxybenzamido)pyridin-3-yl)boronic acid a) N-(5-Bromopyridin-3-yl)-4-methoxybenzamide 5-Bromopyridin-3-amine (1.2 g, 6.94 mmol) was dissolved in dichloromethane (30 ml). Diisopropylethylamine (1.45 ml, 8.32 mmol) first and then a solution of 4-methoxybenzoyl chloride (1.18 g, 6.92 mmol) in dichloromethane (20 ml) were added. After stirring 1 h at room temperature the reaction mixture was diluted with ethyl acetate and washed with water and brine, dried over sodium sulphate, filtered and evaporated under reduced pressure to give 2.12 g (80% yield) of the title compound. Purity 78%.

LRMS (m/z): 307, 309 (M+1)+ b) (5-(4-Methoxybenzamido)pyridin-3-yl)boronic acid

N-(5-Bromopyridin-3-yl)-4-methoxybenzamide (2.18 g, 7.06 mmol), 4,4,4',4',5,5,5',5'-octamethyl-2,2'-bi(1,3,2-dioxaborolane) (5.6 g, 22 mmol), potassium acetate (2.7 g, 27.55 mmol), bis(diphenylphosphino)ferrocene-palladium(II) dichloride dichloromethane complex (680 mg, 0.83 mmol) and 1,1'-bis(diphenylphosphino)ferrocene (460 mg, 0.83 mmol) were suspended in dioxane (50 ml) and stirred at 90° C. overnight. The mixture was diluted with ethyl acetate and washed with water and brine, dried over sodium sulphate, filtered and evaporated under reduced pressure to give 2.12 g (100% yield) of the title compound. Purity (UPLC 92%, estimated 71%).

LRMS (m/z): 273 (M+1)+ c) (5-(4-Hydroxybenzamido)pyridin-3-yl)boronic acid (5-(4-Methoxybenzamido)pyridin-3-yl)boronic acid (300 mg, 0.79 mmol) was dissolved in dichloromethane (15 ml). A solution of boron tribromide (1M in dichloromethane, 3.93 mL, 3.93 mmol) was added dropwise and the reaction was stirred at room temperature overnight. The mixture was diluted with dichloromethane and washed with a solution of 4% sodium bicarbonate, water, brine and dried over sodium sulphate, filtered and evaporated under reduced pressure. The product was purified by reverse phase using SP1® Purification System to give 225 mg (100% yield) of the title compound. Purity 98%.

LRMS (m/z): 257 (M−1)−

Preparation 197

N'-[3-Methoxy-5-(4-{[(1S)-1-(5-methyl-4-oxo-3-phenyl-3,4-dihydropyrrolo[2,1-f][1,2,4]triazin-2-yl) ethyl]amino}-7-{[2-(trimethylsilyl)ethoxy]methyl}-7H-pyrrolo[2,3-d]pyrimidin-5-yl)phenyl]-N,N-dimethylsulfamide (S)-2-(1-((5-(3-Amino-5-methoxyphenyl)-7-((2-(trimethylsilyl)ethoxy)methyl)-7H-pyrrolo[2,3-d]pyrimidin-4-yl) amino)ethyl)-5-methyl-3-phenylpyrrolo[2,1-f][1,2,4]triazin-4(3H)-one (50 mg, 0.08 mmol) was treated with dimethylsulfamoyl chloride (25 μL, 0.23 mmol) and 200 μL pyridine according to the method described in Preparation 15b but stirring at 45° C. during 48 h. The residue was purified using SP1® Purification System (0% to 100% hexane-ethyl acetate) to obtain 30 mg (44% yield, 85% purity) of the title compound.

LRMS (m/z): 744 (M+1)+.

Preparation 198

(3-(Methylsulfonamido)-5-(trifluoromethyl)phenyl) boronic acid a) N-(3-Bromo-5-(trifluoromethyl)phenyl)methanesulfonamide 3-Bromo-5-(trifluoromethyl)aniline (1 g, 4.17 mmol) was treated with methanesulfonyl chloride (480 μl, 6.25 mmol) according to the method described in Preparation 15b to give 1.35 g (97% yield) of the title compound. Purity 96%.

LRMS (m/z): 318, 320 (M+1)+.

b) (3-(Methylsulfonamido)-5-(trifluoromethyl)phenyl)boronic acid

N-(3-Bromo-5-(trifluoromethyl)phenyl)methanesulfonamide (1.33 g, 4.06 mmol), bis(pinacolato)diboron (4.12 g, 16.22 mmol), potassium acetate (2 g, 20.38 mmol), bis(diphenylphosphino)ferrocene-palladium(II)dichloride dichloromethane complex (500 mg, 0.61 mmol) and 1,1'-bis(diphenylphosphino)ferrocene (340 mg, 0.61 mmol) were suspended in dioxane (35 ml) and stirred at 90° C. for 48 h. After evaporation of the solvent under reduced pressure, ethyl acetate (100 ml) was added to the residue and the precipitated salts were eliminated by filtration. The solvent was evaporated under reduced pressure to give 6.39 g (100% yield) of the title compound as a mixture of (3-(methylsulfonamido)-

5-(trifluoromethyl)phenyl)boronic acid and N-(3-(4,4,5,5-tetramethyl-1,3,2-dioxaborolan-2-yl)-5-(trifluoromethyl)phenyl)methanesulfonamide that was used in next step without further purification. (1:1). Estimated Purity: 24%

LRMS (m/z): 284, 366 (M+1)$^+$

Preparation 199

3-Bromo-5-(difluoromethyl)aniline a) 1-Bromo-3-(difluoromethyl)-5-nitrobenzene

A mixture of 3-bromo-5-nitrobenzaldehyde (850 mg, 3.70 mmol) and DAST (2.42 ml, 18.47 mmol) in anhydrous dichloromethane (25 ml) was stirred at 40° C. overnight in a pressure vessel. The mixture was diluted with dichloromethane and washed with a solution of 4% sodium bicarbonate, water, brine and dried over sodium sulphate, filtered and evaporated under reduced pressure to give 944 mg (97% yield) of the title compound as an oil. This crude was used in the following step without further purification. Purity 96%.

LRMS (m/z): 252, 254 (M+1)$^+$ b) 3-Bromo-5-(difluoromethyl)aniline

1-Bromo-3-(difluoromethyl)-5-nitrobenzene (944 mg, 3.60 mmol) was treated with iron powder (804 mg, 23.43 mmol) in a mixture of acetic acid (1.35 ml) and ethanol (25 ml) and stirred at 80° C. for 3 h. The crude was filtered over Celite and the solvent was removed in vacuum. A mixture of a solution of sodium bicarbonate 4% and ethyl acetate was added and the resulting mixture was filtered over Celite. The organic phase was washed with water and brine, dried over magnesium sulphate and the solvent was remove to give 855 mg (100% yield) of the title compound as a dark solid, that was used in the next step without further purification. Purity 96%.

LRMS (m/z): 222, 224 (M+1)$^+$

Preparation 200

N-(3-(Difluoromethyl)-5-(4,4,5,5-tetramethyl-1,3,2-dioxaborolan-2-yl)phenyl) methanesulfonamide a) N-(3-Bromo-5-(difluoromethyl)phenyl)methanesulfonamide 3-Bromo-5-(difluoromethyl)aniline (876 mg, 3.95 mmol) was treated with methanesulfonyl chloride (458 µl, 5.92 mmol) according to the method described in Preparation 15b to give 1.24 g (100% yield) of the title compound. Purity 95%.

LRMS (m/z): 300, 302 (M+1)$^+$.

b) N-(3-(Difluoromethyl)-5-(4,4,5,5-tetramethyl-1,3,2-dioxaborolan-2-yl)phenyl) methanesulfonamide N-(3-Bromo-5-(difluoromethyl)phenyl)methanesulfonamide (1.24 g, 3.95 mmol), bis(pinacolato)diboron (4 g, 15.75 mmol), potassium acetate (1.94 g, 19.77 mmol), bis(diphenylphosphino)ferrocene-palladium(II)dichloride dichloromethane complex (480 mg, 0.59 mmol) and 1,1'-bis(diphenylphosphino)ferrocene (330 mg, 0.59 mmol) were suspended in dioxane (30 ml) and stirred at 90° C. for 48 h. After evaporation of the solvent under reduced pressure, ethyl acetate (100 ml) was added to the residue and the precipitated salts were eliminated by filtration. The solvent was evaporated under reduced pressure to give 6.69 g (100% yield) of the title compound as a mixture of (3-(methylsulfonamido)-5-(difluoromethyl)phenyl)boronic acid and N-(3-(4,4,5,5-tetramethyl-1,3,2-dioxaborolan-2-yl)-5-(difluoromethyl)phenyl)methanesulfonamide that was used in next step without further purification. Estimated Purity: 20%

LRMS (m/z): 284, 366 (M+1)$^+$

Preparation 201

(5-(3-Methoxybenzamido)pyridin-3-yl)boronic acid a) N-(5-Bromopyridin-3-yl)-3-methoxybenzamide 5-Bromopyridin-3-amine (1.5 g, 8.67 mmol) was dissolved in dichloromethane (40 ml). Diisopropylethylamine (1.81 ml, 10.39 mmol) first and then a solution of 3-methoxybenzoyl chloride (1.18 ml, 8.66 mmol) in dichloromethane (25 ml) were added. After 1 h at room temperature the reaction mixture was diluted with ethyl acetate and washed with water and brine, dried over sodium sulphate, filtered and evaporated under reduced pressure to give 3.07 g (89% yield) of the title compound. Purity 77%.

LRMS (m/z): 307, 309 (M+1)$^+$ b) (5-(3-Methoxybenzamido)pyridin-3-yl)boronic acid N-(5-Bromopyridin-3-yl)-3-methoxybenzamide (3.07 g, 7.71 mmol), 4,4,4',4',5,5,5',5'-octamethyl-2,2'-bi(1,3,2-dioxaborolane) (5.88 g, 23.16 mmol), potassium acetate (3.79 g, 38.62 mmol), bis(diphenylphosphino)ferrocene-palladium(II)dichloride dichloromethane complex (950 mg, 1.16 mmol) and 1,1'-bis(diphenylphosphino)ferrocene (640 mg, 1.16 mmol) were suspended in dioxane (60 ml) and stirred at 90° C. overnight. The mixture was diluted with ethyl acetate and washed with water and brine, dried over sodium sulphate, filtered and evaporated under reduced pressure. The crude was purified by reverse phase using SP1® Purification System to give 1 g (44% yield) of the title compound. Purity 93%.

LRMS (m/z): 273 (M+1)$^+$

Preparation 202

N-(3-Methyl-5-(4,4,5,5-tetramethyl-1,3,2-dioxaborolan-2-yl)phenyl)methane sulfonamide a) N-(3-Bromo-5-(methyl)phenyl)methanesulfonamide 3-Bromo-5-(methyl)aniline (2 g, 10.75 mmol) was treated with methanesulfonyl chloride (915 µl, 11.82 mmol) according to the method described in Preparation 15b to give 2.82 g (96% yield) of the title compound. Purity 95%.

LRMS (m/z): 262, 264 (M+1)$^+$.

b) N-(3-Methyl-5-(4,4,5,5-tetramethyl-1,3,2-dioxaborolan-2-yl)phenyl)methane sulfonamide N-(3-Bromo-5-(methyl)phenyl)methanesulfonamide (1 g, 3.79 mmol), bis(pinacolato)diboron (1.92 g, 7.57 mmol), potassium acetate (1.11 g, 11.36 mmol), bis(diphenylphosphino)ferrocene-palladium(II)dichloride dichloromethane complex (310 mg, 0.38 mmol) and 1,1'-bis(diphenylphosphino)ferrocene (210 mg, 0.381 mmol) were suspended in dioxane (37 ml) and stirred at 120° C. for 24 h. After evaporation of the solvent under reduced pressure, ethyl acetate (100 ml) was added to the residue and the precipitated salts were eliminated by filtration. The solvent was evaporated under reduced pressure to give 2.6 g (100% yield) of the title compound. Purity (UPLC 86%, estimated 46%)

LRMS (m/z): 310 (M−1)⁻

Preparation 203

N-(4-(4,4,5,5-Tetramethyl-1,3,2-dioxaborolan-2-yl)-1H-indol-6-yl)methanesulfonamide a) N-(4-Bromo-1H-indol-6-yl)methanesulfonamide 4-Bromo-1H-indol-6-amine (200 mg, 0.81 mmol) was treated with methanesulfonyl chloride (66 μl, 0.85 mmol) according to the method described in Preparation 15b.

The crude was purified using SP1® Purification System (DCM-MeOH) to obtain 226 mg (97% yield, 100% purity) of the title compound.

LRMS (m/z): 289, 291 (M+1)⁺.

b) N-(4-(4,4,5,5-Tetramethyl-1,3,2-dioxaborolan-2-yl)-1H-indol-6-yl)methanesulfonamide N-(4-Bromo-1H-indol-6-yl)methanesulfonamide (226 mg, 0.78 mmol), bis(pinacolato)diboron (398 mg, 1.57 mmol), potassium acetate (235 mg, 2.4 mmol), bis(diphenylphosphino)ferrocene-palladium(II)dichloride dichloromethane complex (32 mg, 0.04 mmol) and 1,1'-bis(diphenylphosphino)ferrocene (21 mg, 0.04 mmol) were suspended in 6 ml dioxane and stirred overnight at 120° C. After evaporation of the solvent under reduced pressure, the residue was partitioned between ethyl acetate and water. The organic phase was washed with brine, dried over sodium sulphate, filtered and evaporated under reduced pressure. The crude was purified using SP1® Purification System (hexane-ethyl acetate) to give 222 mg (78% yield, 92% purity) of the title compound.

LRMS (m/z): 337 (M+1)⁺.

Preparation 204

(S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (101 mg, 0.17 mmol) was treated with N-(4-(4,4,5,5-tetramethyl-1,3,2-dioxaborolan-2-yl)-1H-indol-6-yl)methanesulfonamide (147 mg, 0.44 mmol), sodium carbonate (45 mg, 0.43 mmol), 1,1'-Bis(diphenylphosphino)ferrocene-palladium(II) dichloride dichloromethane complex (41 mg, 0.2 mmol) in 1,2-dimethoxyethane (4 ml) and water (1 ml) according to the method described in Preparation 62. The residue was purified using SP1® Purification System (0% to 100% hexane-ethyl acetate) to obtain 89 mg (50% yield, 69% purity) of the title compound.

LRMS (m/z): 724 (M+1)⁺.

Preparation 205

(S)-4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid a) (S)-Benzyl 4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylate (S)-2-(1-Aminoethyl)-5-methyl-3-phenylpyrrolo[2,1-f][1,2,4]triazin-4(3H)-one (418 mg, 1.56 mmol) and benzyl 4-chloro-7H-pyrrolo[2,3-d]pyrimidine-5-carboxylate (500 mg, 1.74 mmol) were dissolved in tert-butanol (8 ml) and DIEA (2 ml, 11.45 mmol) was added. After stirring the mixture at 80° C. for 12 h, the solvent was evaporated under reduced pressure and the residue was suspended in water, basified with sodium carbonate and extracted with AcOEt (×3). The organic phase was successively washed with water and brine, dried over magnesium sulphate, filtered and the solvent evaporated under reduced pressure. The residue was purified using SP1® Purification System (0% to 50%, hexane-ethyl acetate) to obtain 560 mg (66% yield) of the title compound as a white solid. Purity 96%.

LRMS (m/z): 520 (M+1)⁺.

b) (S)-4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid (S)-Benzyl 4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylate (560 mg, 1.08 mmol) was dissolved in methanol (200 ml) and hydrogenated in a Parr apparatus at 25 psi in the presence of Pd/C 10%. Once the reaction was completed, the mixture was filtered and the solvent evaporated under reduced pressure to yield 376 mg (79% yield) of the final compound, which was used in the next synthetic step without further purification.

LRMS (m/z): 430 (M+1)⁺.

Preparation 206

(S)-2-(1-((5-(1-(2-Hydroxyethyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-(5-(1H-Pyrazol-4-yl)-7-((2-(trimethylsilyl)ethoxy)methyl)-7H-pyrrolo[2,3-d]pyrimidin-4-ylamino)ethyl)-5-methyl-3-phenylpyrrolo[1,2-f][1,2,4]triazin-4(3H)-one (30 mg, 0.05 mmol) and 2-bromoethanol (15 μl, 0.21 mmol) were dissolved in DMF (1.5 ml) and cesium carbonate (102 mg, 0.31 mmol) was added. After stirring the mixture at 75° C. for 12 h, the solvent was evaporated under reduced pressure and the residue was suspended in water, basified with sodium carbonate and extracted with dichloromethane (×3). The organic phase was successively washed with water and brine, dried over magnesium sulphate, filtered and the solvent evaporated under reduced pressure. The residue (33 mg, 93% purity) was used in the next synthetic step without further purification.

LRMS (m/z): 626 (M+1)⁺.

Preparation 207

(S)-2-(1-((5-(1-(2-(Dimethylamino)ethyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (43 mg, 0.07 mmol) and 2-chloro-N,N-dimethylethanamine chlorhydrate (43 mg, 0.30 mmol) were dissolved in DMF (3 ml) and cesium carbonate (240 mg, 0.74 mmol) was added. After stirring the mixture at 75° C. for 3.5 h, the solvent was evaporated under reduced pressure and the residue was suspended in water and extracted with dichloromethane (×3). The organic phase was successively washed with water and brine, dried over magnesium sulphate, filtered and the solvent evaporated under reduced pressure. The residue was purified using SP1® Purification System (0% to 3%, dichloromethane-methanol) to obtain 31 mg (57% yield) of the title compound as a brown solid. Purity 90%.

LRMS (m/z): 653 (M+1)$^+$.

Preparation 208

(S)-5-Methyl-2-(1-((5-(2-methyloxazol-5-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (60 mg, 0.1 mmol) was treated with 2-methyl-5-(4,4,5,5-tetramethyl-1,3,2-dioxaborolan-2-yl)oxazole (52 mg, 0.25 mmol), tetrakistriphenylphosphine palladium (35 mg, 0.03 mmol) and aqueous solution of sodium carbonate (2M, 125 µl, 0.25 mmol) in DMF (1.5 ml). The reaction mixture was submitted at vacuum-argon cycles and stirred at 100° C. for 2 h. The reaction mixture was allowed to cool down to room temperature and poured over ice, basified with potassium carbonate and extracted with ethyl acetate (×3). The organic phase was successively washed with water and brine, dried over magnesium sulphate, filtered and the solvent evaporated under reduced pressure. The residue was purified by normal phase using SP1® Purification System (0% to 100%, hexane-diethyl ether) to obtain 31 mg (52% yield) of the title compound.

LRMS (m/z): 597 (M+1)$^+$.

Preparation 209

(S)-2-(1-((5-(1-(2-Hydroxyethyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (38 mg, 0.07 mmol) and 2-bromoethanol (15 mg, 0.12 mmol) were dissolved in DMF (1.5 ml) and cesium carbonate (102 mg, 0.31 mmol) was added. After stirring the mixture at 75° C. for 2 h, the solvent was evaporated under reduced pressure and the residue was suspended in water, basified with sodium carbonate and extracted with ethyl acetate (×3). The organic phase was successively washed with water and brine, dried over magnesium sulphate, filtered and the solvent evaporated under reduced pressure. The residue (31 mg, 96% purity) was used in the next synthetic step without further purification.

LRMS (m/z): 626 (M+1)$^+$.

Preparation 210

(S)-2-(1-((5-(1-(3-((tert-Butyldimethylsilyl)oxy)propyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (120 mg, 0.2 mmol) was treated with 1-(3-(tert-butyldimethylsilyloxy)propyl)-4-(4,4,5,5-tetramethyl-1,3,2-dioxaborolan-2-yl)-1H-pyrazole (180 mg, 0.49 mmol), tetrakistriphenylphosphine palladium (72 mg, 0.06 mmol) and aqueous solution of sodium carbonate (2M, 250 µl, 0.5 mmol) in DMF (3 ml). The reaction mixture was submitted at vacuum-argon cycles and stirred at 100° C. for 3 h. The reaction mixture was cooled down to room temperature and poured over ice, basified with potassium carbonate and extracted with ethyl acetate (×3). The organic phase was successively washed with water and brine, dried over magnesium sulphate, filtered and the solvent evaporated under reduced pressure. The residue was purified by normal phase using SP1® Purification System (0% to 50%, hexane-diethyl ether) to obtain 124 mg (69% yield) of the title compound. Purity: 85%.

LRMS (m/z): 755 (M+1)$^+$.

Preparation 211

(S)-2-(1-((5-(1-(3-Hydroxy-2,2-dimethylpropyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (70 mg, 0.09 mmol) and 3-bromo-2,2-dimethylpropan-1-ol (30 µl, 0.24 mmol) were dissolved in DMF (2 ml) and cesium carbonate (200 mg, 0.61 mmol) was added. After stirring the mixture at 80° C. for 8 h and subsequent additions of 3-bromo-2,2-dimethylpropan-1-ol until the reaction was completed, the solvent was evaporated under reduced pressure and the residue was suspended in water, basified with sodium carbonate and extracted with ethyl acetate (×3). The organic phase was successively washed with water and brine, dried over magnesium sulphate, filtered and evaporated under reduced pressure. The residue was purified using SP1® Purification System (0% to 20%, hexane-ethyl acetate) to obtain 4 mg (5% yield) of the title compound as a brown solid. Purity 80%.

LRMS (m/z): 668 (M+1)$^+$.

Preparation 212

(S)-2-(1-((5-(1-((3-Methoxyphenyl)sulfonyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-4-yl)-7-((2-(trimethylsilyl)ethoxy)methyl)-7H-pyrrolo[2,3-d]pyrimidin-4-yl)amino)

ethyl)-5-methyl-3-phenylpyrrolo[2,1-f][1,2,4]triazin-4(3H)-one (30 mg, 0.05 mmol) was dissolved in DMF (1 ml) and stirred at 50° C. for 30 min. Once at room temperature, 3-methoxybenzene-1-sulfonyl chloride (90 µl, 0.64 mmol) was added dropwise and the reaction mixture was stirred overnight at room temperature. The crude was poured over ice, basified with potassium carbonate and extracted with ethyl acetate (×3). The organic phase was successively washed with water and brine, dried over magnesium sulphate, filtered and evaporated under reduced pressure. The residue (48.5 mg, 91% purity) was used in the next synthetic step without further purification.

LRMS (m/z): 752 (M+1)+.

Preparation 213

(S)-2-(1-((5-(1H-Pyrrolo[2,3-b]pyridin-5-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (103 mg, 0.17 mmol) was treated with 5-(4,4,5,5-tetramethyl-1,3,2-dioxaborolan-2-yl)-1H-pyrrolo[2,3-b]pyridine (103 mg, 0.42 mmol), sodium carbonate (51 mg, 0.48 mmol), 1,1-bis(diphenylphosphino)ferrocene-palladium(II)dichloride dichloromethane complex (43 mg, 0.05 mmol) in 1,2-dimethoxyethane (4 ml) and water (1 ml) according to the method described in Preparation 62. The residue was purified using SP1® Purification System (0% to 100% hexane-ethyl acetate) to obtain 55 mg (48% yield, 96% purity) of the title compound.

LRMS (m/z): 632 (M+1)+.

Preparation 214

(S)—N-(3-Methyl-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (200 mg, 0.34 mmol) was treated N-(3-methyl-5-(4,4,5,5-tetramethyl-1,3,2-dioxaborolan-2-yl)phenyl)methane sulfonamide (160 mg, 0.51 mmol), tetrakis(triphenylphosphine)palladium (0) (20 mg, 0.02 mmol), aqueous solution 2M of sodium carbonate (260 µl, 0.5 mmol) and 4 ml N,N-dimethylformide according to the method described in Preparation 186 but stirring at 100° C. overnight. The crude was purified using SP1® Purification System (hexane-ethyl acetate) to give 110 mg (38% yield) of the title compound. Purity 80%.

LRMS (m/z): 346 (M+1)+.

Preparation 215

(S)-5-Methyl-2-(1-((5-(3-(morpholinosulfonyl)phenyl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (200 mg, 0.34 mmol) was treated with (3-(morpholinosulfonyl)phenyl)boronic acid (140 mg, 0.52 mmol), tetrakis(triphenylphosphine)palladium(0) (195 mg, 0.5 mmol), aqueous solution 2M of sodium carbonate (260 µl, 0.5 mmol) and 5 ml N,N-dimethylformide as a solvent according to the method described in Preparation 186 but stirring at 100° C. overnight. The crude was purified using SP1® Purification System (hexane-ethyl acetate) to give 90 mg (58% yield) of the title compound. Purity 80%.

LRMS (m/z): 742 (M+1)+.

Preparation 216

N-(4-Methyl-3-(4,4,5,5-tetramethyl-1,3,2-dioxaborolan-2-yl)phenyl)methanesulfonamide 4-Methyl-3-(4,4,5,5-tetramethyl-1,3,2-dioxaborolan-2-yl)aniline (500 mg, 2.14 mmol) was treated with methanesulfonyl chloride (162 µl, 2.10 mmol) according to the method described in Preparation 15b to give 550 mg (83% yield) of the title compound. Purity 98%.

LRMS (m/z): 312 (M+1)+.

Preparation 217

(S)—N-(4-Methyl-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (120 mg, 0.2 mmol) was treated with N-(4-methyl-3-(4,4,5,5-tetramethyl-1,3,2-dioxaborolan-2-yl)phenyl)methanesulfonamide (100 mg, 0.32 mmol), tetrakis(triphenylphosphine)palladium(0) (30 mg, 0.03 mmol), aqueous solution 2M of sodium carbonate (200 µl, 0.4 mmol) and 5 ml N,N-dimethylformide as a solvent according to the method described in Preparation 186 but stirring at 100° C. overnight. The crude was purified using SP1® Purification System (hexane-ethyl acetate) to obtain 50 mg (35% yield) of the title compound as a yellow oil. Purity 98%.

LRMS (m/z): 699 (M+1)+.

Preparation 218

(S)-2-(1-((5-((3-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 3-((4-Chloro-7-((2-(trimethylsilyl)ethoxy)methyl)-7H-pyrrolo[2,3-d]pyrimidin-5-yl)thio)aniline 4-Chloro-5-iodo-7-((2-(trimethylsilyl)ethoxy)methyl)-7H-pyrrolo[2,3-d]pyrimidine (400 mg, 0.98 mmol) was treated with 3-aminobenzenethiol (120 mg, 0.96 mmol), copper(I) iodide (300 mg, 1.58 mmol), potassium carbonate (300 mg, 2.17 mmol) and 8 ml N,N-dimethylformamide as solvent according to Preparation 86. The residue was purified using SP1® Purification System (hexane-ethyl acetate) to obtain 100 mg (25% yield) of the title compound. Purity 98%.

LRMS (m/z): 408 (M+1)+.

201 b) (S)-2-(1-((5-((3-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one 3-((4-Chloro-7-((2-(trimethylsilyl)ethoxy)methyl)-7H-pyrrolo[2,3-d]pyrimidin-5-yl)thio)aniline (100 mg, 0.25 mmol) was treated with (S)-1-(5-methyl-4-oxo-3-phenyl-3,4-dihydropyrrolo[2,1-f][1,2,4]triazin-2-yl)ethanaminium chloride (67 mg, 0.25 mmol), cesium fluoride (15 mg, 0.10 mmol), N,N-diisopropylethylamine (400 µl, 2.3 mmol) and tert-butanol (0.78 ml) according to Preparation 163. The residue (100 mg, 80% purity) was used in the next synthetic step without further purification.
LRMS (m/z): 639 (M+1)$^+$.

Preparation 219

(S)—N-(3-((4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)thio)phenyl)methanesulfonamide (S)-2-(1-((5-((3-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.13 mmol) was treated with methanesulfonyl chloride (10 µl, 0.14 mmol) according to the method described in Preparation 15b. The residue was purified by reverse phase using SP1® Purification System to give 20 mg (23% yield) of the title compound. Purity 98%.
LRMS (m/z): 718 (M+1)$^+$.

Preparation 220

(S)-2-(1-((5-((4-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one a) 4-((4-Chloro-7-((2-(trimethylsilyl)ethoxy)methyl)-7H-pyrrolo[2,3-d]pyrimidin-5-yl)thio)aniline 4-Chloro-5-iodo-7-((2-(trimethylsilyl)ethoxy)methyl)-7H-pyrrolo[2,3-d]pyrimidine (400 mg, 0.98 mmol) was treated with 4-aminobenzenethiol (130 mg, 1.04 mmol), copper(I) iodide (400 mg, 2.1 mmol), potassium carbonate (300 mg, 2.17 mmol) in N,N-dimethylformamide (8 ml) according to Preparation 86 but stirring at 100° C. for 2 h. The residue was purified using SP1® Purification System (hexane-ethyl acetate) to obtain 350 mg (75% yield) of the title compound. Purity 85%.
LRMS (m/z): 408 (M+1)$^+$.

b)(S)-2-(1-((5-((4-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one 4-((4-Chloro-7-((2-(trimethylsilyl)ethoxy)methyl)-7H-pyrrolo[2,3-d]pyrimidin-5-yl)thio)aniline (350 mg, 0.73 mmol) was treated with (S)-1-(5-methyl-4-oxo-3-phenyl-3,4-dihydropyrrolo[2,1-f][1,2,4]triazin-2-yl)ethanaminium chloride (215 mg, 0.80 mmol), cesium fluoride (11 mg, 0.07 mmol), N,N-diisopropylethylamine (318 µl, 1.83 mmol) and tert-butanol (4 ml) as a solvent according to Preparation 163. The residue was purified by reverse phase using SP1® Purification System to obtain 200 mg (40% yield) of the title compound. Yield 98%.
LRMS (m/z): 468 (M+1)$^+$.

Preparation 221

(S)—N-(4-((4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)thio)phenyl)methanesulfonamide (S)-2-(1-((5-((4-Aminophenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with methanesulfonyl chloride (10 µl, 0.14 mmol) according to the method described in Preparation 15b. The residue (15 mg, 85% purity) was used in the next synthetic step without further purification.
LRMS (m/z): 718 (M+1)$^+$.

Preparation 222

1-(Methylsulfonyl)-4-(4,4,5,5-tetramethyl-1,3,2-dioxaborolan-2-yl)-1H-pyrrolo[2,3-b]pyridine a) 4-Bromo-1-(methylsulfonyl)-1H-pyrrolo[2,3-b]pyridine 4-Bromo-1H-pyrrolo[2,3-b]pyridine (250 mg, 1.27 mmol) was dissolved in 5 ml N—N, dimethylformamide. Sodium hydride was slowly added and the mixture was stirred for 15 minutes. Methanesulfonyl chloride (66 µl, 0.85 mmol) was added and the reaction mixture was stirred at room temperature overnight. The reaction was extracted with ethyl acetate and washed with water. The organic phase was dried over sodium sulphate, filtered and evaporated under reduced pressure. The residue (200 mg) was used in the next synthetic step without further purification.
LRMS (m/z): 275, 277 (M+1)$^+$.

b) 1-(Methylsulfonyl)-4-(4,4,5,5-tetramethyl-1,3,2-dioxaborolan-2-yl)-1H-pyrrolo[2,3-b]pyridine 4-Bromo-1-(methylsulfonyl)-1H-pyrrolo[2,3-b]pyridine (200 mg, 0.73 mmol) was treated with bis(pinacolato)diboron (275 mg, 1.08 mmol), potassium acetate (220 mg, 2.2 mmol) and bis(diphenylphosphino)ferrocene-palladium(II)dichloride dichloromethane complex (20 mg, 0.034 mmol) in dioxane (7 ml) according to the method described in Preparation 174a. The crude was purified by reverse phase using SP1® Purification System to obtain 100 mg (42% yield) of the title compound as a white solid. Purity 98%.
LRMS (m/z): 323 (M+1)$^+$.

Preparation 223

(S)-5-Methyl-2-(1-((5-(1-(methylsulfonyl)-1H-pyrrolo[2,3-b]pyridin-4-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (150 mg, 0.25 mmol) was treated with 1-(methylsulfonyl)-4-(4,4,5,5-tetramethyl-1,3,2-dioxaborolan-2-yl)-1H-pyrrolo[2,3-b]pyridine (100 mg, 0.31 mmol), tetrakis(triphenylphosphine)palladium(0) (15 mg, 0.01 mmol) and aqueous solution 2M of sodium carbonate (200 µl, 0.4 mmol) in N,N-dimethylformide (5 ml) according to the method described in Preparation 186 but stirring at 100° C. overnight. The crude was purified using SP1® Purification System (hexane-ethyl acetate) to obtain 90 mg (50% yield) of the title compound as a oil. Purity 99%.

LRMS (m/z): 710 (M+1)$^+$.

Preparation 224

N-(4-(4,4,5,5-Tetramethyl-1,3,2-dioxaborolan-2-yl)-1H-indazol-6-yl)methanesulfonamide a)
N-(4-Bromo-1H-indazol-6-yl)methanesulfonamide 4-Bromo-1H-indazol-6-amine (500 mg, 2.36 mmol) was treated with methanesulfonyl chloride (130 µl, 1.68 mmol) and triethylamine (49 µl, 3.55 mmol) according to the method described in Preparation 15b. The residue was purified using SP1® Purification System to give 300 mg (49% yield) of the title compound. Purity 80%.

LRMS (m/z): 489 (M+1)$^+$.

b) N-(4-(4,4,5,5-Tetramethyl-1,3,2-dioxaborolan-2-yl)-1H-indazol-6-yl)methanesulfonamide N-(4-Bromo-1H-indazol-6-yl)methanesulfonamide (300 mg, 1.03 mmol) was treated with bis(pinacolato)diboron (525 mg, 2.07 mmol), potassium acetate (300 mg, 3.06 mmol), bis(diphenylphosphino)ferrocene-palladium(II)dichloride dichloromethane complex (40 mg, 0.05 mmol) and 1,1'-bis(diphenylphosphino)ferrocene (30 mg, 0.05 mmol) according to the method described in Preparation 203. The crude was purified by reverse phase using SP1® Purification System to give 50 mg (14% yield) of the title compound. Purity 100%.

LRMS (m/z): 349 (M+1)$^+$.

Preparation 225

(S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indazol-6-yl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (25 mg, 0.04 mmol) was treated with N-(4-(4,4,5,5-tetramethyl-1,3,2-dioxaborolan-2-yl)-1H-indazol-6-yl)methanesulfonamide (35 mg, 0.10 mmol), sodium carbonate (11 mg, 0.10 mmol), 1,1'-Bis(diphenylphosphino)ferrocene-palladium(II)dichloride dichloromethane complex (10 mg, 0.01 mmol) and 2 ml 1,2-dimethoxyethane and 1 ml water as a solvents according to the method described in Preparation 62. The residue was purified using SP1® Purification System (hexane-ethyl acetate) to obtain 13 mg (42% yield) of the title compound. Purity 98%.

LRMS (m/z): 726 (M+1)$^+$.

Preparation 226

2-Methyl-5-(3-(4,4,5,5-tetramethyl-1,3,2-dioxaborolan-2-yl)phenyl)-1,3,4-oxadiazole a) 3-Bromobenzohydrazide Methyl 3-bromobenzoate (2 g, 9.3 mmol) was dissolved in 25 ml ethanol. Hydrazine hydrate (4.5 ml, 92.9 mmol) was added and the reaction was stirred at 80° C. overnight. The reaction mixture was evaporated under reduced pressure and a white solid was formed. This solid was washed with water and diethyl ether and dried in the vacuum oven to afford 1.8 g (90% yield) of the title compound. Purity 100%.

LRMS (m/z): 216 (M+1)$^+$.

b) 2-(3-Bromophenyl)-5-methyl-1,3,4-oxadiazole

In a pressure vessel was suspended 3-bromobenzohydrazide (1.8 g, 8.37 mmol) in 14 ml acetic acid. 1,1,1-Triethoxyethane (4.6 ml, 25 mmol) was added and the reaction was stirred at 150° C. for 3 h. The solvent was concentrated under reduced pressure and the crude was washed with sodium bicarbonate and brine. The organic layer was dried over sodium sulphate, filtered and evaporated under reduced pressure. The residue was re-dissolved in dichloromethane, concentrated under reduced pressure and a solid was precipitated. This solid was washed with diethylether, filtered and dried in the vacuum oven at 40° C. to obtain 670 mg (35% yield) of the title compound. Purity 100%.

LRMS (m/z): 240 (M+1)$^+$.

c) 2-Methyl-5-(3-(4,4,5,5-tetramethyl-1,3,2-dioxaborolan-2-yl)phenyl)-1,3,4-oxadiazole 2-(3-Bromophenyl)-5-methyl-1,3,4-oxadiazole (670 mg, 2.80 mmol) was treated with bis(pinacolato)diboron (1 g, 4.2 mmol), potassium acetate (825 mg, 8.41 mmol), bis(diphenylphosphino)ferrocene-palladium(II)dichloride dichloromethane complex (115 mg, 0.14 mmol) and 1,1'-bis(diphenylphosphino)ferrocene (78 mg, 0.14 mmol) according to the method described in Preparation 203. The crude was purified by SP1® Purification System (hexane-ethyl acetate) to give 350 mg (44% yield) of the title compound. Purity 100%.

LRMS (m/z): 287 (M+1)$^+$.

Preparation 227

(S)-5-Methyl-2-(1-((5-(3-(5-methyl-1,3,4-oxadiazol-2-yl)phenyl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with 2-methyl-5-(3-(4,4,5,5-tetramethyl-1,3,2-dioxaborolan-2-yl)phenyl)-1,3,4-oxadiazole (96 mg, 0.34 mmol), tetrakis(triphenylphosphine)palladium(0) (20 mg, 0.02 mmol), aqueous solution 2M of sodium carbonate (200 µl, 0.4 mmol) in N,N-dimethylformide (5 ml) according to the method described in Preparation 186 but stirring at 100° C. overnight. The crude was purified using SP1® Purification System (hexane-ethyl acetate) to obtain 90 mg (72% yield) of the title compound as a oil. Purity 90%.
LRMS (m/z): 674 (M+1)+.

Preparation 228

(S)-3-Methoxy-N-methyl-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl) benzenesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with 3-methoxy-N-methyl-4-(4,4,5,5-tetramethyl-1,3,2-dioxaborolan-2-yl)benzenesulfonamide (72 mg, 0.22 mmol), sodium carbonate (23 mg, 0.22 mmols) and 1,1'-bis(diphenylphosphino)ferrocene-palladium(II)dichloride dichloromethane complex (21 mg, 0.03 mmol) in 1,2-dimethoxyethane (1.60 ml) and water (0.40 ml) according to the method described in Preparation 62. The residue was purified using SP1® Purification System (0% to 50%, hexane-ethyl acetate) to give 46 mg (73% yield) of the title compound.
LRMS (m/z): 715 (M+1)+.

Preparation 229

N-[4-(4-{[(1S)-1-(5-Methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)-1H-indol-6-yl] sulfamide a) 4-(4,4,5,5-Tetramethyl-1,3,2-dioxaborolan-2-yl)-1H-indol-6-amine 4-Bromo-1H-indol-6-amine (300 mg, 1.42 mmol) was dissolved in 3.4 mL tert-butanol and 308 µl water. Bis(pinacolato)diboron (348 mg, 1.37 mmol), 1,1'-bis(diphenylphosphino)ferrocene (39 mg, 0.07 mmol) and potassium acetate (417 mg, 4.25 mmol) were added and the mixture was submitted to three vacuum-argon cycles. 1,1'-Bis(diphenylphosphino)ferrocene-palladium(II)dichloride dichloromethane complex (58 mg, 0.07 mmol) was added under argon conditions. The mixture was stirred at 90° C. overnight. The reaction was poured into a 4% aqueous solution of sodium bicarbonate and extracted twice with ethyl acetate. The organics were combined and washed with water, brine, dried over sodium sulphate, filtered and evaporated under reduced pressure. The residue was purified using SP1® Purification System (0% to 20%, dichloromethane diethyl ether) to give 110 mg (30% yield) of the title compound.
LRMS (m/z): 259 (M+1)+.

b) (S)-2-(1-((5-(6-Amino-1H-indol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (125 mg, 0.21 mmol) was treated with 4-(4,4,5,5-tetramethyl-1,3,2-dioxaborolan-2-yl)-1H-indol-6-amine (110 mg, 0.43 mmol), sodium carbonate (55 mg, 0.52 mmols) and 1,1'-bis(diphenylphosphino)ferrocene-palladium(II)dichloride dichloromethane complex (52 mg, 0.06 mmol) in 1,2-dimethoxyethane (5.0 ml) and water (0.125 ml) according to the method described in Preparation 62. The residue was purified using SP1® Purification System (0% to 50%, hexane-ethyl acetate) to give 84 mg (56% yield) of the title compound.
LRMS (m/z): 646 (M+1)+.

c) N-[4-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)-1H-indol-6-yl] sulfamide (S)-2-(1-((5-(6-Amino-1H-indol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (84 mg, 0.13 mmol) was treated with pyridine (15 µL, 0.18 mmol) and sulfamoyl chloride (18 mg, 0.16 mmol) in tetrahydrofuran (1.0 ml) according to the method described in Preparation 175 but stirring at room temperature during 48 h. The residue was purified using SP1® Purification System (0% to 50% hexane-ethyl acetate) to obtain 47 mg (49% yield) of the title compound.
LRMS (m/z): 725 (M+1)+.

Preparation 230

(S)-1-(2-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)urea a) (S)-2-(1-((5-(5-Amino-6-methoxypyridin-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (200 mg, 0.34 mmol) was treated with 2-methoxy-5-(4,4,5,5-tetramethyl-1,3,2-dioxaborolan-2-yl)pyridin-3-amine (202 mg, 0.81 mmol), sodium carbonate (86 mg, 0.81 mmols) and bis(triphenylphosphine)palladium(II) dichloride (31 mg, 0.04 mmol) in 1,2-dimethoxyethane (3.6 ml) and water (0.40 ml) according to the method described in Preparation 62. The residue was purified using SP1® Purification System (0% to 30%, hexane-ethyl acetate) to give 93 mg (40% yield) of the title compound.
LRMS (m/z): 638 (M+1)+.

b) (S)-1-(2-methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)urea To a suspension of (S)-2-(1-((5-(5-amino-6-methoxypyridin-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (92 mg, 0.14 mmol) in water (0.75 mL) and acetic acid (1.2 mL) was added potassium isocyanate (20 mg, 0.25 mmol) according to the method described in Preparation 181. The residue was purified using Preparation 231

N-[3-Fluoro-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]sulfamide a) (S)-2-(1-((5-(3-Amino-5-fluorophenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (250 mg, 0.42 mmol) was treated with 3-fluoro-5-(4,4,5,5-tetramethyl-1,3,2-dioxaborolan-2-yl)aniline (250 mg, 1.05 mmol), sodium carbonate (110 mg, 1.05 mmol) and 1,1'-Bis(diphenylphosphino)ferrocene-palladium(II)dichloride dichloromethane complex (100 mg, 0.12 mmol) in a mixture of 1,2-dimethoxyethane (10.6 ml) and water (2.4 ml) according to the method described in Preparation 62. The residue was purified using SP1® Purification System (0% to 70% n-hexane-ethyl acetate) to obtain 170 mg (53% yield, 82% purity) of the title compound.
LRMS (m/z): 625 (M+1)$^+$ b) N-[3-Fluoro-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]sulfamide (S)-2-(1-((5-(3-Amino-5-fluorophenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (40 mg, 0.06 mmol) was treated with pyridine (20 µL, 0.25 mmol) and sulfamoyl chloride (24 mg, 0.21 mmol) in tetrahydrofuran (0.5 ml) according to the method described in Preparation 175 but stirring at room temperature overnight. The title compound was obtained (46 mg, 93% yield) without further purification.
LRMS (m/z): 704 (M+1)$^+$ Preparation 232

(S)-2-(1-((5-(4-Amino-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (400 mg, 0.67 mmol) was dissolved in 6 mL N,N-dimethylformamide. 3-Methoxy-4-(4,4,5,5-tetramethyl-1,3,2-dioxaborolan-2-yl)aniline (490 mg, 1.77 mmol, 90% purity), 2M sodium carbonate aqueous solution (0.81 mL, 1.62 mmols) and tetrakis(triphenylphosphine)palladium(0) (233 mg, 0.2 mmol) were added under argon atmosphere and the reaction mixture was stirred at 90° C. for 5 h. The reaction mixture was poured into a saturated ammonium chloride solution and extracted twice with water. The organics were washed with water, brine, dried over sodium sulphate, filtered and evaporated under reduced pressure. The residue was purified using SP1® Purification System (0% to 100%, hexane-ethyl acetate) to give 383 mg (81% yield) of the title compound.
LRMS (m/z): 637 (M+1)$^+$.

Preparation 233

(S)—N-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-1-(tetrahydro-2H-pyran-4-yl)methanesulfonamide (S)-2-(1-((5-(4-Amino-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with pyridine (19 µL, 0.23 mmol) and (tetrahydro-2H-pyran-4-yl)methanesulfonyl chloride (31 mg, 0.16 mmol) in tetrahydrofuran (0.5 ml) according to the method described in Preparation 175 but stirring at 50° C. overnight. The title compound was obtained (54 mg, 68% yield, 80% purity) without further purification.
LRMS (m/z): 800 (M+1)$^+$ Preparation 234

N'-[3-Methoxy-4-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]-N,N-dimethylsulfamide (S)-2-(1-((5-(4-Amino-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with pyridine (19 µL, 0.23 mmol) and dimethylsulfamoyl chloride (23 mg, 0.16 mmol) in tetrahydrofuran (0.5 ml) according to the method described in Preparation 175 but stirring at 50° C. overnight. The title compound was obtained (76 mg, 74% yield, 57% purity) without further purification.
LRMS (m/z): 744 (M+1)$^+$ Preparation 235

(S)-1-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)urea To a suspension of (S)-2-(1-((5-(4-amino-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) in water (0.40 mL) and acetic acid (0.20 mL) was added potassium isocyanate (19 mg, 0.23 mmol) according to the method described in Preparation 181 but stirring at 60° C. overnight. The residue was purified using SP1® Purification System (0% to 100% n-hexane-ethyl acetate) to obtain 34 mg (61% yield) of the title compound.
LRMS (m/z): 680 (M+1)+.

Preparation 236

(S)—N-(3-(Dimethylamino)-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide a) 3-Iodo-N,N-dimethyl-5-nitroaniline

1-Fluoro-3-iodo-5-nitrobenzene (500 mg, 1.87 mmol), and potassium carbonate (260 mg, 1.88 mmol) were suspended in DMSO (7 ml) and dimethylamine (2M in THF, 3 ml, 6 mmol) was added. The vial was sealed under argon and stirred for 15 min at 125° C. under microwave conditions. The reaction mixture was poured into 50 ml of water and extracted with ethyl acetate (3×40 ml). The organic phase was washed with brine (1×100 ml), dried over magnesium sulphate and concentrated under reduced pressure. The residue was purified using SP1® Purification System (0% to 30%, hexane-ethyl acetate) to obtain 320 mg (59% yield) of the title compound as a brown solid. Purity 100%.

LRMS (m/z): 293 (M+1)$^+$.

b) N,N-Dimethyl-3-nitro-5-(4,4,5,5-tetramethyl-1,3,2-dioxaborolan-2-yl)aniline 3-Iodo-N,N-dimethyl-5-nitroaniline (380 mg, 1.3 mmol) was dissolved in 8 ml DMF. Bis(pinacolato)diboron (496 mg, 1.95 mmol) and potassium acetate (638 mg, 6.5 mmol) were added and the mixture was submitted to three vacuum-argon cycles. Bis(diphenylphosphino)ferrocene-palladium(II)dichloride dichloromethane complex (0.11 g, 0.16 mmol) was added under argon conditions. The mixture was then stirred at 100° C. for 30 min. The reaction mixture was partitioned between ethyl acetate and water. The organic phase was dried over sodium sulphate, filtered and evaporated under reduced pressure. The residue was purified using SP1® Purification System (0% to 10%, dichloromethane-methanol) to obtain 356 mg (94% yield) of the title compound as a brown solid. Purity 100%.

LRMS (m/z): 293 (M+1)$^+$.

c) N$^1$,N$^1$-Dimethyl-5-(4,4,5,5-tetramethyl-1,3,2-dioxaborolan-2-yl)benzene-1,3-diamine N,N-Dimethyl-3-nitro-5-(4,4,5,5-tetramethyl-1,3,2-dioxaborolan-2-yl)aniline (356 mg, 1.22 mmol) was dissolved in 50 ml of ethyl acetate. This mixture was hydrogenated in an H-Cube® apparatus using 10% palladium on carbon as catalyst at 2-3 bar. The solvent was evaporated to give 324 mg (99% yield) of the title compound as a white solid. Purity 100%.

LRMS (m/z): 263 (M+1)$^+$.

d) N-(3-(Dimethylamino)-5-(4,4,5,5-tetramethyl-1,3,2-dioxaborolan-2-yl)phenyl)methanesulfonamide N$^1$,N$^1$-Dimethyl-5-(4,4,5,5-tetramethyl-1,3,2-dioxaborolan-2-yl)benzene-1,3-diamine (324 mg, 1.24 mol) was dissolved in 11 mL pyridine. The mixture was submitted to three vacuum-argon cycles and was cooled at 0° C. with an ice bath. Methanesulfonyl chloride (110 µl, 1.42 mol) was added dropwise and the reaction mixture was stirred overnight. The solvent was concentrated and the residue was partitioned between dichloromethane and a saturated sodium bicarbonate solution. The organic phase was dried over sodium sulphate and evaporated under reduced pressure. The semi-solid was crystallized in hexane to obtain a solid that was filtered off and dried in the oven to give 365 mg (87% yield) of the final compound as a mixture of boronic acid and boronate ester. Purity 100%.

LRMS (m/z): 341 (M+1)$^+$.

e) (S)—N-(3-(Dimethylamino)-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (100 mg, 0.17 mmol) was treated with N-(3-(dimethylamino)-5-(4,4,5,5-tetramethyl-1,3,2-dioxaborolan-2-yl)phenyl)methanesulfonamide (145 mg, 0.43 mmol), bis(diphenylphosphino)ferrocene-palladium(II)dichloride dichloromethane complex (42 mg, 0.05 mmol) and sodium carbonate (45 mg, 0.42 mmol) in DME (1.6 ml) and water (0.4 ml). The reaction mixture was submitted to vacuum-argon cycles and stirred at 70° C. for 1.5 h. The reaction mixture was cooled down to room temperature and poured into ice-water, basified with potassium carbonate and extracted with ethyl acetate (×3). The organic phase was successively washed with water and brine, dried over magnesium sulphate, filtered and the solvent evaporated under reduced pressure. The residue was purified by normal phase using SP1® Purification System (0% to 10%, hexane-ethyl acetate) to obtain 89.5 mg (73% yield) of the title compound. Purity: 100%.

LRMS (m/z): 728 (M+1)$^+$.

Preparation 237

(S)—N-(3-Hydroxy-5-(4-((3-hydroxy-1-(5-methyl-4-oxo-3-phenyl-3,4-dihydropyrrolo[2,1-f][1,2,4]triazin-2-yl)propyl)amino)-7-((2-(trimethylsilyl)ethoxy)methyl)-7H-pyrrolo[2,3-d]pyrimidin-5-yl)phenyl)methanesulfonamide a) (S)-2-(1-((5-Bromo-7-((2-(trimethylsilyl)ethoxy)methyl)-7H-pyrrolo[2,3-d]pyrimidin-4-yl)amino)-3-hydroxypropyl)-5-methyl-3-phenylpyrrolo[2,1-f][1,2,4]triazin-4(3H)-one (S)-3-Hydroxy-1-(5-methyl-4-oxo-3-phenyl-3,4-dihydropyrrolo[2,1-f][1,2,4]triazin-2-yl)propan-1-aminium chloride (228 mg, 0.68 mmol) was treated with 5-bromo-4-chloro-7-((2-(trimethylsilyl)ethoxy)methyl)-7H-pyrrolo[2,3-d]pyrimidine (495 mg, 1.36 mmol), cesium fluoride (41 mg, 0.27 mmol) and N,N-diisopropylethylamine (1.60 ml, 9.19 mmol) in tert-butanol (5.0 ml) according to Preparation 13 but stirring the reaction mixture at 100° C. during 96 h. The residue was purified using SP1® Purification System (0% to 100%, hexane-ethyl acetate) to give 249 mg (57% yield) of the title compound.

LRMS (m/z): 625 (M+1)$^+$.

b) (S)—N-(3-Hydroxy-5-(4-((3-hydroxy-1-(5-methyl-4-oxo-3-phenyl-3,4-dihydropyrrolo[2,1-f][1,2,4]triazin-2-yl)propyl)amino)-7-((2-(trimethylsilyl)ethoxy)methyl)-7H-pyrrolo[2,3-d]pyrimidin-5-yl)phenyl)methanesulfonamide (S)-2-(1-((5-Bromo-7-((2-(trimethylsilyl)ethoxy)methyl)-7H-pyrrolo[2,3-d]pyrimidin-4-yl)amino)-3-hydroxypropyl)-5-methyl-3-phenylpyrrolo[2,1-f][1,2,4]triazin-4 (3H)-one (50 mg, 0.08 mmol) was treated with N-(3-hydroxy-5-(4,4,5,5-tetramethyl-1,3,2-dioxaborolan-2-yl) phenyl)methanesulfonamide (85 mg, 0.21 mmol), sodium carbonate (23 mg, 0.22 mmols) and 1,11-bis(diphenylphosphino)ferrocene-palladium(II)dichloride dichloromethane complex (21 mg, 0.03 mmol) in 1,2-dimethoxyethane (1.6 ml) and water (0.40 ml) according to the method described in Preparation 62. The residue was purified using SP1® Purification System (0% to 100%, hexane-ethyl acetate) to give 35 mg (39% yield, 65% purity) of the title compound.
LRMS (m/z): 731 (M+1)+.

Preparation 238

(S)-5-Methyl-2-(1-((5-(1-methyl-3-(trifluoromethyl)-1H-pyrazol-5-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with 1-methyl-5-(4,4,5,5-tetramethyl-1,3,2-dioxaborolan-2-yl)-3-(trifluoromethyl)-1H-pyrazole (58 mg, 0.21 mmol), sodium carbonate (22 mg, 0.21 mmols), and bis(triphenylphosphine)palladium(II) dichloride (6 mg, 0.01 mmol) in 1,2-dimethoxyethane (2.0 ml) and water (0.50 ml) according to the method described in Preparation 62. The residue was purified using SP1® Purification System (0% to 100%, dichloromethane diethyl ether) to give 38 mg (45% yield, 66% purity) of the title compound.
LRMS (m/z): 664 (M+1)+.

Preparation 239

(S)-2-(1-((5-(1-(2-Methoxybenzyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (80 mg, 0.14 mmol) was dissolved in N,N-dimethylformamide (2.0 ml). 1-(Chloromethyl)-2-methoxybenzene (43 ml, 0.27 mmol) and cesium carbonate (200 mg, 0.61 mmol) were added and the mixture was stirred at 75° C. during 2 h. The reaction was poured into ice-water mixture, basified to pH 10 with sodium carbonate and extracted twice with ethyl acetate. The organics were combined and washed with water, brine, dried over sodium sulphate, filtered and evaporated under reduced pressure. The residue was purified using SP1® Purification System (0% to 30%, hexane-ethyl acetate) to give 86 mg (83% yield, 93% purity) of the title compound.
LRMS (m/z): 702 (M+1)+.

Preparation 240

(S)-2-(1-((5-(1-(3-Methoxyphenyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino) ethyl)-5-methyl-3-phenylpyrrolo[2,1-f][1,2,4]triazin-4(3H)-one (88 mg, 0.15 mmol) was dissolved in N,N-dimethylformamide (1.5 ml). (3-Methoxyphenyl)boronic acid (46 mg, 0.30 mmol), copper(II) acetate (4 mg, 0.02 mmol) and pyridine (28 μL, 0.34 mmol) were added and the mixture was stirred at 75° C. during 96 h. The reaction was poured into ice-water mixture, basified to pH 10 with sodium carbonate and extracted twice with ethyl acetate. The organics were combined and washed with water, brine, dried over sodium sulphate, filtered and evaporated under reduced pressure. The residue was purified using SP1® Purification System (0% to 50%, hexane-ethyl acetate) to give 9 mg (9% yield) of the title compound.
LRMS (m/z): 688 (M+1)+.

Preparation 241

4-(4,4,5,5-Tetramethyl-1,3,2-dioxaborolan-2-yl)pyridin-2-amine

4-Bromopyridin-2-amine (500 mg, 2.89 mmol) was treated with bis(pinacolato)diboron (2 g, 7.8 mmol), potassium acetate (1 g, 10.2 mmol), bis(diphenylphosphino)ferrocene-palladium(II)dichloride dichloromethane complex (480 mg, 0.59 mmol) in dioxane (7 ml) according to the method described in Preparation 174a. The reaction mixture was concentrated under reduced pressure and ethyl acetate was added. A black oil was formed and the crude was filtered, washing with more ethyl acetate. The filtered was concentrated and precipitated with hexane to obtain the title compound (800 mg, 94% yield) as a solid.
LRMS (m/z): 221 (M+1)+.

Preparation 242

(S)-2-(1-((5-(2-Aminopyridin-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (250 mg, 0.42 mmol) was treated with 4-(4,4,5,5-tetramethyl-1,3,2-dioxaborolan-2-yl)pyridin-2-amine (200 mg, 0.91 mmol), tetrakis(triphenylphosphine)palladium(0) (90 mg, 0.08 mmol), and aqueous solution 2M of sodium carbonate (200 μl, 0.4 mmol) in N,N-dimethylformide (5 ml) according to the method described in Preparation 186 heating at 100° C. overnight. The crude was purified using SP1® Purification System (hexane-ethyl acetate) to obtain 100 mg (40% yield) of the title compound. Purity 98%.
LRMS (m/z): 608 (M+1)+.

Preparation 243

(S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-2-yl)-1-(tetrahydro-2H-pyran-4-yl)methanesulfonamide (S)-2-(1-((5-(2-Aminopyridin-4-yl)-7-((2-(trimethylsilyl)ethoxy)methyl)-7H-pyrrolo[2,3-d]pyrimidin-4-yl)amino) ethyl)-5-methyl-3-phenylpyrrolo[2,1-f][1,2,4]triazin-4(3H)-one (80 mg, 0.13 mmol) was treated with (tetrahydro-2H-pyran-4-yl)methanesulfonyl chloride (26 mg, 0.13 mmol)

and triethylamine (36 µl, 0.26 mmol) in pyridine (2 ml) according to the method described in Preparation 15b. The residue was purified using SP1® Purification System (hexane-ethyl acetate) to give 55 mg (53% yield) of the title compound. Purity 98%.

LRMS (m/z): 770 (M+1)$^+$.

Preparation 244

3-(5-Methyl-1,3,4-oxadiazol-2-yl)-5-(4,4,5,5-tetramethyl-1,3,2-dioxaborolan-2-yl)phenol a) 3-Bromo-5-hydroxybenzohydrazide Methyl 3-bromo-5-hydroxybenzoate (1 g, 4.33 mmol) was treated with hydrazine hydrate (1 ml, 20.5 mmol) and acetonitrile (5 ml) as a solvent according the method described in Preparation 226a to obtain 0.8 g (64% yield) of the title compound that was used in the next synthetic step without further purification. Purity 80%.

LRMS (m/z): 232 (M+1)$^+$.

b) 3-Bromo-5-(5-methyl-1,3,4-oxadiazol-2-yl)phenol

Bromo-5-hydroxybenzohydrazide (400 mg, 1.73 mmol) was treated with 1,1,1-triethoxyethane (842 mg, 5.19 mmol) and acetic acid (7 ml) as a solvent according to the method described in Preparation 226b. The residue was purified using SP1® Purification System (hexane-ethyl acetate) to give 290 mg of the title compound as a white solid.

LRMS (m/z): 256 (M+1)$^+$.

c) 3-(5-Methyl-1,3,4-oxadiazol-2-yl)-5-(4,4,5,5-tetramethyl-1,3,2-dioxaborolan-2-yl)phenol 3-Bromo-5-(5-methyl-1,3,4-oxadiazol-2-yl)phenol (150 mg, 0.59 mmol) was treated with bis(pinacolato)diboron (300 mg, 1.18 mmol), potassium acetate (180 mg, 1.83 mmol), bis(diphenylphosphino)ferrocene-palladium(II)dichloride dichloromethane complex (49 mg, 0.06 mmol) and dioxane (10 ml) as a solvent according to the method described in Preparation 174a to give 200 mg (90% yield) of the title compound that was used in the next synthetic step without further purification. Purity 80%.

LRMS (m/z): 303 (M+1)$^+$.

Preparation 245

(S)-2-(1-((5-(3-Hydroxy-5-(5-methyl-1,3,4-oxadiazol-2-yl)phenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (250 mg, 0.42 mmol) was treated with 3-(5-methyl-1,3,4-oxadiazol-2-yl)-5-(4,4,5,5-tetramethyl-1,3,2-dioxaborolan-2-yl)phenol (200 mg, 0.66 mmol), tetrakis(triphenylphosphine)palladium(0) (40 mg, 0.03 mmol) and aqueous solution 2M of sodium carbonate (500 µl, 4.7 mmol) in N,N-dimethylformide (5 ml) according to the method described in Preparation 186 but stirring at 100° C. for 48 h. The crude was purified using SP1® Purification System (hexane-ethyl acetate) to obtain 50 mg (16% yield) of the title compound as a oil. Purity 95%.

LRMS (m/z): 690 (M+1)$^+$.

Preparation 246

3-(5-Amino-1,3,4-oxadiazol-2-yl)-5-(4,4,5,5-tetramethyl-1,3,2-dioxaborolan-2-yl)phenol a) 3-(5-Amino-1,3,4-oxadiazol-2-yl)-5-bromophenol 3-Bromo-5-hydroxybenzohydrazide (400 mg, 1.04 mmol) was suspended in 5 ml dioxane. Cyanogen bromide (110 mg, 1.04 mmol) and sodium bicarbonate (4%, 1 ml, 12 mmol) were added and the reaction was stirred at room temperature overnight. The reaction mixture was concentrated under reduced pressure and re-dissolved in ethyl acetate. The organic was washed with water, brine and dried over sodium sulphate, filtered and evaporated under reduced pressure. The oil obtained was precipitate with hexane and filtered to give 126 mg (43% yield) of the title compound. Purity 90%.

LRMS (m/z): 257 (M+1)$^+$.

b) 3-(5-Amino-1,3,4-oxadiazol-2-yl)-5-(4,4,5,5-tetramethyl-1,3,2-dioxaborolan-2-yl)phenol 3-(5-Amino-1,3,4-oxadiazol-2-yl)-5-bromophenol (126 mg, 0.49 mmol) was treated with bis(pinacolato)diboron (350 mg, 1.38 mmol), potassium acetate (50 mg, 0.51 mmol), bis(diphenylphosphino)ferrocene-palladium(II)dichloride dichloromethane complex (0.4 mg, 0.4 mmol) and dioxane (10 ml) as a solvent according to the method described in Preparation 174a to give 200 mg (85% yield) of the title compound that was used in the next synthetic step without further purification. Purity 85%.

Preparation 247

(S)-2-(1-((5-(3-(5-Amino-1,3,4-oxadiazol-2-yl)-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (250 mg, 0.42 mmol) was treated with 3-(5-amino-1,3,4-oxadiazol-2-yl)-5-(4,4,5,5-tetramethyl-1,3,2-dioxaborolan-2-yl)phenol (200 mg, 0.66 mmol), tetrakis(triphenylphosphine)palladium(0) (40 mg, 0.03 mmol), aqueous solution 2M of sodium carbonate (300 µl, 2.83 mmol) and 5 ml N,N-dimethylformide as a solvent according to the method described in Preparation 186 heating at 100° C. for 48 h. The crude was purified using SP1® Purification System (hexane-ethyl acetate) to obtain 40 mg (13% yield) of the title compound. Purity 95%.

LRMS (m/z): 691 (M+1)$^+$.

Preparation 248

(2-(4-(Dimethylamino)piperidin-1-yl)pyridin-4-yl)boronic acid a) 1-(4-Bromopyridin-2-yl)-N,N-dimethylpiperidin-4-amine In a pressure vessel were dissolved 4-bromo-2-fluoropyridine (1 g, 5.68 mmol) and N,N-dimethylpiperidin-4-amine (1.1 g, 8.58 mmol) in DMSO (7 ml). Potassium carbonate (2.4 g, 17.36 mmol) was added and the reaction was heated at 100° C. overnight. The reaction mixture was poured into water and extracted twice with diethylether. The organics were combined, washed with brine, dried over magnesium sulphate, filtered and concentrated under reduced pressure to give 1.55 g (91% yield) of the title compound as a oil. Purity 95%.
LRMS (m/z): 285 (M+1)$^+$.

b) (2-(4-(Dimethylamino)piperidin-1-yl)pyridin-4-yl)boronic acid

In a Schlenck vessel 1-(4-bromopyridin-2-yl)-N,N-dimethylpiperidin-4-amine (1.55 g, 5.45 mmol) was treated with bis(pinacolato)diboron (1.65 g, 6.50 mmol), potassium acetate (1.6 g, 16.3 mmol), bis(diphenylphosphino)ferrocene-palladium(II)dichloride dichloromethane complex (0.22 mg, 0.24 mmol) and dioxane (20 ml) as a solvent according to the method described in Preparation 174a to give 1.71 g (85% yield) of the title compound that was used in the next synthetic step without further purification. Purity 90%.
LRMS (m/z): 250 (M+1)$^+$.

Preparation 249

(S)-2-(1-((5-(2-(4-(Dimethylamino)piperidin-1-yl)pyridin-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-Bromo-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with (2-(4-(dimethylamino)piperidin-1-yl)pyridin-4-yl)boronic acid (43 mg, 0.17 mmol), tetrakis(triphenylphosphine)palladium(0) (15 mg, 0.01 mmol), aqueous solution 2M of sodium carbonate (200 µl, 0.4 mmol) and 5 ml N,N-dimethylformide as a solvent according to the method described in Preparation 186 but stirring at 100° C. overnight. The crude was purified by reverse phase using SP1® Purification System (hexane-ethyl acetate) to obtain 60 mg (75% yield) of the title compound. Purity 75%.
LRMS (m/z): 719 (M+1)$^+$.

Preparation 250

N-(5-Bromo-2-chloropyridin-3-yl)-4-hydroxybenzamide a) N-(5-Bromo-2-chloropyridin-3-yl)-4-methoxybenzamide

5-Bromo-2-chloropyridin-3-amine (1.5 g, 7.23 mmol) was dissolved in dichloromethane (30 ml). Diisopropylethylamine (1.52 ml, 8.67 mmol) first and then a solution of 3-methoxybenzoyl chloride (1.08 ml, 7.95 mmol) in dichloromethane (20 ml) were added. After 1 h at room temperature the reaction mixture was diluted with ethyl acetate and washed with water and brine, dried over sodium sulphate, filtered and evaporated under reduced pressure to give 2.8 g (92% yield) of the title compound. Purity 81%.
LRMS (m/z): 341, 343 (M+1)$^+$ b) N-(5-Bromo-2-chloropyridin-3-yl)-4-hydroxybenzamide

N-(5-Bromo-2-chloropyridin-3-yl)-4-methoxybenzamide (1.4 g, 81% purity, 3.32 mmol) was dissolved in 80 mL dichloromethane. A solution of boron tribromide (1M in dichloromethane, 16.6 ml, 16.6 mmol) was added dropwise and the reaction was stirred at room temperature overnight. The mixture was diluted with ethyl acetate and washed with a solution of 4% sodium bicarbonate, water, brine and dried over sodium sulphate, filtered and evaporated under reduced pressure to give 1.2 g (100% yield) of the title compound as an orange solid. Purity 91%.
LRMS (m/z): 325, 327 (M−1)$^-$

Preparation 251

4-Hydroxy-N-(2-methoxy-5-(4,4,5,5-tetramethyl-1,3,2-dioxaborolan-2-yl)pyridin-3-yl)benzamide a) N-(5-Bromo-2-methoxypyridin-3-yl)-4-hydroxybenzamide

N-(5-Bromo-2-chloropyridin-3-yl)-4-hydroxybenzamide (600 mg, 1.83 mmol) was suspended in a solution of sodium methoxide 25% in methanol (12 ml, 55 mmol and the reaction mixture was stirred at 50° C. overnight. The solvent was removed and the crude poured into water. The precipitate was filtered off and discarded and the filtrate was brought to pH7 by adding hydrogen chloride 2N. The precipitate was then filtered and washed with water and was purified using SP1® Purification System (0% to 25%, hexane-ethyl acetate) to give 74 mg (8% yield) of the title compound. Purity 62%.
LRMS (m/z): 323, 325 (M+1)$^+$ b) 4-Hydroxy-N-(2-methoxy-5-(4,4,5,5-tetramethyl-1,3,2-dioxaborolan-2-yl)pyridin-3-yl)benzamide N-(5-bromo-2-methoxypyridin-3-yl)-4-hydroxybenzamide (74 mg, 0.22 mmol), bis(pinacolato)diboron (174 mg, 0.66 mmol), potassium acetate (112 mg, 1.14 mmol), bis(diphenylphosphino)ferrocene-palladium(II)dichloride dichloromethane complex (19 mg, 0.03 mmol) and 1,1'-bis(diphenylphosphino)ferrocene (19 mg, 0.03 mmol) were suspended in dioxane (5 ml) and heated to 90° C. overnight. The mixture was diluted with ethyl acetate and washed with water and brine, dried over sodium sulphate, filtered and evaporated under reduced pressure to give 397 mg (100% yield) of the title compound. Purity 45%.
LRMS (m/z): 371 (M+1)$^+$

Preparation 252

N-(3-Amino-5-methoxyphenyl)methanesulfonamide a) N-(3-Methoxy-5-nitrophenyl)methanesulfonamide

3-Methoxy-5-nitroaniline (2 g, 11.89 mmol) was treated with methanesulfonyl chloride (1.01 ml, 13.08 mmol) according to the method described in Preparation 15b to give 3 g (100% yield) of the title compound. Purity 97%.
LRMS (m/z): 245 (M−1)$^-$.

b) N-(3-Amino-5-methoxyphenyl)methanesulfonamide

N-(3-Methoxy-5-nitrophenyl)methanesulfonamide (3 g, 11.82 mmol) was treated with iron powder (3.3 g, 59.09 mmol) in acetic acid (120 ml) and stirred at 40° C. for 2 h. The crude was then filtered over Celite and the solvent was removed in vacuum. A mixture of a solution of sodium bicarbonate 4% and ethyl acetate was added and the resulting mixture was filtered over Celite. The organic phase was washed with water and brine, dried over magnesium sulphate and the solvent was remove to give 2.53 g (86% yield) of the title compound as a dark solid, that was used in the next step without further purification. Purity 87%.

LRMS (m/z): 217 (M+1)$^+$.

Preparation 253

4-Amino-6-chloro-N-(3-methoxy-5-(methylsulfonamido)phenyl)pyrimidine-5-carboxamide a) 4,6-Dichloro-N-(3-methoxy-5-(methylsulfonamido)phenyl)pyrimidine-5-carboxamide N-(3-Amino-5-methoxyphenyl)methanesulfonamide (1 g, 87% purity, 4.02 mmol) was dissolved in dichloromethane (36 ml) and triethylamine (1.35 ml, 9.65 mmol) was added. Then a solution of 4,6-dichloropyrimidine-5-carbonyl chloride (1.52 g, 67% purity, 4.82 mmol, prepared according to E. V. Tarasov et al. *Synlett* 2000, 5, 625-626) was added dropwise and the reaction mixture was stirred at room temperature overnight. The reaction mixture was then diluted with dichloromethane, washed with 4% sodium bicarbonate solution, dried over magnesium sulphate, filtered and evaporated. The crude was purified by flash chromatography (0% to 40%, hexane-ethyl acetate) using an Isolera® Purification System to give 617 mg (28% yield) of the title compound as a reddish oil. Purity 73%.

LRMS (m/z): 392 (M+1)$^+$ b) 4-Amino-6-chloro-N-(3-methoxy-5-(methylsulfonamido)phenyl)pyrimidine-5-carboxamide 4,6-Dichloro-N-(3-methoxy-5-(methylsulfonamido)phenyl)pyrimidine-5-carboxamide (617 mg, 73% purity, 1.14 mmol) was dissolved in dioxane (5 ml) and cooled in an ice bath. Ammonia (819 µl, 7N in MeOH, 5.7 mmol) was added dropwise and the mixture stirred at 0° C. for 6 h and at room temperature overnight. The solvent was removed and ethyl acetate added. The solid precipitate was filtered off and the filtrate was concentrated to give 660 mg (100% yield) of the title compound as an oil that was used in the next step without further purification. Purity 65%

LRMS (m/z): 372, 373 (M+1)$^+$

Preparation 254

N-(3-Methoxy-5-(4,4,5,5-tetramethyl-1,3,2-dioxaborolan-2-yl)phenyl)butane-1-sulfonamide 3-Methoxy-5-(4,4,5,5-tetramethyl-1,3,2-dioxaborolan-2-yl)aniline (822 mg, 3.29 mmol), was treated with 1-butanesulfonyl chloride (638 µl, 4.93 mmol) according to the method described in Preparation 15b to give 1.1 g (94% yield) of the title compound. Purity 97%.

LRMS (m/z): 370 (M+1)$^+$.

Preparation 255

1-(4-Fluorophenyl)-N-(3-methoxy-5-(4,4,5,5-tetramethyl-1,3,2-dioxaborolan-2-yl)phenyl)methanesulfonamide 3-Methoxy-5-(4,4,5,5-tetramethyl-1,3,2-dioxaborolan-2-yl)aniline (822 mg, 3.29 mmol), was treated with (4-fluorophenyl)methanesulfonyl chloride (1.03 ml, 4.93 mmol) according to the method described in Preparation 15b to give 1.26 g (94% yield) of the title compound. Purity 97%.

LRMS (m/z): 422 (M+1)$^+$.

Preparation 256

2-Fluoro-4-hydroxy-N-(5-(4,4,5,5-tetramethyl-1,3,2-dioxaborolan-2-yl)pyridin-3-yl)benzenesulfonamide a) N-(5-Bromopyridin-3-yl)-2-fluoro-4-methoxybenzenesulfonamide 5-Bromopyridin-3-amine (500 mg, 2.89 mmol) was dissolved in dichloromethane (14 ml) and pyridine (4 ml) was added. To this mixture 2-fluoro-4-methoxybenzene-1-sulfonyl chloride (1 g, 4.45 mmol) was added dropwise and the mixture stirred at reflux for 5 h. Once at room temperature, the reaction mixture was washed with water and brine, dried over magnesium sulphate, filtered and the solvents were removed under reduced pressure. The product was purified by flash chromatography (0% to 50% DCM/AcOEt) to give 792 mg (76% yield) of the title compound as a white solid.

LRMS (m/z): 362 (M+1)$^+$.

b) N-(5-Bromopyridin-3-yl)-2-fluoro-4-hydroxybenzenesulfonamide

N-(5-Bromopyridin-3-yl)-2-fluoro-4-methoxybenzenesulfonamide (692 mg, 1.92 mmol) was dissolved in DCM (10 ml), the reaction flask was sealed and boron tribromide (5 ml, 1M solution in DCM) was added dropwise under an argon atmosphere. After stirring overnight at reflux, more boron tribromide was added (5 ml) and the mixture was refluxed for 18 h. After cooling in an ice bath, methanol was added dropwise and evaporated under reduced pressure. The mixture was poured into ice and extracted with ethyl acetate. The resulting organic solution was washed with water and brine, dried over magnesium sulphate, filtered and the solvents were removed under reduced pressure. The product was purified by flash chromatography (0% to 5% DCM/MeOH) to give 414 mg (62% yield) of the title compound as a white solid.

LRMS (m/z): 348 (M+1)$^+$.

c) 2-Fluoro-4-hydroxy-N-(5-(4,4,5,5-tetramethyl-1,3,2-dioxaborolan-2-yl)pyridin-3-yl)benzenesulfonamide N-(5-Bromopyridin-3-yl)-2-fluoro-4-hydroxybenzenesulfonamide (414 mg, 1.19 mmol) was dissolved in 10 ml dioxane. Bis(pinacolato)diboron (335 mg, 1.32 mmol) and potassium acetate (325 mg, 3.31 mmol) were added and the mixture was submitted to three vacuum-argon cycles. Bis(diphenylphosphino)ferrocene-palladium(II)dichloride dichloromethane complex (50 mg, 0.06 mmol) was added under argon conditions. The mixture was stirred at 100° C. for 2 days. Dioxane was evaporated under reduced pressure. Ethyl acetate was added to the residue and the precipitated salts were separated by filtration. The solvent was evaporated under reduced pressure and hexane was added to the residue. The title compound (385 mg, 82% yield) was filtered and used in the next synthetic step without further purification. Purity 100%.

LRMS (m/z): 395 (M+1)$^+$.

Preparation 257

(S)—N-(3-Methoxy-5-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-pyrazol-1-yl)phenyl)methanesulfonamide a) (S)-2-(1-((5-(1-(3-Amino-5-methoxyphenyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (67 mg, 0.12 mmol) was treated with 3-methoxy-5-(4,4,5,5-tetramethyl-1,3,2-dioxaborolan-2-yl)aniline (57 mg, 0.23 mmol), Cu(AcO)$_2$ (32 mg, 0.18 mmol) and pyridine (20 µl, 0.25 mmol) in DMF (1.5 ml). The reaction mixture was submitted at vacuum-argon cycles and stirred at 100° C. under microwave conditions for 2 h. More pyridine and Cu(AcO)$_2$ were added, and the reaction mixture stirred at 100° C. until the reaction was over. The solvent was cooled at room temperature and poured into ice-water, basified with potassium carbonate and extracted with ethyl acetate (×3). The organic phase was successively washed with water and brine, dried over magnesium sulfate, filtered and the solvent evaporated under reduced pressure. The residue (15.3 mg, 14% yield, 75% purity) was used in the next synthetic step without further purification.

LRMS (m/z): 704 (M+1)$^+$.

b) (S)—N-(3-Methoxy-5-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-pyrazol-1-yl)phenyl)methanesulfonamide (S)-2-(1-((5-(1-(3-Amino-5-methoxyphenyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (15.3 mg, 0.02 mol) was dissolved in 2 ml pyridine and triethylamine (5 µl, 0.04 mol). The mixture was submitted to three vacuum-argon cycles and was cooled at 0° C. with an ice bath. Methanesulfonyl chloride (2 µl, 0.03 mol) was added dropwise and the reaction mixture was stirred for 2 h. The solvent was concentrated and the residue was partitioned between ethyl acetate and a saturated sodium bicarbonate solution. The organic phase was dried over sodium sulphate and evaporated under reduced pressure, to obtain 16.6 mg (94% yield) of the title compound. Purity 72%.

LRMS (m/z): 781 (M+1)$^+$.

Preparation 258

(S)-2-(1-((5-(1-(3-(Dimethylamino)propyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (43 mg, 0.07 mmol) and 3-chloro-N,N-dimethylpropan-1-amine (47 mg, 0.39 mmol) were dissolved in DMF (3 ml) and cesium carbonate (240 mg, 0.74 mmol) was added. After stirring the mixture at 75° C. for 3.5 h, the solvent was evaporated under reduced pressure and the residue was suspended in water and extracted with dichloromethane (×3). The organic phase was successively washed with water and brine, dried over magnesium sulfate, filtered and the solvent evaporated under reduced pressure, to obtain 50 mg (70% yield) of the title compound as a brown solid. Purity 69%.

LRMS (m/z): 668 (M+1)$^+$.

Preparation 259

(S)-2-(1-((5-Iodopyrimidin-4-yl)amino)ethyl)-3-phenylpyrrolo[2,1-f][1,2,4]triazin-4(3H)-one (S)-2-(1-Aminoethyl)-3-phenylpyrrolo[2,1-f][1,2,4]triazin-4(3H)-one (110 mg, 0.43 mmol) was treated with 4-chloro-5-iodopyrimidine (166 mg, 0.69 mmol), cesium fluoride (131 mg, 0.86 mmol) and N,N-diisopropylethylamine (377 µL, 2.16 mmol) according to Preparation 13. The residue was purified by reverse phase using SP1® Purification System to give 30 mg (13% yield) of the title compound as a solid. Purity 86%.

LRMS (m/z): 459 (M+1)$^+$

Example 1

(S)-2-(1-(6-Amino-5-(1H-tetrazol-5-yl)pyrimidin-4-ylamino)ethyl)-3-phenylpyrrolo[1,2-f][1,2,4]triazin-4(3H)-one 162 mg (0.44 mmol) of (S)-4-amino-6-(1-(4-oxo-3-phenyl-3,4-dihydropyrrolo[1,2-f][1,2,4]triazin-2-yl)ethylamino)pyrimidine-5-carbonitrile (synthesized as described in Eur. Pat. Appl., 2518070, 31 Oct. 2012) were dissolved in a mixture of 4 mL toluene and 1 mL dimethylformamide. 179 mg (0.87 mmol) of azidotrimethylstannane were added and the mixture was stirred at 110° C. under nitrogen atmosphere for 20 hours. Additional 179 mg (0.87 mmol) of azidotrimethylstannane and 4 mL of dimethylformamide were added and the heating was kept for 24 hours more. The volatiles were removed under reduced pressure and the residue was partitioned between 2M aqueous solution of sodium hydroxide and ethyl acetate. The organic layer was extracted twice more with sodium hydroxide and the combined aqueous solutions were acidified with 5M aqueous HCl solution. The product was extracted three times with dichloromethane and the combined organic solutions were washed with brine, dried over magnesium sulphate, filtered and the solvent was removed under reduced pressure. The oil that was obtained was vigorously stirred in 5 mL of diethyl ether until a solid was formed. The product was filtered off and washed with diethyl ether and 10 mg (6% yield) of the title compound were isolated as a yellowish solid.

LRMS (m/z): 414 (M−1)$^-$.

$^1$H NMR (400 MHz, DMSO-d6) δ 10.53 (s, 1H), 8.17 (s, 1H), 7.73-7.36 (m, 5H), 6.95 (dd, 1H), 6.59 (dd, 1H), 5.13-4.65 (m, 1H), 1.51 (d, 3H).

Example 2

(S)-2-(1-((6-Amino-5-(thiazol-2-yl)pyrimidin-4-yl)amino)ethyl)-3-phenylpyrrolo[2,1-f][1,2,4]triazin-4(3H)-one 60 mg (0.07 mmol) of (S)-2-(1-((6-amino-5-iodopyrimidin-4-yl)amino)ethyl)-5-methyl-3-phenylpyrrolo[2,1-f][1,2, 4]triazin-4(3H)-one, 43 mg (0.11 mmol) of 2-(tributylstannyl)thiazole, 2.0 mg (0.01 mmol) of bis-triphenylphosphinepalladium(II) chloride, 4.4 mg (0.02 mmol) of copper (I) iodide and 32 µl (0.23 mmol) of triethylamine in dimethylformamide (1.5 mL) were heated to 120° C. for 20 minutes with microwave irradiation under nitrogen atmosphere. The reaction mixture was filtered through Celite® and washed with methanol. The solvent of the filtrates were evaporated in vacuum and the residue was dissolved in ethyl acetate and washed with brine, dried over magnesium sulphate, filtered and the solvent was removed. The product was purified first by reverse phase chromatography (C-18 silica from Waters®, water/1:1 acetonitrile-methanol as eluents [0.1% v/v formic acid buffered] 0% to 100%) and then by preparative HPLC (Waters XBridge C18 OBD column, mixture of eluents NB from 50% B to 65% B, in a 10 min. gradient) to give 4 mg (13% yield) of the title compound.

LRMS (m/z): 431 (M+1)$^+$.

Example 3

(S)-2-(1-((6-Amino-5-(6-aminopyridin-3-yl)pyrimidin-4-yl)amino)ethyl)-3-phenylpyrrolo[2,1-f][1,2,4]triazin-4(3H)-one To a solution of (S)-2-(1-((6-amino-5-iodopyrimidin-4-yl)amino)ethyl)-5-methyl-3-phenylpyrrolo[2,1-f][1,2,4]triazin-4(3H)-one (100 mg, 0.21 mmol) were added 70 mg (0.32 mmol) of 5-(4,4,5,5-tetramethyl-1,3,2-dioxaborolan-2-yl)pyridin-2-amine, 19 mg (0.02 mmol) of 1,1'-bis(diphenylphosphino)ferrocene-palladium(II)dichloride dichloromethane complex and 317 µl of a 2M aqueous solution of sodium carbonate in dioxane. The mixture was stirred under argon atmosphere at 80° C. for 18 hours and then diluted with ethyl acetate. The resulting solution was washed with water and brine, dried over magnesium sulphate, filtered and the solvents were removed under reduced pressure. The product was purified first by flash chromatography (0% to 15% MeOH/DCM) and then by reverse phase chromatography (C-18 silica from Waters®, water/1:1 acetonitrile-methanol as eluents [0.1% v/v formic acid buffered] 0% to 100%) to give 28 mg (30% yield) of the title compound as a white solid.

LRMS (m/z): 440 (M+1)$^+$.

$^1$H NMR (400 MHz, DMSO-d6) δ 7.77 (s, 1H), 7.74 (s, 1H), 7.58-7.52 (m, 1H), 7.51-7.36 (m, 5H), 7.21 (s, 1H), 6.90 (dd, 1H), 6.61-6.52 (m, 2H), 6.05 (s, 2H), 5.59 (d, 1H), 5.51 (s, 2H), 4.81-4.72 (m, 1H), 1.23 (d, 3H).

Example 4

(S)-2-(1-((6-Amino-5-(1H-pyrazol-4-yl)pyrimidin-4-yl)amino)ethyl)-3-phenylpyrrolo[2,1-f][1,2,4]triazin-4(3H)-one The title compound was prepared following the experimental procedure described in Example 3 from 100 mg (0.21 mmol) of (S)-2-(1-((6-amino-5-iodopyrimidin-4-yl)amino)ethyl)-5-methyl-3-phenylpyrrolo[2,1-f][1,2,4]triazin-4(3H)-one and 62 mg (0.32 mmol) of 4-(4,4,5,5-tetramethyl-1,3,2-dioxaborolan-2-yl)-1H-pyrazole. The mixture was stirred at 80° C. for 18 hours and then an excess of 4-(4,4,5,5-tetramethyl-1,3,2-dioxaborolan-2-yl)-1H-pyrazole (62 mg), palladium catalyst (19 mg) and aqueous sodium carbonate solution (320 µl) were added and the reaction mixture was stirred at 80° C. for 24 hours more. The product was purified by flash chromatography (0% to 15%, dichloromethane-methanol) to obtain 25 mg (29% yield) of the title compound.

LRMS (m/z): 414 (M+1)$^+$.

$^1$H NMR (400 MHz, DMSO-d6) δ 13.10 (s, 1H), 7.81 (s, 1H), 7.78 (s, 1H), 7.58 (s, 1H), 7.53 (s, 1H), 7.51-7.33 (m, 5H), 6.91 (d, 1H), 6.58 (d, 1H), 5.58 (d, 2H), 4.78-4.67 (m, 1H), 1.24 (d, 3H).

Example 5

(S)-2-(1-((6-Amino-5-(1-(2-hydroxyethyl)-1H-pyrazol-4-yl)pyrimidin-4-yl)amino)ethyl)-3-phenylpyrrolo[2,1-f][1,2,4]triazin-4(3H)-one The title compound was prepared following the experimental procedure described in Example 3 from 100 mg (0.21 mmol) of (S)-2-(1-((6-amino-5-iodopyrimidin-4-yl)amino)ethyl)-5-methyl-3-phenylpyrrolo[2,1-f][1,2,4]triazin-4(3H)-one and 76 mg (0.32 mmol) of 2-(4-(4,4,5,5-tetramethyl-1,3,2-dioxaborolan-2-yl)-1H-pyrazol-1-yl)ethanol. After 18 hours heating, an excess of 2-(4-(4,4,5,5-tetramethyl-1,3,2-dioxaborolan-2-yl)-1H-pyrazol-1-yl)ethanol (76 mg), palladium catalyst (19 mg) and aqueous sodium carbonate solution (317 µl) were added and the reaction mixture was stirred at 80° C. for 24 hours more. The product was purified by flash chromatography (0% to 15%, dichloromethane-methanol) to obtain 46 mg (48% yield) of the title compound.

LRMS (m/z): 458 (M+1)$^+$.

$^1$H NMR (400 MHz, DMSO-d6) δ 7.79 (s, 1H), 7.76 (s, 1H), 7.60 (dd, 1H), 7.53-7.38 (m, 6H), 6.91 (dd, 1H), 6.58 (dd, 1H), 5.69 (d, 3H), 4.86 (t, 1H), 4.79-4.68 (m, 1H), 4.19 (t, 2H), 3.79 (q, 2H), 1.25 (d, 3H).

Example 6

(S)-2-(1-((6-Amino-5-(3-hydroxyphenyl)pyrimidin-4-yl)amino)ethyl)-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (134 mg, 0.28 mol) was treated with 3-(4,4,5,5-tetramethyl-1,3,2-dioxaborolan-2-yl)phenol (94 mg, 0.43 mmol), 1,1'-bis(diphenylphosphino)ferrocene-palladium(II)dichloride dichloromethane complex (25 mg, 0.03 mol) and sodium carbonate (2M, 425 µl, 0.85 mol) according to the method described in Example 3 to give 26 mg (21% yield) of the title compound as a white solid. Purity 98%.

LRMS (m/z): 440 (M+1)$^+$.

$^1$H NMR (400 MHz, DMSO-d6) δ 9.59 (s, 1H), 7.82 (s, 1H), 7.58-7.53 (m, 1H), 7.46 (ddt, J=12.0, 9.0, 5.8 Hz, 5H), 7.34 (s, 1H), 6.91 (dd, J=4.3, 1.7 Hz, 1H), 6.80 (dd, J=8.2, 1.6 Hz, 1H), 6.68 (s, 2H), 6.58 (dd, J=4.3, 2.7 Hz, 1H), 5.47 (s, 2H), 5.40 (d, J=8.0 Hz, 1H), 4.83-4.69 (m, 1H), 1.21 (d, J=6.7 Hz, 3H).

Example 7

(S)-2-(1-((6-Amino-5-(3-fluoro-5-hydroxyphenyl)pyrimidin-4-yl)amino)ethyl)-3-phenylpyrrolo[2,1-f][1,2,4]triazin-4(3H)-one (S)-2-(1-(6-Amino-5-iodopyrimidin-4-ylamino)ethyl)-3-phenylpyrrolo[2,1-f][1,2,4]triazin-4(3H)-one and 3-fluoro-5-hydroxyphenylboronic acid (34 mg, 0.22 mmol) were stirred at 80° C. following the experimental procedure described in Example 3. 5 mg (3% yield) of the title compound were obtained as a solid.

LRMS (m/z): 458 (M+1)+.

$^1$H NMR (400 MHz, CDCl$_3$) δ ppm 8.12 (s, 1H), 7.92 (m, 2H), 7.63-7.56 (m, 3H), 7.54-7.49 (m, 2H), 7.29 (dd, J=5.5, 2.8 Hz, 2H), 6.56 (d, J=2.9 Hz, 1H), 5.01-4.86 (m, 1H), 4.77 (m, 2H), 4.10 (s, 3H), 3.09 (s, 3H), 1.24 (d, J=6.7 Hz, 3H).

Example 8

(S)—N-(5-(4-Amino-6-((1-(5-bromo-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide (S)-2-(1-((6-Amino-5-iodopyrimidin-4-yl)amino)ethyl)-5-bromo-3-phenylpyrrolo[2,1-f][1,2,4]triazin-4(3H)-one (90 mg, 0.16 mmol) and N-(2-methoxy-5-(4,4,5,5-tetramethyl-1,3,2-dioxaborolan-2-yl)pyridin-3-yl)methanesulfonamide (80 mg, 0.24 mmol) were stirred at 80° C. following the experimental procedure described in Example 3. 10 mg (3% yield) of the title compound were obtained as a solid.

LRMS (m/z): 627 (M+1)+

$^1$H NMR (400 MHz, CDCl$_3$) δ ppm 7.52 (d, J=12.4 Hz, 3H), 7.34 (dd, J=2.5, 1.7 Hz, 1H), 7.31 (s, 1H), 7.18 (s, 1H), 7.06 (s, 1H), 6.75 (s, 1H), 6.67 (d, J=11.2 Hz, 1H), 6.61 (s, 1H), 6.51 (d, J=29.5 Hz, 2H), 5.28 (s, 1H), 4.90 (dd, J=89.5, 45.0 Hz, 4H), 1.28 (d, J=29.3 Hz, 3H).

Example 9

(S)-2-(1-((6-Amino-5-(3-fluoro-4-hydroxyphenyl)pyrimidin-4-yl)amino)ethyl)-3-phenylpyrrolo[2,1-f][1,2,4]triazin-4(3H)-one (S)-2-(1-((6-Amino-5-(3-fluoro-4-hydroxyphenyl)pyrimidin-4-yl)amino)ethyl)-5-bromo-3-phenylpyrrolo[2,1-f][1,2,4]triazin-4(3H)-one (150 mg, 0.28 mol) was dissolved in 10 mL methanol and 2 mL dimethylformamide. Triethylamine and palladium on carbon were added under nitrogen atmosphere and the mixture was submitted at 30 psi of hydrogen conditions for 4 h. Further catalyst was added and the mixture was hydrogenated at 30 psi for 48 h. The reaction mixture was filtered off and evaporated to dryness. The residue was purified by reverse phase using SP1® Purification System and then was purified by normal phase (0% to 100%, hexane-ethyl acetate) to give 5 mg (4%) of the title compound as a solid. Purity 99%.

LRMS (m/z): 458 (M+1)+

$^1$H NMR (400 MHz, CDCl$_3$) δ 8.08 (s, 1H), 7.63-7.47 (m, 4H), 7.31-7.27 (m, 2H), 7.21 (s, 2H), 7.05 (dd, J=4.3, 1.6 Hz, 2H), 6.53 (dd, J=4.3, 2.7 Hz, 1H), 5.01 (s, 1H), 4.85 (d, J=8.5 Hz, 1H), 4.45 (s, 2H), 1.25 (d, J=6.8 Hz, 3H).

Example 10

(S)-2-(1-((6-Amino-5-(4-hydroxyphenyl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with (4-hydroxyphenyl)boronic acid (21 mg, 0.15 mmol), 1,1'-bis(diphenylphosphino)ferrocene-palladium(II)dichloride dichloromethane complex (14 mg, 0.02 mol) and sodium carbonate (2M, 231 μl, 0.46 mol) according to the method described in Example 3 to give 5 mg (11% yield) of the title compound as a white solid. Purity 100%.

LRMS (m/z): 454 (M+1)+

$^1$H NMR (400 MHz, CDCl$_3$) δ 8.04 (s, 1H), 7.59-7.42 (m, 4H), 7.28 (d, J=7.0 Hz, 1H), 7.13 (d, J=2.6 Hz, 2H), 7.01 (s, 2H), 6.31 (d, J=2.2 Hz, 1H), 5.10-4.72 (m, 3H), 2.66 (d, J=22.3 Hz, 3H), 2.49 (d, J=6.7 Hz, 3H), 1.24 (d, J=6.4 Hz, 3H).

Example 11

(S)-2-(1-((6-Amino-5-(3-fluoro-5-hydroxyphenyl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with (3-fluoro-5-hydroxyphenyl)boronic acid (24 mg, 0.15 mmol), 1,1'-bis(diphenylphosphino)ferrocene-palladium(II)dichloride dichloromethane complex (14 mg, 0.02 mol) and sodium carbonate (2M, 231 μl, 0.46 mol) according to the method described in Example 3 to give 17 mg (35% yield) of the title compound as a white solid. Purity 100%.

LRMS (m/z): 472 (M+1)+

$^1$H NMR (400 MHz, CDCl$_3$) δ 8.45 (s, 1H), 8.04 (s, 1H), 7.59-7.42 (m, 3H), 7.28 (d, J=7.0 Hz, 1H), 7.13 (d, J=2.6 Hz, 2H), 7.01 (s, 2H), 6.31 (d, J=2.2 Hz, 1H), 5.10-4.72 (m, 3H), 2.66 (d, J=22.3 Hz, 2H), 2.49 (d, J=6.7 Hz, 3H), 1.24 (d, J=6.4 Hz, 3H).

Example 12

(S)-4-Amino-6-((1-(5-((3-hydroxyphenyl)thio)-4-oxo-3-phenyl-3,4-dihydropyrrolo[2,1-f][1,2,4]triazin-2-yl)ethyl)amino)pyrimidine-5-carbonitrile (S)-4-Amino-6-((1-(5-((3-methoxyphenyl)thio)-4-oxo-3-phenyl-3,4-dihydropyrrolo[2,1-f][1,2,4]triazin-2-yl)ethyl)amino)pyrimidine-5-carbonitrile (70 mg, 0.14 mmol) was treated with boron tribromide (1M in dichloromethane, 411 μl, 0.41 mmol) with dichloromethane as a solvent according to the method described in Example 23. The residue was purified by reverse phase using SP1® Purification System to give 33 mg (49% yield) as a solid. Purity 100%.

LRMS (m/z): 497 (M+1)+

$^1$H NMR (400 MHz, DMSO-d6) δ 9.60 (s, 1H), 7.75 (d, J=13.0 Hz, 2H), 7.67 (d, J=6.6 Hz, 1H), 7.54-7.38 (m, 2H), 7.31 (d, J=11.7 Hz, 3H), 7.22 (s, 1H), 7.12 (t, J=7.8 Hz, 1H), 6.76-6.57 (m, 3H), 6.46 (s, 1H), 5.03-4.79 (m, 1H), 1.36 (d, J=6.2 Hz, 3H).

Example 13

(S)-2-(1-((6-Amino-5-(3-fluoro-4-hydroxyphenyl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with (3-fluoro-4-hydroxyphenyl)boronic acid (24 mg, 0.15 mmol), 1,1'-bis(diphenylphosphino)ferrocene-palladium(II)dichloride dichloromethane complex (14 mg, 0.02 mol) and sodium carbonate (2M, 231

µl, 0.46 mol) according to the method described in Example 3 to give 4 mg (9% yield) of the title compound as a white solid. Purity 100%.

LRMS (m/z): 472 (M+1)$^+$ $^1$H NMR (400 MHz, CDCl$_3$) δ 8.06 (s, 1H), 7.64-7.42 (m, 4H), 7.29 (d, J=7.2 Hz, 1H), 7.08 (d, J=67.0 Hz, 3H), 6.32 (d, J=2.3 Hz, 1H), 4.99 (s, 1H), 4.91 (s, 1H), 4.72 (s, 2H), 2.49 (s, 3H), 1.67 (s, 2H), 1.23 (t, J=7.2 Hz, 3H).

Example 14

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)methanesulfonamide (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with N-(2-methoxy-5-(4,4,5,5-tetramethyl-1,3,2-dioxaborolan-2-yl)pyridin-3-yl)methanesulfonamide (51 mg, 0.16 mmol), 1,1'-bis(diphenylphosphino)ferrocene-palladium(II)dichloride dichloromethane complex (14 mg, 0.02 mol) and sodium carbonate (2M, 231 µl, 0.46 mol) according to the method described in Example 3 to give 8 mg (14% yield) of the title compound as a white solid. Purity 97%.

LRMS (m/z): 562 (M+1)$^+$ $^1$H NMR (400 MHz, CDCl$_3$) δ 8.10 (s, 1H), 7.92 (d, J=2.3 Hz, 1H), 7.61-7.44 (m, 4H), 7.29 (ddd, J=5.0, 3.0, 1.4 Hz, 1H), 6.31 (dd, J=2.6, 0.6 Hz, 1H), 5.04-4.90 (m, 1H), 4.81 (d, J=26.9 Hz, 1H), 4.59 (s, 2H), 4.10 (s, 3H), 3.07 (s, 3H), 2.49 (d, J=6.8 Hz, 3H), 2.10-1.78 (m, 3H), 1.23 (d, J=6.8 Hz, 3H).

Example 15

(S)-2-(1-((6-Amino-5-(1H-indol-6-yl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with (1H-indol-6-yl)boronic acid (23 mg, 0.14 mmol), 1,1'-bis(diphenylphosphino)ferrocene-palladium(II)dichloride dichloromethane complex (14 mg, 0.02 mol) and sodium carbonate (2M, 231 µl, 0.43 mol) according to the method described in Example 3 to give 7 mg (14% yield) of the title compound as a white solid. Purity 98%.

LRMS (m/z): 477 (M+1)$^+$ $^1$H NMR (400 MHz, CDCl$_3$) δ 8.52 (s, 1H), 8.03 (d, J=11.4 Hz, 1H), 7.83 (dd, J=24.4, 8.0 Hz, 1H), 7.59-7.40 (m, 4H), 7.33 (s, 1H), 7.13 (dd, J=10.1, 5.3 Hz, 1H), 7.08-6.95 (m, 1H), 6.65 (s, 1H), 6.29 (d, J=6.6 Hz, 1H), 5.21-4.87 (m, 4H), 4.39 (s, 2H), 2.47 (d, J=1.8 Hz, 3H), 1.22 (dd, J=10.2, 6.1 Hz, 3H).

Example 16

(S)-2-(1-((2',6-Diamino-[5,5'-bipyrimidin]-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (50 mg, 0.10 mol) was treated with 5-(4,4,5,5-tetramethyl-1,3,2-dioxaborolan-2-yl)pyrimidin-2-amine (34 mg, 0.15 mmol), 1,1% bis(diphenylphosphino)ferrocene-palladium (II)dichloride dichloromethane complex (14 mg, 0.02 mol) and sodium carbonate (2M, 231 µl, 0.43 mol) according to the method described in Example 3 to give 13 mg (28% yield) of the title compound as a white solid. Purity 100%.

LRMS (m/z): 455 (M+1)$^+$ $^1$H NMR (400 MHz, CDCl$_3$) δ 8.31 (s, 2H), 8.09 (s, 1H), 7.63-7.43 (m, 4H), 7.29 (d, J=7.3 Hz, 1H), 7.15 (d, J=2.4 Hz, 1H), 6.30 (s, 1H), 5.39 (d, J=23.1 Hz, 2H), 5.12-4.80 (m, 2H), 4.63 (d, J=22.9 Hz, 2H), 2.48 (s, 3H), 1.25 (d, J=6.7 Hz, 3H).

Example 17

(S)-2-(1-((6-Amino-5-cyanopyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile In a reactor vessel (S)-2-(1-amino-3-(benzyloxy)propyl)-3-(3,5-difluorophenyl)-4-oxo-3,4-dihydropyrrolo[2,1-f][1,2,4]triazine-5-carbonitrile (42 mg, 0.1 mmol) and 4-amino-6-chloropyrimidine-5-carbonitrile (16 mg, 0.1 mmol) were dissolved in 1-butanol (840 µl) under argon atmosphere. N,N-Diisopropylethylamine (76 µl, 0.87 mmol) was added and the reaction mixture was heated at 120° C. overnight. Further N,N-diisopropylethylamine (76 µl, 0.87 mmol) was added afterwards and the reaction mixture was stirred at 120° C. overnight. The crude was evaporated and purified using SP1® Purification System (0% to 100%, hexane-ethyl acetate) to obtain 34 mg (64% yield) of the title compound as a yellow solid. Purity 97%.

LRMS (m/z): 554 (M+1)$^+$ $^1$H NMR (400 MHz, DMSO-d6) δ 7.86 (d, J=3.0, 1H), 7.84 (s, 1H), 7.55 (d, J=7.4 Hz, 1H), 7.41 (d, J=8.8 Hz, 1H), 7.35-7.14 (m, 10H), 5.18-5.06 (m, 1H), 4.31 (m, 2H), 3.52-3.36 (m, 2H), 2.30-2.17 (m, 1H), 2.14-2.03 (m, 1H).

Example 18

(S)-2-(1-((5-(3-Fluoro-5-hydroxyphenyl)pyrimidin-4-yl)amino)ethyl)-3-phenylpyrrolo[2,1-f][1,2,4]triazin-4(3H)-one (S)-2-(1-((5-Iodopyrimidin-4-yl)amino)ethyl)-3-phenylpyrrolo[2,1-f][1,2,4]triazin-4(3H)-one (30 mg, 0.07 mol) was treated with (3-fluoro-5-hydroxyphenyl)boronic acid (15 mg, 0.10 mmol), 1,1'-bis(diphenylphosphino)ferrocene-palladium(II)dichloride dichloromethane complex (87 mg, 0.1 mmol) and sodium carbonate (2M, 147 µl, 0.29 mmol) according to the method described in Example 3 to give 15 mg (52% yield) of the title compound as a white solid. Purity 99%.

LRMS (m/z): 443 (M+1)$^+$ $^1$H NMR (400 MHz, CDCl$_3$) δ 9.96 (s, 1H), 8.50 (d, J=3.3 Hz, 1H), 8.13 (d, J=5.1 Hz, 1H), 7.55 (ddd, J=7.7, 4.6, 2.0 Hz, 1H), 7.52-7.44 (m, 2H), 7.42-7.37 (m, 1H), 7.36-7.30 (m, 2H), 7.07 (td, J=4.1, 1.7 Hz, 1H), 6.84-6.77 (m, 1H), 6.73-6.68 (m, 1H), 6.65-6.61 (m, 1H), 6.57-6.52 (m, 1H), 5.99 (t, J=6.7 Hz, 1H), 5.21-5.02 (m, 1H), 1.68 (d, J=36.6 Hz, 3H), 1.34 (t, J=5.1 Hz, 3H).

Example 19

(S)-4-Amino-6-((3-(benzylthio)-1-(4-oxo-3-phenyl-3,4-dihydropyrrolo[2,1-f][1,2,4]triazin-2-yl)propyl)amino)pyrimidine-5-carbonitrile (S)-2-(1-Amino-3-(benzylthio)propyl)-3-phenylpyrrolo[2,1-f][1,2,4]triazin-4(3H)-one (10 mg, 0.02 mmol) was treated with 4-amino-6-chloropyrimidine-5-carbonitrile (4 mg, 0.03 mmol) and N,N-diisopropylethylamine (24 µl, 0.14 mmol) according to the method described in Example 17. The residue was purified using SP1® Purification System (0% to 100% hexane-ethyl acetate) to obtain 8 mg (66% yield) of the title compound as a yellow solid. Purity 90%.

LRMS (m/z): 509 (M+1)+.

$^1$H NMR (400 MHz, CDCl$_3$) δ 8.04 (s, 1H), 7.59-7.45 (m, 3H), 7.43-7.32 (m, 2H), 7.31-7.15 (m, 6H), 7.12-7.05 (m, 1H), 6.61-6.54 (m, 1H), 5.72 (d, J=8.8 Hz, 1H), 5.34 (bs, 2H), 5.28-5.19 (m, 1H), 3.55 (s, 2H), 2.43-2.32 (m, 1H), 2.32-2.21 (m, 1H), 2.15-2.03 (m, 1H), 1.93-1.80 (m, 1H).

Example 20

(S)-4-Amino-6-((1-(4-oxo-3-phenyl-3,4-dihydropyrrolo[2,1-f][1,2,4]triazin-2-yl)-3-phenoxypropyl)amino)pyrimidine-5-carbonitrile (S)-2-(1-Amino-3-phenoxypropyl)-3-phenylpyrrolo[2,1-f][1,2,4]triazin-4(3H)-one was treated with 4-amino-6-chloropyrimidine-5-carbonitrile (6 mg, 0.02 mmol) and N,N-diisopropylethylamine (16 µl, 0.09 mmol) according to the method described in Example 17. The residue was purified using SP1® Purification System (0% to 50%, dichloromethane-acetonitrile) to obtain 4 mg (55% yield) of the title compound as a yellow solid. Purity 89%.

LRMS (m/z): 479 (M+1)+.

$^1$H NMR (400 MHz, DMSO-d6) δ 7.84 (s, 1H), 7.75 (d, J=7.2 Hz, 1H), 7.67-7.64 (m, 1H), 7.54-7.36 (m, 7H), 7.27-7.18 (m, 2H), 6.98-6.93 (m, 1H), 6.91-6.84 (m, 1H), 6.77-6.71 (m, 2H), 6.63-6.57 (m, 1H), 5.07-4.96 (m, 1H), 4.20-4.08 (m, 1H), 3.97-3.85 (m, 1H), 2.42-2.31 (m, 1H), 2.31-2.21 (m, 1H).

Example 21

(S)-3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxybenzoic acid (S)-Methyl 3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxybenzoate (35 mg, 0.07 mmol) was dissolved in 5 mL tetrahydrofuran. Lithium hydroxide in 5 mL water was added and the mixture was stirred at 50° C. for 4 h. The solvent was evaporated and the residue was re-dissolved in dichloromethane. The aqueous phase was acidified with 2N hydrochloric acid. The aqueous was further extracted with dichloromethane and was washed with water and brine, dried over sodium sulphate, filtered and evaporated under reduced pressure. The residue was purified by reverse phase using SP1 ® Purification System to obtain 25 mg (72% yield) of the title compound as a white solid. Purity 97%.

LRMS (m/z): 498 (M+1)+

$^1$H NMR (400 MHz, CDCl$_3$) δ 8.37 (s, 3H), 7.81 (s, 1H), 7.56-7.18 (m, 8H), 6.93 (s, 1H), 6.76 (s, 1H), 6.28 (s, 1H), 4.85 (dd, J=16.3, 9.7 Hz, 1H), 2.35 (s, 3H), 1.23-1.05 (m, 3H).

Example 22

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-fluorobenzenesulfonamide (S)-2-(1-((6-Amino-5-iodopyrimidin-4-yl)amino)ethyl)-5-methyl-3-phenylpyrrolo[2,1-f][1,2,4]triazin-4(3H)-one (100 mg, 0.16 mmol) was treated with 4-fluoro-N-(2-methoxy-5-(4,4,5,5-tetramethyl-1,3,2-dioxaborolan-2-yl)pyridin-3-yl)benzenesulfonamide (124 mg, 0.27 mmol), a solution of sodium carbonate (2 M, 365 µl, 0.73 mmol) and 2'-(dimethylamino)-2-biphenylyl-palladium(II) chloride dinorbornylphosphine complex (5 mg, 0.01 mmol) according to the method described in Preparation 17. The residue was purified by reverse phase using SP1® Purification System to give 5 mg (5% yield) of the title compound as a solid.

LRMS (m/z): 642 (M+1)+

$^1$H NMR (400 MHz, CDCl$_3$) δ 8.11 (s, 1H), 7.90 (s, 4H), 7.53 (dt, J=9.5, 8.0 Hz, 4H), 7.30 (d, J=6.4 Hz, 1H), 7.18-7.09 (m, 2H), 6.31 (d, J=2.1 Hz, 1H), 4.96 (s, 2H), 4.62 (s, 1H), 4.40 (s, 2H), 3.97 (s, 3H), 2.62 (s, 1H), 2.49 (s, 3H), 1.23 (d, J=6.8 Hz, 3H).

Example 23

(S)-2-(1-((6-Amino-5-(3,4-difluoro-5-hydroxyphenyl)pyrimidin-4-yl)amino)ethyl)-5-methyl-3-phenylpyrrolo[2,1-f][1,2,4]triazin-4(3H)-one (S)-2-(1-((6-Amino-5-(3,4-difluoro-5-methoxyphenyl)pyrimidin-4-yl)amino)ethyl)-5-methyl-3-phenylpyrrolo[2,1-f][1,2,4]triazin-4(3H)-one (87 mg, 0.17 mmol) was dissolved in 3 mL dichloromethane. A solution of boron tribromide (1M, 520 µl, 0.52 mmol) was added dropwise and the reaction was stirred at room temperature overnight. Further tribromide (1M in dichloromethane, 260 µl, 0.26 mmol) was added dropwise and stirred for 2 h more. The mixture was diluted with ethyl acetate and washed with a solution of 4% sodium bicarbonate, water, brine and dried over sodium sulphate, filtered and evaporated under reduced pressure. The residue was purified by reverse phase using SP1® Purification System to give 25 mg (44% yield) of the title compound as a solid. Purity 99%.

LRMS (m/z): 490 (M+1)+

$^1$H NMR (400 MHz, DMSO-d6) δ 10.51 (bs, 1H), 7.75 (s, 1H), 7.53-7.32 (m, 6H), 6.61 (bs, 2H), 6.39 (d, J=2.6 Hz, 1H), 5.69 (d, J=7.6 Hz, 1H), 5.61 (s, 2H), 4.86-4.71 (m, 1H), 2.37 (s, 3H), 1.22 (d, J=6.7 Hz, 3H).

Example 24

(S)-2-(1-((6-Amino-5-(3-fluoro-5-hydroxyphenyl)pyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile (S)-2-(1-((6-Amino-5-iodopyrimidin-4-yl)amino)-3-(benzyloxy)propyl)-3-(3,5-difluorophenyl)-4-oxo-3,4-dihydropyrrolo[2,1-f][1,2,4]triazine-5-carbonitrile (12 mg, 0.02 mmol) was treated with (3-fluoro-5-hydroxyphenyl)boronic acid (4.5 mg, 0.03 mmol), sodium carbonate (2 M, 55 µl, 0.11 mmol) and 2'-(dimethylamino)-2-biphenylyl-palladium(II) chloride dinorbornylphosphine complex (2 mg, 0.001 mmol) according to the method described in the Preparation 17. The residue was purified by reverse phase using SP1® Purification System to give 2 mg (18% yield) of the title compound as a white solid. Purity 97%.

LRMS (m/z): 639 (M+1)+

$^1$H NMR (400 MHz, DMSO-d6) δ ppm 0.86 (dd, J=2.15, 0.98 Hz, 3H), 1.72-1.80 (m, 1H), 1.81-1.94 (m, 2H), 2.04-2.21 (m, 1H), 4.07-4.18 (m, 1H), 4.29 (s, 1H), 4.96-5.14 (m, 1H), 5.62-5.74 (m, 1H), 5.73-5.87 (m, 1H), 6.49-6.61 (m, 1H), 7.11-7.37 (m, 6H), 7.37-7.47 (m, 1H), 7.62-7.86 (m, 3H), 8.23-8.39 (m, 1H).

Example 25

(S)-4-Amino-6-((3-(benzyloxy)-1-(5-methyl-4-oxo-3-phenyl-3,4-dihydropyrrolo[2,1-f][1,2,4]triazin-2-yl)propyl)amino)pyrimidine-5-carbonitrile (S)-2-(1-Amino-3-(benzyloxy)propyl)-5-methyl-3-phenylpyrrolo[2,1-f][1,2,4]triazin-4(3H)-one (24 mg, 0.06 mmol) was treated with 4-amino-6-chloropyrimidine-5-carbonitrile (10 mg, 0.06 mmol), N,N-diisopropylethylamine (59 μl, 0.34 mmol) according to the method described in Example 17. The residue was purified using SP1® Purification System (0% to 80%, hexane-ethyl acetate) to obtain 21 mg (73% yield) of the title compound as a yellow solid. Purity 100%.

LRMS (m/z): 507 (M+1)$^+$
$^1$H NMR (400 MHz, DMSO-d6) δ 7.85 (s, 1H), 7.60 (d, J=7.2 Hz, 1H), 7.47 (d, J=2.6 Hz, 1H), 7.46-7.20 (m, 10H), 7.17-7.12 (m, 2H), 6.41 (dd, J=2.7, 0.7 Hz, 1H), 4.97-4.87 (m, 1H), 4.29 (s, 2H), 3.43-3.34 (m, 2H), 2.39 (s, 3H), 2.22-2.10 (m, 1H), 2.09-1.98 (m, 1H).

Example 26

(S)-2-(1-((6-Amino-5-(3,5-difluoro-4-hydroxyphenyl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino)ethyl)-5-methyl-3-phenylpyrrolo[2,1-f][1,2,4]triazin-4(3H)-one (260 mg, 0.59 mmol) was treated with (3,5-difluoro-4-hydroxyphenyl)boronic acid (154 mg, 0.89 mmol), sodium carbonate (2 M, 1.33 mL, 2.66 mmol) and 2'-(dimethylamino)-2-biphenylyl-palladium(II) chloride dinorbornylphosphine complex (17 mg, 0.03 mmol) according to the method described in the Preparation 17. The residue was purified using SP1® Purification System (0% to 60%, hexane-ethyl acetate) to give 44 mg (15% yield) of the title compound as a white solid. Purity 95%.

LRMS (m/z): 490 (M+1)$^+$
$^1$H NMR (400 MHz, CDCl$_3$) δ 8.11 (s, 1H), 7.63-7.44 (m, 3H), 7.36-7.27 (m, 1H), 7.18 (d, J=2.6 Hz, 1H), 7.07 (s, 1H), 6.91 (s, 1H), 6.39-6.30 (m, 1H), 5.05-4.89 (m, 2H), 4.55 (s, 2H), 2.65 (s, 2H), 2.49 (s, 3H), 1.25 (dd, J=6.9, 3.0 Hz, 3H).

Example 27

(S)-2-(1-((5-(3-Fluoro-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Fluoro-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (37 mg, 0.06 mmol) was dissolved in 740 μl trifluoroacetic acid under argon conditions and was stirred at 30° C. for 2 h. The solvent was evaporated and the crude was re-dissolved in 370 μl methanol and a solution of ammonia (7N in methanol, 740 μl, 5.18 mmol) was added and stirred at room temperature 2 h more.

The reaction mixture was evaporated to dryness and the residue was suspended in 5 mL water and extracted twice with ethyl acetate. The organics were washed with water, brine, dried over sodium sulphate, filtered and concentrated under pressure to give 27 mg (90% yield) of the title compound as a yellow solid. Purity 97%.

LRMS (m/z): 496 (M+1)$^+$
$^1$H NMR (400 MHz, DMSO-d6) δ 11.96 (s, 1H), 10.16 (bs, 1H), 8.15 (s, 1H), 7.65-7.48 (m, 5H), 7.34 (d, J=2.4 Hz, 1H), 7.28 (d, J=2.6 Hz, 1H), 6.88-6.75 (m, 2H), 6.67-6.57 (m, 1H), 6.41 (d, J=2.6, 1 H), 6.11 (d, J=7.4 Hz, 1H), 4.92-4.79 (m, 1H), 2.38 (s, 3H), 1.31 (d, J=6.6 Hz, 3H).

Example 28

(S)-2-(1-((6-Amino-5-(3-hydroxy-5-(trifluoromethyl)phenyl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino)ethyl)-5-methyl-3-phenylpyrrolo[2,1-f][1,2,4]triazin-4(3H)-one (100 mg, 0.23 mmol) was treated with (3-hydroxy-5-(trifluoromethyl)phenyl)boronic acid (70 mg, 0.34 mmol), sodium carbonate (108 mg, 1.02 mmol) and 2'-(dimethylamino)-2-biphenylyl-palladium(II) chloride dinorbornylphosphine complex (6 mg, 0.01 mmol) according to the method described in the Preparation 17. The residue was purified by reverse phase using SP1® Purification System to give 30 mg (25% yield) of the title compound as a solid. Purity 98%.

LRMS (m/z): 522 (M+1)$^+$
$^1$H NMR (400 MHz, DMSO-d6) δ 10.28 (s, 1H), 7.80 (s, 1H), 7.57-7.32 (m, 6H), 6.96 (d, J=58.4 Hz, 3H), 6.40 (d, J=2.5 Hz, 1H), 5.78-5.55 (m, 3H), 4.88-4.69 (m, 1H), 2.36 (s, 3H), 1.20 (d, J=6.7 Hz, 3H).

Example 29

(S)-2-(1-((5-(2-Hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-Hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (52 mg, 0.09 mmol) was treated with trifluoroacetic acid (1.04 mL, 13.50 mmol) and a solution of ammonia (7N in methanol, 1.04 mL, 7.28 mmol) according to the method described in Example 27 to give 23 mg (56% yield) of the title compound. Purity 98%.

LRMS (m/z): 478 (M+1)$^+$
$^1$H NMR (400 MHz, DMSO-d6) δ 11.75 (s, 1H), 9.86 (s, 1H), 8.08 (s, 1H), 7.62-7.47 (m, 5H), 7.31-7.21 (m, 3H), 7.12 (d, J=2.4 Hz, 1H), 7.03 (d, J=7.8 Hz, 1H), 6.96-6.88 (m, 1H), 6.40 (d, J=2.6 Hz, 1H), 6.37 (d, J=7.3 Hz, 1H), 4.79-4.67 (m, 1H), 2.37 (s, 3H), 1.27 (d, J=6.3 Hz, 3H).

Example 30

(S)-2-(1-((5-(4-Hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(4-Hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (48 mg, 0.08 mmol) was treated with trifluoroacetic acid (960 μl, 12.46 mmol) and a solution of ammonia (7N in methanol, 960 μl, 6.72 mmol) according to the method described in Example 27 to give 26 mg (69% yield) of the title compound. Purity 95%.

LRMS (m/z): 478 (M+1)$^+$
$^1$H NMR (400 MHz, DMSO-d6) δ 11.77 (bs, 1H), 9.65 (s, 1H), 8.12 (s, 1H), 7.64-7.47 (m, 5H), 7.36 (d, J=8.4 Hz, 2H), 7.26 (d, J=2.5 Hz, 1H), 7.15 (d, J=2.2 Hz, 1H), 6.92 (d, J=8.4 Hz, 2H), 6.41 (d, J=2.1 Hz, 1H), 5.92 (d, J=7.5 Hz, 1H), 4.89-4.76 (m, 1H), 2.38 (s, 3H), 1.26 (d, J=6.5 Hz, 3H).

Example 31

(S)-2-(1-((6-Amino-5-(3-chloro-5-hydroxyphenyl) pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino) ethyl)-5-methyl-3-phenylpyrrolo[2,1-f][1,2,4]triazin-4(3H)-one (100 mg, 0.23 mmol) was treated with (3-chloro-5-hydroxyphenyl)boronic acid (59 mg, 0.34 mmol), sodium carbonate (2M, 510 µl, 1.02 mmol) and 1,1'-bis(diphenylphosphino)ferrocene-palladium(II)dichloride dichloromethane complex (9 mg, 0.01 mmol) according to the method described in Example 3 to give 15 mg (32% yield) of the title compound as a solid. Purity 100%.

LRMS (m/z): 488 (M+1)⁺

¹H NMR (400 MHz, DMSO-d6) δ 10.07 (s, 1H), 7.78 (s, 1H), 7.55-7.31 (m, 6H), 6.81 (d, J=2.0 Hz, 1H), 6.63 (s, 2H), 6.40 (d, J=2.4 Hz, 1H), 5.63 (d, J=7.8 Hz, 3H), 4.91-4.68 (m, 1H), 2.35 (d, J=15.2 Hz, 3H), 1.21 (d, J=6.7 Hz, 3H.

Example 32

(S)—N-(5-(4-Amino-6-((1-(5-methyl-4-oxo-3-phenyl-3,4-dihydropyrrolo[2,1-f][1,2,4]triazin-2-yl) ethyl)amino)pyrimidin-5-yl)-2-hydroxypyridin-3-yl)-4-methoxybenzenesulfonamide (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-methoxybenzenesulfonamide (82 mg, 0.13 mmol) was treated with a solution of boron tribromide (1M in dichloromethane, 190 µl, 0.19 mmol) according to the method described in Example 23. The residue was purified using SP1® Purification System (0% to 100%, hexane-ethyl acetate) to give 37 mg (46% yield) of the title compound as a solid.

LRMS (m/z): 640 (M+1)⁺

¹H NMR (400 MHz, CDCl₃) δ 8.11 (s, 1H), 7.85 (s, 2H), 7.68-7.46 (m, 5H), 7.40 (s, 1H), 7.30 (d, J=7.3 Hz, 1H), 7.15 (s, 1H), 6.89 (d, J=8.8 Hz, 2H), 6.31 (s, 1H), 4.82 (d, J=43.5 Hz, 4H), 3.79 (s, 3H), 2.47 (s, 3H), 1.69 (s, 2H), 1.27-1.23 (m, 3H).

Example 33

(S)-2-(1-((5-(1H-Pyrazol-4-yl)-7H-pyrrolo[2,3-d] pyrimidin-4-yl)amino)ethyl)-5-methyl-3-phenylpyrrolo[2,1-f][1,2,4]triazin-4(3H)-one (S)-2-(1-((5-(1H-Pyrazol-4-yl)-7-((2-(trimethylsilyl) ethoxy)methyl)-7H-pyrrolo[2,3-d]pyrimidin-4-yl)amino) ethyl)-5-methyl-3-phenylpyrrolo[2,1-f][1,2,4]triazin-4(3H)-one (23 mg, 0.04 mmol) was treated with trifluoroacetic acid (460 µl, 5.97 mmol) and a solution of ammonia (7N in methanol, 460 µl, 3.22 mmol) according to the method described in Example 27 to give 12 mg (66% yield) of the title compound. Purity 98%.

LRMS (m/z): 452 (M+1)⁺

¹H NMR (400 MHz, DMSO-d6) δ 13.15 (bs, 1H), 11.76 (s, 1H), 8.11 (s, 1H), 8.01-7.95 (m, 1H), 7.79-7.72 (m, 1H), 7.63-7.50 (m, 5H), 7.48 (d, J=2.6 Hz, 1H), 7.15 (d, J=2.4 Hz, 1H), 6.43 (d, J=2.4 Hz, 1H), 6.17 (d, J=7.4 Hz, 1H), 4.89-4.79 (m, 1H), 2.38 (s, 3H), 1.28 (d, J=6.6 Hz, 3H).

Example 34

(S)-2-(1-((6-Amino-5-(3-fluoro-5-hydroxyphenyl) pyrimidin-4-yl)amino)ethyl)-3-phenyl-5-(phenylthio)pyrrolo[2,1-f][1,2,4]triazin-4(3H)-one (S)-2-(1-((6-Amino-5-bromopyrimidin-4-yl)amino) ethyl)-3-phenyl-5-(phenylthio)pyrrolo[2,1-f][1,2,4]triazin-4 (3H)-one (230 mg, 0.29 mmol) was treated with (3-fluoro-5-hydroxyphenyl)boronic acid (68 mg, 0.44 mmol), sodium carbonate (2M, 660 µl, 1.32 mmol) and 1,1'-bis(diphenylphosphino)ferrocene-palladium(II)dichloride dichloromethane complex (36 mg, 0.04 mmol) according to the method described in Example 3 to give 4 mg (3% yield) of the title compound as a solid. Purity 91%.

LRMS (m/z): 566 (M+1)⁺

Example 35

(S)-2-(1-((5-(3-Fluoro-5-hydroxyphenyl)pyrimidin-4-yl)amino)ethyl)-5-methyl-3-phenylpyrrolo[2,1-f][1,2,4]triazin-4(3H)-one (S)-2-(1-((5-Iodopyrimidin-4-yl)amino)ethyl)-5-methyl-3-phenylpyrrolo[2,1-f][1,2,4]triazin-4(3H)-one (115 mg, 0.24 mmol) was treated with (3-fluoro-5-hydroxyphenyl)boronic acid (57 mg, 0.37 mmol), sodium carbonate (2M, 548 µl, 1.10 mmol) and 1,1'-bis(diphenylphosphino)ferrocene-palladium(II)dichloride dichloromethane complex (30 mg, 0.04 mmol) according to the method described in Example 3 to give 60 mg (54% yield) of the title compound. Purity 100%.

LRMS (m/z): 457 (M+1)⁺

¹H NMR (400 MHz, CDCl₃) δ 9.75 (s, 1H), 8.49 (s, 1H), 8.13 (s, 1H), 7.58-7.51 (m, 1H), 7.50-7.44 (m, 2H), 7.43-7.38 (m, 1H), 7.36-7.31 (m, 1H), 7.22 (d, J=2.6 Hz, 1H), 6.86-6.79 (m, 1H), 6.70 (dt, J=10.4, 2.2 Hz, 1H), 6.64-6.60 (m, 1H), 6.34 (dd, J=2.7, 0.6 Hz, 1H), 6.02 (d, J=8.4 Hz, 1H), 5.09 (dq, J=13.5, 6.8 Hz, 1H), 2.49 (s, 3H), 1.32 (d, J=6.7 Hz, 3H).

Example 36

(S)-4-Amino-N-(3-hydroxyphenyl)-6-((1-(5-methyl-4-oxo-3-phenyl-3,4-dihydropyrrolo[2,1-f][1,2,4] triazin-2-yl)ethyl)amino)pyrimidine-5-carboxamide (S)-4-Amino-N-(3-methoxyphenyl)-6-((1-(5-methyl-4-oxo-3-phenyl-3,4-dihydropyrrolo[2,1-f][1,2,4]triazin-2-yl) ethyl)amino)pyrimidine-5-carboxamide (27 mg, 0.05 mmol) was treated with boron tribromide (1M in dichloromethane, 160 µl, 0.16 mmol) in dichloromethane according to the method described in Example 23. The residue was purified by reverse phase using SP1® Purification System to give 6 mg (23% yield) as a white solid. Purity 100%.

LRMS (m/z): 457 (M+1)⁺

¹H NMR (400 MHz, CDCl₃) δ 8.99 (s, 1H), 8.03 (s, 1H), 7.62-7.44 (m, 5H), 7.37-7.29 (m, 2H), 7.20-7.05 (m, 2H), 7.01-6.90 (m, 1H), 6.71-6.53 (m, 2H), 6.28 (d, 1H), 6.02 (s, 2H), 5.15-4.94 (m, 1H), 2.46 (s, 3H), 1.35 (d, 3H).

Example 37

(S)-Benzyl 4-((1-(5-methyl-4-oxo-3-phenyl-3,4-dihydropyrrolo[2,1-f][1,2,4]triazin-2-yl)ethyl) amino)-7H-pyrrolo[2,3-d]pyrimidine-5-carboxylate (S)-2-(1-Aminoethyl)-5-methyl-3-phenylpyrrolo[2,1-f] [1,2,4]triazin-4(3H)-one (56 mg, 0.21 mmol) was treated with benzyl 4-chloro-7H-pyrrolo[2,3-d]pyrimidine-5-carboxylate (70 mg, 0.24 mmol), cesium fluoride (14 mg, 0.09 mmol), N,N-diisopropylethylamine (163 µl, 0.94 mol) according to Preparation 13 to give 27 mg (25% yield) of the title compound as a white solid.

LRMS (m/z): 520 (M+1)$^+$ $^1$H NMR (400 MHz, CDCl$_3$) δ 11.62 (s, 1H), 8.90 (d, J=7.4 Hz, 1H), 8.17 (s, 1H), 7.79 (s, 1H), 7.55-7.27 (m, 10H), 6.31 (d, J=2.6 Hz, 1H), 5.37 (s, 2H), 5.10 (p, J=6.8 Hz, 1H), 2.50 (s, 3H), 1.52 (d, J=6.8 Hz, 3H).

Example 38

(S)-2-(1-((5-(2-Methoxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-Methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.08 mmol) was treated with trifluoroacetic acid (1 mL, 12.98 mmol) and a solution of ammonia (7N in methanol, 1 mL, 7.0 mmol) according to the method described in Example 27 to give 34 mg (85% yield) of the title compound as a white solid. Purity 98%.

LRMS (m/z): 492 (M+1)$^+$ $^1$H NMR (400 MHz, DMSO-d6) δ 11.81 (bs, 1H), 8.10 (s, 1H), 7.61-7.42 (m, 6H), 7.35-7.29 (m, 1H), 7.29-7.23 (m, 2H), 7.13 (d, J=2.3 Hz, 1H), 7.11-7.03 (m, 1H), 6.41 (d, J=2.7 Hz, 1H), 6.02 (d, J=7.7 Hz, 1H), 4.79-4.68 (m, 1H), 3.82 (s, 3H), 2.37 (s, 3H), 1.26 (d, J=6.5 Hz, 3H).

Example 39

(S)-2-(1-((5-(2-Fluorophenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-Fluorophenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (35 mg, 0.06 mmol) was treated with trifluoroacetic acid (600 µl, 7.79 mmol) and a solution of ammonia (7N in methanol, 600 µl, 4.2 mmol) according to the method described in Example 27 to give 15 mg (54% yield) of the title compound as a white solid. Purity 89%.

LRMS (m/z): 480 (M+1)$^+$ $^1$H NMR (400 MHz, CDCl$_3$) δ 9.98 (s, 1H), 8.27 (s, 1H), 7.64-7.37 (m, 5H), 7.35-7.18 (m, 4H), 7.16 (s, 1H), 7.04 (d, J=2.6 Hz, 1H), 6.30 (d, J=2.5 Hz, 1H), 5.67 (d, J=8.0 Hz, 1H), 5.12 (dq, J=13.3, 6.7 Hz, 1H), 2.48 (s, 3H), 1.30 (d, J=6.6 Hz, 3H).

Example 40

(S)-4-Amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile (S)-2-(1-Aminoethyl)-5-(3-methoxybenzyl)-3-phenylpyrrolo[2,1-f][1,2,4]triazin-4(3H)-one (120 mg, 0.29 mmol) was treated with 4-amino-6-chloropyrimidine-5-carbonitrile (49 mg, 0.32 mmol), and N,N-diisopropylethylamine (152 µl, 0.87 mmol) in tert-butanol according to the method described in Example 17. The crude was purified by reverse phase using SP1® Purification System to give 82 mg (57% yield) of the title compound as solid. Purity 99%.

LRMS (m/z): 493 (M+1)$^+$ $^1$H NMR (400 MHz, CDCl$_3$) δ ppm 1.40 (d, J=6.64 Hz, 3H) 3.76 (s, 3H) 4.27 (s, 2H) 4.97-5.09 (m, 1H) 5.38 (s, 2H) 5.79 (d, J=7.82 Hz, 1H) 6.33 (d, J=2.74 Hz, 1H) 6.67-6.76 (m, 1H) 6.82-6.87 (m, 1H) 6.90 (dd, J=7.23, 1.37 Hz, 1H) 7.13-7.21 (m, 1H) 7.27 (d, J=2.74 Hz, 1H) 7.30-7.35 (m, 1H) 7.40-7.46 (m, 1H) 7.48-7.59 (m, 3H) 8.07 (s, 1H).

Example 41

(S)-2-(1-((5-(4-Fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(4-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (65 mg, 0.10 mmol) was dissolved in 1.3 ml dichloromethane and the reaction mixture was cooled at 0$^a$C. Boron tribromide (1M in dichloromethane, 1 mL, 1.02 mmol) was added dropwise and the reaction mixture was stirred overnight. The reaction mixture was poured into a 4% sodium bicarbonate solution and extracted twice with dichloromethane. The organics were combined, dried, filtered and concentrated under reduced pressure. The white solid formed was re-dissolved in 650 µl anhydrous methanol and ammonia solution (7M in methanol, 1.3 ml, 9.1 mmol) was added. The reaction mixture was stirred at room temperature for 2 h and then concentrated to dryness, suspended in water and extracted twice with ethyl acetate. The organics were combined, dried over sodium sulphate, filtered and evaporated under reduced pressure. The crude was purified using SP1® Purification System (0% to 10%, hexane-ethyl acetate) to obtain 27 mg (53% yield) of the title compound as a white solid. Purity 96%.

LRMS (m/z): 496 (M+1)$^+$ $^1$H NMR (400 MHz, DMSO-d6) δ 11.74 (s, 1H), 10.37 (bs, 1H), 8.06 (s, 1H), 7.60-7.44 (m, 5H), 7.28-7.21 (m, 1H), 7.18 (d, J=2.6 Hz, 1H), 7.09 (d, J=2.3 Hz, 1H), 6.85-6.66 (m, 2H), 6.40 (d, J=2.4 Hz, 1H), 6.19 (bs, 1H), 4.77-4.64 (m, 1H), 2.36 (s, 3H), 1.24 (d, J=6.5 Hz, 3H).

Example 42

(S)-2-(1-((5-(4-Fluoro-2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(4-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (21 mg, 0.03 mmol) was treated with trifluoroacetic acid (420 µl, 5.45 mmol) and a solution of ammonia (7N in methanol, 420 µl, 2.94 mmol) according to the method described in Example 27 to give 10 mg (59% yield) of the title compound as a white solid. Purity 98%.

LRMS (m/z): 510 (M+1)$^+$ $^1$H NMR (400 MHz, DMSO-d6) δ 11.82 (bs, 1H), 8.10 (s, 1H), 7.64-7.46 (m, 5H), 7.38-7.17 (m, 3H), 7.13 (d, J=2.2 Hz, 1H), 6.96-6.83 (m, 1H), 6.44 (d, J=2.2 Hz, 1H), 5.88 (d, J=7.7 Hz, 1H), 4.82-4.65 (m, 1H), 3.83 (s, 3H), 2.37 (s, 3H), 1.27 (d, J=6.5 Hz, 3H).

Example 43

(S)-2-(1-((5-(3-Hydroxybenzyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Methoxybenzyl)-7-((2-(trimethylsilyl)ethoxy)methyl)-7H-pyrrolo[2,3-d]pyrimidin-4-yl)amino)

ethyl)-5-methyl-3-phenylpyrrolo[2,1-f][1,2,4]triazin-4(3H)-one (55 mg, 0.04 mmol) was treated with boron tribromide (1M in dichloromethane, 1.7 mL, 1.7 mmol) and a solution of ammonia (7N in methanol, 1 mL, 7 mmol) according to the method described in Example 41 to give 16 mg (75% yield) of the title compound as a white solid. Purity 100%.

LRMS (m/z): 492 (M+1)$^+$ $^1$H NMR (400 MHz, CDCl$_3$) δ 8.71 (s, 1H), 7.98 (s, 1H), 7.46 (m, 1H), 7.34 (m, 1H), 7.29 (d, J=2.6 Hz, 1H), 7.14 (m, 3H), 6.92 (m, 1H), 6.84 (m, 1H), 6.76 (s, 1H), 6.65 (s, 1H), 6.58 (d, J=7.6 Hz, 1H), 6.34 (d, J=2.7 Hz, 1H), 5.12 (d, J=8.3 Hz, 1H), 4.91 (m, 1H), 4.05 (dd, J=41.2, 16.7 Hz, 2H), 2.50 (s, 3H), 1.22 (d, J=6.7 Hz, 3H).

Example 44

(S)-2-(1-((6-Amino-5-((3-hydroxyphenyl)thio)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (100 mg, 0.21 mmol) was treated with 3-mercaptophenol (39 mg, 0.31 mmol), potassium carbonate (128 mg, 0.93 mmol) and copper(I) iodide (59 mg, 0.31 mmol) in a microwave vessel with dichloromethane as a solvent according to the method described in Preparation 44. The residue was purified using SP1® Purification System (0% to 100%, hexane-ethyl acetate) to give 30 mg (30% yield) of the title compound.

LRMS (m/z): 486 (M+1)$^+$ $^1$H NMR (400 MHz, CDCl$_3$) δ 7.57 (s, 1H), 7.53-7.35 (m, 4H), 7.30-7.28 (m, 1H), 7.16-7.12 (m, 2H), 6.82 (ddd, J=7.8, 1.7, 0.9 Hz, 1H), 6.66 (ddd, J=8.1, 2.4, 0.9 Hz, 1H), 6.44-6.37 (m, 1H), 6.32 (dd, J=2.7, 0.6 Hz, 1H), 6.24 (d, J=8.4 Hz, 1H), 5.25 (s, 2H), 4.90 (dq, J=13.6, 6.8 Hz, 1H), 2.50 (s, 3H), 1.31-1.27 (m, 3H).

Example 45

(S)—N-(2-Methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide (S)—N-(2-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)methanesulfonamide (82.5 mg, 0.12 mmol) was treated with trifluoroacetic acid (1.4 ml, 18.17 mmol) and a solution of ammonia (7N in methanol, 1.4 ml, 9.8 mmol) according to the method described in Example 27 to give 22 mg (32% yield) of the title compound as a white solid. Purity 95%.

LRMS (m/z): 586 (M+1)$^+$ $^1$H NMR (400 MHz, DMSO-d6) δ 11.97 (s, 1H), 9.36 (bs, 1H), 8.15 (s, 2H), 7.77 (s, 1H), 7.53 (m, 5H), 7.39-7.18 (m, 2H), 6.38 (s, 1H), 5.94 (d, J=7.0 Hz, 1H), 4.96-4.61 (m, 1H), 3.98 (s, 3H), 3.06 (s, 3H), 2.37 (s, 3H), 1.03 (d, J=6.1 Hz, 3H).

Example 46

(S)-2-(1-((5-(3-Fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Fluoro-2-methoxyphenyl)-7-((2-(trimethylsilyl)ethoxy)methyl)-7H-pyrrolo[2,3-d]pyrimidin-4-yl) amino)ethyl)-5-methyl-3-phenylpyrrolo[2,1-f][1,2,4]triazin-4(3H)-one (79 mg, 0.12 mmol) was treated with boron tribromide (1 M in dichloromethane, 1.23 mL, 1.23 mmol) and a solution of ammonia (7N in methanol, 1.6 mL, 11.2 mmol) according to the method described in Example 41 to give 45 mg (73% yield) of the title compound as a white solid. Purity 99%.

LRMS (m/z): 496 (M+1)$^+$ $^1$H NMR (400 MHz, DMSO-d6) δ 11.82 (s, 1H), 9.86 (bs, 1H), 8.08 (s, 1H), 7.61-7.45 (m, 5H), 7.31-7.21 (m, 1H), 7.19 (d, J=2.6 Hz, 1H), 7.16 (d, J=2.0 Hz, 1H), 7.09 (d, J=7.3 Hz, 1H), 6.98-6.83 (m, 1H), 6.39 (d, J=2.5 Hz, 1H), 6.15 (bs, 1H), 4.80-4.67 (m, 1H), 2.36 (s, 3H), 1.24 (d, J=6.5 Hz, 3H).

Example 47

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)methanesulfonamide (S)-2-(1-((5-Iodopyrimidin-4-yl)amino)ethyl)-5-methyl-3-phenylpyrrolo[2,1-f][1,2,4]triazin-4(3H)-one (100 mg, 0.21 mmol) was treated with N-(3-(4,4,5,5-tetramethyl-1,3,2-dioxaborolan-2-yl)phenyl)methanesulfonamide (92 mg, 0.31 mmol), sodium carbonate (2M, 462 μl, 0.92 mmol) and 1,1'-bis(diphenylphosphino)ferrocene-palladium(II)dichloride dichloromethane complex (25 mg, 0.03 mmol) according to the method described in Example 3 to give 20 mg (18% yield) of the title compound. Purity 99%.

LRMS (m/z): 531 (M+1)$^+$ $^1$H NMR (400 MHz, CDCl$_3$) δ 8.07 (s, 1H), 7.51 (d, J=7.2 Hz, 5H), 7.38-7.20 (m, 5H), 7.13 (s, 1H), 6.31 (d, J=2.6 Hz, 1H), 4.92 (dd, J=31.2, 24.6 Hz, 2H), 4.54 (s, 2H), 3.08 (s, 3H), 2.48 (s, 3H), 1.24 (d, J=6.6 Hz, 3H).

Example 48

(S)-4-Amino-6-((1-(5-((2-hydroxyphenyl)thio)-4-oxo-3-phenyl-3,4-dihydropyrrolo[2,1-f][1,2,4]triazin-2-yl)ethyl)amino)pyrimidine-5-carbonitrile (S)-2-(1-Aminoethyl)-5-((2-hydroxyphenyl)thio)-3-phenylpyrrolo[2,1-f][1,2,4]triazin-4(3H)-one (183 mg, 0.36 mmol) was treated with 4-amino-6-chloropyrimidine-5-carbonitrile (84 mg, 0.54 mmol), and N,N-diisopropylethylamine (380 μl, 2.18 mmol) in tert-butanol according to the method described in Example 17. The crude was purified by reverse phase using SP1® Purification System to give 69 mg (38% yield) of the title compound as a white solid. Purity 100%.

LRMS (m/z): 497 (M+1)$^+$ $^1$H NMR (400 MHz, DMSO-d6) δ 9.84 (s, 1H), 7.78 (s, 1H), 7.66 (t, J=4.8 Hz, 2H), 7.49 (d, J=8.0 Hz, 1H), 7.46-7.38 (m, 1H), 7.37-7.26 (m, 3H), 7.20 (s, 2H), 7.15-7.03 (m, 2H), 6.88 (dd, J=8.0, 1.0 Hz, 1H), 6.80-6.71 (m, 1H), 6.25 (d, J=2.8 Hz, 1H), 4.88 (p, J=6.6 Hz, 1H), 1.36 (d, J=6.6 Hz, 3H).

Example 49

(S)-2-(1-((5-(5-Amino-6-methoxypyridin-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(5-Amino-6-methoxypyridin-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2, 4]triazin-4(3H)-one (63 mg, 0.10 mmol) was treated with trifluoroacetic acid (1.4 mL, 18.17 mmol) and a solution of ammonia (7N in methanol, 1.4 mL, 9.8 mmol) at room temperature for 2 h according to the method described in Example 27 to give 43 mg (85% yield) of the title compound as a white solid. Purity 95%.

LRMS (m/z): 508 (M+1)$^+$ $^1$H NMR (400 MHz, DMSO-d6) δ 11.84 (s, 1H), 8.13 (s, 1H), 7.64-7.47 (m, 6H), 7.32 (d, J=2.6 Hz, 1H), 7.19 (d, J=2.4 Hz, 1H), 7.01 (d, J=2.1 Hz, 1H), 6.39 (d, J=2.6 Hz, 1H), 6.02 (d, J=7.3 Hz, 1H), 5.18 (s, 2H), 4.89-4.70 (m, 1H), 3.94 (s, 3H), 2.37 (s, 3H), 1.29 (d, J=6.6 Hz, 3H).

Example 50

2-((1S)-1-((5-(2-Fluoro-6-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one 2-((1S)-1-((5-(2-Fluoro-6-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.07 mmol) was treated with boron tribromide (1M in dichloromethane, 680 μl, 0.68 mmol) and a solution of ammonia (7N in methanol, 1 mL, 7 mmol) according to the method described in Example 41 to give 12 mg (36% yield) of the title compound as a white solid. Purity 97%.

LRMS (m/z): 496 (M+1)$^+$ $^1$H NMR (400 MHz, DMSO-d6) δ 11.81 (bs, 1H), 10.14 (bs, 1H), 8.06 (s, 1H), 7.61-7.40 (m, 5H), 7.36-7.07 (m, 3H), 6.97-6.65 (m, 2H), 6.39 (d, J=2.3 Hz, 1H), 5.96 (bs, 1H), 4.83-4.64 (m, 1H), 2.35 (s, 3H), 1.21 (d, J=6.4 Hz, 3H).

Example 51

(S)-2-(1-((5-(6-Methoxypyridin-2-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(6-Methoxypyridin-2-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (17 mg, 0.02 mmol) was treated with trifluoroacetic acid (340 μl, 4.41 mmol), a solution of ammonia (7N in methanol, 340 μl, 2.38 mmol) in 370 μl methanol according to the method described in Example 27 to give 5 mg (59% yield) of the title compound. Purity 100%.

LRMS (m/z): 493 (M+1)$^+$

Example 52

(S)-2-(1-((5(1H-Indazol-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Indazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.06 mmol) was treated with trifluoroacetic acid (1.4 mL, 18.17 mmol) and a solution of ammonia (7N in methanol, 1.4 mL, 9.8 mmol) according to the method described in Example 27 to give 15 mg (50% yield) of the title compound as a white solid. Purity 98%.

LRMS (m/z): 502 (M+1)$^+$ $^1$H NMR (400 MHz, CDCl$_3$) δ 10.40 (bs, 1H), 9.86 (s, 1H), 8.33 (s, 1H), 8.14 (d, J=0.9 Hz, 1H), 7.54 (m, 5H), 7.32 (m, 4H), 7.00 (d, J=2.6 Hz, 1H), 6.28 (d, J=2.0 Hz, 1H), 5.72 (d, J=7.7 Hz, 1H), 5.05 (m, 1H), 2.47 (s, 3H), 1.21 (d, J=6.7 Hz, 3H).

Example 53

(S)-2-(1-((5-(1H-Pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (39 mg, 0.07 mmol) was treated with trifluoroacetic acid (1.4 mL, 18.17 mmol) and a solution of ammonia (7N in methanol, 1.4 mL, 9.8 mmol) according to the method described in Example 27 to give 18 mg (60% yield) of the title compound. Purity 100%.

LRMS (m/z): 452 (M+1)$^+$ $^1$H NMR (400 MHz, DMSO-d6) δ 12.87 (s, 1H), 11.71 (s, 1H), 10.24 (d, J=6.2 Hz, 1H), 8.06 (s, 1H), 7.85-7.74 (m, 1H), 7.70-7.36 (m, 7H), 6.68 (t, J=2.1 Hz, 1H), 6.35 (d, J=2.6 Hz, 1H), 4.91-4.49 (m, 1H), 2.38 (s, 3H), 1.48 (d, J=6.8 Hz, 3H).

Example 54

(S)-5-(4-Amino-6-((1-(5-methyl-4-oxo-3-phenyl-3,4-dihydropyrrolo[2,1-f][1,2,4]triazin-2-yl)ethyl)amino)pyrimidin-5-yl)benzo[d]oxazol-2(3H)-one (S)-2-(1-((6-Amino-5-iodopyrimidin-4-yl)amino)ethyl)-5-methyl-3-phenylpyrrolo[2,1-f][1,2,4]triazin-4(3H)-one (35 mg, 0.07 mmol) was treated with 1-(2-hydroxy-5-(4,4,5,5-tetramethyl-1,3,2-dioxaborolan-2-yl)phenyl)urea (38 mg, 0.11 mmol), sodium carbonate (2M, 34 μl, 0.07 mmol) and 1,1'-bis(diphenylphosphino)ferrocene-palladium(11)dichloride dichloromethane complex (9 mg, 0.01 mmol) according to the method described in Example 3 to give 17 mg (48% yield) of the title compound. Purity 97%

LRMS (m/z): 495 (M+1)$^+$ $^1$H NMR (400 MHz, DMSO-d6) δ 7.81 (d, J=15.0 Hz, 1H), 7.67-7.26 (m, 7H), 6.96 (s, 1H), 6.82 (s, 1H), 6.41 (d, J=19.8 Hz, 1H), 5.57 (s, 3H), 4.76 (s, 2H), 2.38 (d, J=12.6 Hz, 3H), 1.22 (dd, J=16.9, 6.7 Hz, 3H).

Example 55

(S)-2-(1-((5-(5-Fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(5-Fluoro-2-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (55 mg, 0.09 mmol) was treated with boron tribromide (1 M in dichloromethane, 1 mL, 1 mmol) and a solution of ammonia (7N in methanol, 1 mL, 7 mmol) according to the method described in Example 27 to give 20 mg (47% yield) of the title. Purity 94%.

LRMS (m/z): 496 (M+1)$^+$ $^1$H NMR (400 MHz, DMSO-d6) δ 11.81 (bs, 1H), 9.90 (s, 1H), 8.07 (s, 1H), 7.60-7.43 (m, 5H), 7.23 (d, J=2.6 Hz, 1H), 7.18 (d, J=2.3 Hz, 1H), 7.13-6.95 (m, 3H), 6.42 (d, J=7.6 Hz, 1H), 6.39 (d, J=2.2 Hz, 1H), 4.79-4.66 (m, 1H), 2.36 (s, 3H), 1.26 (d, J=6.5 Hz, 3H).

Example 56

(S)-5-Methyl-2-(1-((6-methylthieno[2,3-d]pyrimidin-4-yl)amino)ethyl)-3-phenylpyrrolo[2,1-f][1,2,4]triazin-4(3H)-one (S)-2-(1-((6-Bromothieno[2,3-d]pyrimidin-4-yl)amino)ethyl)-5-methyl-3-phenylpyrrolo[2,1-f][1,2,4]triazin-4(3H)-one (50 mg, 0.10 mmol) was dissolved in 3 mL dimethylformamide. Potassium carbonate (287 mg, 2.08 mmol), tetrakis(triphenylphosphine)palladium(0) (12 mg, 0.01 mmol) and trimethylboroxine (130 μl, 0.93 mmol) were added under argon conditions. The reaction mixture was stirred at 130° C. for 2 h. The crude was poured into 25 mL saturated ammonium chloride solution and extracted twice with ethyl acetate. The organics were dried over magnesium sulphate, filtered and evaporated under reduced pressure. The residue was purified using SP1® Purification System by reverse phase to obtain 26 mg (60% yield) of a yellow solid as a title compound. Purity 100%.

LRMS (m/z): 417 (M+1)$^+$
$^1$H NMR (400 MHz, CDCl$_3$) δ 8.32 (s, 1H), 7.62-7.46 (m, 4H), 7.39-7.29 (m, 1H), 7.22 (d, J=2.6 Hz, 1H), 6.85 (s, 1H), 6.33 (dd, J=2.7, 0.7 Hz, 1H), 5.60 (d, J=8.3 Hz, 1H), 5.24-5.08 (m, 1H), 2.58 (s, 3H), 2.49 (s, 3H), 1.45 (d, J=6.8 Hz, 3H).

Example 57

(S)-2-(1-((2-Butyl-6-methylthieno[2,3-d]pyrimidin-4-yl)amino)ethyl)-5-methyl-3-phenylpyrrolo[2,1-f][1,2,4]triazin-4(3H)-one (S)-2-(1-((6-Bromo-2-butylthieno[2,3-d]pyrimidin-4-yl)amino)ethyl)-5-methyl-3-phenylpyrrolo[2,1-f][1,2,4]triazin-4(3H)-one (obtained as by-product in Preparation 82, 53 mg, 0.10 mmol) was treated with potassium carbonate (273 mg, 1.97 mmol), tetrakis(triphenylphosphine)palladium(0) (11 mg, 0.01 mmol) and trimethylboroxine (124 μl, 0.89 mmol) according to the method described in Example 56. The residue was purified using SP1® Purification System (0% to 35%, hexane-ethyl acetate) to obtain 17 mg (37% yield) of the title compound as a white solid. Purity 86%.

LRMS (m/z): 473 (M+1)$^+$
$^1$H NMR (400 MHz, DMSO-d6) δ 7.96 (d, J=6.8 Hz, 1H), 7.57-7.40 (m, 4H), 7.39-7.32 (m, 1H), 7.30 (d, J=1.3 Hz, 1H), 7.25-7.17 (m, 1H), 6.39 (d, J=2.7 Hz, 1H), 4.87-4.77 (m, 1H), 2.63-2.53 (m, 2H), 2.50 (s, 3H), 2.38 (s, 3H), 1.56-1.45 (m, 2H), 1.40 (d, J=6.8 Hz, 3H), 1.22-1.13 (m, 2H), 0.77 (t, J=7.3 Hz, 3H).

Example 58

(S)-2-(1-((2,6-Dimethylthieno[2,3-d]pyrimidin-4-yl)amino)ethyl)-5-methyl-3-phenylpyrrolo[2,1-f][1,2,4]triazin-4(3H)-one (S)-2-(1-((6-Bromo-2-methylthieno[2,3-d]pyrimidin-4-yl)amino)ethyl)-5-methyl-3-phenylpyrrolo[2,1-f][1,2,4]triazin-4(3H)-one (obtained as a by-product in Preparation 82, 53 mg, 0.10 mmol) was treated with potassium carbonate (273 mg, 1.97 mmol), tetrakis(triphenylphosphine)palladium(0) (11 mg, 0.01 mmol) and trimethylboroxine (124 μl, 0.89 mmol) according to the method described in Example 56. The residue was purified using SP1® Purification System (0% to 35%, hexane-ethyl acetate) to obtain 24 mg of the title compound as a solid. Purity 99%.

LRMS (m/z): 431 (M+1)$^+$
$^1$H NMR (400 MHz, DMSO-d6) δ 8.13 (s, 1H), 7.58-7.41 (m, 4H), 7.36-7.27 (m, 1H), 7.26-7.18 (m, 1H), 6.66 (d, J=7.4 Hz, 1H), 6.41 (d, J=2.7 Hz, 1H), 5.07-4.95 (m, 1H), 2.49 (s, 3H), 2.40 (s, 3H), 2.39 (s, 3H), 1.43 (d, J=6.7 Hz, 3H).

Example 59

(S)-5-Methyl-3-phenyl-2-(1-(thieno[2,3-d]pyrimidin-4-ylamino)ethyl)pyrrolo[2,1-f][1,2,4]triazin-4(3H)-one (S)-2-(1-Aminoethyl)-5-methyl-3-phenylpyrrolo[2,1-f][1,2,4]triazin-4(3H)-one (50 mg, 0.16 mmol) was treated with 4-chlorothieno[2,3-d]pyrimidine (31 mg, 0.18 mmol) and N,N-diisopropylethylamine (171 μl, 0.98 mmol) in 1-butanol according to the method described in Example 17. The crude was purified using SP1® Purification (0% to 60%, hexane-ethyl acetate) to give 37 mg (56% yield) of the title compound as a solid. Purity 99%.

LRMS (m/z): 403 (M+1)$^+$
$^1$H NMR (400 MHz, DMSO-d6) δ 8.29 (d, J=6.9 Hz, 1H), 8.19 (s, 1H), 7.65 (d, J=6.0 Hz, 1H), 7.59 (d, J=6.0 Hz, 1H), 7.56-7.51 (m, 1H), 7.51 (d, J=2.6 Hz, 1H), 7.48-7.42 (m, 1H), 7.40-7.34 (m, 1H), 7.30-7.24 (m, 1H), 7.12-7.04 (m, 1H), 6.42 (dd, J=2.7, 0.6 Hz, 1H), 4.95-4.84 (m, 1H), 2.39 (s, 3H), 1.45 (d, J=6.8 Hz, 3H).

Example 60

(S)-2-(1-((5-(2-Hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-Methoxy-5-methylphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (45 mg, 0.07 mmol) was treated with boron tribromide (1M in dichloromethane, 1.6 mL, 1.6 mmol) and a solution of ammonia (7N in methanol, 1.6 mL, 11.2 mmol) according to the method described in Example 41 to give 23.6 mg (72% yield) of the title. Purity 97%.

LRMS (m/z): 492 (M+1)$^+$
$^1$H NMR (400 MHz, DMSO-d6) δ 11.74 (bs, 1H), 9.59 (bs, 1H), 8.09 (s, 1H), 7.62-7.47 (m, 5H), 7.27 (d, J=2.3 Hz, 1H), 7.16-7.01 (m, 3H), 6.96-6.87 (m, 1H), 6.40 (d, J=2.3 Hz, 1H), 6.36 (d, J=7.8 Hz, 1H), 4.82-4.61 (m, 1H), 2.38 (s, 3H), 2.23 (s, 3H), 1.27 (d, J=6.4 Hz, 3H).

Example 61

(S)-5-Methyl-2-(1-((2-methylthieno[2,3-d]pyrimidin-4-yl)amino)ethyl)-3-phenylpyrrolo[2,1-f][1,2,4]triazin-4(3H)-one (S)-2-(1-Aminoethyl)-5-methyl-3-phenylpyrrolo[2,1-f][1,2,4]triazin-4(3H)-one (50 mg, 0.16 mmol) was treated with 4-chloro-2-methylthieno[2,3-d]pyrimidine (45 mg, 0.25 mmol), N,N-diisopropylethylamine (257 μl, 1.48 mmol) according to the method described in Example 17. The crude was purified using SP1® Purification System by reverse phase to give 27 mg (40% yield) of the title compound as a white solid. Purity 100%.

LRMS (m/z): 417 (M+1)$^+$
$^1$H NMR (400 MHz, DMSO-d6) δ 8.15 (d, J=7.5 Hz, 1H), 7.61 (d, J=6.0 Hz, 1H), 7.58-7.47 (m, 3H), 7.45 (d, J=6.0 Hz,

1H), 7.36-7.26 (m, 2H), 7.13-7.06 (m, 1H), 6.41 (d, J=2.1 Hz, 1H), 5.05-4.95 (m, 1H), 2.39 (s, 3H), 2.33 (s, 3H), 1.42 (d, J=6.8 Hz, 3H).

Example 62

(S)-5-Methyl-2-(1-((5-(6-oxo-1,6-dihydropyridin-2-yl)-7H-pyrrolo[2,3-d]pyrimidin-4-yl)amino)ethyl)-3-phenylpyrrolo[2,1-f][1,2,4]triazin-4(3H)-one (S)-2-(1-((5-(6-Methoxypyridin-2-yl)-7H-pyrrolo[2,3-d]pyrimidin-4-yl)amino)ethyl)-5-methyl-3-phenylpyrrolo[2,1-f][1,2,4]triazin-4(3H)-one (22 mg, 0.02 mmol) was dissolved in 440 μl acetonitrile. Sodium iodide (35 md, 0.24 mmol) and chlorotrimethylsilane (30 μl, 0.24 mmol) were added. The reaction mixture was stirred at 40° C. for 8 h. The mixture was poured into 10 mL of sodium bicarbonate solution and extracted twice with ethyl acetate. The organics were dried over sodium sulphate, filtered and concentrated under reduced pressure. The residue was purified using SP1® purification system (0% to 10%, dichloromethane-2-propanol) to give 4 mg (34% yield) of the title compound as a solid. Purity 93%.

LRMS (m/z): 479 (M+1)$^+$
$^1$H NMR (400 MHz, DMSO-d6) δ 11.18 (bs, 1H), 10.61 (bs, 1H), 8.05 (s, 1H), 7.98-7.89 (m, 1H), 7.70-7.31 (m, 9H), 6.50 (d, J=8.1 Hz, 1H), 6.35 (d, J=2.6 Hz, 1H), 4.73-4.57 (m, 1H), 2.38 (s, 3H), 1.52 (d, J=6.7 Hz, 3H).

Example 63

(S)-2-(1-((5-(1H-Indol-7-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Indol-7-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (91 mg, 0.14 mmol) was treated with trifluoroacetic acid (1.82 mL, 23.62 mmol) and a solution of ammonia (7N in methanol, 1.82 mL, 12.74 mmol) according to the method described in Example 27 to give 8 mg (11% yield) of the title compound. Purity 98%.

LRMS (m/z): 501 (M+1)$^+$
$^1$H NMR (400 MHz, DMSO-d6) δ 11.97 (bs, 1H), 10.98 (bs, 1H), 8.17 (s, 1H), 7.68-7.61 (m, 1H), 7.60-7.46 (m, 5H), 7.37 (d, J=2.3 Hz, 1H), 7.33-7.28 (m, 1H), 7.19-7.11 (m, 3H), 6.56-6.48 (m, 1H), 6.37 (d, J=2.6 Hz, 1H), 5.71 (d, J=7.3 Hz, 1H), 4.78-4.65 (m, 1H), 2.35 (s, 3H), 1.25 (d, J=6.3 Hz, 3H).

Example 64

(S)-2-(1-((6-Amino-5-(3-hydroxybenzyl)pyrimidin-4-yl)amino)ethyl)-5-methyl-3-phenylpyrrolo[2,1-f][1,2,4]triazin-4(3H)-one (S)-2-(1-((6-Amino-5-(3-methoxybenzyl)pyrimidin-4-yl)amino)ethyl)-5-methyl-3-phenylpyrrolo[2,1-f][1,2,4]triazin-4(3H)-one (70 mg, 0.15 mmol) was treated with boron tribromide (1M in dichloromethane, 436 μl, 0.44 mmol) with dichloromethane as a solvent according to the method described in Example 23. The residue was purified by reverse phase using SP1® Purification System to give 37 mg (54% yield) as a solid. Purity 98%.

LRMS (m/z): 468 (M+1)$^+$
$^1$H NMR (400 MHz, CDCl$_3$) δ 7.92 (s, 1H), 7.56-7.38 (m, 5H), 7.23-7.15 (m, 2H), 6.83 (d, J=7.6 Hz, 1H), 6.74 (dd, J=8.1, 1.9 Hz, 1H), 6.63 (s, 1H), 6.31 (d, J=2.2 Hz, 1H), 5.14 (d, J=8.6 Hz, 1H), 5.01-4.80 (m, 3H), 3.71-3.58 (m, 2H), 2.62 (s, 1H), 2.52-2.43 (m, 3H), 1.25 (d, J=6.7 Hz, 3H).

Example 65

(S)—N-(3-(4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (79 mg, 0.12 mmol) was treated with trifluoroacetic acid (1.58 mL, 20.51 mmol) and a solution of ammonia (7N in methanol, 1.58 mL, 11.06 mmol) according to the method described in Example 27 to give 23 mg (36% yield) of the title compound. Purity 97%.

LRMS (m/z): 555 (M+1)$^+$
$^1$H NMR (400 MHz, DMSO-d6) δ 11.89 (bs, 1H), 8.14 (s, 1H), 7.62-7.49 (m, 5H), 7.45-7.34 (m, 2H), 7.32-7.21 (m, 2H), 7.21-7.09 (m, 2H), 6.38 (d, J=2.7 Hz, 1H), 5.98 (bs, 1H), 4.87-4.75 (m, 1H), 3.00-2.85 (m, 4H), 2.37 (s, 3H), 1.30 (d, J=6.6 Hz, 3H).

Example 66

(S)-2-(1-((5-(2-Hydroxy-5-(trifluoromethyl)phenyl)-7H-pyrrolo[2,3-d]pyrimidin-4-yl)amino)ethyl)-5-methyl-3-phenylpyrrolo[2,1-f][1,2,4]triazin-4(31-1)-one (S)-2-(1-((5-(2-Methoxy-5-(trifluoromethyl)phenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (99 mg, 0.14 mmol) was treated with boron tribromide (1M in dichloromethane, 1.4 mL, 1.44 mmol) and a solution of ammonia (7N in methanol, 1.98 mL, 14 mmol) according to the method described in Example 41 to give 8 mg (10% yield) of the title compound as a solid. Purity 95%.

LRMS (m/z): 546 (M+1)$^+$
$^1$H NMR (600 MHz, DMSO-d6) δ 11.83 (bs, 1H), 10.89 (bs, 1H), 8.08 (s, 1H), 7.65-7.42 (m, 6H), 7.30-6.99 (m, 4H), 6.38 (d, J=2.3 Hz, 1H), 6.03 (bs, 1H), 4.79-4.61 (m, 1H), 2.37 (s, 3H), 1.27 (d, J=6.6 Hz, 3H).

Example 67

(S)-2-(1-((5-(2-Hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-Hydroxy-3-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (71 mg, 0.08 mmol) was treated with trifluoroacetic acid (2 mL, 25.96 mmol) and a solution of ammonia (7N in methanol, 2 mL, 14 mmol) according to the method described in Example 27 to give 19.5 mg (48% yield) of the title compound. Purity 94%.

LRMS (m/z): 508 (M+1)$^+$
$^1$H NMR (400 MHz, DMSO-d6) δ 11.75 (bs, 1H), 8.90 (bs, 1H), 8.08 (s, 1H), 7.59-7.47 (m, 5H), 7.22 (d, J=2.3 Hz, 1H), 7.13-7.02 (m, 2H), 6.94-6.85 (m, 2H), 6.41 (d, J=2.3 Hz, 1H), 6.26 (d, J=6.3 Hz, 1H), 4.82-4.64 (m, 1H), 3.83 (s, 3H), 2.38 (s, 3H), 1.26 (d, J=6.3 Hz, 3H).

Example 68

(S)-2-(1-((5-((3-Hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((3-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (36.4 mg, 0.06 mmol) was treated with boron tribromide (1M in dichloromethane, 1 mL, 1 mmol) and a solution of ammonia (7N in methanol, 3 mL, 21 mmol) according to the method described in Example 41 to give 21 mg (75% yield) of the title compound. Purity 88%.
LRMS (m/z): 510 (M+1)+
$^1$H NMR (400 MHz, DMSO-d6) δ 12.23 (bs, 1H), 9.50 (bs, 1H), 8.08 (s, 1H), 7.62 (s, 1H), 7.58-7.35 (m, 4H), 7.34 (d, J=2.4 Hz, 1H), 7.30-7.23 (m, 1H), 6.94-6.86 (m, 1H), 6.67-6.56 (m, 2H), 6.51-6.43 (m, 2H), 6.41 (d, J=2.4 Hz, 1H), 4.84-4.71 (m, 1H), 2.38 (s, 3H), 1.19 (d, J=6.6 Hz, 3H).

Example 69

(S)-2-(1-((5-((3-Methoxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((3-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (10.2 mg, 0.02 mmol) was treated with trifluoroacetic acid (1 mL, 12.98 mmol) and a solution of ammonia (7N in methanol, 1 mL, 7 mmol) according to the method described in Example 27 to give 19.5 mg (83% yield) of the title compound. Purity 100%.
LRMS (m/z): 524 (M+1)+

Example 70

(S)-2-(1-((5-(1H-Indol-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Indol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (75 mg, 0.11 mmol) was treated with trifluoroacetic acid (1.50 mL, 19.47 mmol) and a solution of ammonia (7N in methanol, 1.50 mL, 10.50 mmol) according to the method described in Example 27 to give 19.5 mg (44% yield) of the title compound. Purity 97%.
LRMS (m/z): 501 (M+1)+
$^1$H NMR (400 MHz, DMSO-d6) δ 11.89 (bs, 1H), 11.32 (bs, 1H), 8.15 (s, 1H), 7.60-7.46 (m, 6H), 7.41-7.36 (m, 1H), 7.33-7.28 (m, 1H), 7.26-7.20 (m, 1H), 7.13 (d, J=2.5 Hz, 1H), 7.09 (d, J=7.1 Hz, 1H), 6.44-6.39 (m, 1H), 6.37 (d, J=2.7 Hz, 1H), 5.89 (d, J=7.3 Hz, 1H), 4.77-4.66 (m, 1H), 2.35 (s, 3H), 1.13 (d, J=6.4 Hz, 3H).

Example 71

(S)-2-(1-((5-(2,4-Di hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2,4-Dimethoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (95 mg, 0.14 mmol) was treated with boron tribromide (1M in dichloromethane, 1.46 mL, 14.6 mmol) and a solution of ammonia (7N in methanol, 1.96 mL, 13.72 mmol) according to the method described in Example 41 to give 15 mg (21% yield) of the title compound. Purity 100%.
LRMS (m/z): 494 (M+1)+
$^1$H NMR (400 MHz, DMSO-d6) δ 11.60 (bs, 1H), 9.67 (bs, 1H), 9.49 (bs, 1H), 8.05 (s, 1H), 7.61-7.47 (m, 5H), 7.29 (d, J=2.6 Hz, 1H), 7.05-6.96 (m, 2H), 6.55-6.48 (m, 1H), 6.41 (d, J=2.7 Hz, 1H), 6.37-6.31 (m, 2H), 4.79-4.67 (m, 1H), 2.38 (s, 3H), 1.26 (d, J=6.7 Hz, 3H).

Example 72

(S)-5-Methyl-2-(1-((5-(1-methyl-1H-pyrazol-4-yl)-7H-pyrrolo[2,3-d]pyrimidin-4-yl)amino)ethyl)-3-phenylpyrrolo[2,1-f][1,2,4]triazin-4(3H)-one (S)-5-Methyl-2-(1-((5-(1-methyl-1H-pyrazol-4-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (37 mg, 0.06 mmol) was treated with trifluoroacetic acid (1 mL, 12.98 mmol) and a solution of ammonia (7N in methanol, 1 mL, 7 mmol) according to the method described in Example 27 to give 25 mg (85% yield) of the title compound. Purity 98%.
LRMS (m/z): 466 (M+1)+
$^1$H NMR (400 MHz, DMSO-d6) δ 11.75 (bs, 1H), 8.11 (s, 1H), 7.89 (s, 1H), 7.69 (d, J=0.8 Hz, 1H), 7.62-7.50 (m, 5H), 7.45 (d, J=2.6 Hz, 1H), 7.13 (d, J=1.9 Hz, 1H), 6.42 (d, J=2.6 Hz, 1H), 6.12 (d, J=7.3 Hz, 1H), 4.90-4.78 (m, 1H), 3.92 (s, 3H), 2.39 (s, 3H), 1.30 (d, J=6.6 Hz, 3H).

Example 73

N'-[3-Methoxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide N'-[3-Methoxy-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]-N,N-dimethylsulfamide (30 mg, 0.03 mmol, 85% purity) was treated with trifluoroacetic acid (600 μl, 7.79 mmol) and a solution of ammonia (7N in methanol, 600 μl, 4.20 mmol) according to the method described in Example 27. The residue was purified using SP1® Purification System (0% to 15% dichloromethane-2-propanol) to obtain 23 mg (93% yield, 85% purity) of the title compound.
LRMS (m/z): 614 (M+1)+.
$^1$H NMR (400 MHz, DMSO-d6) δ 11.88 (bs, 1H), 9.99 (bs, 1H), 8.12 (s, 1H), 7.61-7.46 (m, 5H), 7.25-7.19 (m, 2H), 6.88-6.72 (m, 3H), 6.38 (d, J=2.6 Hz, 1H), 6.04 (d, J=7.2 Hz, 1H), 4.85-4.72 (m, 1H), 3.77 (s, 3H), 2.67 (s, 6H), 2.35 (s, 3H), 1.30 (d, J=6.6 Hz, 3H).

Example 74

(S)-4-Amino-6-((1-(5-(3-hydroxybenzyl)-4-oxo-3-phenyl-3,4-dihydropyrrolo[2,1-f][1,2,4]triazin-2-yl)ethyl)amino)pyrimidine-5-carbonitrile (S)-4-Amino-6-((1-(5-(3-methoxybenzyl)-4-oxo-3-phenyl-3,4-dihydropyrrolo[2,1-f][1,2,4]triazin-2-yl)ethyl)amino)pyrimidine-5-carbonitrile (72 mg, 0.15 mmol) was treated with boron tribromide (1M in dichloromethane, 580 μl, 0.58 mmol) with dichloromethane as a solvent according to the method described in Example 23. The residue was purified by reverse phase using SP1® Purification System to give 27 mg (39% yield) as a solid. Purity 98%.

LRMS (m/z): 479 (M+1)$^+$ $^1$H NMR (400 MHz, CDCl$_3$) δ 8.05 (s, 1H), 7.50 (dd, J=18.0, 5.5 Hz, 3H), 7.42 (d, J=6.5 Hz, 1H), 7.35-7.23 (m, 2H), 7.10 (t, J=7.8 Hz, 1H), 6.85 (d, J=7.4 Hz, 1H), 6.79 (s, 1H), 6.62 (d, J=7.6 Hz, 1H), 6.34 (d, J=2.4 Hz, 1H), 5.85 (d, J=7.6 Hz, 2H), 5.42 (s, 2H), 5.09-4.95 (m, 1H), 4.21 (d, J=2.0 Hz, 2H), 1.39 (d, J=6.7 Hz, 3H).

Example 75

(S)—N—Benzyl-4-((1-(5-methyl-4-oxo-3-phenyl-3, 4-dihydropyrrolo[2,1-f][1,2,4]triazin-2-yl)ethyl) amino)-7H-pyrrolo[2,3-d]pyrimidine-5-carboxamide (S)-4-((1-(5-Methyl-4-oxo-3-phenyl-3,4-dihydropyrrolo [2,1-f][1,2,4]triazin-2-yl)ethyl)amino)-7H-pyrrolo[2,3-d] pyrimidine-5-carboxylic acid (30 mg, 0.07 mmol), benzylamine (20 mg, 0.19 mmol) and diisopropylethylamine (50 μl, 0.29 mmol) were dissolved in DMF (1.5 ml) and stirred for 30 min. The reaction flask was then sealed and T3P® (50% in DMF, 50 μl) was added dropwise and the reaction mixture was stirred overnight at room temperature. The mixture was poured into ice-water and extracted with ethyl acetate. The resulting organic solution was washed with water and brine, dried over magnesium sulphate, filtered and the solvents were removed under reduced pressure. The product was purified by flash chromatography (0% to 5% DCM/MeOH) to give 17 mg (46% yield) of the title compound as a white solid.

LRMS (m/z): 519 (M+1)$^+$.

$^1$H NMR (400 MHz, DMSO-d6) δ 12.11 (s, 1H), 9.86 (d, J=6.7 Hz, 1H), 8.94 (t, J=5.9 Hz, 1H), 8.06 (s, 1H), 8.02 (s, 1H), 7.57-7.48 (m, 3H), 7.48-7.30 (m, 7H), 7.29-7.20 (m, 1H), 6.37 (dd, J=2.7, 0.6 Hz, 1H), 4.73 (p, J=6.9 Hz, 1H), 4.51 (d, J=5.9 Hz, 2H), 2.38 (s, 3H), 1.41 (d, J=6.8 Hz, 3H).

Example 76

(S)—N-(3-(Dimethylamino)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-(Dimethylamino)-5-(4-(1-(5-methyl-4-oxo-3-phenyl-3,4-dihydropyrrolo[1,2-f][1,2,4]triazin-2-yl)ethylamino)-7-((2-(trimethylsilyl)ethoxy)methyl)-7H-pyrrolo[2, 3-d]pyrimidin-5-yl)phenyl)methanesulfonamide (89.5 mg, 0.12 mmol) was treated with trifluoroacetic acid (2 mL, 26 mmol) and a solution of ammonia (7N in methanol, 3 mL, 215 mmol) according to the method described in Example 27 to give 56 mg (76% yield) of the title compound. Purity 100%.

LRMS (m/z): 598 (M+1)$^+$ $^1$H NMR (400 MHz, CDCl$_3$) δ 10.09 (s, 1H), 8.27 (s, 1H), 7.62-7.41 (m, 4H), 7.38-7.27 (m, 2H), 7.09-7.04 (m, 2H), 6.73-6.64 (m, 3H), 6.28 (d, J=2.6 Hz, 1H), 6.10 (d, J=7.7 Hz, 1H), 5.08 (p, J=6.7 Hz, 1H), 3.05 (s, 3H), 3.02 (s, 6H), 2.45 (s, 3H), 1.21 (d, J=6.1 Hz, 3H).

Example 77

(S)-2-(1-((6-Amino-5-((3-fluoro-4-hydroxyphenyl) thio)pyrimidin-4-yl)amino)ethyl)-5-methyl-3-phenylpyrrolo[2,1-f][1,2,4]triazin-4(3H)-one (S)-2-(1-((6-Amino-5-((3-fluoro-4-methoxyphenyl)thio) pyrimidin-4-yl)amino)ethyl)-5-methyl-3-phenylpyrrolo[2, 1-f][1,2,4]triazin-4(3H)-one (233 mg, 0.45 mmol) was treated with boron tribromide (1M in dichloromethane, 1.35 ml, 1.35 mmol) with dichloromethane as a solvent according to the method described in Example 23. The residue was purified by reverse phase using SP1® Purification System to give 40 mg (18% yield) as a solid. Purity 99%.

LRMS (m/z): 504 (M+1)$^+$ $^1$H NMR (400 MHz, CDCl$_3$) δ 8.04 (s, 1H), 7.56-7.46 (m, 3H), 7.41 (dd, J=5.9, 3.6 Hz, 1H), 7.32-7.27 (m, 1H), 7.13 (d, J=2.7 Hz, 1H), 6.96-6.82 (m, 3H), 6.31 (dd, J=2.7, 0.6 Hz, 1H), 6.22 (d, J=8.5 Hz, 1H), 5.28 (s, 2H), 4.94 (dq, J=13.6, 6.8 Hz, 1H), 3.49 (s, 1H), 2.49 (s, 3H), 1.33 (d, J=6.8 Hz, 3H).

Example 78

(S)-2-(1-((5-(3-Fluoro-5-hydroxybenzyl)-7H-pyrrolo [2,3-d]pyrimidin-4-yl)amino)ethyl)-5-methyl-3-phenylpyrrolo[2,1-f][1,2,4]triazin-4(3H)-one (S)-2-(1-((5-(3-Fluoro-5-methoxybenzyl)-7-((2-(trimethylsilyl)ethoxy)methyl)-7H-pyrrolo[2,3-d]pyrimidin-4-yl) amino)ethyl)-5-methyl-3-phenylpyrrolo[2,1-f][1,2,4]triazin-4(3H)-one (3 mg, 0.01 mmol) was treated with boron tribromide (1M in dichloromethane, 148 μL, 0.15 mmol) in dichloromethane (280 μL) and then with a solution of ammonia (7N in methanol, 280 μl, 1.96 mmol) according to the method described in Example 41. The residue was purified using SP1® Purification System (0% to 100% dichloromethane-ethyl acetate) to obtain 3 mg (38% yield) of the title compound.

LRMS (m/z): 510 (M+1)+.

Example 79

(S)—N-(3-Methyl-5-(4-((1-(5-methyl-4-oxo-3-phenyl-3,4-dihydropyrrolo[2,1-f][1,2,4]triazin-2-yl) ethyl)amino)-7H-pyrrolo[2,3-d]pyrimidin-5-yl)phenyl)methanesulfonamide (S)—N-(3-Methyl-5-(4-((1-(5-methyl-4-oxo-3-phenyl-3, 4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (110 mg, 0.16 mmol) was treated with trifluoroacetic acid (2 ml, 26 mmol) and a solution of ammonia (7N in methanol, 2 ml, 90 mmol) according to the method described in Example 27 to give 25 mg (28% yield) of the title compound. Purity 98%.

LRMS (m/z): 569 (M+1)+.

$^1$H NMR (400 MHz, CDCl$_3$) δ ppm 1.35 (d, J=6.64 Hz, 2H) 2.44 (s, 3H) 2.48 (s, 3H) 3.07 (s, 3H) 3.49 (q, J=7.03 Hz, 1H) 5.05-5.15 (m, 1H) 5.84 (d, J=7.82 Hz, 1H) 6.31 (d, J=3.13 Hz, 1H) 6.81 (s, 1H) 7.06 (s, 1H) 7.09 (d, J=2.34 Hz, 1H) 7.11 (s, 1H) 7.20 (s, 1H) 7.29-7.35 (m, J=7.03, 1.95 Hz, 1H) 7.49-7.58 (m, 3H) 8.27 (s, 1H) 9.62 (s, 1H)

Example 80

(S)-5-Methyl-3-phenyl-2-(1-((5-(phenylethynyl)-7H-pyrrolo[2,3-d]pyrimidin-4-yl)amino)ethyl)pyrrolo[2, 1-f][1,2,4]triazin-4(3H)-one (S)-5-Methyl-3-phenyl-2-(1-((5-(phenylethynyl)-7-((2-(trimethylsilyl)ethoxy)methyl)-7H-pyrrolo[2,3-d]pyrimidin-4-yl)amino)ethyl)pyrrolo[2,1-f][1,2,4]triazin-4(3H)-one (9 mg, 0.01 mmol) was treated with trifluoroacetic acid (180 μl, 2.34 mmol) and a solution of ammonia (7N in methanol, 180 μl, 1.26 mmol) according to the method described in Example 27. The residue was purified using SP1® Purification System (0% to 100% n-hexane-ethyl acetate) to obtain 7 mg (98% yield) of the title compound.

LRMS (m/z): 486 (M+1)+.

¹H NMR (400 MHz, DMSO-d6) δ 12.18 (bs, 1H), 8.09 (s, 1H), 7.60-7.34 (m, 11H), 6.90 (d, J=2.7 Hz, 1H), 6.65 (d, J=7.9 Hz, 1H), 6.32 (d, J=2.7 Hz, 1H), 5.04-4.94 (m, 1H), 2.36 (s, 3H), 1.43 (d, J=6.6 Hz, 3H).

Example 81

(S)-4-Amino-6-((1-(5-((3-fluoro-4-hydroxyphenyl) thio)-4-oxo-3-phenyl-3,4-dihydropyrrolo[2,1-f][1,2,4]triazin-2-yl)ethyl)amino)pyrimidine-5-carbonitrile (S)-4-Amino-6-(1-(5-(3-fluoro-4-methoxyphenylthio)-4-oxo-3-phenyl-3,4-dihydropyrrolo[1,2-f][1,2,4]triazin-2-yl) ethylamino)pyrimidine-5-carbonitrile (158 mg, 0.30 mmol) was treated with boron tribromide (1M in dichloromethane, 0.9 ml, 0.9 mmol) in dichloromethane according to the method described in Example 23. The residue was purified by reverse phase using SP1® Purification System to give 42 mg (27% yield) as a solid. Purity 99%.

LRMS (m/z): 516 (M+1)⁺

¹H NMR (400 MHz, CDCl₃) δ 10.18 (s, 1H), 7.77 (s, 1H), 7.64 (d, J=2.8 Hz, 2H), 7.53-7.40 (m, 2H), 7.37-7.28 (m, 3H), 7.26-7.16 (m, 3H), 7.10 (d, J=8.4 Hz, 1H), 6.96 (t, J=8.8 Hz, 1H), 6.20 (d, J=2.8 Hz, 1H), 5.01-4.59 (m, 1H), 1.35 (d, J=6.6 Hz, 3H).

Example 82

(S)—N-(3-Hydroxyphenyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide (S)-4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid (25 mg, 0.06 mmol), 3-aminophenol (7 mg, 0.07 mmol) and diisopropylethylamine (41 μl, 0.23 mmol) were dissolved in DMF (1.5 ml) and stirred for 30 min. The reaction flask was then sealed and T3P® (50% in DMF, 140 μl, 0.24 mmol) was added dropwise and the reaction mixture stirred overnight at room temperature. The mixture was poured into ice and extracted with ethyl acetate. The resulting organic solution was washed with water and brine, dried over magnesium sulphate, filtered and the solvents were removed under reduced pressure. The product was purified by flash chromatography using SP1® Purification System (0% to 5% DCM/MeOH) to give 2 mg (6% yield) of the title compound as a white solid.

LRMS (m/z): 521 (M+1)⁺.

Example 83

(S)-4-Amino-N-(3-fluoro-4-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (100 mg, 0.37 mmol), 4-amino-6-bromo-N-(3-fluoro-4-hydroxyphenyl)pyrimidine-5-carboxamide (183 mg, 0.56 mmol), DIEA (325 μl, 1.87 mmol) and cesium fluoride (113 mg, 0.74 mmol) were suspended in tert-butanol (5 ml) and the mixture was stirred overnight at 120° C. in a sealed tube. The reaction mixture was diluted with ethyl acetate and washed with water and brine. After evaporation of the solvent, the residue was purified by reverse phase using SP1® Purification System to give 15 mg (8% yield) as a solid. Purity 99%.

LRMS (m/z): 515 (M+1)⁺

¹H NMR (400 MHz, CDCl₃) δ 8.98 (s, 1H), 8.07 (s, 1H), 7.74 (dd, J=12.2, 2.5 Hz, 1H), 7.64-7.49 (m, 4H), 7.33 (dd, J=10.1, 8.5 Hz, 1H), 7.09 (t, J=5.0 Hz, 2H), 6.99 (t, J=9.0 Hz, 1H), 6.52 (d, J=8.2 Hz, 1H), 6.31 (d, J=2.1 Hz, 1H), 5.93 (d, J=10.4 Hz, 2H), 5.21-5.04 (m, 1H), 3.49 (s, 1H), 2.49 (s, 3H), 1.38 (d, J=6.8 Hz, 3H).

Example 84

(S)-4-Amino-N-(3-fluoro-5-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (100 mg, 0.37 mmol), 4-amino-6-bromo-N-(3-fluoro-5-hydroxyphenyl)pyrimidine-5-carboxamide (183 mg, 0.56 mmol), DIEA (325 μl, 1.87 mmol) and cesium fluoride (113 mg, 0.74 mmol) were suspended in tert-butanol (5 ml) and the mixture was stirred overnight at 120° C. in a sealed tube. The reaction mixture was diluted with ethyl acetate and washed with water and brine. After evaporation of the solvent, the residue was purified by reverse phase using SP1® Purification System to give 15 mg (8% yield) as a solid. Purity 97%.

LRMS (m/z): 515 (M+1)⁺

¹H NMR (400 MHz, CDCl₃) δ 9.11 (s, 1H), 8.06 (s, 1H), 7.61-7.47 (m, 4H), 7.35 (d, J=7.7 Hz, 1H), 7.12 (d, J=2.6 Hz, 1H), 7.00 (dd, J=11.9, 7.9 Hz, 2H), 6.45 (d, J=7.5 Hz, 1H), 6.40-6.35 (m, 1H), 6.31 (d, J=2.4 Hz, 1H), 6.09 (s, 2H), 5.22-4.96 (m, 1H), 2.62 (s, 2H), 2.54-2.39 (m, 3H), 1.37 (d, J=6.8 Hz, 3H).

Example 85

(S)-5-Methyl-2-(1-((5-(3-(morpholinosulfonyl)phenyl)-7H-pyrrolo[2,3-d]pyrimidin-4-yl)amino)ethyl)-3-phenylpyrrolo[2,1-f][1,2,4]triazin-4(3H)-one (S)-5-Methyl-2-(1-((5-(3-(morpholinosulfonyl)phenyl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (90 mg, 0.12 mmol) was treated with trifluoroacetic acid (2 ml, 25 mmol) and a solution of ammonia (7N in methanol, 2 ml, 91 mmol) according to the method described in Example 27. The residue was purified by reverse phase using SP1® Purification System to obtain 19 mg (25% yield) of the title compound. Purity 98%.

LRMS (m/z): 611 (M+1)+.

¹H NMR (400 MHz, CDCl₃) δ 1.10-1.31 (m, 2H) 1.36 (d, J=6.64 Hz, 3H) 2.40-2.52 (m, 2H) 3.00-3.12 (m, 3H) 3.68-3.83 (m, 3H) 5.00-5.18 (m, 1H) 5.54 (d, J=7.82 Hz, 1H) 6.28 (d, J=2.74 Hz, 1H) 7.03 (d, J=2.74 Hz, 1H) 7.14 (s, 1H) 7.29-7.36 (m, 1H) 7.49-7.59 (m, 3H) 7.71 (t, J=7.62 Hz, 1H) 7.81 (d, J=7.82 Hz, 1H) 7.89 (d, J=7.42 Hz, 1H) 7.95 (s, 1H) 8.32 (s, 1H) 9.65 (s, 1H)

Example 86

2-((1S)-1-((6-Amino-5-(1H-indol-4-yl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino) ethyl)-5-methyl-3-phenylpyrrolo[2,1-f][1,2,4]triazin-4(3H)- one (140 mg, 0.32 mmol) was treated with 4-(4,4,5,5-tetramethyl-1,3,2-dioxaborolan-2-yl)-1H-indole (116 mg, 0.48 mmol), sodium carbonate (2M, 715 µl, 1.43 mmol) and 1,1'-bis(diphenylphosphino)ferrocene-palladium(II)dichloride dichloromethane complex (40 mg, 0.05 mmol) according to the method described in Example 3 to give 6 mg (4% yield) of the title compound as a mixture of diastereoisomers. Purity 99%.

LRMS (m/z): 478 (M+1)$^+$

Example 87

(S)-4-Amino-N-(3-hydroxybenzyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-4-Amino-N-(3-methoxybenzyl)-6-((1-(5-methyl-4-oxo-3-phenyl-3,4-dihydropyrrolo[2,1-f][1,2,4]triazin-2-yl)ethyl)amino)pyrimidine-5-carboxamide (103 mg, 0.20 mmol) was treated with boron tribromide (1M in dichloromethane, 0.85 ml, 0.85 mmol) in dichloromethane (8 ml) according to the method described in Example 23. The residue was purified by reverse phase using SP1® Purification System to give 37 mg (36% yield) as a solid. Purity 98%.

LRMS (m/z): 511 (M+1)$^+$
$^1$H NMR (400 MHz, CDCl$_3$) δ 7.87-7.67 (m, 2H), 7.16-7.06 (m, 2H), 7.01 (dd, J=2.5, 0.7 Hz, 1H), 6.92 (t, J=2.3 Hz, 1H), 6.81 (dd, J=2.1, 0.7 Hz, 1H), 6.41 (s, 1H), 4.97 (s, 1H), 1.30 (s, J=2.5 Hz, 12H).

Example 88

(S)—N-((1H-Pyrazol-4-yl)ethyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide (S)-4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid (50 mg, 0.12 mmol), (1H-pyrazol-4-yl)methanamine (11 mg, 0.11 mmol) and diisopropylethylamine (163 µl, 0.94 mmol) were dissolved in DMF (2 ml) and stirred for 30 min. The reaction flask was then sealed and T3P® (50% in DMF, 270 µl, 0.46 mmol) was added dropwise and the reaction mixture stirred overnight at room temperature. The mixture was poured into ice-water and extracted with ethyl acetate. The resulting organic solution was washed with water and brine, dried over magnesium sulphate, filtered and the solvents were removed under reduced pressure. The product was purified by flash chromatography using SP1® Purification System (0% to 10% DCM/MeOH) to give 1.5 mg (2% yield) of the title compound as a white solid.

LRMS (m/z): 509 (M+1)$^+$.

Example 89

(S)-4-Amino-N-(2-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-4-Amino-N-(2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (72 mg, 0.14 mmol) was treated with boron tribromide (1M in dichloromethane, 0.43 ml, 0.43 mmol) in dichloromethane (8 ml) according to the method described in Example 23. The crude was purified using SP1® Purification (40% to 100%, hexane-ethyl acetate) to give 24 mg (34% yield) of the title compound as a solid. Purity 99%.

LRMS (m/z): 497 (M+1)$^+$
$^1$H-RMN (400 MHz, CD$_3$OD) δ 7.88 (s, 1H), 7.83 (dd, J=7.9, 1.6 Hz, 1H), 7.60-7.44 (m, 4H), 7.44-7.37 (m, J=8.0, 1.4 Hz, 1H), 7.29 (d, J=2.7 Hz, 1H), 7.04 (ddd, J=8.1, 7.4, 1.6 Hz, 1H), 6.94-6.80 (m, 2H), 6.35 (dd, J=2.7, 0.6 Hz, 1H), 4.92 (q, J=6.8 Hz, 1H), 2.44 (s, 3H), 1.42 (d, J=6.8 Hz, 3H).

Example 90

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)methanesulfonamide (S)-2-(1-(6-Amino-5-bromopyrimidin-4-ylamino)ethyl)-5-methyl-3-phenylpyrrolo[1,2-f][1,2,4]triazin-4(3H)-one (125 mg, 0.28 mol) was treated with N-(3-hydroxy-5-(4,4,5,5-tetramethyl-1,3,2-dioxaborolan-2-yl)phenyl)methanesulfonamide (133 mg, 0.42 mmol), tetrakis(triphenylphospino)palladium(0) (16 mg, 0.01 mol) and sodium carbonate (2M, 427 µl, 0.85 mol) according to the method described in Example 3 to give 50 mg (32% yield) of the title compound as a white solid. Purity 98%.

LRMS (m/z): 548 (M+1)$^+$
$^1$H NMR (400 MHz, DMSO-d6) δ 9.73 (s, 1H), 8.34 (s, 1H), 7.80 (d, J=7.1 Hz, 1H), 7.65-7.26 (m, 6H), 6.74-6.64 (m, 1H), 6.48 (d, J=17.6 Hz, 1H), 6.39 (dd, J=2.6, 0.6 Hz, 1H), 6.30 (s, 1H), 5.53 (d, J=20.9 Hz, 3H), 4.74 (s, 1H), 3.00 (s, 3H), 2.37 (d, J=5.1 Hz, 3H), 1.26-1.09 (m, 3H).

Example 91

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-1,1,1-trifluoromethanesulfonamide (S)-2-(1-(6-Amino-5-bromopyrimidin-4-ylamino)ethyl)-5-methyl-3-phenylpyrrolo[1,2-f][1,2,4]triazin-4(3H)-one (125 mg, 0.28 mol) was treated with 1,1,1-trifluoro-N-(2-methoxy-5-(4,4,5,5-tetramethyl-1,3,2-dioxaborolan-2-yl)pyridin-3-yl)methanesulfonamide (145 mg, 0.38 mmol, described at Appl. (2012), WO 2012087938 A1 20120628), tetrakis(triphenylphospino)palladium(0) (15 mg, 0.01 mol) and sodium carbonate (2M, 427 µl, 0.85 mol) according to the method described in Example 3 to give 25 mg (16% yield) of the title compound as a white solid. Purity 99%.

LRMS (m/z): 617 (M+1)$^+$
$^1$H NMR (400 MHz, CDCl$_3$) δ 8.00 (s, 1H), 7.74 (s, 1H), 7.49 (s, 5H), 7.19 (d, J=61.5 Hz, 1H), 6.26 (s, 1H), 5.23 (bs, 2H), 4.93 (bs, 2H), 3.93 (bs, 2H), 3.48 (s, 3H), 2.44 (s, 3H), 1.26 (s, 3H).

Example 92

(S)-4-Amino-6-((1-(5-((2-((2-(dimethylamino)ethyl)amino)phenyl)thio)-4-oxo-3-phenyl-3,4-dihydropyrrolo[2,1-f][1,2,4]triazin-2-yl)ethyl)amino)pyrimidine-5-carbonitrile (S)-2-(1-Aminoethyl)-5-((2-((2-(dimethylamino)ethyl)amino)phenyl)thio)-3-phenylpyrrolo[2,1-f][1,2,4]triazin-4(3H)-one (267 mg, 0.54 mmol), 4-amino-6-chloropyrimidine-5-carbonitrile (123 mg, 0.81 mmol) and DIEA (280 µl, 1.61 mmol) in 10 ml of tert-BuOH were stirred overnight at 80° C. After evaporation of the solvent under reduced pressure, the residue was purified using SP1® Purification System (0% to 20%, DCM-MeOH) to obtain 9 mg of the title compound as a solid. Purity 99%.

LRMS (m/z): 568 (M+1)$^+$ $^1$H NMR (400 MHz, CDCl$_3$) δ 8.08 (s, 1H), 7.60-7.50 (m, 4H), 7.45 (dt, J=4.9, 2.2 Hz, 1H), 7.37-7.32 (m, 1H), 7.27 (m, 1H), 7.21 (d, J=2.9 Hz, 1H), 6.65 (dd, J=11.8, 4.4 Hz, 2H), 6.10 (d, J=2.8 Hz, 1H), 5.74 (d, J=8.1 Hz, 1H), 5.58 (s, 1H), 5.38 (s, 2H), 5.03 (dq, J=13.5, 6.8 Hz, 1H), 3.26 (d, J=4.8 Hz, 2H), 2.56 (s, 2H), 2.25 (s, 6H), 1.37 (t, J=13.2 Hz, 3H).

Example 93

(S)-1-(3-Hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea (S)-1-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)urea (34 mg, 0.05 mmol) was treated with boron tribromide (1M in dichloromethane, 1.5 mL, 1.5 mmol) in dichloromethane (1.0 mL) and then with a solution of ammonia (7N in methanol, 5.0 mL, 35.0 mmol) according to the method described in Example 41. The residue was purified using SP1® Purification System (0% to 10% dichloromethane-methanol) to obtain 3 mg (12% yield) of the title compound.

LRMS (m/z): 536 (M+1)+.

Example 94

(S)—N-(3-Hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (40 mg, 0.05 mmol) was treated with trifluoroacetic acid (920 μl, 11.94 mmol) and a solution of ammonia (7N in methanol, 920 μl, 6.44 mmol) according to the method described in Example 27. The residue was purified using SP1® Purification System (0% to 6% dichloromethane-2-propanol) to obtain 24 mg (78% yield) of the title compound.

LRMS (m/z): 571 (M+1)$^+$ $^1$H NMR (400 MHz, DMSO-d6) δ 11.83 (bs, 1H), 9.75 (bs, 1H), 8.10 (s, 1H), 7.59-7.45 (m, 6H), 7.29 (d, J=2.6 Hz, 1H), 7.20 (d, J=2.2 Hz, 1H), 6.77-6.69 (m, 2H), 6.62 (s, 1H), 6.37 (d, J=2.6 Hz, 1H), 6.05 (d, J=7.3 Hz, 1H), 4.85-4.74 (m, J=6.6 Hz, 1H), 2.97 (s, 3H), 2.35 (s, 3H), 1.30 (d, J=6.6 Hz, 3H).

Example 95

(S)-2-(1-((5-(4-Hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(4-Hydroxy-3-methoxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (63 mg, 0.10 mmol) was treated with trifluoroacetic acid (1.26 ml, 16.36 mmol) and a solution of ammonia (7N in methanol, 1.26 ml, 8.82 mmol) according to the method described in Example 27. The residue was purified using SP1® Purification System (0% to 6% n-hexane-ethyl acetate) to obtain 23 mg (46% yield) of the title compound.

LRMS (m/z): 508 (M+1)+.

$^1$H NMR (400 MHz, DMSO-d6) δ 11.77 (bs, 1H), 9.21 (bs, 1H), 8.13 (s, 1H), 7.65-7.48 (m, 5H), 7.24 (d, J=2.4 Hz, 1H), 7.18 (d, J=2.0 Hz, 1H), 7.10 (s, 1H), 6.91 (s, 2H), 6.40 (d, J=2.0 Hz, 1H), 6.10 (d, J=7.3 Hz, 1H), 4.87-4.74 (m, 1H), 3.85 (s, 3H), 2.37 (s, 3H), 1.29 (d, J=6.5 Hz, 3H).

Example 96

(S)-2-(1-((5-((2-Hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((2-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (57 mg, 0.09 mmol) was treated with boron tribromide (1M in dichloromethane, 872 μL, 0.87 mmol) in dichloromethane (1.14 mL) and then with a solution of ammonia (7N in methanol, 1.14 ml, 7.98 mmol) according to the method described in Example 27. The residue was purified using SP1® Purification System (0% to 100% dichloromethane ethyl acetate) to obtain 23 mg (47% yield, 90% purity) of the title compound.

LRMS (m/z): 510 (M+1)+.

$^1$H NMR (400 MHz, DMSO-d6) δ 12.17 (Bs, 1H), 10.19 (bs, 1H), 8.08 (s, 1H), 7.56-7.36 (m, 5H), 7.27 (d, J=2.6 Hz, 1H), 6.95-6.86 (m, 2H), 6.82 (d, J=7.3 Hz, 1H), 6.76 (d, J=7.9 Hz, 1H), 6.64 (d, J=4.1 Hz, 2H), 6.38 (d, J=2.6, 1H), 4.81-4.70 (m, 1H), 2.37 (s, 3H), 1.17 (d, J=6.6 Hz, 3H).

Example 97

(S)-2-(1-((5-((4-Hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((4-Methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (65 mg, 0.10 mmol) was treated with boron tribromide (1M in dichloromethane, 894 μL, 0.99 mmol) in dichloromethane (1.3 mL) and then with a solution of ammonia (7N in methanol, 1.3 ml, 9.10 mmol) according to the method described in Example 41. The residue was purified using SP1® Purification System (0% to 100% dichloromethane ethyl acetate) to obtain 24 mg (48% yield) of the title compound.

LRMS (m/z): 510 (M+1)+.

$^1$H NMR (400 MHz, DMSO-d6) δ 12.12 (bs, 1H), 9.52 (bs, 1H), 8.04 (s, 1H), 7.62-7.30 (m, 6H), 7.22 (d, J=8.1 Hz, 1H), 7.09-7.05 (m, 2H), 6.75 (d, J=8.0 Hz, 1H), 6.66-6.55 (m, 2H), 6.46-6.38 (m, 1H), 4.88-4.71 (m, J=14.1, 7.4 Hz, 1H), 2.40 (s, 3H), 1.25 (d, J=6.6 Hz, 3H).

Example 98

(S)-4-Amino-N-(3,5-dihydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-4-Amino-N-(3,5-dimethoxyphenyl)-6-((1-(5-methyl-4-oxo-3-phenyl-3,4-dihydropyrrolo[2,1-f][1,2,4]triazin-2- yl)ethyl)amino)pyrimidine-5-carboxamide (720 mg, 33% purity, 0.43 mmol) was treated with boron tribromide (1M in dichloromethane, 2.60 ml, 2.6 mmol) in dichloromethane (10 ml) according to the method described in Example 23. The residue was purified by reverse phase using SP1® Purification System to give 36 mg (3% yield) as a solid. Purity 99%.

LRMS (m/z): 514 (M+1)$^+$ $^1$H NMR (400 MHz, DMSO-d6) δ 9.69 (s, 1H), 9.05 (s, 2H), 8.21 (s, 2H), 7.87 (s, 1H), 7.50 (d, J=14.6 Hz, 4H), 6.67 (s, 2H), 6.56 (s, 2H), 6.33 (s, 1H), 5.96 (s, 1H), 4.71 (d, J=5.7 Hz, 2H), 2.39 (s, 3H), 1.33 (d, J=6.6 Hz, 3H).

Example 99

(S)-4-Amino-N-(5-carbamoyl-2-hydroxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-4-Amino-N-(5-carbamoyl-2-methoxyphenyl)-6-((1-(5-methyl-4-oxo-3-phenyl-3,4-dihydropyrrolo[2,1-f][1,2,4]triazin-2-yl)ethyl)amino)pyrimidine-5-carboxamide (400 mg, 49% purity, 0.35 mmol) was treated with boron tribromide (1M in dichloromethane, 1.1 ml, 1 mmol) in dichloromethane (8 ml) according to the method described in Example 23. The residue was purified by reverse phase using SP1® Purification System to give 10 mg (5% yield) as a solid. Purity 90%.

LRMS (m/z): 541 (M+1)$^+$ $^1$H NMR (400 MHz, DMSO-d6) δ 10.61 (s, 1H), 9.24 (s, 1H), 8.43 (d, J=2.0 Hz, 1H), 7.90 (s, 1H), 7.85-7.68 (m, 2H), 7.60-7.40 (m, 7H), 7.14 (d, J=14.3 Hz, 2H), 6.97-6.78 (m, 3H), 6.38 (d, J=2.4 Hz, 1H), 4.80-4.59 (m, 1H), 2.38 (s, 3H), 1.34 (d, J=6.7 Hz, 3H).

Example 100

(S)-2-(1-((5-(1-(2-Hydroxyethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(2-Hydroxyethyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (33 mg, 0.05 mmol) was treated with trifluoroacetic acid (1.5 mL, 19.47 mmol) and a solution of ammonia (7N in methanol, 2 mL, 14 mmol) according to the method described in Example 27 to give 22 mg (84% yield) of the title compound. Purity 100%.

LRMS (m/z): 496 (M+1)$^+$ $^1$H NMR (400 MHz, DMSO-d6) δ 11.76 (s, 1H), 8.14 (s, 1H), 7.93 (d, J=0.4 Hz, 1H), 7.71 (d, J=0.7 Hz, 1H), 7.65-7.51 (m, 5H), 7.45 (d, J=2.6 Hz, 1H), 7.16 (s, 1H), 6.40 (dd, J=2.7, 0.6 Hz, 1H), 6.12 (d, J=7.5 Hz, 1H), 4.97 (t, J=5.3 Hz, 1H), 4.85-4.76 (m, 1H), 4.22 (td, J=5.6, 3.9 Hz, 2H), 3.79 (q, J=5.3 Hz, 2H), 2.38 (s, 3H), 1.31 (d, J=6.7 Hz, 3H).

Example 101

(S)-2-(1-((5-(3-Amino-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Amino-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (36 mg, 0.06 mmol) was treated with trifluoroacetic acid (720 µl, 9.35 mmol) and a solution of ammonia (7N in methanol, 720 µl, 6.04 mmol) according to the method described in Example 27. The residue was purified using SP1® Purification System (0% to 20% dichloromethane-methanol) to obtain 22 mg (75% yield) of the title compound.

LRMS (m/z): 493 (M+1)+.

$^1$H NMR (400 MHz, DMSO-d6) δ 11.69 (bs, 1H), 9.11 (bs, 1H), 8.10 (s, 1H), 7.61-7.47 (m, 5H), 7.40 (d, J=2.6 Hz, 1H), 7.10 (d, J=1.9 Hz, 1H), 6.35 (d, J=2.6 Hz, 1H), 6.31 (d, J=8.1 Hz, 1H), 6.16-6.12 (m, 1H), 6.11-6.07 (m, 1H), 6.07-6.04 (m, 1H), 5.09 (bs, 2H), 4.80-4.69 (m, 1H), 2.35 (s, 3H), 1.30 (d, J=6.5 Hz, 3H).

Example 102

(S)—N-(3-Hydroxyphenyl)-4-((1-(5-methyl-4-oxo-3-phenyl-3,4-dihydropyrrolo[2,1-f][1,2,4]triazin-2-yl)ethyl)amino)pyrimidine-5-carboxamide (S)—N-(3-Methoxyphenyl)-4-((1-(5-methyl-4-oxo-3-phenyl-3,4-dihydropyrrolo[2,1-f][1,2,4]triazin-2-yl)ethyl)amino)pyrimidine-5-carboxamide (80 mg, 72% purity, 0.12 mmol) was treated with boron tribromide (1M in dichloromethane, 0.6 ml, 0.6 mmol) in dichloromethane (2 ml) according to the method described in Example 23. The residue was purified using SP1® Purification System (0% to 10%, DCM-MeOH) to give 8 mg (14% yield) as a solid. Purity 95%.

LRMS (m/z): 482 (M+1)$^+$ $^1$H NMR (400 MHz, CD$_3$OD) δ 8.57 (s, 1H), 8.31 (s, 1H), 7.45 (dd, J=6.9, 2.3 Hz, 1H), 7.36 (ddt, J=4.3, 3.0, 1.7 Hz, 4H), 7.32-7.27 (m, 1H), 7.13 (ddd, J=8.7, 4.5, 2.3 Hz, 2H), 7.05 (dt, J=8.5, 5.3 Hz, 1H), 6.97 (ddd, J=8.1, 2.0, 1.0 Hz, 1H), 6.87 (s, 1H), 6.51 (ddd, J=8.1, 2.4, 1.0 Hz, 1H), 6.29 (dd, J=2.7, 0.6 Hz, 1H), 4.95 (q, J=6.7 Hz, 1H), 4.48 (s, 1H), 4.19 (t, J=6.6 Hz, 1H), 2.36 (s, 2H), 1.38 (d, J=6.7 Hz, 3H).

Example 103

(S)—N-(3-Hydroxy-5-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-pyrazol-1-yl)phenyl)methanesulfonamide (S)—N-(3-Methoxy-5-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-pyrazol-1-yl)phenyl)methanesulfonamide (15 mg, 0.01 mmol) was treated with boron tribromide (1M in dichloromethane, 1 ml, 1 mmol) in dichloromethane (1 ml) and then with a solution of ammonia (7N in methanol, 10 ml, 70 mmol) according to the method described in Example 41 to give 4.2 mg (44% yield) of the title compound. Purity 92%.

LRMS (m/z): 638 (M+1)$^+$

Example 104

(S)-2-(1-((5-(3-Chloro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Chloro-2-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (58 mg, 0.07 mmol) was treated with trifluoroacetic acid (1.20 ml, 15.58 mmol) and a solution of ammonia (7N in methanol, 1.20 ml, 8.40 mmol) according to the method described in Example 27. The residue was purified using SP1® Purification System (0% to 5% dichloromethane-2-propanol) to obtain 8 mg (21% yield) of the title compound.

LRMS (m/z): 512 (M+1)+.

$^1$H NMR (400 MHz, DMSO-d6) δ 11.84 (bs, 1H), 9.38 (bs, 1H), 8.10 (s, 1H), 7.63-7.39 (m, 7H), 7.31-7.13 (m, 2H), 6.96 (bs, 1H), 6.40 (s, 1H), 5.94 (bs, 1H), 4.86-4.67 (m, 1H), 2.37 (s, 3H), 1.25 (d, J=6.3 Hz, 3H).

Example 105

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzamide To a solution of (S)-2-(1-((6-amino-5-bromopyrimidin-4-yl)amino)ethyl)-5-methyl-3-phenylpyrrolo[2,1-f][1,2,4]triazin-4(3H)-one (84 mg, 0.19 mmol) were added 4-hydroxy-N-(2-methoxy-5-(4,4,5,5-tetramethyl-1,3,2-dioxaborolan-2-yl)pyridin-3-yl)benzamide (85 mg, 0.23 mmol), 1,1'-bis(diphenylphosphino)ferrocene-palladium(II)dichloride dichloromethane complex (16 mg, 0.02 mmol) and 191 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1 ® Purification System (0 to 65%, hexane-ethyl acetate) to give 25 mg (22% yield) of the title compound as a white solid. Purity 100%.

LRMS (m/z): 604 (M+1)$^+$ $^1$H NMR (400 MHz, DMSO-d6) δ 9.20 (s, 1H), 7.82 (d, J=8.5 Hz, 2H), 7.77 (s, 1H), 7.51-7.28 (m, 7H), 6.86 (d, J=8.7 Hz, 2H), 6.33 (s, 1H), 5.75 (d, J=7.8 Hz, 1H), 5.61 (s, 2H), 4.80 (q, 1H), 4.01 (s, 3H), 2.32 (s, 3H), 1.21 (d, J=6.7 Hz, 3H).

Example 106

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide (S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-methoxybenzenesulfonamide (145 mg, 0.23 mmol) was treated with boron tribromide (1M in dichloromethane, 0.7 ml, 0.7 mmol) IN dichloromethane (5 ml) according to the method described in Example 23. The residue was purified by reverse phase using SP1® Purification System to give 40 mg (28% yield) as a solid. Purity 99%.

LRMS (m/z): 609 (M+1)$^+$ $^1$H NMR (400 MHz, DMSO-d6) δ 10.39 (s, 1H), 10.21 (s, 1H), 7.85 (s, 1H), 7.61 (s, 2H), 7.45 (d, J=8.6 Hz, 7H), 7.12 (s, 2H), 6.81 (d, J=7.7 Hz, 3H), 6.39 (s, 1H), 5.48 (s, 2H), 5.24 (s, 1H), 4.72 (s, 1H), 2.37 (s, 3H), 1.15 (d, J=5.6 Hz, 3H).

Example 107

(S)-2-(1-((5-(1-(2-(Dimethylamino)ethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(2-(Dimethylamino)ethyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (30 mg, 0.04 mmol) was treated with trifluoroacetic acid (1.5 mL, 19.47 mmol) and a solution of ammonia (7N in methanol, 2 mL, 14 mmol) according to the method described in Example 27 to give 17 mg (74% yield) of the title compound. Purity 99%.

LRMS (m/z): 523 (M+1)$^+$ $^1$H NMR (400 MHz, DMSO-d6) δ 11.75 (s, 1H), 8.12 (s, 1H), 7.95 (s, 1H), 7.69 (s, 1H), 7.62-7.50 (m, 4H), 7.47 (d, J=2.6 Hz, 1H), 7.14 (d, J=2.3 Hz, 1H), 6.41 (d, J=2.0 Hz, 1H), 6.02 (d, J=7.8 Hz, 1H), 4.92-4.76 (m, 1H), 4.27 (m, 2H), 2.70 (t, J=6.5 Hz, 2H), 2.38 (s, 3H), 2.16 (s, 6H), 1.30 (d, J=6.6 Hz, 3H).

Example 108

(S)—N-(5-(4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide (S)—N-(5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)methanesulfonamide (53 mg, 0.06 mmol) was treated with trifluoroacetic acid (1.05 ml, 13.63 mmol) and a solution of ammonia (7N in methanol, 1.05 ml, 7.35 mmol) according to the method described in Example 27. The residue was purified using SP1® Purification System (0% to 10% dichloromethane-2-propanol) to obtain 22 mg (68% yield) of the title compound.

LRMS (m/z): 556 (M+1)+.

$^1$H NMR (400 MHz, DMSO-d6) δ 12.05 (Bs, 1H), 10.12 (Bs, 1H), 8.55-8.49 (m, 1H), 8.45-8.40 (m, 1H), 8.14 (s, 1H), 7.68-7.63 (m, 1H), 7.58-7.43 (m, 5H), 7.42 (d, J=2.4 Hz, 1H), 7.32 (d, J=2.6 Hz, 1H), 6.42-6.35 (m, 1H), 6.13 (d, J=7.1 Hz, 1H), 4.93-4.81 (m, 1H), 3.08 (s, 3H), 2.37 (s, 3H), 1.32 (d, J=6.7 Hz, 3H).

Example 109

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)butane-1-sulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (120 mg, 0.27 mmol) were added N-(3-methoxy-5-(4,4,5,5-tetramethyl-1,3,2-dioxaborolan-2-yl)phenyl)butane-1-sulfonamide (121 mg, 0.33 mmol), 1,1'-bis(diphenylphosphino)ferrocene-palladium(II)dichloride dichloromethane complex (22 mg, 0.03 mmol) and 273 µl of a 2M aqueous solution of cesium carbonate in dioxane (5 ml). The mixture was stirred under argon atmosphere at 100° C.

for 18 hours and then diluted with ethyl acetate. The resulting solution was washed with water and brine, dried over magnesium sulphate, filtered and the solvents were removed under reduced pressure. The crude was purified using SP1® Purification System (0 to 80%, hexane-ethyl acetate) to give 130 mg (79% yield) of the title compound as a white solid. Purity 100%.

LRMS (m/z): 603 (M+1)$^+$ $^1$H NMR (400 MHz, DMSO-d6) δ 9.80 (s, 1H), 7.76 (s, 1H), 7.54-7.19 (m, 7H), 6.77 (s, 2H), 6.36 (d, J=2.6 Hz, 1H), 5.70-5.41 (m, 2H), 4.75 (q, 1H), 3.75 (s, 3H), 3.17-2.98 (m, 2H), 2.33 (d, J=13.3 Hz, 3H), 1.68-1.50 (m, 2H), 1.23-1.13 (m, J=14.9, 7.7 Hz, 2H), 0.86-0.63 (m, 3H).

Example 110

(S)-4-Hydroxy-N-(3-(4-((1-(5-methyl-4-oxo-3-phenyl-3,4-dihydropyrrolo[2,1-f][1,2,4]triazin-2-yl) ethyl)amino)-7H-pyrrolo[2,3-d]pyrimidin-5-yl)phenyl)benzenesulfonamide (S)-4-Methoxy-N-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)benzenesulfonamide (57 mg, 0.05 mmol) was treated with boron tribromide (1M in dichloromethane, 536 μL, 0.54 mmol) in dichloromethane (1.15 mL) and then with a solution of ammonia (7N in methanol, 1.15 ml, 6.05 mmol) according to the method described in Example 27. The residue was purified using SP1 ® Purification System (0% to 6% dichloromethane-2-propanol) to obtain 25 mg (72% yield) of the title compound.

LRMS (m/z): 623 (M+1)$^+$.

Example 111

(S)-4-Methoxy-N-(3-(4-((1-(5-methyl-4-oxo-3-phenyl-3,4-dihydropyrrolo[2,1-f][1,2,4]triazin-2-yl) ethyl)amino)-7H-pyrrolo[2,3-d]pyrimidin-5-yl)phenyl)benzenesulfonamide (S)-4-Methoxy-N-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)benzenesulfonamide (25 mg, 0.02 mmol) was treated with trifluoroacetic acid (500 μl, 6.49 mmol) and a solution of ammonia (7N in methanol, 500 μl, 3.50 mmol) according to the method described in Example 27. The residue was purified using SP1® Purification System (0% to 100% n-hexane-ethyl acetate) to obtain 13 mg (86% yield) of the title compound.

LRMS (m/z): 647 (M+1)+.

$^1$H NMR (400 MHz, DMSO-d6) δ 11.87 (bs, 1H), 10.31 (bs, 1H), 8.12 (s, 1H), 7.74-7.65 (m, 2H), 7.59-7.44 (m, 5H), 7.33 (t, 1H), 7.20 (s, 1H), 7.17-7.08 (m, 4H), 7.02-6.94 (m, 2H), 6.35 (d, J=2.7, 1H), 5.81 (d, J=7.1 Hz, 1H), 4.83-4.71 (m, 1H), 3.73 (s, 3H), 2.35 (s, 3H), 1.23 (d, J=6.4 Hz, 3H).

Example 112

(S)-2-(1-((5-(1-(3-(Dimethylamino)propyl)-1H-pyrazol-4-yl)-7H-pyrrolo[2,3-d]pyrimidin-4-yl)amino) ethyl)-5-methyl-3-phenylpyrrolo[2,1-f][1,2,4]triazin-4(3H)-one (S)-2-(1-((5-(1-(3-(Dimethylamino)propyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.05 mmol) was treated with trifluroacetic acid (2 ml, 26 mmol) and a solution of ammonia (7N in methanol, 5 ml, 35 mmol) according to the method decried in Example 27 to give 12 mg (42% yield) of the title compound. Purity 97%.

LRMS (m/z): 538 (M+1)$^+$ $^1$H NMR (400 MHz, DMSO-d6) δ 11.73 (d, J=2.0 Hz, 1H), 8.09 (s, 1H), 7.91 (d, J=0.6 Hz, 1H), 7.68 (d, J=0.7 Hz, 1H), 7.58-7.49 (m, 4H), 7.44 (d, J=2.6 Hz, 1H), 7.12 (d, J=2.3 Hz, 1H), 6.39 (dd, J=2.6, 0.7 Hz, 1H), 6.02 (d, J=7.7 Hz, 1H), 4.83 (p, J=6.4 Hz, 1H), 4.18 (td, J=6.9, 2.5 Hz, 2H), 2.36 (s, 3H), 2.22 (t, J=6.8 Hz, 2H), 2.11 (s, 6H), 1.99-1.89 (m, 2H), 1.28 (d, J=6.6 Hz, 3H)

Example 113

(S)-4-Amino-N-(3-hydroxy-4-(oxazol-5-yl)phenyl)-6-((1-(5-methyl-4-oxo-3-phenyl-3,4-dihydropyrrolo [2,1-f][1,2,4]triazin-2-yl)ethyl)amino)pyrimidine-5-carboxamide (S)-2-(1-Aminoethyl)-5-methyl-3-phenylpyrrolo[2,1-f] [1,2,4]triazin-4(3H)-one (100 mg, 0.37 mmol), 4-amino-6-bromo-N-(3-hydroxy-4-(oxazol-5-yl)phenyl)pyrimidine-5-carboxamide (220 mg, 0.58 mmol), DIEA (325 μl, 1.87 mmol) and cesium fluoride (113 mg, 0.74 mmol) were suspended in tert-butanol (10 ml) and the mixture was stirred overnight at 120° C. in a sealed tube. The reaction mixture was diluted with ethyl acetate and washed with water and brine. After evaporation of the solvent, the residue was purified by reverse phase using SP1® Purification System to give 3 mg (1% yield) of the title compound as a solid. Purity 97%.

LRMS (m/z): 564 (M+1)$^+$ $^1$H NMR (400 MHz, CDCl$_3$) δ 9.15 (s, 1H), 8.08 (s, 1H), 7.94 (s, 1H), 7.68 (dd, J=18.5, 9.6 Hz, 3H), 7.52 (ddt, J=8.6, 6.0, 3.9 Hz, 4H), 7.38-7.27 (m, 1H), 7.12 (d, J=2.6 Hz, 1H), 7.03-6.85 (m, 1H), 6.68 (d, J=7.9 Hz, 1H), 6.29 (d, J=2.2 Hz, 1H), 6.00 (d, J=1.3 Hz, 2H), 5.17-4.97 (m, 1H), 2.62 (s, 1H), 2.47 (s, 2H), 2.42 (d, J=4.8 Hz, 1H), 1.37 (d, J=6.8 Hz, 3H).

Example 114

(S)-2-(1-((6-Amino-5-(5-(trifluoromethyl)pyridin-3-yl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino) ethyl)-5-methyl-3-phenylpyrrolo[2,1-f][1,2,4]triazin-4(3H)-one (83 mg, 0.19 mmol) was treated with 3-(4,4,5,5-tetramethyl-1,3,2-dioxaborolan-2-yl)-5-(trifluoromethyl)pyridine (130 mg, 0.47 mmol, prepared according to J. Aebi et al US 20090048238 19 Feb. 2009), sodium carbonate (2M, 350 μl, 0.70 mmol) and 1,1'-bis(diphenylphosphino)ferrocene-palladium(II)dichloride dichloromethane complex (15 mg, 0.02 mmol) according to the method described in Example 3 to give 37 mg (39% yield) of the title compound. Purity 99%.

LRMS (m/z): 507 (M+1)$^+$ $^1$H NMR (400 MHz, CDCl$_3$) δ 9.00 (s, 1H), 8.88 (s, 1H), 8.16 (s, 1H), 8.05 (s, 1H), 7.63-7.45 (m, 4H), 7.34-7.27 (m, 1H), 7.11 (s, 1H), 6.31 (d, J=2.6 Hz, 1H), 5.00 (d, J=6.9 Hz, 1H), 4.73 (d, J=8.9 Hz, 1H), 4.45 (s, 2H), 2.47 (s, 3H), 1.21 (dd, J=6.9, 1.2 Hz, 3H).

Example 115

(S)—N-(3-(2-(Dimethylamino)ethoxy)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (6 mg, 0.01 mmol) was dissolved in 120 μl N,N-dimethylformamide. Sodium carbonate (8 mg, 0.07 mmol) and 2-chloro-N,N-dimethylethanaminium chloride (4 mg, 0.03 mmol) were added and the mixture was stirred at 50° C. overnight. The reaction was poured into water and extracted twice with ethyl acetate. The organics were combined and washed with brine, dried over sodium sulphate, filtered and evaporated under reduced pressure. The residue was purified using SP1® Purification System (0% to 100%, dichloromethane-dichloromethane/2-propanol 85:15) to give 4 mg (56% yield) of the title compound.

LRMS (m/z): 642 (M+1)$^+$.

$^1$H NMR (400 MHz, DMSO-d6) δ 11.90 (bs, 1H), 9.98 (bs, 1H), 8.14 (s, 1H), 7.58-7.44 (m, 5H), 7.31-7.25 (m, 2H), 7.00-6.94 (m, 1H), 6.93-6.89 (m, 1H), 6.85-6.79 (m, 1H), 6.35 (d, J=2.1 Hz, 1H), 5.93 (d, J=7.5 Hz, 1H), 4.90-4.79 (m, 1H), 3.68 (t, J=6.9 Hz, 2H), 3.01 (s, 3H), 2.34 (s, 3H), 2.27 (t, J=6.9 Hz, 2H), 2.07 (s, 6H), 1.29 (d, J=6.6 Hz, 3H).

Example 116

(S)-2-(1-((6-Amino-5-(1-(2-hydroxyethyl)-1H-pyrazol-4-yl)pyrimidin-4-yl)amino)ethyl)-5-methyl-3-phenylpyrrolo[2,1-f][1,2,4]triazin-4(3H)-one (S)-2-(1-((6-Amino-5-iodopyrimidin-4-yl)amino)ethyl)-5-methyl-3-phenylpyrrolo[2,1-f][1,2,4]triazin-4(3H)-one (70 mg, 0.12 mmol) was treated with 2-(4-(4,4,5,5-tetramethyl-1,3,2-dioxaborolan-2-yl)-1H-pyrazol-1-yl)ethanol (66 mg, 0.28 mmol, prepared according to Perry, Benjamin Garfield; Sabin, Verity Margaret from PCT Int. Appl. (2009), WO 2009122148 A1 20091008), sodium carbonate (2M, 565 μl, 1.13 mmol) and 1,1'-bis(diphenylphosphino)ferrocene-palladium(II)dichloride dichloromethane complex (13 mg, 0.02 mmol) according to the method described in Example 3 to give 5 mg (8% yield) of the title compound. Purity 92%.

LRMS (m/z): 472 (M+1)$^+$ $^1$H NMR (400 MHz, CDCl$_3$) δ 8.02 (s, 1H), 7.65 (t, J=2.1 Hz, 1H), 7.60 (d, J=4.3 Hz, 1H), 7.57-7.44 (m, 4H), 7.28 (dt, J=3.6, 2.1 Hz, 1H), 7.17 (t, J=3.1 Hz, 1H), 6.35-6.25 (m, 1H), 5.13-4.90 (m, 2H), 4.53 (s, 1H), 4.39-4.33 (m, 2H), 4.25 (dd, J=9.2, 4.5 Hz, 1H), 4.11 (dd, J=9.7, 4.7 Hz, 2H), 4.02 (dd, J=8.8, 3.9 Hz, 1H), 2.48 (s, 3H), 1.27 (t, J=5.3 Hz, 3H).

Example 117

(S)-2-(1-((6-Amino-5-(3-hydroxy-5-(trifluoromethoxy)phenyl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino)ethyl)-5-methyl-3-phenylpyrrolo[2,1-f][1,2,4]triazin-4(3H)-one (82 mg, 0.19 mmol) was treated with 3-hydroxy-5-(trifluoromethoxy)phenylboronic acid (124 mg, 0.56 mmol), sodium carbonate (2M, 375 μl, 0.75 mmol) and 1,1'-bis(diphenylphosphino)ferrocene-palladium(II)dichloride dichloromethane complex (15 mg, 0.02 mmol) according to the method described in Example 3 to give 52 mg (51% yield) of the title compound. Purity 98%.

LRMS (m/z): 538 (M+1)$^+$ $^1$H NMR (400 MHz, DMSO-d6) δ 10.17 (s, 1H) 7.78 (s, 1H), 7.50-7.25 (m, 6H), 6.69 (d, J=0.9 Hz, 3H), 6.42-6.31 (m, 1H), 5.67-5.49 (m, 3H), 4.75 (p, J=6.7 Hz, 1H), 2.35 (s, 3H), 1.19 (d, J=6.7 Hz, 3H).

Example 118

(S)-4-Amino-N-(4-(3-(dimethylamino)propoxy)-3-hydroxyphenyl)-6-((1-(8-methyl-1-oxo-2-phenyl-1,2-dihydropyrrolo[2,1-f][1,2,4]triazin-3-yl)ethyl)amino)pyrimidine-5-carboxamide (S)-4-Amino-6-((1-(8-methyl-1-oxo-2-phenyl-1,2-dihydropyrrolo[2,1-f][1,2,4]triazin-3-yl)ethyl)amino)pyrimidine-5-carboxylic acid (50 mg, 0.11 mmol) was dissolved in 3 mL dimethylformamide. N,N-Diisopropylethylamine (43 μl, 0.25 mmol) and HATU (85 mg, 0.22 mmol) were added and was stirred at room temperature for 30 min. 5-Amino-2-(3-(dimethylamino)propoxy)phenol (75 mg, 0.22 mmol) was added. The reaction mixture was stirred at room temperature overnight and then diluted with water and extracted with ethyl acetate. The organic was washed with water, brine, dried over sodium sulphate and concentrated under reduced pressure. The semi-solid was purified by reverse phase using SP1® Purification System to obtain 19 mg (29% yield) of the title compound. Purity 100%.

LRMS (m/z): 598 (M+1)$^+$ $^1$H NMR (400 MHz, CDCl$_3$) δ 8.76 (s, 1H), 8.37 (s, 1H), 8.02 (s, 1H), 7.65-7.44 (m, 4H), 7.32 (dt, J=12.2, 6.0 Hz, 1H), 7.14 (ddd, J=22.1, 14.0, 2.5 Hz, 3H), 6.87 (d, J=8.6 Hz, 1H), 6.61 (d, J=8.3 Hz, 1H), 6.30 (d, J=2.7 Hz, 1H), 6.16 (s, 1H), 5.08 (dd, J=14.3, 7.3 Hz, 1H), 4.06-3.99 (m, 3H), 2.99 (t, J=6.7 Hz, 2H), 2.61 (d, J=5.9 Hz, 6H), 2.50 (d, J=15.5 Hz, 3H), 2.20-2.05 (m, 2H), 1.38 (t, J=9.3 Hz, 3H).

Example 119

3-((S)-1-((6-Amino-5-((S)-3-hydroxypyrrolidine-1-carbonyl)pyrimidin-4-yl)amino)ethyl)-8-methyl-2-phenylpyrrolo[2,1-f][1,2,4]triazin-1 (2H)-one (S)-4-Amino-6-((1-(8-methyl-1-oxo-2-phenyl-1,2-dihydropyrrolo[2,1-f][1,2,4]triazin-3-yl)ethyl)amino)pyrimidine-5-carboxylic acid (50 mg, 0.11 mmol) was dissolved in 3 ml dimethylformamide. N,N-Diisopropylethylamine (86 μl, 0.49 mmol) and HATU (85 mg, 0.22 mmol) were added and the mixture was stirred at room temperature for 30 min. Then, (S)-Pyrrolidin-3-ol (HCl, 22 mg, 0.18 mmol) was added. The reaction mixture was stirred at room temperature overnight and then diluted with water and extracted with ethyl acetate. The organic layer was washed with water, brine, dried over sodium sulphate and concentrated under reduced pressure. The semi-solid was purified by reverse phase using SP1® Purification System to obtain 20 mg (34% yield) of the title compound. Purity 99%.

LRMS (m/z): 475 (M+1)$^+$ $^1$H NMR (400 MHz, DMSO-d6) δ 7.80 (d, J=3.8 Hz, 1H), 7.58-7.26 (m, 6H), 6.37 (d, J=2.6 Hz, 1H), 6.28 (s, 1H), 6.16 (s, 1H), 4.99 (s, 1H), 4.64 (s, 1H), 4.25 (d, J=15.1 Hz, 1H), 3.57 (dd, J=19.3, 8.2 Hz, 1H), 3.42 (s, 2H), 2.33 (d, J=20.5 Hz, 3H), 1.84 (d, J=71.7 Hz, 3H), 1.27 (d, J=6.7 Hz, 3H), 1.09 (s, 1H).

Example 120

(S)-2-(1-((5-(5-(Ethylamino)-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one To a suspension of (S)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid (50 mg, 0.12 mmol) and N-ethylhydrazinecarbothioamide (21 mg, 0.18 mmol) in 1 ml 1,4-dioxane was added phosphorus (V) oxychloride (12.5 µL, 0.13 mmol). The mixture was stirred at 80° C. overnight. The solvent was evaporated and the residue was poured into water and ethyl acetate. The mixture was basified to pH 10 with sodium carbonate and extracted twice with ethyl acetate. The organics were combined and washed with water, brine, dried over sodium sulphate, filtered and evaporated under reduced pressure. The residue was precipitated using diethyl ether, filtered, washed with cold diethyl ether and dried in a vacuum oven to obtain 14 mg (29% yield) of the title compound.

LRMS (m/z): 513 (M+1)$^+$.
$^1$H NMR (400 MHz, DMSO-d6) δ 12.08 (s, 1H), 9.99 (d, J=6.3 Hz, 1H), 8.07 (s, 1H), 7.82 (t, J=5.4 Hz, 1H), 7.68 (s, 1H), 7.59 (d, J=2.6 Hz, 1H), 7.57-7.51 (m, 3H), 7.45 (dd, J=6.4, 3.5 Hz, 2H), 6.36 (d, J=2.1 Hz, 1H), 4.78-4.66 (m, 1H), 3.40-3.32 (m, 2H), 2.36 (s, 3H), 1.40 (d, J=6.7 Hz, 3H), 1.20 (t, J=7.2 Hz, 3H).

Example 121

(S)-2-(1-((6-Amino-5-(5-(difluoromethyl)pyridin-3-yl)pyrimidin-4-yl)amino)ethyl)-5-methyl-3-phenylpyrrolo[2,1-f][1,2,4]triazin-4(3H)-one (S)-2-(1-((6-Amino-5-bromopyrimidin-4-yl)amino)ethyl)-5-methyl-3-phenylpyrrolo[2,1-f][1,2,4]triazin-4(3H)-one (81 mg, 0.18 mmol) was treated with 3-(difluoromethyl)-5-(4,4,5,5-tetramethyl-1,3,2-dioxaborolan-2-yl)pyridine (237 mg, 0.93 mmol, prepared according to WO2012/087237), sodium carbonate (2M, 700 µl, 1.40 mmol) and 1,1-bis(diphenylphosphino)ferrocene-palladium(II)dichloride dichloromethane complex (20 mg, 0.02 mmol) according to the method described in Example 3 to give 3 mg (3% yield) of the title compound. Purity 98%.

LRMS (m/z): 489 (M+1)$^+$
$^1$H NMR (400 MHz, CDCl$_3$) δ 8.88 (s, 1H), 8.81 (s, 1H), 8.15 (s, 1H), 7.98 (s, 1H), 7.54 (m, 2H), 7.28 (d, J=17.1 Hz, 1H), 7.15 (s, 1H), 6.99 (s, 1H), 6.83 (s, 1H), 6.69 (s, 1H), 6.31 (s, 1H), 5.01 (m, 1H), 4.72 (d, J=9.2 Hz, 1H), 4.47 (s, 2H), 2.48 (s, 3H), 1.21 (d, J=6.8 Hz, 3H).

Example 122

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-1,1,1-trifluoromethanesulfonamide (S)-2-(1-((6-Amino-5-iodopyrimidin-4-yl)amino)ethyl)-5-methyl-3-phenylpyrrolo[2,1-f][1,2,4]triazin-4(3H)-one (70 mg, 0.14 mmol) was treated with 1,1,1-trifluoro-N-(3-(4,4,5,5-tetramethyl-1,3,2-dioxaborolan-2-yl)phenyl)methanesulfonamide (124 mg, 0.22 mmol, prepared according to WO 2012013727 A1 20120202), sodium carbonate (2M, 215 µl, 0.43 mmol) and 1,1'-bis(diphenylphosphino)ferrocene-palladium(II)dichloride dichloromethane complex (8.3 mg, 0.01 mmol) according to the method described in Example 3 to give 35 mg (42% yield) of the title compound. Purity 99%.

LRMS (m/z): 585 (M+1)$^+$
$^1$H NMR (400 MHz, DMSO-d6) δ 7.95 (s, 1H), 7.61-7.26 (m, 7H), 7.14 (d, J=7.3 Hz, 2H), 6.92 (s, 2H), 6.37 (d, J=1.9 Hz, 1H), 6.18 (s, 3H), 4.86 (s, 1H), 2.34 (s, 3H), 1.21 (d, J=6.3 Hz, 3H).

Example 123

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-hydroxybenzenesulfonamide (S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-methoxybenzenesulfonamide (25 mg, 0.04 mmol) was treated with boron tribromide (1M in dichloromethane, 118 µl, 0.12 mmol) in dichloromethane (3 ml) according to the method described in Example 23. The residue was purified by reverse phase using SP1® Purification System to give 10 mg (38% yield) as a solid. Purity 93%.

LRMS (m/z): 625 (M+1)$^+$
$^1$H NMR (400 MHz, CD$_3$OD) δ 7.86 (s, 2H), 7.46 (ddd, J=84.3, 45.5, 37.9 Hz, 8H), 6.92-6.19 (m, 7H), 4.88 (dd, J=9.7, 4.0 Hz, 1H), 4.80 (s, 1H), 2.72-2.58 (m, 2H), 2.43 (d, J=4.0 Hz, 3H), 1.25 (t, J=11.7 Hz, 3H).

Example 124

((S)-2-(1-((6-Amino-5-(5-hydroxypyridin-3-yl)pyrimidin-4-yl)amino)ethyl)-3-phenylpyrrolo[2,1-f][1,2,4]triazin-4(3H)-one To a solution of (S)-2-(1-((6-amino-5-iodopyrimidin-4-yl)amino)ethyl)-5-methyl-3-phenylpyrrolo[2,1-f][1,2,4]triazin-4(3H)-one (183 mg, 0.31 mmol) was added 5-(4,4,5,5-tetramethyl-1,3,2-dioxaborolan-2-yl)pyridin-3-ol (102 mg, 0.46 mmol), (1,1-bis(diphenylphosphino)ferrocene-palladium(II)dichloride dichloromethane complex 25 mg, 0.03 mmol) and a 2M aqueous solution of cesium carbonate in dioxane (462 µl). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by flash chromatography (0% to 100% hexane/AcOEt, 0-8% AcOEt/MeOH) to give 56 mg (40% yield) of the title compound as a white solid.

LRMS (m/z): 441 (M+1)$^+$.
$^1$H NMR (400 MHz, DMSO-d6) δ 9.98 (s, 1H), 8.11 (d, J=2.7 Hz, 1H), 7.83 (s, 1H), 7.77 (s, 1H), 7.46-7.27 (m, 5H), 6.97 (s, 1H), 6.36 (dd, J=2.6, 0.6 Hz, 1H), 5.68 (d, J=7.6 Hz, 1H), 5.59 (s, 1H), 4.76 (q, 1H), 2.34 (s, 3H), 1.21-1.16 (m, 2H).

Example 125

(S)-4-Hydroxy-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide (S)—N-(3-Hydroxy-5-(4-((1-(5-methyl-4-oxo-3-phenyl-3,4-dihydropyrrolo[2,1-f][1,2,4]triazin-2-yl)ethyl)amino)-

7-((2-(trimethylsilyl)ethoxy)methyl)-7H-pyrrolo[2,3-d]pyrimidin-5-yl)phenyl)-4-methoxybenzenesulfonamide (40 mg, 0.04 mmol) was treated with boron tribromide (1M in dichloromethane, 388 µl, 0.39 mmol) in dichloromethane (800 µl) and then with a solution of ammonia (7N in methanol, 800 µl, 5.60 mmol) according to the method described in Example 41. The residue was purified using SP1® Purification System (0% to 10% dichloromethane-2-propanol) to obtain 3 mg (11% yield, 88% purity) of the title compound.
LRMS (m/z): 649 (M+1)+.

Example 126

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-hydroxybenzenesulfonamide (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-methoxybenzenesulfonamide (132 mg, 0.11 mmol) was treated with boron tribromide (1M in dichloromethane, 337 µl, 0.34 mmol) in dichloromethane (10 ml) according to the method described in Example 23. The residue was purified by reverse phase using SP1® Purification System to give 10 mg (15% yield) as a solid. Purity 99%.
LRMS (m/z): 610 (M+1)+
$^1$H NMR (400 MHz, CD$_3$OD) δ 8.41-8.09 (m, 2H), 7.89 (s, 1H), 7.65 (dd, J=19.8, 10.3 Hz, 2H), 7.58-7.28 (m, 6H), 6.81 (d, J=8.8 Hz, 2H), 6.36 (t, J=9.4 Hz, 1H), 4.92 (dd, J=13.5, 6.7 Hz, 2H), 3.32-3.28 (m, 4H), 2.48-2.37 (m, 3H), 2.01 (d, J=8.4 Hz, 1H), 1.34-1.18 (m, 3H).

Example 127

(S)-2-(1-((6-Amino-5-(5-(difluoromethoxy)pyridin-3-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (75 mg, 0.17 mmol) were added 48 mg (0.26 mmol) of (5-(difluoromethoxy)pyridin-3-yl)boronic acid, 13 mg (0.02 mmol) of 1,1'-bis(diphenylphosphino)ferrocene-palladium(II)dichloride dichloromethane complex and 170 µl of a 2M aqueous solution of cesium carbonate in dioxane. The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by flash chromatography (0% to 100% hexane/AcOEt, 0-8% AcOEt/MeOH) to give 70 mg (81% yield) of the title compound as a white solid.
LRMS (m/z): 505 (M+1)+
$^1$H NMR (400 MHz, DMSO-d6) δ ppm 1.20 (d, 3H) 2.27-2.38 (m, 3H) 4.76 (q, 1H) 5.71-5.81 (m, 2H) 5.92 (d, 1H) 6.32-6.39 (m, 1H) 7.27-7.52 (m, 7H) 7.76-7.84 (m, 1H) 8.21-8.30 (m, 1H) 8.41-8.50 (m, 1H)

Example 128

(S)-4-Amino-6-((1-(5-(6-(4-isopropylpiperazin-1-yl)-6-oxohex-1-yn-1-yl)-4-oxo-3-phenyl-3,4-dihydropyrrolo[2,1-f][1,2,4]triazin-2-yl)ethyl)amino)pyrimidine-5-carbonitrile To a solution of (S)-2-(1-aminoethyl)-5-(6-(4-isopropylpiperazin-1-yl)-6-oxohex-1-yn-1-yl)-3-phenylpyrrolo[2,1-f][1,2,4]triazin-4(3H)-one (120 mg, purity 10%, 0.03 mmol) and 4-amino-6-chloropyrimidine-5-carbonitrile (6 mg, 0.04 mmol) in tert-butanol (3 ml) was added DIEA (44 µl, 0.25 mmol) and the reaction mixture was stirred at 120° C. for 2 days. The solvent was removed under reduced pressure. Ethyl acetate was added and the organic phase was washed with water and brine, dried over magnesium sulphate, filtered and the solvents were removed under reduced pressure. The product was purified by flash chromatography using SP1® Purification System (0% to 100% hexane/AcOEt, 0-8% AcOEt/MeOH) to give 4 mg (25% yield) of the title compound as a white solid. Purity 96%.
LRMS (m/z): 593 (M+1)+
$^1$H NMR (400 MHz, CDCl$_3$) δ ppm 1.03 (d, 6H) 1.40 (d, J=7.03 Hz, 3H) 1.85-1.94 (m, 2H) 2.34 (t, 2H) 2.51 (t, 4H) 2.56-2.63 (m, 2H) 3.45-3.74 (m, J=46.89 Hz, 4H) 4.93-5.04 (m, 1H) 5.35 (s, 2H) 5.72 (d, J=7.82 Hz, 1H) 6.57 (d, J=2.74 Hz, 1H) 7.26-7.27 (m, 1H) 7.30 (d, J=7.42 Hz, 1H) 7.40-7.48 (m, 1H) 7.47-7.63 (m, 3H) 8.07 (s, 1H)

Example 129

(S)-2-(1-((5-((5-Fluoro-2-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((5-Fluoro-2-methoxyphenyl)thio)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (63 mg, 0.09 mmol) was treated with boron tribromide (1M in dichloromethane, 938 µl, 0.94 mmol) in dichloromethane (1.30 ml) and then with a solution of ammonia (7N in methanol, 1.30 ml, 9.10 mmol) according to the method described in Example 41. The residue was purified using SP1® Purification System (0% to 10% dichloromethane-2-propanol) to obtain 33 mg (64% yield) of the title compound.
LRMS (m/z): 528 (M+1)+.
$^1$H NMR (400 MHz, DMSO-d6) δ 12.22 (bs, 1H), 10.25 (bs, 1H), 8.09 (s, 1H), 7.65-7.56 (m, 1H), 7.55-7.34 (m, 5H), 7.22 (d, J=2.5 Hz, 1H), 6.83-6.66 (m, 3H), 6.36 (d, J=2, 5 Hz, 1H), 6.27 (d, J=10.0 Hz, 1H), 4.84-4.67 (m, 1H), 2.35 (s, 3H), 1.16 (d, J=6.5 Hz, 3H).

Example 130

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-2,4-difluorobenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (80 mg, 0.18 mmol) was treated with 2,4-difluoro-N-(3-hydroxy-5-(4,4,5,5-tetramethyl-1,3,2-dioxaborolan-2-yl)phenyl)benzenesulfonamide (180 mg, 0.37 mmol), sodium carbonate (2M, 200 µl, 0.40 mmol) and 1,1'-bis(diphenylphosphino)ferrocene-palladium(II)dichloride dichloromethane complex (30 mg, 0.04 mmol) according to the method described in Example 3 to give 10 mg (8% yield) of the title compound. Purity 94%.
LRMS (m/z): 645 (M+1)+
$^1$H NMR (400 MHz, CD$_3$OD) δ 7.90 (s, 1H), 7.81 (d, J=15.4 Hz, 1H), 7.72-7.60 (m, 1H), 7.60-7.30 (m, 7H), 7.25 (s, 1H), 7.11-6.92 (m, 2H), 6.79 (s, 1H), 6.61 (dd, J=39.0, 22.2 Hz, 2H), 6.38 (d, J=16.7 Hz, 2H), 2.43 (s, 3H), 1.25 (d, J=6.4 Hz, 3H).

Example 131

(S)-5-Methyl-2-(1-((5-(2-methyloxazol-5-yl)-7H-pyrrolo[2,3-d]pyrimidin-4-yl)amino)ethyl)-3-phenylpyrrolo[2,1-f][1,2,4]triazin-4(3H)-one (S)-5-Methyl-2-(1-((5-(2-methyloxazol-5-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (31 mg, 0.05 mmol) was treated with trifluoroacetic acid (1 ml, 13 mmol) and a solution of ammonia (7N in methanol, 2 ml, 14 mmol) according to the method described in Example 27 to give 22.5 mg (87% yield) of the title compound. Purity 94%.

LRMS (m/z): 467 (M+1)$^+$ $^1$H NMR (400 MHz, DMSO-d6) δ 12.10 (s, 1H), 8.10 (m, 1H), 7.59 (m, 1H), 7.52 (m, 3H), 7.42 (m, 3H), 7.23 (s, 1H), 6.80 (m, 1H), 6.38 (m, 1H), 4.94-4.84 (m, 1H), 2.44 (s, 3H), 2.37 (s, 3H), 1.41 (d, J=6.7 Hz, 3H).

Example 132

(S)-2-(1-((6-Amino-5-(5-(2,2,2-trifluoroethoxyl)pyridin-3-yl)pyrimidin-4-yl)amino)ethyl)-5-methyl-3-phenylpyrrolo[2,1-f][1,2,4]triazin-4(3H)-one A mixture of (S)-2-(1-((6-amino-5-(5-hydroxypyridin-3-yl)pyrimidin-4-yl)amino)ethyl)-5-methyl-3-phenylpyrrolo[2,1-f][1,2,4]triazin-4(3H)-one (49 mg, 0.11 mmol), 1,1,1-trifluoro-2-iodoethane (13 μl, 0.13 mmol) and potassium carbonate (30 mg, 0.22 mmol) in N,N-dimethylformamide (3 ml) was stirred at 120° C. under microwave irradiation for 2 h. Further 1,1,1-trifluoro-2-iodoethane (13 μl, 0.13 mmol) and potassium carbonate (15 mg, 0.11 mmol) were added and the reaction mixture was stirred at 120° C. under microwave irradiation for 2 h. The residue was purified by reverse phase using SP1® Purification System to give 32 mg (55% yield) as a solid. Purity 100%.

LRMS (m/z): 537 (M+1)$^+$ $^1$H NMR (400 MHz, DMSO-d6) δ 8.37 (d, J=2.9 Hz, 1H), 8.08 (s, 1H), 7.81 (s, 1H), 7.49-7.33 (m, 7H), 6.36 (dd, J=2.6, 0.6 Hz, 1H), 5.80 (d, J=7.5 Hz, 1H), 5.73 (s, 2H), 4.85 (d, J=8.8 Hz, 2H), 4.75 (q, 1H), 2.34 (s, 3H), 1.20 (d, J=6.7 Hz, 3H).

Example 133

(S)-2-(1-((5-(1-(2-Hydroxyethyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(2-Hydroxyethyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (30 mg, 0.05 mmol) was treated with trifluoroacetic acid (1 ml, 13 mmol) and a solution of ammonia (7N in methanol, 2 ml, 14 mmol) according to the method described in Example 27 to give 23.8 mg (100% yield) of the title compound. Purity 98%.

LRMS (m/z): 496 (M+1)$^+$ $^1$H NMR (400 MHz, DMSO-d6) δ 11.69 (s, 1H), 10.11 (d, J=6.3 Hz, 1H), 7.94 (s, 1H), 7.68 (m, 1H), 7.59 (d, J=2.5 Hz, 1H), 7.52 (m, 2H), 7.47 (m, 1H), 7.45-7.35 (m, 2H), 7.26 (t, J=7.8 Hz, 1H), 6.60 (d, J=2.2 Hz, 1H), 6.38 (d, J=2.5 Hz, 1H), 4.89 (m, 1H), 4.80 (m, 1H), 3.97 (m, 2H), 3.68-3.56 (m, 2H), 2.37 (s, 3H), 1.46 (d, J=6.6 Hz, 3H).

Example 134

(S)-2-(1-((5-(5-Amino-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one (S)-4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylic acid (50 mg, 0.12 mmol) was treated with hydrazinecarbothioamide (20 mg, 0.22 mmol) and phosphorus (V) oxychloride (12.5 μl, 0.13 mmol) in 1,4-dioxane (1 ml) according to the method described in Example 120 but stirring at 110° C. overnight. The residue was purified using SP1® Purification System (reverse phase, 0% to 100%, water-methanol/acetonitrile 1:1) to give 11 mg (19% yield) of the title compound.

LRMS (m/z): 485 (M+1)$^+$.

$^1$H NMR (400 MHz, DMSO-d6) δ 10.40 (d, J=6.3 Hz, 1H), 9.98 (d, J=6.5 Hz, 1H), 9.20 (s, 1H), 8.05 (d, J=1.4 Hz, 1H), 7.67 (d, J=1.4 Hz, 1H), 7.56 (m, 3H), 7.47-7.36 (m, 2H), 7.31 (s, 1H), 6.40-6.30 (m, 1H), 4.72 (m, 1H), 2.34 (s, 3H), 1.40 (dd, J=6.7, 4.3 Hz, 3H).

Example 135

(S)-2-(1-((6-Amino-5-(3-(difluoromethyl)-5-hydroxyphenyl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (65 mg, 0.15 mmol) were added 3-(difluoromethyl)-5-(4,4,5,5-tetramethyl-1,3,2-dioxaborolan-2-yl)phenol (91 mg, 0.15 mmol), 1,1'-bis(diphenylphosphino)ferrocene-palladium(II)dichloride dichloromethane complex (12 mg, 0.01 mmol) and 147 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 48 mg (64% yield) as a solid. Purity 99%.

LRMS (m/z): 504 (M+1)$^+$.

$^1$H NMR (400 MHz, DMSO-d6) δ ppm 1.18 (d, J=4.69 Hz, 3H) 2.35 (s, 3H) 4.77 (q, 1H) 5.44-5.60 (m, 2H) 6.38 (s, 1H) 6.67-6.88 (m, 2H) 6.94 (s, 1H) 7.27-7.53 (m, 4H) 7.80 (s, 1H) 10.00 (s, 1H)

Example 136

(S)—N-(4-(4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide (S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)methanesulfonamide (87 mg, 0.12 mmol) was treated with trifluoroacetic acid (2.5 ml, 32 mmol) and a solution of ammonia (7N in methanol, 1.25 ml, 17 mmol) according to the method described in Example 27. The residue was purified using SP1® Purification System (0% to 50% dichloromethane-2-propanol) to obtain 60 mg (80% yield) of the title compound. Purity 95%.

LRMS (m/z): 594 (M+1)⁺.

¹H NMR (400 MHz, DMSO-d6) δ ppm 1.00-1.08 (m, 3H) 2.35 (s, 3H) 2.93 (s, 3H) 4.72 (t, 1H) 5.83 (d, J=7.03 Hz, 1H) 6.31-6.39 (m, J=2.34 Hz, 2H) 6.96 (s, 1H) 7.13 (d, J=2.74 Hz, 1H) 7.29 (d, J=2.34 Hz, 1H) 7.35 (d, J=2.74 Hz, 1H) 7.44 (s, 1H) 7.47-7.58 (m, 5H) 8.14 (s, 1H) 9.55 (s, 1H) 11.28 (s, 1H) 11.90 (s, 1H)

Example 137

(S)-2-(1-((6-Amino-5-(2-methoxy-6-(trifluoromethyl)pyridin-4-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (70 mg, 0.16 mmol) were added (2-methoxy-6-(trifluoromethyl)pyridin-4-yl)boronic acid (53 mg, 0.24 mmol), 1,1'-bis(diphenylphosphino)ferrocene-palladium(II) dichloride dichloromethane complex (12 mg, 0.01 mmol) and 159 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 72 mg (82% yield) of the title compound as a white solid. Purity 98%.

LRMS (m/z): 537 (M+1)⁺.

¹H NMR (400 MHz, CDCl₃) δ ppm 1.25 (d, J=3.52 Hz, 3H) 2.49 (s, 3H) 4.09 (s, 3H) 4.50 (s, 2H) 4.93 (d, J=8.99 Hz, 1H) 5.03 (q, J=7.03 Hz, 1H) 6.34 (d, J=1.95 Hz, 1H) 6.98-7.11 (m, 1H) 7.18 (s, 1H) 7.30 (d, J=6.64 Hz, 1H) 7.34-7.45 (m, 1H) 7.47-7.64 (m, 4H) 8.13 (s, 1H)

Example 138

(S)—N-Methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide (S)—N-Methyl-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzenesulfonamide (76 mg, 0.08 mmol) was treated with trifluoroacetic acid (1.52 ml, 18.73 mmol) and a solution of ammonia (7N in methanol, 1.52 ml, 10.64 mmol) according to the method described in Example 27. The residue was purified using SP1® Purification System (0% to 15% dichloromethane-2-propanol) to obtain 34 mg (71% yield) of the title compound.

LRMS (m/z): 555 (M+1)+.

¹H NMR (400 MHz, DMSO-d6) δ 12.03 (bs, 1H), 8.17 (s, 1H), 7.92-7.87 (m, 1H), 7.87-7.76 (m, 3H), 7.72 (t, J=7.7 Hz, 1H), 7.60-7.45 (m, 5H), 7.42 (s, 1H), 7.21 (d, J=2.6 Hz, 1H), 6.35 (d, J=2.6 Hz, 1H), 5.84 (d, J=7.3 Hz, 1H), 4.87-4.76 (m, 1H), 2.44 (s, 3H), 2.35 (s, 3H), 1.30 (d, J=6.7 Hz, 3H).

Example 139

(S)-2-(1-((5-(1H-Pyrrolo[2,3-b]pyridin-5-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1H-Pyrrolo[2,3-b]pyridin-5-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (51 mg, 0.08 mmol) was treated with trifluoroacetic acid (2 ml, 25 mmol) and a solution of ammonia (7N in methanol, 2 ml, 14 mmol) according to the method described in Example 27. The residue was purified using SP1® Purification System (0% to 50% dichloromethane-2-propanol) to obtain 18 mg (44% yield) of the title compound. Purity 100%.

LRMS (m/z): 502 (M+1)+.

¹H NMR (400 MHz, DMSO-d6) δ ppm 1.1 (m, 3H) 2.35 (s, 3H) 3.04-3.11 (m, 1H) 4.80-4.91 (m, 1H) 5.95 (d, J=5.86 Hz, 1H) 6.33 (s, 1H) 6.49 (s, 1H) 6.92 (s, 1H) 7.26-7.33 (m, J=1.56 Hz, 1H) 7.49-7.61 (m, 3H) 8.05-8.17 (m, 2H) 8.43 (s, 1H) 11.86 (d, J=20.71 Hz, 2H)

Example 140

(S)-2-(1-((5-(1-(3-Hydroxypropyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(3-((tert-Butyldimethylsilyl)oxy)propyl)-1H-pyrazol-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (124 mg, 0.14 mmol) was treated with trifluoroacetic acid (1 ml, 13 mmol) and a solution of ammonia (7N in methanol, 2 ml, 14 mmol) according to the method described in Example 27 to give 48 mg (68% yield) of the title compound. Purity 99%.

LRMS (m/z): 510 (M+1)⁺

¹H NMR (400 MHz, DMSO-d6) δ 11.74 (s, 1H), 8.10 (s, 1H), 7.92 (s, 1H), 7.69 (s, 1H), 7.61-7.49 (m, 5H), 7.44 (d, J=2.6 Hz, 1H), 7.13 (d, J=2.3 Hz, 1H), 6.40 (d, J=2.5 Hz, 1H), 6.03 (d, J=7.5 Hz, 1H), 4.89-4.78 (m, 1H), 4.61 (t, J=5.0 Hz, 1H), 4.23 (m, 2H), 3.42 (q, J=6.1 Hz, 2H), 2.37 (s, 3H), 2.03-1.90 (m, 2H), 1.29 (d, J=6.6 Hz, 3H).

Example 141

(S)—N-(5-(4-amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-2,4-difluorobenzenesulfonamide (S)-2-(1-(6-Amino-5-bromopyrimidin-4-ylamino)ethyl)-5-methyl-3-phenylpyrrolo[1,2-f][1,2,4]triazin-4(3H)-one (50 mg, 0.11 mol) was treated with 2,4-difluoro-N-(5-(4,4,5,5-tetramethyl-1,3,2-dioxaborolan-2-yl)pyridin-3-yl)benzenesulfonamide (140 mg, 0.35 mmol), bis(diphenylphosphino)ferrocene-palladium(II)dichloride dichloromethane complex (10 mg, 0.01 mol) and cesium carbonate (2M, 180 µl, 0.36 mol) according to the method described in Example 3 to give 38 mg (53% yield) of the title compound as a white solid. Purity 99%.

LRMS (m/z): 630 (M+1)⁺

¹H NMR (400 MHz, CDCl₃) δ 8.38 (s, 2H), 8.09 (s, 1H), 7.91 (dd, J=14.1, 8.1 Hz, 1H), 7.84-7.59 (m, 1H), 7.59-7.39 (m, 5H), 7.36-7.25 (m, 1H), 7.24-7.04 (m, 1H), 6.92 (dt, J=18.1, 7.8 Hz, 2H), 6.30 (s, 1H), 4.96 (q, J=6.3 Hz, 1H), 4.71 (s, 1H), 4.54 (s, 2H), 2.47 (s, 3H), 1.21 (d, J=6.3 Hz, 3H).

Example 142

(S)-2-(1-((6-Amino-5-(2-hydroxy-6-(trifluoromethyl)pyridin-4-yl)pyrimidin-4-yl)amino)ethyl)-5-methyl-3-phenylpyrrolo[2,1-f][1,2,4]triazin-4(3H)-one (S)-2-(1-((6-Amino-5-(2-methoxy-6-(trifluoromethyl)pyridin-4-yl)pyrimidin-4-yl)amino)ethyl)-5-methyl-3-phenylpyrrolo[2,1-f][1,2,4]triazin-4(3H)-one (40 mg, 0.07 mmol) was dissolved in dichloromethane (1 ml). A solution of boron tribromide (1M in dichloromethane, 223 μl, 0.22 mmol) was added dropwise and the reaction mixture was stirred at room temperature overnight. Further boron tribromide (1M in dichloromethane, 223 μl, 0.22 mmol) was added and the reaction mixture stirred at room temperature an extra night. The reaction mixture was then diluted with dichloromethane and washed with a solution of 4% sodium bicarbonate, water, brine and dried over sodium sulphate, filtered and evaporated under reduced pressure. The product was purified by reverse phase using SP1® Purification System to give 8 mg (20% yield) of the title compound as a white solid. Purity 99%.

LRMS (m/z): 523 (M+1)⁺.
¹H NMR (400 MHz, DMSO-d6) δ ppm 1.21 (d, 3H) 2.33-2.39 (s, 3H) 4.79 (q, 1H) 5.79-5.87 (s, 2H) 6.05 (d, 1H) 6.37 (d, 1H) 6.67-6.77 (s, 1H) 6.98-7.09 (d, 1H) 7.27-7.48 (m, 5H) 7.74-7.81 (s, 1H)

Example 143

N-[3-Hydroxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]sulfamide N-[3-hydroxy-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]sulfamide (38 mg, 0.05 mmol) was treated with trifluoroacetic acid (760 μl, 9.86 mmol) and a solution of ammonia (7N in methanol, 780 μl, 5.32 mmol) according to the method described in Example 27. The residue was purified using SP1® Purification System (0% to 15% dichloromethane-2-propanol) to obtain 20 mg (63% yield) of the title compound.

LRMS (m/z): 572 (M+1)⁺.
¹H NMR (400 MHz, DMSO-d6) δ 11.81 (bs, 1H), 9.58 (bs, 2H), 8.12 (s, 1H), 7.60-7.46 (m, 5H), 7.33 (d, J=2.6 Hz, 1H), 7.19 (s, 1H), 7.08 (bs, 2H), 6.77-6.72 (m, 1H), 6.68-6.62 (m, 1H), 6.56-6.50 (m, 1H), 6.36 (d, J=2.7 Hz, 1H), 6.12 (d, J=7.1 Hz, 1H), 4.80-4.69 (m, 1H), 2.36 (s, 3H), 1.31 (d, J=6.6 Hz, 3H).

Example 144

(S)-5-Methyl-2-(1-((5-(1-(2-morpholinoethyl)-1H-pyrazol-3-yl)-7H-pyrrolo[2,3-d]pyrimidin-4-yl)amino)ethyl)-3-phenylpyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.07 mmol) and 4-(2-chloroethyl)morpholine (30 mg, 0.20 mmol) were dissolved in DMF (2 ml) and cesium carbonate (240 mg, 0.74 mmol) was added. After heating the mixture at 80° C. for 2 h, the solvent was evaporated under reduced pressure and the residue was suspended in water and extracted with ethyl acetate (×3). The organic phase was successively washed with water and brine, dried over magnesium sulphate, filtered and the solvent evaporated under reduced pressure. The residue was purified using SP1® Purification System (0% to 5%, dichloromethane-methanol) to obtain 49 mg of an intermediate that was treated with trifluoroacetic acid (1 mL, 13 mmol) and a solution of ammonia (7N in methanol, 2 mL, 14 mmol) according to the method described in Example 27 to give 14 mg (37% yield) of the title compound. Purity 99%.

LRMS (m/z): 565 (M+1)⁺.
¹H NMR (400 MHz, DMSO-d6) δ 11.68 (s, 1H), 10.04 (d, J=6.7 Hz, 1H), 7.91 (s, 1H), 7.74 (d, J=2.3 Hz, 1H), 7.60 (s, 1H), 7.51 (m, 3H), 7.38-7.29 (m, 2H), 7.18 (m, 1H), 6.61 (d, J=2.4 Hz, 1H), 6.40 (d, J=2.7 Hz, 1H), 4.91-4.83 (m, 1H), 4.12-4.02 (m, 2H), 3.48 (t, J=4.6 Hz, 2H), 3.36 (m, 2H), 3.27-3.23 (m, 2H), 2.61-2.52 (m, 2H), 2.37 (s, 3H), 2.27 (m, 2H), 1.48 (d, J=6.7 Hz, 3H)

Example 145

(S)-5-Methyl-3-phenyl-2-(1-((5-(1-(2,2,2-trifluoroethyl)-1H-pyrazol-3-yl)-7H-pyrrolo[2,3-d]pyrimidin-4-yl)amino)ethyl)pyrrolo[2,1-f][1,2,4]triazin-4(3H)-one (S)-2-(1-((5-(1H-Pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.07 mmol) and 1,1,1-trifluoro-2-iodoethane (36 mg, 0.17 mmol) were dissolved in DMF (2 ml) and cesium carbonate (140 mg, 0.43 mmol) was added. After stirring the mixture at 80° C. for 2 h, the solvent was evaporated under reduced pressure and the residue was suspended in water and extracted with ethyl acetate (×3). The organic phase was successively washed with water and brine, dried over magnesium sulphate, filtered and the solvent evaporated under reduced pressure. The residue (54 mg) was treated with trifluoroacetic acid (1 mL, 13 mmol) and a solution of ammonia (7N in methanol, 10 ml, 70 mmol) according to the method described in Example 27 to give 4.6 mg (12% yield) of the title compound. Purity 93%.

LRMS (m/z): 534 (M+1)⁺.

Example 146

(S)—N-(5-(4-Amino-6-(1-(5-methyl-4-oxo-3-phenyl-3,4-dihydropyrrolo[1,2-f][1,2,4]triazin-2-yl)ethylamino)pyrimidin-5-yl)pyridin-3-yl)-2-fluoro-4-hydroxybenzenesulfonamide (S)-2-(1-(6-Amino-5-bromopyrimidin-4-ylamino)ethyl)-5-methyl-3-phenylpyrrolo[1,2-f][1,2,4]triazin-4(3H)-one (50 mg, 0.11 mmol) was treated with 2-fluoro-4-hydroxy-N-(5-(4,4,5,5-tetramethyl-1,3,2-dioxaborolan-2-yl)pyridin-3-yl)benzenesulfonamide (145 mg, 0.37 mmol), PdCl₂dppf.CH₂Cl₂ (10 mg, 0.01 mmol) and aqueous solution of sodium carbonate (2M, 180 μl, 0.36 mmol) in DMF (3 ml). The reaction mixture was submitted to vacuum-argon cycles and stirred at 80° C. for 3 h. The reaction mixture was then cooled at room temperature and the solvents evaporated under reduced pressure. Water was added and the mixture was extracted with ethyl acetate (×3). The organic phase was successively washed with water and brine, dried over magnesium sulphate, filtered and the solvent evaporated under reduced pressure. The residue was purified by reverse phase using SP1® Purification System to obtain 12 mg (16% yield) of the title compound. Purity: 95%.

LRMS (m/z): 628 (M+1)$^+$.

$^1$H-RMN (400 MHz, CD$_3$OD) δ 8.33 (d, J=2.1 Hz, 1H), 8.14 (s, 1H), 7.88 (s, 1H), 7.70 (t, J=8.7 Hz, 1H), 7.57-7.34 (m, 6H), 7.29 (br s, 1H), 6.63 (dd, J=8.8, 2.2 Hz, 1H), 6.52 (d, J=12.5 Hz, 1H), 6.34 (d, J=2.4 Hz, 1H), 4.94 (q, J=6.7 Hz, 1H), 2.42 (s, 3H), 1.25 (d, J=6.7 Hz, 3H).

Example 147

(S)-3-Methoxy-5-(4-((1-(5-methyl-4-oxo-3-phenyl-3,4-dihydropyrrolo[2,1-f][1,2,4]triazin-2-yl)ethyl) amino)-7H-pyrrolo[2,3-d]pyrimidin-5-yl)benzonitrile (S)-3-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzonitrile (24 mg, 0.04 mmol) was treated with trifluoroacetic acid (480 μl, 6.23 mmol) and a solution of ammonia (7N in methanol, 480 μl, 3.36 mmol) according to the method described in Example 27. The residue was purified using SP1® Purification System (0% to 15% dichloromethane-2-propanol) to obtain 11 mg (56% yield) of the title compound.

LRMS (m/z): 517 (M+1)$^+$ $^1$H NMR (400 MHz, DMSO-d6) δ 12.05 (bs, 1H), 8.16 (s, 1H), 7.62-7.46 (m, 8H), 7.43 (d, J=5.0 Hz, 1H), 7.24 (s, 1H), 6.38 (s, 1H), 6.02 (d, J=7.1 Hz, 1H), 4.89-4.77 (m, 1H), 3.86 (s, 3H), 2.36 (s, 3H), 1.31 (d, J=6.5 Hz, 3H).

Example 148

(S)-3-Hydroxy-5-(4-((1-(5-methyl-4-oxo-3-phenyl-3,4-dihydropyrrolo[2,1-f][1,2,4]triazin-2-yl)ethyl) amino)-7H-pyrrolo[2,3-d]pyrimidin-5-yl)benzonitrile (S)-3-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzonitrile (34 mg, 0.05 mmol) was treated with boron tribromide (1M in dichloromethane, 526 μL, 0.53 mmol) in dichloromethane (680 μL) and then with a solution of ammonia (7N in methanol, 680 μl, 4.76 mmol) according to the method described in Example 41. The residue was purified using SP1® Purification System (0% to 15% dichloromethane-2-propanol) to obtain 19 mg (69% yield) of the title compound.

LRMS (m/z): 503 (M+1)$^+$.

$^1$H NMR (400 MHz, CDCl$_3$) δ 8.17 (s, 1H), 7.62-7.48 (m, 5H), 7.47-7.39 (m, 2H), 7.29 (d, J=2.6 Hz, 1H), 7.26-7.22 (m, 1H), 7.19-7.14 (m, 1H), 6.39 (d, J=2.7, 1H), 5.97 (d, J=7.4 Hz, 1H), 4.90-4.79 (m, 1H), 2.37 (s, 3H), 1.32 (d, J=6.6 Hz, 3H).

Example 149

(S)-2-(1-((6-Amino-5-(2-(trifluoromethyl)pyridin-4-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]tri-azin-4(3H)-one (60 mg, 0.14 mmol) were added 2-(trifluoromethyl)pyridin-4-ylboronic acid (39 mg, 0.20 mmol), 1,1'-bis(diphenylphosphino)ferrocene-palladium(II)dichloride dichloromethane complex (11 mg, 0.01 mmol) and 204 μl of a 2M aqueous solution of cesium carbonate in dioxane (2.5 ml). The mixture was stirred under argon atmosphere at 90° C. for 18 hours and then diluted with ethyl acetate. The resulting solution was washed with water and brine, dried over magnesium sulphate, filtered and the solvents were removed under reduced pressure. The product was purified by flash chromatography using SP1® Purification System (0% to 70% hexane/AcOEt in 25 CV, 70% AcOEt in 10 CV) to give 33 mg (48% yield) of the title compound as a white solid. Purity 100%.

LRMS (m/z): 507 (M+1)$^+$.

$^1$H NMR (400 MHz, DMSO-d6) δ 8.81 (d, J=4.9 Hz, 1H), 7.81 (s, 1H), 7.64 (s, 1H), 7.55 (d, J=4.8 Hz, 1H), 7.46-7.28 (m, 5H), 6.37 (d, J=2.2 Hz, 1H), 6.07 (d, J=7.4 Hz, 1H), 5.87 (s, 2H), 4.80 (q, 1H), 2.35 (s, 3H), 1.20 (d, J=6.7 Hz, 3H).

Example 150

(S)-2-(Dimethylamino)-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)ethanesulfonamide (S)-2-(Dimethylamino)-N-(3-hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl) ethanesulfonamide (15 mg, 0.02 mmol, 77% purity) was treated with trifluoroacetic acid (300 μl, 3.89 mmol) and a solution of ammonia (7N in methanol, 300 μl, 2.10 mmol) according to the method described in Example 27. The residue was purified using SP1® Purification System (0% to 40% dichloromethane methanol) to obtain 5 mg (52% yield) of the title compound.

LRMS (m/z): 628 (M+1)+.

Example 151

(S)-5-Methyl-2-(1-((5-(1-methyl-3-(trifluoromethyl)-1H-pyrazol-5-yl)-7H-pyrrolo[2,3-d]pyrimidin-4-yl) amino)ethyl)-3-phenylpyrrolo[2,1-f][1,2,4]triazin-4 (3H)-one (S)-5-Methyl-2-(1-((5-(1-methyl-3-(trifluoromethyl)-1H-pyrazol-5-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (38 mg, 0.04 mmol, 66% purity) was treated with trifluoroacetic acid (760 μl, 9.86 mmol) and a solution of ammonia (7N in methanol, 760 μl, 5.32 mmol) according to the method described in Example 27. The residue was purified using SP1® Purification System (reverse phase, 0% to 100% water-methanol/acetonitrile 1:1) to obtain 14 mg (69% yield) of the title compound.

LRMS (m/z): 534 (M+1)+.

Example 152

(S)-tert-Butyl 4-(4-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)piperazine-1-carboxylate To a solution of (S)-2-(1-((6-amino-5-bromopyrimidin-4-yl)amino)ethyl)-5-methyl-3-phenylpyrrolo[2,1-f][1,2,4]triazin-4(3H)-one (70 mg, 0.16 mmol) in dioxane (2 ml) was added (4-(4-(tert-butoxycarbonyl)piperazin-1-yl)phenyl)boronic acid (73 mg, 0.24 mmol), 1,1'-bis(diphenylphosphino)ferrocene-palladium(II)dichloride dichloromethane complex (12 mg, 0.01 mmol) and 159 µl of a 2M aqueous solution of cesium carbonate. The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 75 mg (74% yield) as a white solid. Purity 99%.

LRMS (m/z): 622 (M+1)$^+$.

Example 153

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (65 mg, 0.08 mmol, 82% purity) was treated with trifluoroacetic acid (1.30 ml, 16.87 mmol) and a solution of ammonia (7N in methanol, 1.30 ml, 8.10 mmol) according to the method described in Example 27. The residue was purified using SP1® Purification System (0% to 15% dichloromethane-2-propanol) to obtain 31 mg (70% yield) of the title compound.

LRMS (m/z): 555 (M+1)$^+$.
$^1$H NMR (400 MHz, DMSO-d6) δ 11.84 (bs, 1H), 8.12 (s, 1H), 7.59-7.45 (m, 7H), 7.31 (d, J=8.3 Hz, 2H), 7.28 (d, J=2.6 Hz, 1H), 7.22 (d, J=2.2 Hz, 1H), 6.78 (bs, 1H), 6.37 (d, J=2.6 Hz, 1H), 5.87 (d, J=7.5 Hz, 1H), 4.90-4.77 (m, 1H), 2.99 (s, 3H), 2.35 (s, 3H), 1.26 (d, J=6.6 Hz, 3H).

Example 154

(S)-2-(1-((5-(1-(2-Methoxybenzyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(2-Methoxybenzyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (16 mg, 0.02 mmol) was treated with trifluoroacetic acid (500 µl, 6.49 mmol) and a solution of ammonia (7N in methanol, 500 µl, 3.50 mmol) according to the method described in Example 27 to obtain 12 mg (87% yield) of the title compound without further purification.

LRMS (m/z): 572 (M+1)+.

Example 155

(S)-2-(1-((5-(1-(3-Hydroxy-2,2-dimethylpropyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(3-Hydroxy-2,2-dimethylpropyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (4 mg, 0.01 mmol) was treated with trifluoroacetic acid (1 mL, 13 mmol) and a solution of ammonia (7N in methanol, 5 mL, 35 mmol) according to the method described in Example 27 to give 3.2 mg (100% yield) of the title compound. Purity 85%.

LRMS (m/z): 538 (M+1)$^+$

Example 156

(S)-3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxy-N,N-dimethyl benzamide (S)-2-(1-((6-Amino-5-bromopyrimidin-4-yl)amino)ethyl)-5-methyl-3-phenylpyrrolo[2,1-f][1,2,4]triazin-4(3H)-one (70.5 mg, 0.16 mmol) was treated with 3-hydroxy-N,N-dimethyl-5-(4,4,5,5-tetramethyl-1,3,2-dioxaborolan-2-yl)benzamide (113 mg, 0.39 mmol, prepared from 3-bromo-5-hydroxy-N,N-dimethylbenzamide, as described at WO 2009077385 A1 20090625, and bis(pinacolate)diboron according to the method describe at Preparation 119b), sodium carbonate (40.55 mg, 0.38 mmol) and 1,1'-bis(diphenylphosphino)ferrocene-palladium(II)dichloride dichloromethane complex (39.2 mg, 0.05 mmol) in water (1.7 ml) and dimethoxyethane (6.5 ml) according to the method described in Example 3 to give 40.7 mg (44% yield) of the title compound. Purity 90%.

LRMS (m/z): 525 (M+1)$^+$
$^1$H NMR (400 MHz, CDCl$_3$) δ 8.05 (d, J=14.8 Hz, 1H), 7.46 (d, J=23.2 Hz, 4H), 7.26 (s, 1H), 7.13 (d, J=9.8 Hz, 1H), 6.97 (s, 1H), 6.93-6.82 (m, 1H), 6.74 (d, J=26.0 Hz, 1H), 6.25 (d, J=34.0 Hz, 1H), 5.01 (d, J=31.3 Hz, 2H), 4.58 (s, 2H), 3.15 (d, J=9.3 Hz, 3H), 3.01 (s, 2H), 2.46 (d, J=7.3 Hz, 3H), 1.35 (d, J=8.2 Hz, 2H), 1.21 (dd, J=21.4, 6.4 Hz, 3H).

Example 157

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-4-hydroxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (50 mg, 0.11 mmol) was treated with 4-hydroxy-N-(2-methoxy-5-(4,4,5,5-tetramethyl-1,3,2-dioxaborolan-2-yl)pyridin-3-yl)benzenesulfonamide (70 mg, 0.17 mmol) and bis(pinacolato)diboron according to the method described at Preparation 119b), cesium carbonate (2M, 120 µl, 0.24 mmol) and 1,1'-bis(diphenylphosphino)ferrocene-palladium (II)dichloride dichloromethane complex (10 mg, 0.01 mmol) according to the method described in Example 3 to give 37 mg (51% yield) of the title compound. Purity 100%.

LRMS (m/z): 640 (M+1)$^+$
$^1$H NMR (400 MHz, CD$_3$OD) δ 7.93-7.84 (m, 1H), 7.72 (s, 1H), 7.64 (d, J=8.6 Hz, 2H), 7.58-7.42 (m, 6H), 7.39 (d, J=7.6 Hz, 1H), 6.78 (d, J=8.5 Hz, 2H), 6.34 (s, 1H), 4.93 (q, J=6.4 Hz, 1H), 3.85 (s, 3H), 2.43 (s, 3H), 1.30 (d, J=6.6 Hz, 3H).

Example 158

(S)—N-(3-Hydroxy-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-hydroxy-5-(4-((1-(4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (160 mg, 0.22 mmol) was treated with trifluoroacetic acid (4.1 mL, 53.22 mmol) and a solution of ammonia (7N in methanol, 4.1 mL, 28.7 mmol) according to the method described in Example 27 to give 34 mg (28% yield) of the title compound. Purity 99%.

LRMS (m/z): 557 (M+1)⁺.

¹H NMR (400 MHz, CD₃OD) δ 8.10 (d, J=9.1 Hz, 1H), 7.63-7.39 (m, 6H), 7.13 (s, 1H), 6.99 (dd, J=4.4, 1.7 Hz, 1H), 6.94-6.73 (m, 3H), 6.58 (dd, J=4.4, 2.7 Hz, 1H), 5.08 (q, J=6.6 Hz, 1H), 2.95 (s, 3H), 1.42 (d, J=6.6 Hz, 3H).

Example 159

(S)-2-(1-((5-(1-(2-Hydroxybenzyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(2-Methoxybenzyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (53 mg, 0.08 mmol) was treated with boron tribromide (1M in dichloromethane, 750 μL, 0.75 mmol) in dichloromethane (1.0 mL) and then with a solution of ammonia (7N in methanol, 750 μl, 5.25 mmol) according to the method described in Example 41. The residue was purified using SP1® Purification System (reverse phase, 0% to 100% water-methanol/acetonitrile 1:1) to obtain 20 mg (48% yield) of the title compound.

LRMS (m/z): 558 (M+1)⁺.

¹H NMR (400 MHz, DMSO-d6) δ 11.70 (s, 1H), 10.02 (d, J=6.6 Hz, 1H), 9.80 (s, 1H), 7.97 (s, 1H), 7.72 (d, J=2.3 Hz, 1H), 7.60 (d, J=2.0 Hz, 1H), 7.48 (m, 3H), 7.43-7.37 (m, 1H), 7.33 (m, 2H), 7.11-7.01 (m, 1H), 6.85 (dd, J=7.6, 1.6 Hz, 1H), 6.80 (dd, J=8.1, 1.0 Hz, 1H), 6.70-6.66 (m, 1H), 6.65 (d, J=2.3 Hz, 1H), 6.31 (dd, J=2.7, 0.7 Hz, 1H), 5.17 (d, J=3.5 Hz, 2H), 4.73 (p, J=7.0 Hz, 1H), 2.34 (s, 3H), 1.33 (d, J=6.8 Hz, 3H).

Example 160

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)-1-(4-fluorophenyl)methanesulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (120 mg, 0.27 mmol) were added 1-(4-fluorophenyl)-N-(3-methoxy-5-(4,4,5,5-tetramethyl-1,3,2-dioxaborolan-2-yl)phenyl)methanesulfonamide (138 mg, 0.33 mmol), 1,1'-bis(diphenylphosphino)ferrocene-palladium(II)dichloride dichloromethane complex (22 mg, 0.03 mmol) and 273 μl of a 2M aqueous solution of cesium carbonate in dioxane (5 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1® Purification System (0 to 80%, hexane-ethyl acetate) to give 155 mg (85% yield) of the title compound as a white solid. Purity 98%.

LRMS (m/z): 655 (M+1)⁺.

¹H NMR (400 MHz, DMSO-d6) δ 9.90 (s, 1H), 7.54-7.25 (m, 10H), 7.21-7.04 (m, J=8.2 Hz, 3H), 6.87-6.71 (m, J=2.1 Hz, 2H), 4.74 (q, 1H), 4.48 (d, J=5.3 Hz, 2H), 3.73 (s, 3H), 2.33 (s, 3H), 1.20 (d, J=6.4 Hz, 3H).

Example 161

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)-4-fluorobenzenesulfonamide (S)-2-(1-(((6-Amino-5-bromopyrimidin-4-yl)amino)ethyl)-5-methyl-3-phenylpyrrolo[2,1-f][1,2,4]triazin-4(3H)-one (50 mg, 0.11 mmol) was treated with 4-fluoro-N-(3-hydroxy-5-(4,4,5,5-tetramethyl-1,3,2-dioxaborolan-2-yl)phenyl)benzenesulfonamide (69 mg, 0.18 mmol), cesium carbonate (2M, 180 μl, 0.36 mmol) and 1,1'-bis(diphenylphosphino)ferrocene-palladium(II)dichloride dichloromethane complex (10 mg, 0.01 mmol) according to the method described in Example 3 to give 42 mg (56% yield) of the title compound. Purity 95%.

LRMS (m/z): 627 (M+1)⁺.

¹H NMR (400 MHz, CD₃OD) δ 9.46-9.35 (m, 3H), 9.18-8.62 (m, 8H), 8.30 (d, J=11.7 Hz, 1H), 8.16 (d, J=7.9 Hz, 1H), 7.98 (d, J=6.7 Hz, 1H), 7.92 (d, J=2.1 Hz, 1H), 4.00 (s, 3H), 2.81 (d, J=6.7 Hz, 3H).

Example 162

(S)-2-(1-(((6-Amino-5-(4-(piperazin-1-yl)phenyl)pyrimidin-4-yl)amino)ethyl)-5-methyl-3-phenylpyrrolo[2,1-f][1,2,4]triazin-4(3H)-one (S)-tert-Butyl 4-(4-(4-amino-6-((1-(5-methyl-4-oxo-3-phenyl-3,4-dihydropyrrolo[2,1-f][1,2,4]triazin-2-yl)ethyl)amino)pyrimidin-5-yl)phenyl)piperazine-1-carboxylate (75 mg, 0.12 mmol) was dissolved in 2 ml dioxane. A solution of hydrochloric acid (4M in dioxane, 30 μL, 0.12 mol) was added and the reaction was stirred at room temperature for 2 h. The solvent was removed and the residue was purified by preparative HPLC-MS to give 12 mg (19% yield) of the title compound as a solid. Purity 100%.

LRMS (m/z): 522 (M+1)⁺.

¹H NMR (400 MHz, DMSO-d6) δ ppm 1.14 (d, J=6.64 Hz, 3H) 2.33 (s, 3H) 2.84 (t, 4H) 3.11 (t, J=4.69 Hz, 4H) 4.68 (q, 1H) 5.24 (d, J=7.82 Hz, 1H) 5.40 (s, 2H) 6.35 (d, J=2.34 Hz, 1H) 6.98-7.19 (m, J=1.95 Hz, 4H) 7.36 (d, J=2.34 Hz, 1H) 7.38-7.50 (m, 4H) 7.79 (s, 1H) 8.23 (s, 1H)

Example 163

(S)-2-(1-((5-(1-(3-Hydroxyphenyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-(3-Methoxyphenyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (9 mg, 0.01 mmol) was treated with boron tribromide (1M in dichloromethane, 1 mL, 1.00 mmol) in dichloromethane (1.0 mL) and then with a solution of ammonia (7N in methanol, 5.0 ml, 35.0 mmol) according to the method described in Example 41. The residue was purified using SP1® Purification System (reverse phase, 0% to 100% water-methanol/acetonitrile 1:1) to obtain 4 mg (47% yield) of the title compound.

LRMS (m/z): 544 (M+1)+.

Example 164

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-fluorophenyl)-4-hydroxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (30 mg, 0.07 mmol) was treated with N-(3-fluoro-5-(4,4,5,5-tetramethyl-1,3,2-dioxaborolan-2-yl)phenyl)-4-hydroxybenzenesulfonamide (42 mg, 0.11 mmol), cesium carbonate (2M, 120 µl, 0.24 mmol) and 1,1'-bis(diphenylphosphino)ferrocene-palladium(II)dichloride dichloromethane complex (8 mg, 0.01 mmol) according to the method described in Example 3 to give 22 mg (52% yield) of the title compound. Purity 100%.

LRMS (m/z): 627 (M+1)$^+$ $^1$H-NMR (400 MHz, CD3OD) δ 7.84 (d, J=5.2 Hz, 1H), 7.71-7.62 (m, 2H), 7.58-7.40 (m, 4H), 7.36 (d, J=7.9 Hz, 1H), 7.31-6.60 (m, 6H), 6.34 (d, J=2.0 Hz, 1H), 4.87 (q, J=6.5 Hz, 1H), 2.42 (s, 3H), 1.23 (d, J=6.7 Hz, 3H).

Example 165

(S)—N-(4-(4-((1-(4-Oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide (S)—N-(4-(4-((1-(4-Oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)methanesulfonamide (152 mg, 0.21 mmol) was treated with trifluoroacetic acid (1 ml, 12.9 mmol) and a solution of ammonia (7N in methanol, 5 mL, 35 mmol) according to the method described in Example 27 to give 23 mg (18% yield) of the title compound. Purity 98%.

LRMS (m/z): 580 (M+1)$^+$ $^1$H NMR (400 MHz, CD$_3$OD) δ 8.04 (s, 1H), 7.56-7.21 (m, 8H), 7.19 (s, 1H), 7.17 (s, 1H), 7.01 (d, J=1.8 Hz, 1H), 6.93 (dd, J=4.3, 1.6 Hz, 1H), 6.54 (dd, J=4.4, 2.7 Hz, 1H), 6.36-6.30 (m, 1H), 4.93 (q, J=6.6 Hz, 1H), 2.86 (s, 3H), 1.22 (d, J=6.6 Hz, 3H).

Example 166

(S)—N-(3-(4-amino-6-((1-(5-methyl-4-oxo-3-phenyl-3,4-dihydropyrrolo[2,1-f][1,2,4]triazin-2-yl)ethyl)amino)pyrimidin-5-yl)-5-fluorophenyl)methanesulfonamide (S)-2-(1-((6-Amino-5-bromopyrimidin-4-yl)amino)ethyl)-5-methyl-3-phenylpyrrolo[2,1-f][1,2,4]triazin-4(3H)-one (30 mg, 0.07 mmol) was treated with N-(3-fluoro-5-(4,4,5,5-tetramethyl-1,3,2-dioxaborolan-2-yl)phenyl)methanesulfonamide (34 mg, 0.11 mmol, prepared as described at WO 2004052847 A2 20040624), cesium carbonate (2M, 110 µl, 0.22 mmol) and 1,1'-bis(diphenylphosphino)ferrocene-palladium(II)dichloride dichloromethane complex (6 mg, 0.01 mmol) according to the method described in Example 3 to give 22 mg (59% yield) of the title compound. Purity 100%.

LRMS (m/z): 549 (M+1)$^+$ $^1$H-RMN (400 MHz, CD$_3$OD) δ 7.86 (s, 1H), 7.68-7.43 (m, 4H), 7.43-7.23 (m, 2H), 6.99 (dd, J=94.2, 48.7 Hz, 3H), 6.35 (dd, J=2.7, 0.6 Hz, 1H), 4.92 (q, J=6.7 Hz, 1H), 3.02 (s, 3H), 2.43 (s, 3H), 1.28 (d, J=6.8 Hz, 3H).

Example 167

(S)-2-(1-((5-(1-((3-Hydroxyphenyl)sulfonyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(1-((3-Methoxyphenyl)sulfonyl)-1H-pyrazol-3-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (48.5 mg, 0.06 mmol) was treated with boron tribromide (1M in dichloromethane, 0.75 ml, 0.75 mmol) in dichloromethane (2 ml) and then with a solution of ammonia (7N in methanol, 5 ml, 35 mmol) according to the method described in Example 41 to give 6.7 mg (17% yield) of the title compound. Purity 98%.

LRMS (m/z): 608 (M+1)$^+$

Example 168

(S)-3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-N-(3-hydroxyphenyl)benzamide (S)-2-(1-((6-Amino-5-bromopyrimidin-4-yl)amino)ethyl)-5-methyl-3-phenylpyrrolo[2,1-f][1,2,4]triazin-4(3H)-one (55 mg, 0.12 mmol) was treated with N-(3-hydroxyphenyl)-3-(4,4,5,5-tetramethyl-1,3,2-dioxaborolan-2-yl)benzamide (106 mg, 0.31 mmol, prepared from 3-bromo-N-(3-hydroxyphenyl)benzamide and bis(pinacolato)diboron according to Preparation 119b), sodium carbonate (40 mg, 0.38 mmol) and 1,1'-bis(diphenylphosphino)ferrocene-palladium(II)dichloride dichloromethane complex (6 mg, 0.01 mmol) in water (1 ml) and dimethoxyethane (3 ml) according to the method described in Example 3 to give 11 mg (15% yield) of the title compound. Purity 100%.

LRMS (m/z): 573 (M+1)$^+$ $^1$H NMR (400 MHz, CDCl$_3$) δ 8.70 (s, 1H), 8.01-7.64 (m, 3H), 7.58-7.31 (m, 7H), 7.22 (s, 1H), 7.10 (d, J=1.8 Hz, 1H), 6.97 (s, 1H), 6.81 (s, 1H), 6.49 (s, 1H), 6.27 (s, 1H), 6.10 (s, 1H), 5.20 (s, 3H), 4.88 (q, J=6.8 Hz, 1H), 2.38 (d, J=29.5 Hz, 3H), 1.19 (s, 3H).

Example 169

2-(((6-Amino-5-(5-(difluoromethyl)pyridin-3-yl)pyrimidin-4-yl)amino)methyl)-5-methyl-3-phenylpyrrolo[2,1-f][1,2,4]triazin-4(3H)-one To a solution of 2-(((6-amino-5-bromopyrimidin-4-yl)amino)methyl)-5-methyl-3-phenylpyrrolo[2,1-f][1,2,4]triazin-4(3H)-one (50 mg, 0.12 mmol) were added (5-(difluoromethyl)pyridin-3-yl)boronic acid (31 mg, 0.18 mmol), 1,1'-bis(diphenylphosphino)ferrocene-palladium(II)dichloride dichloromethane complex (9 mg, 0.01 mmol) and 117 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 33 mg (59% yield) as a white solid. Purity 100%.

LRMS (m/z): 475 (M+1)⁺.
¹H NMR (400 MHz, DMSO-d6) δ ppm 2.35 (s, 3H) 3.99 (d, J=5.08 Hz, 2H) 5.81-5.87 (m, 1H) 5.91 (s, 2H) 6.37 (d, J=2.74 Hz, 1H) 7.03-7.22 (m, 1H) 7.31-7.36 (m, 2H) 7.38 (d, J=2.74 Hz, 1H) 7.40-7.52 (m, 3H) 7.82 (s, 1H) 7.87 (s, 1H) 8.56 (s, 1H) 8.79 (s, 1H)

Example 170

(S)—N-(4-Hydroxy-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(4-Hydroxy-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (102 mg, 0.15 mmol) was treated with trifluoroacetic acid (2.7 ml, 35.05 mmol) and a solution of ammonia (7N in methanol, 2.7 ml, 19 mmol) according to the method described in Example 27 to give 26 mg (29% yield) of the title compound. Purity 93%.
LRMS (m/z): 571 (M+1)⁺
¹H NMR (400 MHz, CD₃OD) δ 8.06 (s, 2H), 8.00 (s, 1H), 7.53 (d, J=1.3 Hz, 1H), 7.44 (s, 1H), 7.40-7.28 (m, 3H), 7.23 (d, J=2.7 Hz, 1H), 7.17 (dd, J=7.5, 2.3 Hz, 2H), 7.08 (s, 1H), 6.91 (d, J=9.1 Hz, 1H), 6.43-6.28 (m, 1H), 4.95 (d, J=6.6 Hz, 1H), 3.32 (s, 1H), 2.83 (s, 3H), 2.41 (s, 3H), 2.13 (s, 1H), 1.35 (d, J=6.6 Hz, 3H).

Example 171

(S)-2-(1-((6-Amino-5-(1-((2-fluoro-4-hydroxyphenyl)sulfonyl)-4-hydroxy-1H-indol-6-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (28 mg, 0.06 mmol) were added (1-((2-fluoro-4-hydroxyphenyl)sulfonyl)-4-hydroxy-1H-indol-6-yl)boronic acid (22 mg, 0.06 mmol), 1,1'-bis(diphenylphosphino)ferrocene-palladium(II)dichloride dichloromethane complex (5 mg, 0.01 mmol) and 63 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 8 mg (19% yield) as a white solid. Purity 99%.
LRMS (m/z): 665 (M−1)⁻.
¹H NMR (400 MHz, CD₃OD) δ 8.51-8.33 (m, 1H), 7.96-7.79 (m, 2H), 7.54 (t, J=20.5 Hz, 6H), 7.37 (s, 2H), 7.16 (s, 1H), 6.84 (s, 1H), 6.62 (s, 2H), 6.49 (s, 1H), 6.34 (d, J=17.3 Hz, 2H), 4.64-4.55 (m, 1H), 2.42 (d, J=13.2 Hz, 3H), 1.28 (s, 1H), 1.21 (t, J=7.6 Hz, 3H). A mixture of atropoisomers is observed Example 172

N-(3-(4-Amino-6-(((5-methyl-4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide To a solution of 2-(((6-amino-5-bromopyrimidin-4-yl)amino)methyl)-5-methyl-3-phenylpyrrolo[2,1-f][1,2,4]triazin-4(3H)-one (32 mg, 0.08 mmol) in dioxane (2 ml) were added (3-(4-hydroxyphenylsulfonamido)phenyl)boronic acid (26 mg, 0.09 mmol), 1,1-bis(diphenylphosphino)ferrocene-palladium(II)dichloride dichloromethane complex (6 mg, 0.01 mmol) and 75 μl of a 2M aqueous solution of cesium carbonate. The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 36 mg (80% yield) as a white solid. Purity 100%.
LRMS (m/z): 595 (M+1)⁺.
¹H NMR (400 MHz, DMSO-d6) δ ppm 2.36 (s, 3H) 5.43 (s, 2H) 6.37 (d, J=2.74 Hz, 1H) 6.75 (d, J=8.21 Hz, 2H) 6.92 (d, J=7.42 Hz, 1H) 6.97 (s, 1H) 7.13 (d, J=8.99 Hz, 1H) 7.31 (d, J=2.34 Hz, 1H) 7.33-7.39 (m, 3H) 7.42-7.52 (m, 3H) 7.55 (d, J=8.21 Hz, 2H) 7.83 (s, 1H) 8.23 (s, 1H)

Example 173

(S)-1-(4-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-fluorophenyl)-3-(pyridin-4-yl)urea To a solution of (S)-2-(1-((6-amino-5-bromopyrimidin-4-yl)amino)ethyl)-5-methyl-3-phenylpyrrolo[2,1-f][1,2,4]triazin-4(3H)-one (40 mg, 0.09 mmol) in dioxane (2 ml) were added 1-(2-fluoro-4-(4,4,5,5-tetramethyl-1,3,2-dioxaborolan-2-yl)phenyl)-3-(pyridin-4-yl)urea (62 mg, 0.14 mmol), 1,1'-bis(diphenylphosphino)ferrocene-palladium(11)dichloride dichloromethane complex (7.5 mg, 0.01 mmol) and 136 μl of a 2M aqueous solution of cesium carbonate. The mixture was stirred under argon atmosphere at 100° C. for 18 hours and then diluted with ethyl acetate. The resulting solution was washed with water and brine, dried over magnesium sulphate, filtered and the solvents were removed under reduced pressure. The product was purified by reverse phase using SP1® Purification System to give 25 mg (45% yield) as a white solid. Purity 97%.
LRMS (m/z): 591 (M+1)⁺.
¹H NMR (400 MHz, DMSO-d6) δ 9.48 (s, 1H), 8.85 (d, J=2.5 Hz, 1H), 8.37 (dd, J=4.8, 1.6 Hz, 2H), 8.28 (dd, J=8.4 Hz, 1H), 7.78 (s, 1H), 7.48-7.30 (m, 7H), 7.16-6.95 (m, 2H), 6.36 (d, J=2.6 Hz, 1H), 5.60 (d, J=7.6 Hz, 2H), 4.73 (q, 1H), 2.32 (d, J=13.9 Hz, 3H), 1.20 (t, J=6.0 Hz, 3H).

Example 174

2-(((6-Amino-5-(3-(difluoromethyl)-5-hydroxyphenyl)pyrimidin-4-yl)amino)methyl)-5-methyl-3-phenylpyrrolo[2,1-f][1,2,4]triazin-4(3H)-one To a solution of 2-(((6-amino-5-bromopyrimidin-4-yl)amino)methyl)-5-methyl-3-phenylpyrrolo[2,1-f][1,2,4]triazin-4(3H)-one (70 mg, 0.16 mmol) in dioxane (2 ml) were added 3-(difluoromethyl)-5-(4,4,5,5-tetramethyl-1,3,2-dioxaborolan-2-yl)phenol (67 mg, 0.25 mmol), 1,1'-bis(diphenylphosphino)ferrocene-palladium(II)dichloride dichloromethane complex (13 mg, 0.02 mmol) and 246 μl of a 2M aqueous solution of cesium carbonate. The mixture was stirred under argon atmosphere at 90° C. for 18 hours and then diluted with ethyl acetate. The resulting solution was washed with water and brine, dried over magnesium sulphate, filtered and the solvents were removed under reduced pressure. The crude was purified using SP1® Purification System (0% to 100%, hexane-ethyl acetate) to obtain 34 mg (42% yield) of the title compound as a white solid. Purity 100%.

LRMS (m/z): 4690 (M+1)⁺.

¹H NMR (400 MHz, DMSO-d6) δ 10.00 (s, 1H), 7.83 (s, 1H), 7.53-7.41 (m, 3H), 7.37 (d, J=1.6 Hz, 1H), 7.35 (t, J=1.4 Hz, 1H), 7.32 (d, J=2.6 Hz, 1H), 6.97 (s, 1H), 6.96-6.94 (m, 1H), 6.88-6.85 (m, 1H), 6.81 (d, J=0.9 Hz, 1H), 6.37 (d, J=2.6 Hz, 1H), 5.62 (s, 2H), 5.51 (dd, J=5.1 Hz, 1H), 3.98 (d, J=5.2 Hz, 2H), 2.35 (s, 3H).

Example 175

(S)-1-(3-Hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea (S)-1-(3-Hydroxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)urea (18 mg, 0.03 mmol) was treated with trifluoroacetic acid (360 μl, 4.07 mmol) and a solution of ammonia (7N in methanol, 360 μl, 2.52 mmol) according to the method described in Example 27. The residue was purified using SP1® Purification System (0% to 15% dichloromethane-2-propanol) to obtain 13 mg (90% yield) of the title compound.

LRMS (m/z): 536 (M+1)⁺

¹H NMR (400 MHz, DMSO-d6) δ 11.79 (d, J=2.3 Hz, 1H), 9.49 (s, 1H), 8.54 (s, 1H), 8.11 (s, 1H), 7.61-7.45 (m, 5H), 7.30 (d, J=2.6 Hz, 1H), 7.18 (d, J=2.4 Hz, 1H), 7.02-6.94 (m, 2H), 6.49-6.41 (m, 1H), 6.34 (d, J=2.6 Hz, 1H), 6.19 (d, J=7.2 Hz, 1H), 5.78 (bs, 2H), 4.81-4.69 (m, 1H), 2.35 (s, 3H), 1.30 (d, J=6.6 Hz, 3H).

Example 176

(S)-3-(Methylsulfonamido)-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl methanesulfonate (S)-3-(Methylsulfonamido)-5-(4-((1-(4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl methanesulfonate (82 mg, 0.07 mmol) was treated with trifluoroacetic acid (3 ml, 39 mmol) and a solution of ammonia (7N in methanol, 2.5 ml, 18 mmol) according to the method described in Example 27 to give 23 mg (52% yield) of the title compound. Purity 99%.

LRMS (m/z): 635 (M+1)⁺

¹H NMR (400 MHz, CD₃OD) δ 8.10 (s, 1H), 7.64-7.53 (m, 1H), 7.53-7.41 (m, 4H), 7.38 (ddd, J=3.5, 2.3, 1.6 Hz, 2H), 7.28 (dd, J=2.2, 1.5 Hz, 1H), 7.25 (s, 1H), 7.22 (t, J=2.1 Hz, 1H), 6.99 (dd, J=4.4, 1.6 Hz, 1H), 6.57 (dd, J=4.4, 2.7 Hz, 1H), 5.12 (q, J=6.6 Hz, 1H), 3.23 (s, 3H), 3.02 (s, 3H), 1.42 (d, J=6.7 Hz, 3H). δ 8.06 (s, 2H), 8.00 (s, 1H), 7.53 (d, J=1.3 Hz, Example 177

(S)—N-(3-Hydroxy-5-(4-((3-hydroxy-1-(5-methyl-4-oxo-3-phenyl-3,4-dihydropyrrolo[2,1-f][1,2,4]triazin-2-yl)propyl)amino)-7H-pyrrolo[2,3-d]pyrimidin-5-yl)phenyl)methanesulfonamide (S)—N-(3-Hydroxy-5-(4-((3-hydroxy-1-(5-methyl-4-oxo-3-phenyl-3,4-dihydropyrrolo[2,1-f][1,2,4]triazin-2-yl)propyl)amino)-7-((2-(trimethylsilyl)ethoxy)methyl)-7H-pyrrolo[2,3-d]pyrimidin-5-yl)phenyl)methanesulfonamide (35 mg, 0.03 mmol, 65% purity) was treated with trifluoroacetic acid (1.0 ml, 12.98 mmol) and a solution of ammonia (7N in methanol, 5.0 ml, 35.0 mmol) according to the method described in Example 27. The residue was purified using SP1® Purification System (0% to 5% dichloromethane-methanol) to obtain 11 mg (59% yield) of the title compound.

LRMS (m/z): 601 (M+1)+.

Example 178

(S)-3-Hydroxy-N-methyl-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide (S)-3-Methoxy-N-methyl-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzenesulfonamide (45 mg, 0.06 mmol) was treated with boron tribromide (1M in dichloromethane, 2.0 mL, 2.00 mmol) in dichloromethane (1 mL) and then with a solution of ammonia (7N in methanol, 5.0 mL, 35.0 mmol) according to the method described in Example 41. The residue was purified using SP1® Purification System (reverse phase, 0% to 100% water methanol/acetonitrile 1:1) to obtain 8 mg (22% yield) of the title compound.

LRMS (m/z): 571 (M+1)⁺.

Example 179

(S)-3-Hydroxy-N,N-dimethyl-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzamide (S)-3-Hydroxy-N,N-dimethyl-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)benzamide (44 mg, 0.06 mmol, 89% purity) was treated with trifluoroacetic acid (880 μl, 11.42 mmol) and a solution of ammonia (7N in methanol, 880 μl, 6.16 mmol) according to the method described in Example 27. The residue was purified using SP1® Purification System (0% to 15% dichloromethane-2-propanol) to obtain 27 mg (85% yield) of the title compound.

LRMS (m/z): 549 (M+1)⁺.

¹H NMR (400 MHz, DMSO-d6) δ 11.90 (bs, 1H), 9.93 (bs, 1H), 8.14 (s, 1H), 7.60-7.45 (m, 5H), 7.29 (d, J=2.6 Hz, 1H), 7.00-6.91 (m, J=4.1, 1.7 Hz, 2H), 6.78-6.72 (m, J=2.2, 1.5 Hz, 1H), 6.36 (dd, J=2.6, 0.7 Hz, 1H), 5.92 (d, J=7.7 Hz, 1H), 4.87-4.75 (m, 1H), 2.92 (s, 6H), 2.34 (s, 3H), 1.26 (d, J=6.7 Hz, 2H).

Example 180

(S)—N-(3-Fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Fluoro-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (36 mg, 0.05 mmol) was treated with trifluoroacetic acid (1 ml, 13 mmol) and a solution of ammonia (7N in methanol, 1 ml, 7 mmol) according to the method described in Example 27 to give 22 mg (75% yield) of the title compound. Purity 100%.

LRMS (m/z): 573 (M+1)+.

$^1$H-NMR (400 MHz, CDCl$_3$) δ 11.04 (br. s, 1H), 9.20 (br. s, 1H), 8.31 (s, 1H), 7.60-7.42 (m, 3H), 7.38 (t, J=7.8 Hz, 1H), 7.29 (d, J=7.7 Hz, 1H), 7.19 (d, J=9.9 Hz, 1H), 7.13 (d, J=2.5 Hz, 1H), 7.12-7.06 (m, 2H), 7.05 (s, 1H), 6.26 (d, J=2.6 Hz, 1H), 5.84 (d, J=8.0 Hz, 1H), 5.17 (p, J=6.7 Hz, 1H), 3.03 (s, 3H), 2.37 (s, 3H), 1.29 (d, J=6.6 Hz, 3H)

Example 181

(S)—N-(4-(4-((1-(5-Methyl-4-oxo-3-phenyl-3,4-dihydropyrrolo[2,1-f][1,2,4]triazin-2-yl)ethyl) amino)-7H-pyrrolo[2,3-d]pyrimidin-5-yl)-1H-indazol-6-yl)methanesulfonamide (S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indazol-6-yl)methanesulfonamide (13 mg, 0.02 mmol) was treated with trifluoroacetic acid (2 ml, 26 mmol) and a solution of ammonia (7N in methanol, 2 ml, 117 mmol) according to the method described in Example 27 to give 7 mg (66% yield) of the title compound. Purity 100%.

LRMS (m/z): 595 (M+1)+.

Example 182

(S)—N-Methyl-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-Methyl-N-(3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (143 mg, 0.20 mmol) was treated with trifluoroacetic acid (3.8 ml, 49 mmol) and a solution of ammonia (7N in methanol, 3.8 ml, 27 mmol) according to the method described in Example 27 to give 103 mg (86% yield) of the title compound. Purity 96%.

LRMS (m/z): 569 (M+1)+.

$^1$H NMR (400 MHz, DMSO-d6) δ 11.97 (d, J=2.3 Hz, 1H), 8.15 (d, J=5.4 Hz, 1H), 7.71-7.38 (m, 9H), 7.35 (d, J=2.5 Hz, 1H), 7.24 (d, J=2.6 Hz, 1H), 6.37 (dd, J=2.7, 0.6 Hz, 1H), 5.88 (d, J=7.3 Hz, 1H), 4.85 (p, J=6.6 Hz, 1H), 3.30-3.27 (m, 3H), 2.97 (d, J=7.2 Hz, 3H), 2.36 (s, 3H), 1.29 (d, J=6.7 Hz, 3H).

Example 183

(S)—N-(3-(4-((1-(5-Methyl-4-oxo-3-phenyl-3,4-dihydropyrrolo[2,1-f][1,2,4]triazin-2-yl)ethyl) amino)-7H-pyrrolo[2,3-d]pyrimidin-5-yl)-5-morpholinophenyl)methanesulfonamide (S)—N-(3-(4-((1-(5-Methyl-4-oxo-3-phenyl-3,4-dihydropyrrolo[2,1-f][1,2,4]triazin-2-yl)ethyl)amino)-7-((2-(trimethylsilyl)methyl)-7H-pyrrolo[2,3-d]pyrimidin-5-yl)-5-morpholinophenyl)methanesulfonamide (27 mg, 0.02 mmol) was treated with trifluoroacetic acid (0.45 ml, 5.84 mmol) and a solution of ammonia (7N in methanol, 0.45 ml, 3.15 mmol) according to the method described in Example 27 to give 11 mg (71% yield) of the title compound. Purity 100%.

LRMS (m/z): 640 (M+1)+.

$^1$H NMR (400 MHz, CD$_3$OD) δ 8.22-7.95 (m, 1H), 7.74-7.31 (m, 6H), 7.23 (t, J=7.8 Hz, 1H), 7.15 (s, 1H), 6.98-6.78 (m, 2H), 6.36 (dt, J=14.9, 7.5 Hz, 1H), 5.09-4.94 (m, 1H), 4.60 (s, 1H), 3.80-3.67 (m, 3H), 3.25-3.08 (m, 3H), 3.08-2.83 (m, 3H), 2.43 (s, 3H), 1.36 (dd, J=7.3, 4.1 Hz, 3H), 1.32-1.26 (m, 2H), 1.23 (dd, J=9.5, 4.7 Hz, 1H), 0.90 (dd, J=12.8, 5.7 Hz, 1H).

Example 184

N-[4-(4-{[(1S)-1-(5-Methyl-4-oxo-3-phenyl-3,4-dihydropyrrolo[2,1-f][1,2,4]triazin-2-yl)ethyl] amino}-7H-pyrrolo[2,3-d]pyrimidin-5-yl)-1H-indol-6-yl]sulfamide N-[4-(4-{[(1S)-1-(5-Methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)-1H-indol-6-yl]sulfamide (48 mg, 0.06 mmol) was treated with trifluoroacetic acid (1.0 ml, 12.98 mmol) and a solution of ammonia (7N in methanol, 5.0 ml, 35.0 mmol) according to the method described in Example 27. The title compound was obtained (33 mg, 80% yield) without further purification.

LRMS (m/z): 595 (M+1)+.

$^1$H NMR (400 MHz, DMSO-d6) δ 11.86 (bs, 1H), 11.16 (bs, 1H), 9.24 (bs, 1H), 8.14 (s, 1H), 7.58-7.44 (m, 7H), 7.38-7.33 (m, 1H), 7.28-7.24 (m, 1H), 7.22 (d, J=2.3 Hz, 1H), 7.14 (d, J=2.6 Hz, 1H), 6.93 (bs, 2H), 6.32 (d, J=2.0 Hz, 1H), 5.84 (d, J=6.7 Hz, 1H), 4.68-4.57 (m, 1H), 2.33 (s, 3H), 1.15 (d, J=6.5 Hz, 3H).

Example 185

(S)—N-(2-Hydroxy-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide N-(2-Hydroxy-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (12 mg, 0.02 mmol) was treated with trifluoroacetic acid (1 ml, 13 mmol) and a solution of ammonia (7N in methanol, 1 ml, 7 mmol) according to the method described in Example 27 to give 4 mg (41% yield) of the title compound. Purity 100%.

LRMS (m/z): 571 (M+1)+.

$^1$H NMR (400 MHz, CDCl$_3$) δ 8.11 (s, 1H), 7.63 (d, J=8.2 Hz, 1H), 7.58-7.45 (m, 3H), 7.38 (s, 1H), 7.30 (d, J=7.3 Hz, 1H), 7.26 (d, J=0.6 Hz, 2H), 7.17 (d, J=7.0 Hz, 1H), 7.09 (dd, J=9.3, 6.3 Hz, 2H), 6.92 (s, 1H), 6.33 (d, J=2.5 Hz, 1H), 5.97 (d, J=7.2 Hz, 1H), 5.02 (d, J=6.7 Hz, 2H), 3.05 (s, 3H), 2.46 (s, 3H), 1.27 (d, J=8.6 Hz, 3H).

Example 186

(S)-2-(1-((6-Amino-5-(1-((4-methoxyphenyl)sulfonyl)-1H-indazol-6-yl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added 1-((4-methoxyphenyl)sulfonyl)-6-(4,4,5,5-tetramethyl-1,3,2-dioxaborolan-2-yl)-1H-indazole (201 mg, 0.34 mmol), 1,1'- bis(diphenylphosphino)ferrocene-palladium(II)dichloride dichloromethane complex (18 mg, 0.02 mmol) and 227 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1® Purification System (50% to 75%, hexane-ethyl acetate) to obtain 97 mg (66% yield) of the title compound as a white solid. Purity 100%. LRMS (m/z): 648 (M−1)$^-$.

$^1$H NMR (400 MHz, DMSO-d6) δ ppm 1.21 (d, J=6.25 Hz, 3H), 2.32-2.39 (m, 3H), 3.76 (s, 3H), 4.85 (q, 1H), 5.59-5.66 (m, 2H), 5.78 (s, 1H), 6.36 (s, 1H), 6.96-7.04 (m, 1H), 7.09-7.14 (m, 1H), 7.33-7.50 (m, 5H), 7.79 (s, 1H), 7.90 (d, J=6.64 Hz, 2H), 8.09 (s, 1H), 8.53 (s, 1H).

Example 187

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethoxypyridin-3-yl)-4-hydroxybenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (54 mg, 0.12 mmol) was treated with N-(2-ethoxy-5-(4,4,5,5-tetramethyl-1,3,2-dioxaborolan-2-yl)pyridin-3-yl)-4-hydroxybenzenesulfonamide (116 mg, 0.18 mmol), sodium carbonate (30 mg, 0.28 mmol) and 1,1'-bis(diphenylphosphino)ferrocene-palladium(II)dichloride dichloromethane complex (32 mg, 0.04 mmol) according to the method described in Example 3 to give 22 mg (27% yield) of the title compound. Purity 100%. LRMS (m/z): 654 (M+1)$^+$. $^1$H NMR (400 MHz, CD$_3$OD δ 7.88 (m, 1H), 7.79 (s, 1H), 7.71 (s, 1H), 7.65-7.42 (m, 7H), 7.38 (dd, J=7.6, 1.2 Hz, 2H), 6.76 (d, J=8.8 Hz, 2H), 6.33 (m, 1H), 4.23 (q, J=6.9 Hz, 2H), 2.42 (s, 3H), 1.30 (d, J=6.8 Hz, 3H), 1.25 (t, J=7.1 Hz, 3H).

Example 188

(S)-5-Methyl-2-(1-((5-(3-(5-methyl-1,3,4-oxadiazol-2-yl)phenyl)-7H-pyrrolo[2,3-d]pyrimidin-4-yl)amino)ethyl)-3-phenylpyrrolo[2,1-f][1,2,4]triazin-4(3H)-one (S)-5-Methyl-2-(1-((5-(3-(5-methyl-1,3,4-oxadiazol-2-yl)phenyl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (90 mg, 0.13 mmol) was treated with trifluoroacetic acid (2 ml, 25 mmol) and a solution of ammonia (7N in methanol, 2 ml, 100 mmol) according to the method described in Example 27 to give 15 mg (20% yield) of the title compound. Purity 95%.

LRMS (m/z): 544 (M+1)$^+$.

$^1$H NMR (400 MHz, CDCl$_3$) δ ppm 1.17-1.24 (s, 1H), 1.32 (d, J=6.64 Hz, 3H), 2.47 (s, 3H), 2.56 (s, 3H), 5.07-5.18 (m, 1H), 5.76 (d, J=8.21 Hz, 1H), 6.27 (d, J=1.95 Hz, 1H), 6.97 (d, J=2.74 Hz, 1H), 7.16 (d, J=1.95 Hz, 1H), 7.29-7.34 (m, 1H), 7.51-7.59 (m, 3H), 7.66 (t, J=7.62 Hz, 1H), 7.78 (d, J=7.82 Hz, 1H), 8.11 (d, J=7.82 Hz, 1H), 8.26 (s, 1H), 8.32 (s, 1H), 10.06 (s, 1H).

Example 189

N'-[3-Hydroxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide N'-[3-Hydroxy-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]-N,N-dimethylsulfamide (8 mg, 0.01 mmol) was treated with trifluoroacetic acid (160 μl, 2.08 mmol) and a solution of ammonia (7N in methanol, 160 μl, 1.12 mmol) according to the method described in Example 27. The residue was purified using SP1® Purification System (0% to 15% dichloromethane-2-propanol) to obtain 6 mg (91% yield) of the title compound.

LRMS (m/z): 600 (M+1)$^+$.

Example 190

(S)—N-(6-(4-Amino-6-((1-(5-methyl-4-oxo-3-phenyl-3,4-dihydropyrrolo[2,1-f][1,2,4]triazin-2-yl)ethyl)amino)pyrimidin-5-yl)-1H-indol-4-yl)-4-hydroxybenzenesulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (80 mg, 0.18 mmol) were added 4-methoxy-N-(6-(4,4,5,5-tetramethyl-1,3,2-dioxaborolan-2-yl)-1H-indol-4-yl)benzenesulfonamide (137 mg, 0.27 mmol), 1,1'-bis(diphenylphosphino)ferrocene-palladium(II)dichloride dichloromethane complex (14 mg, 0.02 mmol) and 182 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude product was purified using SP1® Purification System (50% to 100%, hexane-ethyl acetate) to obtain 27 mg (21% yield, 95% purity) and 98 mg (72% yield, 88% purity) of the title compound as a white solid.

LRMS (m/z): 662 (M+1)$^+$.

$^1$H NMR (400 MHz, DMSO-d6 at 80° C.) δ ppm 1.16 (d, J=6.64 Hz, 3H), 2.36 (s, 3H), 4.77 (q, J=8.21 Hz, 1H), 5.04-5.11 (m, 1H), 5.14 (s, 1H), 6.33 (d, J=2.74 Hz, 1H), 6.67 (s, 1H), 6.89 (d, J=8.99 Hz, 2H), 7.22 (d, J=2.74 Hz, 1H), 7.26-7.32 (m, 1H), 7.36-7.52 (m, 4H), 7.67 (d, J=8.60 Hz, 2H), 7.86 (s, 1H), 9.74 (s, 1H). At room temperature a mixture of atropoisomers is observed.

Example 191

(S)—N-(6-(4-Amino-6-((1-(5-methyl-4-oxo-3-phenyl-3,4-dihydropyrrolo[2,1-f][1,2,4]triazin-2-yl)ethyl)amino)pyrimidin-5-yl)-1H-indol-4-yl)-4-hydroxybenzenesulfonamide (S)—N-(6-(4-Amino-6-((1-(5-methyl-4-oxo-3-phenyl-3,4-dihydropyrrolo[2,1-f][1,2,4]triazin-2-yl)ethyl)amino)pyrimidin-5-yl)-1-((2-(trimethylsilyl)ethoxy)methyl)-1H-indol-4-yl)-4-methoxybenzenesulfonamide (56 mg, 0.07 mmol) was dissolved in dichloromethane (1 ml). A solution of boron tribromide (1M in dichloromethane, 707 μl, 0.71 mmol) was added dropwise and the reaction was stirred at room temperature overnight. Methanol was added and the solvents were removed. Then ammonia (7N in methanol) (1.5 ml) was added and the mixture was stirred at room temperature overnight. The solvent was removed and the residue was purified by reverse phase chromatography using SP1® Purification System to give 6 mg (20% yield) of the title compound as a white solid. Purity 97%.

LRMS (m/z): 648 (M+1)$^+$.

Example 192

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethylpyridin-3-yl)-4-hydroxybenzenesulfonamide (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethylpyridin-3-yl)-4-methoxybenzenesulfonamide (146 mg, 0.22 mmol) was treated with boron tribromide (1M in dichloromethane, 700 µl, 0.70 mmol) in dichloromethane (1 ml) as a solvent according to the method described in Example 23. The residue was purified by reverse phase chromatography using SP1® Purification System to give 31 mg (22% yield) as a solid. Purity 100%.

LRMS (m/z): 638 (M+1)$^+$.

$^1$H NMR (400 MHz, CD$_3$OD) δ 8.20 (bs, 1H), 7.84 (s, 1H), 7.59-7.49 (m, 4H), 7.49-7.33 (m, 5H), 7.30 (s, 1H), 6.86-6.73 (m, 2H), 6.38-6.28 (m, 1H), 4.95 (m, 1H), 2.66 (q, J=7.5 Hz, 2H), 2.41 (s, 3H), 1.30 (d, J=6.7 Hz, 3H), 1.10 (t, J=7.4 Hz, 3H).

Example 193

(S)—N-(3-Cyano-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Cyano-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (145 mg, 0.20 mmol) was treated with trifluoroacetic acid (3.8 ml, 49 mmol) and a solution of ammonia (7N in methanol, 3.8 ml, 27 mmol) according to the method described in Example 27 to give 78 mg (66% yield) of the title compound. Purity 100%.

LRMS (m/z): 580 (M+1)$^+$.

$^1$H NMR (400 MHz, DMSO-d6) δ 12.07 (d, J=2.3 Hz, 1H), 10.26 (s, 1H), 8.16 (s, 1H), 7.75 (s, 1H), 7.64-7.37 (m, 7H), 7.27 (d, J=2.6 Hz, 1H), 6.37 (d, J=2.5 Hz, 1H), 6.11 (d, J=6.9 Hz, 1H), 4.81 (p, J=6.6 Hz, 1H), 3.12 (s, 3H), 2.36 (s, 3H), 1.35 (d, J=6.7 Hz, 3H), 1.23 (s, 1H).

Example 194

(S)-2-(1-((6-Amino-5-(1H-indazol-6-yl)pyrimidin-4-yl)amino)ethyl)-5-methyl-3-phenylpyrrolo[2,1-f][1,2,4]triazin-4(3H)-one (S)-2-(1-((6-amino-5-(1-((4-methoxyphenyl)sulfonyl)-1H-indazol-6-yl)pyrimidin-4-yl)amino)ethyl)-5-methyl-3-phenylpyrrolo[2,1-f][1,2,4]triazin-4(3H)-one (77 mg, 0.12 mmol) was treated with pyridine hydrochloride (2.7 g, 115 mmol) and heated at 180° C. for 2 h. Water and ethyl acetate were added and the organic phase was washed with water and brine and then concentrated. The residue was purified using SP1® Purification System (0% to 75%, hexane-ethyl acetate) to obtain 12 mg (22% yield) of the title compound as a white solid. Purity 98%.

LRMS (m/z): 478 (M+1)$^+$.

$^1$H NMR (400 MHz, DMSO-d6) δ ppm 1.18 (d, J=6.64 Hz, 3H), 2.28-2.39 (m, 3H), 4.81 (q, 1H), 5.71-5.77 (m, 2H), 6.36 (d, J=1.95 Hz, 1H), 7.30-7.52 (m, 7H), 7.87 (s, 1H), 8.05-8.14 (m, 1H), 13.09 (d, 1H).

Example 195

(S)-3-Hydroxy-5-(methylsulfonamido)phenyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate (S)-2-(1-Aminoethyl)-5-methyl-3-phenylpyrrolo[2,1-f][1,2,4]triazin-4(3H)-one (81 mg, 0.27 mmol), 3-hydroxy-5-(methylsulfonamido)phenyl 4-amino-6-chloropyrimidine-5-carboxylate (104 mg, 0.29 mmol), DIEA (323 µl, 1.85 mmol) and cesium fluoride (121 mg, 0.80 mmol) were suspended in tert-butanol (8 ml) and the mixture was heated at 70° C. in a sealed tube for 24 h. The solvent was evaporated under reduced pressure and the reaction mixture was diluted with ethyl acetate and washed with saturated ammonium chloride solution and brine. After evaporation of the solvent, the residue was purified by reverse phase chromatography using SP1® Purification System to give 50 mg (31% yield) as a solid. Purity 97%.

LRMS (m/z): 591 (M+1)$^+$.

$^1$H NMR (400 MHz, DMSO-d6) δ 9.90 (s, 1H), 8.58 (d, J=7.1 Hz, 1H), 7.90 (s, 1H), 7.58-7.40 (m, 5H), 7.35 (d, J=2.7 Hz, 1H), 6.63 (dd, J=2.0 Hz, 1H), 6.50 (dd, J=2.0 Hz, 1H), 6.41-6.33 (m, 2H), 4.82 (q, J=6.8 Hz, 1H), 3.00 (s, 3H), 2.36 (d, J=5.5 Hz, 3H), 1.32 (d, J=8.0 Hz, 3H).

Example 196

(S)-2-(1-((5-((2-Hydroxyphenyl)sulfonyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-((2-Hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one (5.6 mg, 0.01 mmol) was dissolved in 2 ml N,N-dimethylformamide. The mixture was cooled in an ice bath and Oxone® (18 mg, 0.03 mmol) was added dropwise. The reaction was stirred overnight at room temperature. More Oxone® (9 mg, 0.015 mmol) was added and the mixture was heated at 30° C. overnight. The reaction mixture was partitioned between ethyl acetate and water. The organic layer was dried over magnesium sulphate, filtered and evaporated under reduced pressure. The crude was purified using SP1® Purification System to give 2 mg (31% yield) of the title compound. Purity 95%.

LRMS (m/z): 542 (M+1)$^+$.

$^1$H NMR (400 MHz, CDCl$_3$) δ 0.80-0.92 (m, 1H), 1.52 (s, 3H), 1.54 (s, 3H), 5.13-5.19 (m, 1H), 6.33 (d, J=2.34 Hz, 1H), 6.90 (t, J=7.62 Hz, 1H), 6.96 (d, J=8.21 Hz, 1H), 7.25 (s, 1H), 7.36 (d, J=7.42 Hz, 1H), 7.39-7.60 (m, 4H), 7.77 (s, 1H), 7.81 (d, J=8.21 Hz, 1H), 7.98 (d, J=7.42 Hz, 1H), 8.24 (s, 1H).

Example 197

(S)—N-(3-(4-Amino-6-((1-(4-oxo-3-phenyl-3,4-dihydropyrrolo[2,1-f][1,2,4]triazin-2-yl)ethyl)amino)pyrimidin-5-yl)phenyl)-4-hydroxybenzenesulfonamide (S)—N-(3-(4-Amino-6-((1-(4-oxo-3-phenyl-3,4-dihydropyrrolo[2,1-f][1,2,4]triazin-2-yl)ethyl)amino)pyrimidin-5-yl)phenyl)-4-methoxybenzenesulfonamide (126 mg, 0.21 mmol) was treated with boron tribromide (1M in dichloromethane, 0.62 ml, 0.62 mmol) with dichloromethane (1.5 ml) as a solvent according to the method described in Example 23. The residue was purified by reverse phase chromatography using SP1® Purification System to give 47 mg (38% yield) as a solid. Purity 99%.
LRMS (m/z): 595 (M+1)⁺.
¹H NMR (400 MHz, CD₃OD) δ 7.87 (s, 1H), 7.62 (d, J=8.5 Hz, 2H), 7.58-7.34 (m, 8H), 7.32-7.04 (m, 3H), 6.98 (s, 2H), 6.76 (d, J=6.7 Hz, 2H), 6.62-6.47 (m, 1H), 4.99-4.89 (m, 3H), 1.26 (d, J=6.7 Hz, 3H).

Example 198

(S)-2-(1-((5-(2-Aminopyridin-4-yl)-7H-pyrrolo[2,3-d]pyrimidin-4-yl)amino)ethyl)-5-methyl-3-phenylpyrrolo[2,1-f][1,2,4]triazin-4(3H)-one The title compound was isolated (20 mg) as a by-product in the experiment described in Example 210. Purity 99%.
LRMS (m/z): 478 (M+1)⁺.
¹H NMR (400 MHz, CDCl₃) δ ppm 1.37 (d, J=6.64 Hz, 3H), 2.13 (s, 2H), 3.50 (s, 1H), 5.04-5.21 (m, 3H), 6.09 (d, J=7.82 Hz, 1H), 6.32 (d, J=2.34 Hz, 1H), 6.75 (s, 1H), 6.90 (d, J=5.08 Hz, 1H), 7.14-7.22 (m, 2H), 7.32-7.38 (m, 1H), 7.46-7.62 (m, 4H), 8.13 (d, J=5.08 Hz, 1H), 8.27 (d, 1H), 10.81 (d, 1H).

Example 199

(S)-2-(1-((6-Amino-5-(1-((4-methoxyphenyl)sulfonyl)-1H-indol-6-yl)pyrimidin-4-yl)amino)ethyl)-5-methyl-3-phenylpyrrolo[2,1-f][1,2,4]triazin-4(3H)-one ((S)-2-(1-((6-Amino-5-(1H-indol-6-yl)pyrimidin-4-yl)amino)ethyl)-5-methyl-3-phenylpyrrolo[2,1-f][1,2,4]triazin-4(3H)-one (126 mg, 0.26 mmol) was added to a suspension of sodium hydride (14 mg, 0.37 mmol, 60% dispersion in mineral oil) at 0° C. After 30 min., 4-methoxybenzene-1-sulfonyl chloride was added dropwise. After 10 min. the reaction was let to warm to room temperature. After 1 h the crude was poured over a mixture of ice and water. Ethyl acetate was added and the organic phase was washed with water and brine. After evaporation of the solvent, the residue was purified by flash chromatography using SP1® Purification System (50-100% hexane/Ethyl acetate) to give 75 mg (42% yield). Purity 97%.
LRMS (m/z): 648 (M+1)⁺.
¹H NMR (400 MHz, DMSO-d6) δ ppm 1.18 (d, 3H), 2.26-2.40 (m, 3H), 3.70-3.80 (m, 3H), 4.76 (q, 1H), 5.36-5.49 (m, 2H), 5.54 (d, 1H), 6.35 (d, 1H), 6.85 (d, 1H), 6.96-7.08 (m, 2H), 7.33-7.55 (m, 5H), 7.66-7.73 (m, 1H), 7.76-7.85 (m, 2H), 7.93-8.03 (m, 2H).

Example 200

(S)-4-(N-Methylsulfamoyl)phenyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate (S)-2-(1-Aminoethyl)-5-methyl-3-phenylpyrrolo[2,1-f][1,2,4]triazin-4(3H)-one (81 mg, 0.27 mmol), 4-(N-methylsulfamoyl)phenyl 4-amino-6-chloropyrimidine-5-carboxylate (135 mg, 0.39 mmol), DIEA (344 µl, 1.97 mmol) and cesium fluoride (150 mg, 0.99 mmol) were suspended in tert-butanol (10 ml) and the mixture was heated at 80° C. in a sealed tube for 24 h. The solvent was evaporated under reduced pressure and the reaction mixture was diluted with ethyl acetate and washed with saturated ammonium chloride solution and brine. After evaporation of the solvent, the residue was purified by reverse phase chromatography using SP1® Purification System to give 27 mg (14% yield) as a solid. Purity 99%.
LRMS (m/z): 575 (M+1)⁺.
¹H NMR (400 MHz, DMSO-d6) δ 8.57 (d, J=7.2 Hz, 1H), 7.91 (s, 1H), 7.85 (d, 2H), 7.55-7.42 (m, 8H), 7.35 (d, J=2.7 Hz, 1H), 6.36 (d, J=2.7 Hz, 1H), 4.84 (q, 1H), 2.43 (d, J=5.0 Hz, 3H), 2.35 (s, 3H), 1.32 (d, J=6.7 Hz, 2H).

Example 201

(S)-3-(4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-(methylsulfonamido)phenyl methanesulfonate (S)-3-(Methylsulfonamido)-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl methanesulfonate (169 mg, 0.19 mmol) was treated with trifluoroacetic acid (4.7 ml, 61 mmol) and a solution of ammonia (7N in methanol, 4.0 ml, 17 mmol) according to the method described in Example 27 to give 102 mg (83% yield) of the title compound. Purity 99%.
LRMS (m/z): 649 (M+1)⁺.
¹H NMR (400 MHz, DMSO-d6) δ 12.01 (d, J=2.3 Hz, 1H), 10.18 (s, 1H), 8.14 (s, 1H), 7.64-7.49 (m, 3H), 7.49-7.41 (m, 2H), 7.37 (d, J=2.5 Hz, 1H), 7.28 (t, J=1.6 Hz, 1H), 7.24-7.21 (m, 2H), 7.16 (t, J=2.1 Hz, 1H), 6.35 (dd, J=2.6, 0.6 Hz, 1H), 6.00 (d, J=7.1 Hz, 1H), 4.82 (p, J=6.6 Hz, 1H), 3.41 (s, 3H), 3.08 (s, 3H), 2.35 (s, 3H), 1.32 (d, J=6.7 Hz, 3H).

Example 202

(S)-2-(1-((5-(3-Hydroxy-5-(5-methyl-1,3,4-oxadiazol-2-yl)phenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-Hydroxy-5-(5-methyl-1,3,4-oxadiazol-2-yl)phenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (50 mg, 0.07 mmol) was treated with trifluoroacetic acid (2 ml, 25 mmol) and a solution of ammonia (7N in methanol, 3 ml, 135 mmol) according to the method described in Example 27. The residue was purified using SP1® Purification System (DCM to DCM-Isopropyl alcohol 15%) to give 10 mg (67% yield) of the title compound. Purity 98%.
LRMS (m/z): 560 (M+1)⁺.
¹H NMR (400 MHz, DMSO-d6) δ ppm 1.29 (d, J=6.64 Hz, 3H), 2.35 (s, 3H), 3.26-3.29 (m, 3H), 3.36-3.40 (m, 3H), 4.80-4.87 (m, 1H), 6.01 (d, J=7.42 Hz, 1H), 6.35 (d, J=2.74 Hz, 1H), 7.13 (d, J=2.74 Hz, 1H), 7.16-7.18 (m, 1H), 7.38-7.41 (m, 1H), 7.42 (s, 1H), 7.50-7.60 (m, 6H), 8.16 (s, 1H), 10.22 (s, 1H).

Example 203

(S)-2-(1-((5-(3-(5-Amino-1,3,4-oxadiazol-2-yl)-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(3-(5-Amino-1,3,4-oxadiazol-2-yl)-5-hydroxyphenyl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (40 mg, 0.06 mmol) was treated with trifluoroacetic acid (1 ml, 13 mmol) and a solution of ammonia (7N in methanol, 1 ml, 59 mmol) according to the method described in Example 27. The residue was purified by reverse phase chromatography using SP1® Purification System to give 5 mg (15% yield) of the title compound. Purity 98%.

LRMS (m/z): 561 (M+1)$^+$.

$^1$H NMR (400 MHz, DMSO-d6) δ ppm 1.30 (d, J=6.64 Hz, 3H), 2.33-2.39 (m, 3H), 3.28 (s, 3H), 3.37-3.41 (m, 3H), 4.81 (q, J=6.77 Hz, 1H), 6.03 (d, J=7.82 Hz, 1H), 6.35 (d, J=3.13 Hz, 1H), 7.07 (d, J=1.95 Hz, 1H), 7.16 (d, J=2.74 Hz, 1H), 7.19 (s, 2H), 7.26 (s, 1H), 7.35-7.40 (m, 2H), 7.50-7.60 (m, 5H), 8.17 (s, 1H), 10.11 (s, 1H).

Example 204

(S)—N-(3-Hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (159 mg, 0.02 mmol) was treated with boron tribromide (1M in dichloromethane, 0.61 ml, 0.61 mmol) in dichloromethane (1 ml) as a solvent and then with a solution of ammonia (7N in methanol, 4 ml, 28 mmol) according to the method described in Example 41 to give 53 mg (46% yield) of the title compound. Purity 100%.

LRMS (m/z): 571 (M+1)$^+$ $^1$H NMR (400 MHz, DMSO-d6) δ 11.69 (s, 1H), 10.05 (s, 1H), 9.82 (s, 1H), 8.05 (s, 1H), 7.65-7.37 (m, 5H), 7.29 (d, J=2.6 Hz, 1H), 7.17 (d, J=8.2 Hz, 1H), 7.05 (d, J=2.2 Hz, 1H), 7.00 (d, J=1.9 Hz, 1H), 6.76 (dd, J=8.2, 2.0 Hz, 1H), 6.37 (d, J=2.3 Hz, 1H), 6.33 (d, J=7.5 Hz, 1H), 4.75 (p, J=6.4 Hz, 1H), 2.99 (s, 3H), 2.36 (s, 3H), 1.26 (d, J=6.5 Hz, 3H).

Example 205

(S)—N-(4-Methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(4-Methyl-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (50 mg, 0.07 mmol) was treated with trifluoroacetic acid (2 ml, 25 mmol) and a solution of ammonia (7N in methanol, 2 ml, 117 mmol) according to the method described in Example 27 to give 30 mg (73% yield) of the title compound as a yellow solid. Purity 99%.

LRMS (m/z): 569 (M+1)$^+$.

$^1$H NMR (400 MHz, DMSO-d6) δ ppm 1.18 (d, 3H), 2.11-2.24 (m, J=21.49 Hz, 3H), 2.36 (s, 3H), 2.88-3.00 (m, 3H), 4.73-4.81 (m, 1H), 5.45 (d, J=7.03 Hz, 1H), 6.40 (s, 1H), 7.12-7.21 (m, J=2.74 Hz, 3H), 7.29 (dd, J=8.21, 2.34 Hz, 1H), 7.34-7.44 (m, J=2.74 Hz, 1H), 7.48-7.59 (m, 5H), 8.12 (s, 1H), 9.74 (s, 1H).

Example 206

(S)—N-(3-((4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide (S)—N-(3-((4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)thio)phenyl)methanesulfonamide (10 mg, 0.01 mmol) was treated with trifluoroacetic acid (1 ml, 14 mmol) and a solution of ammonia (7N in methanol, 1 ml, 59 mmol) according to the method described in Example 27 to give 3 mg (37% yield) of the title compound as a white solid. Purity 99%.

LRMS (m/z): 587 (M+1)$^+$.

$^1$H NMR (400 MHz, DMSO-d6) δ ppm 1.17 (d, J=6.64 Hz, 3H), 2.38 (s, 3H), 2.79 (s, 3H), 4.75-4.85 (m, 1H), 6.40 (d, J=2.74 Hz, 1H), 6.63 (d, J=8.21 Hz, 1H), 6.87 (d, J=7.82 Hz, 1H), 6.90-6.96 (m, 1H), 7.06 (t, J=7.82 Hz, 1H), 7.24 (d, J=7.82 Hz, 1H), 7.31 (d, J=2.74 Hz, 1H), 7.38 (t, J=7.42 Hz, 1H), 7.42-7.57 (m, 4H), 7.63 (d, J=1.95 Hz, 1H), 8.07 (s, 1H), 9.77 (s, 1H), 12.26 (s, 1H).

Example 207

(S)-4-Amino-6-((1-(5-methyl-4-oxo-3-phenyl-3,4-dihydropyrrolo[2,1-f][1,2,4]triazin-2-yl)ethyl)amino)-N-(4-(N-methylsulfamoyl)phenyl)pyrimidine-5-carboxamide (S)-2-(1-Aminoethyl)-5-methyl-3-phenylpyrrolo[2,1-f][1,2,4]triazin-4(3H)-one (100 mg, 0.33 mmol), 4-amino-6-chloro-N-(4-(N-methylsulfamoyl)phenyl)pyrimidine-5-carboxamide (123 mg, 0.36 mmol), DIEA (344 μl, 1.97 mmol) and cesium fluoride (150 mg, 0.99 mmol) were suspended in tert-butanol (10 ml) and the mixture was heated at 80° C. in a sealed tube for 24 h. The solvent was evaporated under reduced pressure and the reaction mixture was diluted with ethyl acetate and washed with saturated ammonium chloride solution and brine. After evaporation of the solvent, the residue was purified by reverse phase chromatography using SP1® Purification System to give 47 mg (23% yield) as a solid. Purity 94%.

LRMS (m/z): 574 (M+1)$^+$.

$^1$H NMR (400 MHz, DMSO-d6) δ 8.39 (s, 1H), 7.87 (s, 1H), 7.82 (d, J=8.8 Hz, 2H), 7.68 (d, J=8.9 Hz, 2H), 7.52-7.41 (m, 5H), 7.37 (d, J=2.6 Hz, 1H), 6.78 (d, J=12.1 Hz, 2H), 6.36 (d, J=2.1 Hz, 1H), 4.63 (q, J=6.6 Hz, 1H), 2.37 (s, 2H), 2.36 (s, 2H), 1.29 (d, J=6.8 Hz, 2H).

Example 208

(S)-2-(1-((6-Amino-5-(1-((4-hydroxyphenyl)sulfonyl)-1H-indol-6-yl)pyrimidin-4-yl)amino)ethyl)-5-methyl-3-phenylpyrrolo[2,1-f][1,2,4]triazin-4(3H)-one (S)-2-(1-((6-Amino-5-(1-((4-methoxyphenyl)sulfonyl)-1H-indol-6-yl)pyrimidin-4-yl)amino)ethyl)-5-methyl-3-phenylpyrrolo[2,1-f][1,2,4]triazin-4(3H)-one (100 mg, 0.14 mmol) was dissolved in dichloromethane (1 ml). A solution of boron tribromide (1M in dichloromethane, 952 μL, 0.95 mmol) was added dropwise and the reaction was stirred at room temperature overnight. A solution of boron tribromide (1M in dichloromethane, 1.4 ml, 1.4 mmol) was added dropwise and the reaction was heated at 60° C. overnight. The mixture was diluted with ethyl acetate and washed with a 4% solution of sodium bicarbonate, water, brine and dried over sodium sulphate, filtered and evaporated under reduced pressure. The product was purified by reverse phase chromatography using SP1® Purification System to give 53 mg (61% yield) of the title compound. Purity 99%. LRMS (m/z): 633 (M+1)$^+$.

$^1$H NMR (400 MHz, DMSO-d6) δ ppm 1.12-1.25 (m, 3H), 2.27-2.40 (m, 3H), 4.61-4.84 (m, 1H), 5.35-5.51 (m, 3H), 6.26-6.42 (m, 1H), 6.78-6.89 (m, 3H), 6.94-7.23 (m, 1H), 7.26-7.61 (m, 6H), 7.63-7.95 (m, 5H), 7.94-8.17 (m, 1H).

Example 209

(S)—N-(6-(4-((1-(5-Methyl-4-oxo-3-phenyl-3,4-dihydropyrrolo[2,1-f][1,2,4]triazin-2-yl)ethyl) amino)-7H-pyrrolo[2,3-d]pyrimidin-5-yl)-1H-indol-4-yl)methanesulfonamide (S)—N-(6-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-4-yl)methanesulfonamide (37 mg, 0.05 mmol) was treated with trifluoroacetic acid (1 ml, 13 mmol) and a solution of ammonia (7N in methanol, 1 ml, 7 mmol) according to the method described in Example 27 to give 17 mg (53% yield) of the title compound. Purity 95%. LRMS (m/z): 594 (M+1)$^+$.

$^1$H NMR (400 MHz, DMSO-d6) δ 11.79 (d, J=2.2 Hz, 1H), 11.30 (s, 1H), 9.64 (s, 1H), 8.12 (s, 1H), 7.59-7.41 (m, 5H), 7.39-7.34 (m, 1H), 7.31 (s, 1H), 7.20 (d, J=2.4 Hz, 1H), 7.14 (d, J=1.2 Hz, 1H), 6.88-6.83 (m, 1H), 6.54 (d, J=2.6 Hz, 1H), 6.25 (dd, J=2.7, 0.5 Hz, 1H), 6.08 (d, J=7.4 Hz, 1H), 4.77 (q, 1H), 2.97-2.92 (m, 3H), 2.31 (s, 3H), 1.26 (d, J=6.6 Hz, 3H).

Example 210

(S)—N-(4-(4-((1-(5-Methyl-4-oxo-3-phenyl-3,4-dihydropyrrolo[2,1-f][1,2,4]triazin-2-yl)ethyl) amino)-7H-pyrrolo[2,3-d]pyrimidin-5-yl)pyridin-2-yl)-1-(tetrahydro-2H-pyran-4-yl) methanesulfonamide (S)—N-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-2-yl)-1-(tetrahydro-2H-pyran-4-yl) methanesulfonamide (55 mg, 0.07 mmol) was treated with trifluoroacetic acid (2 ml, 26 mmol) and a solution of ammonia (7N in methanol, 2 ml, 91 mmol) according to the method described in Example 27 to give 5 mg (11% yield) of the title compound. Purity 99%.

LRMS (m/z): 640 (M+1)$^+$.

$^1$H NMR (400 MHz, CDCl$_3$) δ ppm 1.33-1.52 (m, 4H), 1.88 (d, J=12.50 Hz, 2H), 2.22-2.39 (m, 2H), 2.46 (s, 3H), 3.19 (d, J=5.86 Hz, 2H), 3.38 (t, J=11.53 Hz, 2H), 3.85-3.98 (m, 2H), 5.09-5.22 (m, 1H), 5.85 (d, J=7.03 Hz, 1H), 6.25 (s, 1H), 7.12 (d, J=2.34 Hz, 1H), 7.17 (d, J=5.86 Hz, 1H), 7.30-7.37 (m, 2H), 7.47 (s, 1H), 7.51-7.59 (m, 3H), 8.26 (d, J=5.86 Hz, 1H), 8.38 (s, 1H), 11.11-11.23 (m, 1H).

Example 211

(S)—N-(5-(4-Amino-6-((1-(5-methyl-4-oxo-3-phenyl-3,4-dihydropyrrolo[2,1-f][1,2,4]triazin-2-yl) ethyl)amino)pyrimidin-5-yl)-2-methoxypyridin-3-yl)-4-hydroxy-3-methylbenzenesulfonamide (S)-2-(1-(((6-Amino-5-bromopyrimidin-4-yl)amino) ethyl)-5-methyl-3-phenylpyrrolo[2,1-f][1,2,4]triazin-4(3H)-one (63 mg, 0.14 mmol) was treated with 4-hydroxy-N-(2-methoxy-5-(4,4,5,5-tetramethyl-1,3,2-dioxaborolan-2-yl) pyridin-3-yl)-3-methylbenzenesulfonamide (90 mg, 0.21 mmol), 2M cesium carbonate (430 μl, 0.86 mmol) and 1,1'-bis(diphenylphosphino)ferrocene-palladium(II)dichloride dichloromethane complex (12 mg, 0.01 mmol) according to the method described in Example 3 to give 48 mg (51% yield) of the title compound. Purity 100%.

LRMS (m/z): 654 (M+1)$^+$.

$^1$H NMR (400 MHz, CD$_3$OD) δ 7.89 (s, 2H), 7.83-7.64 (m, 1H), 7.65-7.41 (m, 7H), 7.38 (d, J=7.7 Hz, 2H), 7.12 (s, 1H), 6.72 (d, J=8.5 Hz, 1H), 6.31 (s, 1H), 4.98-4.85 (m, 1H), 3.84 (s, 3H), 2.42 (s, 3H), 1.27 (d, J=7.0 Hz, 4H).

Example 212

(S)-4-Methoxybenzyl 4-amino-6-((1-(5-methyl-4-oxo-3-phenyl-3,4-dihydropyrrolo[2,1-f][1,2,4]triazin-2-yl)ethyl)amino)pyrimidine-5-carboxylate (S)-2-(1-Aminoethyl)-5-methyl-3-phenylpyrrolo[2,1-f] [1,2,4]triazin-4(3H)-one (515 mg, 0.27 mmol), 4-methoxybenzyl 4-amino-6-chloropyrimidine-5-carboxylate (691 mg, 1.86 mmol), DIEA (1.77 ml, 10.16 mmol) and cesium fluoride (770 mg, 5.07 mmol) were suspended in tert-butanol (50 ml) and the mixture was heated at 80° C. in a sealed tube for 24 h. The solvent was evaporated under reduced pressure and the reaction mixture was diluted with ethyl acetate and washed with saturated ammonium chloride solution and brine. After evaporation of the solvent, the residue was purified by flash chromatography (0 to 50%, hexane-ethyl acetate) using SP1® Purification System to give 459 mg (51% yield) of the title compound as a solid. Purity 99%.

LRMS (m/z): 526 (M+1)$^+$.

$^1$H NMR (400 MHz, DMSO-d6) δ 8.45 (d, J=7.1 Hz, 1H), 7.83 (s, 1H), 7.52-7.21 (m, 12H), 6.89 (d, J=8.8 Hz, 2H), 6.39 (dd, J=2.7, 0.7 Hz, 1H), 5.27 (d, J=5.4 Hz, 2H), 4.73 (q, 1H), 3.72 (s, 3H), 2.37 (s, 3H), 1.27 (d, J=6.7 Hz, 3H).

Example 213

(S)-1-(3-(4-Amino-6-((1-(5-methyl-4-oxo-3-phenyl-3,4-dihydropyrrolo[2,1-f][1,2,4]triazin-2-yl)ethyl) amino)pyrimidin-5-yl)-5-methoxyphenyl)urea (S)-2-(1-((6-Amino-5-(3-amino-5-methoxyphenyl)pyrimidin-4-yl)amino)ethyl)-5-methyl-3-phenylpyrrolo[2,1-f] [1,2,4]triazin-4(3H)-one (87 mg, 0.18 mmol) was suspended in a mixture of water (1.5 ml) and acetic acid (1.5 ml) and cooled in an ice bath to 0° C. This mixture was treated with a solution of potassium isocyanate (29 mg, 0.36 mmol) in water (0.5 ml). The reaction mixture was stirred at 0° C. for 1 h and then led to warm to room temperature. The crude was diluted with ethyl acetate and washed with saturated ammonium chloride solution and brine. After evaporation of the solvent, the residue was purified by flash chromatography (50 to 100%, hexane-ethyl acetate) using SP1® Purification System to give 54 mg (57% yield) of the title compound as a solid. Purity 99%

LRMS (m/z): 526 (M+1)$^+$.

$^1$H NMR (400 MHz, DMSO-d6) δ ppm 1.16 (d, 3H), 2.35 (s, 3H), 3.65-3.82 (m, 3H), 4.72 (q, 1H), 5.40 (s, 1H), 5.51 (s, 2H), 5.88 (s, 2H), 6.36 (s, 1H), 6.41-6.76 (m, 1H), 6.98-7.09 (m, 1H), 7.13-7.36 (m, 1H), 7.36-7.53 (m, 5H), 7.81 (s, 1H), 8.57-8.70 (m, 1H).

Example 214

(S)-2-(1-((6-Amino-5-(3-(morpholinosulfonyl)phenyl)pyrimidin-4-yl)amino)ethyl)-5-methyl-3-phenylpyrrolo[2,1-f][1,2,4]triazin-4(3H)-one To a solution of (S)-2-(1-((6-amino-5-bromopyrimidin-4-yl)amino)ethyl)-5-methyl-3-phenylpyrrolo[2,1-f][1,2,4]triazin-4(3H)-one (60 mg, 0.13 mmol) were added (3-(morpholinosulfonyl)phenyl)boronic acid (54 mg, 0.2 mmol), 1,1'-bis(diphenylphosphino)ferrocene-palladium(II)dichloride dichloromethane complex (11 mg, 0.01 mmol) and 133 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified using SP1® Purification System (50 to 100%, hexane-ethyl acetate) to give 58 mg (73% yield) of the title compound as a white solid. Purity 100%.

LRMS (m/z): 587 (M+1)+.

$^1$H NMR (400 MHz, DMSO-d6) δ ppm 1.18 (d, J=6.64 Hz, 3H), 2.31-2.37 (m, 3H), 2.96 (t, J=3.91 Hz, 4H), 3.60 (t, J=4.30 Hz, 4H), 4.78 (q, 1H), 5.69 (s, 2H), 5.79 (d, J=7.42 Hz, 1H), 6.36 (d, J=2.74 Hz, 1H), 7.36-7.48 (m, 6H), 7.67-7.79 (m, 2H), 7.81-7.84 (m, 1H), 8.18 (s, 1H).

Example 215

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-methoxypyridin-3-yl)-2,4-difluorobenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (150 mg, 0.34 mmol) was treated with 2,4-difluoro-N-(2-methoxy-5-(4,4,5,5-tetramethyl-1,3,2-dioxaborolan-2-yl)pyridin-3-yl)benzenesulfonamide (280 mg, 0.51 mmol), 2M cesium carbonate (350 µl, 0.70 mmol) and 1,1'-bis(diphenylphosphino)ferrocene-palladium(II)dichloride dichloromethane complex (30 mg, 0.04 mmol) according to the method described in Example 3 to give 117 mg (50% yield) of the title compound. Purity 97%.

LRMS (m/z): 660 (M+1)+.

$^1$H NMR (400 MHz, DMSO-d6) δ 10.27 (s, 1H), 7.73 (q, J=8.6 Hz, 3H), 7.58-7.19 (m, 9H), 7.10 (s, 1H), 6.36 (d, J=2.6 Hz, 1H), 5.62 (s, 1H), 5.57 (s, 2H), 4.76 (m, 1H), 3.70 (s, 3H), 2.36 (s, 3H), 1.19 (d, J=6.6 Hz, 3H).

Example 216

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-2,4-dihydroxybenzenesulfonamide (S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-2,4-dimethoxybenzenesulfonamide (108 mg, 0.17 mmol) was treated with boron tribromide (1M in dichloromethane, 0.90 ml, 0.9 mmol) with dichloromethane (20 ml) as a solvent at 100° C. for 2 h under microwave conditions. After evaporation of the solvent and usual workup with ethyl acetate and water, the residue was purified by reverse phase chromatography using SP1® Purification System to give 48 mg (55% yield) as a solid. Purity 99%.

LRMS (m/z): 655 (M+1)+.

$^1$H NMR (400 MHz, CD$_3$OD) δ 7.84 (s, 1H), 7.58-7.28 (m, 8H), 7.28-6.87 (m, 3H), 6.36 (s, 1H), 6.26 (d, J=2.2 Hz, 1H), 6.20 (dd, J=8.7, 2.1 Hz, 1H), 4.57 (br. s, 1H), 2.43 (s, 3H), 1.23 (d, J=6.7 Hz, 3H).

Example 217

(S)-1-(2-Methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)urea (S)-1-(2-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)pyridin-3-yl)urea (60 mg, 0.08 mmol, 86% purity) was treated with trifluoroacetic acid (2.0 ml, 26.0 mmol) and a solution of ammonia (7N in methanol, 5.0 ml, 35.0 mmol) according to the method described in Example 27. The residue was purified using SP1® Purification System (reverse phase, 0% to 100% water-methanol/acetonitrile 1:1) to obtain 18 mg (43% yield) of the title compound.

LRMS (m/z): 551 (M+1)+.

Example 218

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-(ethylamino)pyridin-3-yl)-4-hydroxybenzenesulfonamide (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-(ethylamino)pyridin-3-yl)-4-methoxybenzenesulfonamide (18 mg, 0.03 mmol) was treated with boron tribromide (1M in dichloromethane, 0.1 ml, 0.10 mmol) with dichloromethane (1 ml) as a solvent according to the method described in Example 23. The residue was purified by reverse phase using SP1® Purification System to give 6 mg (32% yield) as a solid. Purity 93%.

LRMS (m/z): 653 (M+1)+

$^1$H NMR (400 MHz, CD$_3$OD) δ 7.79 (d, J=12.3 Hz, 2H), 7.54 (dd, J=19.8, 8.3 Hz, 4H), 7.48-7.26 (m, 6H), 6.79 (d, J=8.7 Hz, 3H), 6.34 (d, J=2.6 Hz, 1H), 4.58 (s, 1H), 3.45-3.24 (m, 6H), 2.42 (s, 3H), 1.28 (d, J=6.6 Hz, 3H), 1.16 (t, J=6.8 Hz, 3H).

Example 219

(S)—N,N-dimethyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-(methylsulfonamido)benzamide (S)—N,N-Dimethyl-3-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-5-(methylsulfonamido)benzamide (215 mg, 0.28 mmol) was treated with trifluoroacetic acid (3.0 ml, 39 mmol) and a solution of ammonia (7N in methanol, 3.0 ml, 21 mmol) according to the method described in Example 27 to give 144 mg (81% yield) of the title compound. Purity 99%.

LRMS (m/z): 626 (M+1)+

¹H NMR (400 MHz, DMSO-d6) δ 8.11 (s, 1H), 7.59-7.53 (m, 1H), 7.52-7.44 (m, 4H), 7.43-7.39 (m, 1H), 7.39 (t, J=1.5 Hz, 1H), 7.28 (dd, J=2.1, 1.4 Hz, 1H), 7.23 (t, J=1.2 Hz, 2H), 6.35 (dd, J=2.7, 0.7 Hz, 1H), 5.06 (q, J=6.7 Hz, 1H), 3.08 (s, 3H), 3.04 (s, 3H), 2.99 (s, 3H), 2.43 (s, 3H), 1.37 (d, J=6.7 Hz, 3H).

Example 220

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-4-hydroxybenzamide To a solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added (5-(4-hydroxybenzamido)pyridin-3-yl)boronic acid (88 mg, 0.34 mmol), 1,1'-bis(diphenylphosphino)ferrocene-palladium(II) dichloride dichloromethane complex (19 mg, 0.02 mmol) and 227 μl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by reverse phase using SP1® Purification System to give 29 mg (21% yield) of the title compound as a white solid. Purity 96%.

LRMS (m/z): 574 (M+1)⁺.

¹H NMR (400 MHz, DMSO-d6) δ 10.26 (s, 1H), 8.98 (s, 1H), 7.87 (d, J=7.8 Hz, 2H), 7.77 (s, 1H), 7.41 (dt, J=25.3, 8.4 Hz, 6H), 6.87 (d, J=8.7 Hz, 2H), 6.34 (d, J=2.5 Hz, 1H), 5.81 (d, J=7.6 Hz, 1H), 5.65 (s, 2H), 4.81 (q, 1H), 2.34 (s, 3H), 1.21 (d, J=6.7 Hz, 3H).

Example 221

(S)-4-Amino-N-(3-methoxy-5-(methylsulfonamido)phenyl)-6-((1-(5-methyl-4-oxo-3-phenyl-3,4-dihydropyrrolo[2,1-f][1,2,4]triazin-2-yl)ethyl)amino)pyrimidine-5-carboxamide (S)-2-(1-Aminoethyl)-5-methyl-3-phenylpyrrolo[2,1-f][1,2,4]triazin-4(3H)-one (117 mg, 0.38 mmol), 4-amino-6-chloro-N-(3-methoxy-5-(methylsulfonamido)phenyl)pyrimidine-5-carboxamide (266 mg, 65% purity, 0.46 mmol), DIEA (404 μl, 2.32 mmol) and cesium fluoride (175 mg, 1.14 mmol) were suspended in tert-butanol (12 ml) and the mixture was heated at 80° C. in a sealed tube for 3 days. The solvent was evaporated under reduced pressure and the reaction mixture was diluted with ethyl acetate and washed with saturated ammonium chloride solution and brine. After evaporation of the solvent, the residue was purified by reverse phase using SP1® Purification System to give 54 mg (23% yield) as a solid. Purity 97%.

LRMS (m/z): 604 (M+1)⁺

¹H NMR (400 MHz, DMSO-d6) δ 10.00 (s, 1H), 9.78-9.51 (m, 1H), 7.86 (s, 1H), 7.54-7.41 (m, 4H), 7.38 (d, J=2.6 Hz, 1H), 7.19 (dd, J=1.8 Hz, 1H), 7.11 (dd, 1H), 6.64 (s, 2H), 6.48 (dd, J=2.1 Hz, 1H), 6.36 (dd, J=2.7, 0.7 Hz, 1H), 4.61 (q, J=6.9 Hz, 1H), 3.68 (s, 3H), 2.98 (s, 3H), 2.36 (s, 3H), 1.29 (d, J=6.8 Hz, 3H).

Example 222

N-[3-Fluoro-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]sulfamide N-[3-Fluoro-5-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]sulfamide (46 mg, 0.06 mmol) was treated with trifluoroacetic acid (2.0 ml, 26.0 mmol) and a solution of ammonia (7N in methanol, 10 ml, 70.0 mmol) according to the method described in Example 27. The residue was purified using SP1® Purification System (0% to 5% dichloromethane-methanol) to obtain 20 mg (57% yield) of the title compound.

LRMS (m/z): 574 (M+1)+.

¹H NMR (400 MHz, DMSO-d6) δ 11.95 (s, 1H), 9.94 (s, 1H), 8.14 (s, 1H), 7.67-7.44 (m, 5H), 7.32 (s, 3H), 7.22 (d, J=2.6 Hz, 1H), 7.07 (s, 1H), 6.97 (t, J=10.0 Hz, 2H), 6.36 (d, J=2.6 Hz, 1H), 5.99 (d, J=7.4 Hz, 1H), 4.91-4.67 (m, 1H), 2.35 (s, 3H), 1.30 (d, J=6.6 Hz, 3H).

Example 223

(S)—N-(4-((4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide (S)—N-(4-((4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)thio)phenyl)methanesulfonamide (15 mg, 0.02 mmol) was treated with trifluoroacetic acid (2 ml, 25 mmol) and a solution of ammonia (7N in methanol, 2 ml, 120 mmol) according to the method described in Example 27 to give 5 mg (40% yield) of the title compound as a white solid. Purity 99%.

LRMS (m/z): 587 (M+1)⁻.

¹H NMR (400 MHz, CDCl₃) δ ppm 1.38 (d, J=6.64 Hz, 3H) 2.55 (s, 3H) 2.88 (s, 3H) 5.08 (q, J=8.79, 6.84 Hz, 1H) 6.39-6.42 (m, 1H) 6.59 (d, J=8.60 Hz, 1H) 6.65 (d, J=9.77 Hz, 1H) 6.86-6.91 (m, 2H) 7.08-7.13 (m, 3H) 7.21-7.25 (m, 2H) 7.31-7.39 (m, 3H) 7.46-7.53 (m, 1H) 8.08 (s, 1H) 9.54 (s, 1H)

Example 224

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-(trifluoromethyl)phenyl)methanesulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added (3-(methylsulfonamido)-5-(trifluoromethyl)phenyl)boronic acid (529 mg, 24% purity, 0.45 mmol), 1,1'-bis(diphenylphosphino)ferrocene-palladium(II)dichloride dichloromethane complex (19 mg, 0.02 mmol) and 284 μl of a 2M aqueous solution of cesium carbonate in dioxane (3 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by flash chromatography (0 to 80%, hexane-ethyl acetate) using SP1® Purification System to give 52 mg (38% yield) of the title compound as a white solid. Purity 98%.

LRMS (m/z): 599 (M+1)$^+$.

$^1$H NMR (400 MHz, DMSO-d6) δ 10.24 (s, 1H), 7.80 (s, 1H), 7.57-7.25 (m, 6H), 6.37 (d, J=2.6 Hz, 1H), 5.91 (s, 1H), 5.77 (s, 2H), 4.81 (q, 1H), 3.06 (s, 3H), 2.34 (s, 3H), 1.19 (d, J=6.7 Hz, 3H).

Example 225

(S)-2-(1-((5-(2-(4-(Dimethylamino)piperidin-1-yl)pyridin-4-yl)-7H-pyrrolo[2,3-d]pyrimidin-4-yl)amino)ethyl)-5-methyl-3-phenylpyrrolo[2,1-f][1,2,4]triazin-4(3H)-one (S)-2-(1-((5-(2-(4-(Dimethylamino)piperidin-1-yl)pyridin-4-yl)-7-((2-(trimethylsilyl)ethoxy)methyl)-7H-pyrrolo[2,3-d]pyrimidin-4-yl)amino)ethyl)-5-methyl-3-phenylpyrrolo[2,1-f][1,2,4]triazin-4(3H)-one (12 mg, 0.02 mmol) was treated with trifluoroacetic acid (1 ml, 13 mmol) and a solution of ammonia (7N in methanol, 1 ml, 60 mmol) according to the method described in Example 27 to give 5 mg (50% yield) of the title compound as a solid. Purity 98%.

LRMS (m/z): 589 (M+1)$^+$.

$^1$H NMR (400 MHz, DMSO-d6) δ ppm 1.25-1.38 (m, 4H) 1.69-1.83 (m, 1H) 2.02-2.08 (m, 1H) 2.13-2.23 (m, 5H) 2.28-2.39 (m, 4H) 2.61-2.82 (m, 3H) 4.42 (t, 2H) 4.70-4.92 (m, 1H) 6.15 (d, J=7.03 Hz, 1H) 6.38 (d, J=2.74 Hz, 1H) 6.79 (d, J=5.08 Hz, 1H) 6.86-6.92 (m, 1H) 7.17-7.25 (m, 1H) 7.40-7.63 (m, 6H) 8.09-8.21 (m, 3H) 12.01 (s, 1H)

Example 226

(S)-5-Methyl-2-(1-((5-(1-(methylsulfonyl)-1H-pyrrolo[2,3-b]pyridin-4-yl)-7H-pyrrolo[2,3-d]pyrimidin-4-yl)amino)ethyl)-3-phenylpyrrolo[2,1-f][1,2,4]triazin-4(3H)-one (S)-5-Methyl-2-(1-((5-(1-(methylsulfonyl)-1H-pyrrolo[2,3-b]pyridin-4-yl)-7-((2-(trimethylsilyl)ethoxy)methyl)-7H-pyrrolo[2,3-d]pyrimidin-4-yl)amino)ethyl)-3-phenylpyrrolo[2,1-f][1,2,4]triazin-4(3H)-one (30 mg, 0.04 mmol) was treated with trifluoroacetic acid (1 ml, 13 mmol) and a solution of ammonia (7N in methanol, 1 ml, 60 mmol) according to the method described in Example 27 to give 22 mg (88% yield) of the title compound as a white solid. Purity 98%.

LRMS (m/z): 580 (M+1)$^-$.

$^1$H NMR (400 MHz, CDCl$_3$) δ 1.30 (d, J=6.64 Hz, 3H) 2.48 (s, 3H) 3.66 (s, 3H) 5.08-5.17 (m, 1H) 5.76 (d, J=7.82 Hz, 1H) 6.80 (d, J=3.91 Hz, 1H) 7.04 (d, J=2.74 Hz, 1H) 7.29-7.35 (m, 2H) 7.46-7.51 (m, J=5.08 Hz, 2H) 7.51-7.59 (m, 3H) 7.71 (d, J=4.30 Hz, 1H) 8.36 (s, 1H) 8.62 (d, J=5.08 Hz, 1H) 11.05 (s, 1H)

Example 227

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-(difluoromethyl)phenyl)methanesulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added (3-(methylsulfonamido)-5-(difluoromethyl)phenyl)boronic acid (598 mg, 20% purity, 0.34 mmol), 1,1'-bis(diphenylphosphino) ferrocene-palladium(II)dichloride dichloromethane complex (19 mg, 0.02 mmol) and 284 µl of a 2M aqueous solution of cesium carbonate in dioxane (3 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by flash chromatography (0 to 85%, hexane-ethyl acetate) using SP1® Purification System to give 22 mg (17% yield) of the title compound as a white solid. Purity 100%.

LRMS (m/z): 581 (M+1)$^+$.

$^1$H NMR (400 MHz, DMSO-d6) δ 10.26 (s, 1H), 8.98 (s, 1H), 7.87 (d, J=7.8 Hz, 2H), 7.77 (s, 1H), 7.41 (dt, J=25.3, 8.4 Hz, 6H), 6.87 (d, J=8.7 Hz, 2H), 6.34 (d, J=2.5 Hz, 1H), 5.81 (d, J=7.6 Hz, 1H), 5.65 (s, 2H), 4.81 (q, 1H), 2.34 (s, 3H), 1.21 (d, J=6.7 Hz, 3H).

Example 228

(S)-1-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-hydroxyphenyl)urea (S)-1-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-methoxyphenyl)urea (50 mg, 0.10 mmol) was dissolved in dichloromethane (1.5 ml). A solution of boron tribromide (1M in dichloromethane, 285 µl, 0.29 mmol) was added dropwise and the reaction was stirred at room temperature overnight. The mixture was diluted with dichloromethane and washed with a solution of 4% sodium bicarbonate, water, brine and dried over sodium sulphate, filtered and evaporated under reduced pressure. The product was purified by reverse phase using SP1® Purification System to give 27 mg (55% yield) of the title compound. Purity 100%.

LRMS (m/z): 513 (M+1)$^+$.

$^1$H NMR (400 MHz, DMSO-d6) δ 9.43 (d, J=29.9 Hz, 1H), 8.51 (d, J=18.1 Hz, 1H), 7.83 (s, 1H), 7.54-7.28 (m, 5H), 6.90 (d, J=8.4 Hz, 1H), 6.54 (s, 1H), 6.33 (d, J=24.7 Hz, 1H), 6.09 (s, 1H), 5.81 (d, J=16.5 Hz, 2H), 5.66 (s, 2H), 4.89-4.64 (m, 1H), 2.88-1.86 (m, 19H), 2.35 (s, 3H), 1.20 (d, J=10.2 Hz, 3H).

Example 229

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-3-methoxybenzamide To a solution of (S)-2-(1-((6-amino-5-bromopyrimidin-4-yl)amino)ethyl)-5-methyl-3-phenylpyrrolo[2,1-f][1,2,4]triazin-4(3H)-one (100 mg, 0.23 mmol) were added (5-(3-methoxybenzamido)pyridin-3-yl)boronic acid (120 mg, 0.34 mmol), 1,1'-bis(diphenylphosphino)ferrocene-palladium(II) dichloride dichloromethane complex (19 mg, 0.02 mmol) and 148 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by flash chromatography (50 to 100%, hexane-ethyl acetate) phase using SP1® Purification System to give 113 mg (85% yield) of the title compound as a white solid. Purity 100%.

LRMS (m/z): 588 (M+1)⁺.

¹H NMR (400 MHz, DMSO-d6) δ 10.50 (s, 1H), 9.01 (s, 1H), 7.78 (s, 1H), 7.60-7.26 (m, J=31.6, 7.3 Hz, 11H), 7.16 (dd, J=15.8, 14.1 Hz, 1H), 6.34 (s, 1H), 5.84 (d, J=7.5 Hz, 1H), 5.66 (s, 2H), 4.82 (q, 1H), 3.81 (s, 3H), 2.34 (s, 3H), 1.21 (d, J=6.6 Hz, 3H).

Example 230

(S)—N-(3-Methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide (S)—N-(3-Methoxy-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)methanesulfonamide (42 mg, 0.05 mmol) was treated with trifluoroacetic acid (840 μl, 10.80 mmol) and a solution of ammonia (7N in methanol, 840 μl, 5.88 mmol) according to the method described in Example 27. The residue was purified using SP1® Purification System (0% to 15% dichloromethane-2-propanol) to obtain 28 mg (87% yield) of the title compound.

LRMS (m/z): 585 (M+1)+.

Example 231

(S)-1-(4-(4-((1-(5-Methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)urea (S)-1-(4-(4-((1-(5-Methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)-1H-indol-6-yl)urea (40 mg, 0.06 mmol) was treated with trifluoroacetic acid (800 μl, 10.38 mmol) and a solution of ammonia (7N in methanol, 800 μl, 5.60 mmol) according to the method described in Example 27. The residue was purified using SP1® Purification System (0% to 20% dichloromethane methanol) to obtain 26 mg (80% yield) of the title compound.

LRMS (m/z): 559 (M+1)+.

¹H NMR (400 MHz, DMSO-d6) δ 11.83 (s, 1H), 11.02 (s, 1H), 8.48 (s, 1H), 8.13 (s, 1H), 7.59-7.43 (m, 5H), 7.25 (s, 1H), 7.21-7.17 (m, 1H), 7.14 (d, J=2.7 Hz, 1H), 7.09 (d, J=2.0 Hz, 1H), 7.02 (s, 1H), 6.92 (d, J=1.7 Hz, 1H), 6.31 (d, J=2.7 Hz, 1H), 5.96 (d, J=6.6 Hz, 1H), 5.72 (s, 2H), 4.66 (m, 1H), 2.32 (s, 3H), 1.18 (d, J=6.5 Hz, 3H).

Example 232

(S)—N-(3-Fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-hydroxyethanesulfonamide (S)—N-(3-Fluoro-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-2-methoxyethanesulfonamide (29 mg, 0.03 mmol, 78% purity) was treated with boron tribromide (1M in dichloromethane, 303 μl, 0.30 mmol) with dichloromethane (580 μl) as a solvent according to the method described in Example 23. and then with a solution of ammonia (7N in methanol, 600 μl, 4.20 mmol) according to the method described in Example 27. The residue was purified using SP1® Purification System (0% to 15% dichloromethane-2-propanol) to obtain 15 mg (82% yield) of the title compound.

LRMS (m/z): 603 (M+1)+.

¹H NMR (400 MHz, DMSO-d6) δ 11.97 (bs, 1H), 8.14 (s, 1H), 7.59-7.45 (m, 5H), 7.33 (d, J=2.4 Hz, 1H), 7.23 (d, J=2.6 Hz, 1H), 7.13-6.96 (m, 3H), 6.36 (d, J=2.7 Hz, 1H), 6.01 (d, J=7.2 Hz, 1H), 4.87-4.76 (m, 1H), 3.73 (t, J=6.5 Hz, 2H), 2.35 (s, 3H), 1.32 (d, J=6.6 Hz, 3H).

Example 233

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-3-hydroxybenzamide (S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)pyridin-3-yl)-3-methoxybenzamide (95 mg, 0.16 mmol) was dissolved in dichloromethane (3 ml). A solution of boron tribromide (1M in dichloromethane, 480 μl, 0.48 mmol) was added dropwise and the reaction was stirred at room temperature overnight. More solution of boron tribromide (1M in dichloromethane, 240 μL, 0.24 mmol) was added and the reaction was stirred at room temperature for 4 h. The mixture was diluted with dichloromethane and washed with a solution of 4% sodium bicarbonate, water, brine and dried over sodium sulphate, filtered and evaporated under reduced pressure. The product was purified by reverse phase using SP1® Purification System to give 45 mg (49% yield) of the title compound as a white solid. Purity 100%.

LRMS (m/z): 574 (M+1)⁺.

¹H NMR (400 MHz, DMSO-d6) δ 10.45 (s, 1H), 9.80 (s, 1H), 8.99 (s, 1H), 8.12 (s, 1H), 7.77 (s, 1H), 7.51-7.26 (m, 9H), 6.98 (d, 1H), 6.34 (d, J=2.1 Hz, 1H), 5.83 (d, J=7.7 Hz, 1H), 5.65 (s, 2H), 4.81 (q, 1H), 2.32 (s, 3H), 1.21 (d, J=6.7 Hz, 3H).

Example 234

(S)—N-(3-Fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-methoxyethanesulfonamide (S)—N-(3-Fluoro-5-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-2-methoxyethanesulfonamide (30 mg, 0.03 mmol, 78% purity) was treated with trifluoroacetic acid (600 μl, 7.79 mmol) and a solution of ammonia (7N in methanol, 600 μl, 4.20 mmol) according to the method described in Example 27. The residue was purified using SP1® Purification System (0% to 15% dichloromethane-2-propanol) to obtain 14 mg (73% yield) of the title compound.

LRMS (m/z): 617 (M+1)+.

¹H NMR (400 MHz, DMSO-d6) δ 11.96 (bs, 1H), 8.13 (s, 1H), 7.58-7.45 (m, 5H), 7.32 (d, J=2.5 Hz, 1H), 7.22 (d, J=2.6 Hz, 1H), 7.11-6.95 (m, 3H), 6.37 (d, J=2.7 Hz, 1H), 6.00 (d, J=7.2 Hz, 1H), 4.87-4.77 (m, 1H), 3.62 (t, J=6.1 Hz, 2H), 3.41 (t, J=5.9 Hz, 2H), 3.13 (s, 3H), 2.35 (s, 3H), 1.31 (d, J=6.6 Hz, 3H).

Example 235

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)phenyl)-4-hydroxy-3-methylbenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (100 mg, 0.23 mmol) was treated with 4-hydroxy-3-methyl-N-(3-(4,4,5,5-tetramethyl-1,3,2-dioxaborolan-2-yl)phenyl)benzenesulfonamide (133 mg, 0.34 mmol), 2M cesium carbonate (340 µl, 0.68 mmol) and 1,1'-bis(diphenylphosphino)ferrocene-palladium(II)dichloride dichloromethane complex (19 mg, 0.02 mmol) according to the method described in Example 3 to give 76 mg (53% yield) of the title compound. Purity 98%.

LRMS (m/z): 623 (M+1)+

$^1$H NMR (400 MHz, CD$_3$OD) δ 7.86 (s, 1H), 7.47-7.25 (m, 10H), 7.27 (s, 1H), 7.25-6.90 (m, 4H), 6.71 (d, J=8.5 Hz, 1H), 6.35 (bs, 1H), 2.42 (s, 3H), 2.10 (s, 3H), 1.21 (d, J=6.5 Hz, 3H).

Example 236

(S)—N-(3-(4-Amino-6-((1-(5-methyl-4-oxo-3-phenyl-3,4-dihydropyrrolo[2,1-f][1,2,4]triazin-2-yl)ethyl)amino)pyrimidin-5-yl)-5-methylphenyl)methanesulfonamide To a solution of (S)-2-(1-((6-amino-5-bromopyrimidin-4-yl)amino)ethyl)-5-methyl-3-phenylpyrrolo[2,1-f][1,2,4]triazin-4(3H)-one (60 mg, 0.14 mmol) were added N-(3-methyl-5-(4,4,5,5-tetramethyl-1,3,2-dioxaborolan-2-yl)phenyl)methane sulfonamide (141 mg, 45% purity, 0.20 mmol), 1,1'-bis(diphenylphosphino)ferrocene-palladium(II)dichloride dichloromethane complex (11 mg, 0.01 mmol) and 136 µl of a 2M aqueous solution of cesium carbonate in dioxane (2 ml). The mixture was stirred under argon atmosphere at 100° C. for 18 hours and then diluted with ethyl acetate. The resulting solution was washed with water and brine, dried over magnesium sulphate, filtered and the solvents were removed under reduced pressure. The crude was purified by flash chromatography (50 to 100%, hexane-ethyl acetate) phase using SP1® Purification System to give 42 mg (55% yield) of the title compound as a white solid. Purity 98%.

LRMS (m/z): 545 (M+1)+.

$^1$H NMR (400 MHz, DMSO-d6) δ 9.73 (s, 1H), 7.82 (s, 1H), 7.55-7.27 (m, J=10.4, 8.3 Hz, 5H), 7.01 (s, 1H), 6.93-6.64 (m, J=42.9 Hz, 1H), 6.37 (dd, J=2.7, 0.7 Hz, 1H), 5.65-5.36 (m, 3H), 4.73 (q, 1H), 3.02 (s, 3H), 2.49 (s, 3H), 2.32 (s, 3H), 1.17 (d, J=6.7 Hz, 3H).

Example 237

(S)—N-(5-(4-Amino-6-((1-(5-methyl-4-oxo-3-phenyl-3,4-dihydropyrrolo[2,1-f][1,2,4]triazin-2-yl)ethyl)amino)pyrimidin-5-yl)-2-ethoxypyridin-3-yl)-4-hydroxy-3-methylbenzenesulfonamide (S)-2-(1-((6-Amino-5-bromopyrimidin-4-yl)amino)ethyl)-5-methyl-3-phenylpyrrolo[2,1-f][1,2,4]triazin-4(3H)-one (100 mg, 0.23 mmol) was treated with N-(2-ethoxy-5-(4,4,5,5-tetramethyl-1,3,2-dioxaborolan-2-yl)pyridin-3-yl)-4-hydroxy-3-methylbenzenesulfonamide (149 mg, 0.34 mmol), 2M cesium carbonate (340 µl, 0.68 mmol) and 1,1'-bis(diphenylphosphino)ferrocene-palladium(II)dichloride dichloromethane complex (19 mg, 0.02 mmol) according to the method described in Example 3 to give 47 mg (27% yield) of the title compound. Purity 85%.

LRMS (m/z): 668 (M+1)+

$^1$H NMR (400 MHz, DMSO-d6) δ 7.89 (s, 1H), 7.85-7.60 (m, 2H), 7.60-7.44 (m, 6H), 7.44-7.33 (m, 3H), 6.72 (d, J=8.5 Hz, 1H), 6.32 (s, 1H), 4.24 (q, J=7.0 Hz, 2H), 2.42 (s, J=11.6 Hz, 3H), 2.13 (s, 3H), 1.29 (d, J=6.2 Hz, 3H), 1.25 (t, J=7.2 Hz, 3H).

Example 238

(S)—N-(3-Hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-1-(tetrahydro-2H-pyran-4-yl)methanesulfonamide (S)—N-(3-Methoxy-4-(4-((1-(5-methyl-4-oxo-3-phenyl-3,4-dihydropyrrolo[2,1-f][1,2,4]triazin-2-yl)ethyl)amino)-7-((2-(trimethylsilyl)ethoxy)methyl)-7H-pyrrolo[2,3-d]pyrimidin-5-yl)phenyl)-1-(tetrahydro-2H-pyran-4-yl)methanesulfonamide (50 mg, 0.05 mmol, 80% purity) was treated with boron tribromide (1M in dichloromethane, 2.0 ml, 2.0 mmol) with dichloromethane (1.0 ml) as a solvent according to the method described in Example 23. and then with a solution of ammonia (7N in methanol, 5.0 ml, 35.0 mmol) according to the method described in Example 27. The residue was purified using SP1® Purification System (reverse phase, 0% to 100% water-acetonitrile/methanol 1:1) to obtain 6 mg (16% yield) of the title compound.

LRMS (m/z): 655 (M+1)+.

Example 239

N'-[3-Hydroxy-4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide N'-[3-Methoxy-4-(4-{[(1S)-1-(5-methyl-4-oxo-3-phenyl-3,4-dihydropyrrolo[2,1-f][1,2,4]triazin-2-yl)ethyl]amino}-7-{[2-(trimethylsilyl)ethoxy]methyl}-7H-pyrrolo[2,3-d]pyrimidin-5-yl)phenyl]-N,N-dimethylsulfamide (73 mg, 0.06 mmol, 57% purity) was treated with boron tribromide (1M in dichloromethane, 2.0 ml, 2.0 mmol) with dichloromethane (1.0 ml) as a solvent according to the method described in Example 23. and then with a solution of ammonia (7N in methanol, 5.0 ml, 35.0 mmol) according to the method described in Example 27. The residue was purified using SP1® Purification System (reverse phase, 0% to 100% water-acetonitrile/methanol 1:1) to obtain 1 mg (2% yield) of the title compound.

LRMS (m/z): 600 (M+1)+.

REFERENCES

1.—Tehrani, A. K.; Borremans D.; De Kimpe N. *Tetrahedron* 1999, 55, 4133-4152

2.—Ohta, T.; Fukuda, T.; Ishibashi, F., Iwao, M. *J. Org. Chem.* 2009, 74, 8143-8153

3.—Leroy, J.; Porthiel, E.; Bondon, A. *Tetrahedron* 2002, 58, 6713-6722

Pharmacological Activity
PI3K α, β, δ and γ Enzymatic Inhibition Assays

Compounds were screened for their ability to inhibit PI3Kα (PI3Ka), PI3Kβ (PI3Kb), PI3Kδ (PI3Kd) and PI3Kγ (PI3Kg) using a cell-free based PI3K HTRF™ assay (Millipore, ref. #33-017).

PI-3 Kinase HTRF kit (ref. #33-037) and the different PI3K recombinant isoforms (ref. #14-602, ref. #14-603, ref. #14-604, ref. #15-558 for Alpha, Beta, Delta and Gamma respectively) were purchased at Millipore (expressed in insect cells). ATP was purchased at Sigma Aldrich (ref. #A7699).

The compounds were pre-incubated with the enzyme for 30 min before starting of the catalytic reaction. [PIP2] was used at its Km. [ATP] was used at 15 μM for all isoforms for technical reasons (Km values varied between 10 and 20 μM depending on the isoform). Time of assay and [Enzyme] were optimized to work in the linear range. Stop and Detection mixtures were used as specified in the Millipore PI-3 Kinase kit.

Final Assay Conditions

| PI3K | Reaction Time (min) | [Enz] (nM) | [ATP] (μM) | [PIP2] (μM) | Preincubation Time (min) | Reading (hours) |
|---|---|---|---|---|---|---|
| ALPHA | 6 | 0.30 | 15 | 2 | 30 | 1-18 |
| BETA | 6 | 0.75 | 15 | 5 | 30 | 1-18 |
| DELTA | 8 | 0.35 | 15 | 2 | 30 | 1-18 |
| GAMMA | 8 | 2.5 | 15 | 10 | 30 | 1-18 |

Reaction time and enzyme concentration in the assay will depend of each batch.

All experiments were analysed using Activity Base software from IDBS and the four-parameter log equation.

The results are shown in Table 1.

| Example | $IC_{50}$ PI3Kd HTRF (nM) |
|---|---|
| 1 | 15 |
| 2 | 22 |
| 3 | 40 |
| 5 | 17 |
| 7 | 11 |
| 8 | 25 |
| 15 | 3 |
| 16 | 5 |
| 17 | 6 |
| 19 | 95 |
| 20 | 1 |
| 22 | 12 |
| 24 | 97 |
| 27 | 1 |
| 28 | 5 |
| 34 | 12 |
| 35 | 4 |
| 36 | 3 |
| 37 | 5 |
| 40 | 30 |
| 43 | 3 |
| 45 | 2 |
| 52 | 1 |
| 59 | 10 |
| 64 | 16 |
| 74 | 36 |
| 76 | 0.8 |
| 78 | 0.4 |
| 80 | 0.3 |
| 81 | 2 |
| 83 | 0.6 |
| 85 | 0.3 |
| 88 | 41 |
| 91 | 1 |
| 97 | 2 |
| 99 | 3 |
| 104 | 1 |
| 106 | 0.4 |
| 107 | 2 |
| 114 | 0.5 |
| 116 | 1 |
| 119 | 156 |
| 120 | 0.4 |
| 125 | 0.7 |
| 127 | 0.4 |
| 128 | 4 |
| 130 | 1 |
| 132 | 2 |
| 137 | 4 |
| 139 | 0.2 |
| 140 | 0.2 |
| 144 | 2 |
| 145 | 0.2 |
| 147 | 0.4 |
| 150 | 1 |
| 151 | 5 |
| 152 | 100 |
| 155 | 0.3 |
| 156 | 1 |
| 157 | 0.2 |
| 159 | 4 |
| 162 | 132 |
| 163 | 0.2 |
| 165 | 5 |
| 168 | 2 |
| 169 | 3 |
| 171 | 5 |
| 175 | 0.3 |
| 176 | 1 |
| 181 | 5 |
| 186 | 0.4 |
| 187 | 0.7 |
| 188 | 0.4 |
| 190 | 0.8 |
| 195 | 0.2 |
| 199 | 3 |
| 209 | 0.2 |
| 218 | 5 |
| 219 | 0.3 |
| 225 | 0.4 |
| 239 | 2 |

It can be seen from Table 1 that the compounds of formula (I) are potent inhibitors of Phosphoinositide 3-kinase delta (PI3kd). Preferred compounds of the invention possess an $IC_{50}$ value for the inhibition of PI3Kd (determined as defined above) of less than 10 μM (10,000 nM), preferably less than 1 μM (1,000 nM), even more preferably of less than 0.2 μM (200 nM), most preferably less than 0.05 μM (50 nM).

The invention is also directed to a compound of the invention as described herein for use in the treatment of the human or animal body by therapy. Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Combinations

The pyrrolotriazinone derivatives defined herein may also be combined with other active compounds in the treatment of a pathological condition or disease susceptible to amelioration by inhibition of PI3Ks.

The combinations of the invention can optionally comprise one or more additional active substances which are known to be useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS); cancer and hematologic malignancies, leukemia, lymphomas and solid tumors.

Particularly, the combinations of the invention can optionally comprise one or more additional active substances which are known to be useful in the treatment of neoplastic diseases (e.g. leukemia, lymphomas, solid tumors); transplant rejection, bone marrow transplant applications (e.g., graft-versus-host disease); autoimmune diseases (e.g. rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis and blistering diseases including but not limited to *pemphigus vulgaris*, bullous pemphigoid and epidermolysis bullosa; respiratory inflammation diseases (e.g. asthma, chronic obstructive pulmonary disease, cystic fibrosis, idiopathic pulmonary fibrosis, sarcoidosis); skin inflammatory diseases (e.g., atopic dermatitis, contact dermatitis, eczema or psoriasis); premalignant and malignant skin conditions (e.g. basal cell carcinoma (BCC), squamous cell carcinoma (SCC) or actinic keratosis (AK)); neurological disorders and pain (such as pain associated with rheumatoid arthritis or osteoarthritis, back pain, general inflammatory pain, inflammatory neuropathic pain, trigeminal neuralgia or central pain).

Preferably, the combinations of the invention can optionally comprise one or more additional active substances which are known to be useful in the treatment of neoplastic diseases leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular, the combinations of the invention can optionally comprise one or more additional active substances which are known to be useful in the treatment of neoplastic diseases leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis The combinations of the invention comprise (i) a compound of the invention as defined above; and (ii) another compound selected from the group consisting of an Adenoside $A_{2A}$ agonist, an agent for treating cardiovascular disorders, an agent for treating diabetes, and an agent for treating liver disease, an anti-allergic agent, an anti-cholinergic agent, an anti-inflammatory agent, an anti-infective agent, a β2-adrenergic agonist, a Chemoattractant receptor homologous molecule expressed on $TH_2$ cells (CRTH2) inhibitor, a chemotherapeutic agent, a corticosteroid, an IKKβ/IKBKB (IkB kinase beta or IKK2) inhibitor, an immunosuppressant, a Janus kinase (JAK) inhibitor, a topically acting p38 Mitogen-Activated Protein Kinase (p38 MAPK) inhibitor, a Phosphosdiesterase (PDE) IV inhibitor, and a Spleen tyrosine kinase (Syk) inhibitor, for simultaneous, separate or sequential use in the treatment of the human or animal body.

In a particular embodiment, the combinations of the invention can optionally comprise one or more additional active substances selected from a) Dyhydrofolate reductase inhibitors, such as Methotrexate or CH-1504;

b) Dihydroorotate dehydrogenase (DHODH) inhibitors such as leflunomide, teriflunomide, or the compounds described in the International Patent Application Nos. WO2008/077639 and WO2009/021696;

c) Immunomodulators such as Glatiramer acetate (Copaxone), Laquinimod or Imiquimod;

d) Inhibitors of DNA synthesis and repair, such as Mitoxantrone or Cladribine;

e) Immunosuppressants, such as Imuran (azathioprine) or Purinethol (6-mercaptopurine or 6-MP);

f) Anti-alpha 4 integrin antibodies, such as Natalizumab (Tysabri);

g) Alpha 4 integrin antagonists such as R-1295, TBC-4746, CDP-323, ELND-002, Firategrast or TMC-2003;

h) Corticoids and glucocorticoids such as prednisone or methylprednisolone, fluticasone, mometasone, budesonide, ciclesonide or beta-metasone;

i) Fumaric acid esters, such as BG-12;

j) Anti-tumor necrosis factor-alpha (Anti-TNF-alpha) monoclonal antibodies such as Infliximab, Adalimumab or Certolizumab pegol;

k) Soluble Tumor necrosis factor-alpha (TNF-alpha) Antagonists such as Ethanercept;

l) Anti-CD20 (lymphocyte protein) monoclonal antibodies such as Rituximab, Ocrelizumab Ofatumumab or TRU-015;

m) Anti-CD52 (lymphocyte protein) monoclonal antibodies such as alemtuzumab;

n) Anti-CD25 (lymphocyte protein) such as daclizumab;

o) Anti-CD88 (lymphocyte protein), such as eculizumab or pexilizumab;

p) Anti-Interleukin 6 Receptor (IL-6R), such as tocilizumab;

q) Anti-Interleukin 12 Receptor (IL-12R)/Interleukin 23 Receptor (IL-23R), such as ustekinumab;

r) Calcineurin inhibitors such as cyclosporine A or tacrolimus;

s) Inosine-monophosphate dehydrogenase (IMPDH) inhibitors, such as mycophenolate mophetyl, ribavirin, mizoribine or mycophenolic acid;

t) Cannabinoid receptor agonists such as Sativex;

u) Chemokine CCR1 antagonists such as MLN-3897 or PS-031291;

v) Chemokine CCR2 antagonists such as INCB-8696;

w) Necrosis factor-kappaB (NF-kappaB or NFKB) Activation Inhibitors such as Sulfasalazine, Iguratimod or MLN-0415;

x) Adenosine $A_{2A}$ agonists, such as ATL-313, ATL-146e, CGS-21680, Regadenoson or UK-432,097;

y) Sphingosine-1 (S1P) phosphate receptor agonists such as fingolimod, BAF-312, or ACT128800;

z) Sphingosine-1 (S1P) liase inhibitors such as LX2931;

aa) Spleen tyrosine kinase (Syk) inhibitors, such as R-112;

bb) Protein Kinase Inhibitors (PKC) inhibitors, such as NVP-AEB071;

cc) Anti-cholinergic agents such as tiotropium or aclidinium;
dd) Beta adrenergic agonists such as formoterol, indacaterol or LAS100977 (abediterol);
ee) MABA (molecules with dual activity: beta-adrenergic agonists and muscarinic receptor antagonists)
ff) Histamine 1 (H1) receptor antagonists, such as azelastine or ebastine;
gg) Cysteinyl leukotriene (CysLT) receptor antagonists, such as montelukast;
hh) Mast cell stabilizers, such as nedocromil or chromoglycate;
ii) 5-lipoxygenase-activating protein (FLAP) inhibitors, such as MK886 or BAY X 1005;
jj) 5-lipoxygenase (5-LO) inhibitors, such as WY-50295T;
kk) Chemoattractant receptor homologous molecule expressed on $TH_2$ cells (CRTH2) inhibitors, such as OC-459, AZD-1981, ACT-129968, QAV-680;
ll) Vitamin D derivatives like calcipotriol (Daivonex);
mm) Anti-inflammatory agents, such as non-steroidal anti-inflammatory drugs (NSAIDs) or selective cyclooxygenase-2 (COX-2) inhibitors such as aceclofenac, diclofenac, ibuprofen, naproxen, apricoxib, celecoxib, cimicoxib, deracoxib, etoricoxib, lumiracoxib, parecoxib sodium, rofecoxib, selenocoxib-1 or valdecoxib;
nn) Anti-allergic agents;
oo) Anti-viral agents;
pp) Phosphodiestearase (PDE) III inhibitors;
qq) Phosphosdiesterase (PDE) IV inhibitors such as roflumilast or GRC-4039;
rr) Dual Phosphodiestearase (PDE) III/IV inhibitors;
ss) Xanthine derivatives, such as theophylline or theobromine;
tt) p38 Mitogen-Activated Protein Kinase (p38 MAPK) Inhibitors such as ARRY-797;
uu) Mitogen-activated extracellular signal regulated kinase kinase (MEK) inhibitor, such as ARRY-142886 or ARRY-438162;
vv) Janus kinase (JAK) inhibitors, such as tofacitinib (previously known as tasocitinib or CP-690,550) from Pfizer and INCB-18424, from Incyte;
ww) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex;
xx) Interferon alpha such as Sumiferon MP;
yy) Epidermal Growth Factor Receptor (EGFR) inhibitors such as erlotinib, Trastuzumab, Herceptin, Avastin, Platins (cisplatin, carboplatin) or Temazolamide;
zz) Antineoplastic agents such as Docetaxel, Estramustine, Anthracyc lines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda), 5 fluorouracil (5 FU), Gemcitabine (Gemzar) or Vinorelbine (Navelbine);

Specific examples of suitable corticoids and glucocorticoids that can be combined with the PI3K inhibitors of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Specific examples of suitable Syk kinase inhibitors that can be combined with the PI3K inhibitors of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide (QAB-205 from Novartis), 2-[7-(3,4-Dimethoxyphenyl)imidazo[1,2-c]pyrimidin-5-ylamino]pyridine-3-carboxamide dihydrochloride (BAY-61-3606 from Bayer) and AVE-0950 (from Sanofi-Aventis).

Specific examples of suitable M3 antagonists (anticholinergics) that can be combined with the PI3K inhibitors of the present invention are tiotropium salts, oxitropium salts, flutropium salts, ipratropium salts, glycopyrronium salts, trospium salts, zamifenacin, revatropate, espatropate, darotropium bromide, CI-923, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenyl-propionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1-[2-oxo-2-(3-thienyl)ethyl]pyrrolidinium iodide, N-[1-(3-Hydroxybenzyl)-1-methylpiperidinium-3(S)-yl]-N—[N-[4-(isopropoxycarbonyl)phenyl]carbamoyl]-L-tyrosinamide trifluoroacetate, UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 3(R)-[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl) piperidinium bromide from Novartis (412682), 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Specific examples of suitable beta adrenergic agonists (β2-agonists) that can be combined with the PI3K inhibitors of the present invention are terbutaline sulphate, eformoterol fumarate, formoterol fumarate, bambuterol, ibuterol, isoprenaline hydrochloride, dopexamine, metaproterenol, tulobuterol, procaterol hydrochloride, sibenadet hydrochloride, mabuterol hydrochloride, albuterol sulphate, salbutamol sulphate, salmefamol, salmeterol xinafoate, carmoterol hydrochloride, (R)-albuterol hydrochloride, Levalbuterol hydrochloride; Levosalbutamol hydrochloride; (−)-Salbutamol hydrochloride, formoterol, (R,R)-Formoterol tartrate; Arformoterol tartrate, sulfonterol, Bedoradrine sulphate, Indacaterol, Trantinterol hydrochloride, Milveterol hydrochloride, Olodaterol, fenoterol hydrobromide, rimoterol hydrobromide, riproterol hydrochloride, Vilanterol broxaterol, pirbuterol hydrochloride, bitolterol mesylate, clenbuterol hydrochloride, AZD-3199, GSK-159802; GSK-597901, GSK-678007, GSK-961081; 4-[2-[3-(1H-Benzimidazol-1-yl)-1,1-dimethylpropylamino]-1-hydroxyethyl]-2-(4-methoxybenzylamino)phenol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-domethoxyphenyl)-2-methyl-2-propylamino]ethanol, 1-[2H-5-hydroxy-3-oxo-4H-1,4-benzoxazin-8-yl]-2-[3-(4-n-butyloxyhenyl)-2-methyl-2-propylamino]ethanol, KUL-1248, HOKU-81, SM-110444, RP-58802B, LAS100977 (abediterol) and compounds described in PCT patent applications Nos. WO 2007/124898, WO 2006/122788A1, WO 2008/046598, WO 2008095720, WO 2009/068177 and WO 2010/072354.

Specific examples of suitable anti-allergic agents that can be combined with the PI3K inhibitors of the present invention are anti-histamines (e.g. Methapyrilene, Mequitazine, Azelastine hydrochloride, Acrivastine, Emedastine difumarate, Emedastine fumarate, Loratadine, Cyproheptadine hydrochloride, Diphenhydramine hydrochloride, Doxepin hydrochloride, Prometriazine hydrochloride, Levocabastine hydrochloride, Desloratadine, Cinnarizine, Setastine hydrochloride, Mizolastine, Ebastine, Cetirizine hydrochloride, Epinastine hydrochloride, Olopatadine hydrochloride, Bepotastine besilate, Triprolidine hydrochloride, Rupatadine fumarate, Fexofenadine hydrochloride, Levocetirizine dihydrochloride, Ketotifen, Azatadine maleate, Dimethindene maleate, Clemastine fumarate, Alcaftadine, Bilastine, Vapitadine hydrochloride, AZD-1744, GSK-1004723D, GSK-835726 or SUN-1334H.

Specific examples of suitable Phosphosdiesterase IV (PDE IV) inhibitors that can be combined with the PI3K inhibitors of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)padenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl) pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid, MK-0873, CDC-801, UK-500001, BLX-914, 2-carbomethoxy-4-cyano-4-(3-cyclopropylmethoxy-4-difluromethoxyphenyl)cyclohexan1-one, cis[4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22 (Suppl. 45): Abst 2557) and the compounds claimed in the PCT patent applications number WO 03/097613, WO 2004/058729, WO 2005/049581, WO 2005/123693, WO 2005/123692, and WO 2010/069504.

Specific examples of suitable immunosupressants that can be combined with the PI3K inhibitors of the present invention are picremolimus, tacrolimus, cyclosporine A, leflunomide, teriflunomide, vidofludimus, laquinimod, methotrexate, 5-fluorouracil (5-FU), anti-TNF agents and compounds described in PCT patent applications Nos. WO 2008/077639, WO 2009/021696, WO 2009/153043, and WO2010083975 (in particular amino(iso)nicotinic acid derivatives selected from the group consisting of 2-(3'-ethoxy-3-(trifluoromethoxy)biphenyl-4-ylamino)nicotinic acid, 2-(3,5-difluoro-3'-methoxybiphenyl-4-ylamino)nicotinic acid and 2-(3,5-difluoro-2-methylbiphenyl-4-ylamino)nicotinic acid; and azabiphenylaminobenzoic acid derivatives selected from the group consisting of 5-cyclopropyl-2-(2-(2,6-difluorophenyl)pyrimidin-5-ylamino)benzoic acid, 5-cyclopropyl-2-((2-(2-(trifluoromethyl)phenyl)pyrimidin-5-yl)amino)benzoic acid and 5-methyl-2-((6-(2,3-difluorophenyl)pyridin-3-yl) amino)benzoic acid)

Specific examples of suitable anti-infectives that can be combined with the PI3K inhibitors of the present invention are aclarubicin, actinomycin D, amrubicin, annamycin, adhamycin, bleomycin, daunorubicin, doxorubicin, elsamitrucin, epirubicin, galarubicin, idarubicin, mitomycin C, mupiricin, nemorubicin, neocarzinostatin, peplomycin, pirarubicin, rebeccamycin, retapamulin, stimalamer, streptozocin, valrubicin, zinostatin, amphotericin B, bifonazole, caspofungin, clotrimazole, echinocandin B, econazole, fluconazole, flucytosine, itraconazole, ketoconazole, miconazole, posaconazole, ravuconazole, terbinafine, tioconazole, voriconazole and combinations thereof.

Particularly preferred combination products according to the invention comprise a compound of formula (I) and a therapeutically effective amount of one or more additional therapeutic agents selected from the group consisting of mometasone furoate, ciclesonide, budesonide, fluticasone propionate, fluticasone furoate, betamethasone valerate, clobetasol propionate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo [2.2.2]octane salts, formoterol, salmeterol, indacaterol, carmoterol, LAS 100977 (abediterol), compounds described in PCT patent applications Nos. WO 2008/077639, WO 2009/021696, WO 2009/153043, and WO 2010/083975 (in particular amino(iso)nicotinic acid derivatives selected from the group consisting of 2-(3'-ethoxy-3-(trifluoromethoxy)biphenyl-4-ylamino)nicotinic acid, 2-(3,5-difluoro-3'-methoxybiphenyl-4-ylamino)nicotinic acid and 2-(3,5-difluoro-2- methylbiphenyl-4-ylamino)nicotinic acid; and azabiphenylaminobenzoic acid derivatives selected from the group consisting of 5-cyclopropyl-2-(2-(2,6-difluorophenyl) pyrimidin-5-ylamino)benzoic acid, 5-cyclopropyl-2-((2-(2-(trifluoromethyl)phenyl)pyrimidin-5-yl)amino)benzoic acid and 5-methyl-2-((6-(2,3-difluorophenyl)pyridin-3-yl) amino)benzoic acid), methapyrilene, cetirizine, loratadine, ebastine, desloratadine, fexofenadine, azelastine, levocabastine, olopatadine, Montelukast, picremolimus, tacrolimus, mupiricin, retapamulin, clotrimazole, ketoconazole and terbinafine.

The compounds of formula (I) and the combinations of the invention may be used in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors, wherein the use of a PI3K inhibitor is expected to have a beneficial effect, for example leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the compounds of the invention together with one or more other therapeutic agents for use in the treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The invention also encompasses the use of a combination of the compounds of the invention together with one or more other therapeutic agents for the manufacture of a formulation or medicament for treating these diseases.

The invention also provides a method of treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the pyrrolotriazinone derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a imidazopyridine derivative of the invention together with instructions for simultaneous, concurrent, separate or sequential use in combination with another active compound useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosus, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosus, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

Another execution of the present invention consists of a package comprising a imidazopyridine derivative of the invention and another active compound useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

Pharmaceutical Compositions

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The invention further provides pharmaceutical compositions comprising the compounds of the invention in association with a pharmaceutically acceptable diluent or carrier together with one or more other therapeutic agents for use in the treatment of a pathological condition or disease susceptible to amelioration by inhibition of Phosphoinositide 3-Kinases (PI3Ks), such as the ones previously described.

The invention is also directed to pharmaceutical compositions of the invention for use in the treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelodysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis. The invention also encompasses the use of a pharmaceutical composition of the invention for the manufacture of a medicament for treating these diseases.

The invention also provides a method of treatment of a pathological condition or disease susceptible to amelioration by inhibition of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to *pemphigus vulgaris*, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis; more in particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis; comprising administering a therapeutically effective amount of a pharmaceutical composition of the invention.

The present invention also provides pharmaceutical compositions which comprise, as an active ingredient, at least a compound of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

Additional suitable carriers for formulations of the compounds of the present invention can be found in Remington: The Science and Practice of Pharmacy, 21st Edition, Lippincott Williams & Wilkins, Philadelphia, Pa., 2001.

i) Oral Administration

The compounds of the invention may be administered orally (peroral administration; per os (latin)). Oral administration may involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, *acacia*, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.001-50 mg, more preferably 0.01-5 mg of active ingredient or the equivalent amount of a pharmaceutically acceptable salt thereof. Alternatively, the active ingredient(s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants (eg oleic acid or lecithin) and cosolvens (eg ethanol). Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 min, preferably 2-5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

iv) Nasal Mucosal Administration

The compounds of the invention may also be administered via the nasal mucosal. Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semisolid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the pharmaceutical compositions of the invention are made up in a form suitable for oral, inhalation or topical administration, being particularly preferred oral or inhalation administration.

The pharmaceutical formulations may conveniently be presented in unit dosage form and may be prepared by any of the methods well known in the art of pharmacy.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

The following preparations forms are cited as formulation examples:

FORMULATION EXAMPLES

Formulation Example 1

Oral Suspension

| Ingredient | Amount |
| --- | --- |
| Active Compound | 3 mg |
| Citric acid | 0.5 g |
| Sodium chloride | 2.0 g |

325
-continued

| Ingredient | Amount |
| --- | --- |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

Gelatin Cartridge for Inhalation

| Ingredient | Amount |
| --- | --- |
| Active Compound (micronized) | 0.2 mg |
| Lactose | 25 mg |

Formulation Example 4

Formulation for Inhalation with a DPI

| Ingredient | Amount |
| --- | --- |
| Active Compound (micronized) | 15 mg |
| Lactose | 3000 mg |

Formulation Example 5

Formulation for a MDI

| Ingredient | Amount |
| --- | --- |
| Active Compound (micronized) | 10 g |
| 1,1,1,2,3,3,3-heptafluoro-n-propane | q.s. to 200 mL |

In all the formulation examples, active compound is (S)-2-(1-(6-Amino-5-(1H-tetrazol-5-yl)pyrimidin-4-ylamino)ethyl)-3-phenylpyrrolo[1,2-f][1,2,4]triazin-4(3H)-one.

Modifications, which do not affect, alter, change or modify the essential aspects of the compounds, combinations or pharmaceutical compositions described, are included within the scope of the present invention.

326

The invention claimed is:

1. A compound of Formula (I), or a pharmaceutically acceptable salt or N-oxide thereof, comprising:

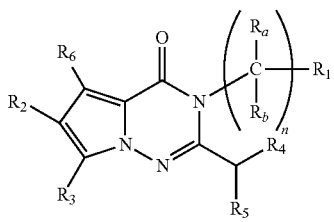

Formula (I)

wherein:

n is 0, 1, 2 or 3;

$R_a$ and $R_b$ are independently chosen from a hydrogen atom, a $C_1$-$C_4$ haloalkyl group, a $C_1$-$C_4$ hydroxyalkyl group, and a linear or branched $C_1$-$C_4$ alkyl group;

$R_1$ is chosen from a $C_3$-$C_{10}$ cycloalkyl group; a $C_3$-$C_{10}$ cycloalkenyl group; a phenyl group; a 5- to 7-membered heteroaryl group containing at least one heteroatom chosen from O, S, and N; and a 5- to 7-membered heterocyclyl group containing at least one heteroatom chosen from O, S, and N;

wherein the cycloalkyl, cycloalkenyl, phenyl, heteroaryl, and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_3$-$C_4$ cycloalkyl group, $R_2$ and $R_3$ are independently chosen from a hydrogen atom, a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a $C_1$-$C_4$ alkoxy group, a —$NH_2$ group, a —$N(CH_3)H$ group, and a —$N(CH_3)_2$ group;

$R_7$ and $R_8$ are independently chosen from a hydrogen atom, a $C_1$-$C_4$ haloalkyl group, a $C_1$-$C_4$ hydroxyalkyl group, and a linear or branched $C_1$-$C_4$ alkyl group;

$R_4$ is chosen from a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom chosen from O, S, and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom chosen from O, S, and N), a —$(CH_2)_{0-3}$-(phenyl group), a —$(CH_2)_{0-3}$-(5- to 14-membered monocyclic or bicyclic heteroaryl group containing at least one heteroatom chosen from O, S, and N), and a linear or branched $C_1$-$C_4$ alkyl group, wherein the $C_1$-$C_4$ alkyl group is unsubstituted or substituted by at least one substituent chosen from a $C_1$-$C_4$ alkoxy group, a cyano group, a $C_3$-$C_4$ cycloalkyl group, a —$C(O)$—$(CH_2)_{0-3}$—$R_6$ group, and a —$C(O)$—$(CH_2)_{0-3}$—$NR_7R_8$ group;

wherein the phenyl and heteroaryl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group;

$R_6$ is chosen from a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}NR_7R_8$ group; a —$(CH_2)_{1-3}$—O($C_1$-$C_4$ alkyl group); a —$(CH_2)_{0-3}$—OC(O)—($C_1$-$C_4$ alkyl group); a —$(CH_2)_{0-3}$—C(O)O—($C_1$-$C_4$ alkyl group); a —C(O)—$(CH_2)_{0-3}$—$NR_7R_8$ group; a —$(CH_2)_{0-3}$—C(O)OH group; a —$(CH_2)_{0-3}$—S—$(CH_2)_{0-3}$-(phenyl group); a —$(CH_2)_{0-3}$—S—$(CH_2)_{0-3}$-(5- to 14-membered monocyclic or bicyclic heteroaryl group containing at least one heteroatom chosen from O, S and N); a —$(CH_2)_{0-3}$—O—$(CH_2)_{0-3}$-(phenyl group); a —$(CH_2)_{0-3}$—O—$(CH_2)_{0-3}$-(5- to 14-membered monocyclic or bicyclic heteroaryl group containing at least one heteroatom chosen from O, S, and N); a —$(CH_2)_{0-3}$-(phenyl group); a —$(CH_2)_{0-3}$-(5- to 14-membered monocyclic or bicyclic heteroaryl group containing at least one heteroatom chosen from O, S, and N); a —$(CH_2)_{0-3}$-(5- to 14-membered monocyclic or bicyclic heterocyclyl group containing at least one heteroatom chosen from O, S, and N); a $C_2$-$C_4$ alkynyl group or a linear or branched $C_1$-$C_4$ alkyl group, wherein the $C_1$-$C_4$ alkyl group is unsubstituted or substituted by at least one substituent chosen from a $C_1$-$C_4$ alkoxy group, a cyano group; and a $C_3$-$C_4$ cycloalkyl group;
wherein the phenyl, heteroaryl, heterocyclyl and alkynyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group, a —$(CH_2)_{0-3}$—$NR_7$—$(CH_2)_{0-3}$—$NR_7R_8$ group, a —$(CH_2)_{0-3}$—C(O)—$(CH_2)_{0-3}$-(5- to 7-membered heteroaryl group containing at least one heteroatom chosen from O, S, and N), and a —$(CH_2)_{0-3}$-(5- to 7-membered heterocyclyl group containing at least one heteroatom chosen from O, S, and N); wherein the heteroaryl and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group; and $R_5$ has formula (II-2)

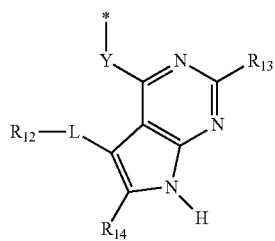

wherein:
$R_{13}$ and $R_{14}$ are independently chosen from a hydrogen atom, a —$(CH_2)_{0-3}CN$ group, a —$(CH_2)_{0-3}NR'R''$ group, and a linear or branched $C_1$-$C_4$ alkyl group; wherein R' and R'' are independently chosen from a hydrogen atom, a hydroxyl group, a $C_1$-$C_4$ alkoxy group, a $C_1$-$C_4$ hydroxyalkyl group or a linear, and branched $C_1$-$C_4$ alkyl group;
$R_{12}$ is chosen from a phenyl group, or a 5- to 14-membered heteroaryl group containing at least one heteroatom chosen from O, S, and N, wherein the phenyl and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a linear or branched $C_1$-$C_6$ hydroxyalkyl group, a $C_3$-$C_7$ cycloalkyl group, a —$(CH_2)_{0-3}$-(phenyl group), a —$(CH_2)_{0-3}$-(5- to 14-membered heteroaryl group containing at least one heteroatom chosen from O, S, and N), a —$(CH_2)_{0-3}$-(5- to 14-membered heterocyclyl group containing at least one heteroatom chosen from O, S, and N), a —$(CH_2)_{1-3}CN$ group, a —$(CH_2)_{0-3}$—O—$(CH_2)_{0-3}$—R' group, a —C(O) group, a —$(CH_2)_{0-3}NR'R''$ group, a —$(CH_2)_{0-3}$—C(O)—$(CH_2)_{1-3}$—CN group, a —$(CH_2)_{0-3}$—C(O)OH group, a —$(CH_2)_{0-3}$—C(O)—$(CH_2)_{0-3}$—R' group, a —$(CH_2)_{0-3}$—C(O)—$(CH_2)_{0-3}$—NR'R'' group, a —$(CH_2)_{0-3}NR'$—C(O)—$(CH_2)_{0-3}$—NR'R'' group, a —$(CH_2)_{0-3}NR'$—C(O)—$(CH_2)_{0-3}$—R'' group, a —$(CH_2)_{0-3}NR'$—S(O)$_2$—$(CH_2)_{0-3}$—R'' group, a —$(CH_2)_{0-3}NR'$—SO$_2$—$(CH_2)_{0-3}$—NR'R'' group, a —$(CH_2)_{0-3}$—S(O)$_2$—$(CH_2)_{0-3}$—R'' group, and a —$(CH_2)_{0-3}$—S(O)$_2$—$(CH_2)_{0-3}NR'R''$ group; wherein the phenyl, heterocyclyl, and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a $C_1$-$C_4$ alkoxy group, a —$NH_2$ group, a —$NH(C_1$-$C_4$ alkyl) group, a —$N(C_1$-$C_4$ alkyl)$_2$ group, and a linear or branched $C_1$-$C_6$ hydroxyalkyl group; and wherein R' and R'' are independently chosen from a hydrogen atom; a hydroxyl group; a $C_1$-$C_4$ haloalkyl group; a $C_1$-$C_4$ alkoxy group; a $C_1$-$C_4$ hydroxyalkyl group; a linear or branched $C_1$-$C_4$ alkyl group; a —$N(C_1$-$C_4$ alkyl)$_2$ group; a 5- to 7-membered heteroaryl group containing at least one heteroatom chosen from O, S, and N; a 5- to 7-membered heterocyclyl group containing at least one heteroatom chosen from O, S, and N; and a phenyl group, wheerein the phenyl group is unsubstituted or substituted by at least one substituent chosen from a halogen atom, a hydroxyl group, a cyano group, a $C_1$-$C_4$ hydroxyalkyl group, a $C_1$-$C_4$ haloalkyl group, a $C_1$-$C_4$ alkoxy group, a $C_3$-$C_4$ cycloalkyl group, and a linear or branched $C_1$-$C_4$ alkyl group;

L is chosen from a direct bound or a linker chosen from —O—, —S—, a —$(CH_2)_{0-3}$—SO$_2$—$(CH_2)_{0-3}$ group, a —$(CH_2)_{0-3}$—SO$_2$—NR'—$(CH_2)_{0-3}$, a —$(CH_2)_{0-3}NR'$—$(CH_2)_{0-3}$— group, a —C(O)—$(CH_2)_{0-3}$ group, a —C(O)—NR'—$(CH_2)_{0-3}$ group, a —$(CH_2)_{0-3}$ NR'—C(O)—$(CH_2)_{0-3}$ group, a —$(CH_2)_{0-3}$ —C(O)—O—$(CH_2)_{0-3}$ group, a —$(CH_2)_{0-3}$ —O—C(O)—$(CH_2)_{0-3}$ group, and a —$(CH_2)_{1-4}$ group; wherein R' is chosen from a hydrogen atom and a linear or branched $C_1$-$C_4$ alkyl group;

Y is chosen from a —NR'— group; wherein R' is chosen from a hydrogen atom and a linear or branched $C_1$-$C_4$ alkyl group; and (*) represents a point of attachment of $R_5$ to the remainder of formula (I).

2. The compound according to claim 1, wherein
n is 0, 1, 2 or 3;
$R_a$ and $R_b$ are independently chosen from a hydrogen atom, a $C_1$-$C_4$ haloalkyl group, a $C_1$-$C_4$ hydroxyalkyl group, and a linear or branched $C_1$-$C_4$ alkyl group;
$R_1$ is chosen from a $C_3$-$C_{10}$ cycloalkyl group; a $C_3$-$C_{10}$ cycloalkenyl group, a phenyl group; a 5- to 7-membered heteroaryl group containing at least one heteroatom chosen from O, S, and N; and a 5- to 7-membered heterocyclyl group containing at least one heteroatom chosen from O, S, and N;
wherein the cycloalkyl, cycloalkenyl, phenyl, heteroaryl, and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_3$-$C_4$ cycloalkyl group, $R_2$ and $R_3$ are independently chosen from a hydrogen atom, a halogen atom, a hydroxyl group, a $C_1$-$C_3$ alkoxy group, a linear or branched $C_1$-$C_4$ alkyl group, a $C_1$-$C_3$ haloalkyl group, a $C_3$-$C_4$ cycloalkyl group, and a —$NH_2$ group;
$R_7$ and $R_8$ are independently chosen from a hydrogen atom, a $C_1$-$C_4$ haloalkyl group, a $C_1$-$C_4$ hydroxyalkyl group, and a linear or branched $C_1$-$C_4$ alkyl group;
$R_4$ is chosen from a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom chosen from O, S, and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom chosen from O, S, and N), a —$(CH_2)_{0-3}$-(phenyl group), a —$(CH_2)_{0-3}$-(5- to 14-membered monocyclic or bicyclic heteroaryl group containing at least one heteroatom chosen from O, S, and N), and a linear or branched $C_1$-$C_4$ alkyl group;
wherein the phenyl and heteroaryl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group;
$R_6$ is chosen from a hydrogen atom; a halogen atom; a hydroxyl group; a cyano group; a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom chosen from O, S, and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom chosen from O, S, and N); a —$(CH_2)_{0-3}$-(phenyl group); a —$(CH_2)_{0-3}$-(5- to 14-membered monocyclic or bicyclic heteroaryl group containing at least one heteroatom chosen from O, S, and N); a —$(CH_2)_{0-3}$-(5- to 14-membered monocyclic or bicyclic heterocyclyl group containing at least one heteroatom chosen from O, S, and N); a $C_2$-$C_4$ alkynyl group or a linear or branched $C_1$-$C_4$ alkyl group, which alkyl group is unsubstituted or substituted by at least one substituent chosen from a $C_1$-$C_4$ alkoxy group, a cyano group, and a $C_3$-$C_4$ cycloalkyl group;
wherein the phenyl, heteroaryl, heterocyclyl and alkynyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group, a —$(CH_2)_{0-3}$—$NR_7$—$(CH_2)_{0-3}$—$NR_7R_8$ group, a —$(CH_2)_{0-3}$—C(O)—$(CH_2)_{0-3}$-(5- to 7-membered heteroaryl group containing at least one heteroatom chosen from O, S, and N), and a —$(CH_2)_{0-3}$-(5- to 7-membered heterocyclyl group containing at least one heteroatom chosen from O, S, and N);

wherein the heteroaryl and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group; and
$R_5$ has formula (II-2)

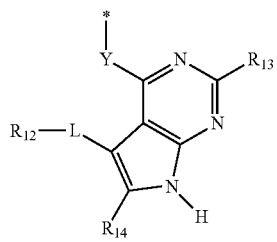

wherein:
$R_{13}$ and $R_{14}$ are independently chosen from a hydrogen atom, a —$(CH_2)_{0-3}$CN group, a —$(CH_2)_{0-3}$NR'R" group, and a linear or branched $C_1$-$C_4$ alkyl group; wherein R' and R" are independently chosen from a hydrogen atom, a hydroxyl group, a $C_1$-$C_4$ alkoxy group, a $C_1$-$C_4$ hydroxyalkyl group, and a linear or branched $C_1$-$C_4$ alkyl group;
$R_{12}$ is chosen from a phenyl group or a 5- to 14-membered heteroaryl group containing at least one heteroatom chosen from O, S, and N,
wherein the phenyl and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a linear or branched $C_1$-$C_6$ hydroxyalkyl group, a $C_3$-$C_7$ cycloalkyl group, a —$(CH_2)_{0-3}$-(phenyl group), a —$(CH_2)_{0-3}$-(5- to 14-membered heteroaryl group containing at least one heteroatom chosen from O, S, and N), a —$(CH_2)_{0-3}$-(5- to 14-membered heterocyclyl group containing at least one heteroatom chosen from O, S, and N), a —$(CH_2)_{0-3}$CN group, a —$(CH_2)_{0-3}$—O—$(CH_2)_{0-3}$—R' group, a —C(O) group, a —$(CH_2)_{0-3}$NR'R" group, a —$(CH_2)_{0-3}$—C(O)—$(CH_2)_{1-3}$—CN group, a —$(CH_2)_{0-3}$—C(O)OH group, a —$(CH_2)_{0-3}$—C(O)—$(CH_2)_{0-3}$—R' group, a —$(CH_2)_{0-3}$—C(O)—$(CH_2)_{0-3}$—NR'R" group, a —$(CH_2)_{0-3}$NR'—C(O)—$(CH_2)_{0-3}$—NR'R" group, a —$(CH_2)_{0-3}$NR'—C(O)—$(CH_2)_{0-3}$—R" group, a —$(CH_2)_{0-3}$NR'—S(O)$_2$—$(CH_2)_{0-3}$—R" group, a —$(CH_2)_{0-3}$—NR'—SO$_2$—$(CH_2)_{0-3}$—NR'R" group, a —$(CH_2)_{0-3}$—S(O)$_2$—$(CH_2)_{0-3}$—R" group, and a —$(CH_2)_{0-3}$—S(O)$_2$—$(CH_2)_{0-3}$NR'R" group; wherein the phenyl, heterocyclyl and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a $C_1$-$C_4$ alkoxy group, a —$NH_2$ group, a —$NH(C_1$-$C_4$ alkyl) group, a —$N(C_1$-$C_4$ alkyl)$_2$ group, and a linear or branched $C_1$-$C_6$ hydroxyalkyl group; and wherein R' and R" are independently chosen from a hydrogen atom; a hydroxyl group; a $C_1$-$C_4$ haloalkyl group; a $C_1$-$C_4$ alkoxy group; a $C_1$-$C_4$ hydroxyalkyl group; a linear or branched $C_1$-$C_4$ alkyl group; a —$N(C_1$-$C_4$ alkyl)$_2$ group; a 5- to 7-membered heteroaryl group containing at least one heteroatom chosen from O, S, and N; a 5- to 7-membered heterocyclyl group containing at least one heteroatom chosen from O, S, and N; and a phenyl group, wherein the phenyl group is unsubstituted or substituted by at least one substituent chosen from a halogen atom, a hydroxyl group, a cyano group, a $C_1$-$C_4$ hydroxyalkyl group, a $C_1$-$C_4$ haloalkyl group, a $C_1$-$C_4$ alkoxy group, a $C_3$-$C_4$ cycloalkyl group, and a linear or branched $C_1$-$C_4$ alkyl group;

L is chosen from a direct bound or a linker chosen from —O—, —S—, a —$(CH_2)_{0-3}$—$SO_2$—$(CH_2)_{0-3}$ group, a —$(CH_2)_{0-3}$—$SO_2$—NR'—$(CH_2)_{0-3}$, a —$(CH_2)_{0-3}$ NR'—$(CH_2)_{0-3}$— group, a —C(O)—$(CH_2)_{0-3}$ group, a —C(O)—NR'—$(CH_2)_{0-3}$ group, a —$(CH_2)_{0-3}$ NR'—C(O)—$(CH_2)_{0-3}$ group, a —$(CH_2)_{0-3}$—C(O)—O—$(CH_2)_{0-3}$ group, a —$(CH_2)_{0-3}$—O—C(O)—$(CH_2)$ group, and a —$(CH_2)_{1-4}$ group; wherein R' is chosen from a hydrogen atom and a linear or branched $C_1$-$C_4$ alkyl group;

Y is chosen from a —NR'— group; wherein R' is chosen from a hydrogen atom and a linear or branched $C_1$-$C_4$ alkyl group.

3. The compound according to claim 1, wherein $R_1$ is chosen from a $C_3$-$C_7$ cycloalkyl group, a phenyl group, a 5- to 10-membered heteroaryl group containing one, two or three heteroatoms chosen from O, S, and N, a pyrrolidinyl group, a piperidinyl group, a piperazinyl group, a tetrahydropyranyl group, and a morpholinyl group, wherein the cycloalkyl, phenyl, heteroaryl, pyrrolidinyl, piperidinyl, piperazinyl, tetrahydropyranyl, and morpholinyl groups are unsubstituted or substituted by at least one substituent chosen from a halogen atom, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group, and a —C(O)—$(CH_2)_{0-3}$—$NR_7R_8$ group; wherein $R_7$ and $R_8$ are independently chosen from a hydrogen atom and a $C_1$-$C_4$ alkyl group.

4. The compound according to claim 1, wherein $R_2$ is chosen from a hydrogen atom, a halogen atom, a hydroxyl group, and a linear or branched $C_1$-$C_4$ alkyl group.

5. The compound according to claim 1, wherein $R_3$ is chosen from a hydrogen atom, a halogen atom, a hydroxyl group, and a linear or branched $C_1$-$C_4$ alkyl group.

6. The compound according to claim 1, wherein $R_4$ is chosen from a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$—S—$(CH_2)_{0-3}$-(phenyl group), a —$(CH_2)_{0-3}$—S—$(CH_2)_{0-3}$-(5- to 14-membered monocyclic or bicyclic heteroaryl group containing at least one heteroatom chosen from O, S, and N), a —$(CH_2)_{0-3}$—O—$(CH_2)_{0-3}$-(phenyl group), a —$(CH_2)_{0-3}$—O—$(CH_2)_{0-3}$-(5- to 14-membered monocyclic or bicyclic heteroaryl group containing at least one heteroatom chosen from O, S, and N), a —$(CH_2)_{0-3}$-(phenyl group), a —$(CH_2)_{0-3}$-(5- to 14-membered monocyclic or bicyclic heteroaryl group containing at least one heteroatom chosen from O, S, and N), and a linear or branched $C_1$-$C_4$ alkyl group;

wherein the phenyl and heteroaryl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group;

$R_6$ is chosen from a hydrogen atom; a halogen atom; a hydroxyl group; a cyano group; a —$(CH_2)_{0-3}$—S—$(CH_2)_{0-3}$-(phenyl group); a —$(CH_2)_{0-3}$—S$(CH_2)_{0-3}$-(5- to 14-membered monocyclic or bicyclic heteroaryl group containing at least one heteroatom chosen from O, S, and N); a —$(CH_2)_{0-3}$—O—$(CH_2)_{0-3}$-(phenyl group); a —$(CH_2)_{0-3}$—O—$(CH_2)_{0-3}$-(5- to 14-membered monocyclic or bicyclic heteroaryl group containing at least one heteroatom chosen from O, S, and N); a —$(CH_2)_{0-3}$-(phenyl group); a —$(CH_2)_{0-3}$-(5- to 14-membered monocyclic or bicyclic heteroaryl group containing at least one heteroatom chosen from O, S, and N); a —$(CH_2)_{0-3}$-(5- to 14-membered monocyclic or bicyclic heterocyclyl group containing at least one heteroatom chosen from O, S, and N); a $C_2$-$C_4$ alkynyl group; and a linear or branched $C_1$-$C_4$ alkyl group, wherein the $C_1$-$C_4$ alkyl group is unsubstituted or substituted by at least one substituent chosen from a $C_1$-$C_4$ alkoxy group, a cyano group, and a $C_3$-$C_4$ cycloalkyl group;

wherein the phenyl, heteroaryl, heterocyclyl, and alkynyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_1$-$C_4$ alkoxy group, a —$(CH_2)_{0-3}$—$NR_7$—$(CH_2)_{0-3}$—$NR_7R_8$ group, a —$(CH_2)_{0-3}$—C(O)—$(CH_2)_{0-3}$-(5- to 7-membered heteroaryl group containing at least one heteroatom chosen from O, S, and N), and a —$(CH_2)_{0-3}$-(5- to 7-membered heterocyclyl group containing at least one heteroatom chosen from O, S and N); wherein the heteroaryl and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, and a $C_1$-$C_4$ alkoxy group.

7. The compound according to claim 1, wherein:

n is 0 or 1;

$R_1$ is chosen from a phenyl group, unsubstituted or substituted by at least one substituent chosen from a halogen atom and a linear or branched $C_1$-$C_3$ alkyl group;

$R_2$ and $R_3$ are independently chosen from a hydrogen atom and a linear or branched $C_1$-$C_3$ alkyl group;

$R_4$ is chosen from a hydrogen atom, a linear or branched $C_1$-$C_3$ alkyl group, a —$(CH_2)_{0-3}$—S—$(CH_2)_{0-3}$-(phenyl) group, and a —$(CH_2)_{0-3}$—O—$(CH_2)_{0-3}$-(phenyl) group;

$R_6$ is chosen from a hydrogen atom, a halogen atom, a cyano group, a linear or branched $C_1$-$C_3$ alkyl group, and a —S-phenyl group;

$R_5$ has formula (II-2)

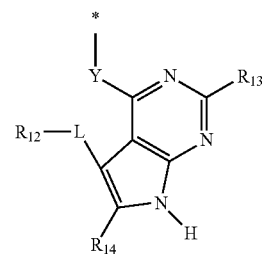

wherein:

$R_{13}$ and $R_{14}$ are independently chosen from a hydrogen atom, a —$NH_2$ group, and a linear or branched $C_1$-$C_4$ alkyl group;

$R_{12}$ is chosen from a phenyl group or a 5- to 9-membered heteroaryl group containing at least one heteroatom chosen from O, S, and N, wherein the phenyl and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a linear or branched $C_1$-$C_6$ hydroxyalkyl group, a —$(CH_2)_{0-3}$-(phenyl) group, a —$(CH_2)_{0-3}$-(morpholinyl) group, a —$(CH_2)_{0-3}$-(piperidinyl)-$N(C_1$-$C_3$ alkyl$)_2$ group, a —$(CH_2)_{0-3}$-(oxazolyl) group, a —$(CH_2)_{0-3}$-(oxadiazolyl)-R' group, a —O—$(C_1$-$C_3$ alkyl) group, a —O—$(C_1$-$C_3$ haloalkyl) group, a —$(CH_2)_{0-3}$—O—$(CH_2)_{0-3}$—$N(C_1$-$C_3$ alkyl$)_2$ group, a —C(O) group, a —$NH_2$ group, a —$NH(C_1$-$C_3$ alkyl) group, a —$N(C_1$-$C_3$ alkyl$)_2$ group, a —$(CH_2)_{0-3}$—C(O)OH group, a —C(O)—$N(C_1$-$C_3$ alkyl$)_2$ group, a —C(O)—NH-(phenyl) group, a —NH—C(O)—$NH_2$— group, a —NH—C(O)—NH-(pyridine) group, a —NH—C(O)-(phenyl) group, a —$N(CH_3)$—$S(O)_2$—$CH_3$ group, a —NH—S$(O)_2$—$(CH_2)_{0-3}$—R" group, a —$S(O)_2$R" group, or a —$S(O)_2NH(C_1$-$C_3$ alkyl) group; wherein R' is chosen from a linear or branched $C_1$-$C_4$ alkyl group, and a —$NH_2$ group, and wherein R" is chosen from a hydroxyl group, a $C_1$-$C_4$ haloalkyl group, a $C_1$-$C_4$ alkoxy group, a linear or branched $C_1$-$C_4$ alkyl group, a —$NH_2$ group, a —$N(C_1$-$C_3$ alkyl$)_2$ group, a phenyl group, a tetrahydropyranyl group, and a morpholinyl group; and wherein each phenyl group independently is unsubstituted or substituted by at least one substituent chosen from a halogen atom, a hydroxyl group, a $C_1$-$C_4$ haloalkyl group, a $C_1$-$C_4$ alkoxy group, a linear or branched $C_1$-$C_4$ alkyl group, a $C_1$-$C_4$ haloalkyl group, and a linear or branched $C_1$-$C_6$ hydroxyalkyl group;

L is chosen from a direct bound or a linker chosen from —S—, a —$SO_2$— group, a —C(O)—NH—$(CH_2)_{0-3}$ group, a —$(CH_2)_{0-3}$—C(O)—O—$(CH_2)_{0-3}$ group, and a —$(CH_2)_{1-3}$ group;

Y is a —NH— group.

8. The compound according to claim 1,
wherein,
n is 0 or 1;
$R_a$ and $R_b$ are independently chosen from a hydrogen atom and a linear or branched $C_1$-$C_4$ alkyl group;
$R_1$ is chosen from a phenyl group unsubstituted or substituted by at least one substituent chosen from a halogen atom and a linear or branched $C_1$-$C_3$ alkyl group;
$R_2$ and $R_3$ are independently chosen from a hydrogen atom and a linear or branched $C_1$-$C_3$ alkyl group;
and
$R_4$ is chosen from a hydrogen atom, a linear or branched $C_1$-$C_3$ alkyl group, a —$(CH_2)_{0-3}$—S—$(CH_2)_{0-3}$-(phenyl) group, and a —$(CH_2)_{0-3}$—O—$(CH_2)_{0-3}$-(phenyl) group;

$R_6$ is chosen from a hydrogen atom, a halogen atom, a cyano group, a linear or branched $C_1$-$C_3$ alkyl group, and a —S-phenyl group;

$R_5$ has formula (II-2):

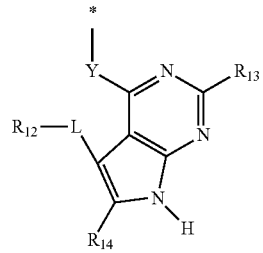

wherein:
$R_{13}$ and $R_{14}$ are independently chosen from a hydrogen atom, a —$NH_2$ group, and a linear or branched $C_1$-$C_4$ alkyl group;
$R_{12}$ is chosen from a phenyl group and a 5- to 9-membered heteroaryl group containing at least one heteroatom chosen from O, S, and N, wherein the phenyl and heteroaryl groups are unsubstituted or substituted by at least one substituent chosen from a halogen atom, a hydroxyl group, a cyano group, a linear or branched $C_1$-$C_6$ alkyl group, a $C_1$-$C_4$ haloalkyl group, a linear or branched $C_1$-$C_6$ hydroxyalkyl group, a —$(CH_2)_{0-3}$-(phenyl) group, a —$(CH_2)_{0-3}$-(morpholinyl) group, a —$(CH_2)_{0-3}$-(piperidinyl)-$N(C_1$-$C_3$ alkyl$)_2$ group, a —$(CH_2)_{0-3}$-(oxazolyl) group, a —$(CH_2)_{0-3}$-(oxadiazolyl)-R' group, a —O—$(C_1$-$C_3$ alkyl) group, a —O—$(C_1$-$C_3$ haloalkyl) group, a —$(CH_2)_{0-3}$—O—$(CH_2)_{0-3}$—$N(C_1$-$C_3$ alkyl$)_2$ group, a —C(O) group, a —$NH_2$ group, a —$NH(C_1$-$C_3$ alkyl) group, a —$N(C_1$-$C_3$ alkyl$)_2$ group, a —$(CH_2)_{0-3}$—C(O)OH group, a —C(O)—$N(C_1$-$C_3$ alkyl$)_2$ group, a —C(O)—NH-(phenyl) group, a —NH—C(O)—$NH_2$— group, a —NH—C(O)—NH-(pyridine) group, a —NH—C(O)-(phenyl) group, a —$N(CH_3)$—$S(O)_2$—$CH_3$ group, a —NH—S$(O)_2$—$(CH_2)_{0-3}$—R" group, a —$S(O)_2$R" group, and a —$S(O)_2NH(C_1$-$C_3$ alkyl) group;

wherein R' is chosen from a linear or branched $C_1$-$C_4$ alkyl group and a —$NH_2$ group, and wherein R" is chosen from a hydroxyl group, a $C_1$-$C_4$ haloalkyl group, a $C_1$-$C_4$ alkoxy group, a linear or branched $C_1$-$C_4$ alkyl group, a —$NH_2$ group, a —$N(C_1$-$C_3$ alkyl$)_2$ group, a phenyl group, a tetrahydropyranyl group, and a morpholinyl group; wherein each phenyl group independently is unsubstituted or substituted by at least one substituent chosen from a halogen atom, a hydroxyl group, a $C_1$-$C_4$ haloalkyl group, a $C_1$-$C_4$ alkoxy group, a linear or branched $C_1$-$C_4$ alkyl group, a $C_1$-$C_4$ haloalkyl group, and a linear or branched $C_1$-$C_6$ hydroxyalkyl group;

L is chosen from a direct bound and a linker chosen from —S—, a —$SO_2$— group, a —C(O)—NH—$(CH_2)_{0-3}$ group, a —$(CH_2)_{0-3}$—C(O)—O—$(CH_2)_{0-3}$ group, and a —$(CH_2)_{1-3}$ group;

Y is a —NH— group.

9. The compound according to claim 1 chosen from:
(S)-2-(1-((5-(3-fluoro-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;
(S)-2-(1-((5-(2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-hydroxyphenyl)-7H-pyrrolo[2,3-]pyrimidin-4-yl)amino)ethyl)-5-methyl-3-phenylpyrrolo[2,1-f][1,2,4]triazin-4(3H)-one;

(S)-2-(1-((5-(1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-benzyl 4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxylate;

(S)-2-(1-((5-(2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-fluorophenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(4-fluoro-2-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(2-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide;

(S)-2-(1-((5-(3-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(5-amino-6-methoxypyridin-3-yl)-7H-pyrrolo[2,3-d]pyrimidin-4-yl)amino)ethyl)-5-methyl-3-phenylpyrrolo[2,1-f][1,2,4]triazin-4(3H)-one;

2-(1S)-1-((5-(2-fluoro-6-hydroxyphenyl)-7H-pyrrolo[2,3-d]pyrimidin-4-yl)amino)ethyl)-5-methyl-3-phenylpyrrolo[2,1-f][1,2,4]triazin-4(3H-one;

(S)-2-(1-((5-(6-methoxypyridin-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(5-fluoro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-5-methylphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(6-oxo-1,6-dihydropyridin-2-yl)-7H-pyrrolo[2,3-d]pyrimidin-4-yl)amino)ethyl)-3-phenylpyrrolo[2,1-f][1,2,4]triazin-4(3H)-one;

(S)-2-(1-((5-(1H-indol-7-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(2-hydroxy-5-(trifluoromethyl)phenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((3-methoxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1H-indol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2,4-dihydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(1-methyl-1H-pyrazol-4-yl)-7H-pyrrolo[2,3-d]pyrimidin-4-yl)amino)ethyl)-3-phenylpyrrolo[2,1-f][1,2,4]triazin-4(3H)-one;

N'-[3-methoxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

(S)—N-benzyl-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)—N-(3-(dimethylamino)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(3-fluoro-5-hydroxybenzyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-methyl-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-hydroxyphenyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)-5-methyl-2-(1-((5-(3-(morpholinosulfonyl)phenyl)-7H-pyrrolo[2,3-d]pyrimidin-4-yl)amino)ethyl)-3-phenylpyrrolo[2,1-f][1,2,4]triazin-4(3H)-one;

(S)—N-((1H-pyrazol-4-yl)methyl)-4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidine-5-carboxamide;

(S)-1-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea;

(S)—N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(4-hydroxy-3-methoxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-((2-hydroxyphenyl)thio)-7H-pyrrolo[2,3-d]pyrimidin-4-yl)amino)ethyl) 5-methyl-3-phenylpyrrolo[2,1-f][1,2,4]triazin-4(3H)-one;

(S)-2-(1-((5-((4-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1-(2-hydroxyethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-amino-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-chloro-2-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1-(2-(dimethylamino)ethyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)methanesulfonamide;

(S)-4-hydroxy-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)-4-methoxy-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)-2-(1-((5-(1-(3-(dimethylamino)propyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-(2-(dimethylamino)ethoxy)-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(5-ethylamino)-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)-4-hydroxy-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)benzenesulfonamide;

(S)-2-(1-((5-((5-fluoro-2-hydroxyphenyl)thio)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(2-methyloxazol-5-yl)-7H-pyrrolo[2,3-d]pyrimidin-4-yl)amino)ethyl)-3-phenylpyrrolo[2,1-f][1,2,4]triazin-4(3H)-one;

(S)-2-(1-((5-(1-(2-hydroxyethyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(5-amino-1,3,4-thiadiazol-2-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide;

(S)—N-methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide;

(S)-2-(1-((5-(1H-pyrrolo[2,3-b]pyridin-5-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1-(3-hydroxypropyl)-1H-pyrazol-4-yl)-7H-pyrrolo[2,3-d]pyrimidin-4-yl)amino)ethyl)-5-methyl-3-phenylpyrrolo[2,1-f][1,2,4]triazin-4(3H)-one;

N-[3-hydroxy-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]sulfamide;

(S)-5-methyl-2-(1-((5-(1-(2-morpholinoethyl)-1H-pyrazol-3-yl)-7H-pyrrolo[2,3-d]pyrimidin-4-yl)amino)ethyl)-3-phenylpyrrolo[2,1-f][1,2,4]triazin-4(3H)-one;

(S)-5-methyl-3-phenyl-2-(1-((5-(1-(2,2,2-trifluoroethyl)-1H-pyrazol-3-yl)-7H-pyrrolo[2,3-d]pyrimidin-4-yl)amino)ethyl)pyrrolo[2,1-f][1,2,4]triazin-4(3H)-one;

(S)-3-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzonitrile;

(S)-3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzonitrile;

(S)-2-(dimethylamino)-N-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)ethanesulfonamide;

(S)-5-methyl-2-(1-((5-(1-methyl-3-(trifluoromethyl)-1H-pyrazol-5-yl)-7H-pyrrolo[2,3-d]pyrimidin-4-yl)amino)ethyl)-3-phenylpyrrolo[2,1-f][1,2,4]triazin-4(3H)-one;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(1-(2-methoxybenzyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(1-(3-hydroxy-2,2-dimethylpropyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-hydroxy-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-(1-(2-hydroxybenzyl)-1H-pyrazol-3-yl)-7H-pyrrolo[2,3-d]pyrimidin-4-yl)amino)ethyl)-3-phenylpyrrolo[2,1-f][1,2,4]triazin-4(3H)-one;

(S)-2-(1-((5-(1-(3-hydroxyphenyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(4-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)methanesulfonamide;

(S)-2-(1-((5-(1-((3-hydroxyphenyl)sulfonyl)-1H-pyrazol-3-yl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(4-hydroxy-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-1-(3-hydroxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)urea;

(S)-3-(Methylsulfonamido)-5-(4-((1-(4-oxo-3-phenyl-3,4-dihydropyrrolo[2,1-f][1,2,4]triazin-2-yl)ethyl)amino)-7H-pyrrolo[2,3-d]pyrimidin-5-yl)phenyl methanesulfonate;

(S)—N-(3-hydroxy-5-(4-((3-hydroxy-1-(5-methyl-4-oxo-3-phenyl-3,4-dihydropyrrolo[2,1-f][1,2,4]triazin-2-yl)propyl)amino)-7H-pyrrolo[2,3-d]pyrimidin-5-yl)phenyl)methanesulfonamide;

(S)-3-hydroxy-N-methyl-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzenesulfonamide;

(S)-3-hydroxy-N, N-dimethyl-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)benzamide;

(S)—N-(3-Fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indazol-6-yl)methanesulfonamide;

(S)—N-methyl-N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-5-morpholinophenyl)methanesulfonamide;

N-[4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)-1H-indol-6-yl]sulfamide;

(S)—N-(2-hydroxy-3-(4-((1-(5-methyl-4-oxo-3-phenyl-3,4-dihydropyrrolo[2,1-][1,2,4]triazin-2-yl)ethyl)amino)-7H-pyrrolo[2,3-d]pyrimidin-5-yl)phenyl)methanesulfonamide;

(S)-5-methyl-2-(1-((5-(3-(5-methyl-1,3,4-oxadiazol-2-yl)phenyl)-7H-pyrrolo[2,3-d]pyrimidin-4-yl)amino)ethyl)-3-phenylpyrrolo[2,1-f][1,2,4]triazin-4(3H)-one;

N'-[3-hydroxy-5-(4-{[(1 S)-1-(5-methyl-4-oxo-3-phenyl-3,4-dihydropyrrolo[2,1-][1,2,4]triazin-2-yl)ethyl]amino}-7H-pyrrolo[2,3-d]pyrimidin-5-yl)phenyl]-N,N-dimethylsulfamide;

(S)—N-(3-cyano-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-2-(1-((5-((2-hydroxyphenyl)sulfonyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(2-aminopyridin-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-hydroxy-5-(5-methyl-1,3,4-oxadiazol-2-yl)phenyl)-7H-pyrrolo[2,3-d]pyrimidin-4-yl)amino)ethyl)-5-methyl-3-phenylpyrrolo[2,1-f][1,2,4]triazin-4(3H)-one;

(S)-2-(1-((5-(3-(5-amino-1,3,4-oxadiazol-2-yl)-5-hydroxyphenyl)-7H-pyrrolo[2,3-d]pyrimidin-4-yl)amino)ethyl)-5-methyl-3-phenylpyrrolo[2,1-f][1,2,4]triazin-4(3H)-one;

(S)—N-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(4-methyl-3-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)—N-(3-((4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide;

(S)—N-(6-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-4-yl)methanesulfonamide;

(S)—N-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-2-yl)-1-(tetrahydro-2H-pyran-4-yl)methanesulfonamide;

(S)-1-(2-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)pyridin-3-yl)urea;

N-[3-fluoro-5-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]sulfamide;

(S)—N-(4-((4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)thio)phenyl)methanesulfonamide;

(S)-2-(1-((5-(2-(4-(dimethylamino)piperidin-1-yl)pyridin-4-yl)-7H-pyrrolo[2,3-d]pyrimidin-4-yl)amino)ethyl)-5-methyl-3-phenylpyrrolo[2,1-f][1,2,4]triazin-4(3H)-one;

(S)-5-methyl-2-(1-((5-(1-(methylsulfonyl)-1H-pyrrolo[2,3-b]pyridin-4-yl)-7H-pyrrolo[2,3-d]pyrimidin-4-yl)amino)ethyl)-3-phenylpyrrolo[2,1-f][1,2,4]triazin-4(3H)-one;

(S)—N-(3-methoxy-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)methanesulfonamide;

(S)-1-(4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)-1H-indol-6-yl)urea;

(S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-hydroxyethanesulfonamide;

(S)—N-(3-fluoro-5-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-2-methoxyethanesulfonamide;

(S)—N-(3-hydroxy-4-(4-((1-(5-methyl-4-oxo-3-phenyl-3,4-dihydropyrrolo[2,1-f][1,2,4]triazin-2-yl)ethyl)amino)-7H-pyrrolo[2,3-d]pyrimidin-5-yl)phenyl)-1-(tetrahydro-2H-pyran-4-yl)methanesulfonamide; and N'-[3-hydroxy-4-(4-{[(1S)-1-(5-methyl-4-oxo-3-phenyl-3,4-dihydropyrrolo[2,1-f][1,2,4]triazin-2-yl)ethyl]amino}-7H-pyrrolo[2,3-d]pyrimidin-5-yl)phenyl]-N,N-dimethylsulfamide;

or a pharmaceutically acceptable salt or N-oxide thereof.

10. A pharmaceutical composition comprising the compound according to claim 1 and a pharmaceutically acceptable diluent or carrier.

11. A method for treating a subject afflicted with asthma, chronic obstructive pulmonary disease, cystic fibrosis and idiopathic pulmonary fibrosis, comprising administering to the subject a therapeutically effective amount of the compound according to claim 1.

12. A combination product comprising (i) the compound according to claim 1; and (ii) at least one additional compound chosen from the group consisting of an Adenoside $A_{2A}$ agonist, an agent for treating cardiovascular disorders, an agent for treating diabetes, and an agent for treating liver disease, an anti-allergic agent, an anti-cholinergic agent, an anti-inflammatory agent, an anti-infective agent, a β2-adrenergic agonist, a Chemoattractant receptor homologous molecule expressed on $TH_2$ cells (CRTH2) inhibitor, a chemotherapeutic agent, a corticosteroid, an IKKβ/IKBKB (IkB kinase beta or IKK2) inhibitor, an immunosuppressant, a Janus kinase (JAK) inhibitor, a topically acting p38 Mitogen-Activated Protein Kinase (p38 MAPK) inhibitor, a Phosphodiesterase (PDE) IV inhibitor, and a Spleen tyrosine kinase (Syk) inhibitor, for simultaneous, separate or sequential use in the treatment of the human or animal body.

13. The compound according to claim 3, wherein $R_1$ is a phenyl group unsubstituted or substituted by one, two, or three substituents chosen from a halogen atom and a linear or branched $C_1$-$C_3$ alkyl group.

14. The compound according to claim 3, wherein $R_1$ is a phenyl group directly bonded to the pyrrolotriazinone group.

15. The compound according to claim 1, wherein the compound is N'-[3-methoxy-5-(4-{[(1S)-1-(5-methyl-4-oxo-3-phenyl-3,4-dihydropyrrolo[2,1-f][1,2,4]triazin-2-ethyl]amino)-7H-pyrrolo(2,3-d]pyrimidin-5-yl)phenyl]-N,N-dimethylsulfamide or a pharmaceutically acceptable salt or N-oxide thereof.

16. The compound according to claim 1, wherein the compound is (S)-5-methyl-2-(1-((5-(3-(morpholinosulfonyl)phenyl)-7H-pyrrolo[2,3-d]pyrimidin-4-yl) amino)ethyl)-3-phenylpyrrolo[2,1-f][1,2,4]triazin-4(3H)-one or a pharmaceutically acceptable salt or N-oxide thereof.

17. The compound according to claim 1, wherein the compound is (S)-2-(1-((5-(5-(ethylamino)-1,3,4-thiadiazol-2-yl)-7H-pyrrolo[2,3-d]pyrimidin-4-yl)amino) ethyl)-5-methyl-3-phenylpyrrolo[2,1-f][1,2,4]triazin-4(3H)-one or a pharmaceutically acceptable salt or N-oxide thereof.

18. The compound according to claim 1, wherein the compound is (S)-2-(1-((5-((5-fluoro-2-hydroxyphenyl)thio)-7H-pyrrolo[2,3-d]pyrimidin-4-yl)amino) ethyl)-5-methyl-3-phenylpyrrolo[2,1-f][1,2,4]triazin-4(3H)-one or a pharmaceutically acceptable salt or N-oxide thereof.

19. The compound according to claim 1, wherein the compound is N-[4-(4-{[(1S)-1-(5-methyl-4-oxo-3-phenyl-3,4-dihydropyrrolo[2,1-f][1,2,4]triazin-2-yl]ethyl]amino)-7H-pyrrolo[2,3-d]pyrimidin-5-yl)-1H-indol-6-yl]sulfamide or a pharmaceutically acceptable salt or N-oxide thereof.

20. The compound according to claim 1, wherein the compound is (S)-N-(3-fluoro-5-(4((1-(5-methyl-4-oxo-3-phenyl-3,4-dihydropyrollo[2,1-f][1,2,4]triazin-2-yl)ethyl)amino)-7H-pyrrolo[2,3-d]pyrimidin-5-yl)phenyl)-2-hydroxyethanesulfonamide or a pharmaceutically acceptabe salt or N-oxide thereof.

* * * * *